US008178557B2

(12) United States Patent
Potashman et al.

(10) Patent No.: US 8,178,557 B2
(45) Date of Patent: *May 15, 2012

(54) COMPOUNDS AND METHODS OF USE

(75) Inventors: Michele Potashman, Cambridge, MA (US); Tae-Seong Kim, Thousand Oaks, CA (US); Steven Bellon, Wellesley, MA (US); Shon Booker, Thousand Oaks, CA (US); Yuan Cheng, Newbury Park, CA (US); Joseph L. Kim, Wayland, MA (US); Andrew Tasker, Simi Valley, CA (US); Ning Xi, Thousand Oaks, CA (US); Shimin Xu, San Diego, CA (US); Jean-Christophe Harmange, Andover, MA (US); George Borg, Somerville, MA (US); Matthew Weiss, Boston, MA (US); Brian L. Hodous, Cambridge, MA (US); Russell Graceffa, Hampton, NH (US); William H. Buckner, Kittery, ME (US); Craig E. Masse, Cambridge, MA (US); Deborah Choquette, Medford, MA (US); Matthew W. Martin, Arlington, MA (US); Julie Germain, Quebec (CA); Lucian V. DiPietro, Gloucester, MA (US); Stuart C. Chaffee, Boston, MA (US); Joseph J. Nunes, Andover, MA (US); John L. Buchanan, Newton, MA (US); David C. McGowan, Brussels (BE); Douglas A. Whittington, Waltham, MA (US); Gregory J. Habgood, Merrimac, MA (US); Vinod F. Patel, Acton, MA (US); Daniel La, Brookline, MA (US)

(73) Assignee: Amgen Inc., Thousand Oaks, CA (US)

( * ) Notice: Subject to any disclaimer, the term of this patent is extended or adjusted under 35 U.S.C. 154(b) by 777 days.

This patent is subject to a terminal disclaimer.

(21) Appl. No.: 12/157,303

(22) Filed: Jun. 9, 2008

(65) Prior Publication Data

US 2009/0176774 A1 Jul. 9, 2009

Related U.S. Application Data

(62) Division of application No. 11/042,634, filed on Jan. 24, 2005, now Pat. No. 7,435,823.

(60) Provisional application No. 60/538,691, filed on Jan. 23, 2004.

(51) Int. Cl.
*A61K 31/04* (2006.01)
(52) U.S. Cl. ........................................ 514/312
(58) Field of Classification Search .................. 514/312, 514/314
See application file for complete search history.

(56) References Cited

U.S. PATENT DOCUMENTS

| 3,755,332 | A | 8/1973 | Wasley et al. |
|---|---|---|---|
| 4,266,060 | A | 5/1981 | Bisagni et al. |
| 4,916,135 | A | 4/1990 | Effland et al. |
| 5,580,870 | A | 12/1996 | Barker et al. |
| 5,866,572 | A | 2/1999 | Barker et al. |
| 5,965,563 | A | 10/1999 | Buzzetti et al. |
| 6,143,764 | A | 11/2000 | Kubo et al. |
| 6,265,398 | B1 | 7/2001 | Braun et al. |
| 6,313,129 | B1 | 11/2001 | Uckun et al. |
| 6,358,962 | B2 | 3/2002 | Uckun et al. |
| 6,399,602 | B1 | 6/2002 | Barker et al. |
| 6,469,013 | B2 | 10/2002 | Uckun et al. |
| 6,495,556 | B2 | 12/2002 | Uckun et al. |
| 6,573,289 | B1 | 6/2003 | Tasaka et al. |
| 6,939,874 | B2 | 9/2005 | Harmange et al. |
| 7,435,823 | B2 * | 10/2008 | Potashman et al. ........... 546/153 |
| 2003/0018029 | A1 | 1/2003 | Barker et al. |
| 2003/0165873 | A1 | 9/2003 | Come et al. |
| 2004/0053908 | A1 | 3/2004 | Funahashi et al. |
| 2004/0242603 | A1 | 12/2004 | Fujiwara et al. |
| 2006/0128734 | A1 | 6/2006 | Floersheimer et al. |

FOREIGN PATENT DOCUMENTS

| EP | 860433 A1 | 8/1998 |
|---|---|---|
| EP | 1411046 A1 | 4/2004 |
| EP | 1415987 A1 | 5/2004 |
| EP | 1 548 008 A1 | 6/2005 |
| WO | WO 96/23774 | 8/1996 |
| WO | WO 96/29301 | 9/1996 |
| WO | WO 96/29305 | 9/1996 |
| WO | WO 97/03069 | 1/1997 |
| WO | 9718208 A1 | 5/1997 |
| WO | WO97/22596 | 6/1997 |
| WO | WO 99/35132 | 7/1999 |
| WO | WO 99/54309 | 10/1999 |
| WO | WO 99/61428 | 12/1999 |

(Continued)

OTHER PUBLICATIONS

Carvalho, J Clin Immunology, vol. 27, No. 3, May 2007, pp. 246-256.*
Anderson et al., Involvement of the protein tyrosine kinase p56$^{lck}$ in T cell signaling and thymocyte development, Advances in Immunology, 56:151-178 (1994).
Appleby et al., Defective T cell receptor signaling in mice lacking the thymic isoform of p59$^{fyn}$, Cell, 70:751-763 (1992).
Asami et al., Purification and characterization of hepatocyte growth factor from injured liver of carbon tetrachloride-treated rats, Journal of Biochemistry, 109:8-13 (1991).
Asano et al., Silver halide color photographic materials, Abstract 113:181318 (1990).

(Continued)

*Primary Examiner* — D M Seaman
(74) *Attorney, Agent, or Firm* — Joseph W. Bulock

(57) ABSTRACT

Selected compounds are effective for prophylaxis and treatment of diseases, such as HGF mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

21 Claims, No Drawings

FOREIGN PATENT DOCUMENTS

| | | |
|---|---|---|
| WO | WO 00/10981 | 3/2000 |
| WO | WO 00/47212 | 8/2000 |
| WO | WO 00/56720 | 9/2000 |
| WO | WO 00/61580 | 10/2000 |
| WO | WO 01/70673 | 9/2001 |
| WO | WO 01/70734 | 9/2001 |
| WO | WO 02/22607 | 3/2002 |
| WO | WO 02/22608 | 3/2002 |
| WO | WO 02/30924 | 4/2002 |
| WO | WO 02/076976 | 10/2002 |
| WO | WO02/098426 | 12/2002 |
| WO | WO 03/040108 | 5/2003 |
| WO | WO 03/040109 | 5/2003 |
| WO | WO 03/064413 | 8/2003 |
| WO | WO 03/082272 | 10/2003 |
| WO | WO 2004/029045 | 4/2004 |
| WO | WO2004/043379 | 5/2004 |
| WO | WO 2004/078114 | 9/2004 |
| WO | WO 2004/085425 | 10/2004 |
| WO | WO 2004/098604 | 11/2004 |
| WO | WO2005/021553 | 3/2005 |
| WO | WO2005/037285 | 4/2005 |

OTHER PUBLICATIONS

Boehm et al., Antiangiogenic therapy of experimental cancer does not induce acquired drug resistance, Nature, 390:404-407 (1997).

Bolen et al., Leukocyte protein tyrosine kinases: Potential targets for drug discovery, Annu. Rev. Immunology, 15:371-404 (1997).

Brazhko et al., Investigations of the biological activity 4-thioquinolines. Abstract 135:189745, 2001.

Bussolino et al., Hepatocyte growth factor is a potent angiogenic factor which stimulates endothelial cell motility and growth, The Journal of Cell Biology, 119(3):629-641 (1992).

Chan et al., Isoforms of human HGF and their biological activities, Hepatocyte Growth Factor-Scatter Factor (HGF-SF) and the C-*Met* Receptor, pp. 67-79, Goldberg and Rosen (Eds.), Birkhauser Verlag Basel, Switzerland (1993).

Chatterjee, A.K., 4-Aminoquinolines. III. Some 4-(quinolylamino)quinolines, Science and Culture 23:195 (1957).

Cockerill et al., Indazolylamino quinazolines and pyridopyrimidines as inhibitors of the EGFr and C-erbB-2, Bioorganic & Medicinal Chemistry Letters, 11:1401-1405 (2001).

Di Renzo et al., Selective expression of the *Met*/HGF receptor in human central nervous system microglia, Oncogene, 8:219-222 (1992).

Gibson et al., Epidermal growth factor receptor tyrosine kinase: Structure-activity relationships and antitumor activity of novel quinazolines, Bioorganic & Medicinal Chemistry Letters, 7(21):2723-2728 (1997).

Giordano et al., Transfer of motogenic and invasive response to scatter factor/hepatocyte growth factor by transfection of human *MET* protooncogene, Proceedings of the National Academy of Sciences, USA, 90:649-653 (1993).

Goldman et al, Defective expression of p56lck in an infant with severe combined immunodeficiency, Journal of Clinical Investigations, 102(2):421-429 (1998).

Han et al., Characterization of the DNF15S2 locus on human chromosome 3: Identification of a gene coding for four kringle domains with homology to hepatocyte growth factor, Biochemistry, 30:9768-9780 (1991).

Igawa et al., Hepatocyte growth factor is a potent mitogen for cultured rabbit renal tubular epithelial cells, Biochemical and Biophysical Research Communications, 174(2):831-838 (1991).

Jeffers et al., Hepatocyte growth factor/scatter factor-Met signaling in tumorigenicity and invasion/metastasis, J. Mol. Med., 74:505-513 (1996).

Kane et al., Signal transduction by the TCR for antigen, Current Opinion in Immunology, 12:242-249 (2000).

Kasai et al., Flexible coordination networks with fluorinated backbones, remarkable ability for induced-fit enclathration of organic molecules, Journal of American Chemical Society, 122:2140-2141 (2000).

Konishi et al., Preparation of thioquinoline derivatives as antibacterial agents for *Helicobacter pylori*, Chemical Abstracts 125:247631, 1996.

Lempert-Sreter et al., the synthesis of di(1-isoquinolinyl) and di(4-quinazolinyl) disulfides form 1(2H)-isoquinolinethiones and 4(3H)-quinazolinethiones, respectively, with tosyl chloride and sodium ethoxide, Acta Chemica Hungarica, 112(1):83-87 (1983).

Makisumi, Yasuo, The Thio-claisen rearrangement of allyl 4-quinolyl sulfides, Tetrahedron Letters, 51:6399-6403 (1966).

Maslankiewicz, M.J., Reactions of β- and γ-quinolinyl sulfides with a nitrating mixture, Polish Journal of Chemistry, 68(12):2545-2552 (1994).

Matsumoto et al., Hepatocyte growth factor is a potent stimulator of human melanocyte DNA synthesis and growth, Biochemical and Biophysical Research Communications, 176(1):45-51 (1991).

Matsunaga et al., $C_{17,20}$-lyase inhibitors. Part 2:Design, synthesis and structure-activity relationships of (2-naphthylmethyl)-1*H*-imidazoles as novel $C_{17,20}$-lyase inhibitors, Bioorganic & Medicinal Chemistry, 12:4313-4336 (2004).

Maulik et al., Role of the hepatocyte growth factor receptor, c-Met, in oncogenesis and potential for therapeutic inhibition, Cytokine & Growth Factor Reviews, 13:41-59 (2002).

Montesano et al., Induction of epithelial tubular morphogenesis in vitro by fibroblast-derived soluble factors, Cell, 66:697-711 (1991).

Monti et al., IV. Abstract 55:2681, 1959.

Moszew et al., Thermal reactions of γ-thiols in pyridine and quinoline series. Abstract 77:164418, 1972.

Nakamura et al., Partial purification and characterization of hepatocyte growth factor from serum of hepatectomized rats, Biochemical and Biophysical Research Communications, 122(3):1450-1459 (1984).

Naldini et al., Scatter factor and hepatocyte growth factor are indistinguishable ligands for the *MET* receptor, EMBO Journal, 10:2867-2878 (1991).

Park et al., Sequence of *MET* protooncogene cDNA has features characteristic of the tyrosine kinase family of growth-factor receptors, Proceedings of the National Academy of Sciences, USA, 84:6379-6383 (1987).

Renfrew, Alice G., Studies in the Quinoline Series. IV. Quinolyl Mercaptans and Sulfides, J. American Chemical Society, 1433-1436 (1946).

Di Renzo et al., Overexpression of the c-*MET*/HGF receptor gene in human thyroid carcinomas, Oncogene, 7:2549-2553 (1992).

Rubin et al., A broad-spectrum human lung fibroblast-derived mitogen is a variant of hepatocyte growth factor, Proceedings of the National Academy of Sciences, USA, 88:415-419 (1991).

Sinyak et al., The synthesis and biological properties of the derivatives of 4-heterylmercaptoquinazoline, Khimiko-Farmatsevticheskii Zhurnal, 20(2), 168-171 (1986). Abstract 104:199594.

Solbreux et al., Extrahepatic bile duct growth in mice repeatedly injected with human normal serum, IgA-deficient serum or purified secretory IgA, Hepatology, 13:735-742 (1991).

Soriano et al., Targeted disruption of the c-*src* proto-oncogene leads to osteopetrosis in mice, Cell, 64:693-702 (1991).

Stern et al., Epithelial scatter factor and development of the chick embryonic axis, Development 110:1271-1284 (1990).

Stoker et al., Scatter factor is a fibroblast-derived modulator of epithelial cell mobility, Nature, 327:239-242 (1987).

Thakore, P.V. et al., Studies in the synthesis of quinoline derivatives. Part VIII. Synthesis of 4:3'-methylenebis(2,2'-dichloro-4'-methylquinoline) derivatives, Journal of the Indian Chemical Society, 54(12)1204-1206 (1977).

Turner et al., Signalling through the high-affinity IgE receptor FceRI, Nature, 402:B24-B30 (1999).

Vicentini et al., Fgr deficiency results in defective eosinophil recruitment to the lung during allergic airway inflammation, The Journal of Immunology, 168:6446-6454 (2002).

Weidner et al., Scatter Factor: Molecular characteristics and effect on the invasiveness of epithelial cells, The Journal of Cell Biology, 111:2097-2108 (1990).

Wyszomirski et al., Conformations of monosubstituted and disubstituted 3,4'-, 3,3'- and 4,4'-diquinolinyl sulfides studied by NMR spectroscopy, Phosphorus, Sulfur, and Silicon, 95-96:415-416 (1994).

Zhang et al., Synthesis and antimalarial activity of 2-dialkylaminomethyl-4-(heterocyclic amino)-5,6,7,8-tetrahydronaphthol derivatives. Abstract 103:87753, 1985.

Zhang et al., Synthesis and SAR of potent EGFR/erbB2 dual inhibitors, Bioorganic & Medicinal Chemistry Letters, 14:111-114 (2004).

Breier et al., The role of vascular endothelial growth factor in blood vessel formation, Trends in Cell Biology, 6:454-456 (1996).

Paolo M. Comoglio, "Structure, biosynthesis and biochemical properties of the HGF receptor in normal and malignant cells", Hepatocyte Growth Factor-Scatter Factor (HGF-SF) and the C-*Met* Receptor, eds. Goldberg and Rosen, Birkhauser Verlag Basel, Switzerland, 131-165 (1993).

Connell et al., "Patent focus on cancer chemotherapeutics. II Angiogenesis agents: Apr. 2000-Sep. 2000", Expert Opinion on Therapeutic Patents, 11(1):77-114 (2001).

* cited by examiner

COMPOUNDS AND METHODS OF USE

This application is a division of application Ser. No. 11/042,634, filed on Jan. 24, 2005 which claims the benefit of U.S. Provisional Application No. 60/538,691 filed Jan. 23, 2004, which is hereby incorporated by reference.

FIELD OF THE INVENTION

This invention is in the field of pharmaceutical agents and specifically relates to compounds, compositions, uses and methods for treating inflammation, angiogenesis and cancer.

BACKGROUND OF THE INVENTION

Protein kinases represent a large family of proteins which play a central role in the regulation of a wide variety of cellular processes, maintaining control over cellular function. A partial list of such kinases includes ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed 'Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

The hepatocyte growth factor receptor ("c-Met") is a unique receptor tyrosine kinase shown to be overexpressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327:239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Basel, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Overexpression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met protooncogene have been postulated to play a role in microglial reactions to CNS injuries (Oncogene, 8:219-222 (1993)).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound.

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR) which is expressed on the cell surface. This activation triggers a series of intracellular signaling cascades mediated by enzymes expressed within the cell (Kane, L P et al. Current Opinion in Immunol. 200, 12, 242). These cascades lead to gene regulation events that result in the production of cytokines, like interleukin-2 (IL-2). IL-2 is a critical cytokine in T cell activation, leading to proliferation and amplification of specific immune responses.

One class of enzymes shown to be important in signal transduction is the kinase enzymes Members of the Src-family of tyrosine kinases include, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the src family of kinases would potentially lead to therapeutic benefit. Src(−/−) mice have abnormalities in bone remodeling or osteopetrosis (Soriano, P. Cell 1991, 64, 693), suggesting that inhibition of this kinase might be useful in diseases of bone resorption, such as osteoporosis. Lck(−/−) mice have defects in T cell maturation and activation (Anderson, S J et al. Adv. Immunol. 1994, 56, 151), suggesting that inhibition of this kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Without wishing to imply that the compounds disclosed in the present invention possess pharmacological activity only by virtue of an effect on a single biological process, it is believed that the compounds modulate T cell activation by way of inhibition of one or more of the multiple protein tyrosine kinases involved in early signal transduction steps leading to T cell activation, for example by way of inhibition of Lck kinase.

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

PCT publication WO 03/000660 describes substituted phenyl compounds. Substituted quinolines are described in U.S. Pat. No. 6,143,764. WO 02/32872 describes substituted quinolines. WO 00/47212 describes substituted quinazoline derivatives.

Compounds of the current invention have not been described for the treatment of cancer and inflammation.

DESCRIPTION OF THE INVENTION

A class of compounds useful in treating cancer and angiogenesis is defined by Formula I

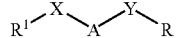

wherein R is selected from substituted or unsubstituted aryl, substituted or unsubstituted heterocyclyl, substituted or unsubstituted cycloalkyl, substituted or unsubstituted cycloalkenyl, H, substituted or unsubstituted alkyl, and substituted or unsubstituted alkenyl and substituted or unsubstituted alkynyl;

wherein $R^1$ is selected from substituted or unsubstituted 5-14-membered nitrogen containing heterocyclyl;
wherein A is an optionally substituted ten membered bicyclic ring comprising at least one aromatic ring;
wherein X is selected from O, S, $NR^2$ and $CR^3R^4$;
wherein Y is selected from $-NR^b(CR^3R^4)_p-$, $-NR^bC(=O)(CR^3R^4)_p-$, $-NR^bC(=O)NR^b(CR^3R^4)_p-$, $-NR^bC(=O)(CR^3R^4)_pO-$, $-NR^bC(=O)O(CR^3R^4)_p-$, $-NR^bC(=S)(CR^3R^4)_p-$, $-NR^bC(=NR^a)(CR^3R^4)_p$, $-NR^bSO_2-(CR^3R^4)_p-$, $-OC(=O)(CR^3R^4)_p-$, $-O(CR^3R^4)_p-$, $-(CR^3R^4)_p-S(=O)_t-$, $-(CR^3R^4)_p-$, $-S(=O)_2NR^b(CR^3R^4)_p-$, $-S(=O)_t(CR^3R^4)_p-$, $-C(=O)(CR^3R^4)_p-$, $-C(=NR^a)NH(CR^3R^4)_p-$, $-C(=S)NH(CR^3R^4)_p-$ and $-C(=O)NH(CR^3R^4)_p-$; wherein Y is in either direction;
wherein $R^a$ and $R^b$ is each independently selected from H, alkyl, heterocyclyl, aryl, arylalkyl, heterocyclylalkyl, cycloalkyl, cycloalkylalkyl, alkenyl, alkynyl, $R^5R^5N-(C=O)-$, and $R^5-(=O)-$;
wherein each of $R^a$ and $R^b$ is optionally substituted;
wherein $R^2$ is selected from H, alkyl, haloalkyl, aryl, heterocyclyl, arylalkyl, heterocyclylalkyl, cycloalkyl, cycloalkylalkyl, alkenyl, alkynyl and $R^5$-carbonyl;
wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;
wherein $R^5$ is selected from H, alkyl, haloalkyl, arylalkyl, heterocyclylalkyl, cycloalkylalkyl, aryl, heterocyclyl, alkenyl, alkynyl and cycloalkyl;
wherein $R^6$ is selected from cyano, $-OR^2$, $-SR^2$, halo, $-SO_2R^2$, $-C(=O)R^2$, $-SO_2NR^2R^5$, $-NR^5C(=O)OR^2$, $-NR^5C(=O)NR^5R^2$, $-NR^5C(=O)R^2$, $-CO_2R^2$, $-C(=O)NR^2R^5$ and $-NR^2R^5$;
wherein p is 0, 1, 2, or 3; and
wherein t is 0, 1 or 2;
and pharmaceutically acceptable derivatives thereof;
provided R is not methyl when Y is $-CO_2-$.

The invention also relates to compounds of Formula I wherein R is selected from H, 6-10 membered aryl, 4-10 membered heterocyclyl, 4-6 membered cycloalkyl, $C_{1-6}$-alkyl, $C_{2-6}$-alkenyl and $C_{2-6}$-alkynyl; wherein R is substituted or unsubstituted; in conjunction with any of the above or below embodiments.

The invention also relates to compounds of Formula I wherein R is phenyl or naphthyl; in conjunction with any of the above or below embodiments.

The invention also relates to compounds of Formula I wherein R is a substituted or unsubstituted heterocyclyl ring selected from pyrrolidinyl, pyrrolyl, imidazolyl, pyrazolyl, pyrazinyl, pyrimidinyl, pyridyl, quinolinyl, isoquinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl, and thienyl; in conjunction with any of the above or below embodiments.

The invention also relates to compounds of Formula I wherein R is 4-6 membered cycloalkyl selected from cyclobutyl, cyclopentyl and cyclohexyl; in conjunction with any of the above or below embodiments.

The invention also relates to compounds of Formula I wherein R is selected from methyl, ethyl, propyl, butyl and pentyl; in conjunction with any of the above or below embodiments.

The invention also relates to compounds of Formula I wherein R is selected from ethenyl and propenyl; in conjunction with any of the above or below embodiments.

The invention also relates to compounds of Formula I wherein R is H; in conjunction with any of the above or below embodiments.

The invention also relates to compounds of Formula I wherein A is selected from

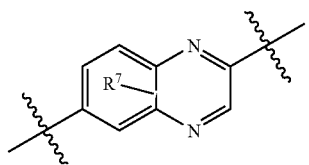

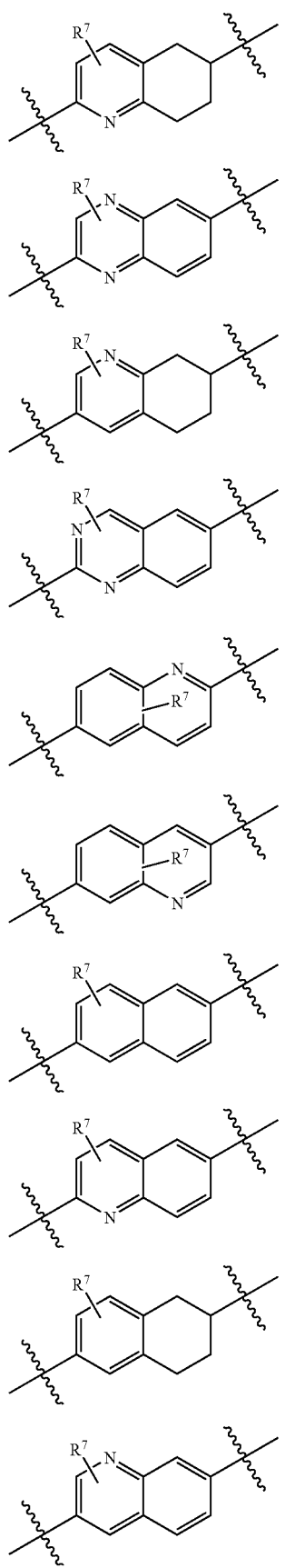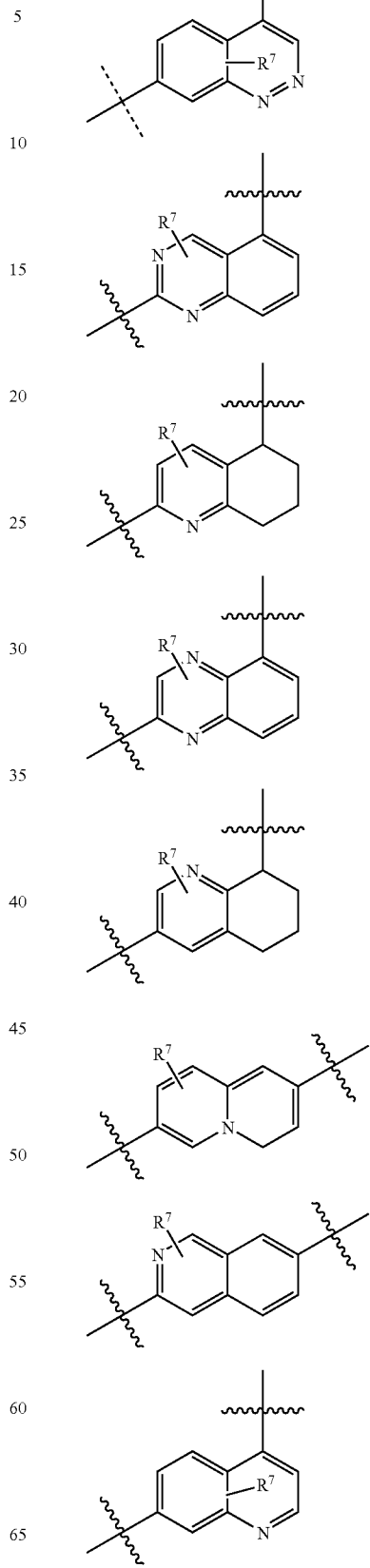

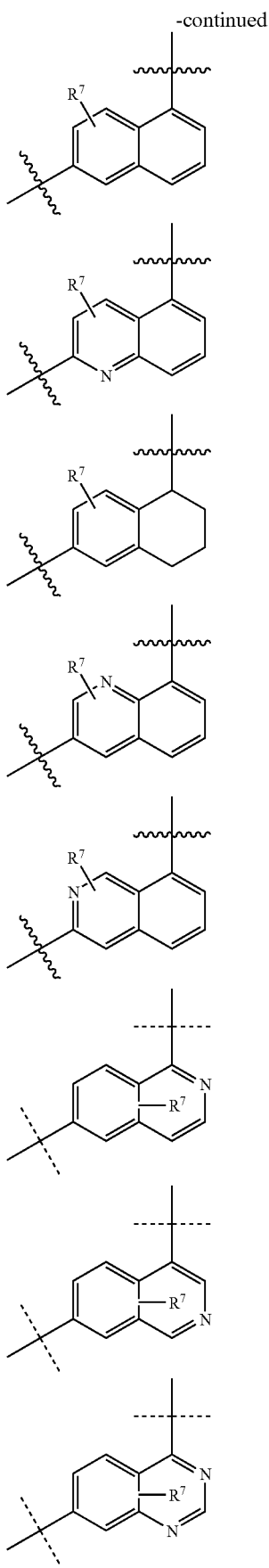

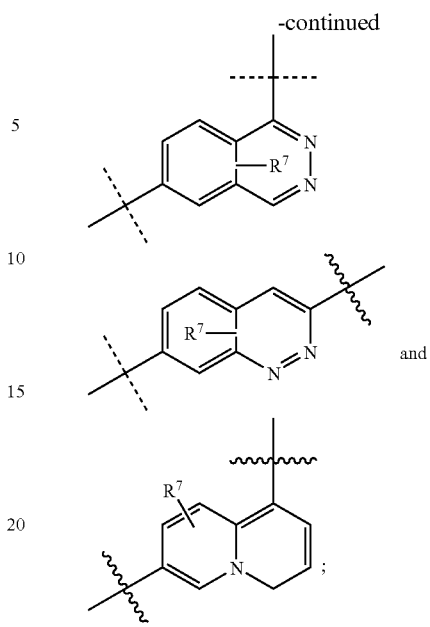

wherein R⁷ is selected from H, halo and $C_{1-3}$-alkyl;
and pharmaceutically acceptable derivatives thereof; in conjunction with any of the above or below embodiments.

The invention also relates to compounds of Formula I wherein $R^1$ is selected from 6-membered heterocyclyl and 9-10-membered bicyclic heterocyclyl; in conjunction with any of the above or below embodiments.

The invention also relates to compounds of Formula I wherein $R^1$ is selected from 9-10-membered bicyclic heteroaryl; in conjunction with any of the above or below embodiments.

The invention also relates to compounds of Formula I wherein $R^1$ is

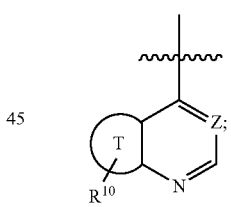

wherein ring T is selected from phenyl and 5-6-membered heteroaryl; wherein Z is selected from N or CH; wherein $R^{10}$ is one or more substituents selected from $R^5O$—; and wherein $R^5$ is selected from $C_{1-6}$-alkyl, $C_{1-6}$-haloalkyl, $C_{1-6}$-alkylamino-$C_{1-6}$-alkyl, aryl-$C_{1-6}$-alkyl, heterocyclyl-$C_{1-6}$-alkyl, cycloalkyl-$C_{1-6}$-alkyl, aryl, heterocyclyl, and cycloalkyl; in conjunction with any of the above or below embodiments.

The invention also relates to compounds of Formula I wherein $R^1$ is selected from

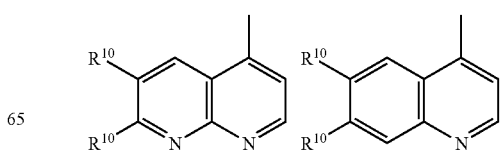

-continued

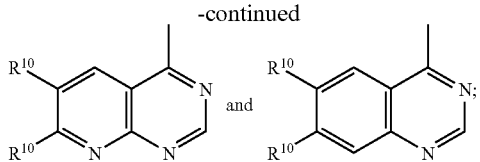

and wherein R[10] is selected from $C_{1-3}$-alkoxy, $C_{1-3}$-alkylamino-$C_{1-3}$-alkoxy, phenyl-$C_{1-3}$-alkoxy, 5-6 membered heterocyclyl-$C_{1-3}$-alkoxy and $C_{4-6}$-cycloalkyl-$C_{1-3}$-alkoxy; in conjunction with any of the above or below embodiments.

The invention also relates to compounds of Formula I wherein R[1] is selected from 6,7-dimethoxy-4-quinolinyl, 6-methoxy-7-(dimethylaminopropoxy)-4-quinolinyl, 6,7-dimethoxy-4-quinazolinyl, and 6-methoxy-7-(dimethylaminopropoxy)-4-quinazolinyl; in conjunction with any of the above or below embodiments.

The invention also relates to compounds of Formula I wherein Y is selected from —NH(CH$_2$)$_p$—, —NHC(=O)(CH$_2$)$_p$—, —NHC(=O)(CH$_2$)$_p$O—, —NHC(=O)O(CH$_2$)$_p$—, —(CH$_2$)$_p$—NHC(=O)—, —NHC(=O)NH—, —C(=O)O—, —NHSO$_2$—, and —C(=O)NH(CH$_2$)$_p$—; and wherein p is 0, 1, or 2; in conjunction with any of the above or below embodiments.

The invention also relates to compounds of Formula I wherein Y is selected from —NH—, —NHCH$_2$—, —NH(CH$_2$)$_2$—, —NH(CH$_2$)$_3$—, —NHC(=O)CH$_2$—, —NHC(=O)(CH$_2$)$_2$—, —NHC(=O)—, —NHC(=O)CH$_2$O—, —NHC(=O)OCH$_2$—, —NHC(=O)NH—, —(CH$_2$)NHC(=O)—, —C(=O)O—, —NHSO$_2$—, and —C(=O)NHCH$_2$—; in conjunction with any of the above or below embodiments.

The invention also relates to compounds of Formula I wherein R is selected from ethyl, isopropyl, (CH$_3$)$_3$CCH$_2$—, ethenyl, and an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; wherein A is naphthyl; wherein X is —O— or —CH$_2$—; wherein Y is selected from —NHC(=O)—, —NHC(=O)(CH$_2$)—, —NHC(=O)(CH$_2$)$_2$—, —CH$_2$)$_p$NHC(=O)—, —NHC(=O)NH— and —NHSO$_2$—; and wherein R[1] is selected from 6,7-dimethoxy-4-quinolinyl, 6-methoxy-7-(dimethylaminopropoxy)-4-quinolinyl, 6,7-dimethoxy-4-quinazolinyl, and 6-methoxy-7-(dimethylaminopropoxy)-4-quinazolinyl; and pharmaceutically acceptable derivatives thereof; in conjunction with any of the above or below embodiments.

The invention also relates to compounds of Formula I and pharmaceutically acceptable salts thereof selected from N-(6-((6,7-bis(methyloxy)-4-quinolinyl)oxy)-2-naphthalenyl)-2-(methyloxy)benzamide;

N-(6-((6,7-bis(methyloxy)-4-quinolinyl)oxy)-5-fluoro-2-naphthalenyl)-2-thiophenecarboxamide;

N-{5-fluoro-6-[6-methoxy-7-(3-morpholin-4-yl-propoxy)-quinolin-4-yloxy]-naphthalen-2-yl}-2-methoxy-benzamide;

N-(6-((6,7-bis(methyloxy)-4-quinolinyl)oxy)-2-naphthalenyl)-7-fluoro-2,3-dihydro-1,4-benzodioxine-5-carboxamide;

N-(6-((6,7-bis(methyloxy)-4-quinolinyl)oxy)-2-naphthalenyl)-5-fluoro-2-(methyloxy)benzamide;

N-(6-((6,7-bis(methyloxy)-4-quinolinyl)oxy)-2-naphthalenyl)-3-cyanobenzamide;

N-(6-((6,7-bis(methyloxy)-4-quinolinyl)oxy)-2-naphthalenyl)cyclobutanecarboxamide;

N-(6-((6,7-bis(methyloxy)-4-quinolinyl)oxy)-2-naphthalenyl)-2-(2-thienyl)acetamide;

N-(6-((6,7-bis(methyloxy)-4-quinolinyl)oxy)-2-naphthalenyl)-2-(ethyloxy)benzamide;

N-(6-((6,7-bis(methyloxy)-4-quinolinyl)oxy)-2-naphthalenyl)-4-(methyloxy)-3-thiophenecarboxamide;

N-(6-((6,7-bis(methyloxy)-4-quinolinyl)oxy)-2-naphthalenyl)-3-methyl-2-thiophenecarboxamide;

N-(6-((6,7-bis(methyloxy)-4-quinolinyl)oxy)-2-naphthalenyl)-5-chloro-2-(methyloxy)benzamide;

N-(6-((6,7-bis(methyloxy)-4-quinolinyl)oxy)-2-naphthalenyl)-2-(methyloxy)-3-pyridinecarboxamide;

N-(6-((6,7-bis(methyloxy)-4-quinolinyl)oxy)-2-naphthalenyl)-2-thiophenecarboxamide;

N-(6-((6,7-bis(methyloxy)-4-quinolinyl)oxy)-2-naphthalenyl)-3-bromobenzamide;

N-(6-((6,7-bis(methyloxy)-4-quinolinyl)oxy)-2naphthalenyl-1methyl-4H-imidazole-5-carboxamide;

N-(6-((6,7-bis(methyloxy)-4-quinolinyl)oxy)-2-naphthalenyl)-4-(methyloxy)benzamide;

N-(6-((6,7-bis(methyloxy)-4-quinolinyl)oxy)-5-fluoro-2-naphthalenyl)-3-thiophenecarboxamide;

N-(6-((6,7-bis(methyloxy)-4-quinolinyl)oxy)-5 fluoro-2-naphthalenyl)-4-(methyloxy)-3-thiophenecarboxamide;

N-(6-((6,7-bis(methyloxy)-4-quinolinyl)oxy)-5-fluoro-2-naphthalenyl)-5-fluoro-2-(methyloxy)benzamide;

N-(6-((6,7-bis(methyloxy)-4-quinolinyl)oxy)-5 fluoro-2-naphthalenyl)-2-(methyloxy)benzamide;

N-(6-((6,7-bis(methyloxy)-4-quinolinyl)oxy)-5-fluoro-2-naphthalenyl)benzamide;

N-(5-fluoro-6-((6-(methyloxy)-7-((3-(4-morpholinyl)propyl)oxy)-4-quinolinyl)oxy)-2-naphthalenyl)-2-thiophenecarboxamide;

N-(5-fluoro-6-((6-(methyloxy)-7-((3-(4-morpholinyl)propyl)oxy)-4-quinolinyl)oxy)-2-naphthalenyl)-3-thiophenecarboxamide;

3-(acetylamino)-N-(6-((6,7-bis(methyloxy)-4-quinolinyl)oxy)-2-naphthalenyl)benzamide;

N-(6-((6,7-bis(methyloxy)-4-quinolinyl)oxy)-5-fluoro-2-naphthalenyl)-2-(methyloxy)-3-pyridinecarboxamide; and N-(6-((6-(methyloxy)-7-((3-(4-morpholinyl)propyl)oxy)-4-quinolinyl)oxy)-2-naphthalenyl)-2-thiophenecarboxamide.

The invention also relates to compounds of Formula I'

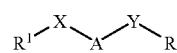

wherein R is selected from
a) substituted or unsubstituted aryl,
b) substituted or unsubstituted heterocyclyl,
c) substituted or unsubstituted cycloalkyl,
d) substituted or unsubstituted cycloalkenyl,
e) H,
f) substituted or unsubstituted alkyl,
g) substituted or unsubstituted alkenyl,
h) substituted or unsubstituted alkynyl,
i) alkylaminocarbonyl,
j) aminocarbonyl, and
k) cyano;

wherein R¹ is a) 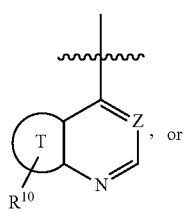, or b) 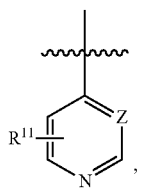, wherein ring T is selected from phenyl and 5-6-membered heteroaryl; wherein Z is selected from N or CR$^x$; wherein R$^x$ is selected from H, CN, NH$_2$, F, alkylcarbonylamino, and alkylaminocarbonyl; wherein R$^{10}$ is one or more substituents selected from H, C$_{1-6}$-alkoxy, C$_{1-6}$-haloalkoxy, C$_{1-6}$-alkylamino-C$_{1-6}$-alkoxy, aryl-C$_{1-6}$-alkoxy, heterocyclyl-C$_{1-6}$-alkoxy, cycloalkyl-C$_{1-6}$-alkoxy, heterocyclyl-C$_{1-6}$-(hydroxyalkoxy), cycloalkyl-C$_{1-6}$-(hydroxyalkoxy), aryl-C$_{1-6}$-(hydroxyalkoxy), C$_{1-6}$-alkoxyalkoxy, aryloxy-C$_{1-6}$-alkoxy, heterocyclyloxy-C$_{1-6}$-alkoxy, cycloalkyloxy-C$_{1-6}$-alkoxy, aryloxy, heterocyclyloxy, and cycloalkyloxy; wherein R$^{11}$ is selected from amino, alkylamino, alkoxy, aminocarbonyl, alkylaminocarbonyl and H, wherein A is selected from the following:

a
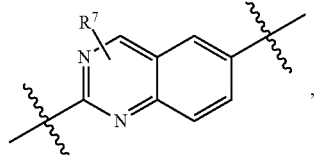, b
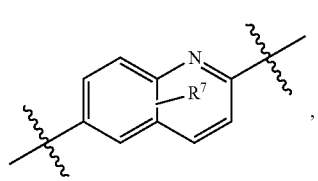, c
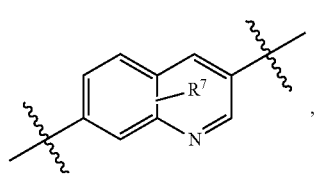, d
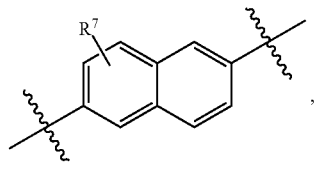, e
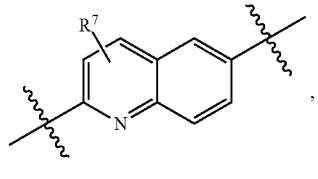, f
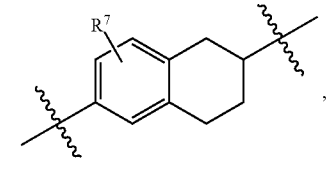, g
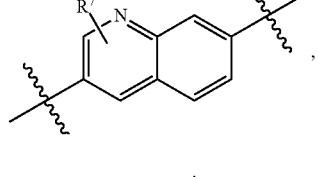, h
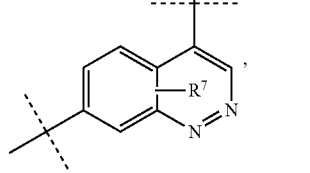, i
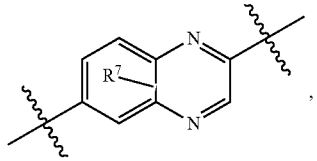, j
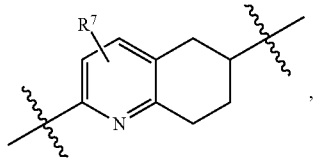, k
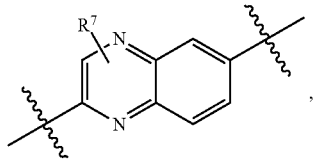, l
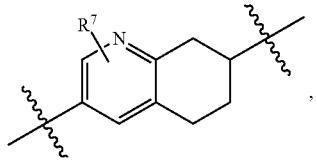, m
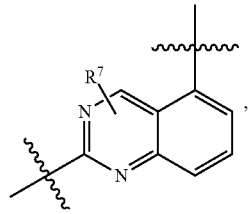,
n
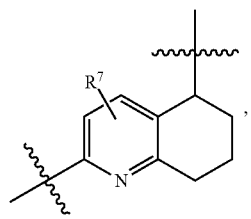,
o
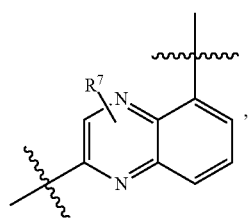,
p
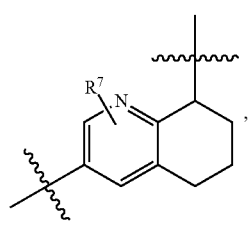,
q
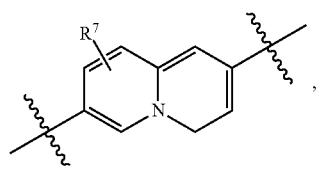,
r
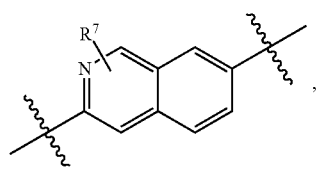,
s
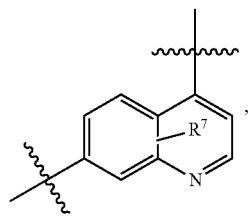,
t
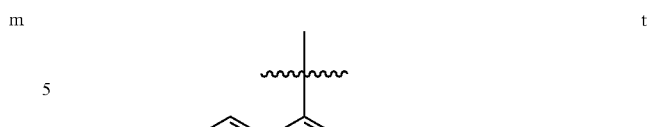,
u
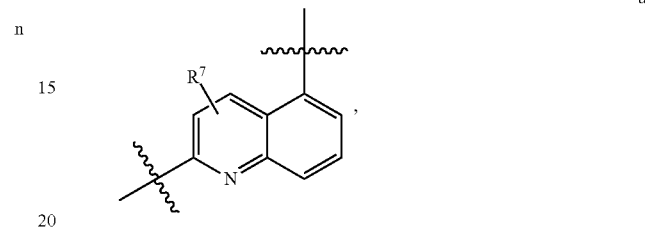,
v
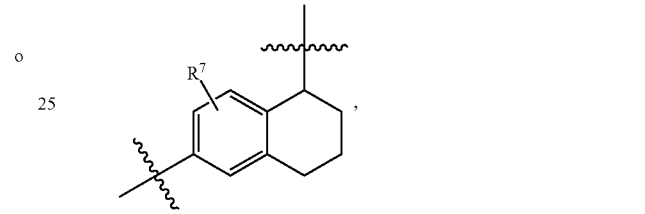,
w
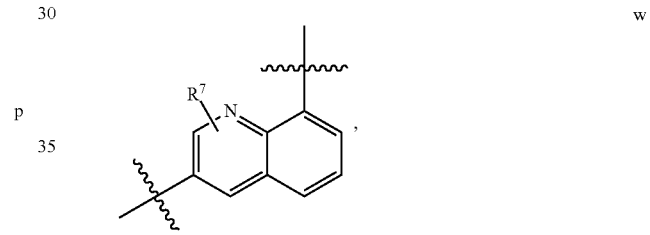,
x
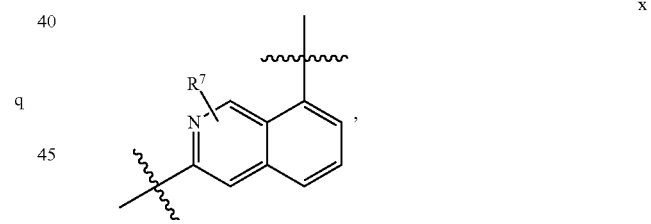,
y
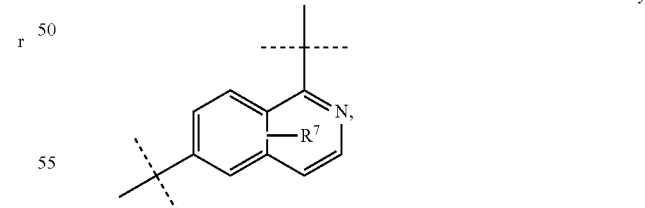,
z
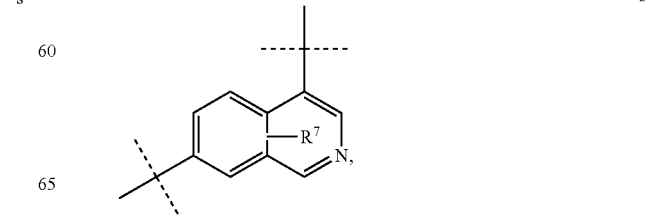,

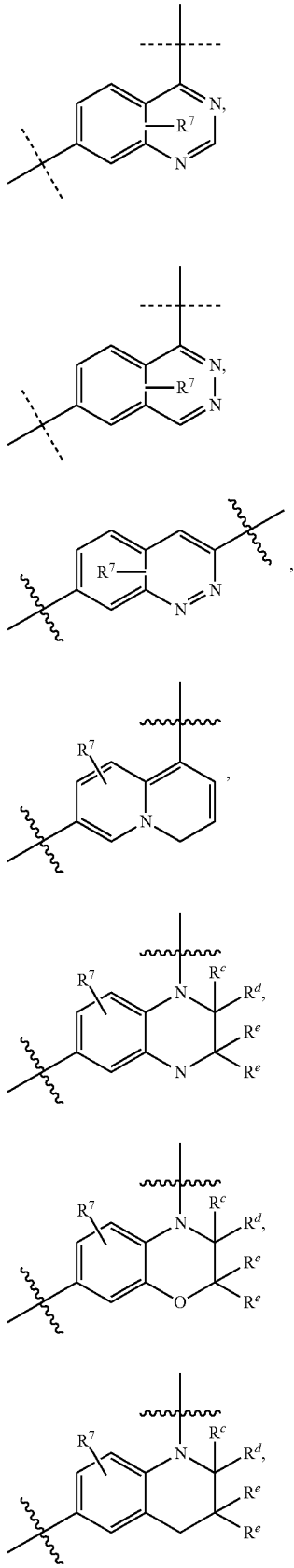

wherein X is selected from O, S, $NR^2$ and $CR^3R^4$;

wherein Y is selected from $-NR^b(CR^3R^4)_p-$, $-NR^bC(=O)(CR^3R^4)_p-$, $-NR^bC(=O)NR^b(CR^3R^4)_p-$, $-NR^bC(=O)(CR^3R^4)_pO-$, $-NR^bC(=O)O(CR^3R^4)_p-$, $NR^bC(=S)(CR^3R^4)_p-$, $-NR^bC(=NR^a)(CR^3R^4)_p-$, $-NR^bSO_2-(CR^3R^4)_p-$, $-OC(=O)(CR^3R^4)_p-$, $-O(CR^3R^4)_p-$, $-(CR^3R^4)_p-S(=O)_t-$, $-(CR^3R^4)_p-$, $-S(=O)_2NR^b(CR^3R^4)_p-$, $-S(=O)_t(CR^3R^4)_p-$, $-C(=O)(CR^3R^4)_p-$, $-C(=O)S(CR^3R^4)_p-$, $-C(=NR^a)NR^b(CR^3R^4)_p-$, $-C(=S)NH(CR^3R^4)_p-$ and $-C(=O)NR^b(CR^3R^4)_p-$; wherein Y is in either direction;

wherein $R^a$ and $R^b$ is each independently selected from H, alkyl, heterocyclyl, aryl, arylalkyl, heterocyclylalkyl, cycloalkyl, cycloalkylalkyl, alkenyl, alkynyl, $R^5R^5N-(C=O)-$, and $R^5-(=O)-$; wherein each of $R^a$ and $R^b$ is optionally substituted;

wherein $R^c$, $R^d$, $R^e$ and $R^f$ is each independently selected from H, and $C_{1-3}$-alkyl; wherein each of $R^c$, $R^d$, $R^e$ and $R^f$ is optionally substituted;

wherein $R^2$ is selected from H, alkyl, haloalkyl, aryl, heterocyclyl, arylalkyl, heterocyclylalkyl, cycloalkyl, cycloalkylalkyl, alkenyl, alkynyl and $R^5$-carbonyl;

wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;

wherein $R^5$ is selected from H, alkyl, haloalkyl, arylalkyl, heterocyclylalkyl, cycloalkylalkyl, aryl, heterocyclyl, alkenyl, alkynyl and cycloalkyl;

wherein $R^6$ is selected from cyano, $-OR^2$, $-SR^2$, halo, $-SO_2R^2$, $-C(=O)R^2$, $-SO_2NR^2R^5$, $-NR^5C(=O)OR^2$, $-NR^5C(=O)NR^5R^2$, $-NR^5C(=O)R^2$, $-CO_2R^2$, $-C(=O)NR^2R^5$ and $-NR^2R^5$;

wherein $R^7$ is selected from H, halo and $C_{1-3}$-alkyl;

wherein $R^{10}$ is one or more substituents selected from $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy;

wherein p is 0, 1, 2, or 3; and
wherein t is 0, 1 or 2;
wherein each alkyl, aryl, heteroaryl, cycloalkyl, alkenyl, alkynyl, heterocyclyl, and alkoxy moiety of any R, $R^1$, $R^2$, $R^3$, $R^4$, $R^5$, $R^a$ and $R^b$ is optionally substituted with one or more groups selected from halo, $-NH_2$, $-OH$, $-CO_2H$, $(C_1-C_6)$alkylamino, $(C_1-C_6)$alkyl, $C_1-C_6)$alkoxy, $C_1-C_6)$haloalkyl, di$(C_1-C_6)$alkylamino, $(C_1-C_6)$alkylamino-$(C_1-$ $C_6$)alkyl, ($C_1$-$C_6$)hydroxyalkylamino, ($C_1$-$C_6$)alkylamino-($C_1$-$C_6$)alkylamino, phenyl, and heterocyclyl;

and pharmaceutically acceptable derivatives thereof;

provided R is not methyl when Y is —$CO_2$— or —O—.

The invention also relates to compounds wherein R is selected from H, 6-10 membered aryl, 4-10 membered heterocyclyl, 3-6 membered cycloalkyl, $C_{1-6}$-alkyl, $C_{2-6}$-alkenyl and $C_{2-6}$-alkynyl; wherein R is substituted or unsubstituted.

The invention also relates to compounds wherein R is optionally substituted phenyl or optionally substituted naphthyl.

The invention also relates to compounds wherein R is a substituted or unsubstituted heterocyclyl ring selected from pyrrolidinyl, pyrrolyl, imidazolyl, pyrazolyl, pyrazinyl, pyrimidinyl, pyridyl, quinolinyl, isoquinolinyl, tetrahydrofuryl, 2,3-dihydrothiazolyl, 2,3-dihydrobenzofuryl, 2,3-dihydro-1,4-benzodioxinyl, 1,3-benzodioxolyl, benzisoxazolyl, benzthiazolyl, benzimidazolyl, benzothiadiazolyl, indolinyl, imidazo[1,2-a]pyridyl, isoxazolyl, isothiazolyl, oxazolyl, thiazolyl, thiadiazolyl, furanyl, and thienyl.

The invention also relates to compounds wherein R is selected from 1-methyl-cyclopropyl, cyclopropyl, 2-fluorocyclopropyl, cyclobutyl, cyclopentyl and cyclohexyl.

The invention also relates to compounds wherein R is selected from methyl, trifluoromethyl, ethyl, propyl, butyl and pentyl.

The invention also relates to compounds wherein R is selected from cyclohexenyl, ethenyl and propenyl.

The invention also relates to compounds wherein R is H.

The invention also relates to compounds wherein R is dimethylamino.

The invention also relates to compounds wherein A is selected from

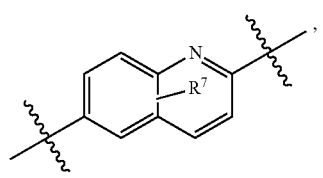
a

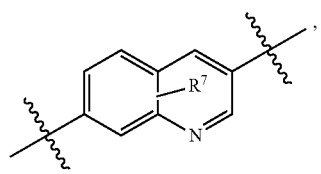
b

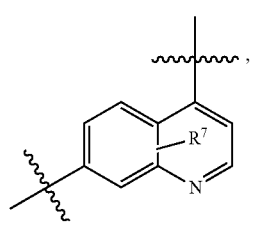
c

-continued

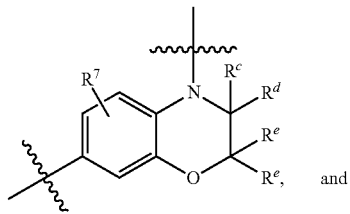
d

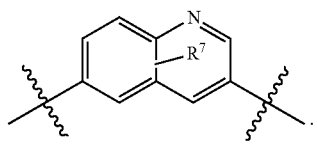
and

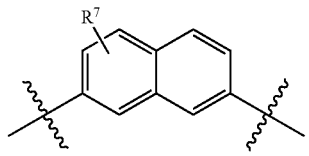
e

The invention also relates to compounds wherein A is

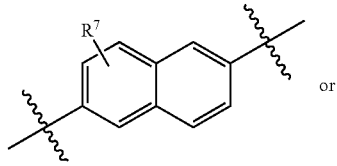

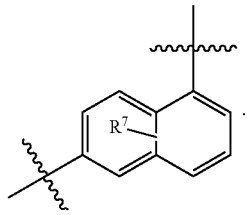
or

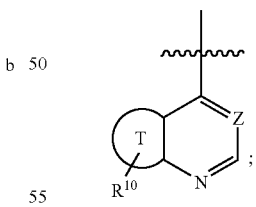

The invention also relates to compounds wherein $R^1$ is selected from wherein ring T is selected from phenyl and 5-6-membered heteroaryl; wherein Z is selected from N or CH; wherein $R^{10}$ is one or more substituents selected from $R^8O$—; and wherein $R^8$ is selected from $C_{1-6}$-alkyl, $C_{1-6}$-haloalkyl, $C_{1-6}$-alkylamino-$C_{1-6}$-alkyl, aryl-$C_{1-6}$-alkyl, heterocyclyl-$C_{1-6}$-alkyl, cycloalkyl-$C_{1-6}$-alkyl, heterocyclyl-$C_{1-6}$-(hydroxyalkyl), cycloalkyl-$C_{1-6}$-(hydroxyalkyl), aryl-$C_{1-6}$-(hydroxyalkyl), $C_{1-6}$-alkoxyalkyl, aryloxy-$C_{1-6}$-alkyl, heterocyclyloxy-$C_{1-6}$-alkyl, cycloalkyloxy-$C_{1-6}$-alkyl, aryl, heterocyclyl, and cycloalkyl.

The invention also relates to compounds wherein $R^1$ is selected from

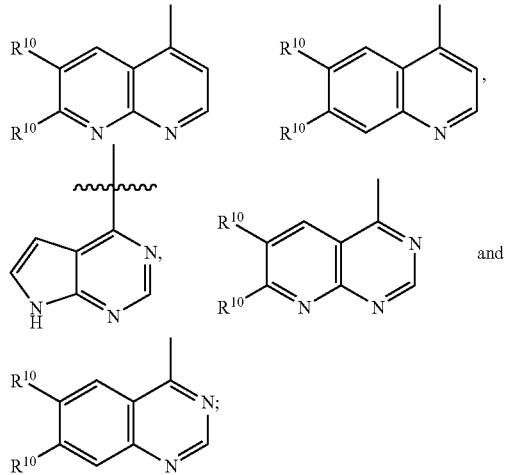

and wherein $R^{10}$ is selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), phenyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-4}$-alkoxy, cycloalkyloxy-$C_{1-3}$-alkoxy, 5-6 membered heterocyclyloxy, and $C_{3-6}$-cycloalkyloxy.

The invention also relates to compounds wherein $R^1$ is selected from pyrrolo[2,3-d]pyrimidin-4-yl, pyrazolo[3,4-b]pyridine-4-yl, 2-aminocarbonyl-4-pyridyl, 2-methylaminocarbonyl-4-pyridyl, 2-methylaminopyrimidin-4-yl, 2-aminopyrimidin-4-yl, 6,7-dimethoxy-4-quinolinyl, 6-methoxy-7-(dimethylaminopropoxy)-4-quinolinyl, 6-methoxy-7-(4-morpholinylpropoxy)-4-quinolinyl, 6,7-dimethoxy-4-quinazolinyl, and 6-methoxy-7-(dimethylaminopropoxy)-4-quinazolinyl.

The invention also relates to compounds wherein Y is selected from —NH(CH$_2$)$_p$—, —NHC(=O)(CH$_2$)$_p$—, —NHC(=O)(CH$_2$)$_p$O—, —NHC(=O)O(CH$_2$)$_p$—, —(CH$_2$)$_p$—NHC(=O)—, —NHC(=O)NH—, —C(=O)O—, —NHSO$_2$—, and —C(=O)NH(CH$_2$)$_p$—; and wherein p is 0, 1, or 2.

The invention also relates to compounds wherein Y is selected from —NH—, —NHCH$_2$—, —NH(CH$_2$)$_2$—, —NH(CH$_2$)$_3$—, —NHC(=O)CH$_2$—, —NHC(=O)(CH$_2$)$_2$—, —NHC(=O)—, —NHC(=O)CH$_2$O—, —NHC(=O)OCH$_2$—, —NHC(=O)NH—, —(CH$_2$)NHC(=O)—, —C(=O)O—, —NHSO$_2$—, and —C(=O)NHCH$_2$—.

The invention also relates to compounds wherein R is selected from ethyl, isopropyl, (CH$_3$)$_3$CCH$_2$—, ethenyl, and an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; wherein A is naphthyl; wherein X is —O— or —CH$_2$—; wherein Y is selected from —NHC(=O)—, —NHC(=O)(CH$_2$)—, —NHC(=O)(CH$_2$)$_2$—, —CH$_2$)$_p$—NHC(=O)—, —NHC(=O)NH— and —NHSO$_2$—; and wherein $R^1$ is selected from 6,7-dimethoxy-4-quinolinyl, 6-methoxy-7-(dimethylaminopropoxy)-4-quinolinyl, 6,7-dimethoxy-4-quinazolinyl, and 6-methoxy-7-(dimethylaminopropoxy)-4-quinazolinyl.

The invention also relates to compounds selected from

N-(6-((6,7-bis(methyloxy)-4-quinolinyl)oxy)-2-naphthalenyl)-2-(methyloxy)benzamide;

N-(6-((6,7-bis(methyloxy)-4-quinolinyl)oxy)-5-fluoro-2-naphthalenyl)-2-thiophenecarboxamide;

N-{5-fluoro-6-[6-methoxy-7-(3-morpholin-4-yl-propoxy)-quinolin-4-yloxy]-naphthalen-2-yl}-2-methoxy-benzamide;

N-(6-((6,7-bis(methyloxy)-4-quinolinyl)oxy)-2-naphthalenyl)-7-fluoro-2,3-dihydro-1,4-benzodioxine-5-carboxamide;

N-(6-((6,7-bis(methyloxy)-4-quinolinyl)oxy)-2-naphthalenyl)-5-fluoro-2-(methyloxy)benzamide;

N-(6-((6,7-bis(methyloxy)-4-quinolinyl)oxy)-2-naphthalenyl)-3-cyanobenzamide;

N-(6-((6,7-bis(methyloxy)-4-quinolinyl)oxy)-2-naphthalenyl)cyclobutanecarboxamide;

N-(6-((6,7-bis(methyloxy)-4-quinolinyl)oxy)-2-naphthalenyl)-2-(2-thienyl)acetamide;

N-(6-((6,7-bis(methyloxy)-4-quinolinyl)oxy)-2-naphthalenyl)-2-(ethyloxy)benzamide;

N-(6-((6,7-bis(methyloxy)-4-quinolinyl)oxy)-2-naphthalenyl)-4-(methyloxy)-3-thiophenecarboxamide;

N-(6-((6,7-bis(methyloxy)-4-quinolinyl)oxy)-2-naphthalenyl)-3-methyl-2-thiophenecarboxamide;

N-(6-((6,7-bis(methyloxy)-4-quinolinyl)oxy)-2-naphthalenyl)-5-chloro-2-(methyloxy)benzamide;

N-(6-((6,7-bis(methyloxy)-4-quinolinyl)oxy)-2-naphthalenyl)-2-(methyloxy)-3-pyridinecarboxamide;

N-(6-((6,7-bis(methyloxy)-4-quinolinyl)oxy)-2-naphthalenyl)-2-thiophenecarboxamide;

N-(6-((6,7-bis(methyloxy)-4-quinolinyl)oxy)-2-naphthalenyl)-3-bromobenzamide;

N-(6-((6,7-bis(methyloxy)-4-quinolinyl)oxy)-2-naphthalenyl)-1-methyl-1H-imidazole-5-carboxamide;

N-(6-((6,7-bis(methyloxy)-4-quinolinyl)oxy)-2-naphthalenyl)-4-(methyloxy)benzamide;

N-(6-((6,7-bis(methyloxy)-4-quinolinyl)oxy)-5-fluoro-2-naphthalenyl)-3-thiophenecarboxamide;

N-(6-((6,7-bis(methyloxy)-4-quinolinyl)oxy)-5-fluoro-2-naphthalenyl)-4-(methyloxy)-3-thiophenecarboxamide;

N-(6-((6,7-bis(methyloxy)-4-quinolinyl)oxy)-5-fluoro-2-naphthalenyl)-5-fluoro-2-(methyloxy)benzamide;

N-(6-((6,7-bis(methyloxy)-4-quinolinyl)oxy)-5-fluoro-2-naphthalenyl)-2-(methyloxy)benzamide;

N-(6-((6,7-bis(methyloxy)-4-quinolinyl)oxy)-5-fluoro-2-naphthalenyl)benzamide;

N-(5-fluoro-6-((6-(methyloxy)-7-((3-(4-morpholinyl)propyl)oxy)-4-quinolinyl)oxy)-2-naphthalenyl)-2-thiophenecarboxamide;

N-(5-fluoro-6-((6-(methyloxy)-7-((3-(4-morpholinyl)propyl)oxy)-4-quinolinyl)oxy)-2-naphthalenyl)-3-thiophenecarboxamide;

3-(acetylamino)-N-(6-((6,7-bis(methyloxy)-4-quinolinyl)oxy)-2-naphthalenyl)benzamide;

N-(6-((6,7-bis(methyloxy)-4-quinolinyl)oxy)-5-fluoro-2-naphthalenyl)-2-(methyloxy)-3-pyridinecarboxamide; and N-(6-((6-(methyloxy)-7-((3-(4-morpholinyl)propyl)oxy)-4-quinolinyl)oxy)-2-naphthalenyl)-2-thiophenecarboxamide.

The invention also relates to compounds of Formula II

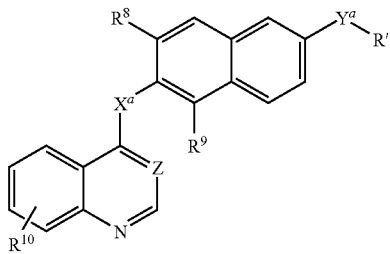

wherein $X^a$ is O or $CH_2$;
wherein $Y^a$ is selected from —NH(CH$_2$)$_p$—, —NHC(=O)(CH$_2$)$_p$—, —NHC(=O)(CH$_2$)$_p$O—, —(CH$_2$)$_p$—NHC(=O)—, —NHC(=O)NH—, —NHC(=O)O(CH$_2$)$_p$—, —C(=O)O—, —NHSO$_2$—, and —C(=O)NH(CH$_2$)$_p$—;
wherein p is 0, 1, 2, or 3; or Y is a bond if R is thienyl;
wherein Z is CH or N;
wherein R' is selected from H, $C_{1-5}$-alkyl, $C_{2-4}$-alkenyl, and an unsubstituted or substituted ring selected from phenyl, $C_{3-6}$-cycloalkyl, pyrrolidinyl, pyrrolyl, imidazolyl, pyrazolyl, pyrazinyl, pyrimidinyl, pyridyl, quinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl and thienyl;
wherein $R^8$ is selected from H, fluoro, chloro and methyl;
wherein $R^9$ is selected from H, methyl and fluoro; and
wherein $R^{10}$ is one or more substituents selected from 5 or 6-membered heterocyclyl-$C_{1-3}$-alkoxy, $C_{1-2}$-alkylamino-$C_{1-4}$-alkoxy, and $C_{1-4}$-alkoxy;
and pharmaceutically acceptable derivatives thereof;
provided R is not methyl when Y is —CO$_2$—.

The invention also relates to compounds of Formula II wherein $X^a$ is O; wherein $Y^a$ is selected from —NHC(=O)(CH$_2$)$_p$—, —NHC(=O)(CH$_2$)$_p$O—, —(CH$_2$)$_p$—NHC(=O)—, —NHC(=O)NH—, —NHC(=O)O(CH$_2$)$_p$—, —NHSO$_2$—, and —C(=O)NH(CH$_2$)$_p$—; wherein p is 0, 1, 2, or 3; wherein R' is selected from ethyl, isopropyl, (CH$_3$)$_3$CCH$_2$—, ethenyl, and an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; wherein $R^{10}$ is one or more substituents selected from 4-morpholinopropoxy, 1-pyrrolidinylethoxy, dimethylaminoethoxy, dimethylaminopropoxy and methoxy; wherein $R^8$ is H; and wherein $R^9$ is H, methyl or fluoro; and pharmaceutically acceptable derivatives thereof; in conjunction with any of the above or below embodiments.

The invention also relates to compounds of Formula II wherein $Y^a$ is selected from —NHC(=O)—, —NHC(=O)(CH$_2$)—, —NHC(=O)(CH$_2$)$_2$—, —(CH$_2$)$_p$—NHC(=O)—, —NHC(=O)NH— and —NHSO$_2$—; and pharmaceutically acceptable derivatives thereof; in conjunction with any of the above or below embodiments.

The invention also relates to compounds of Formula II wherein $Y^a$ is —NHC(=O)—; and pharmaceutically acceptable derivatives thereof; in conjunction with any of the above or below embodiments.

The invention also relates to compounds of Formula II wherein R' is an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; and pharmaceutically acceptable derivatives thereof; in conjunction with any of the above or below embodiments.

The invention also relates to compounds of Formula II wherein $R^8$ is H; and wherein $R^9$ is H or fluoro; and pharmaceutically acceptable derivatives thereof; in conjunction with any of the above or below embodiments.

The invention also relates to compounds of

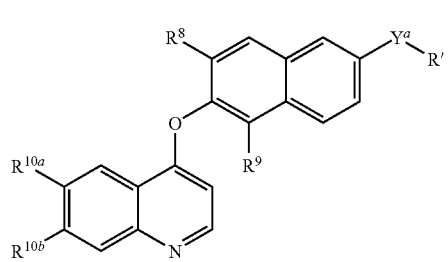

wherein $Y^a$ is selected from —NH(CH$_2$)$_p$—, —NHC(=O)(CH$_2$)$_p$—, —NHC(=O)(CH$_2$)$_p$O—, —(CH$_2$)$_p$—NHC(=O)—, —NHC(=O)NH—, —NHC(=O)O(CH$_2$)$_p$—, —C(=O)O—, —NHSO$_2$—, and —C(=O)NH(CH$_2$)$_p$—;
wherein p is 0, 1, 2, or 3; or Y is a bond if R is thienyl;
wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkylaminocarbonyl-$C_{1-5}$-alkyl, amino-$C_{1-5}$-alkyl, $C_{1-5}$-alkylamino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from
phenyl, naphthyl, 1,3-benzodioxolyl, 2,3-dihydro-1,4-benzodioxinyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, piperidinyl, 1-methyl-oxopyridyl, tetrahydropyran-4-yl, indolinyl, imidazo[1,2-a]pyridinyl, quinolinyl, isoquinolinyl, tetahydroisoquinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;
wherein $R^8$ is selected from H, fluoro, chloro and methyl;
wherein $R^9$ is selected from H, methyl and fluoro; and
wherein $R^{10a}$ is H or methoxy; and
wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy;
and pharmaceutically acceptable derivatives thereof;
provided R is not methyl when Y is —CO$_2$—.

The invention also relates to compounds wherein $Y^a$ is selected from —NHC(=O)—, —NHC(=O)(CH$_2$)—, —NHC(=O)(CH$_2$)$_2$—, —CH$_2$—NHC(=O)—, —NHC(=O)NH— and —NHSO$_2$—.

The invention also relates to compounds wherein $Y^a$ is —NHC(=O)— or —NHC(=O)NH—.

The invention also relates to compounds wherein $R^{10a}$ is methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy.

The invention also relates to compounds wherein $R^8$ is H; and wherein $R^9$ is H, methyl or fluoro; and pharmaceutically acceptable derivatives thereof.

The invention also relates to compounds wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-CH(CH$_3$)—, phenyl-CH(CH$_3$)—, 5-methylisoxazol-3-ylmethyl, pyrrolidin-1-ylethyl, tetrahydrofur-2-ylmethyl, 4-methyl-2-oxo-oxazolidin-5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, (CH$_3$)$_3$CCH$_2$—, pentafluoroethyl, CF$_3$CH$_2$CH$_2$—, cyclopropylmethyl, benzyl, 4-methylbenzyl, 4-chlorobenzyl, (2-methoxyphenyl)ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N(CH$_3$)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ylmethyl)phenyl, 2-(4-methylpiperazin-1-ylmethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methylisothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydro-indol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl.

The invention also relates to compounds wherein R' is an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl.

The invention also relates to compounds wherein $R^8$ is H; and wherein $R^9$ is H or fluoro; and pharmaceutically acceptable derivatives thereof.

The invention also relates to compounds selected from
N-(5-fluoro-6-((6-(methyloxy)-7-((3-(4-morpholinyl)propyl)oxy)-4-quinolinyl)oxy)-2-naphthalenyl)-2-thiophenecarboxamide;
5-fluoro-N-(5-fluoro-6-((6-(methyloxy)-7-((3-(4-morpholinyl)propyl)oxy)-4-quinolinyl)oxy)-2-naphthalenyl)-2-(methyloxy)benzamide;
N-(6-((7-((3-(dimethylamino)propyl)oxy)-6-(methyloxy)-4-quinolinyl)oxy)-2-naphthalenyl)-3-thiophenecarboxamide;
N-(6-((6-(methyloxy)-7-((3-(4-morpholinyl)propyl)oxy)-4-quinolinyl)oxy)-2-naphthalenyl)-3-thiophenecarboxamide;
N-ethyl-N'-(5-fluoro-6-((6-(methyloxy)-7-((3-(4-morpholinyl)propyl)oxy)-4-quinolinyl)oxy)-2-naphthalenyl)urea;
N-(6-((7-((3-(dimethylamino)propyl)oxy)-6-(methyloxy)-4-quinolinyl)oxy)-5-fluoro-2-naphthalenyl)-3-thiophenecarboxamide;
N-ethyl-N'-(6-((6-(methyloxy)-7-((3-(4-morpholinyl)propyl)oxy)-4-quinolinyl)oxy)-2-naphthalenyl)urea;
N-(6-((7-((2-(dimethylamino)ethyl)oxy)-6-(methyloxy)-4-quinolinyl)oxy)-2-naphthalenyl)benzamide;
N-(6-((7-((3-(dimethylamino)propyl)oxy)-6-(methyloxy)-4-quinolinyl)oxy)-5-fluoro-2-naphthalenyl)-2-thiophenecarboxamide;
N-(6-((6-(methyloxy)-7-((3-(4-morpholinyl)propyl)oxy)-4-quinolinyl)oxy)-2-naphthalenyl)-2-thiophenecarboxamide;
N-(5-fluoro-6-((6-(methyloxy)-7-((3-(4-morpholinyl)propyl)oxy)-4-quinolinyl)oxy)-2-naphthalenyl)-3-thiophenecarboxamide;
N-(5-fluoro-6-((6-(methyloxy)-7-((3-(4-morpholinyl)propyl)oxy)-4-quinolinyl)oxy)-2-naphthalenyl)-2-(methyloxy)benzamide;
N-(5-fluoro-6-((7-(((2S)-2-hydroxy-3-(4-morpholinyl)propyl)oxy)-6-(methyloxy)-4-quinolinyl)oxy)-2-naphthalenyl)-3-thiophenecarboxamide;
N-(6-((7-(((2R)-2-hydroxy-3-(4-morpholinyl)propyl)oxy)-6-(methyloxy)-4-quinolinyl)oxy)-2-naphthalenyl)-2-thiophenecarboxamide;
N-(6-((7-((3-(dimethylamino)propyl)oxy)-6-(methyloxy)-4-quinolinyl)oxy)-5-fluoro-2-naphthalenyl)-N'-(2,2,2-trifluoroethyl)urea;
N-(6-((7-(((2S)-2-hydroxy-3-(4-morpholinyl)propyl)oxy)-6-(methyloxy)-4-quinolinyl)oxy)-2-naphthalenyl)-2-thiophenecarboxamide; and
N-(5-fluoro-6-((7-(((2R)-2-hydroxy-3-(4-morpholinyl)propyl)oxy)-6-(methyloxy)-4-quinolinyl)oxy)-2-naphthalenyl)-3-thiophenecarboxamide.

The invention also relates to compounds of Formula III

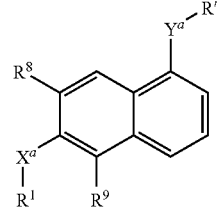

wherein $X^a$ is O, $NR^2$ or $CH_2$; wherein $R^2$ is $C_{1-3}$-alkyl or H; wherein $Y^a$ is selected from $-NH(CH_2)_p-$, $-NHC(=O)(CH_2)_p-$, $-NHC(=O)(CH_2)_pO-$, $-(CH_2)_p-NHC(=O)-$, $-NHC(=O)NH-$, $-NHC(=O)O(CH_2)_p-$, $-C(=O)O-$, $-NHSO_2-$, and $-C(=O)NH(CH_2)_p-$;
wherein Y is in either direction; wherein p is 0, 1, 2, or 3;
wherein R' is lower alkyl or an unsubstituted or substituted ring selected from phenyl, $C_{3-6}$-cycloalkyl, pyrrolidinyl, pyrrolyl, imidazolyl, pyrazolyl, pyrazinyl, pyrimidinyl, pyridyl, quinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl and thienyl;
wherein $R^1$ is selected from
  4-quinolinyl optionally substituted with one or more substituents selected from $C_{1-3}$-alkoxy, $C_{1-3}$-alkylamino-$C_{1-3}$-alkoxy, phenyl-$C_{1-3}$-alkoxy, 5-6 membered heterocyclyl-$C_{1-3}$-alkoxy and $C_{4-6}$-cycloalkyl-$C_{1-3}$-alkoxy,
  4-quinazolinyl optionally substituted with one or more substituents selected from $C_{1-3}$-alkoxy, $C_{1-3}$-alkylamino-$C_{1-3}$-alkoxy, phenyl-$C_{1-3}$-alkoxy, 5-6 membered heterocyclyl-$C_{1-3}$-alkoxy and $C_{4-6}$-cycloalkyl-$C_{1-3}$-alkoxy,
  4-pyrrolo[2,3-b]pyridinyl optionally substituted with one or more substituents selected from is $C_{1-3}$-alkyl, $C_{1-3}$-alkoxy, $C_{1-3}$-alkylamino-$C_{1-3}$-alkoxy, phenyl-$C_{1-3}$-alkoxy, 5-6 membered heterocyclyl-$C_{1-3}$-alkoxy and $C_{4-6}$-cycloalkyl-$C_{1-3}$-alkoxy,
  4-pyrazolo[3,4-b]pyridinyl optionally substituted with one or more substituents selected from is $C_{1-3}$-alkyl, $C_{1-3}$-alkoxy, $C_{1-3}$-alkylamino-$C_{1-3}$-alkoxy, phenyl-$C_{1-3}$-alkoxy, 5-6 membered heterocyclyl-$C_{1-3}$-alkoxy and $C_{4-6}$-cycloalkyl-$C_{1-3}$-alkoxy,
  4-pyrimidinyl optionally substituted with one or more substituents selected from amino, methylamide and methylamino, and
  4-pyridinyl optionally substituted with one or more substituents selected from methylamide and methylamino; and
wherein $R^8$ and $R^9$ are independently selected from H, methyl, trifluoromethyl, chloro and fluoro;
and pharmaceutically acceptable derivatives thereof.

The invention also relates to compounds of Formula III wherein $Y^a$ is selected from $-NHC(=O)-$, $-NHC(=O)(CH_2)-$, $-NHC(=O)(CH_2)_2-$, $-(CH_2)_p-NHC(=O)-$, $-NHC(=O)NH-$ and $-NHSO_2-$; wherein Y is in either direction; and pharmaceutically acceptable derivatives thereof; in conjunction with any of the above or below embodiments.

The invention also relates to compounds of Formula III wherein $Y^a$ is —NHC(=O)— or —C(=O)NH—; and pharmaceutically acceptable derivatives thereof; in conjunction with any of the above or below embodiments.

The invention also relates to compounds of Formula III wherein R' is an unsubstituted or substituted ring selected from phenyl, cyclobutyl, cyclopentyl, cyclohexyl, n-butyl, isobutyl, tert-butyl, isopropyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; and pharmaceutically acceptable derivatives thereof; in conjunction with any of the above or below embodiments.

The invention also relates to compounds of Formula III wherein $Y^a$ is —NHC(=O)— or C(=O)NH—; and R' is selected from n-butyl, isobutyl, tert-butyl, isopropyl, phenyl, 4-methylphenyl, 4-fluorophenyl, 4-bromophenyl, 4-chlorophenyl, 4-trifluoromethoxyphenyl, 4-trifluoromethylphenyl, 4-chloro-3-trifluoromethylphenyl, 3-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 2-[methyl-(1-methylpyrrolidin-3-yl)amino]-5-trifluoromethylphenyl, 5-tert-butyl-isoxazol-3-yl, 5-tert-butyl-pyrazol-3-yl, and 2-methylbenzothiazol-5-yl; and pharmaceutically acceptable derivatives thereof; in conjunction with any of the above or below embodiments.

The invention also relates to compounds of Formula III wherein $R^8$ is H; and wherein $R^9$ is H or fluoro; and pharmaceutically acceptable derivatives thereof; in conjunction with any of the above or below embodiments.

The invention also relates to compounds of Formula III wherein $R^1$ is selected from 2-aminopyrimidin-4-yl, 2-methylamino-pyrimidin-4-yl, 2-methylaminocarbonyl-pyridin-4-yl, 4-pyrazolo[3,4-b]pyridinyl, 4-pyrrolo[2,3-b]pyridinyl, 6,7-dimethoxy-4-quinolinyl, 6-methoxy-7-(dimethylaminopropoxy)-4-quinolinyl, 6,7-dimethoxy-4-quinazolinyl, and 6-methoxy-7-(dimethylaminopropoxy)-4-quinazolinyl; and pharmaceutically acceptable derivatives thereof; in conjunction with any of the above or below embodiments.

The invention also relates to compounds of Formula III wherein $X^a$ is O; wherein $R^1$ is selected from 6,7-dimethoxy-quinolin-4-yl, 2-aminopyrimidin-4-yl, 2-methylamino-pyrimidin-4-yl, 2-methylaminocarbonyl-pyridin-4-yl, 4-pyrazolo[3,4-b]pyridinyl, and 4-pyrrolo[2,3-b]pyridinyl; wherein $R^8$ is H; and wherein $R^9$ is H; and pharmaceutically acceptable derivatives thereof; in conjunction with any of the above or below embodiments.

The invention also relates to compounds of

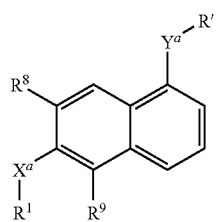

III' wherein $X^a$ is O, $NR^2$ or $CH_2$; wherein $R^2$ is $C_{1-3}$-alkyl or H;

wherein $Y^a$ is selected from —NH(CH$_2$)$_p$—, —NHC(=O)(CH$_2$)$_p$—, —NHC(=O)(CH$_2$)$_p$O—, —CH$_2$)$_p$—NHC(=O)—, —NHC(=O)NH—, —NHC(=O)O(CH$_2$)$_p$—, —C(=O)O—, —NHSO$_2$—, and —C(=O)NH(CH$_2$)$_p$—; wherein Y is in either direction; wherein p is 0, 1, 2, or 3;

wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkyl-aminocarbonyl-$C_{1-5}$-alkyl, amino-$C_{1-5}$-alkyl, $C_{1-5}$-alkyl-amino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from phenyl, naphthyl, 1,3-benzodioxolyl, 2,3-dihydro-1,4-benzodioxinyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, piperidinyl, 1-methyl-oxopyridyl, tetrahydropyran-4-yl, indolinyl, imidazo[1,2-a]pyridinyl, quinolinyl, isoquinolinyl, tetahydroisoquinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;

wherein $R^1$ is selected from 4-quinolinyl optionally substituted with one or more substituents selected from $C_{1-3}$-alkoxy, $C_{1-3}$-alkylamino-$C_{1-3}$-alkoxy, aminocarbonyl, alkylaminocarbonyl, phenyl-$C_{1-3}$-alkoxy, 5-6 membered heterocyclyl-$C_{1-3}$-alkoxy and $C_{4-6}$-cycloalkyl-$C_{1-3}$-alkoxy, 4-quinazolinyl optionally substituted with one or more substituents selected from $C_{1-3}$-alkoxy, $C_{1-3}$-alkylamino-$C_{1-3}$-alkoxy, aminocarbonyl, alkylaminocarbonyl, phenyl-$C_{1-3}$-alkoxy, 5-6 membered heterocyclyl-$C_{1-3}$-alkoxy and $C_{4-6}$-cycloalkyl-$C_{1-3}$-alkoxy, 4-pyrrolo[2,3-b]pyridinyl optionally substituted with one or more substituents selected from is $C_{1-3}$-alkyl, $C_{1-3}$-alkoxy, $C_{1-3}$-alkylamino-$C_{1-3}$-alkoxy, phenyl-$C_{1-3}$-alkoxy, 5-6 membered heterocyclyl-$C_{1-3}$-alkoxy and $C_4"$-cycloalkyl-$C_{1-3}$-alkoxy, 4-pyrazolo[3,4-b]pyridinyl optionally substituted with one or more substituents selected from is $C_{1-3}$-alkyl, $C_{1-3}$-alkoxy, $C_{1-3}$-alkylamino-$C_{1-3}$-alkoxy, phenyl-$C_{1-3}$-alkoxy, 5-6 membered heterocyclyl-$C_{1-3}$-alkoxy and $C_{4-6}$-cycloalkyl-$C_{1-3}$-alkoxy, 4-pyrimidinyl optionally substituted with one or more substituents selected from amino, methylamide and methylamino, and 4-pyridinyl optionally substituted with one or more substituents selected from methylamide and methylamino;

wherein $R^8$ is selected from H, fluoro, chloro and methyl; and wherein $R^9$ is selected from H, methyl and fluoro;

and pharmaceutically acceptable derivatives thereof.

The invention also relates to compounds wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-CH(CH$_3$)—, phenyl-CH(CH$_3$)—, 5-methylisoxazol-3-ylmethyl, pyrrolidin-1-ylethyl, tetrahydrofur-2-ylmethyl, 4-methyl-2-oxo-oxazolidin-5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, (CH$_3$)$_3$CCH$_2$—, pentafluoroethyl, CF$_3$CH$_2$CH$_2$—, cyclopropylmethyl, benzyl, 4-methylbenzyl, 4-chlorobenzyl, (2-methoxyphenyl)

ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N(CH$_3$)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ylmethyl)phenyl, 2-(4-methylpiperazin-1-ylmethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methylisothiazol-5-yl, 3-isothiazolyl, 4,5-dichloro-3-isothiazolyl, isoxazol-5-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydroindol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl.

The invention also relates to compounds wherein $X^a$ is O;

The invention also relates to compounds wherein $R^1$ is selected from 2-aminopyrimidin-4-yl, 2-methylamino-pyrimidin-4-yl, 2-methylaminocarbonyl-pyridin-4-yl, 4-pyrazolo[3,4-b]pyridinyl, and 4-pyrrolo[2,3-b]pyridinyl.

The invention also relates to compounds wherein $R^1$ is

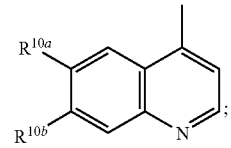

wherein $R^{10a}$ is selected from H, methoxy, aminocarbonyl, and methylaminocarbonyl; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4- methylpiperazin-1-yl)propoxy, 3-(1,2,4-triazol-1-yl) propoxy, triazinylpropoxy, 3-(piperidin-4-yl)propoxy, dimethylaminoethoxy, dimethylaminopropoxy and methoxy.

The invention also relates to compounds selected from

N-(6-((6,7-bis(methyloxy)-4-quinolinyl)oxy)-1-naphthalenyl)benzamide;

6-((6,7-bis(methyloxy)-4-quinolinyl)oxy)-N-(4-chlorophenyl)-1-naphthalenecarboxamide;

6-((6,7-bis(methyloxy)-4-quinolinyl)oxy)-N-(3-(trifluoromethyl)phenyl)-1-naphthalenecarboxamide;

6-((6,7-bis(methyloxy)-4-quinolinyl)oxy)-N-(4-(trifluoromethyl)phenyl)-1-naphthalenecarboxamide;

6-((6,7-bis(methyloxy)-4-quinolinyl)oxy)-N-ethyl-1-naphthalenecarboxamide;

6-((6,7-bis(methyloxy)-4-quinolinyl)oxy)-5-fluoro-N-methyl-1-naphthalenecarboxamide;

4-(5-Carbamoyl-1-fluoro-naphthalen-2-yloxy)-7-methoxy-quinoline-6-carboxylic acid amide;

6-((6,7-bis(methyloxy)-4-quinolinyl)oxy)-N-(3-isoxazolyl)-1-naphthalenecarboxamide;

6-((6,7-bis(methyloxy)-4-quinolinyl)oxy)-N-methyl-1-naphthalenecarboxamide;

6-((6,7-bis(methyloxy)-4-quinolinyl)oxy)-5-fluoro-1-naphthalenecarboxamide;

6-((6,7-bis(methyloxy)-4-quinolinyl)oxy)-N-phenyl-1-naphthalenecarboxamide;

6-((6,7-bis(methyloxy)-4-quinolinyl)oxy)-N-(2-(methyloxy)ethyl)-1-naphthalenecarboxamide;

6-((6,7-bis(methyloxy)-4-quinolinyl)oxy)-5-fluoro-N-(2-(methyloxy)ethyl)-1-naphthalenecarboxamide;

4-(5-Cyclopropylcarbamoyl-1-fluoro-naphthalen-2-yloxy)-7-methoxy-quinoline-6-carboxylic acid amide;

7-(methyloxy)-4-((5-(((2-(methyloxy)ethyl)amino)carbonyl)-2-naphthalenyl)oxy)-6-quinolinecarboxamide;

6-((6,7-bis(methyloxy)-4-quinolinyl)oxy)-N-cyclopropyl-1-naphthalenecarboxamide;

6-((6,7-bis(methyloxy)-4-quinolinyl)oxy)-5-fluoro-N-(3-isoxazolyl)-1-naphthalenecarboxamide;

4-((5-((cyclopropylamino)carbonyl)-2-naphthalenyl)oxy)-N-methyl-7-(methyloxy)-6-quinolinecarboxamide;

4-((5-((cyclopropylamino)carbonyl)-2-naphthalenyl)oxy)-7-(methyloxy)-6-quinolinecarboxamide;

4-(5-Carbamoyl-naphthalen-2-yloxy)-7-methoxy-quinoline-6-carboxylic acid amide;

6-((6,7-bis(methyloxy)-4-quinolinyl)oxy)-N-cyclopropyl-1-naphthalenecarboxamide;

6-((6,7-bis(methyloxy)-4-quinolinyl)oxy)-5-fluoro-N-(1,3-thiazol-2-yl)-1-naphthalenecarboxamide;

6-((6,7-bis(methyloxy)-4-quinolinyl)oxy)-1-naphthalenecarboxamide;

6-((6,7-bis(methyloxy)-4-quinolinyl)oxy)-N-cyclopropyl-5-fluoro-1-naphthalenecarboxamide;

6-((6,7-bis(methyloxy)-4-quinolinyl)oxy)-N-(6-(dimethylamino)-3-pyridinyl)-1-naphthalenecarboxamide;

6-((6,7-bis(methyloxy)-4-quinolinyl)oxy)-N-(4-chloro-3-(trifluoromethyl)phenyl)-1-naphthalenecarboxamide; and 6-((6,7-bis(methyloxy)-4-quinolinyl)oxy)-N-(4-(1,1-dimethylethyl)phenyl)-1-naphthalenecarboxamide.

The invention also relates to compounds of

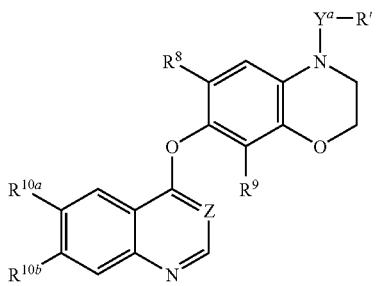

IV wherein $Y^a$ is selected from —$(CH_2)_p$—NH—, —$(CH_2)_p$—C(=O)NH—, —$CH_2)_p$—OC(=O)NH—, —C(=O)O—, and —C(=O)NH($CH_2)_p$—; wherein p is 0, 1, 2, or 3;

wherein Z is $CR^x$ or N;

wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkyl-aminocarbonyl-$C_{1-5}$-alkyl, amino-$C_{1-5}$-alkyl, $C_{1-5}$-alkyl-amino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from phenyl, naphthyl, 1,3-benzodioxolyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, 2,3-dihydro-1,4-benzodioxinyl, piperidinyl, 1-methyl-oxopyridyl, tetrahydropyran-4-yl, indolinyl, imidazo[1,2-a]pyridinyl, quinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;

wherein $R^8$ is selected from H, fluoro, chloro and methyl;

wherein $R^9$ is selected from H, methyl and fluoro; and wherein $R^x$ is selected from H, CN, $NH_2$, F, alkylcarbonylamino, and alkylaminocarbonyl;

wherein $R^{10a}$ is H or methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy;

and pharmaceutically acceptable derivatives thereof.

The invention also relates to compounds wherein Z is CH; wherein $R^{10a}$ is methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl) propoxy, triazinylpropoxy, 3-(piperidin-4-yl)propoxy, dimethylaminoethoxy, dimethylaminopropoxy and methoxy.

The invention also relates to compounds wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-CH($CH_3$)—, phenyl-CH($CH_3$)—, 5-methylisoxazol-3-ylmethyl, pyrrolidin-1-ylethyl, tetrahydrofur-2-ylmethyl, 4-methyl-2-oxo-oxazolidin-5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, (CH$_3$)$_3$CCH$_2$—, pentafluoroethyl, CF$_3$CH$_2$CH$_2$—, cyclopropylmethyl, benzyl, 4-methylbenzyl, 4-chlorobenzyl, (2-methoxyphenyl)ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N(CH$_3$)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ylmethyl)phenyl, 2-(4-methylpiperazin-1-ylmethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-yletoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methylisothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydroindol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl.

The invention also relates to compounds wherein R' is selected from H, isopropyl, (CH$_3$)$_3$CCH$_2$—, benzyl, 4-methylphenylmethyl, 2-thiazolyl-CH(CH$_3$)—, phenyl-CH(CH$_3$)—, phenyl, 4-methylphenyl, 3-methylphenyl, 2-methylphenyl, 4-tert-butyl-phenyl, 4-chlorophenyl, 3-chlorophenyl, 2-chlorophenyl, 4-trifluoromethylphenyl, 3-trifluoromethylphenyl, -chloro-3-trifluoromethylphenyl, 4-dimethylaminophenyl, biphenyl, 3-isothiazolyl, and 2-thiazolyl.

The invention also relates to compounds wherein $Y^a$ is C(=O)NH—.

The invention also relates to compounds wherein $R^8$ and $R^9$ are both H.

The invention also relates to compounds thereof selected from 7-((6,7-bis(methyloxy)-4-quinolinyl)oxy)-N-phenyl-2,3-dihydro-4H-1,4-benzoxazine-4-carboxamide;

7-((6,7-bis(methyloxy)-4-quinolinyl)oxy)-N-(4-methylphenyl)-2,3-dihydro-4H-1,4-benzoxazine-4-carboxamide;

7-((6,7-bis(methyloxy)-4-quinolinyl)oxy)-N-(4-(dimethylamino)phenyl)-2,3-dihydro-4H-1,4-benzoxazine-4-carboxamide;

7-((6,7-bis(methyloxy)-4-quinolinyl)oxy)-N-(3-(trifluoromethyl)phenyl)-2,3-dihydro-4H-1,4-benzoxazine-4-carboxamide;

7-((6,7-bis(methyloxy)-4-quinolinyl)oxy)-N-((1S)-1-phenylethyl)-2,3-dihydro-4H-1,4-benzoxazine-4-carboxamide;

7-((6,7-bis(methyloxy)-4-quinolinyl)oxy)-N-(4-chlorophenyl)-2,3-dihydro-4H-1,4-benzoxazine-4-carboxamide;

7-((6,7-bis(methyloxy)-4-quinolinyl)oxy)-N-(4-(trifluoromethyl)phenyl)-2,3-dihydro-4H-1,4-benzoxazine-4-carboxamide;

7-((6,7-bis(methyloxy)-4-quinolinyl)oxy)-N-(4-(1,1-dimethylethyl)phenyl)-2,3-dihydro-4H-1,4-benzoxazine-4-carboxamide;

7-((6,7-bis(methyloxy)-4-quinolinyl)oxy)-N-(3-isoxazolyl)-2,3-dihydro-4H-1,4-benzoxazine-4-carboxamide;

7-((6,7-bis(methyloxy)-4-quinolinyl)oxy)-N-(3-methylphenyl)-2,3-dihydro-4H-1,4-benzoxazine-4-carboxamide; and 7-((6,7-bis(methyloxy)-4-quinolinyl)oxy)-N-(3-chlorophenyl)-2,3-dihydro-4H-1,4-benzoxazine-4-carboxamide.

The invention also relates to compounds

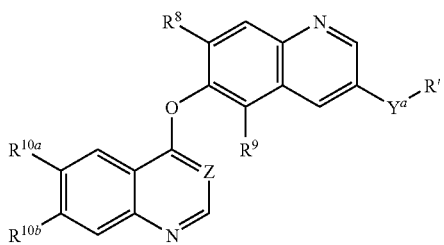

V wherein $Y^a$ is selected from $-NH(CH_2)_p-$, $-NHC(=O)(CH_2)_p-$, $-NHC(=O)(CH_2)_pO-$, $-CH_2)_p-NHC(=O)-$, $-NHC(=O)NH-$, $-NHC(=O)O(CH_2)_p-$, $-C(=O)O-$, $-NHSO_2-$, and $-C(=O)NH(CH_2)_p-$;

wherein p is 0, 1, 2, or 3;

wherein Z is $CR^x$ or N;

wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkylaminocarbonyl-$C_{1-5}$-alkyl, amino-$C_{1-5}$-alkyl, $C_{1-5}$-alkylamino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from phenyl, naphthyl, 1,3-benzodioxolyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, 2,3-dihydro-1,4-benzodioxinyl, piperidinyl, 1-methyl-oxopyridyl, tetrahydropyran-4-yl, indolinyl, imidazo[1,2-a]pyridinyl, quinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;

wherein $R^8$ is selected from H, fluoro, chloro and methyl;

wherein $R^9$ is selected from H, methyl and fluoro; and wherein $R^x$ is selected from H, CN, $NH_2$, F, alkylcarbonylamino, and alkylaminocarbonyl;

wherein $R^{10a}$ is H or methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy;

and pharmaceutically acceptable derivatives thereof.

The invention also relates to compounds wherein Z is CH; wherein $R^{10a}$ is methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy.

The invention also relates to compounds wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-$CH(CH_3)-$, phenyl-$CH(CH_3)-$, 5-methylisoxazol-3-ylmethyl, pyrrolidin-1-ylethyl, tetrahydrofur-2-ylmethyl, 4-methyl-2-oxo-oxazolidin-5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, $(CH_3)_3CCH_2-$, pentafluoroethyl, $CF_3CH_2CH_2-$, cyclopropylmethyl, benzyl, 4-methylbenzyl, 4-chlorobenzyl, (2-methoxyphenyl)ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N(CH_3)]-5-trifluoromethylphenyl, 5-[1-methylpiperazin-4-ylmethyl]-3-trifluoromethylphenyl, 5-[2-oxopyrrolidin-1- yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ylmethyl)phenyl, 2-(4-methylpiperazin-1-ylmethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methylisothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydroindol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl.

The invention also relates to compounds wherein R' is selected from 3-isopropylphenyl, 3-fluorophenyl, 3,4-difluorophenyl, 4-chlorophenyl, 3-chlorophenyl, 3,4-dichlorophenyl, 3-methoxyphenyl, 3-trifluoromethoxyphenyl, and 3,5-di(trifluoromethyl)phenyl.

The invention also relates to compounds wherein $Y^a$ is —C(=O)NH—.

The invention also relates to compounds wherein $R^8$ and $R^9$ are H.

The invention also relates to compounds of

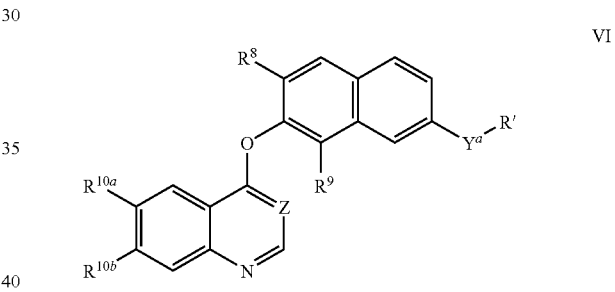

VI wherein $Y^a$ is selected from —NH(CH$_2$)$_p$—, —NHC(=O)(CH$_2$)$_p$—, —NHC(=O)(CH$_2$)$_p$O—, —CH$_2$)$_p$—NHC(=O)—, —NHC(=O)NH—, —NHC(=O)O(CH$_2$)$_p$—, —C(=O)O—, —NHSO$_2$—, and —C(=O)NH(CH$_2$)$_p$—;
wherein p is 0, 1, 2, or 3;
wherein Z is CR$^x$ or N;
wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkylaminocarbonyl-$C_{1-5}$-alkyl, amino-$C_{1-5}$ alkyl, $C_{1-5}$-alkylamino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from
phenyl, naphthyl, 1,3-benzodioxolyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, 2,3-dihydro-1,4-benzodioxinyl, piperidinyl, 1-methyl-oxopyridyl, tetrahydropyran-4-yl, indolinyl, imidazo[1,2-a]pyridinyl, quinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;
wherein $R^8$ is selected from H, fluoro, chloro and methyl;
wherein $R^9$ is selected from H, methyl and fluoro; and wherein R$^x$ is selected from H, CN, NH$_2$, F, alkylcarbonylamino, and alkylaminocarbonyl;

wherein R$^{10a}$ is H or methoxy; and wherein R$^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy;

and pharmaceutically acceptable derivatives thereof.

The invention also relates to compounds wherein Z is CH; wherein R$^{10a}$ is methoxy; and wherein R$^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy.

The invention also relates to compounds wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-CH(CH$_3$)—, phenyl-CH(CH$_3$)—, 5-methylisoxazol-3-ylmethyl, pyrrolidin-1-ylethyl, tetrahydrofur-2-ylmethyl, 4-methyl-2-oxo-oxazolidin-5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, (CH$_3$)$_3$CCH$_2$—, pentafluoroethyl, CF$_3$CH$_2$CH$_2$—, cyclopropylmethyl, benzyl, 4-methylbenzyl, 4-chlorobenzyl, (2-methoxyphenyl)ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 2,4-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N(CH$_3$)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxothiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ylmethyl)phenyl, 2-(4-methylpiperazin-1-ylmethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxin-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methylisothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, S-bromo-2-thienyl, 4-methoxy-5-bromo-3-thienyl, 4-methoxy-3-thienyl, 2-furyl, 2-cyano-5-phenylfur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydroindol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzoxazol-2-yl, benzisoxazol-3-yl, 4-methoxybenzisoxazol-3-yl and 2-methylbenzothiazol-5-yl.

The invention also relates to compounds wherein R' is selected from methoxyethyl, cyclopropyl, 3-isopropylphenyl, 4-tert-butyl-phenyl, 4-isopropyl-3-methylphenyl, 3-chloro-4-methylphenyl, 3-fluorophenyl, 3,4-difluorophenyl, 4-chlorophenyl, 3-chlorophenyl, 3,4-dichlorophenyl, 3-methoxyphenyl, 4-trifluoromethoxyphenyl, 3-trifluoromethoxyphenyl, 3-trifluoromethylphenyl, 3-pyridyl, 4-trifluoromethyl-2-pyridyl, 3-isothiazolyl, and 2-thiazolyl.

The invention also relates to compounds wherein $Y^a$ is —C(=O)NH—.

The invention also relates to compounds wherein $R^8$ and $R^9$ are H.

The invention also relates to compounds selected from 7-((6,7-bis(methyloxy)-4-quinolinyl)oxy)-N-(3-fluorophenyl)-2-naphthalenecarboxamide;

7-((6,7-bis(methyloxy)-4-quinolinyl)oxy)-N-cyclopropyl-2-naphthalenecarboxamide;

7-((6,7-bis(methyloxy)-4-quinolinyl)oxy)-N-(3-(methyloxy)phenyl)-2-naphthalenecarboxamide;

7-((6,7-bis(methyloxy)-4-quinolinyl)oxy)-N-(3-isoxazolyl)-2-naphthalenecarboxamide;

7-((6,7-bis(methyloxy)-4-quinolinyl)oxy)-N-(3-chlorophenyl)-2-naphthalenecarboxamide;

7-((6,7-bis(methyloxy)-4-quinolinyl)oxy)-N-(4-(1,1-dimethylethyl)phenyl)-2-naphthalenecarboxamide;

7-((6,7-bis(methyloxy)-4-quinolinyl)oxy)-N-(5-(1,1-dimethylethyl)-3-isoxazolyl)-2-naphthalenecarboxamide;

7-((6,7-bis(methyloxy)-4-quinolinyl)oxy)-N-(1,3-thiazol-2-yl)-2-naphthalenecarboxamide;

7-((6,7-bis(methyloxy)-4-quinolinyl)oxy)-N-(3-chloro-4-methylphenyl)-2-naphthalenecarboxamide;

7-((6,7-bis(methyloxy)-4-quinolinyl)oxy)-N-(4-(trifluoromethyl)-2-pyridinyl)-2-naphthalenecarboxamide;

7-((6,7-bis(methyloxy)-4-quinolinyl)oxy)-N-(3-((trifluoromethyl)oxy)phenyl)-2-naphthalenecarboxamide;

7-((6,7-bis(methyloxy)-4-quinolinyl)oxy)-N-(3,4-difluorophenyl)-2-naphthalenecarboxamide;

7-((6,7-bis(methyloxy)-4-quinolinyl)oxy)-N-(3-methyl-4-(1-methylethyl)phenyl)-2-naphthalenecarboxamide;

7-((6,7-bis(methyloxy)-4-quinolinyl)oxy)-N-(3,4-dichlorophenyl)-2-naphthalenecarboxamide;

7-((6,7-bis(methyloxy)-4-quinolinyl)oxy)-N-(4-((trifluoromethyl)oxy)phenyl)-2-naphthalenecarboxamide;

7-((6,7-bis(methyloxy)-4-quinolinyl)oxy)-N-(3-(trifluoromethyl)phenyl)-2-naphthalenecarboxamide; and 7-((6,7-bis(methyloxy)-4-quinolinyl)oxy)-N-(3-pyridinyl)-2-naphthalenecarboxamide.

The invention also relates to compounds of

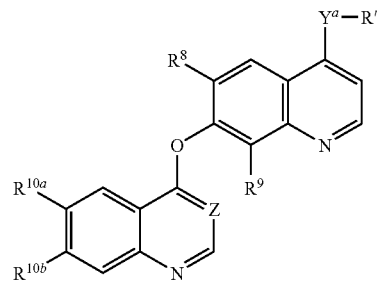

VII wherein $Y^a$ is selected from —NH(CH$_2$)$_p$—, —NHC(=O)(CH$_2$)$_p$—, —NHC(=O)(CH$_2$)$_p$O—, —(CH$_2$)$_p$—NHC(=O)—, —NHC(=O)NH—, —NHC(=O)O(CH$_2$)$_p$—, —C(=O)O—, —NHSO$_2$—, and —C(=O)NH(CH$_2$)$_p$—;

wherein p is 0, 1, 2, or 3;

wherein Z is $CR^x$ or N;

wherein R' is selected from H, $C_{1-5}$-alkyl, $C_{1-3}$-haloalkyl, $C_{1-3}$-alkoxy-$C_{1-3}$-alkyl, $C_{1-3}$-alkoxycarbonyl-$C_{1-3}$-alkyl, $C_{1-5}$-cyanoalkyl, aminocarbonyl-$C_{1-5}$-alkyl, $C_{1-5}$-alkylaminocarbonyl-$C_{1-5}$-alkyl, amino-$C_{1-5}$-alkyl, $C_{1-5}$-alkylamino-$C_{1-5}$-alkyl, $C_{1-5}$-alkylsulfonyl-$C_{1-5}$-alkyl, phenyl-$C_{1-3}$-alkyl, $C_{3-6}$-cycloalkyl-$C_{1-3}$-alkyl, 5-6-membered heterocyclyl-$C_{1-3}$-alkyl, and an unsubstituted or substituted ring selected from phenyl, naphthyl, 1,3-benzodioxolyl, $C_{3-6}$-cycloalkyl, $C_{5-6}$-cycloalkenyl, pyrrolidinyl, pyrrolyl, imidazolyl, pyrazolyl, pyrazinyl, pyrimidinyl, pyridyl, quinolinyl, dihydrothiazolyl, 2,3-dihydrobenzofuryl, 2,3-dihydro-1,4-benzodioxinyl, piperidinyl, 1-methyl-oxopyridyl, tetrahydropyran-4-yl, indolinyl, imidazo[1,2-a]pyridinyl, quinolinyl, benzofuryl, benzo[1,2,5]thiadiazolyl, benzothiazolyl, benzimidazolyl, benzoxazolyl, benzisoxazolyl, isoxazolyl, isothiazolyl, oxazolyl, thiazolyl, thiadiazolyl, furanyl and thienyl;

wherein $R^8$ is selected from H, fluoro, chloro and methyl;

wherein $R^9$ is selected from H, methyl and fluoro; and wherein $R^x$ is selected from H, CN, NH$_2$, F, alkylcarbonylamino, and alkylaminocarbonyl;

wherein $R^{10a}$ is H or methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy;

and pharmaceutically acceptable derivatives thereof.

The invention also relates to compounds wherein Z is CH; wherein $R^{10a}$ is methoxy; and wherein $R^{10b}$ is selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy.

The invention also relates to compounds wherein R' is selected from H, methyl, ethyl, n-butyl, isobutyl, tert-butyl, isopropyl, propyl, cyanomethyl, aminocarbonylmethyl, dimethylaminocarbonylmethyl, dimethylaminoethyl, 2-methoxy-1-methylethyl, methoxycarbonylmethyl, methoxyethyl, methoxypropyl, methylsulfonylethyl, dimethylaminoethyl, methoxycarbonylmethyl, ethenyl, thiazol-2-yl-CH(CH$_3$)—, phenyl-CH(CH$_3$)—, 5-methylisoxazol-3-ylmethyl, pyrrolidin-1-ylethyl, tetrahydrofur-2-ylmethyl, 4-methyl-2-oxo-oxazolidin-5-yl, pyrid-4-ylmethyl, pyrid-2-ylmethyl, 2-trifluoromethylpyrid-5-ylmethyl, trifluoromethyl, 2,2,2-trifluoroethyl, 3,3,3-trifluoropropyl, $(CH_3)_3CCH_2$—, pentafluoroethyl, $CF_3CH_2CH_2$—, cyclopropylmethyl, benzyl, 4-methylbenzyl, 4-chlorobenzyl, (2-methoxyphenyl)ethyl, 1-phenylethyl, phenylethyl, cyclopropyl, 1-methylcyclopropyl, 2-fluorocyclopropyl, 2-phenylcyclopropyl, cyclobutyl, cyclopentyl, cyclohexyl, 5,5-dimethyl-3-oxocyclohexenyl, phenyl, 4-methylphenyl, 3-methylphenyl, 2-methylphenyl, 3,4-dimethylphenyl, 3,5-dimethylphenyl, 4-ethylphenyl, 3-ethylphenyl, 2-ethylphenyl, 4-isopropylphenyl, 4-isopropyl-3-methylphenyl, 3-isopropylphenyl, 4-tert-butylphenyl, 2,3-dimethylphenyl, 3-fluorophenyl, 4-fluorophenyl, 2-fluorophenyl, 24-difluorophenyl, 3,4-difluorophenyl, 2,3-difluorophenyl, 2,6-difluorophenyl, 2,5-difluorophenyl, 3,5-difluorophenyl, 2,4,6-trifluorophenyl, 3-bromophenyl, 4-bromophenyl, 4-chlorophenyl, 3-chlorophenyl, 2-chlorophenyl, 4-methoxyphenyl, 3-methoxyphenyl, 2-methoxyphenyl, 3,4-dimethoxyphenyl, 2,6-dichlorophenyl, 3-fluoro-5-methoxyphenyl, 3-chloro-5-methoxyphenyl, 4-chloro-2-methoxyphenyl, 2,4-dimethoxyphenyl, 2,6-dimethoxyphenyl, 3,5-dimethoxyphenyl, 2-ethoxyphenyl, 4-hydroxyphenyl, 2-hydroxyphenyl, 2,5-dichlorophenyl, 2,4-dichlorophenyl, 2,3-dichlorophenyl, 3,5-dichlorophenyl, 3,4-dichlorophenyl, 3,4-difluorophenyl, 3-trifluoromethoxyphenyl, 4-trifluoromethoxyphenyl, 3-trifluoromethylphenyl, 4-trifluoromethylphenyl, 3,5-di(trifluoromethyl)-phenyl, 3,5-di(trifluoromethyl)-2-methylphenyl, 4-dimethylaminophenyl, 3-dimethylaminophenyl, 3-nitrophenyl, 4-nitrophenyl, 3-cyanophenyl, 4-methylthiophenyl, 3-methylsulfonylphenyl, 2-methylsulfonylphenyl, 3-chloro-4-methylphenyl, 3-chloro-4-fluorophenyl, 4-[1-isopropylpiperazinin-4-yl]phenyl, 2-[(1-methylpyrrolidin-3-yl)-N(CH_3)]-5-trifluoromethylphenyl, 5-[1-methylpiperazin-4-ylmethyl]-3-trifluoromethylphenyl, 5-[2-oxopyrrolidin-1-yl]-3-trifluoromethylphenyl, 2-chloro-4-trifluoromethylphenyl, 4-chloro-3-trifluoromethylphenyl, 4-bromo-2-fluorophenyl, 2-trifluoromethoxyphenyl, 2-trifluoromethylphenyl, 4-pentafluoroethylphenyl, -fluoro-3-trifluoromethylphenyl, 2-fluoro-5-trifluoromethylphenyl, 2-methyl-3-trifluoromethylphenyl, 2-methyl-5-trifluoromethylphenyl, 3-fluoro-5-trifluoromethylphenyl, 2-[methylcarbonylamino]-5-trifluoromethylphenyl, 3-[1-methylpiperidin-4-yl]-5-trifluoromethylphenyl, 2-[1,1-dioxo-thiomorpholin-4-yl]-5-trifluoromethylphenyl, 2-[1-oxothiomorpholin-4-yl]-5-trifluoromethylphenyl, 2-[thiomorpholin-4-yl]-5-trifluoromethylphenyl, 2-piperidin-1-yl-5-trifluoromethyl-phenyl, 2-[(3-dimethylaminopropyl)methylamino]-5-trifluoromethylphenyl, 2-(3-dimethylamino-pyrroldin-1-yl)-5-trifluoromethylphenyl, 3-(methylcarbonylamino)phenyl, 3-(4-methylpiperazin-1-ylmethyl)phenyl, 2-(4-methylpiperazin-1-ylmethyl)phenyl, 2-piperidin-1-yl-5-trifluoromethyl-phenyl, 2-[1-methylpiperidin-4-yloxy]-5-trifluoromethylphenyl, 2-methoxy-5-trifluoromethylphenyl, 2-methoxy-5-phenylphenyl, 2-[3,3-dimethyl-2-oxo-azetidin-1-yl]-5-trifluoromethylphenyl, 2-[morpholin-4-ylethoxy]-5-tert-butylphenyl, 2-methoxy-5-fluorophenyl, 2-methoxy-5-tert-butylphenyl, 3-[dimethylaminomethylcarbonylamino]-4-tert-butylphenyl, 2-methoxy-5-[2-pyridylaminocarbonyl]phenyl, 2-methoxy-5-phenylaminocarbonylphenyl, 2-[methyl-(1-methylpyrrolidin-3-yl)amino]-5-trifluoromethylphenyl, 2,2-difluorobenzodioxol-4-yl, biphenyl, 2-naphthyl, 2,3-dihydro-1,4-benzodioxol-6-yl, 7-fluoro-2,3-dihydro-1,4-benzodioxin-6-yl, 1,3-benzodioxol-4-yl, 1-isopropylpiperidin-4-yl, 2-pyrrolidinyl, 1-methyl-2-pyrrolidinyl, 4-piperazinyl, 1-methylpiperidin-4-yl, 3-methylisothiazol-5-yl, 3-isothiazolyl, 4,5-dichloro-3-isothiazolyl, isoxazol-3-yl, 5-isoxazolyl, 4-isoxazolyl, 5-methyl-isoxazol-3-yl, 3,5-dimethyl-isoxazol-4-yl, 4,5-dimethyl-isoxazol-3-yl, 3-methyl-isoxazol-5-yl, 5-tert-butyl-isoxazol-3-yl, 4-bromo-5-methyl-isoxazol-3-yl, 5-oxazolyl, 1-methylimidazol-5-yl, 5-imidazolyl, 2-thienyl, 3-thienyl, 2-methylcarbonyl-thien-3-yl, 2-methylcarbonyl-5-tert-butyl-thien-3-yl, 2-aminocarbonyl-5-tert-butyl-thien-3-yl, 4-methoxy-5-chloro-3-thienyl, 3-methyl-2-thienyl, 5-methyl-2-thienyl, 5-methylthio-2-thienyl, 5-methylsulfonyl-2-thienyl, 3-ethoxy-2-thienyl, 3-chloro-2-thienyl, 5-chloro-2-thienyl, 3-bromo-2-thienyl, 5-bromo-2-thienyl, 4-methoxy-5-bromo-3-thienyl, 4-methoxy-3-thienyl, 2-furyl, 2-cyano-5-phenyl-fur-3-yl, 4,5-dimethyl-2-furyl, 5-methyl-2-trifluoromethyl-3-furyl, 3-furanyl, 1-methylpyrrol-2-yl, 2-pyrrolyl, 2-pyrazinyl, 5-methyl-2-pyrazinyl, 4-pyrimidinyl, 2,6-dimethoxy-4-pyrimidinyl, 4-methoxy-6-methylpyrimidin-2-yl, 4-chloro-2-methylthiopyrimidin-6-yl, 2-pyridyl, 3-pyridyl, 4-pyridyl, 4-trifluoromethylpyridin-2-yl, 2-trifluoromethylpyridin-5-yl, 2-dimethylaminopyridin-5-yl, 5-chloro-2-pyridyl, 2-fluoro-3-pyridyl, 2-chloro-3-pyridyl, 2-methoxy-3-pyridyl, 2-ethoxy-3-pyridyl, 2-chloro-4-pyridyl, 2,5-dichloro-3-pyridyl, 2-(dimethylaminoethoxy)-3-pyridyl, 2-methoxy-5-pyridyl, 2-methyl-5-pyridyl, 4-chloro-2-pyridyl, 4-methoxy-5-pyridyl, 3-benzyloxypyridin-2-yl, 4-methylpyridin-2-yl, 4-ethylpyridin-2-yl, 2-chloropyridin-4-yl, 3-chloropyridin-5-yl, 3-chloropyridin-6-yl, 2-chloropyridin-5-yl, 4-chloropyridin-2-yl, 1-methyl-2-oxopyrid-5-yl, tetrahydropyran-4-yl, 4,5-dihydrothiazol-2-yl, thiazol-2-yl, 5-methyl-thiazol-2-yl, 4,5-dimethyl-thiazol-2-yl, 4-tert-butyl-thiazol-2-yl, 5-tert-butyl-thiazol-2-yl, 5-nitrothiazol-2-yl, 5-bromothiazol-2-yl, 5-[4-chlorophenyl]-thiazol-2-yl, 4-[4-chlorophenyl]-thiazol-2-yl, 4-[4-nitrophenyl]-thiazol-2-yl, 4-thiazolyl, 2-methyl-4-thiazolyl, 2,5-dimethyl-4-thiazolyl, 2,4-dimethyl-5-thiazolyl, 5-tert-butyl-1,3,4-thiadiazol-2-yl, 5-trifluoromethyl-1,3,4-thiadiazol-2-yl, 5-ethyl-1,3,4-thiadiazol-2-yl, pyrazol-5-yl, 3-pyrazolyl, 1,3-diphenyl-pyrazol-3-yl, 1,3-dimethyl-pyrazol-3-yl, 5-cyano-4-tert-butyl-pyrazol-3-yl, 5-amino-3-methyl-pyrazol-1-yl, 3-methyl-1-tert-butyl-pyrazol-3-yl, 5-amino-3-tert-butyl-pyrazol-1-yl, 1-ethylpyrazol-5-yl, 3-tert-butyl-pyrazol-5-yl, 1-methyl-3-tert-butyl-pyrazol-5-yl, 4,4-dimethyl-1,2,34-tetrahydroisoquinolin-7-yl, 7-quinolinyl, 2,3-dihydrobenzofur-7-yl, 3,3-dimethyl-1-methylcarbonylindolin-6-yl, 3,3-dimethyl-2,3-dihydro-indol-6-yl, 4-tert-butyl-imidazo[1,2-a]pyridin-6-yl, 3-quinolinyl, 2-benzofuryl, benzo[1,2,5]thiadiazol-4-yl, 7-methyl-benzothiazol-2-yl, 6-ethoxy-benzothiazol-2-yl, 6-fluoro-benzothiazol-2-yl, 5,6-dimethyl-benzothiazol-2-yl, benzimidazol-2-yl, 1-methyl-benzimidazol-2-yl, benzokazol-2-yl, benzisoxazol-3-yl, 4-methoxybenzisoxazol-3-yl and 2-methylbenzothiazol-5-yl.

The invention also relates to compounds wherein R' is selected from methoxyethyl, cyclopropyl, and 4-chlorophenyl.

The invention also relates to compounds wherein $Y^a$ is —C(=O)NH—.

The invention also relates to compounds wherein $R^8$ and $R^9$ are H.

The invention also relates to compounds selected from
7-((6,7-bis(methyloxy)-4-quinolinyl)oxy)-N-(4-chlorophenyl)-4-quinolinecarboxamide;
7-((6,7-bis(methyloxy)-4-quinolinyl)oxy)-N-cyclopropyl-4-quinolinecarboxamide; and
7-((6,7-bis(methyloxy)-4-quinolinyl)oxy)-N-(2-(methyloxy)ethyl)-4-quinolinecarboxamide.

The invention also relates to compounds wherein R is not H when Y is $(CH_2)_0$ when A is naphthyl or quinolinyl.

Indications

Compounds of the present invention would be useful for, but not limited to, the prevention or treatment of angiogenesis related diseases. The compounds of the invention have kinase inhibitory activity, such as VEGFR/KDR, c-kit, abl, and/or c-Met inhibitory activity. The compounds of the invention are useful in therapy as antineoplasia agents or to minimize deleterious effects of VEGF and/or HGF. The compounds of the invention also inhibit lck and src activity.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemagiomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

Accordingly, the invention relates to a method of treating inflammation in a mammal, the method comprising administering to the mammal a therapeutically effective amount of a compound according to any one of the above embodiments.

The invention relates to a method of inhibiting T cell activation in a mammal, the method comprising administering to the mammal a therapeutically effective amount of a compound according to any one of the above embodiments.

The invention relates to a method of treating arthritis, rheumatoid arthritis, psoriatic arthritis, or osteoarthritis in a mammal, the method comprising administering to the mammal a therapeutically effective amount of a compound according to any one of the above embodiments.

The invention relates to a method of treating organ transplant, acute transplant or heterograft or homograft rejection, or transplantation tolerance induction in a mammal, the method comprising administering to the mammal a therapeutically effective amount of a compound according to any one of the above embodiments.

The invention relates to a method of treating ischemic or reperfusion injury, myocardial infarction, or stroke in a mammal, the method comprising administering to the mammal a therapeutically effective amount of a compound according to any one of the above embodiments.

The compounds of this invention may also act as inhibitors of other protein kinases, e.g. tie-2, lck, src, fgf, c-Met, ron, and ret, and thus be effective in the treatment of diseases associated with other protein kinases. The compounds of this invention may also act as inhibitors of mutants of the above-identified tyrosine kinases, including c-kit, abl and VEGFR.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a sindle compound, salt and the like.

Definitions

"Angiogenesis" is defined as any alteration of an existing vascular bed or the formation of new vasculature which benefits tissue perfasion. This includes the formation of new vessels by sprouting of endothelial cells from existing blood vessels or the remodeling of existing vessels to alter size, maturity, direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta 5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as $p^{190}$MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, amino, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term heterocyclyl also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heterocyclyl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a] isoquinolyl, 3,4-dihydro-2H-benzo[1,4]oxazinyl, benzo[1,4] dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH₃S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-C₁-C₃-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three CH₂ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-C₁-C₃-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I-VII" includes any sub formulas.

The compounds of the invention are endowed with kinase inhibitory activity, such as Lck, KDR and/or c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of Lck, KDR and/or c-Met.

The present invention comprises a pharmaceutical composition comprising a therapeutically-effective amount of a compound of Formulas I-VII in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I-VII.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimeterxate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE- 21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitertinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimeterxate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemeterxed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors, and anti-inflamatories.

The present invention comprises processes for the preparation of a compound of Formula I-VII.

Also included in the family of compounds of Formula I-VII are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-VII may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-VII include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aisitidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-VII. When a basic group and an acid group are present in the same molecule, a compound of Formula I-VII may also form internal salts.

General Synthetic Procedures

The compounds of the invention can be synthesized according to the following procedures of Schemes 1-16, wherein the substituents are as defined for Formulas I-VII, above, except where further noted.

The following abbreviations are used throughout the specification:

| | |
|---|---|
| AcOH | acetic acid |
| BINAP | 2,2'-bis(diphenylphosphino)-1,1'-binapthyl |
| BBr$_3$ | boron tribromide |
| BH$_3$-THF | borane-tetrahydrofuran complex |
| BOC | t-butoxycarbonyl |
| BSA | bovine serum albumin |
| n-BuLi | n-butyl lithium |
| CO | carbon monoxide |
| C$_2$O$_2$Cl$_2$ or (COCl)$_2$ | oxalyl chloride |
| Cs$_2$CO$_3$ | cesium carbonate |
| CHCl$_3$ | chloroform |
| Et$_2$O | diethyl ether |
| DCM, CH$_2$Cl$_2$ | methylene chloride |
| DIBAL | diisobutylaluminum hydride |
| DIEA, DIPEA, Hunig's base | diisopropylethylamine |
| DMF | dimethylformamide |
| dppa | diphenylphosphoryl azide |
| DPPP | 1,3-diphenylphosphino propane |
| DMAP | 4-dimethylaminopyridine |
| EtOAc, EA | ethyl acetate |
| EtOH | ethanol |
| Et$_2$O | diethyl ether |
| EDC, EDCI | 1-(3-dimethylaminopropyl)-3-ethylcarbodiimide hydrochloride |
| EtNH$_2$ | ethyl amine |
| FBS | fetal bovine serum |
| g | gram |
| h | hour |
| HCl | hydrochloric acid |
| HOAt | 1-hydroxy-7-azabenzotriazole |
| HOBt | 1-hydroxybenzotriazole hydrate |
| H$_2$ | hydrogen |
| H$_2$0 | water |
| H$_2$O$_2$ | hydrogen peroxide |
| HATU | O-(7-azabenzotriazol-1-yl-)N,N,N',N', tetramethyluronium hexafluorophosphate |
| KOH | potassium hydroxide |
| K$_2$CO$_3$ | potassium carbonate |
| K$_3$PO$_4$ | potassium phosphate |
| KMnO$_4$ | potassium permanganate |
| LAH | lithium aluminum hydride |
| LiHMDS | lithium bis(trimethylsilyl)-amide |
| LiOH | lithium hydroxide |
| MgSO$_4$ | magnesium sulfate |
| MCPBA | meta-chloroperbenzoic acid |
| MeOH, CH$_3$OH | methanol |
| MeNH$_2$ | methyl amine |
| NH$_4$Cl | ammonium chloride |
| NH$_4$OH | ammonium hydroxide |
| NMP | N-methylpyrrolidinone |
| NaHCO$_3$ | sodium bicarbonate |
| NaN$_3$ | sodium azide |
| Na$_2$SO | sodium sulfate |
| NaOH | sodium hydroxide |
| NaH | sodium hydride |
| Na$_2$SO$_4$ | sodium sulfate |

-continued

| | |
|---|---|
| NaOt-Bu | sodium tert-butoxide |
| NaHB(OAc)$_3$ | sodium triacetoxyborohydride |
| N$_2$ | nitrogen |
| O/N | overnight |
| POCl$_3$ | phosphorus oxychloride |
| Pd/C | palladium on carbon |
| Pd$_2$(dba)$_3$ | bis(dibenzylideneacetone) palladium |
| Pd(OAC)$_2$ | palladium (II) acetate |
| P(t-bu)$_3$ | tri(tert-butyl)phosphine |
| PBS | phospate buffered saline |

-continued

| | |
|---|---|
| PyBop | Benzotriazol-1-yl-oxy-tripyrrolidino-phosphonium hexafluorophosphate |
| RT | room temperature |
| SOCl$_2$ | thionyl chloride |
| TBTU | O-benzotriazol-1-yl-N,N,N',N'-tetramethyluronium tetrafluoroborate |
| TBAI | tetrabutylammonium iodide |
| TFA | trifluoroacetic acid |
| THF | tetrahydrofuran |
| TEA, Et$_3$N | triethylamine |

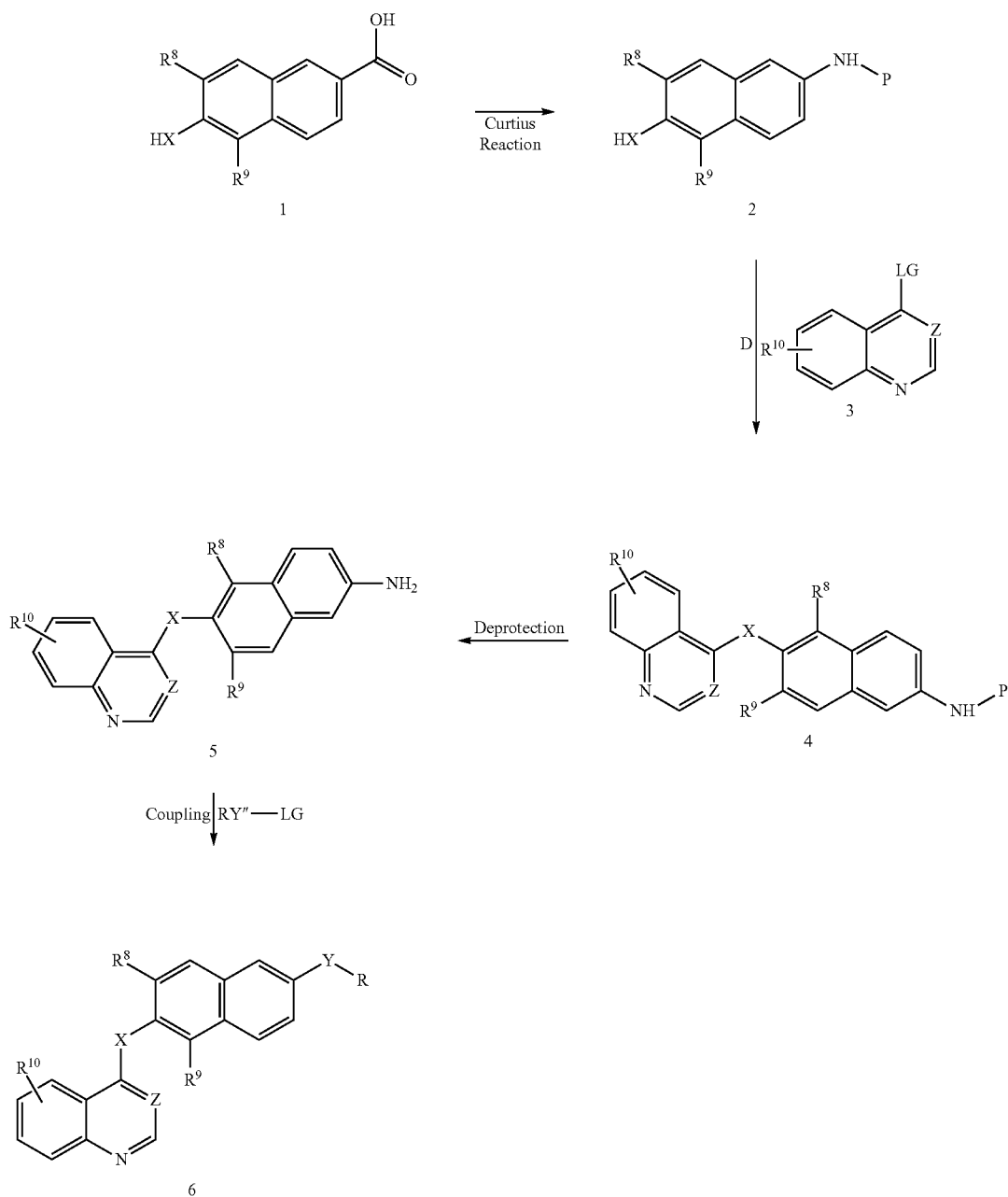

Scheme 1

Substituted bicyclic compounds 6 [where Y is substituted amines or amides] can be prepared by the process outlined in Scheme 1. Disubstituted naphthyl compounds 1, e.g. 6-hydroxy-2-naphthoic acid, is protected, such as with benzyl alcohol in the presence of dppa and a base, such as Et$_3$N at a temperature above RT, preferably at a temperature at about reflux, provide carbamates 2. The protected amine 2 [where X is O] is coupled with a quinoline derivative 3 [where LG is halo, and the like] such as in the presence of DMAP in a solvent such as toluene at a temperature above RT, preferably above about 100° C., more preferably at a temperature of about 180° C., to form the protected linked compound 4. Such heating is preferably heated by microwave. After deprotection, e.g. with H$_2$ in the presence of a catalyst such as Pd/C, amine 5 is formed. Alternatively, the deprotection can be achieved by treatment with K$_2$CO$_3$ and copper, at a temperature above RT, preferably above about 100° C., more preferably at about 120° C. The amine 5 can be coupled with compounds having an active acyl moiety, such as acid chlorides and carboxylic acids, to form naphthyl amides 6 of the present invention.

Alternatively, protected amine 2 can be deprotected and coupled to nitrogen containing heterocyclic compounds such as quinolines and quinzaolines 3 can be achieved by treatment with K$_2$CO$_3$ and copper, at a temperature above RT, preferably above about 100° C., more prefrably at about 120° C.

Scheme 2

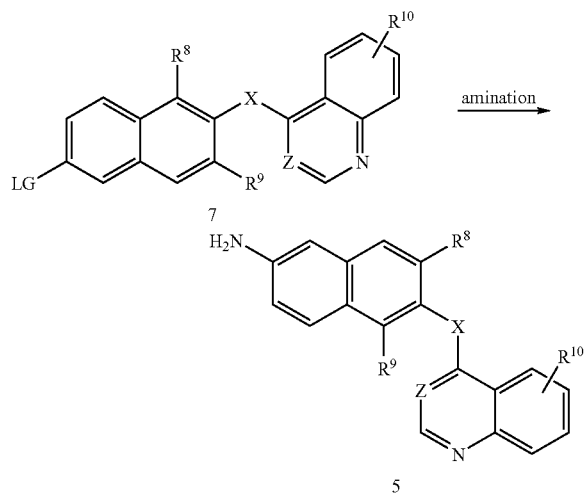

Alternatively, naphthyl amines 5 can be prepared via amination of a bromo-derivative 7 e.g. a halo derivative more preferably a bromo-derivative such as in the presence of Pd and a strong base, e.g. LiHMDS. Preferably Pd$_2$(dba)$_3$ in the presence of P(t-Bu)$_3$ is used. Preferably the reaction is kept at aout RT.

Scheme 3

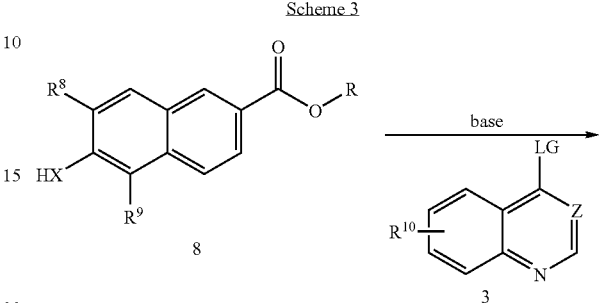

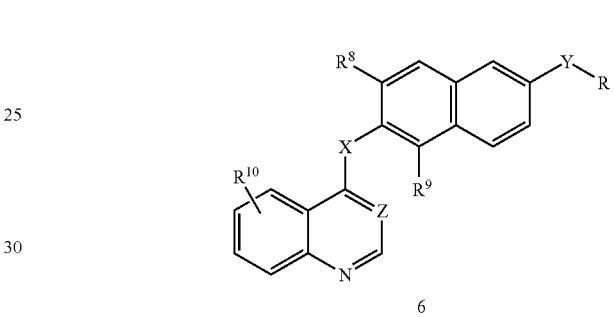

Alternatively, compounds where Y is —CO$_2$— 6 can be prepared as described in Scheme 3. A substituted naphthalene-2-carboxylic acid ester 8 is treated with strong base, such as NaH, preferably in a solvent such as DMF, to form the anion. Preferably the reaction temperature is at about RT. Substituted nitrogen containing heteroaryl compounds 3, such as substituted quinazolines or quinolines, are coupled to the anion to form the compounds of the present invention 6. The reaction temperature is above RT, preferably above about 50° C., more preferably at about 60° C.

Scheme 4

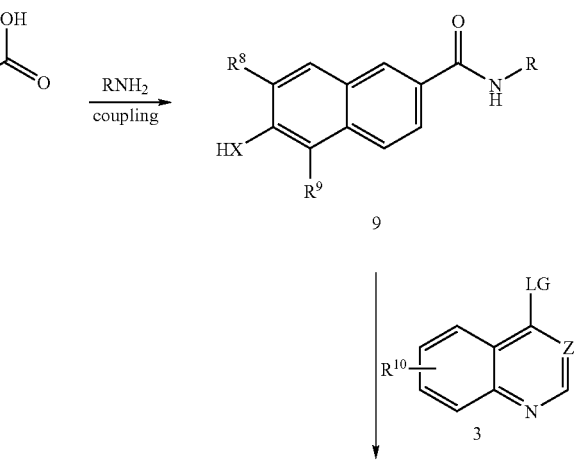

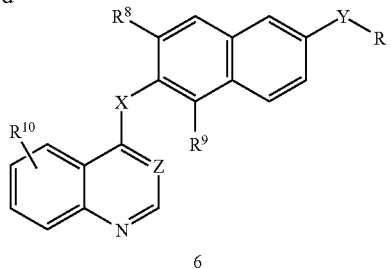

Alternatively, compounds where Y is —C(=O)NH— 6 can be prepared as described in Scheme 4. A substituted naphthalene-2-carboxylic acid 1 can be coupled with an amine under standard coupling chemistry, such as with EDC in the presence of a solvent like DMF, to form amides 9. The reaction temperature is preferably kept at about RT. Coupling the amides 9 with nitrogen-containing heterocyclic compounds, such as quinolines and quinzaolines 3, by the method described above in Scheme 1 provides compounds of the present invention 6 [where Y is —C(=O)NH—].

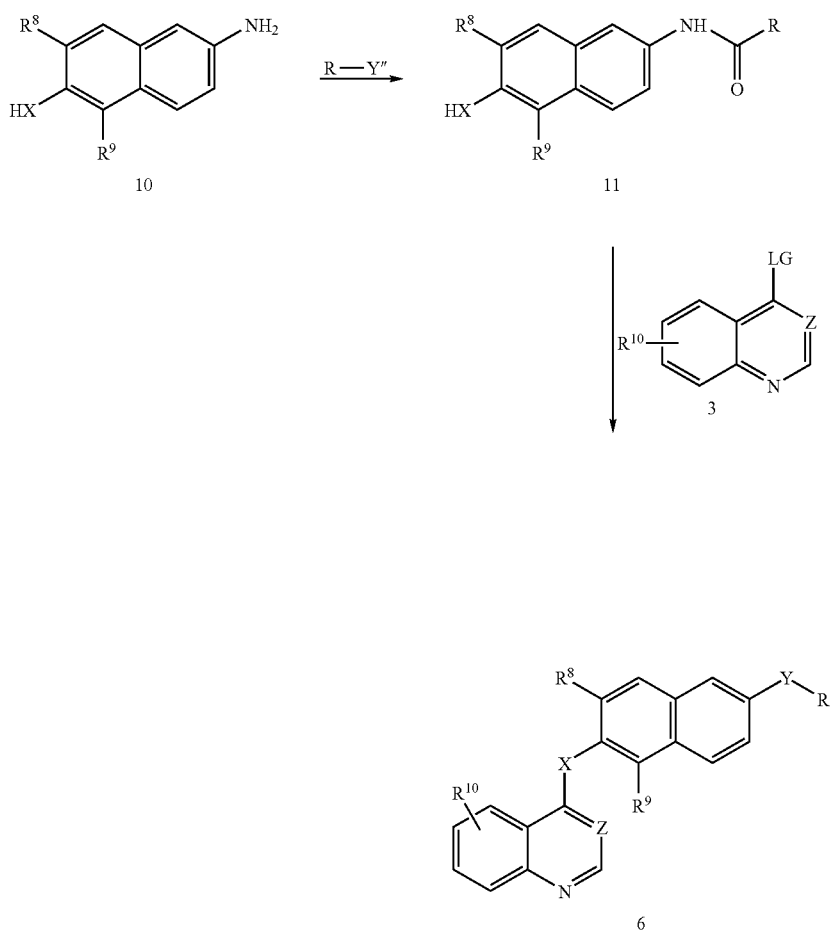

Alternatively, compounds where Y is —C(=O)NH— 6 can be prepared as described in Scheme 5. A substituted naphthylamine 10 can be coupled with an active carbonyl compound (Y"—R) as described in Scheme 1, to form amides 11. Coupling the amides 11 with nitrogen containing heterocyclic compounds, such as quinolines and quinzaolines 3 by the method described in Scheme 4, provides compounds of the present invention 6 [where Y is —NHC(=O)—].

Scheme 6

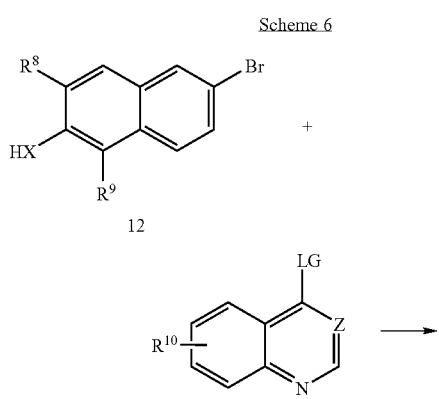

Scheme 7

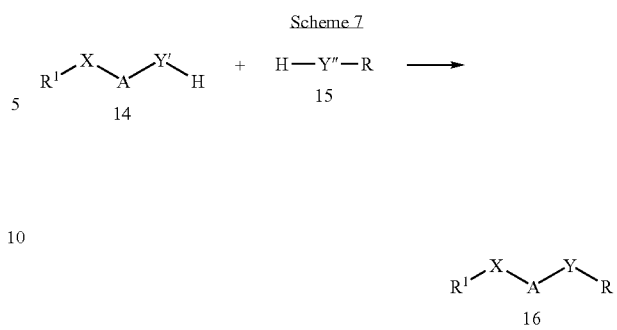

Substituted bicyclic compounds can be prepared by the process outlined in Scheme 7. Coupling of bicyclic compounds (where R is not H) 15 with intermediates 14 (where Y' is a portion of Y, such as NH, C(=O), etc.) yields compounds 16.

Scheme 8

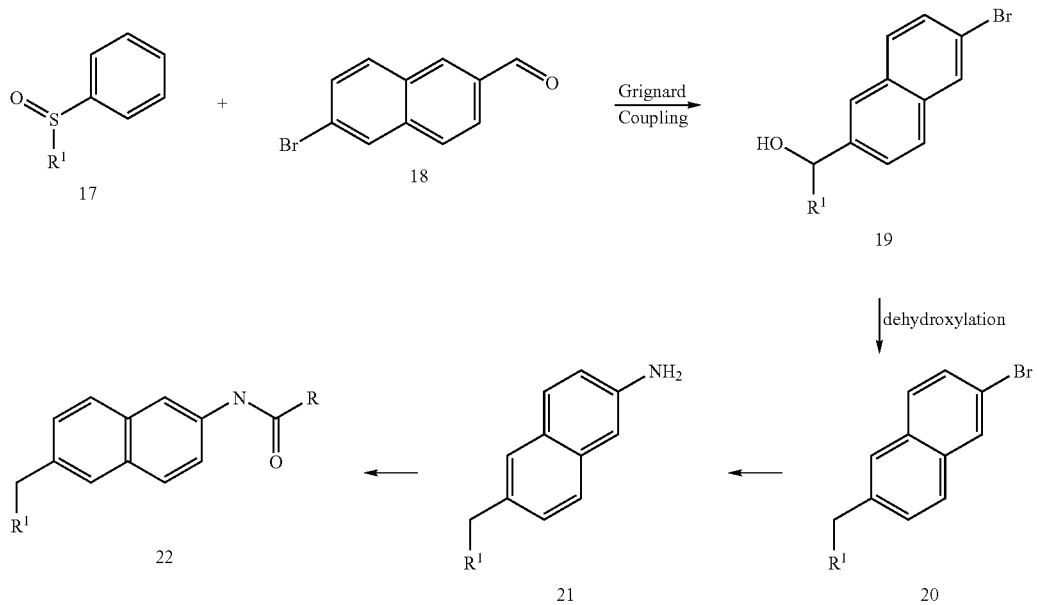

-continued

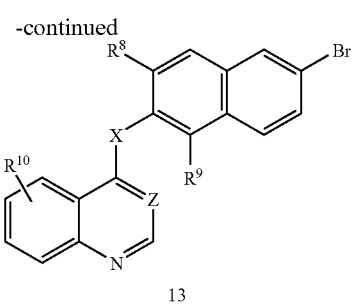

Bromonaphthyl intermediates 13 can be provided by the method described in Scheme 6. A mixture of substituted quinoline 3 [where LG is chloro], 6-bromo-naphthyl compound 12 and DMAP, in a solvent such as toluene, at a temperature above RT, preferably above about 100° C., more preferably at a temperature of about 180° C., to form the intermediates 13.

Substituted bicyclic compounds 22 [where Y is an amide] can be prepared by the process outlined in Scheme 8. 6-Bromo-2-hydroxymethylnaphthalenes 19 are prepared such as by the coupling of 6-bromonaphthyl-2-carbaldehydes 18 and activated $R^1$ containing compounds 17, such as phenylsulfinyl substituted compounds. Preferably the coupling occurs in the presence of a Grignard reagent, such as phenylmagnesium bromide, in an appropriate protic solvent such as THF. The temperature is preferably maintained at about RT. Preferably the Grignard is first added to the $R^1$ containing compound 17 prior to the addition of the carbaldehyde 18. The resulting hydroxymethyl compound 19 is dehydroxylated, such as in the presence of Zn and formic acid. The dehydroxylation preferably occurs at a temperature above RT, more preferably above about 50° C., and most preferably at about reflux temperature. The resulting 6-bromonaphtyl compound 20 is animated similar to that described in Scheme 2 to form naphthyl amine 21 and the amides 22 are consequently formed similar to that described in Scheme 1.

Scheme 9

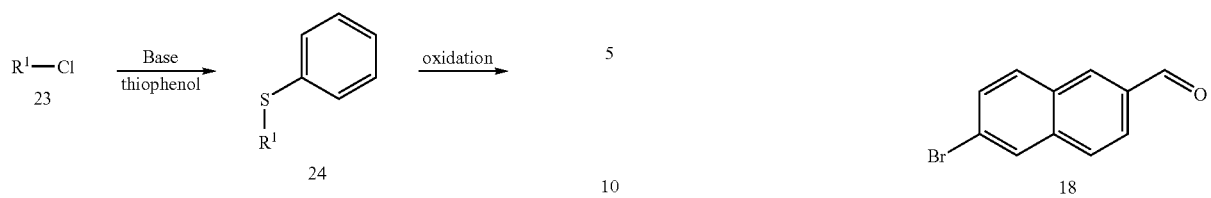

Activated R¹ containing compounds 17 can be prepared such as by the method identified in Scheme 9. Halosubstituted compounds 23 are dehalogenated, such as with aqueous base, e.g. KOH, then treated with a thiol compound, such as thiophenol, at a temperature above RT, preferably above 75° C., more preferably at about 100° C. The thio compound 24 is oxidized, such as with mCPBA, at a temperature below RT, preferably below −23° C., more preferably at about −78° C., to form the sulfinyl compounds 17.

Scheme 10

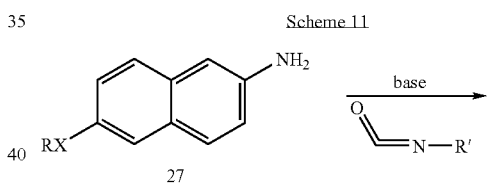

6-Bromonaphthyl-2-carbaldehydes 18 are prepared from the carboxylic acid 25 via reduction of the amide intermediate 26. The amide 26 is formed via peptide type coupling, such as in the presence of EDC, HOBt and base, of a substituted hydroxylamine, at a temperature preferably at about RT. Reduction of the amide 26, such as with DIBAL, in a solvent such as THF, at a temperature between −78° C. and RT, preferably at about RT, provides the desired 6-bromonaphthalene-2-carbaldehyde 18.

Scheme 11

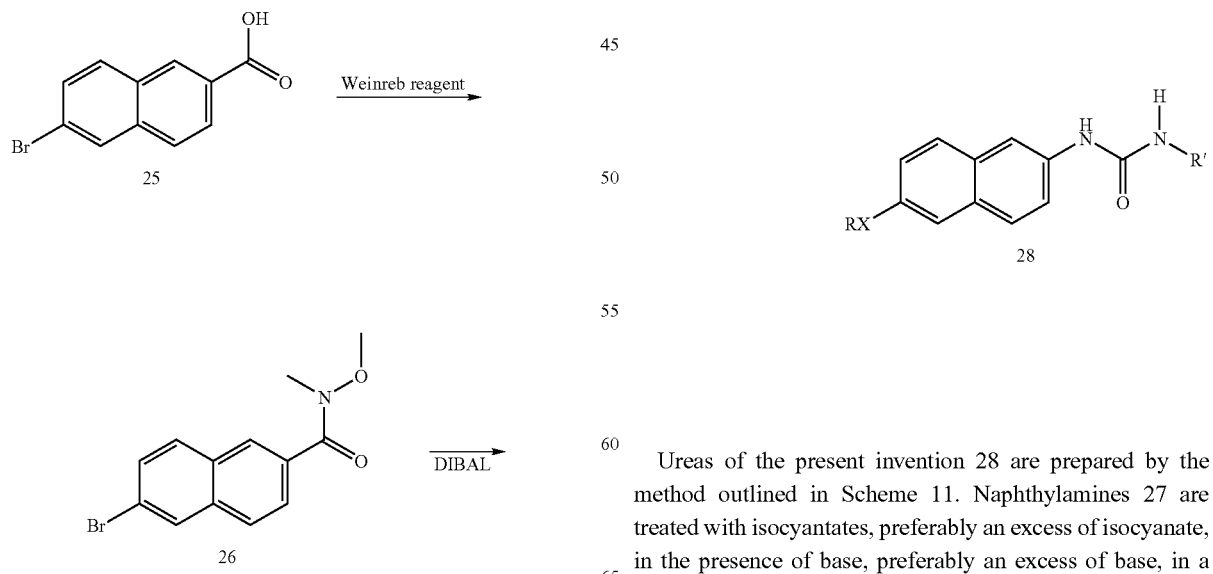

Ureas of the present invention 28 are prepared by the method outlined in Scheme 11. Naphthylamines 27 are treated with isocyantates, preferably an excess of isocyanate, in the presence of base, preferably an excess of base, in a solvent such as DMF to form the ureas 28. Preferably the reaction temperature is maintained at around RT.

Scheme 12

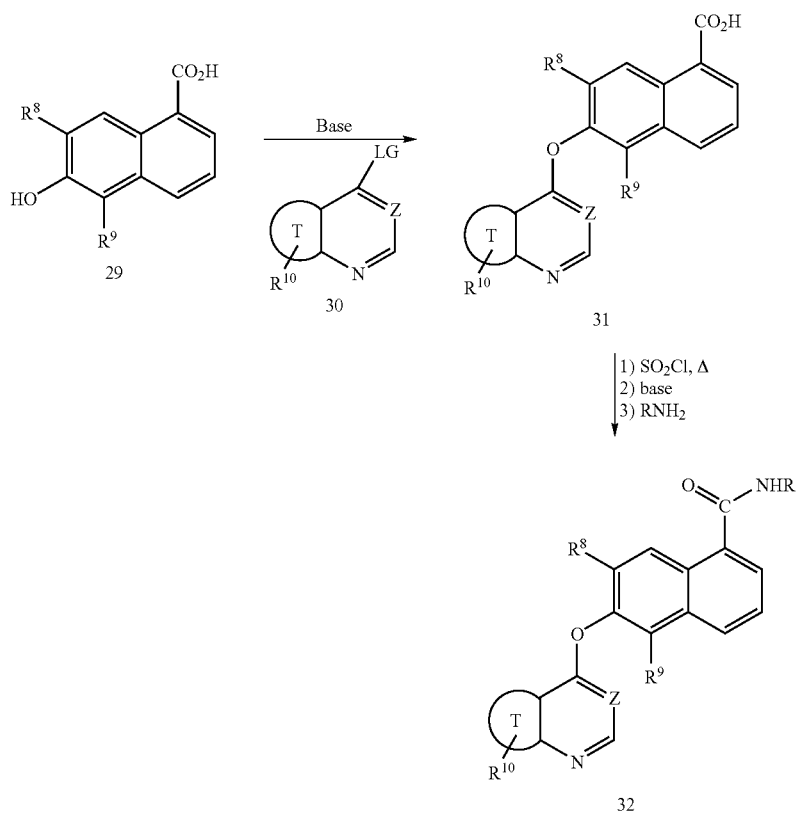

Naphthyl amides of the present invention 32 are prepared by the method outlined in Scheme 12. 6-Hydroxynaphtoic acid 29, is treated with base, such as t-BuOK in an appropriate solvent such as DMSO. The ring 30 (where LG is a leaving group such as chloro) is added and the resulting mixture is heated to at a temperature above RT, preferably above about 50° C., more preferably at a temperature of about 90° C., to form ether 31. The ether is aminated, such as by treatment with SOCl$_2$ and DMF, in an appropriate solvent such as toluene, at a temperature above RT, preferably above about 50° C., more preferably at a temperature of about 100° C. The mixture is treated with base and the appropriate amine to form the desired amides 32.

Scheme 13

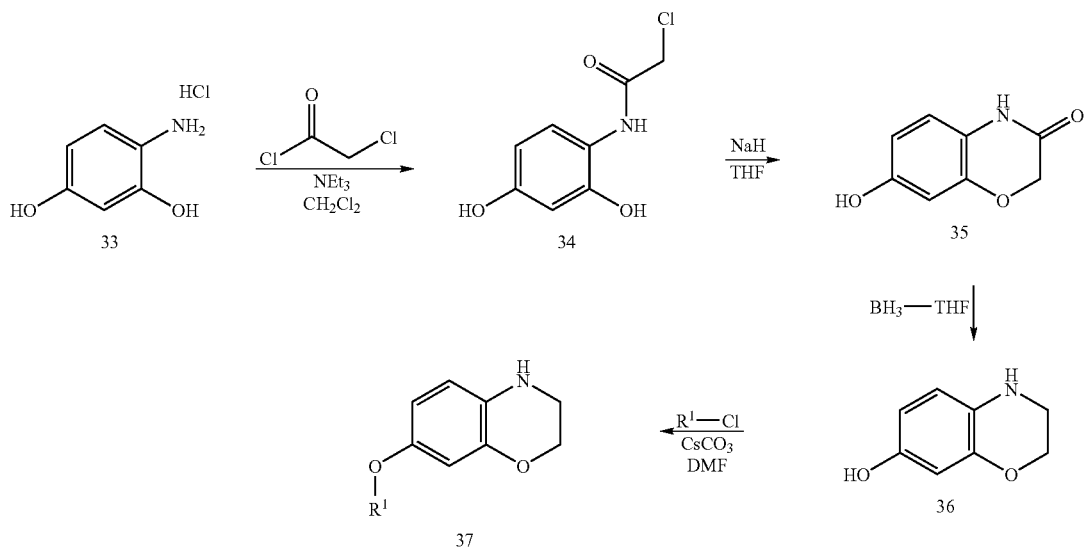

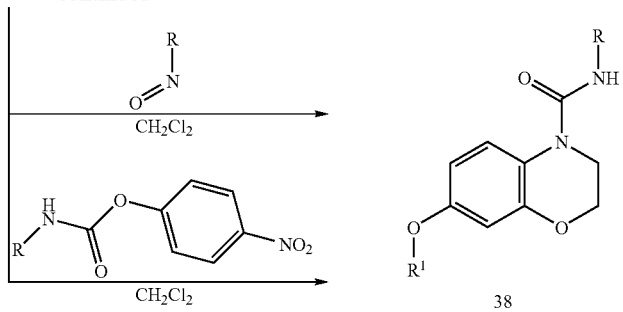

2,3-Dihydrobenzo[b][1,4]oxazine amides 38 of the present invention are prepared by the method outlined in Scheme 13. The 2-chloro-N-(2,4-dihydroxyphenyl)acetamide 34 is formed by treatment of 4-aminoresorcinol hydrochloride 33 with chloroacetyl chloride in a solvent such as $CH_2Cl_2$, in the presence of base, e.g. TEA at a temperature of about RT. The hydroxyl 2H-benzo[b][1,4]oxazin-3(4H)-one 35 is formed from treatment of the acetamide 34 with base, e.g. NaH, in a suitable solvent such as $CH_2Cl_2$ at a temperature of about RT. Reduction of the 2H-benzo[b][1,4]oxazin-3(4H)-one 35, such as with treatment with $BH_3$-THF in a solvent such as THF, at a temperature above RT, preferably above 50° C., and more preferably at about 60° C., provides the 3,4-dihydro-2H-benzo[b][1,4]oxazin-7-ol 36. Coupling of the alcohol 36 with the halide, such as in the presence of cesium carbonate, at a temperature above RT, preferably above 50° C., and more preferably at about 80° C., provides the substituted 3,4-dihydro-2H-benzo[b][1,4]oxazine 37. Treatment with an isocyante or carbamate, yields the desired amides 38.

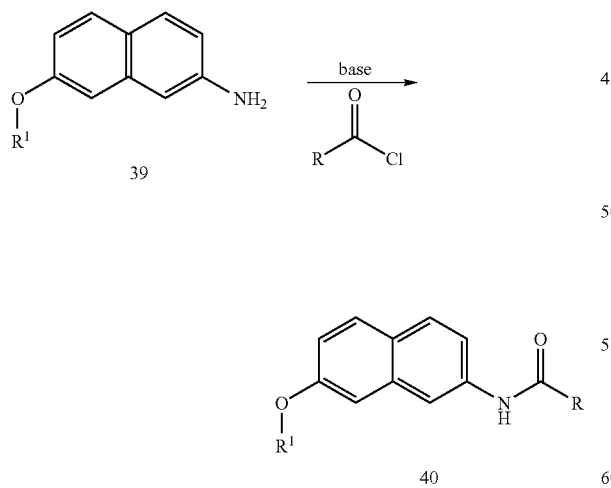

Formation of the desired 3,6-disubstituted naphthalenes 40 using a procedure described above but starting with the 3-amino-naphthalene 39 is shown in Scheme 14.

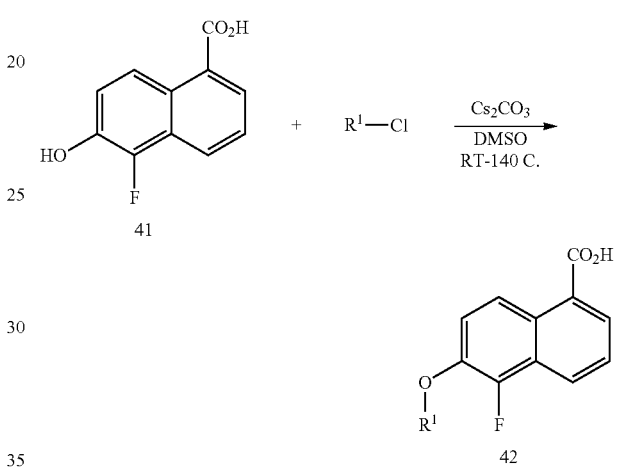

Substituted 5-fluoro-1-carboxy-naphthalenes 42 can be prepared such as by the method described in Scheme 15. Reaction of the alcohol 41, such as with the appropriate halide, in the presence of cesium carbonate, provides the desired ether.

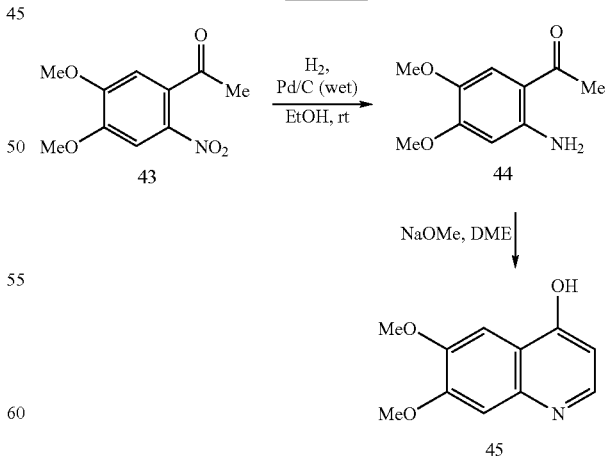

Dimethoxy-quinolines 45 can be prepared from the corresponding nitro 43 compounds via the method described in Scheme 16. Reduction of the nitro compound 43 to the amine 44, such as with $H_2$ in the presence of a catalyst, such as Pd, e.g. Pd/C, followed by treatment with base and dimethyl ether, yields the desired quinolines 45.

Various substituted quinolines and quinazolines can be prepared by the methods described in WO 98/13350.

The starting compounds defined in Schemes 1-16 may also be present with functional groups in protected form if necessary and/or in the form of salts, provided a salt-forming group is present and the reaction in salt form is possible. If so desired, one compound of Formula I can be converted into another compound of Formula I, e.g. an N-oxide thereof; a compound of Formula I can be converted into a salt; a salt of a compound of Formula I can be converted into the free compound or another salt; and/or a mixture of isomeric compounds of Formula I can be separated into the individual isomers.

N-Oxides can be obtained in a known matter by reacting a compound of Formula I with hydrogen peroxide, oxone, or a peracid, e.g. mCPBA, in an inert solvent, e.g. $CH_2Cl_2$, or a mixture of water and an alcohol such as MeOH or EtOH, at a temperature between about $-10\text{-}35°$ C., such as about $0°$ C.-RT.

If one or more other functional groups, for example carboxy, hydroxy, amino, or mercapto, are or need to be protected in a compound of Formula I or in the preparation of compounds of Formula I, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York (1973), in T. W. Greene, "Protective Groups in Organic Synthesis", Wiley, New York (1981), in "The Peptides", Volume 3, E. Gross and J. Meienhofer editors, Academic Press, London and New York (1981), in "Methoden der organischen Chemie" (Methods of Organic Chemistry), Houben Weyl, $4^{th}$ edition, Volume 15/1, Georg Thieme Verlag, Stuttgart (1974), in H.-D. Jakubke and H. Jescheit, "Aminosauren, Peptide, Proteine" (Amino Acids, Peptides, Proteins), Verlag Chemie, Weinheim, Deerfield Beach, and Basel (1982), and in Jochen Lehmann, "Chemie der Kohlenhydrate: Monosaccharide und Derivate" (Chemistry of carbohydrates: monosaccharides and derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the $H^+$ form, depending on the type of reaction and/or reactants at reduced, normal, or elevated temperature, for example in the range from about $-100°$ C. to about 190° C., preferably from about $-80°$ C. to about 150° C., for example at about $-80$ to about 60° C., at room temperature, at about $-20$ to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., EtOAc, ethers, typically aliphatic ethers, e.g., $Et_2O$, or cyclic ethers, e.g., THF, liquid aromatic hydrocarbons, typically benzene or toluene, alcohols, typically MeOH, EtOH or 1-propanol, POH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

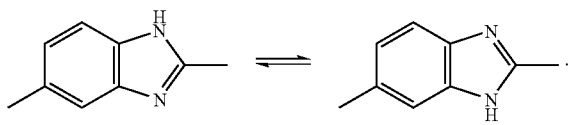

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, "Comprehensive Organic Transformations", VCH Publishers (1989); T. W. Greene and P. G. M. Wuts, "Protective Groups in Organic Synthesis", $3^{rd}$ edition, John Wiley and Sons (1999); L. Fieser and M. Fieser, "Fieser and Fieser's Reagents for Organic Synthesis", John Wiley and Sons (1994); A. Katritzky and A. Pozharski, "Handbook of Heterocyclic Chemistry", $2^{nd}$ edition (2001); M. Bodanszky, A. Bodanszky, "The Practice of Peptide Synthesis", Springer-Verlag, Berlin Heidelberg (1984); J. Seyden-Penne, "Reductions by the Alumino- and Borohydrides in Organic Synthesis", $2^{nd}$ edition, Wiley-VCH, (1997); and L. Paquette, editor, "Encyclopedia of Reagents for Organic Synthesis", John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

These detailed descriptions fall within the scope, and serve to exemplify, the above-described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company.

EXAMPLE 1

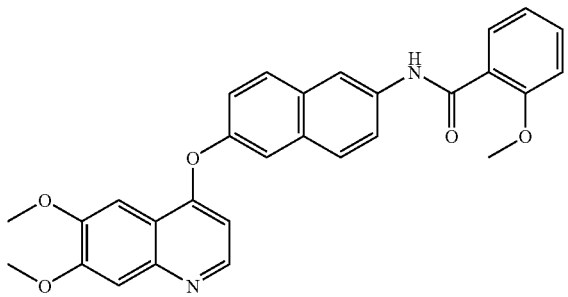

N-(6-((6,7-bis(Methoxy)-4-quinolinyl)oxy)-2-naphthalenyl)-2-(methoxy)benzamide

Step (a) Preparation of N-(6-hydroxy-(2-naphthyl))(benzyloxy)carboxamide

6-Hydroxy-2-naphthoic acid (30 g, 160 mmol, Aldrich), dppa (48.4 g, 176 mmol, Aldrich), benzyl alcohol (51.8 g, 480 mmol, Aldrich) and $Et_3N$ (32.3 g, 320 mmol, Aldrich) were heated at reflux with toluene (500 mL, Aldrich) for 16 h. After cooling to RT, the volatile portion was removed in vacuo. The resulting brown residue was purified by silica gel column chromatography (40% EtOAc/hexane) to give crude compound, which was further purified by crystallization from 50% EtOAc/Hexane to give the title compound as an off-white solid. MS (ESI, pos. ion) m/z: 294.2 (M+1). Mass Calc'd for $C_{18}H_{15}NO_3$: 293.11.

Step (b) Preparation of N-[6-(6,7-dimethoxy(4-quinolyloxy))(2-naphthyl)](phenylmethoxy)carboxamide 4-Chloro-6,7-dimethoxyquinoline (prepared by the method described in WO 03/33472) (223 mg, 1.0 mmol), N-(6-hydroxy-(2-naphthyl))(benzyloxy)carboxamide (Step a, 293 mg, 1.0 mmol) and DMAP (122 mg, 1.0 mmol, Aldrich) in toluene (5 mL, Aldrich) were microwaved (Personal Chemistry, Emrys Optimizer) at 180° C. for 2 h. After cooling to RT, the white precipitate was collected and purified by silica gel column chromatography (80% EtOAc/hexane) to give title compound as a white solid. MS (ESI, pos. ion) m/z: 481.3 (M+1). Mass Calc'd for $C_{29}H_{24}N_2O_5$: 480.17.

Step (c) Preparation of 6-(6,7-dimethoxy-4-quinolyloxy)-2-naphthylamine

A mixture of N-[6-(6,7-dimethoxy(4-quinolyloxy))(2-naphthyl)](phenylmethoxy)carboxamide (Step b, 170 mg, 0.35 mmol) and Pd/C (17 mg, 10%, Aldrich) in 60 mL of EtOAc was stirred at RT under $H_2$ balloon for 16 h. The mixture was filtered through a Celite® pad. The filtrate was concentrated in vacuo to give the title compound as an off-white solid. MS (ESI, pos. ion) m/z: 347.0 (M+1). Mass Calc'd for $C_{21}H_{18}N_2O_3$: 346.13.

Step (d) Preparation of N-(6-((6,7-bis(methoxy)-4-quinolinyl)oxy)-2-naphthalenyl)-2-(methoxy)benzamide To a mixture of 6-(6,7-dimethoxy-4-quinolyloxy)-2-naphthylamine (Step c, 34.6 mg, 0.1 mmol) and $K_2CO_3$ in dry $CH_2Cl_2$ (10 mL, Aldrich) was added 2-methoxybenzoyl chloride (25.5 mg, 0.15 mmol, Aldrich). The reaction was stirred at RT for 3 h. The volatile portion was removed in vacuo. To the residue was added 15 mL of MeOH and the mixture was stirred at RT for 30 min. The MeOH was removed in vacuo. The resulting residue was diluted in EtOAc (50 mL) and washed with water and brine. The organic phase was dried over $MgSO_4$ and concentrated. The resulting brown residue was purified by silica gel column chromatography (EtOAc) to give the title compound as a white solid. MS (ESI, pos. ion) m/z: 481.4 (M+1). Mass Calc'd for $C_{29}H_{24}N_2O_5$: 480.17.

EXAMPLE 2

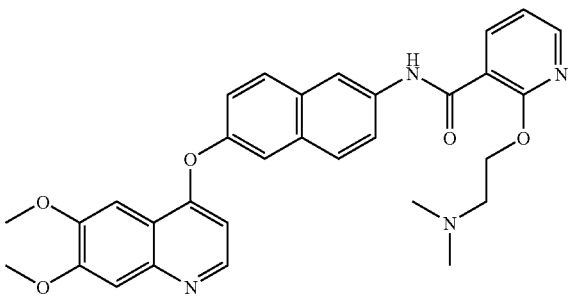

N-(6-((6,7-bis(Methoxy)-4-quinolinyl)oxy)-2-naphthalenyl)-2-((2-(dimethylamino)ethyl)oxy)-3-pyridinecarboxamide Step (a) Preparation of N-[6-((6,7-dimethoxy-4-quinolyl)oxy)(2-naphthyl)](2-fluoro-3-pyridyl)carboxamide 6-(6,7-Dimethoxy-4-quinolyloxy)-2-naphthylamine (69.2 mg, 0.2 mmol, Example 1c), 2-fluoropyridine-3-carboxylic acid (33.8 mg, 0.24 mmol, Maybridge), DIEA (31 mg, 0.24 mmol, Aldrich) and TBTU (91.2 mg, 0.24 mmol, Advanced ChemTech) were stirred in 6 mL of dry DMF at RT for 24 h. The solution was diluted with 50 mL of EtOAc and washed with saturated aqueous $NaHCO_3$ and brine. The organic layer was dried over $MgSO_4$ and concentrated. The residue was purified by silica gel column chromatography (EtOAc) to give title compound as a white solid. MS (ESI, pos. ion) m/z: 470.0 (M+1). Mass Calc'd for $C_{27}H_{20}FN_3O_4$: 469.14.

Step (b) Preparation of N-(6-((6,7-bis(methoxy)-4-quinolinyl)oxy)-2-naphthalenyl)-2-((2-(dimethylamino)ethyl)oxy)-3-pyridinecarboxamide To a mixture of N-[6-(6,7-dimethoxy-(4-quinolyloxy))(2-naphthyl)](2-fluoro-(3-pyridyl))carboxamide (Step a, 62 mg, 0.13 mmol) and $K_2CO_3$ (166 mg, 1.3 mmol) in dry NMP (5 mL, Aldrich) was added N,N-dimethylethanolamine (35 mg, 0.36 mmol, Aldrich) at RT. The reaction was stirred at 110° C. for 16 h. The mixture was cooled and diluted with 60 mL of EtOAc, then washed with water and brine. The organic phase was dried over MgSO₄ and concentrated. The residue was purified by prep-HPLC to give title compound as a white solid. MS (ESI, pos. ion) m/z: 539 (M+1). Mass Calc'd for $C_{31}H_{30}N_4O_5$: 538.22.

EXAMPLE 3

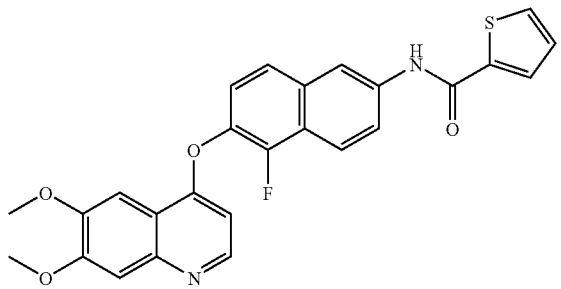

N-(6-((6,7-bis(Methoxy)-4-quinolinyl)oxy)-5-fluoro-2-naphthalenyl)-2-thiophenecarboxamide Step (a) Preparation of 6-bromo-1-fluoro-naphthalen-2-ol To a solution of 6-bromo-naphthalen-2-ol (5 g, 22.4 mmol, Aldrich) in dry DMF (50 mL, Aldrich) was added N-fluorobenzene sulfonimide (21.9 g, 67.2 mmol, Aldrich). The reaction was stirred at RT for 48 h. The volatile portion was removed in vacuo and the residue was purified by silica gel chromatography (CHCl₃) to give title compound as a yellow solid. MS (ESI, neg. ion) m/z: 240.0 (M−1). Mass Calc'd for $C_{10}H_6BrFO$: 239.96.

Step (b) Preparation of 2-(6,7-dimethoxy-4-quinolyloxy)-6-bromo-1-fluoronaphthalene A mixture of 4-chloro-6,7-dimethoxy-quinoline (prepared as in Example 1, Step b)(371 mg, 1.66 mmol), 6-bromo-1-fluoro-naphthalen-2-ol (Step a, 400 mg, 1.66 mmol) and DMAP (203 mg, 1.66 Aldrich) in toluene (in a microwave tube) was heated in a microwave oven (Personal Chemistry, Emrys Optimizer) at 180° C. for 2 h. The mixture was cooled to RT and diluted with 30 mL of EtOAc. The solution was washed with 10 mL of brine twice, dried over Na₂SO₄ and concentrated in vacuo. The residue was further purified with silica gel column chromatography (40-100% EtOAc in hexanes) to give title compound as a white solid. MS (ESI, pos. ion) m/z: 428.0 (M+1). Mass Calc'd for $C_{21}H_{15}BrFNO_3$: 427.02.

Step (c) Preparation of 6-(6,7-dimethoxy-4-quinolyloxy)-5-fluoro-2-naphthylamine A mixture of 2-(6,7-dimethoxy-4-quinolyloxy)-6-bromo-1-fluoronaphthalene (Step b, 1.7 g, 4.0 mmol), Pd₂(dba)₃ (183 mg, 0.2 mmol, Aldrich) and P(t-Bu)₃ (40 mg, 0.2 mmol, Aldrich) in a two-necked round-bottom flask was degassed under vacuum and refilled with N₂. Under N₂, dry toluene and LiHMDS (5 mL, 1M in THF, 5.0 mmol, Aldrich) was added to the mixture via syringe. The reaction was stirred at RT under N₂ for 16 h. To the reaction was added 1N aqueous HCl (10 mL) and a yellow precipitate was collected by filtration. The solid was washed with 10 mL of water and dried in vacuo at 50° C. for 24 h to give title compound as HCl salt in the form of yellow solid. MS (ESI, pos. ion) m/z: 365 (M+1). Mass Calc'd for $C_{21}H_{17}FN_2O_3$: 364.12.

Step (d) Preparation of N-(6-((6,7-bis(methoxy)-4-quinolinyl)oxy)-5-fluoro-2-naphthalenyl)-2-thiophenecarboxamide To a solution of 6-(6,7-dimethoxy-4-quinolyloxy)-5-fluoro-2-naphthylamine 2HCl (Step c, 200 mg, 0.46 mmol), thiophene-2-carboxylic acid (120 mg, 0.91 mmol, Aldrich) and DIEA (353 mg, 2.74 mmol, Aldrich) in dry DMF was added PyBOP (476 mg, 0.91 mmol, Fluka) at RT. The reaction was stirred for 16 h. It was diluted with 40 mL of EtOAc and washed with saturated aqueous NaHCO₃, followed by brine. The organic phase was dried over Na₂SO₄ and concentrated in vacuo. The residue was purified by silica gel column chromatography (EtOAc) to give the title compound as a yellow solid. MS (ESI, pos. ion) m/z: 475.0 (M+1). Mass Calc'd for $C_{26}H_{19}FN_2O_4S$: 474.10.

EXAMPLE 4

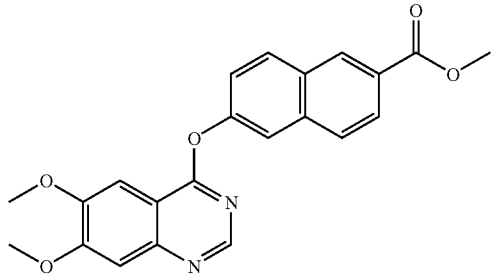

Methyl 6-((6,7-bis(methoxy)-4-quinazolinyl) oxy)-2-naphthalenecarboxylate

Step (a) Preparation of 6-hydroxy-naphthalene-2-carboxylic Acid Methyl Ester

Through a solution of 6-hydroxynaphthalene-2-carboxylic acid (4.87 g, 26 mmol, Aldrich) in MeOH (100 mL, Aldrich) was bubbled HCl gas for 1 h. The resulting mixture was stirred for 10 h at RT. The solution was concentrated in vacuo to give the title compound as a pink powder. MS (ESI, pos. ion) m/z: 203 (M+1). Mass Calc'd for $C_{12}H_{10}O_3$: 202.06.

Step (b)

Preparation of methyl 6-((6,7-bis(methoxy)-4-quinazolinyl)oxy)-2-naphthalenecarboxylate To a stirred mixture of NaH (200 mg, 60% in mineral oil, 5.0 mmol, Aldrich) in 10 mL of DMF at RT was added 6-hydroxy-naphthalene-2-carboxylic acid methyl ester (Step a, 675 mg, 3.34 mmol). After 20 min, 4-chloro-6,7-dimethoxy-quinazoline (750 mg, 3.34 mmol, Oakwood) was added and the reaction was heated to 60° C. for 20 min. The reaction was cooled to RT, quenched with saturated aqueous NH₄Cl solution (30 mL) and extracted with CHCl₃ (30 mL). The organic solution was washed with brine, dried over Na₂SO₄ and concentrated in vacuo. The residue was purified by column chromatography (30% EtOAc/hexane) to give the title compound as a white solid. MS (ESI, pos. ion) m/z: 390.9 (M+1). Mass Calc'd for $C_{22}H_{18}N_2O_5$: 390.12.

EXAMPLE 5

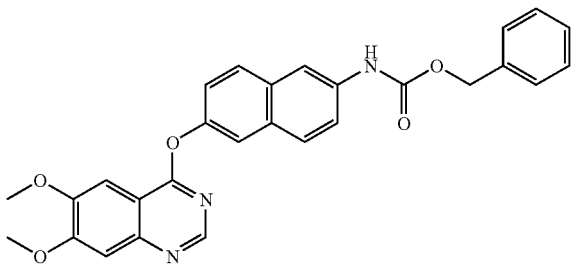

Phenylmethyl 6-((6,7-bis(methoxy)-4-quinazolinyl)oxy)-2-naphthalenylcarbamate

N-(6-Hydroxy-2-naphthyl)(phenylmethoxy)carboxamide (180 mg, 0.61 mmol, Example 1a) was reacted with 4-chloro-6,7-dimethoxy-quinazoline (140 mg, 0.61 mmol, Oakwood) under the conditions of Example 4b to give the title compound as a white solid. MS (ESI, pos. ion) m/z: 482.5 (M+1). Mass Calc'd for $C_{28}H_{23}N_3O_5$: 481.16.

EXAMPLE 6

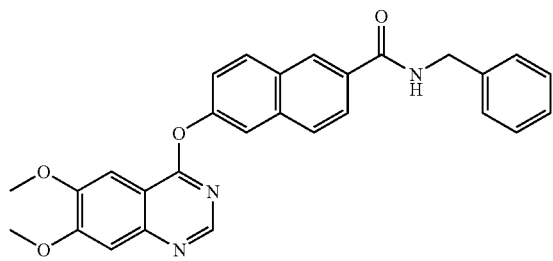

6-((6,7-bis(Methoxy)-4-quinazolinyl)oxy)-N-(phenylmethyl)-2-naphthalenecarboxamide Step (a) Preparation of (6-hydroxy(2-naphthyl))-N-benzylcarboxamide A solution of 6-hydroxy-naphthalene-2-carboxylic acid (2.0 g, 10.6 mmol, Aldrich) and benzylamine (1.7 g, 15.9 mmol, Aldrich) in DMF (40 mL, Aldrich) at 0° C. was added EDC (3.05 g, 15.9 mmol, Aldrich). The reaction was warmed to RT and stirred for 16 h. The volatile portion was removed in vacuo. The residue was diluted with 100 mL of EtOAc and washed with saturated aqueous $NaHCO_3$ and brine. The organic layer was dried over $Na_2SO_4$ and concentrated in vacuo. The residue was dissolved in EtOAc and passed through a short silica gel column and the filtrate was concentrated in vacuo. Recrystallization with 50% EtOAc/hexane provided the title compound as a white solid.

Step (b) Preparation of 6-((6,7-bis(methoxy)-4-quinazolinyl)oxy)-N-(phenylmethyl)-2-naphthalenecarboxamide 6-Hydroxy(2-naphthyl))-N-benzylcarboxamide (Step a, 500 mg, 1.8 mmol) was reacted with 4-chloro-6,7-dimethoxy-quinazoline (400 mg, 1.8 mmol, Oakwood) under the conditions of Example 4b to give the title compound as a white solid. MS (ESI, pos. ion) m/z: 466.2 (M+1). Mass Calc'd for $C_{28}H_{23}N_3O_4$: 465.17.

EXAMPLE 7

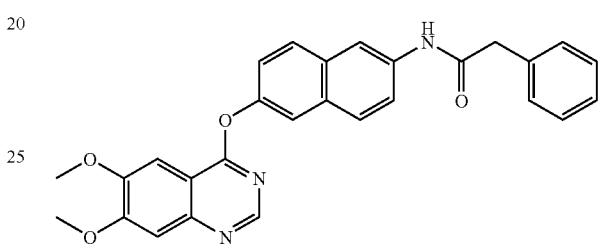

N-(6-((6,7-bis(Methoxy)-4-7 quinazolinyl)oxy)-2-naphthalenyl)-2-phenylacetamide

Step (a) Preparation of 6-aminonaphthalen-2-ol

N-(6-Hydroxy-2-naphthyl)(phenylmethoxy)carboxamide (600 mg, 2.0 mmol) was reacted under conditions of Example 1c to give the title compound as a light yellow solid. MS (ESI, pos. ion) m/z: 160.3 (M+1). Mass Calc'd for $C_{10}H_9NO$: 159.07.

Step (b) Preparation of N-(6-hydroxy-2-naphthyl)-2-phenylacetamide

The 6-aminonaphthalen-2-ol from Step (a) above (320 mg, 2.0 mmol) reacted with phenylacetyl chloride (683 mg, 4.4 mmol, Aldrich) under the conditions of Example 1d to give the title compound as a white solid. MS (ESI, pos. ion) m/z: 278.3 (M+1). Mass Calc'd for $C_{18}H_{15}NO_2$: 277.11.

Step (c) Preparation of N-(6-((6,7-bis(methoxy)-4-quinazolinyl)oxy)-2-naphthalenyl)-2-phenylacetamide N-(6-Hydroxy-2-naphthyl)-2-phenylacetamide from step (b) above (260 mg, 0.9 mmol) reacted with 4-chloro-6,7-dimethoxy-quinazoline (210 mg, 0.9 mmol, Oakwood) under the conditions of Example 4b to give the title compound as a white solid. MS (ESI, pos. ion) m/z: 466.2 (M+1). Mass Calc'd for $C_{28}H_{23}N_3O_4$: 465.17.

EXAMPLE 8

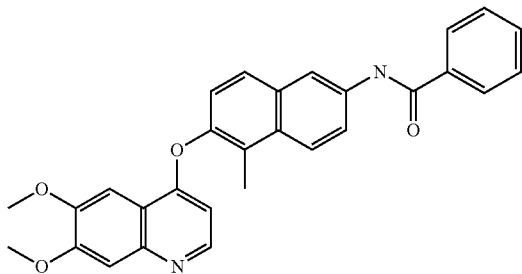

N-[6-(6,7-Dimethoxy-quinolin-4-yloxy)-5-methyl-naphthalen-2-yl]-benzamide

Step (a) Preparation of (6-hydroxy-5-methyl-naphthalen-2-yl)-carbamic acid benzyl ester To a mixture containing 6-hydroxy-5-methyl-naphthalene-2-carboxylic acid (3.42 g, 12.7 mmol), was added dppa (3 mL, 14.0 mmol) and Et$_3$N (3.5 mL, 25.4 mmol) in 50 mL of toluene. After stirring for 10 min, benzyl alcohol (3.9 mL, 38.1 mmol) was added to the mixture and heated at reflux for 4 h. The crude was purified by silica-gel column chromatography in EtOAc/Hexanes to give the titled compound as brown solid. MS (ESI neg. ion) m/z: 306 (M−H). Mass Calc'd for $C_{19}H_{17}NO_3$: 307.12.

Step (b) Preparation of 6-(6,7-dimethoxy-quinolin-4-yloxy)-5-methyl-naphthalen-2-ylamine (6-Hydroxy-5-methyl-naphthalen-2-yl)-carbamic acid benzyl ester (Step a, 0.300 g, 0.9 mmol), 4-chloro-6,7-dimethoxy-quinoline (0.218 g, 0.9 mmol), K$_2$CO$_3$ (0.124 g, 0.9 mmol), and copper (4% by wt.) were added to a vial, then microwaved for 30 min at 120° C. with 150 watts of power (Powermax, CEM). The mixture was diluted with CH$_2$Cl$_2$ and 40 mL of 1N NaOH, then extracted the organics 3 times with CH$_2$Cl$_2$. The organics were combined, dried over Na$_2$SO$_4$, filtered, and concentrated in vacuo. The crude was crystallized from CH$_2$Cl$_2$/Hexanes to give a light brown solid, which was the titled compound. MS (ESI, pos. ion) m/z: 361 (M+1). Mass Calc'd for $C_{22}H_{20}N_2O_3$: 360.15.

Step (c) Preparation of N-[6-(6,7-dimethoxy-quinolin-4-yloxy)-5-methyl-naphthalen-2-yl]-benzamide 6-(6,7-Dimethoxy-quinolin-4-yloxy)-5-methyl-naphthalen-2-ylamine (Step b, 0.100 g, 0.2 mmol), benzoyl chloride (0.04 mL, 0.3 mmol) and K$_2$CO$_3$ (0.116 g, 0.6 mmol) in CH$_2$Cl$_2$ were stirred overnight under inert atmosphere. The reaction was quenched with water and diluted with CH$_2$Cl$_2$. The aqueous layer was extracted 3 times with CH$_2$Cl$_2$. The organics were collected, dried over Na$_2$SO$_4$, filtered, and concentrated in vacuo. The crude was purified by silica-gel column chromatography in EtOAc/Hexanes to give the titled compound as a rust colored film. MS (ESI, pos. ion) m/z: 465 (M+1). Mass Calc'd for $C_{29}H_{24}N_2O_4$: 464.17.

EXAMPL 9

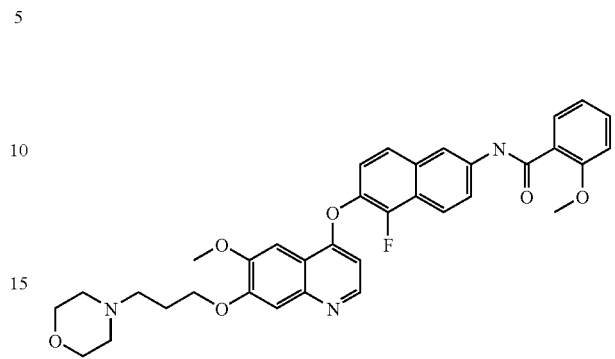

N-{5-Fluoro-6-[6-methoxy-7-(3-morpholin-4-yl-propoxy)-quinolin-4-yloxy]-naphthalen-2-yl}-2-methoxy-benzamide Step (a) Preparation of 4-(6-bromo-1-fluoro-naphthalen-2-yloxy)-6-methoxy-7-(3-morpholin-4-yl-propoxy)-quinoline A mixture of 4-chloro-6-methoxy-7-(3-morpholin-4-yl-propoxy)-quinoline (prepared as described in WO 03/33472) (0.465 mg, 1.93 mmol), 6-bromo-1-fluoro-naphthalen-2-ol (Example 3a) (0.65 mg, 1.93 mmol) and DMAP (0.235 mg, 1.93 mmol, Aldrich) in toluene (in a microwave tube) was heated in a microwave oven (Personal Chemistry, Emrys Optimizer) at 180° C. for 2 h. The mixture was cooled to RT and diluted with 30 mL of EtOAc. The solution was washed with brine (2×10 mL), dried over Na$_2$SO$_4$ and concentrated in vacuo. The residue was further purified with silica gel column chromatography (40% to 100% EtOAc in hexanes) to give the title compound as an orange foam. MS (ESI, pos. ion) m/z: 541.1 (M+1). Mass Calc'd for $C_{27}H_{26}BrFN_2O_4$: 540.11.

Step (b) Preparation of 5-fluoro-6-[6-methoxy-7-(3-morpholin-4-yl-propoxy)-quinolin-4-yloxy]-naphthalen-2-ylamine HCl 4-(6-Bromo-1-fluoro-naphthalen-2-yloxy)-6-methoxy-7-(3-morpholin-4-yl-propoxy)-quinoline (Step a, 0.64 g, 1.17 mmol) was reacted under the conditions of Example 3c to afford a red solid. MS (ESI, pos. ion) m/z: 478.2 (M+1). Mass Calc'd for $C_{27}H_{28}FN_3O_4$: 477.21.

Step (c) Preparation of N-{5-fluoro-6-[6-methoxy-7-(3-morpholin-4-yl-propoxy)-quinolin-4-yloxy]-naphthalen-2-yl}-2-methoxy-benzamide 5-Fluoro-6-[6-methoxy-7-(3-morpholin-4-yl-propoxy)-quinolin-4-yloxy]-naphthalen-2-ylamine (Step b, 0.2 g, 0.34 mmol) was reacted under the conditions of Example 3d to afford a yellow solid. MS (ESI, pos. ion) m/z: 611.7 (M+1). Mass Calc'd for $C_3H_{34}FN_3O_6$: 611.24.

EXAMPLE 10

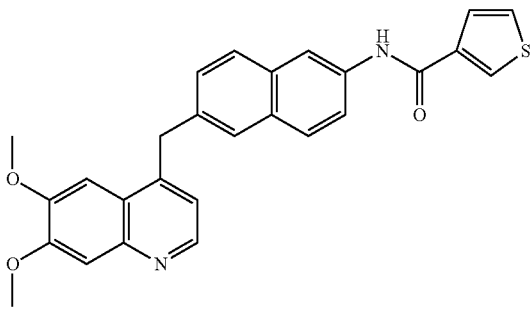

N-(6-((6,7-bis(Methoxy)-4-quinolinyl)methyl)-2-naphthalenyl)-3-thiophenecarboxamide

Step (a) Preparation of 6,7-dimethoxy-4-phenylsulfanyl-quinoline

To a solution of 4-chloro-6,7-dimethoxy-quinoline (214 mg, 0.96 mmol) in EtOH (10 mL) and H$_2$O (10 mL), was added KOH (107 mg, 1.44 mmol). The solution was stirred in a 100° C. bath. Then thiophenol (148 μL, 1.44 mmol) was added. The reaction was stirred at 100° C. for 1 h. The solvent was removed by rotary evaporation. The resulting residue was worked up with water and extracted with EtOAc 3×. The combined organic layer was washed with water and brine, dried over Na$_2$SO$_4$, filtered, and concentrated in vacuo. The crude material was purified by silica gel prep-TLC with 100% EtOAc to give the titled compound. MS (ESI, pos. ion) m/z: 298.1 (M+1).

Step (b) Preparation of 4-benzenesulfinyl-6,7-dimethoxy-quinoline

To a solution of 6,7-dimethoxy-4-phenylsulfanyl-quinoline (Step a, 1.0 g, 3.4 mmol) in CH$_2$Cl$_2$ (30 mL) at −78° C., 3-chloroperoxybenzoic acid (0.64 g, 3.7 mmol) was added in CH$_2$Cl$_2$ dropwise slowly. The reaction was stirred at −78° C. for 2 h. The solution was poured into saturated NaHCO$_3$ and extracted with CH$_2$Cl$_2$ 3×. The combined organic layer was washed with saturated NaHCO$_3$, water and brine, dried over Na$_2$SO$_4$, filtered and concentrated in vacuo. The crude material was purified by silica gel column chromatography with (70-100% EtOAc/Hexane) to give the titled compound as a white solid. MS (ESI, pos. ion) m/z: 314.4 (M+1).

Step (c) Preparation of 6-bromo-naphthalene-2-carboxylic acid methoxy-methyl-amide To a suspension of 6-bromo-naphthalene-2-carboxylic acid (0.6 g, 2.4 mmol) and O,N-dimethyl-hydroxylamine (0.28 g, 2.87 mmol) in CH$_2$Cl$_2$ (20 mL), was added EDC (0.55 g, 2.87 mmol), HOBt (0.39 g, 2.87 mmol) and TEA (0.66 mL, 4.8 mmol). The reaction was stirred at RT overnight. The solvent was removed in vacuo and the crude material was purified by silica gel column chromatography with (20-40% EtOAc/hexane) to give the titled compound as a white solid. MS (ESI, pos. ion) m/z: 294.0 (M+1).

Step (d) Preparation of 6-bromo-naphthalene-2-carbaldehyde

To a solution of 6-bromo-naphthalene-2-carboxylic acid methoxy-methyl-amide (Step c, 6.3 g, 21.4 mmol) in THF (200 mL) at −78° C., DIBAL (1M in THF, 25.7 mL, 25.7 mmol) was added. The mixture was stirred at −78° C. for 10 min, warmed to RT and stirred for 2 h. The reaction was poured into 1N HCl and extracted with EtOAc 3×. The combined organic layer was washed with water and brine, dried over Na$_2$SO$_4$, filtered and concentrated in vacuo. The crude was purified by silica gel column chromatography with (5-20% EtOAc/hexane) to give the titled compound as a white solid. MS (ESI, pos. ion) m/z: 236.0 (M+1).

Step (e) Preparation of (6-bromo-naphthalen-2-yl)-(6,7-dimethoxy-quinolin-4-yl)-methanol To a solution of 4-benzenesulfinyl-6,7-dimethoxy-quinoline (step b, 1 g, 3.2 mmol) in THF (15 mL) at −10° C., was added phenylmagnesium bromide (1M in THF, 3.5 mL, 3.5 mmol). The reaction was warmed to RT and stirred for 20 min. 6-Bromo-naphthalene-2-carbaldehyde (Step d, 0.75 g, 3.2 mmol) was added in THF. The resulting mixture was stirred at RT for 2 h, then poured into saturated NH$_4$Cl solution and extracted with ethyl acetate 3×. The combined organic layer was washed with brine, dried over Na$_2$SO$_4$, filtered and concentrated in vacuo. The crude was purified by silica gel column chromatography (15-35% acetone/CH$_2$Cl$_2$) to give the titled compound. MS (ESI, pos. ion) m/z: 424.1 (M+1).

Step (f) Preparation of 4-(6-bromo-naphthalen-2-ylmethyl)-6,7-dimethoxy-quinoline To a solution of (6-bromo-naphthalen-2-yl)-(6,7-dimethoxy-quinolin-4-yl)-methanol (Step e, 0.55 g, 1.3 mmol) in formic acid (10 mL), was added Zn dust (500 mg, 7.6 mmol). The suspension was heated at reflux for 6 h and the solvent was removed in vacuo. The resulting residue was worked up with 1N NaOH and extracted with CH$_2$Cl$_2$ 3×. The combined organic layer was washed with water and brine, dried over Na$_2$SO$_4$, filtered and concentrated in vacuo. The crude was purified with silica gel column chromatography (40-65% EtOAc/Hexane) to give the titled compound. MS (ESI, pos. ion) m/z: 408.1 (M+1).

Step (g) Preparation of 6-(6,7-dimethoxy-quinolin-4-ylmethyl)-naphthalen-2-ylamine To a sealed tube, 4-(6-bromo-naphthalen-2-ylmethyl)-6,7-dimethoxy-quinoline (Step f, 100 mg, 0.11 mmol), Pd$_2$(dba)$_3$ (5 mg, 0.0055 mmol), P(t-Bu)$_3$ (1.1 mg, 0.0055 mmol), toluene (1 mL) was combined under nitrogen, followed by addition of LiHMDS (1M in THF, 0.137 mL, 0.137 mmol). The reaction was stirred at RT overnight. The suspension was diluted with Et$_2$O and HCl (1M, 1 mL) was added. The crude material was poured into 1N NaOH and extracted with Et$_2$O 3×. The combined organic layer was washed with water and brine, dried on Na$_2$SO$_4$, filtered, concentrated and purified by prep-TLC with 100% EtOAc to give the desired compound. MS (ESI, pos. ion) m/z: 345.1 (M+1).

Step (h) Preparation of N-(6-((6,7-bis(Methoxy)-4-quinolinyl)methyl)-2-naphthalenyl)-3-thiophenecarboxamide To a solution of 6-(6,7-dimethoxy-quinolin-4-ylmethyl)-naphthalen-2-ylamine (Step g, 36 mg, 0.10 mmol) and 3-thiophenecarboxylic acid (15 mg, 0.115 mmol) in CH$_2$Cl$_2$ (1 mL), was added PyBop (163 mg, 0.314 mmol) and Et$_3$N (44 μL, 0.314 mmol). The mixture was stirred at RT overnight. The solvent was evaporated and the crude material was purified by Prep-TLC with EtOAc/CH$_2$Cl$_2$ (3:2) to give the desired product. MS (ESI, pos. ion) m/z: 455.1 (M+1). Calc'd for C$_{27}$H$_{22}$N$_2$O$_3$S: 454.14.

The following Examples were prepared similar to the procedures described in either Example 1 or Example 2.

| Ex. No. | Structure & Name | Mol Formula | Mass | M + H | Proc. No. |
|---|---|---|---|---|---|
| 11 | 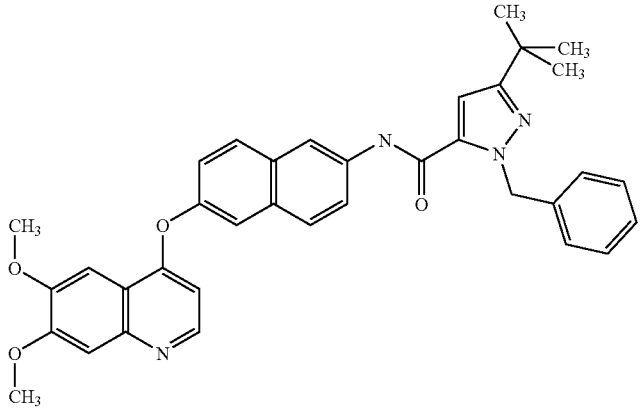<br>N-(6-((6,7-bis(methoxy)-4-quinolinyl)oxy)-2-naphthalenyl)-3-(1,1-dimthylethyl)-1-(phenylmethyl)-1H-pyrazole-5-carboxamide | C$_{36}$H$_{34}$N$_4$O$_4$ | 586.26 | 587.8 | 1 |
| 12 | 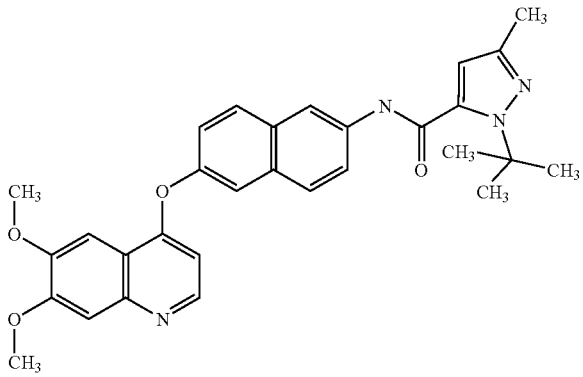<br>N-(6-((6,7-bis(methoxy)-4-quinolinyl)oxy)-2-naphthalenyl)-1-(1,1-dimethylethyl)-3-methyl-1H-pyrazole-5-carboxamide | C$_{30}$H$_{30}$N$_4$O$_4$ | 510.23 | 511.6 | 1 |
| 13 | 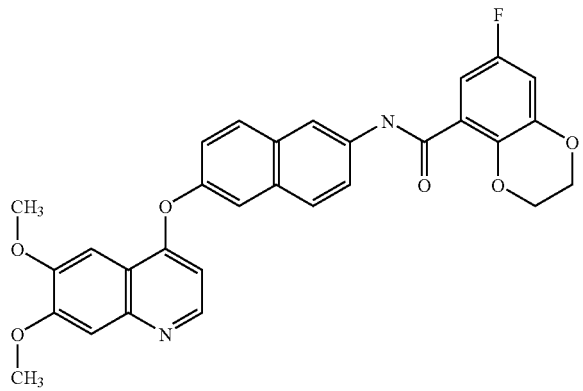<br>N-(6-((6,7-bis(methoxy)-4-quinolinyl)oxy)-2-naphthalenyl)-7-fluoro-2,3-dihydro-1,4-benzodioxine-5-carboxamide | C$_{30}$H$_{23}$FN$_2$O$_6$ | 526.15 | 527.3 | 1 |

| Ex. No. | Structure & Name | Mol Formula | Mass | M + H | Proc. No. |
|---|---|---|---|---|---|
| 14 | 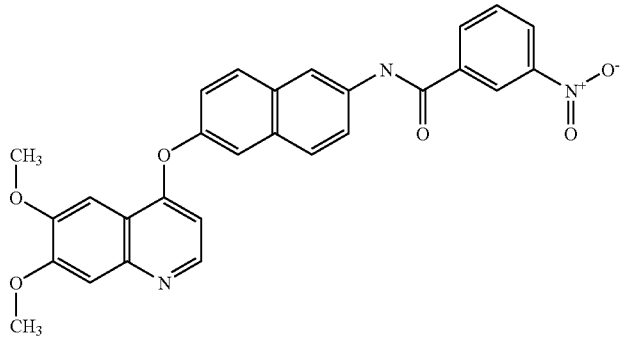<br>N-(6-((6,7-bis(methoxy)-4-quinolinyl)oxy)-2-naphthalenyl)-3-nitrobenzamide | C₂₈H₂₁N₃O₆ | 495.14 | 496.6 | 1 |
| 15 | 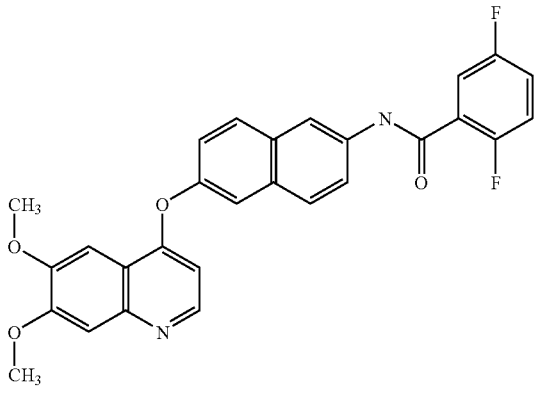<br>N-(6-((6,7-bis(methoxy)-4-quinolinyl)oxy)-2-naphthalenyl)-2,5-difluorobenzamide | C₂₈H₂₀F₂N₂O₄ | 486.14 | 487.6 | 1 |
| 16 | 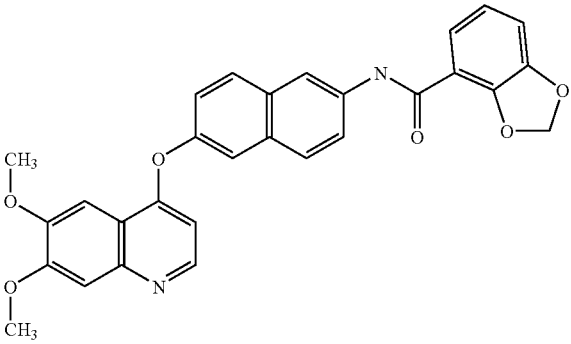<br>N-(6-((6,7-bis(methoxy)-4-quinolinyl)oxy)-2-naphthalenyl)-1,3-benzodioxole-4-carboxamide | C₂₉H₂₂N₂O₆ | 494.15 | 495.3 | 1 |
| 17 | 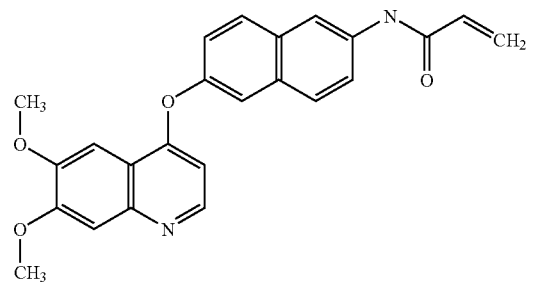<br>N-(6-((6,7-bis(methoxy)-4-quinolinyl)oxy)-2-naphthalenyl)-2-propenamide | C₂₄H₂₀N₂O₄ | 400.14 | 401.2 | 1 |

-continued

| Ex. No. | Structure & Name | Mol Formula | Mass | M + H | Proc. No. |
|---|---|---|---|---|---|
| 18 | 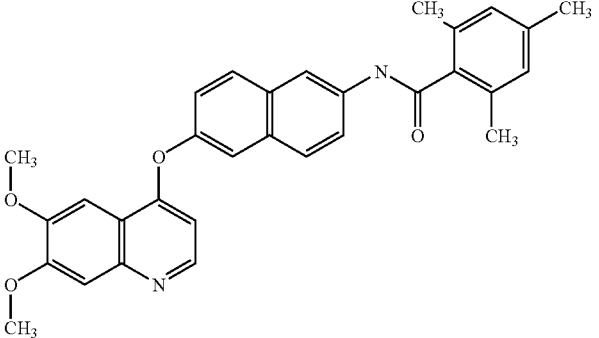<br>N-(6-((6,7-bis(methoxy)-4-quinolinyl)oxy)-2-naphthalenyl)-2,4,6-trimethylbenzamide | $C_{31}H_{28}N_2O_4$ | 492.20 | 493.6 | 1 |
| 19 | 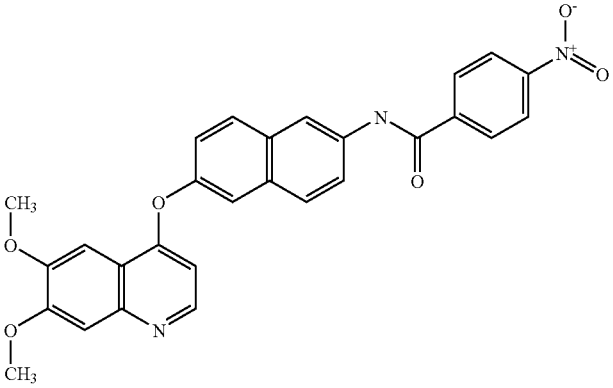<br>N-(6-((6,7-bis(methoxy)-4-quinolinyl)oxy)-2-naphthalenyl)-4-nitrobenzamide | $C_{28}H_{21}N_3O_6$ | 495.14 | 496.6 | 1 |
| 20 | 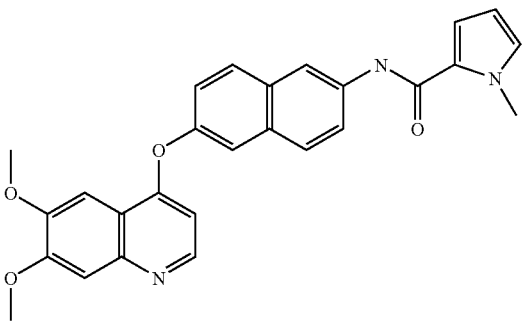<br>N-(6-((6,7-bis(methoxy)-4-quinolinyl)oxy)-2-naphthalenyl)-1-methyl-1H-pyrrole-2-carboxamide | $C_{27}H_{23}N_3O_4$ | 453.17 | 454.6 | 1 |
| 21 | 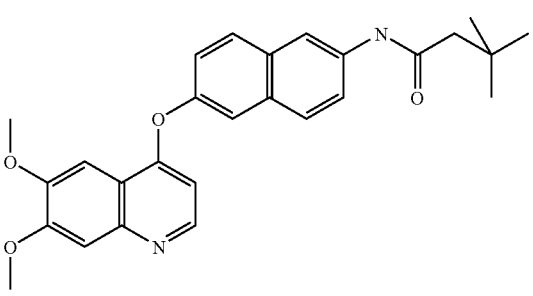<br>N-(6-((6,7-bis(methoxy)-4-quinolinyl)oxy)-2-naphthalenyl)-3,3-dimethylbutanamide | $C_{27}H_{28}N_2O_4$ | 444.20 | 445.4 (M + 1) | 1 |

| Ex. No. | Structure & Name | Mol Formula | Mass | M + H | Proc. No. |
|---|---|---|---|---|---|
| 22 | N-(6-((6,7-bis(methoxy)-4-quinolinyl)oxy)-2-naphthalenyl)-2,4-bis(methoxy)benzamide | $C_{30}H_{26}N_2O_6$ | 510.18 | 511 | 1 |
| 23 | N-(6-((6,7-bis(methoxy)-4-quinolinyl)oxy)-2-naphthalenyl)-2,6-bis(methoxy)benzamide | $C_{30}H_{26}N_2O_6$ | 510.18 | 511 | 1 |
| 24 | N-(6-((6,7-bis(methoxy)-4-quinolinyl)oxy)-2-naphthalenyl)-5-fluoro-2-(methoxy)benzamide | $C_{29}H_{23}F_2N_2O_5$ | | 499 | 1 |
| 25 | N-(6-((6,7-bis(methoxy)-4-quinolinyl)oxy)-2-naphthalenyl)cyclopentanecarboxamide | $C_{27}H_{26}N_2O_4$ | 442.19 | 443.5 (M + 1) | 1 |

| Ex. No. | Structure & Name | Mol Formula | Mass | M + H | Proc. No. |
|---|---|---|---|---|---|
| 26 | 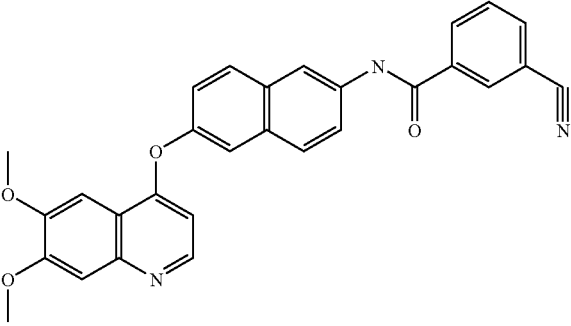<br>N-(6-((6,7-bis(methoxy)-4-quinolinyl)oxy)-2-naphthalenyl)-3-cyanobenzamide | $C_{29}H_{21}N_3O_4$ | 475.15 | 476.5 (M + 1) | 1 |
| 27 | 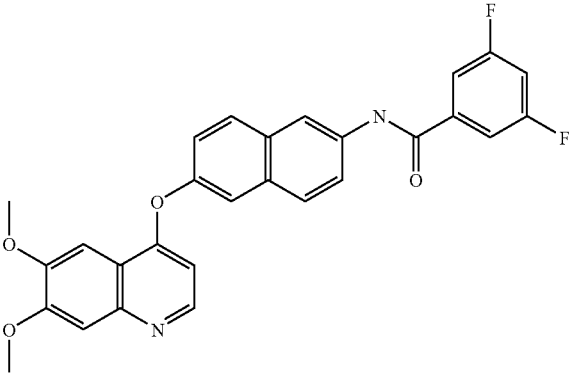<br>N-(6-((6,7-bis(methoxy)-4-quinolinyl)oxy)-2-naphthalenyl)-3,5-difluorobenzamide | $C_{28}H_{20}F_2N_2O_4$ | 486.14 | 487.2 (M + 1) | 1 |
| 28 | 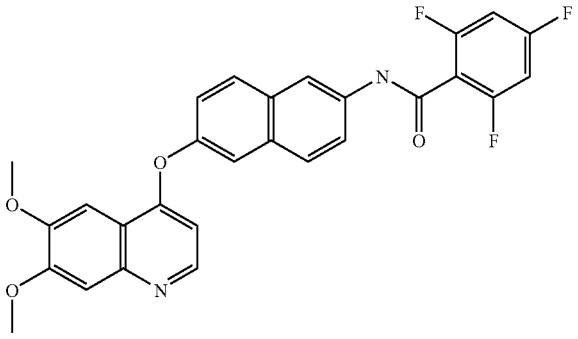<br>N-(6-((6,7-bis(methoxy)-4-quinolinyl)oxy)-2-naphthalenyl)-2,4,6-trifluorobenzamide | $C_{28}H_{19}F_3N_2O_4$ | 504.13 | 505.7 (M + 1) | 1 |
| 29 | 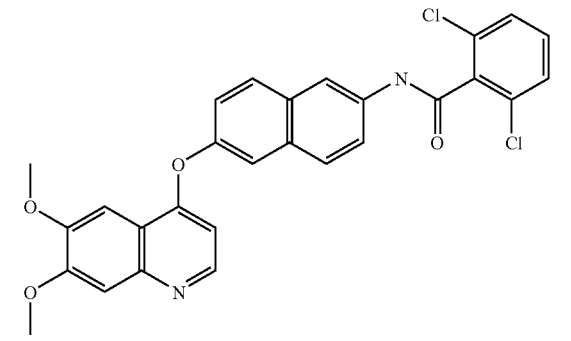<br>N-(6-((6,7-bis(methoxy)-4-quinolinyl)oxy)-2-naphthalenyl)-2,6-dichlorobenzamide | $C_{28}H_{20}Cl_2N_2O_4$ | 518.08 | 520.1 (M + 2) | 1 |

-continued

| Ex. No. | Structure & Name | Mol Formula | Mass | M + H | Proc. No. |
|---|---|---|---|---|---|
| 30 | 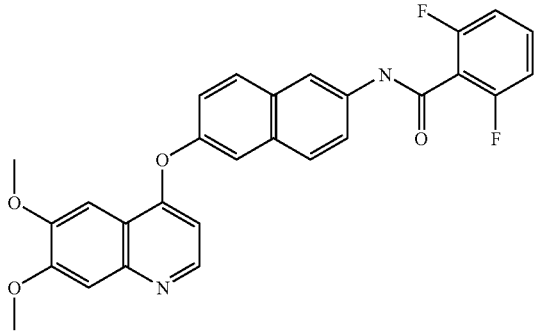<br>N-(6-((6,7-bis(methoxy)-4-quinolinyl)oxy)-2-naphthalenyl)-2,6-difluorobenzamide | $C_{28}H_{20}F_2N_2O_4$ | 486.14 | 487.5 (M + 1) | 1 |
| 31 | 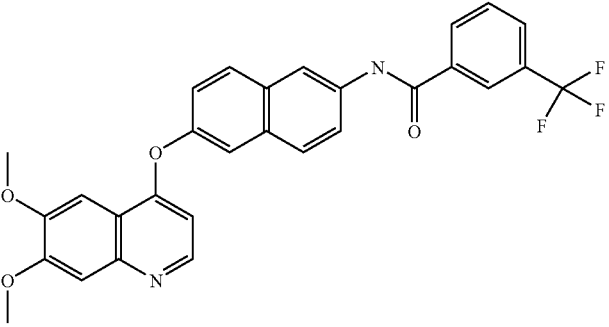<br>N-(6-((6,7-bis(methoxy)-4-quinolinyl)oxy)-2-naphthalenyl)-3-(trifluoromethyl)benzamide | $C_{29}H_{21}F_3N_2O_4$ | 518.15 | 519.4 (M + 1) | 1 |
| 32 | 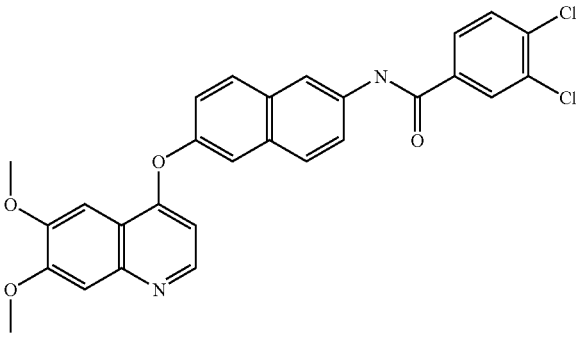<br>N-(6-((6,7-bis(methoxy)-4-quinolinyl)oxy)-2-naphthalenyl)-3,4-dichlorobenzamide | $C_{28}H_{20}Cl_2N_2O_4$ | 518.08 | 520.5 | 1 |
| 33 | 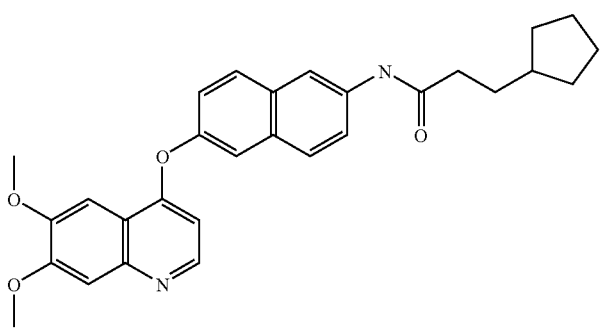<br>N-(6-((6,7-bis(methoxy)-4-quinolinyl)oxy)-2-naphthalenyl)-3-cyclopentylpropanamide | $C_{29}H_{30}N_2O_4$ | 470.22 | 471.6 (M + 1) | 1 |

-continued

| Ex. No. | Structure & Name | Mol Formula | Mass | M + H | Proc. No. |
|---|---|---|---|---|---|
| 34 | 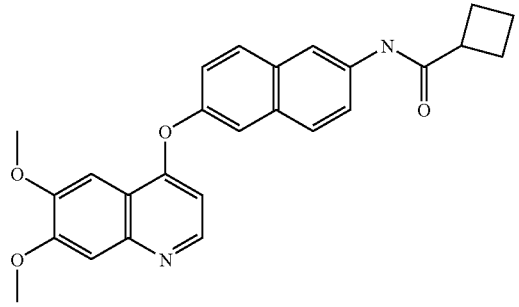 N-(6-(((6,7-bis(methoxy)-4-quinolinyl)oxy)-2-naphthalenyl)cyclobutanecarboxamide | $C_{26}H_{24}N_2O_4$ | 428.17 | 429.5 (M + 1) | 1 |
| 35 | 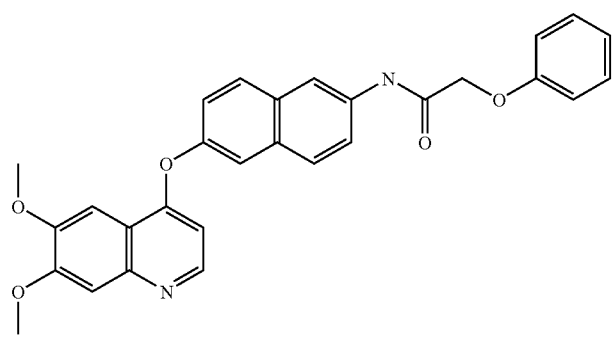 N-(6-(((6,7-bis(methoxy)-4-quinolinyl)oxy)-2-naphthalenyl)-2-(phenyloxy)acetamide | $C_{29}H_{24}N_2O_5$ | 480.17 | 481.5 (M + 1) | 1 |
| 36 | 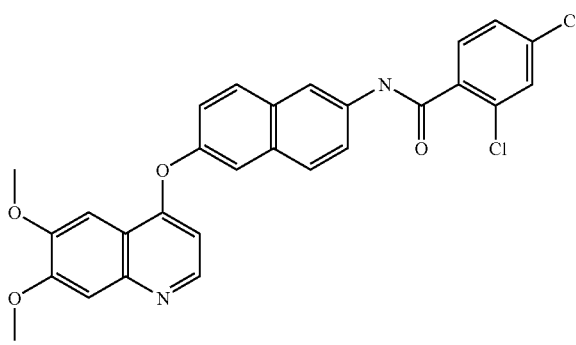 N-(6-(((6,7-bis(methoxy)-4-quinolinyl)oxy)-2-naphthalenyl)-2,4-dichlorobenzamide | $C_{28}H_{20}Cl_2N_2O_4$ | 518.08 | 520.3 (M + 2) | 1 |
| 37 | 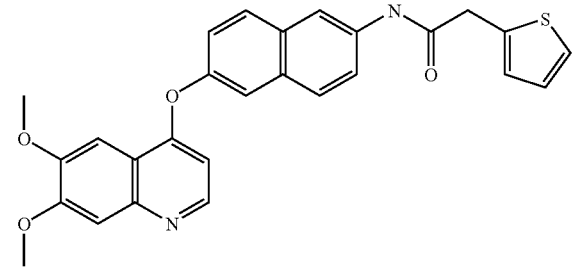 N-(6-(((6,7-bis(methoxy)-4-quinolinyl)oxy)-2-naphthalenyl)-2-(2-thienyl)acetamide | $C_{27}H_{22}N_2O_4S$ | 470.13 | 471.6 (M + 1) | 1 |

| Ex. No. | Structure & Name | Mol Formula | Mass | M + H | Proc. No. |
|---|---|---|---|---|---|
| 38 | 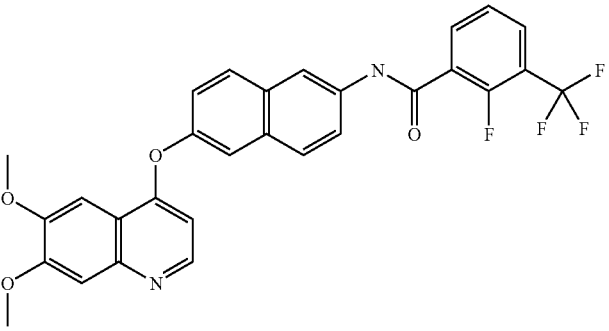<br>N-(6-((6,7-bis(methoxy)-4-quinolinyl)oxy)-2-naphthalenyl)-2-fluoro-3-(trifluoromethyl)benzamide | $C_{29}H_{20}F_4N_2O_4$ | 536.14 | 537.5 (M + 1) | 1 |
| 39 | 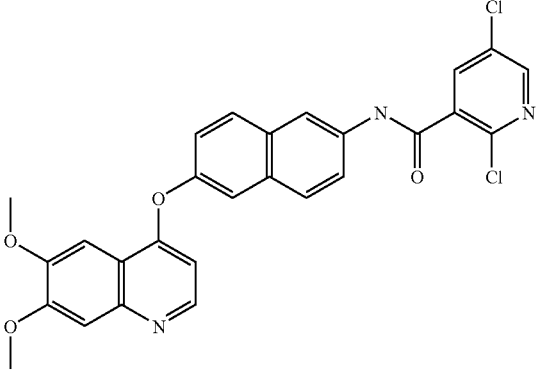<br>N-(6-((6,7-bis(methoxy)-4-quinolinyl)oxy)-2-naphthalenyl)-2,5-dichloro-3-pyridinecarboxamide | $C_{27}H_{19}Cl_2N_3O_4$ | 519.08 | 521.4 (M + 2) | 1 |
| 40 | 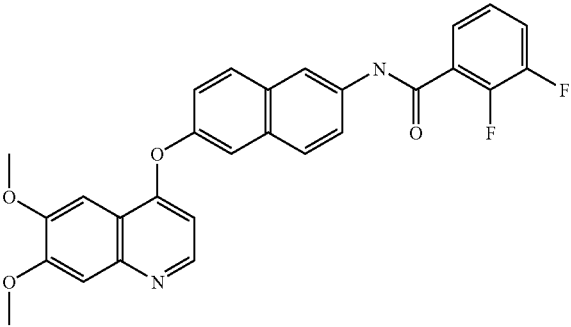<br>N-(6-((6,7-bis(methoxy)-4-quinolinyl)oxy)-2-naphthalenyl)-2,3-dichlorobenzamide | $C_{28}H_{20}F_2N_2O_4$ | 486.14 | 487.5 (M + 1) | 1 |

-continued

| Ex. No. | Structure & Name | Mol Formula | Mass | M + H | Proc. No. |
|---|---|---|---|---|---|
| 41 | N-(6-(((6,7-bis(methoxy)-4-quinolinyl)oxy)-2-naphthalenyl)-2-((trifluoromethyl)oxy)benzamide | C$_{29}$H$_{21}$F$_3$N$_2$O$_5$ | 534.14 | 535.5 (M + 1) | 1 |
| 42 | N-(6-(((6,7-bis(methoxy)-4-quinolinyl)oxy)-2-naphthalenyl)-2-(ethyloxy)benzamide | C$_{30}$H$_{26}$N$_2$O$_5$ | 494.18 | 495.6 (M + 1) | 1 |
| 43 | N-(6-(((6,7-bis(methoxy)-4-quinolinyl)oxy)-2-naphthalenyl)-2,4-dimethyl-1,3-thiazole-5-carboxamide | C$_{27}$H$_{23}$N$_3$O$_4$S | 485.14 | 486 | 1 |
| 44 | N-(6-(((6,7-bis(methoxy)-4-quinolinyl)oxy)-2-naphthalenyl)-2-methyl-1,3-thiazole-4-carboxamide | C$_{26}$H$_{21}$N$_3$O$_4$S | 471.13 | 472 | 1 |

-continued

| Ex. No. | Structure & Name | Mol Formula | Mass | M + H | Proc. No. |
|---|---|---|---|---|---|
| 45 | 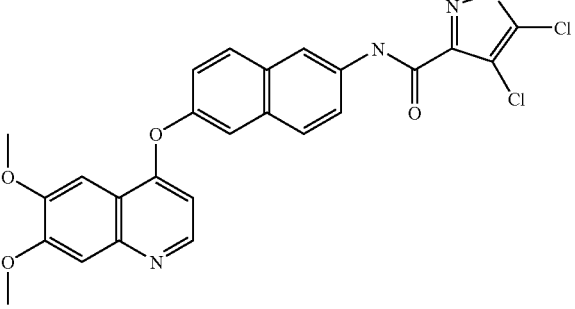<br>N-(6-((6,7-bis(methoxy)-4-quinolinyl)oxy)-2-naphthalenyl)-4,5-dichloro-3-isothiazolecarboxamide | $C_{25}H_{17}Cl_2N_3O_4S$ | 525.03 | 527 | 1 |
| 46 | 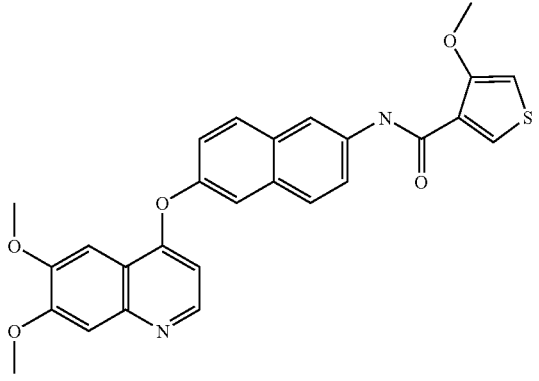<br>N-(6-((6,7-bis(methoxy)-4-quinolinyl)oxy)-2-naphthalenyl)-4-(methoxy)-3-thiophenecarboxamide | $C_{27}H_{22}N_2O_5S$ | 486.12 | 487 | 1 |
| 47 | 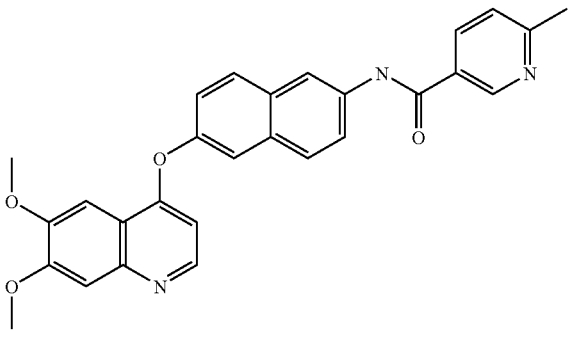<br>N-(6-((6,7-bis(methoxy)-4-quinolinyl)oxy)-2-naphthalenyl)-6-methyl-3-pyridinecarboxamide | $C_{28}H_{23}N_3O_4$ | 465.17 | 466 | 1 |
| 48 | 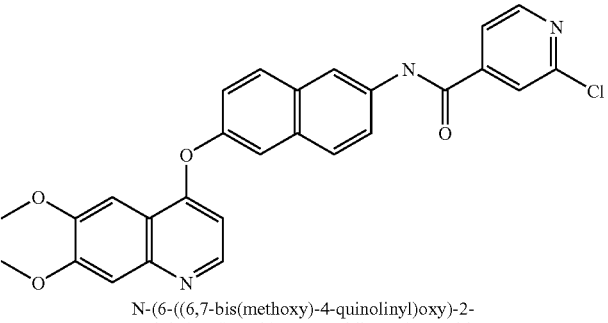<br>N-(6-((6,7-bis(methoxy)-4-quinolinyl)oxy)-2-naphthalenyl)-2-chloro-4-pyridinecarboxamide | $C_{27}H_{20}Cl_1N_3O_4$ | 485.11 | 487 (M + 1) | 1 |

-continued

| Ex. No. | Structure & Name | Mol Formula | Mass | M + H | Proc. No. |
|---|---|---|---|---|---|
| 49 | 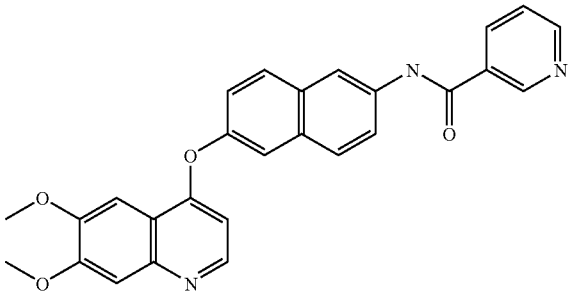<br>N-(6-((6,7-bis(methoxy)-4-quinolinyl)oxy)-2-naphthalenyl)-3-pyridinecarboxamide | $C_{27}H_{21}N_3O_4$ | 451.15 | 452 | 1 |
| 50 | 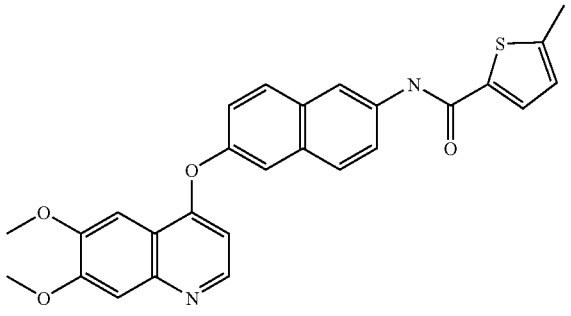<br>N-(6-((6,7-bis(methoxy)-4-quinolinyl)oxy)-2-naphthalenyl)-5-methyl-2-thiophenecarboxamide | $C_{27}H_{22}N_2O_4S$ | 470.13 | 471 | 1 |
| 51 | 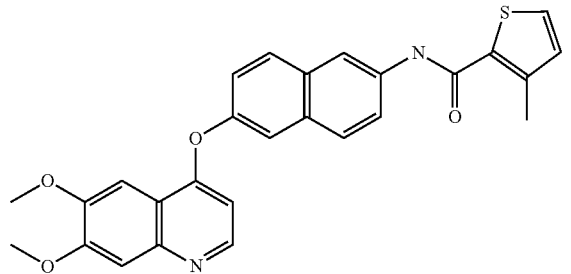<br>N-(6-((6,7-bis(methoxy)-4-quinolinyl)oxy)-2-naphthalenyl)-3-methyl-2-thiophenecarboxamide | $C_{27}H_{22}N_2O_4S$ | 470.13 | 471.4 | 1 |
| 52 | 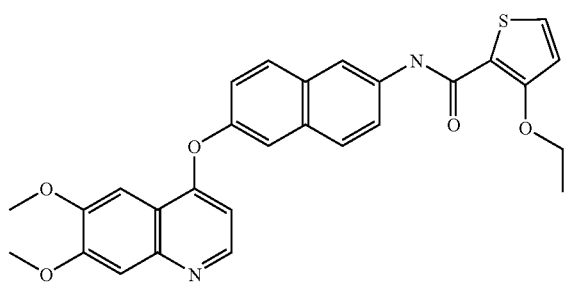<br>N-(6-((6,7-bis(methoxy)-4-quinolinyl)oxy)-2-naphthalenyl)-3-(ethyloxy)-2-thiophenecarboxamide | $C_{28}H_{24}N_2O_5S$ | 500.14 | 501 | 1 |

| Ex. No. | Structure & Name | Mol Formula | Mass | M + H | Proc. No. |
|---|---|---|---|---|---|
| 53 | 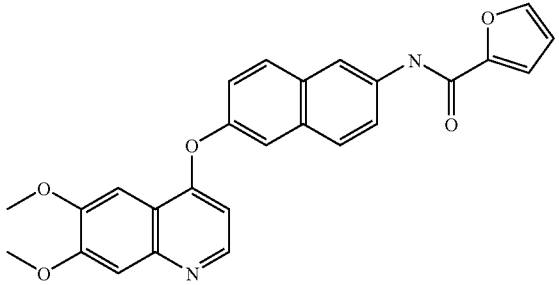<br>N-(6-((6,7-bis(methoxy)-4-quinolinyl)oxy)-2-naphthalenyl)-2-furancarboxamide | $C_{26}H_{20}N_2O_5$ | 440.14 | 441 | 1 |
| 54 | 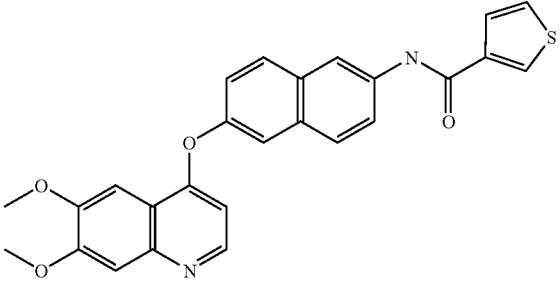<br>N-(6-((6,7-bis(methoxy)-4-quinolinyl)oxy)-2-naphthalenyl)-3-thiophenecarboxamide | $C_{26}H_{20}N_2O_4S$ | 456.11 | 457 | 1 |
| 55 | 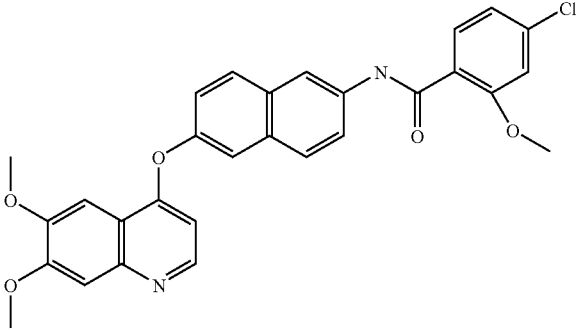<br>N-(6-((6,7-bis(methoxy)-4-quinolinyl)oxy)-2-naphthalenyl)-4-chloro-2-(methoxy)benzamide | $C_{29}H_{23}Cl_1N_2O_5$ | 514.13 | 515.2 | 1 |
| 56 | 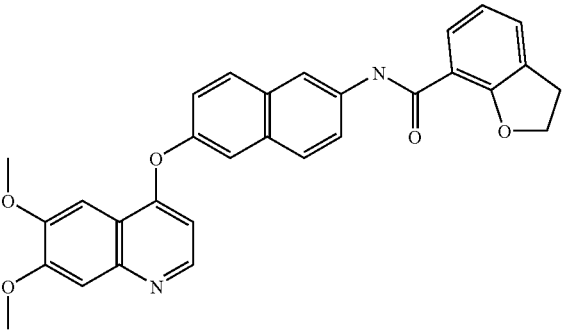<br>N-(6-((6,7-bis(methoxy)-4-quinolinyl)oxy)-2-naphthalenyl)-4-chloro-2-(methoxy)benzamide | $C_{30}H_{24}N_2O_5$ | 492.17 | 493.2 | 1 |

| Ex. No. | Structure & Name | Mol Formula | Mass | M + H | Proc. No. |
|---|---|---|---|---|---|
| 57 | 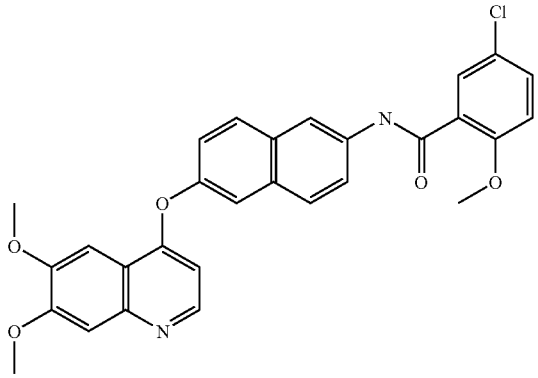<br>N-(6-((6,7-bis(methoxy)-4-quinolinyl)oxy)-2-naphthalenyl)-5-chloro-2-(methoxy)benzamide | $C_{29}H_{23}C_1N_2O_5$ | 514.13 | 515.1 | 1 |
| 58 | 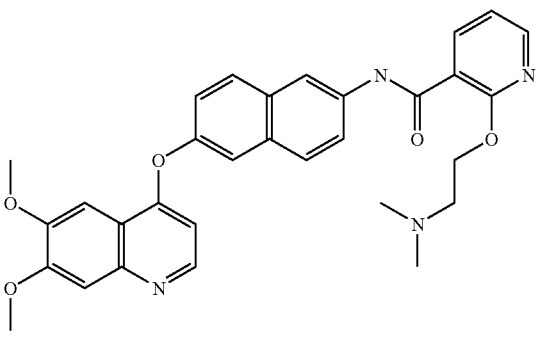<br>N-(6-((6,7-bis(methoxy)-4-quinolinyl)oxy)-2-naphthalenyl)-2-((2-(dimethylamino)ethyl)oxy)-3-pyridinecarboxamide | $C_{31}H_{30}N_4O_5$ | 538.22 | 539.4 | 2 |
| 59 | 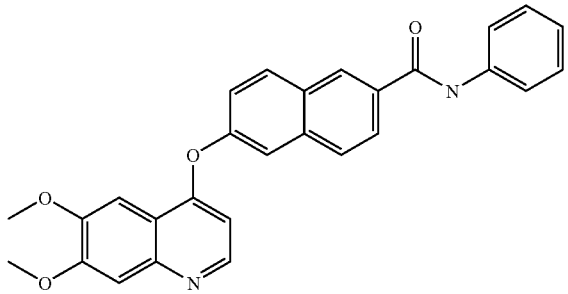<br>6-((6,7-bis(methoxy)-4-quinolinyl)oxy)-N-phenyl-2-naphthalenecarboxamide | $C_{28}H_{22}N_2O_4$ | 450.16 | 451 | 1 |
| 60 | 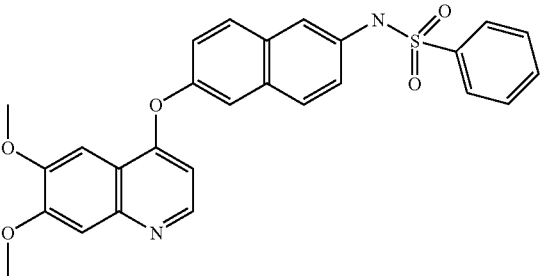<br>N-(6-((6,7-bis(methoxy)-4-quinolinyl)oxy)-2-naphthalenyl)benzenesulfonamide | $C_{27}H_{22}N_2O_5S$ | 486.12 | 487.3 | 1 |

-continued

| Ex. No. | Structure & Name | Mol Formula | Mass | M + H | Proc. No. |
|---|---|---|---|---|---|
| 61 | 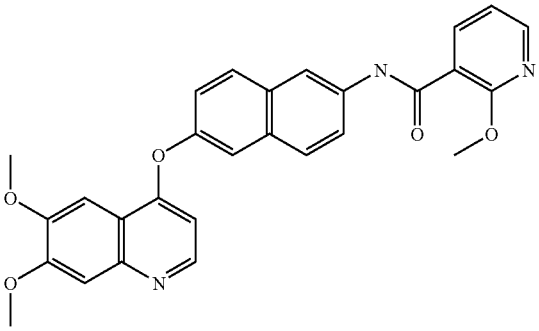 N-(6-((6,7-bis(methoxy)-4-quinolinyl)oxy)-2-naphthalenyl)-2-(methoxy)-3-pyridinecarboxamide | $C_{28}H_{23}N_3O_5$ | 481.16 | 482.1 | 1 |
| 62 | 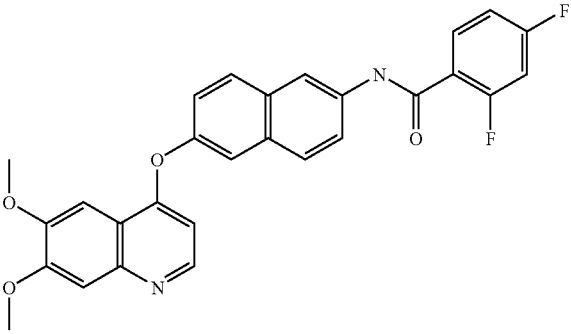 N-(6-((6,7-bis(methoxy)-4-quinolinyl)oxy)-2-naphthalenyl)-2,4-difluorobenzamide | $C_{28}H_{20}F_2N_2O_4$ | 486.14 | 487.3 (M + 1) | 1 |
| 63 | 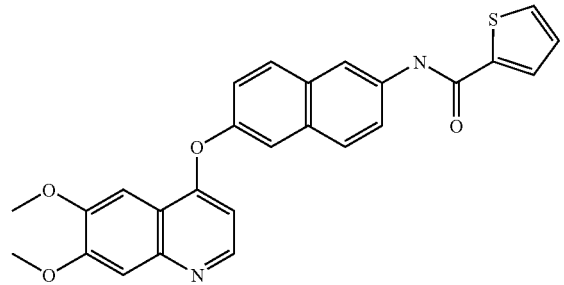 N-(6-((6,7-bis(methoxy)-4-quinolinyl)oxy)-2-naphthalenyl)-2-thiophenecarboxamide | $C_{26}H_{20}N_2O_4S$ | 456.11 | 457.1 | 1 |
| 64 | 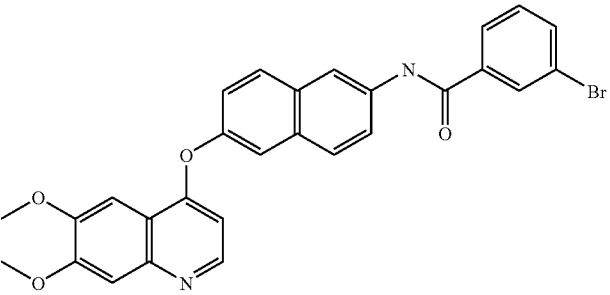 N-(6-((6,7-bis(methoxy)-4-quinolinyl)oxy)-2-naphthalenyl)-3-bromobenzamide | $C_{28}H_{21}BrN_2O_4$ | 528.07 | 531.2 (M + 3) | 1 |

-continued

| Ex. No. | Structure & Name | Mol Formula | Mass | M + H | Proc. No. |
|---|---|---|---|---|---|
| 65 | 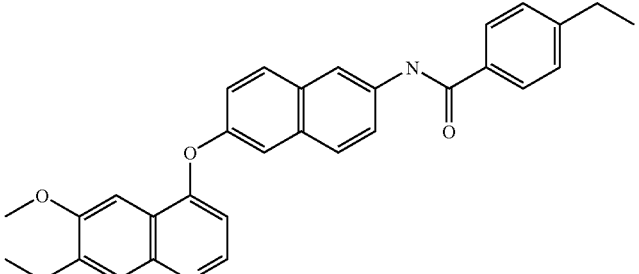<br>N-(6-((6,7-bis(methoxy)-4-quinolinyl)oxy)-2-naphthalenyl)-4-ethylbenzamide | $C_{30}H_{26}N_2O_4$ | 478.19 | 479.2 | 1 |
| 66 | 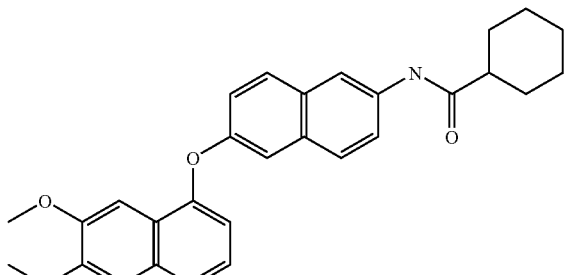<br>N-(6-((6,7-bis(methoxy)-4-quinolinyl)oxy)-2-naphthalenyl)cyclohexanecarboxamide | $C_{28}H_{28}N_2O_4$ | 456.20 | 457.4 | 1 |
| 67 | 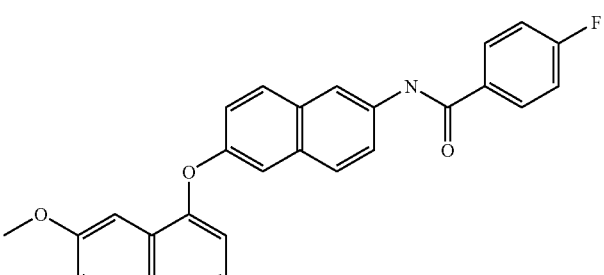<br>N-(6-((6,7-bis(methoxy)-4-quinolinyl)oxy)-2-naphthalenyl)-4-fluorobenzamide | $C_{28}H_{21}FN_2O_4$ | 468.15 | 469.2 | 1 |
| 68 | 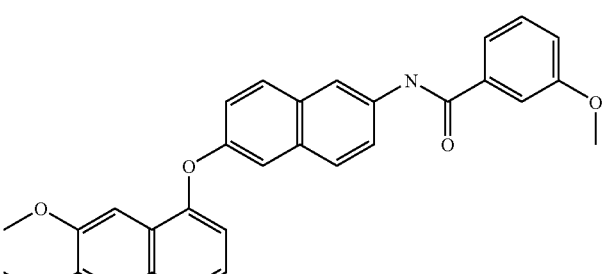<br>N-(6-((6,7-bis(methoxy)-4-quinolinyl)oxy)-2-naphthalenyl)-3-(methoxy)benzamide | $C_{29}H_{24}N_2O_5$ | 480.17 | 481.6 (M + 1) | 1 |

| Ex. No. | Structure & Name | Mol Formula | Mass | M + H | Proc. No. |
|---|---|---|---|---|---|
| 69 | 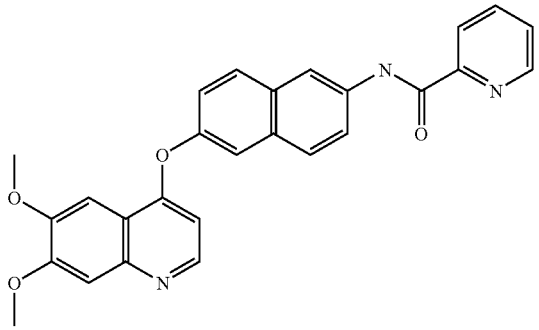<br>N-(6-((6,7-bis(methoxy)-4-quinolinyl)oxy)-2-naphthalenyl)-2-pyridinecarboxamide | $C_{27}H_{21}N_3O_4$ | 451.15 | 454.2 | 1 |
| 70 | 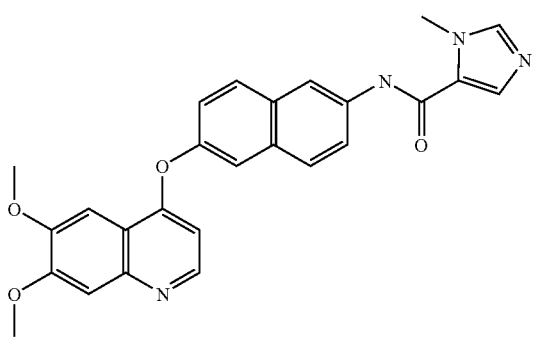<br>N-(6-((6,7-bis(methoxy)-4-quinolinyl)oxy)-2-naphthalenyl)-1-methyl-1H-imidazole-5-carboxamide | $C_{26}H_{22}N_4O_4$ | 454.16 | 455.2 | 1 |
| 71 | 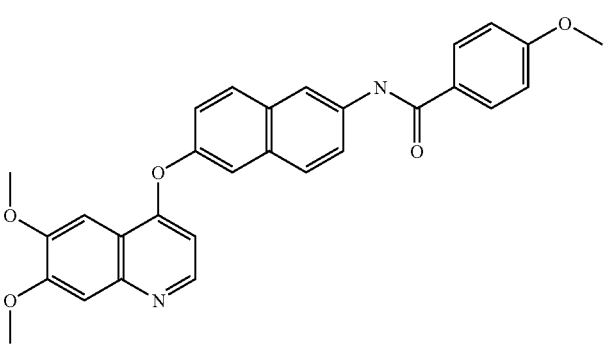<br>N-(6-((6,7-bis(methoxy)-4-quinolinyl)oxy)-2-naphthalenyl)-4-(methoxy)benzamide | $C_{29}H_{24}N_2O_5$ | 480.17 | 481.2 | 1 |
| 72 | 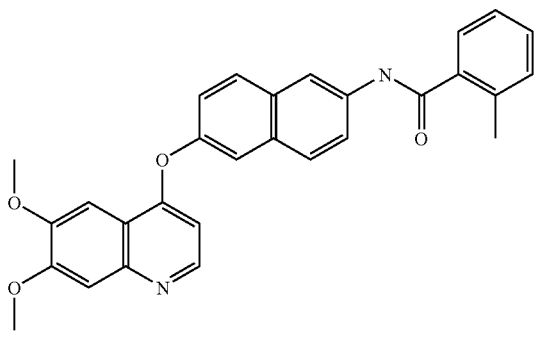<br>N-(6-((6,7-bis(methoxy)-4-quinolinyl)oxy)-2-naphthalenyl)-2-methylbenzamide | $C_{29}H_{24}N_2O_4$ | 464.17 | 465.7 (M + 1) | 1 |

-continued

| Ex. No. | Structure & Name | Mol Formula | Mass | M + H | Proc. No. |
|---|---|---|---|---|---|
| 73 | 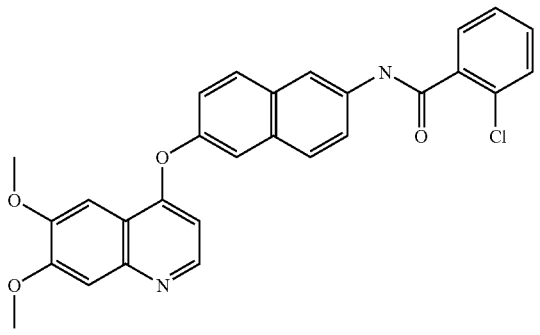<br>N-(6-((6,7-bis(methoxy)-4-quinolinyl)oxy)-2-naphthalenyl)-2-chlorobenzamide | $C_{28}H_{21}ClN_2O_4$ | 484.12 | 485.3 | 1 |
| 74 | 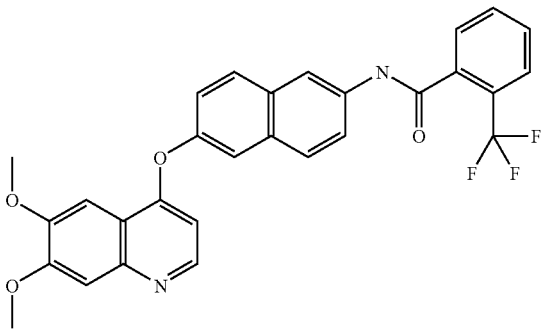<br>N-(6-((6,7-bis(methoxy)-4-quinolinyl)oxy)-2-naphthalenyl)-2-(trifluoromethyl)benzamide | $C_{29}H_{21}F_3N_2O_4$ | 518.15 | 519.4 (M + 1) | 1 |
| 75 | 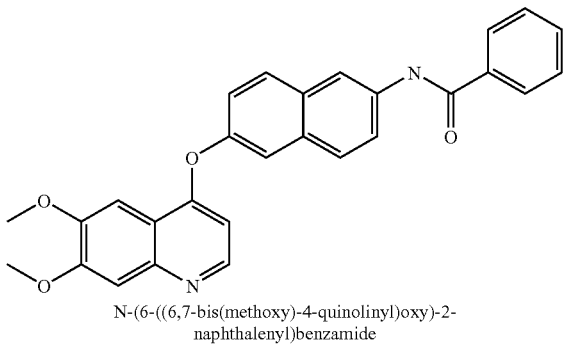<br>N-(6-((6,7-bis(methoxy)-4-quinolinyl)oxy)-2-naphthalenyl)benzamide | $C_{28}H_{22}N_2O_4$ | 450.16 | 451 | 1 |
| 76 | 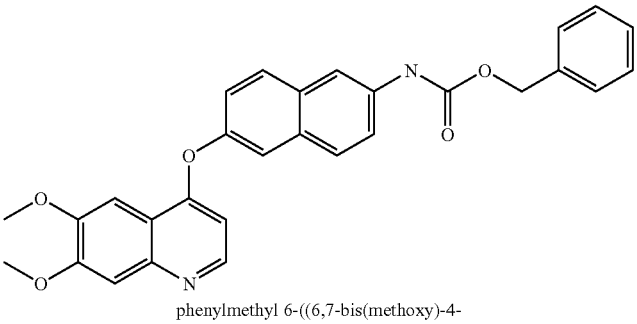<br>phenylmethyl 6-((6,7-bis(methoxy)-4-quinolinyl)oxy)-2-naphthalenylcarboxamide | $C_{29}H_{24}N_2O_5$ | 480.17 | 481 | 1 |

| Ex. No. | Structure & Name | Mol Formula | Mass | M + H | Proc. No. |
|---|---|---|---|---|---|
| 77 | 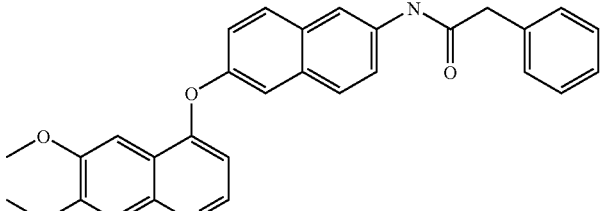<br>N-(6-((6,7-bis(methoxy)-4-quinolinyl)oxy)-2-naphthalenyl)-2-phenylacetamide | $C_{29}H_{24}N_2O_4$ | 464.17 | 465 | 1 |
| 78 | 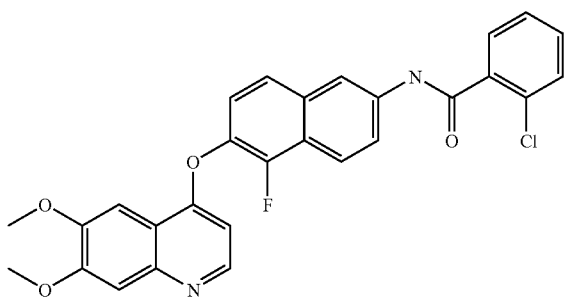<br>N-(6-((6,7-bis(methoxy)-4-quinolinyl)oxy)-5-fluoro-2-naphthalenyl)-2-chlorobenzamide | $C_{28}H_{20}ClFN_2O_4$ | 502.11 | 503 | 3 |
| 79 | 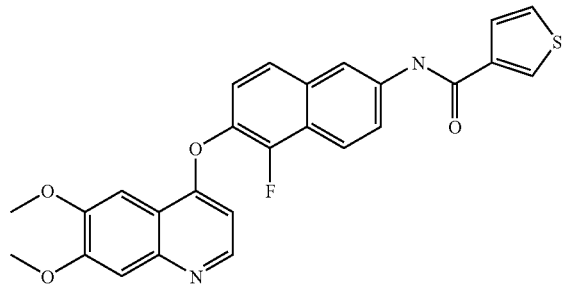<br>N-(6-((6,7-bis(methoxy)-4-quinolinyl)oxy)-5-fluoro-2-naphthalenyl)-3-thiophenecarboxamide | $C_{26}H_{19}FN_2O_4S$ | 474.10 | 475 | 3 |
| 80 | 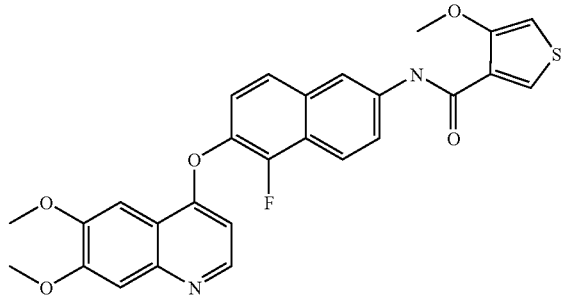<br>N-(6-((6,7-bis(methoxy)-4-quinolinyl)oxy)-5-fluoro-2-naphthalenyl)-4-(methoxy)-3-thiophenecarboxamide | $C_{27}H_{21}FN_2O_5S$ | 504.12 | 505 | 3 |

-continued

| Ex. No. | Structure & Name | Mol Formula | Mass | M + H | Proc. No. |
|---|---|---|---|---|---|
| 81 | 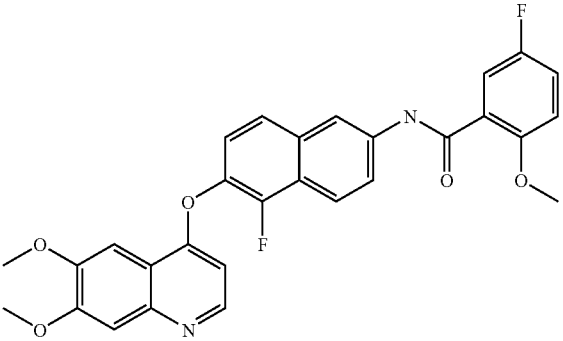<br>N-(6-(((6,7-bis(methoxy)-4-quinolinyl)oxy)-5-fluoro-2-naphthalenyl)-5-fluoro-2-(methoxy)benzamide | $C_{29}H_{22}F_2N_2O_5$ | 516.15 | 517 | 3 |
| 82 | 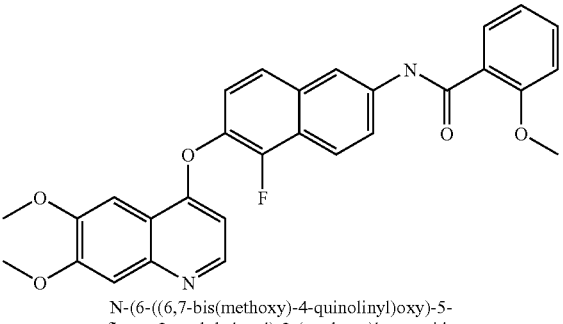<br>N-(6-(((6,7-bis(methoxy)-4-quinolinyl)oxy)-5-fluoro-2-naphthalenyl)-2-(methoxy)benzamide | $C_{29}H_{23}FN_2O_5$ | 498.16 | 499 | 3 |
| 83 | 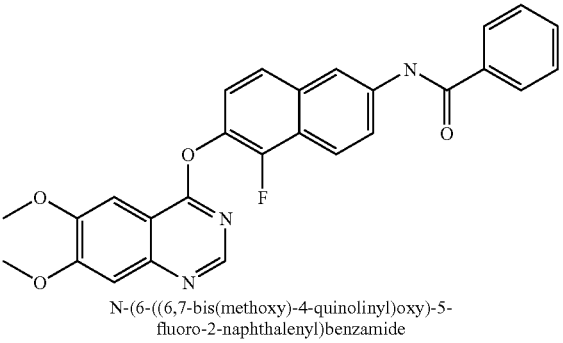<br>N-(6-(((6,7-bis(methoxy)-4-quinolinyl)oxy)-5-fluoro-2-naphthalenyl)benzamide | $C_{27}H_{20}FN_3O_4$ | 469.14 | 470 | 3 |
| 84 | 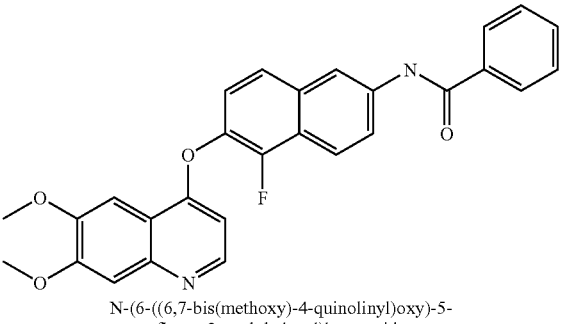<br>N-(6-(((6,7-bis(methoxy)-4-quinolinyl)oxy)-5-fluoro-2-naphthalenyl)benzamide | $C_{28}H_{21}FN_2O_4$ | 468.15 | 469 | 3 |

| Ex. No. | Structure & Name | Mol Formula | Mass | M + H | Proc. No. |
|---|---|---|---|---|---|
| 85 | N-(6-((6,7-bis(methoxy)-4-quinolinyl)oxy)-5-fluoro-2-naphthalenyl)-2,3-difluorobenzamide | $C_{28}H_{19}F_3N_2O_4$ | 504.13 | 505 | 3 |
| 86 | N-(5-fluoro-6-((6-(methoxy)-7-((3-(4-morpholinyl)propyl)oxy)-4-quinolinyl)oxy)-2-naphthalenyl)-2-thiophenecarboxamide | $C_{32}H_{30}FN_3O_5S$ | 587.19 | 588.2 | 9 |
| 87 | N-(5-fluoro-6-((6-(methoxy)-7-((3-(4-morpholinyl)propyl)oxy)-4-quinolinyl)oxy)-2-naphthalenyl)-3-thiophenecarboxamide | $C_{32}H_{30}FN_3O_5S$ | 587.19 | 588 | 9 |
| 88 | 3-(acetylamino)N-(6-((6,7-bis(methoxy)-4-quinolinyl)oxy)-2-naphthalenyl)benzamide | $C_{30}H_{25}N_3O_5$ | 507.18 | 508 | 3 |

-continued

| Ex. No. | Structure & Name | Mol Formula | Mass | M + H | Proc. No. |
|---|---|---|---|---|---|
| 89 | 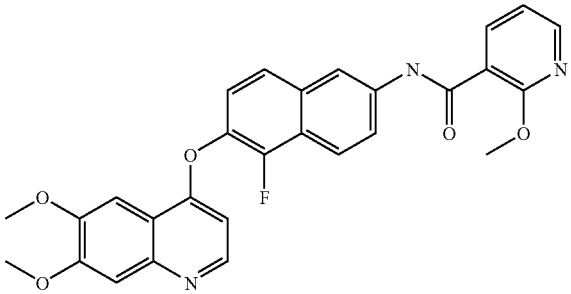<br>N-(6-(((6,7-bis(methoxy)-4-quinolinyl)oxy)-5-fluoro-2-naphthalenyl)-2-(methoxy)-3-pyridinecarboxamide | $C_{28}H_{22}FN_3O_5$ | 499.15 | 500 | 3 |
| 90 | 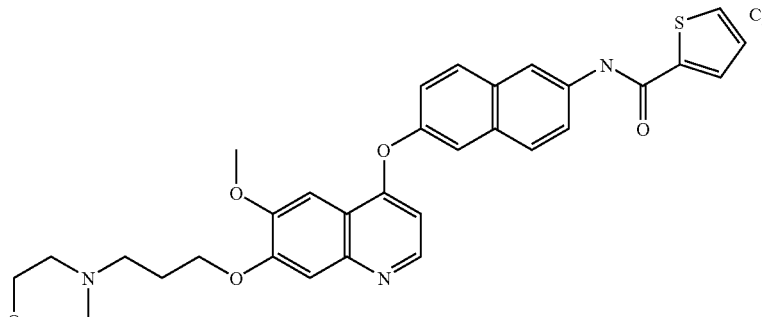<br>N-(6-((6-(methoxy)-7-((3-(4-morpholinyl)propyl)oxy)-4-quinolinyl)oxy)-2-naphthalenyl)-2-thiophenecarboxamide | $C_{32}H_{31}N_3O_5S$ | 569.20 | 570 | 9 |
| 91 | 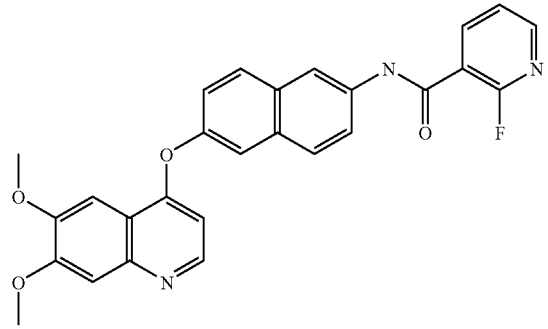<br>N-(6-((6,7-bis(methoxy)-4-quinolinyl)oxy)-2-naphthalenyl)-2-fluoro-3-pyridinecarboxamide | $C_{27}H_{30}FN_3O_4$ | 469.14 | 470 | 3 |
| 92 | 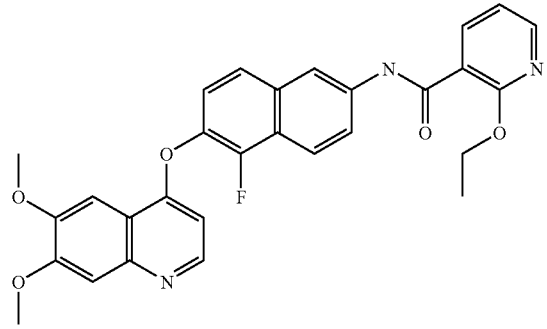<br>N-(6-((6,7-bis(methoxy)-4-quinolinyl)oxy)-2-naphthalenyl)-2-(ethyloxy)-3-pyridinecarboxamide | $C_{29}H_{25}N_3O_5$ | 495.18 | 496 | 3 |

| Ex. No. | Structure & Name | Mol Formula | Mass | M + H | Proc. No. |
|---|---|---|---|---|---|
| 93 | 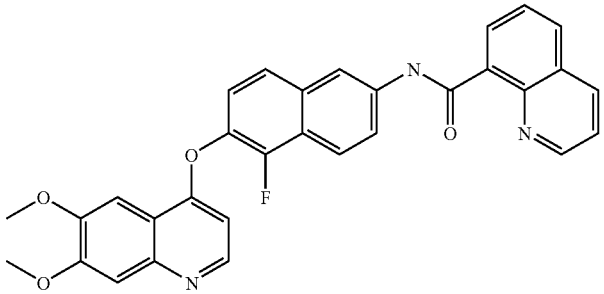<br>N-(6-((6,7-bis(methoxy)-4-quinolinyl)oxy)-2-naphthalenyl)-8-quinolinecarboxamide | $C_{31}H_{23}N_3O_4$ | 501.17 | 502 | 3 |
| 94 | 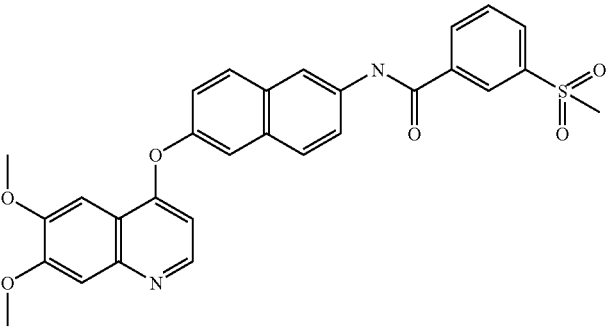<br>N-(6-((6,7-bis(methoxy)-4-quinolinyl)oxy)-2-naphthalenyl)-3-(methylsulfonyl)benzamide | $C_{29}H_{24}N_2O_6S$ | 528.14 | 529 | 3 |
| 95 | 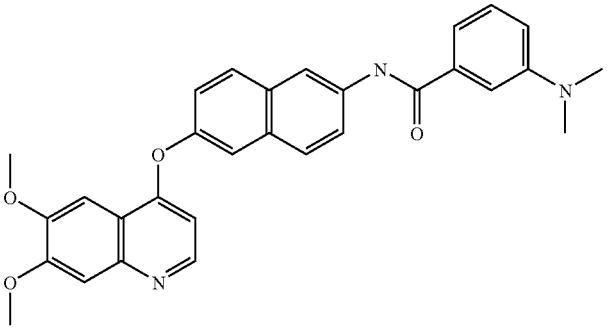<br>N-(6-((6,7-bis(methoxy)-4-quinolinyl)oxy)-2-naphthalenyl)-3-(dimethylamino)benzamide | $C_{30}H_{27}N_3O_4$ | 493.20 | 494 | 3 |
| 96 | 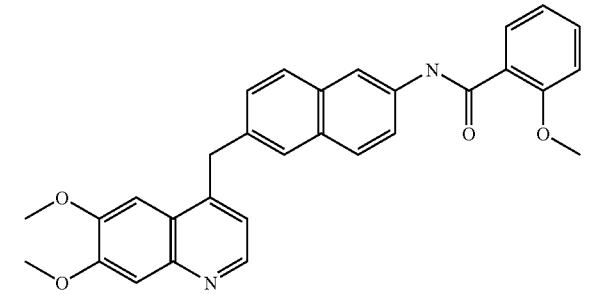<br>N-(6-((6,7-bis(methoxy)-4-quinolinyl)methyl)-2-naphthalenyl)-2-(methoxy)benzamide | $C_{30}H_{26}N_2O_4$ | 478.19 | 479 | |

-continued

| Ex. No. | Structure & Name | Mol Formula | Mass | M + H | Proc. No. |
|---|---|---|---|---|---|
| 97 | 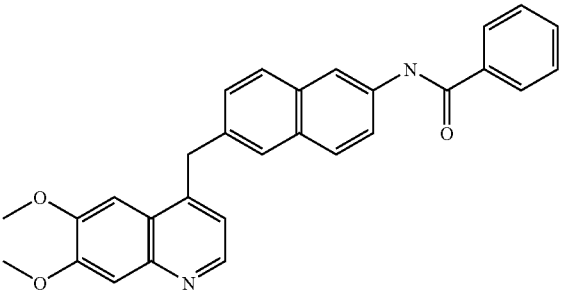<br>N-(6-((6,7-bis(methyoxy)-4-quinolinyl)methyl)-2-naphthalenyl)benzamide | C$_{29}$H$_{24}$N$_2$O$_3$ | 448.18 | 449 | |
| 98 | 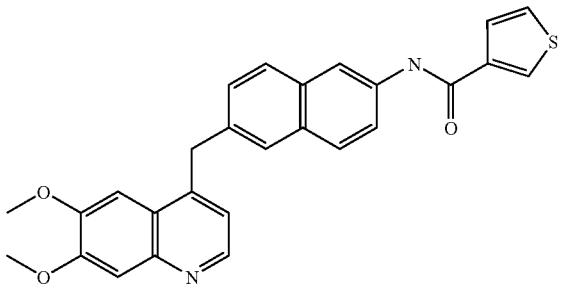<br>N-(6-((6,7-bis(methoxy)-4-quinolinyl)methyl)-2-naphthalenyl)-3-thiophenecarboxamide | C$_{27}$H$_{22}$N$_2$O$_3$S | 454.14 | 45 | |
| 99 | 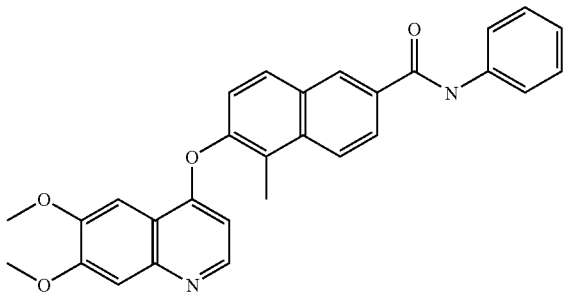<br>6-((6,7-bis(methoxy)-4-quinolinyl)oxy)-5-methyl-N-phenyl-2-naphthalenecarboxamide | C$_{29}$H$_{24}$N$_2$O$_4$ | 464.17 | 456 | |
| 100 | 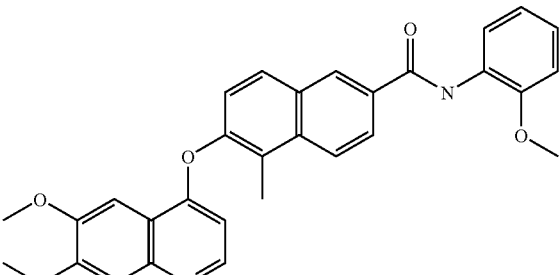<br>6-((6,7-bis(methoxy)-4-quinolinyl)oxy)-5-methyl-N-(2-(methoxy)phenyl)-2-naphthalenecarboxamide | C$_{30}$H$_{26}$N$_2$O$_5$ | 494.18 | 495 | |

| Ex. No. | Structure & Name | Mol Formula | Mass | M + H | Proc. No. |
|---|---|---|---|---|---|
| 101 | N-(6-((6,7-bis(methoxy)-4-quinolinyl)oxy)-5-methyl-2-naphthalenyl)-4-(methoxy)benzamide | $C_{30}H_{26}N_2O_5$ | 494.18 | 495 | |
| 102 | N-((6-((6,7-bis(methoxy)-4-quinolinyl)oxy)-2-naphthalenyl)methyl)benzamide | $C_{29}H_{24}N_2O_4$ | 464.17 | 465 | |
| 103 | 6-((6,7-bis(methoxy)-4-quinolinyl)oxy)-5-methyl-N-(4-(methoxy)phenyl)-2-naphthalenecarboxamide | $C_{30}H_{26}N_2O_5$ | 494.18 | 495 | |
| 104 | N-(6-((7-((3-(dimethylamino)propyl)oxy)-6-(methoxy)-4-quinolinyl)oxy)-2-naphthalenyl)-3-thiophenecarboxamide | $C_{30}H_{29}N_3O_4S$ | 527.19 | 528 | |

| Ex. No. | Structure & Name | Mol Formula | Mass | M + H | Proc. No. |
|---|---|---|---|---|---|
| 105 | 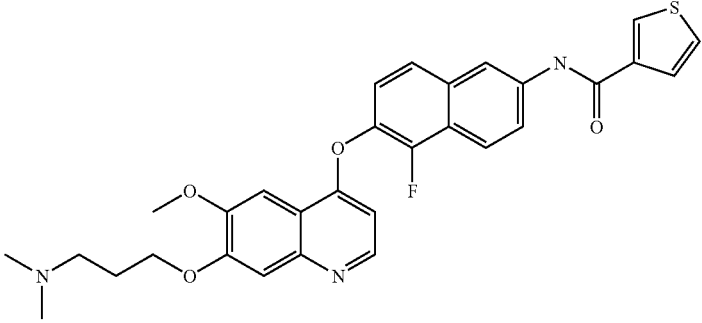 N-(6-((7-((3-(dimethylamino)propyl)oxy)-6-(methoxy)-4-quinolinyl)oxy)-5-fluoro-2-naphthalenyl)-3-thiophenecarboxamide | $C_{30}H_{28}FN_3O_4S$ | 545.18 | 546 | |
| 106 | 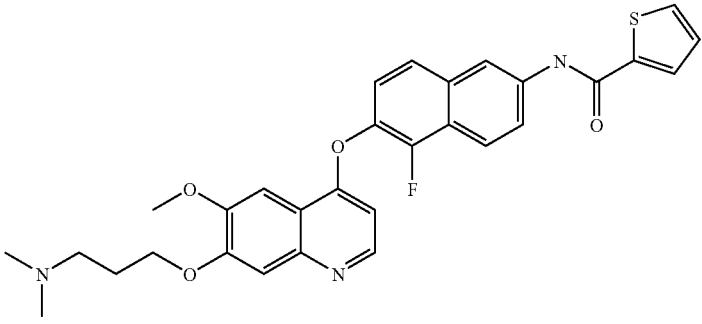 N-(6-((7-((3-(dimethylamino)propyl)oxy)-6-(methoxy)-4-quinolinyl)oxy)-5-fluoro-2-naphthalenyl)-2-thiophenecarboxamide | $C_{30}H_{28}FN_3O_4S$ | 545.18 | 546 | |
| 107 | 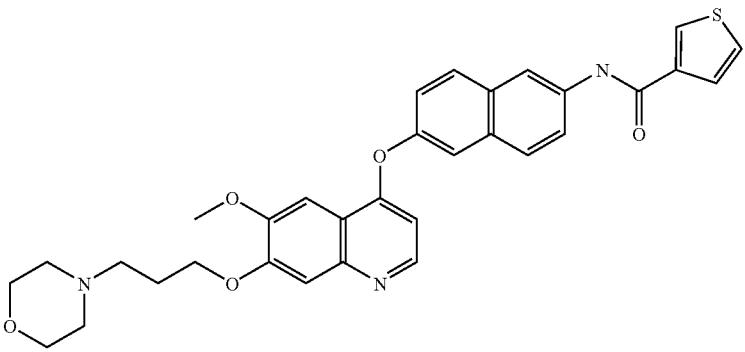 N-(6-((6-(methoxy)-7-((3-(4-morpholinyl)propyl)oxy)-4-quinolinyl)oxy)-2-naphthalenyl)-3-thiophenecarboxamide | $C_{32}H_{31}N_3O_5S$ | 569.67 | 570 | |

| Ex. No. | Structure & Name | Mol Formula | Mass | M + H | Proc. No. |
|---|---|---|---|---|---|
| 108 | 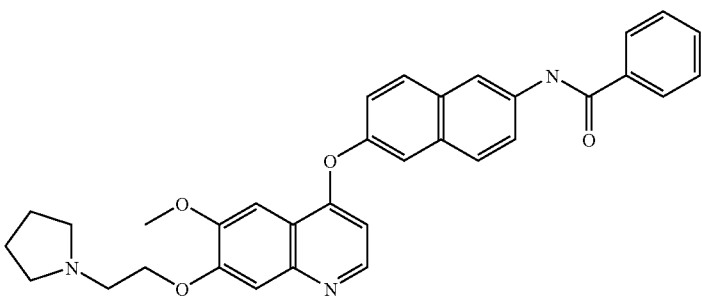<br>N-(6-((6-(methoxy)-7-((2-(1-pyrrolidinyl)ethyl)oxy)-4-quinolinyl)oxy)-2-naphthalenyl)benzamide | $C_{33}H_{31}N_3O_4$ | 533.23 | 534 | |
| 109 | 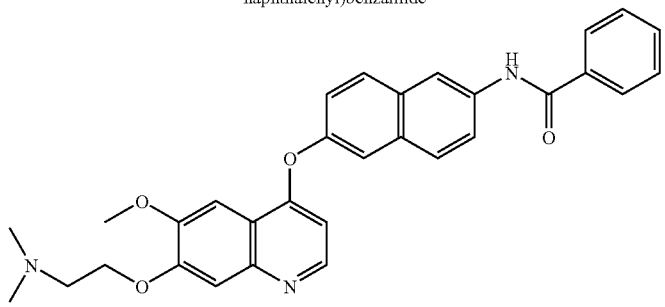<br>N-(6-((7-((2-(dimethylamino)ethyl)oxy)-6-(methoxy)-4-quinolinyl)oxy)-2-naphthalenyl)benzamide | $C_{31}H_{29}N_3O_4$ | 507.22 | 508 | |

EXAMPLE 110

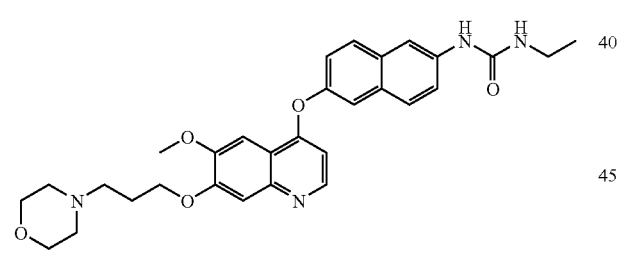

(Ethylamino)-N-{6-[6-methoxy-7-(3-morpholin-4-ylpropoxy)(4-quinolyloxy)](2-naphthyl)}carboxamide To a solution of 6-[6-methoxy-7-(3-morpholin-4-ylpropoxy)-4-quinolyloxy]-2-naphthylamine (prepared similar to that described in Example 1, Step c) (46.0 mg, 0.1 mmol) in anhydrous DMF (5 mL, Aldrich) was added Et₃N (50.5 mg, 0.5 mmol, Aldrich) and ethyl isocyanate (35.5 mg, 0.5 mmol, Aldrich) at RT. The reaction was stirred at RT for 16 h, then was quenched with saturated aqueous solution of NaHCO₃ (20 mL) and extracted with EtOAc (2×30 mL). The combined organic extracts were dried over MgSO₄, filtered and concentrated in vacuo. The residue was purified by column chromatography (FPNH-25S, Biotage, EtOAc) to give the title compound as white solid. MS (ESI, pos. ion) m/z: 531.3 (M+1); 529.3 (M−1). Calc'd for C₃₀H₃₃N₄O₅−530.25.

EXAMPLE 111

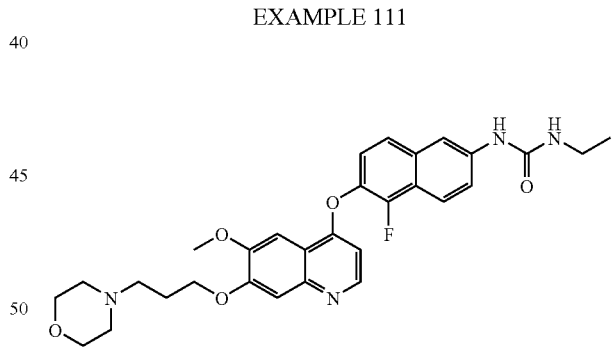

(Ethylamino)-N-{5-fluoro-6-[6-methoxy-7-(3-morpholin-4-ylpropoxy)(4-quinolyloxy)](2-naphthyl)}carboxamide 5-Fluoro-6-[6-methoxy-7-(3-morpholin-4-ylpropoxy)(4-quinolyloxy)]-2-naphthylamine (Example 9, Step b, 47.7 mg, 0.1 mmol) was reacted with Et₃N (55 mg, 0.5 mmol, Aldrich) and ethylisocyanate (35.5 mg, 0.5 mmol, Aldrich) under the conditions of Example 110 to give the title compound as a white solid. M.p. 193.5-196.4° C. MS (ESI, pos. ion) m/z: 549.6 (M+1), 547.4 (M−1). Calc'd for C₃₀H₃₃FN₄O₅−548.24.

Example 112 was prepared similar to the procedure described in either Example 110.

EX. 112

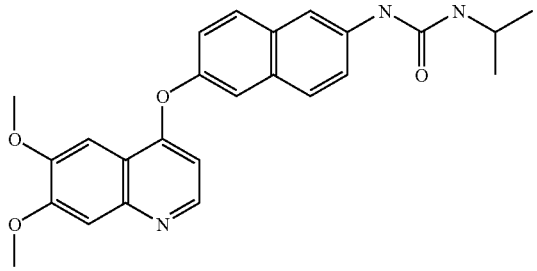

N-(6-((6,7-bis(methoxy)-4-quinolinyl)oxy)-2-naphthalenyl)-N'-(1-methylethyl)urea; Mass calc'd for $C_{25}H_{25}N_3O_4$–431.18.

EXAMPLE 113

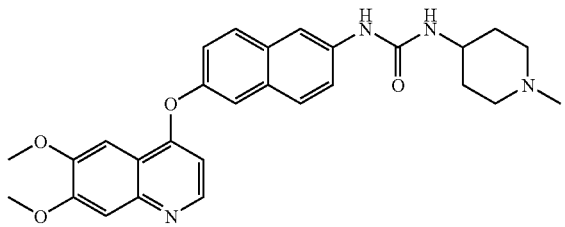

N-[6-(6,7-Dimethoxy(4-quinolyloxy))(2-naphthyl)][(1-methyl(4-piperidyl)) amino]carboxamide To a solution of 6-(6,7-dimethoxy-4-quinolyloxy)-2-naphthylamine (Example 1, Step c, 52 mg, 0.15 mmol) in anhydrous DMF (5 mL, Aldrich) was added Et$_3$N (30.3 mg, 0.3 mmol, Aldrich) and N,N'-disuccinimidyl carbonate (46 mg, 0.18 mmol, Aldrich) at RT. After the reaction was stirred at RT for 16 h, it was treated with 1-methyl 4-piperidylamine (20.5 mg, 0.18 mmol, Aldrich) and stirred at RT for 16 h. The reaction was quenched with saturated aqueous solution of NaHCO$_3$ (20 mL) and extracted with EtOAc (2×30 mL). The combined organic extracts were dried over MgSO$_4$, filtered and concentrated in vacuo. The residue was purified by column chromatography (silica gel, EtOAc) to give the title compound as a white solid. MS (ESI, pos. ion) m/z: 487.5 (M+1); 485.5 (M−1). Calc'd for $C_{28}H_{30}N_4O_4$–486.23.

EXAMPLE 114

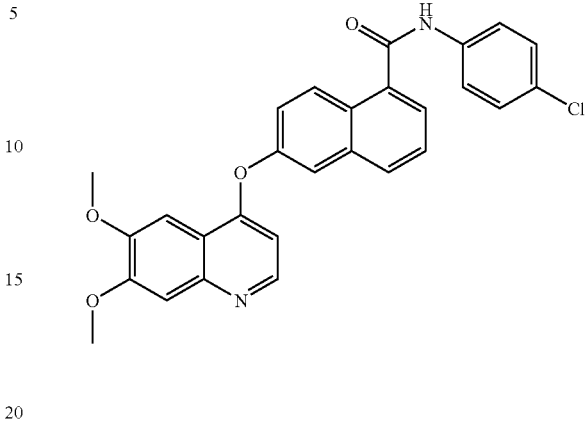

6-(6,7-Dimethoxy-quinolin-4-yloxy)-naphthalene-1-carboxylic acid (4-chloro-phenyl)-amide Step (a) Preparation of 6-Hydroxy-naphthalene-1-carboxylic acid (4-chloro-phenyl)-amide A slurry of 6-hydroxy-naphthalene-1-carboxylic acid (0.2 g, 1.06 mmol) in 10.6 mL of SOCl$_2$ and 1 drop of DMF was heated to 40° C. After 4 h, the solution was concentrated to dryness and placed under high vacuum overnight. The crude residue was dissolved in 3.5 mL of CH$_2$Cl$_2$. To the resulting solution was added DIEA (0.554 mL, 3.18 mmol), 4-chlorophenylamine (0.162 g, 1.27 mmol) and a catalytic amount of DMAP. The reaction was stirred under an argon atmosphere for 2 days. The reaction was diluted with CH$_2$Cl$_2$, washed with saturated aqueous NH$_4$Cl, saturated aqueous NaHCO$_3$, and brine. The organic layer was dried (Na$_2$SO$_4$), filtered and concentrated. The residue was passed through a medium-pressure silica gel column (solvent gradient: 94:6 CH$_2$Cl$_2$:MeOH; 95:5 CH$_2$Cl$_2$:MeOH; 90:10 CH$_2$Cl$_2$:MeOH) to afford the desired crude compound. The fractions were concentrated to dryness to afford a solid residue. The residue was triturated with CHCl$_3$ to afford the desired compound as a pale yellow solid.

Step (b) 6-(6,7-Dimethoxy-quinolin-4-yloxy)-naphthalene-1-carboxylic acid (4-chloro-phenyl)-amide The 6-hydroxy-naphthalene-1-carboxylic acid (4-chlorophenyl)-amide (Step a, 0.076 g, 0.254 mmol), Cs$_2$CO$_3$ (0.248 g, 0.762 mmol), 4-chloro-6,7-dimethoxy-quinoline (0.114 g, 0.508 mmol) and DMF (0.250 mL) were combined in a screw-cap test tube under N$_2$. The tube was sealed and heated to 100° C. After 60 h at 100° C., the reaction was cooled to RT. The solvent was removed in vacuo, dissolved in EtOAc and washed with saturated aqueous NaHCO$_3$ and brine. The organic layer was dried (Na$_2$SO$_4$), filtered and concentrated. The residue remaining after concentration was dissolved in MeOH and purified by reverse-phase HPLC (pH 10 buffer solvent system). The fractions containing the desired product were concentrated, dissolved in EtOAc, and washed with brine. The organic layer was dried (Na$_2$SO$_4$), filtered and concentrated to afford the title compound as a tan solid. M+H −485.1. Calc'd for $C_{28}H_{31}N_2O_4$–484.12.

The following examples were prepared similar to the procedures described in Example 114.

| Example No. | Structure & Name | Mol Formula | Mass | M + H |
|---|---|---|---|---|
| 115 | 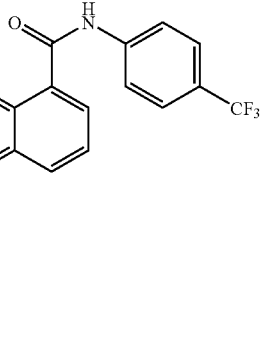<br>6-(6,7-dimethoxy-quinolin-4-yloxy)-naphthalene-1-carboxylic acid (4-trifluoromethyl-phenyl)-amide | $C_{29}H_{21}F_3N_2O_4$ | 518.15 | 517.0 (M − H) |
| 116 | 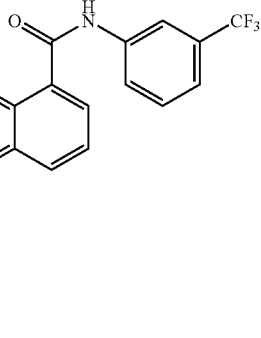<br>6-(6,7-dimethoxy-quinolin-4-yloxy)-naphthalene-1-carboxylic acid (3-trifluoromethyl-phenyl)-amide | $C_{29}H_{21}F_3N_2O_4$ | 518.15 | 519.0 |
| 117 | 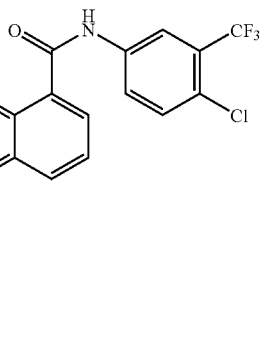<br>6-(6,7-dimethoxy-quinolin-4-yloxy)-naphthalene-1-carboxylic acid (4-chloro-3-trifluoromethyl-phenyl)-amide | $C_{29}H_{20}ClF_3N_2O_4$ | 552.11 | 553.0 |

| Example No. | Structure & Name | Mol Formula | Mass | M + H |
|---|---|---|---|---|
| 118 | 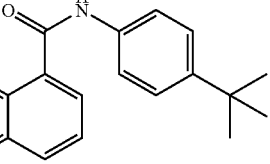<br>6-(6,7-dimethoxy-quinolin-4-yloxy)-naphthalene-1-carboxylic acid (4-tert-butyl-phenyl)-amide | $C_{32}H_{30}N_2O_4$ | 506.22 | 507.1 |

EXAMPLE 119

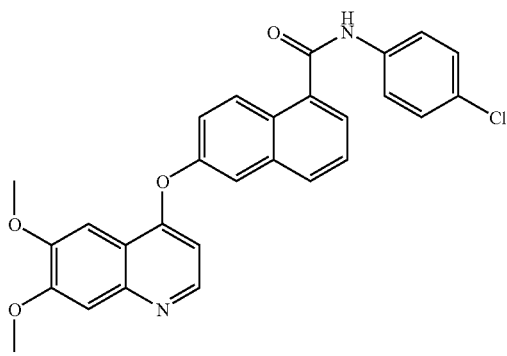

6-(6,7-Dimethoxy-quinolin-4-yloxy)-naphthalene-1-carboxylic acid (4-chloro-phenyl)-amide

Step (a) Preparation of 6-(6,7-Dimethoxy-quinolin-4-yloxy)-naphthalene-1-carboxylic acid hydrochloride A slurry of 6-hydroxy-naphthalene-1-carboxylic acid (0.100 g, 0.531 mmol), 4-chloro-6,7-dimethoxy-quinoline (0.143 g, 0.638 mmol) and $Cs_2CO_3$ (0.519 g, 1.59 mmol) in 2.66 mL of DMSO under argon was stirred for 15 min at RT. The mixture was heated to 140° C. in a microwave. After 1 h, the reaction was diluted with ca. 2.7 mL of water. 6N HCl was added dropwise until the solution was at pH 3-4. The resulting precipitate was filtered and washed with acetone to afford the titled compound as a tan solid.

Step (b) 6-(6,7-Dimethoxy-quinolin-4-yloxy)-naphthalene-1-carboxylic acid (4-chloro-phenyl)-amide A slurry of 6-(6,7-dimethoxy-quinolin-4-yloxy)-naphthalene-1-carboxylic acid hydrochloride (0.200 g, 0.532 mmol, step a), HATU (0.264 g, 0.692 mmol), and $Et_3N$ (0.296 ml, 2.12 mmol) in 1.33 mL of DMF under argon was stirred at RT. After 1 h, 4-hydroxyaniline (0.116 g, 1.064 mmol) was added. The solution was stirred at RT for 0.5 h then at 50° C.

After 2 h, the reaction was diluted with EtOAc and washed with saturated aqueous $NaHCO_3$, water, and brine. The organic layer was dried ($Na_2SO_4$), filtered and concentrated. The residue remaining after concentration was dissolved in acetone and purified by reverse-phase HPLC (pH 1 $CH_3CN$/water solvent system). The fractions containing the desired product were concentrated, dissolved in $CH_2Cl_2$, and washed with saturated aqueous $NaHCO_3$ and brine. The organic layer was dried ($Na_2SO_4$), filtered and concentrated to afford the titled compound as a pale yellow solid. M+H –467.1. Calc'd for $C_{28}H_{22}N_2O_5$–466.49.

EXAMPLE 120

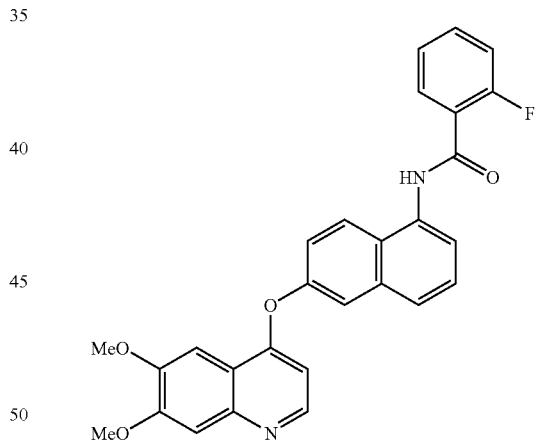

N-[6-(6,7-Dimethoxy-quinolin-4-yloxy)-naphthalen-1-yl]-2-fluoro-benzamide

Step (a) Preparation of 6-(6,7-Dimethoxy-quinolin-4-yloxy)-naphthalen-1-ylamine To a solution of 5-amino-2-naphthol (711 mg, 4.47 mmol) in NMP (3 ml), $Cs_2CO_3$ (4.37 g, 13.41 mmol) was added and the reaction was stirred at RT for 15 min. To the mixture, 4-chloro-6,7-dimethoxy-quinoline (500 mg, 2.23 mmol) was added and the vessel was sealed/clamped shut. The reaction was placed in the microwave and heated at 160° C. for 15 min, then 10 additional min with pre-stirring for 60 sec. The mixture was taken up into water and $CH_2Cl_2$, and filtered through Celite. The aqueous layer was extracted with $CH_2Cl_2$. The combined organic layers were washed with water, 1N NaOH, and brine, dried with Na$_2$SO$_4$, filtered and concentrated in vacuo. The 6-(6,7-dimethoxy-quinolin-4-yloxy)-naphthalen-1-ylamine was purified by column chromatography using 0-10% MeOH in CH$_2$Cl$_2$.

Step (b) Preparation of N-[6-(6,7-dimethoxy-quinolin-4-yloxy)-naphthalen-1-yl]-2-fluoro-benzamide To a solution of 6-(6,7-dimethoxy-quinolin-4-yloxy)-naphthalen-1-ylamine (Step a, 50 mg, 0.14 mmol) and NaHCO$_3$ (38 mg, 0.45 mmol) in CH$_2$Cl$_2$ (1 mL), 2-fluorobenzoyl chloride (18 mL, 0.15 mmol) was added. The reaction was stirred at RT for 20 h. The mixture was taken up into CHCl$_3$ and water, washed with brine, dried with Na$_2$SO$_4$, filtered and concentrated in vacuo. The title compound was purified by column chromatography using 0-100% of a 90:10:1 (CH$_2$Cl$_2$:MeOH: NH$_4$OH) solution as the eluant. M+H 469.1, Calc'd for C$_{28}$H$_{21}$FN$_2$O$_4$–468.49.

The following compounds were prepared similarly to the procedure outlined above:

| Example No. | Structure & Name | Mol Formula | Mass | M + H |
|---|---|---|---|---|
| 121 | 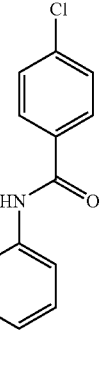<br>N-[6-(6,7-Dimethoxy-quinolin-4-yloxy)-naphthalen-1-yl]-4-chloro-benzamide | C$_{28}$H$_{21}$ClN$_2$O$_4$ | 484.94 | 485.1 |
| 122 | 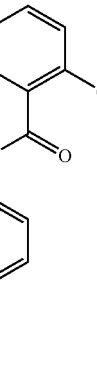<br>N-[6-(6,7-dimethoxy-quinolin-4-yloxy)-naphthalen-1-yl]-2-fluoro-benzamide | C$_{28}$H$_{21}$ClN$_2$O$_4$ | 484.12 | 485.1 |

EXAMPLE 123

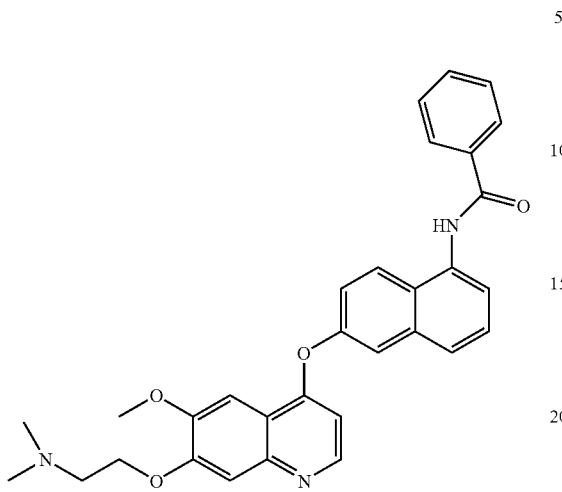

N-{6-[7-(2-Dimethylamino-ethoxy)-6-methoxy-quinolin-4-yloxy]-naphthalen-1-yl}-benzamide Step (a) N-(6-Hydroxy-naphthalen-1-yl)-benzamide To a round bottom flask containing 1.00 g (6.3 mmol) 5-amino-naphthalene-2-ol in 10 mL $CH_2Cl_2$, was added 2.61 g (0.0189 mmol) $K_2CO_3$, followed by 1.46 mL (0.0126 mmol) benzolyl chloride. The solution mixture was stirred under inert atmosphere until completion. After stirring for 18 h, water was added into the mixture and diluted with $CH_2Cl_2$. The organics were separated by sep. funnel, while extracting the organics 3× with $CH_2Cl_2$. The organic layers were combined, dried over $Na_2SO_4$, filtered and concentrated in-vacuo. The crude was purified by crystallization in $CH_2Cl_2$/Hexanes. A gray colored powder was collected, which was titled compound. MS (ESI pos. ion) m/z: 264 (M+H)

Step (b) N-{6-[7-(2-Dimethylamino-ethoxy)-6-methoxy-quinolin-4-yloxy]-naphthalen-1-yl}-benzamide To a microwaveable vial containing 0.300 g (1.1 mmol) of N-(6-hydroxy-naphthalen-1-yl)-benzamide in 1.5 mL DMF and 1.5 mL pyridine, was added 0.771 g (2.8 mmol) of [2-(4-chloro-6-methoxy-quinolin-7-yloxy)-ethyl]-dimethylamine. Then added (5 mmol %) copper grind into the mixture, along with 0.158 g (2.5 mmol) KOH pellets. The vial was heated in a microwave for 18 min at 120° C. (60 Watts constant power, CEM powermax). The mixture was diluted with $CH_2Cl_2$ and water, then transferred to seperatory funnel. The organics were extracted 3× with $CH_2Cl_2$. The organic layers were combined, dried over $Na_2SO_4$, filtered, and concentrated in-vacuo. The crude was purified by reverse-phase HPLC. A tan oil was collected, which was titled product. MS (ESI pos. ion) m/z: 508 (M+H). Calc'd for $C_{31}H_{29}N_3O_4$–507.22.

EXAMPLE 124

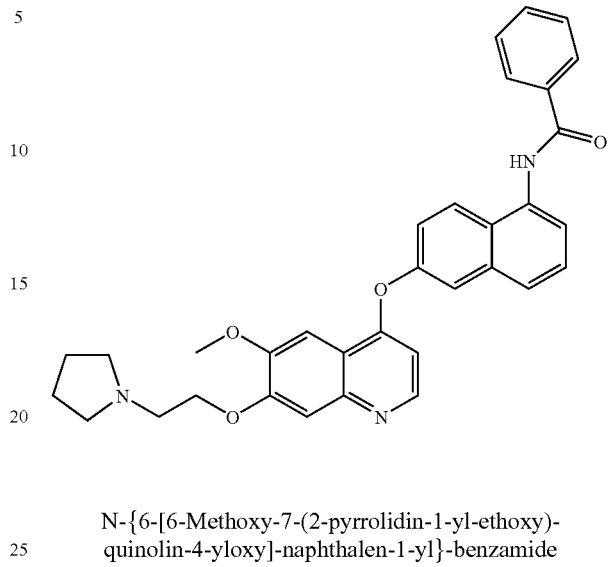

N-{6-[6-Methoxy-7-(2-pyrrolidin-1-yl-ethoxy)-quinolin-4-yloxy]-naphthalen-1-yl}-benzamide To a microwaveable vial containing 0.300 g (0.0011 mmol) of N-(6-hydroxy-naphthalen-1-yl)-benzamide in 1.5 mL DMF and 1.5 mL pyridine, was added 0.858 g (0.0028 mmol) of 4-chloro-6-methoxy-7-(2-pyrrolidin-1-yl-ethoxy)-quinoline. Copper grind was added (5 mmol %) to the mixture, along with 0.158 g (0.0025 mmol) KOH pellets. The vial was heated in a microwave for 18 min at 120° C., (60 Watts of constant power, powermax, CEM). The mixture was diluted with $CH_2Cl_2$ and water, then transferred to a seperatory funnel. The organics were extracted 3× with $CH_2Cl_2$. Then combined all organics, dried over $Na_2SO_4$, filtered, and concentrated in-vacuo. The crude was purified by reverse-phase HPLC. A tan oil was collected, which was the titled product. MS (ESI pos. ion) m/z: 534 (M+H). Calc'd for $C_{33}H_{31}N_3O_4$–533.23.

The following example was prepared similar to the procedures described in either Example 123 or 124.

125)

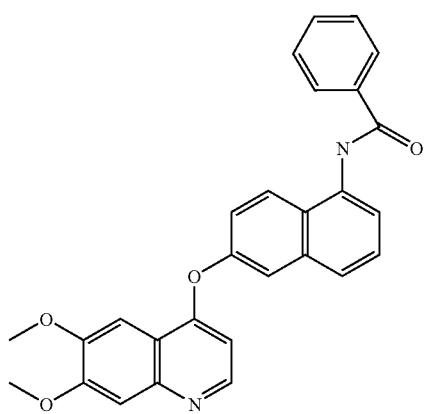

N-(6-((6,7-bis(methoxy)-4-quinolinyl)oxy)-1-naphthalenyl)benzamide Mass Calc'd for $C_{28}H_{22}N_2O_4$ – 450.16.
Other compounds included in this invention are set forth in Tables 1-2 below.
TABLE 1
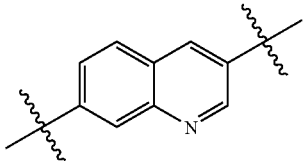
| # | $R^1$ |
|---|---|
| 126. | pyridin-4-yl |
| 127. | 4-pyrimidinyl |
| 128. | quinazolin-4-yl |
| 129. | 6,7-dimethoxyquinazolin-4-yl |
TABLE 2
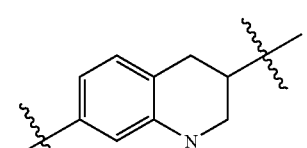
| # | A |
|---|---|
| 130. | 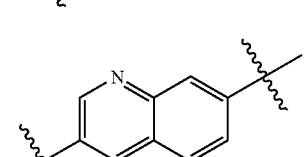 |
| 131. | 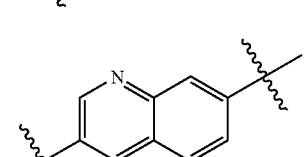 |
| 132. | 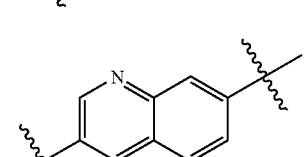 |
TABLE 2-continued
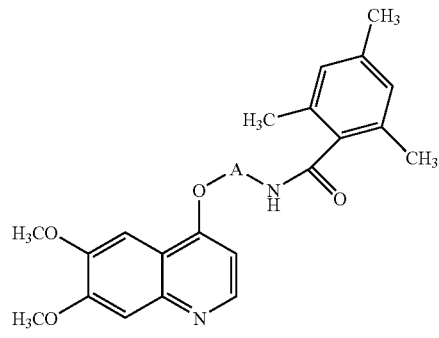
| # | A |
|---|---|
| 133. | 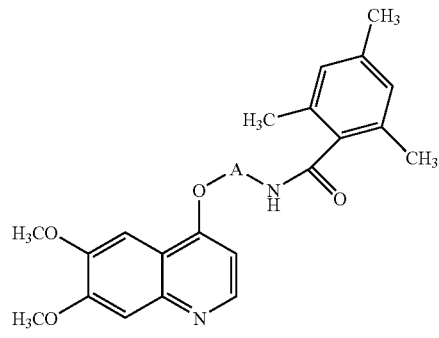 |
| 134. | 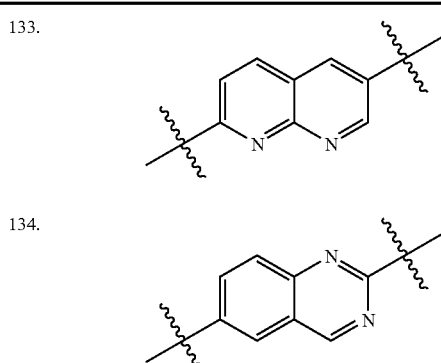 |
| 135. | 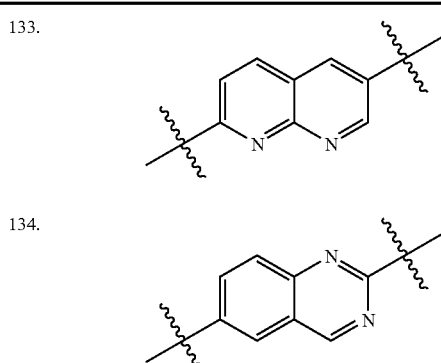 |
| 136. | 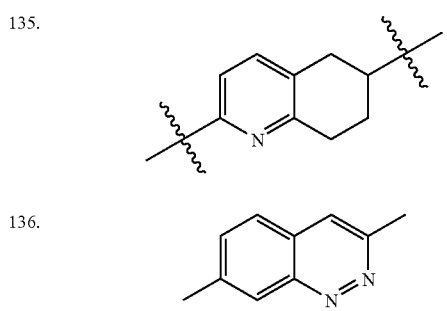 |
| 137. | 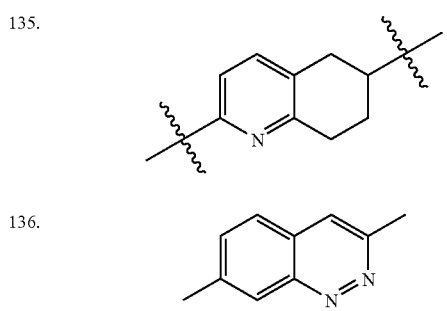 |
| 138. | 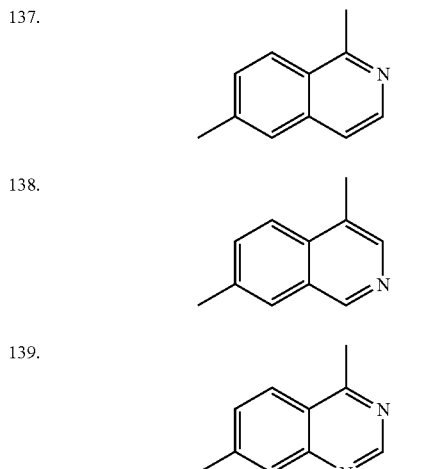 |
| 139. | 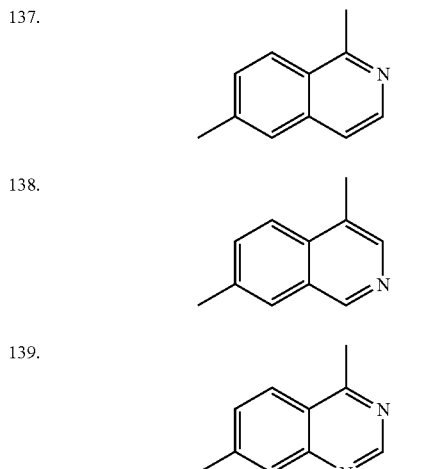 |
The following Examples were prepared similar to the procedures described in either Example 114 or Example 123.

| Example No. | Structure & Name | Mol Formula | Mass |
|---|---|---|---|
| 140 | 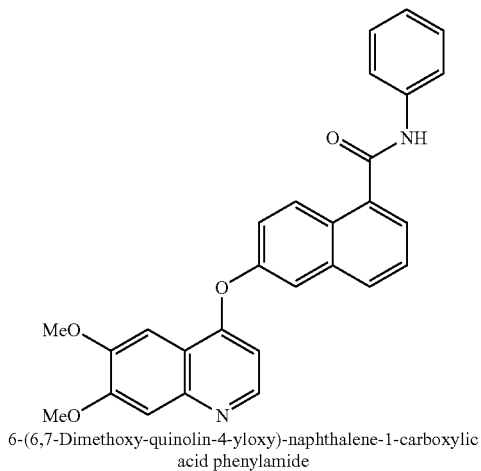<br>6-(6,7-Dimethoxy-quinolin-4-yloxy)-naphthalene-1-carboxylic acid phenylamide | $C_{28}H_{22}N_2O_4$ | 450.50 |
| 141 | 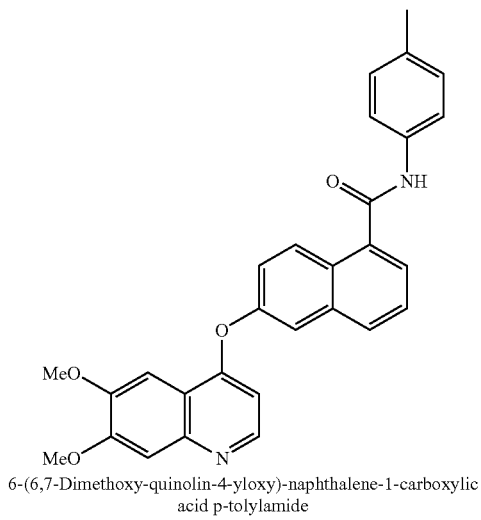<br>6-(6,7-Dimethoxy-quinolin-4-yloxy)-naphthalene-1-carboxylic acid p-tolylamide | $C_{29}H_{24}N_2O_4$ | 464.53 |
| 142 | 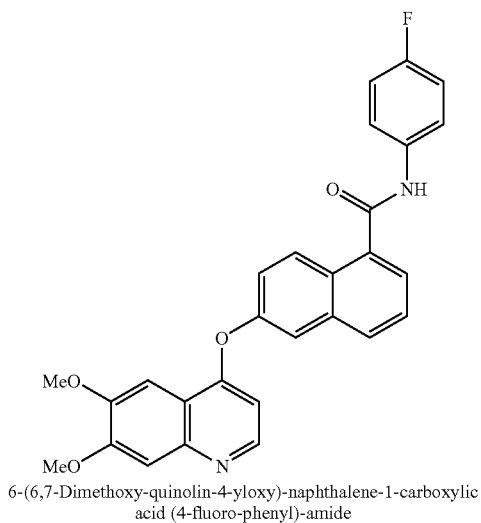<br>6-(6,7-Dimethoxy-quinolin-4-yloxy)-naphthalene-1-carboxylic acid (4-fluoro-phenyl)-amide | $C_{28}H_{21}FN_2O_4$ | 468.49 |

| Example No. | Structure & Name | Mol Formula | Mass |
|---|---|---|---|
| 143 | 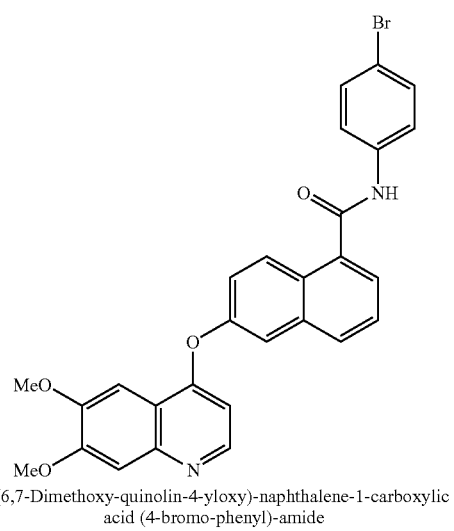<br>6-(6,7-Dimethoxy-quinolin-4-yloxy)-naphthalene-1-carboxylic acid (4-bromo-phenyl)-amide | C$_{28}$H$_{21}$BrN$_2$O$_4$ | 529.39 |
| 144 | 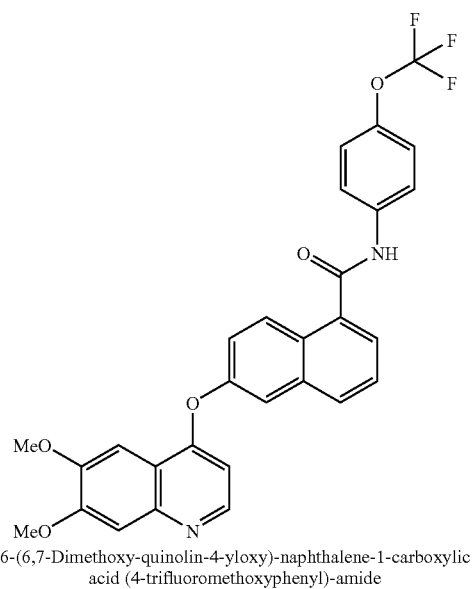<br>6-(6,7-Dimethoxy-quinolin-4-yloxy)-naphthalene-1-carboxylic acid (4-trifluoromethoxyphenyl)-amide | C$_{29}$H$_{21}$F$_3$N$_2$O$_5$ | 534.50 |

| Example No. | Structure & Name | Mol Formula | Mass |
|---|---|---|---|
| 145 | 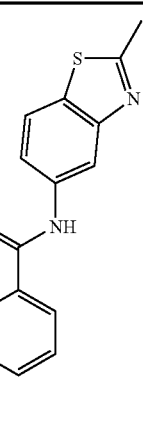<br>6-(6,7-Dimethoxy-quinolin-4-yloxy)-naphthalene-1-carboxylic acid (2-methyl-benzothiazol-5-yl)-amide | C₃₀H₂₃N₃O₄S | 521.60 |
| 146 | 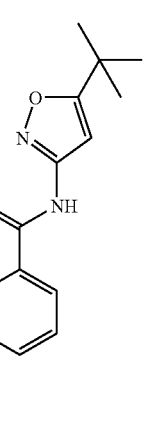<br>6-(6,7-Dimethoxy-quinolin-4-yloxy)-naphthalene-1-carboxylic acid (5-tert-butyl-isoxazol-3-yl)-amide | C₂₉H₂₇N₃O₅ | 497.56 |
| 147 | 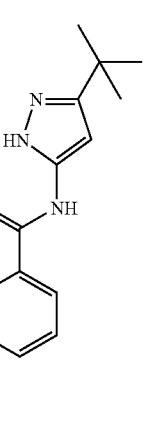<br>6-(6,7-Dimethoxy-quinolin-4-yloxy)-naphthalene-1-carboxylic acid (5-tert-butyl-2H-pyrazol-3-yl)-amide | C₂₉H₂₈N₄O₄ | 496.57 |

| Example No. | Structure & Name | Mol Formula | Mass |
|---|---|---|---|
| 148 | 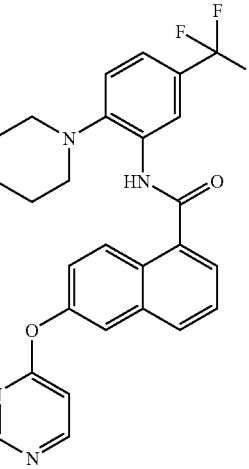<br>6-(2-Amino-pyrimidin-4-yloxy)-naphthalene-1-carboxylic acid (2-piperidin-1-yl-5-trifluoromethyl-phenyl)-amide | $C_{27}H_{24}F_3N_5O_2$ | 507.52 |
| 149 | 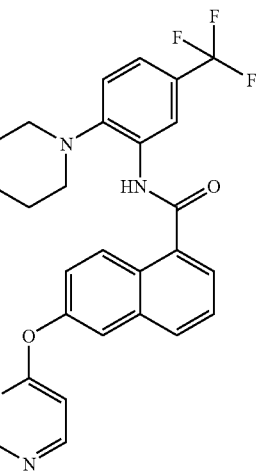<br>6-(2-Methylamino-pyrimidin-4-yloxy)-naphthalene-1-carboxylic acid (2-piperidin-1-yl-5-trifluoromethyl-phenyl)-amide | $C_{28}H_{26}F_3N_5O_2$ | 521.55 |
| 150 | 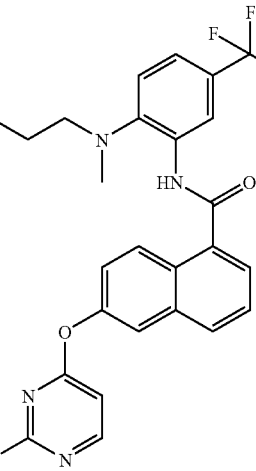<br>6-(2-Amino-pyrimidin-4-yloxy)-naphthalene-1-carboxylic acid {2-[(3-dimethylamino-propyl)-methyl-amino]-5-trifluoromethyl-phenyl}-amide | $C_{28}H_{29}F_3N_6O_2$ | 538.58 |

| Example No. | Structure & Name | Mol Formula | Mass |
|---|---|---|---|
| 151 | 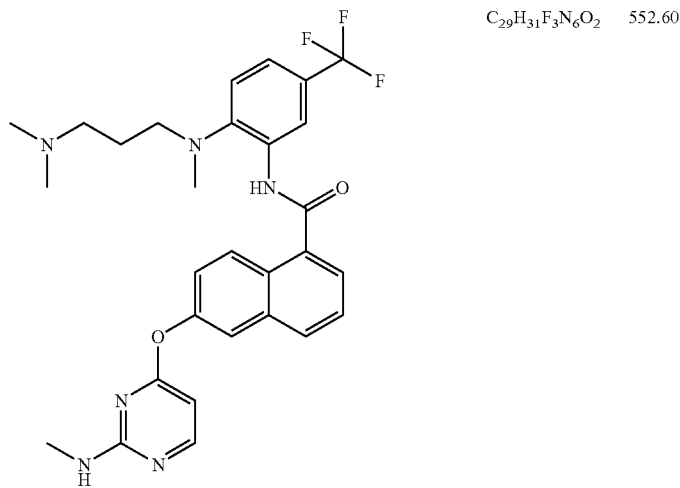<br>6-(2-Methylamino-pyrimidin-4-yloxy)-naphthalene-1-carboxylic acid {2-[(3-dimethylamino-propyl)-methyl-amino]-5-trifluoromethyl-phenyl}-amide | $C_{29}H_{31}F_3N_6O_2$ | 552.60 |
| 152 | 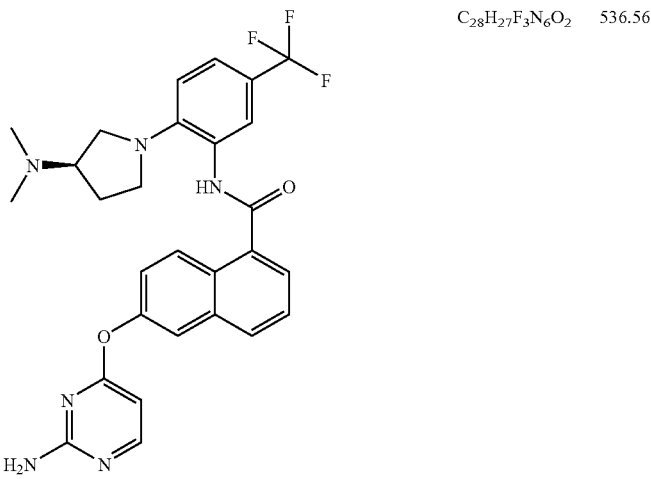<br>6-(2-Amino-pyrimidin-4-yloxy)-naphthalen-1-carboxylic acid [2-(3-dimethylamino-pyrrolidin-1-yl)-5-trifluoromethyl-phenyl]-amide | $C_{28}H_{27}F_3N_6O_2$ | 536.56 |

| Example No. | Structure & Name | Mol Formula | Mass |
|---|---|---|---|
| 153 | 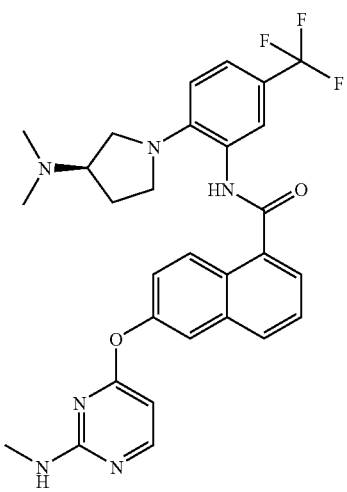<br>6-(2-Methylamino-pyrimidin-4-yloxy)-naphthalen-1-carboxylic acid [2-(3-dimethylamino-pyrrolidin-1-yl)-5-trifluoromethyl-phenyl]-amide | $C_{29}H_{29}F_3N_6O_2$ | 550.59 |
| 154 | 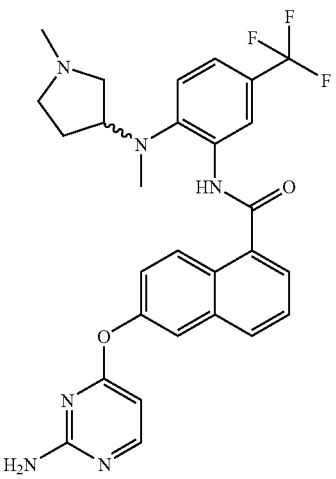<br>6-(2-Amino-pyrimidin-4-yloxy)-naphthalene-1-carboxylic acid {2-[methyl(1-methyl-pyrrolidin-3-yl)-amino]-5-trifluoromethyl-phenyl}-amide | $C_{28}H_{27}F_3N_6O_2$ | 536.56 |

| Example No. | Structure & Name | Mol Formula | Mass |
|---|---|---|---|
| 155 | 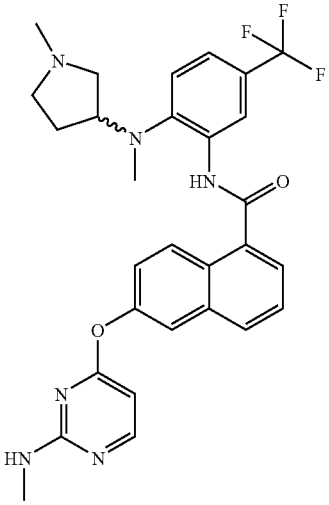<br>6-(2-Methylamino-pyrimidin-4-yloxy)-naphthalene-1-carboxylic acid {2-[methyl(1-methyl-pyrrolidin-3-yl)-amino]-5-trifluoromethyl-phenyl}-amide | $C_{29}H_{29}F_3N_6O_2$ | 550.59 |
| 156 | 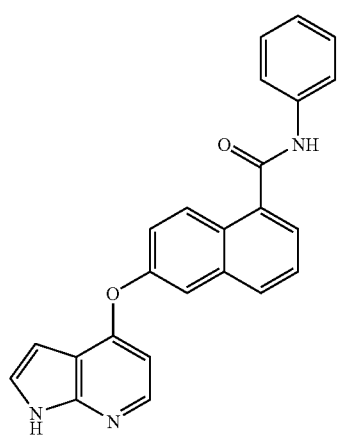<br>6-(1H-Pyrrolo[2,3-b]pyridin-4-yloxy)-naphthalene-1-carboxylic acid phenylamide | $C_{24}H_{17}N_3O_2$ | 379.42 |
| 157 | 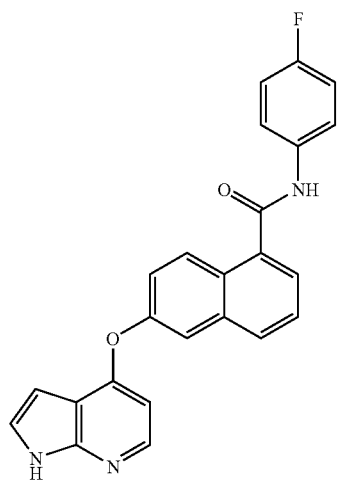<br>6-(1H-Pyrrolo[2,3-b]pyridin-4-yloxy)-naphthalene-1-carboxylic acid (4-fluoro-phenyl)-amide | $C_{24}H_{16}FN_3O_2$ | 397.41 |

| Example No. | Structure & Name | Mol Formula | Mass |
|---|---|---|---|
| 158 | 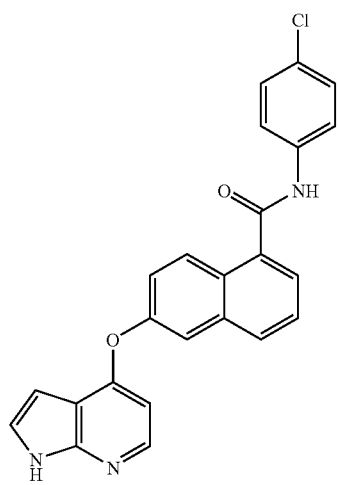<br>6-(1H-Pyrrolo[2,3-b]pyridin-4-yloxy)-naphthalene-1-carboxylic acid (4-chloro-phenyl)-amide | $C_{24}H_{16}ClN_3O_2$ | 413.87 |
| 159 | 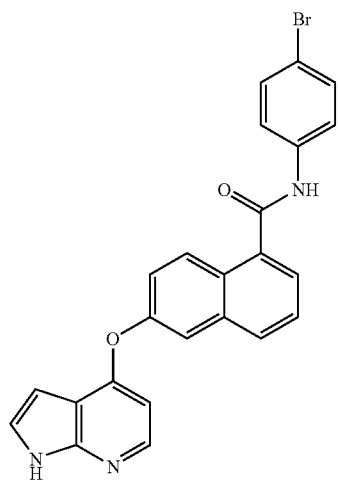<br>6-(1H-Pyrrolo[2,3-b]pyridin-4-yloxy)-naphthalene-1-carboxylic acid (4-bromo-phenyl)-amide | $C_{24}H_{16}BrN_3O_2$ | 458.32 |
| 160 | 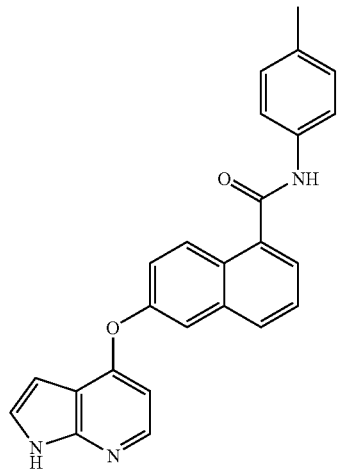<br>6-(1H-Pyrrolo[2,3-b]pyridin-4-yloxy)-naphthalene-1-carboxylic acid p-tolylamide | $C_{25}H_{19}N_3O_2$ | 393.45 |

| Example No. | Structure & Name | Mol Formula | Mass |
|---|---|---|---|
| 161 | 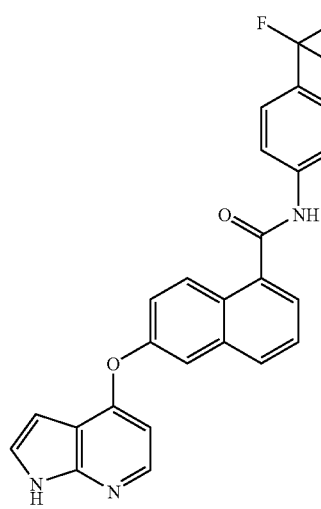<br>6-(1H-Pyrrolo[2,3-b]pyridin-4-yloxy)-naphthalene-1-carboyxlic acid (4-trifluoromethyl-phenyl)-amide | $C_{25}H_{16}F_3N_3O_2$ | 447.42 |
| 162 | 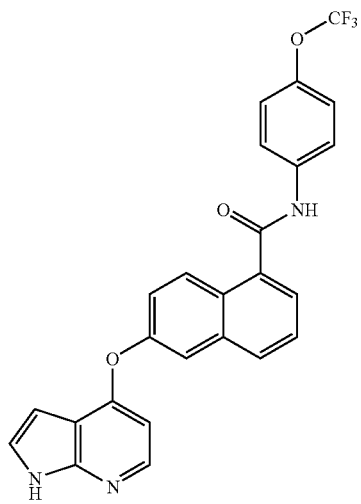<br>6-(1H-Pyrrolo[2,3-b]pyridin-4-yloxy)-naphthalene-1-carboxylic acid (4-trifluoromethoxy-phenyl)-amide | $C_{25}H_{16}F_3N_3O_3$ | 463.42 |
| 163 | 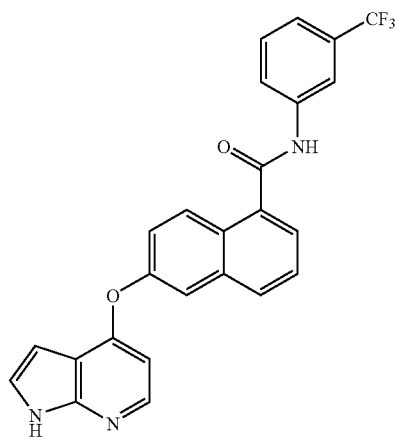<br>6-(1H-Pyrrolo[2,3-b]pyridin-4-yloxy)-naphthalen-1-carboxylic acid (3-trifluoromethyl-phenyl)-amide | $C_{25}H_{16}F_3N_3O_2$ | 447.42 |

| Example No. | Structure & Name | Mol Formula | Mass |
|---|---|---|---|
| 164 | 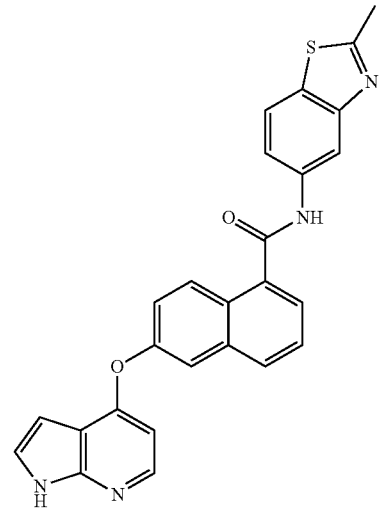<br>6-(1H-Pyrrolo[2,3-b]pyridin-4-yloxy)-naphthalene-1-carboxylic acid (2-methyl-benzothiazol-5-yl)-amide | C<sub>26</sub>H<sub>18</sub>N<sub>4</sub>O<sub>2</sub>S | 450.52 |
| 165 | 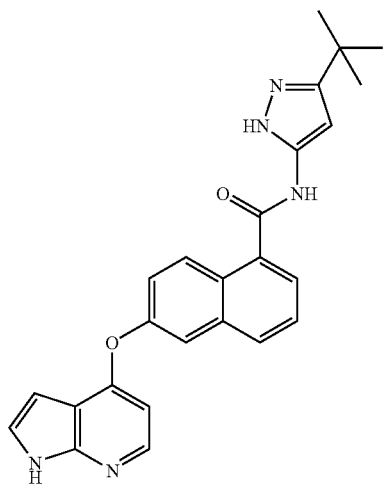<br>6-(1H-Pyrrolo[2,3-b]pyridin-4-yloxy)-naphthalene-1-carboxylic acid (5-tert-butyl-2H-pyrazol-3-yl)-amide | C<sub>25</sub>H<sub>23</sub>N<sub>5</sub>O<sub>2</sub> | 425.49 |
| 166 | 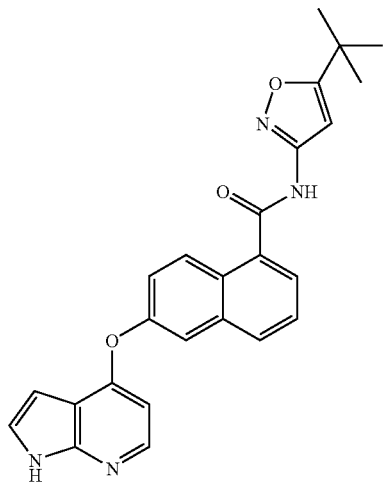<br>6-(1H-Pyrrolo[2,3-b]pyridin-4-yloxy)-naphthalene-1-carboxylic acid (5-tert-butyl-isoxazol-3-yl)-amide | C<sub>25</sub>H<sub>22</sub>N<sub>4</sub>O<sub>3</sub> | 426.48 |

| Example No. | Structure & Name | Mol Formula | Mass |
|---|---|---|---|
| 167 | 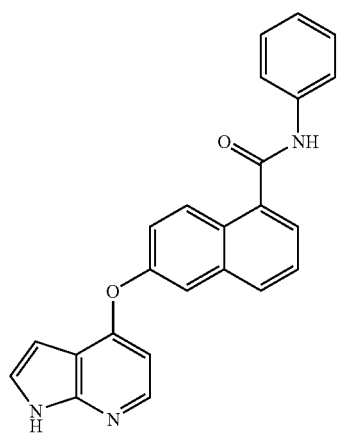<br>6-(1H-Pyrazolo[3,4-b]pyridin-4-yloxy)-naphthalene-1-carboxylic acid phenylamide | $C_{23}H_{16}N_4O_2$ | 380.41 |
| 168 | 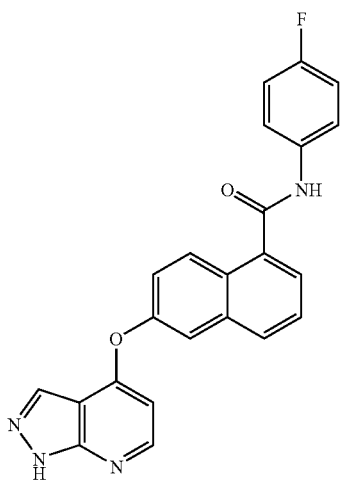<br>6-(1H-Pyrazolo[3,4-b]pyridin-4-yloxy)-naphthalene-1-carboxylic acid (4-fluoro-phenyl)-amide | $C_{23}H_{15}FN_4O_2$ | 398.40 |
| 169 | 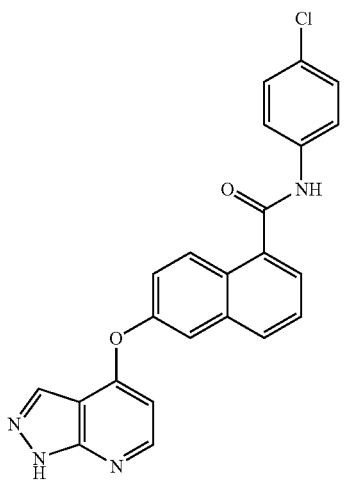<br>6-(1H-Pyrazolo[3,4-b]pyridin-4-yloxy)-naphthalene-1-carboxylic acid (4-chloro-phenyl)-amide | $C_{23}H_{15}ClN_4O_2$ | 414.85 |

| Example No. | Structure & Name | Mol Formula | Mass |
|---|---|---|---|
| 170 | 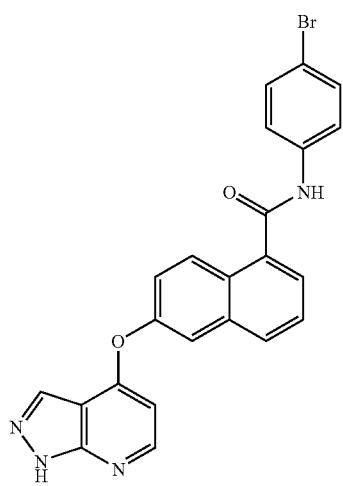<br>6-(1H-Pyrazolo[3,4-b]pyridin-4-yloxy)-naphthalene-1-carboxylic acid (4-bromo-phenyl)-amide | $C_{23}H_{15}BrN_4O_2$ | 459.31 |
| 171 | 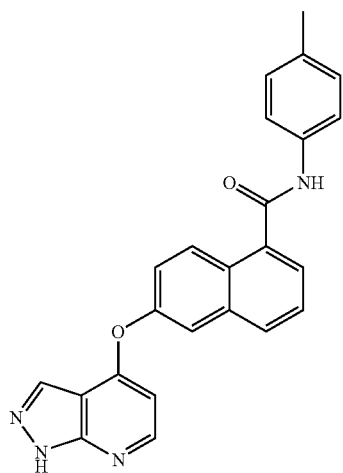<br>6-(1H-Pyrazolo[3,4-b]pyridin-4-yloxy)-naphthalene-1-carboxylic acid p-tolylamide | $C_{24}H_{18}N_4O_2$ | 394.44 |
| 172 | 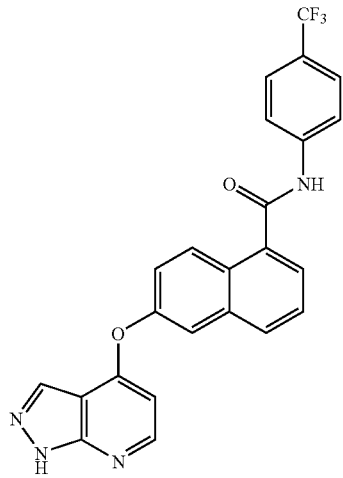<br>6-(1H-Pyrazolo[3,4-b]pyridin-4-yloxy)-naphthalene-1-carboxylic acid (4-trifluoromethyl-phenyl)-amide | $C_{24}H_{15}F_3N_4O_2$ | 448.41 |

| Example No. | Structure & Name | Mol Formula | Mass |
|---|---|---|---|
| 173 | 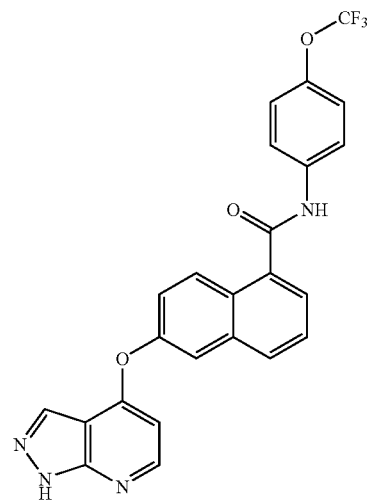<br>6-(1H-Pyrazolo[3,4-b]pyridin-4-yloxy)-naphthalene-1-carboxylic acid (4-trifluoromethoxy-phenyl)-amide | $C_{24}H_{15}F_3N_4O_3$ | 464.41 |
| 174 | 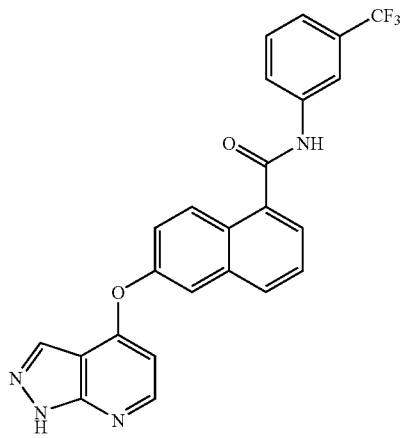<br>6-(1H-Pyrazolo[3,4-b]pyridin-4-yloxy)-naphthalene-1-carboxylic acid (3-trifluoromethyl-phenyl)-amide | $C_{24}H_{15}F_3N_4O_2$ | 448.41 |
| 175 | 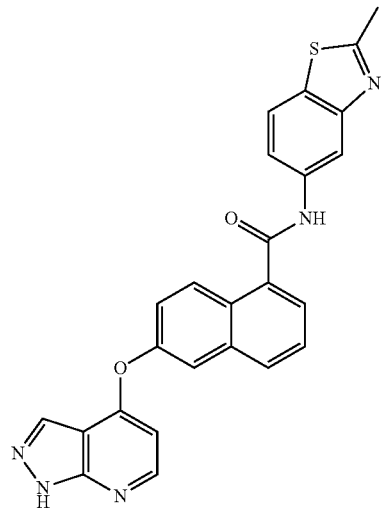<br>6-(1H-Pyrazolo[3,4-b]pyridin-4-yloxy)-naphthalene-1-carboxylic acid (2-methyl-benzothiazol-5-yl)-amide | $C_{25}H_{17}N_5O_2S$ | 451.51 |

| Example No. | Structure & Name | Mol Formula | Mass |
|---|---|---|---|
| 176 | 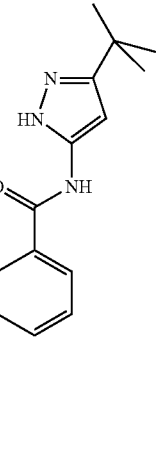<br>6-(1H-Pyrazolo[3,4-b]pyridin-4-yloxy)-naphthalene-1-carboxylic acid (5-tert-butyl-2H-pyrazol-3-yl)-amide | $C_{24}H_{22}N_6O_2$ | 426.48 |
| 177 | 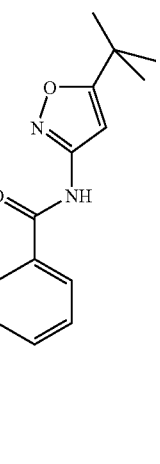<br>6-(1H-Pyrazolo[3,4-b]pyridin-4-yloxy)-naphthalene-1-carboxylic acid (5-tert-butyl-isoxazol-3-yl)-amide | $C_{24}H_{21}N_5O_3$ | 427.47 |
| 178 | 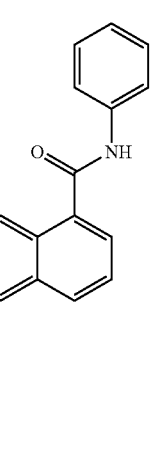<br>4-[5-(4-Fluoro-phenylcarbamoyl)-naphthalen-2-yloxy]-pyridin-2-carboxylic acid methylamide | $C_{24}H_{19}N_3O_3$ | 397.44 |

| Example No. | Structure & Name | Mol Formula | Mass |
|---|---|---|---|
| 179 | 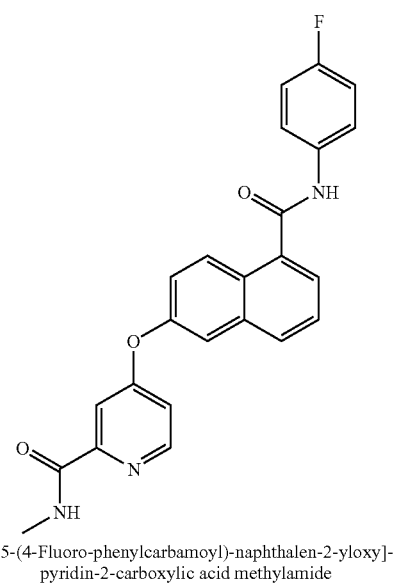<br>4-[5-(4-Fluoro-phenylcarbamoyl)-naphthalen-2-yloxy]-pyridin-2-carboxylic acid methylamide | $C_{24}H_{18}FN_3O_3$ | 415.43 |
| 180 | 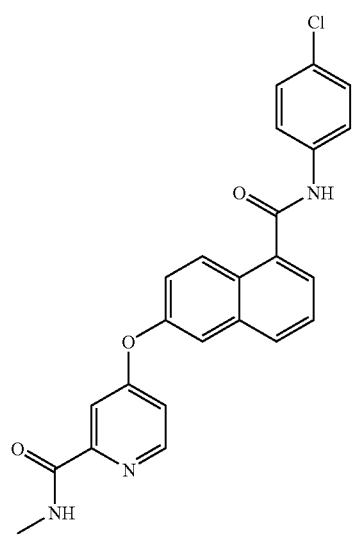<br>4-[5-(4-Chloro-phenylcarbamoyl)-naphthalen-2-yloxy]-pyridin-2-carboxylic acid methylamide | $C_{24}H_{18}ClN_3O_3$ | 431.88 |

| Example No. | Structure & Name | Mol Formula | Mass |
|---|---|---|---|
| 181 | 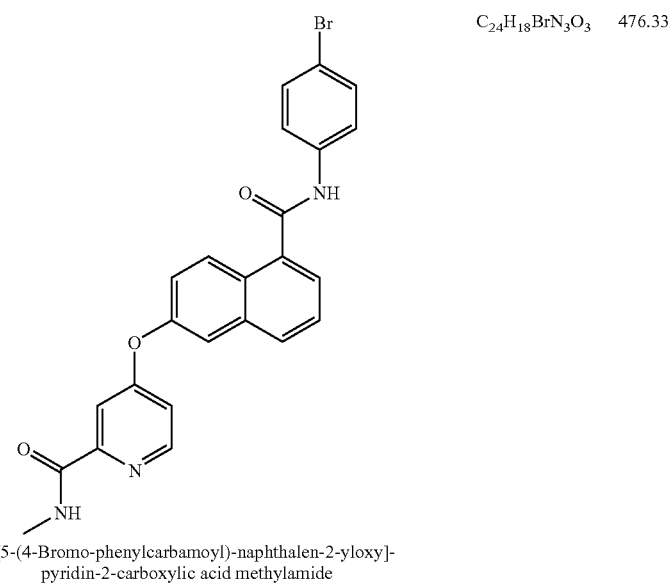<br>4-[5-(4-Bromo-phenylcarbamoyl)-naphthalen-2-yloxy]-pyridin-2-carboxylic acid methylamide | $C_{24}H_{18}BrN_3O_3$ | 476.33 |
| 182 | 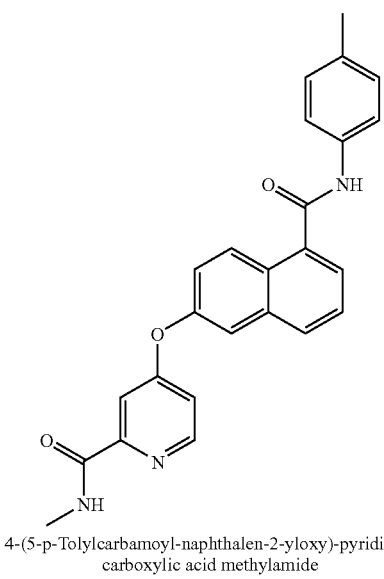<br>4-(5-p-Tolylcarbamoyl-naphthalen-2-yloxy)-pyridin-2-carboxylic acid methylamide | $C_{25}H_{21}N_3O_3$ | 411.46 |

| Example No. | Structure & Name | Mol Formula | Mass |
|---|---|---|---|
| 183 | 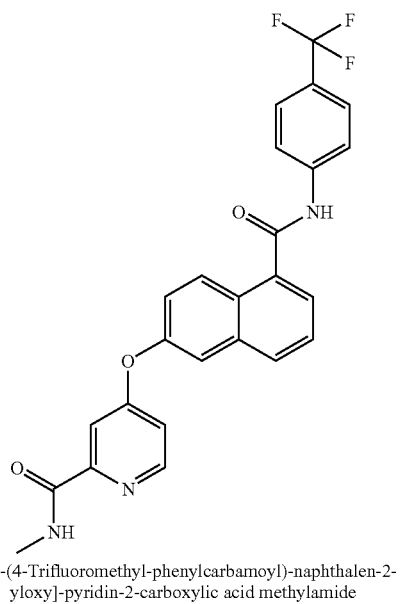<br>4-[5-(4-Trifluoromethyl-phenylcarbamoyl)-naphthalen-2-yloxy]-pyridin-2-carboxylic acid methylamide | $C_{25}H_{18}F_3N_3O_3$ | 465.44 |
| 184 | 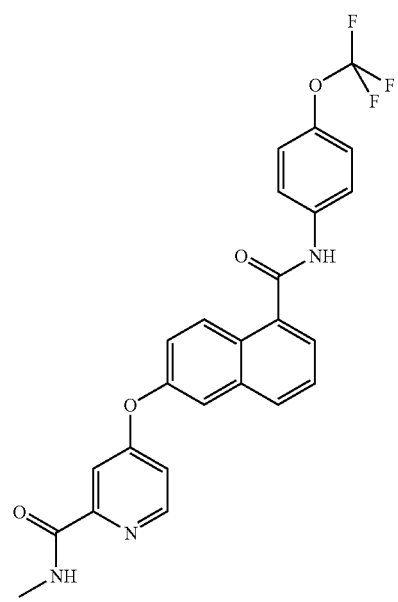<br>4-[5-(4-Trifluoromethoxy-phenylcarbamoyl)-naphthalen-2-yloxy]-pyridin-2-carboxylic acid methylamide | $C_{25}H_{18}F_3N_3O_4$ | 481.44 |

| Example No. | Structure & Name | Mol Formula | Mass |
|---|---|---|---|
| 185 | 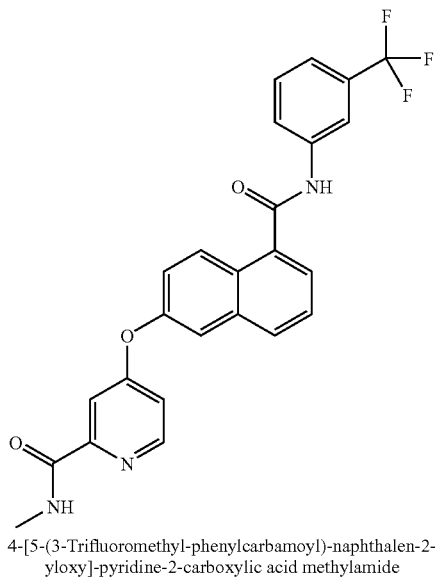<br>4-[5-(3-Trifluoromethyl-phenylcarbamoyl)-naphthalen-2-yloxy]-pyridine-2-carboxylic acid methylamide | $C_{25}H_{18}F_3N_3O_3$ | 465.44 |
| 186 | 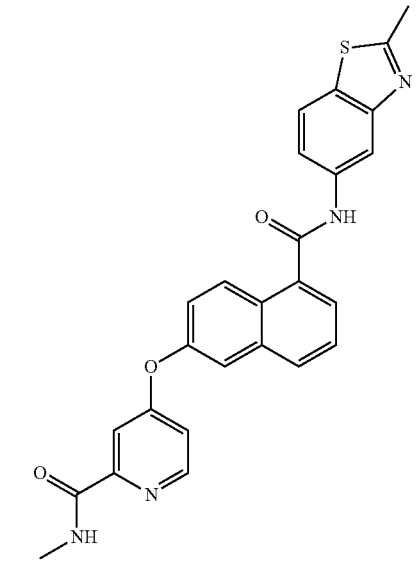<br>4-[5-(2-Methyl-benzothiazol-5-ylcarbamoyl)-naphthalen-2-yloxy]-pyridine-2-carboxylic acid methylamide | $C_{26}H_{20}N_4O_3S$ | 468.54 |

| Example No. | Structure & Name | Mol Formula | Mass |
|---|---|---|---|
| 187 | 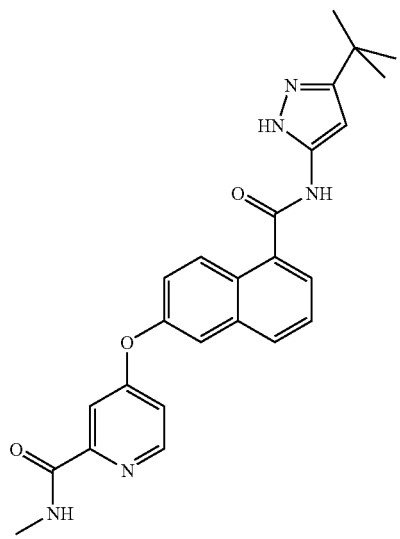<br>4-[5-(5-tert-Butyl-2H-pyrazol-3-ylcarbamoyl)-naphthalen-2-yloxy]-pyridin-2-carboxylic acid methylamide | $C_{25}H_{25}N_5O_3$ | 443.51 |
| 188 | 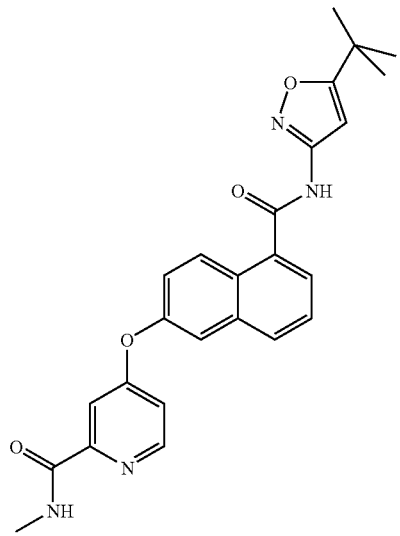<br>4-[5-(5-tert-Butyl-isoxazol-3-ylcarbamoyl)-naphthalen-2-yloxy]-pyridine-2-carboxylic acid methylamide | $C_{25}H_{24}N_4O_4$ | 444.49 |

| Example No. | Structure & Name | Mol Formula | Mass |
|---|---|---|---|
| 189 | 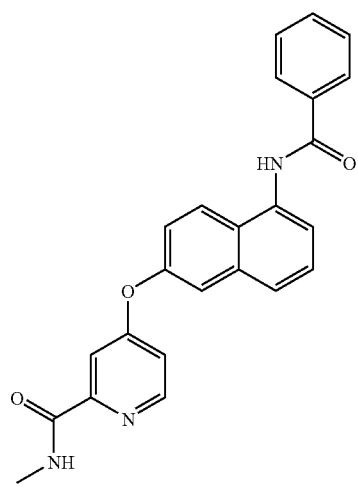<br>4-(5-Benzoylamino-naphthalen-2-yloxy)-pyridin-2-carboxylic acid methylamide | C_{24}H_{19}N_3O_3 | 397.44 |
| 190 | 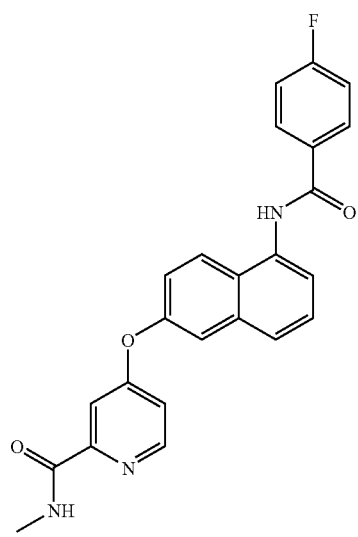<br>4-[5-(4-Fluoro-benzoylamino)-naphthalen-2-yloxy]-pyridine-2-carboxylic acid methylamide | C_{24}H_{18}FN_3O_3 | 415.43 |

| Example No. | Structure & Name | Mol Formula | Mass |
|---|---|---|---|
| 191 | 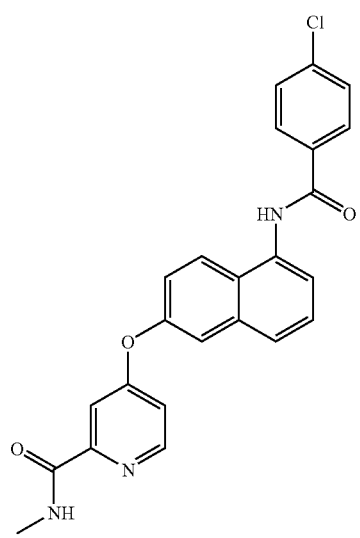<br>4-[5-(4-Chloro-benzoylamino)-naphthalen-2-yloxy]-pyridine-2-carboxylic acid methylamide | $C_{24}H_{18}ClN_3O_3$ | 431.88 |
| 192 | 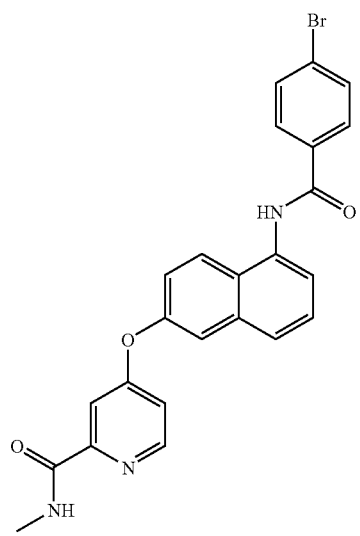<br>4-[5-(4-Bromo-benzoylamino)-naphthalen-2-yloxy]-pyridine-2-carboxylic acid methylamide | $C_{24}H_{18}BrN_3O_3$ | 476.33 |

| Example No. | Structure & Name | Mol Formula | Mass |
|---|---|---|---|
| 193 | 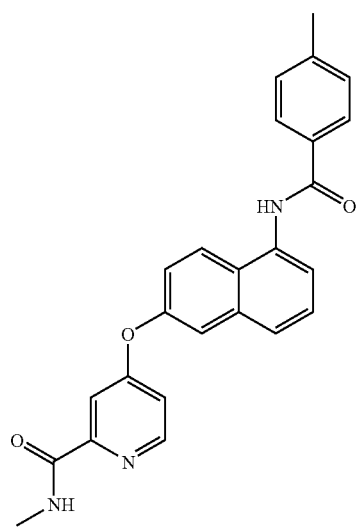<br>4-[5-(4-Methyl-benzoylamino)-naphthalen-2-yloxy]-pyridine-2-carboxylic acid methylamide | $C_{25}H_{21}N_3O_3$ | 411.46 |
| 194 | 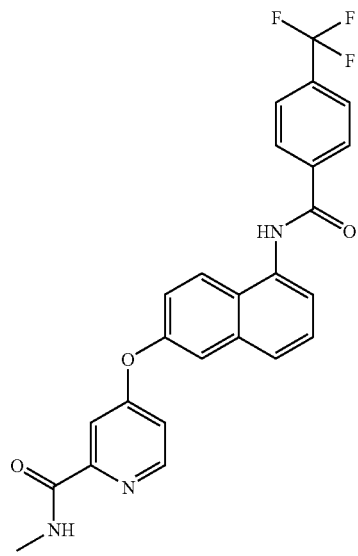<br>4-[5-(4-Trifluoromethyl-benzoylamino)-naphthalen-2-yloxy]-pyridine-2-carboxylic acid methylamide | $C_{25}H_{18}F_3N_3O_3$ | 465.44 |

| Example No. | Structure & Name | Mol Formula | Mass |
|---|---|---|---|
| 195 | 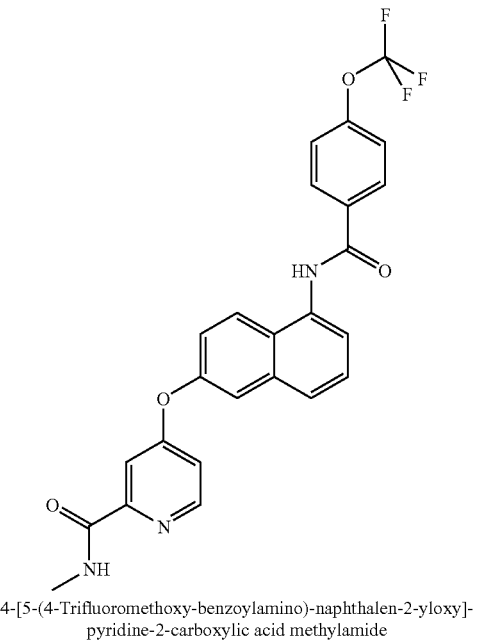<br>4-[5-(4-Trifluoromethoxy-benzoylamino)-naphthalen-2-yloxy]-pyridine-2-carboxylic acid methylamide | $C_{25}H_{18}F_3N_3O_4$ | 481.44 |
| 196 | 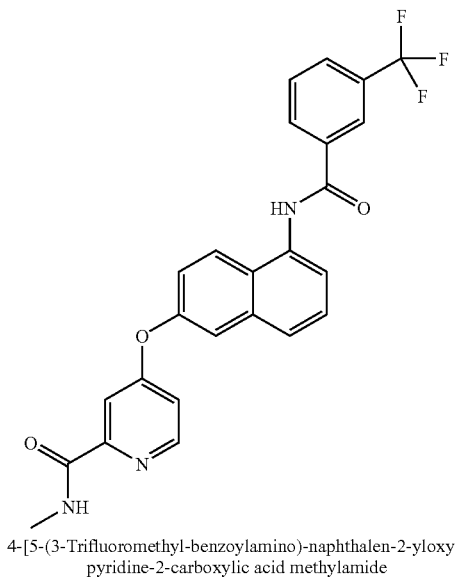<br>4-[5-(3-Trifluoromethyl-benzoylamino)-naphthalen-2-yloxy]-pyridine-2-carboxylic acid methylamide | $C_{25}H_{18}F_3N_3O_3$ | 465.44 |

| Example No. | Structure & Name | Mol Formula | Mass |
|---|---|---|---|
| 197 | 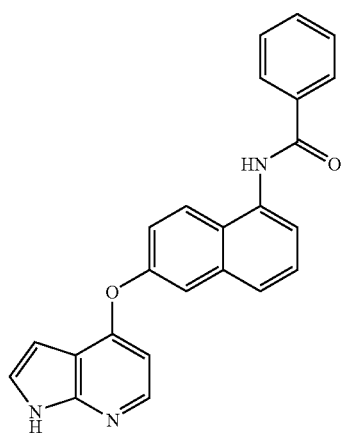<br>N-[6-(1H-Pyrrolo[2,3-b]pyridin-4-yloxy)-naphthalen-1-yl]-benzamide | $C_{24}H_{17}N_3O_2$ | 379.42 |
| 198 | 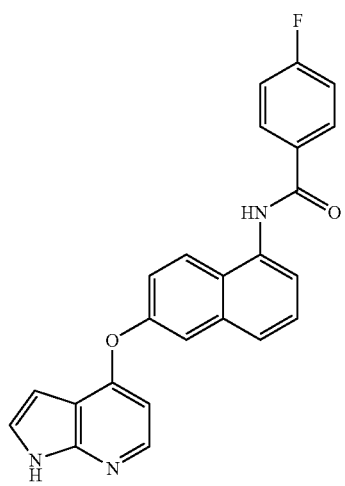<br>4-Fluoro-N-[6-(1H-pyrrolo[2,3-b]pyridin-4-yloxy)-naphthalen-1-yl]-benzamide | $C_{24}H_{16}FN_3O_2$ | 397.41 |
| 199 | 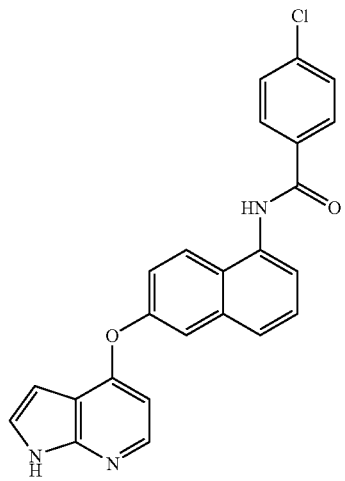<br>4-Chloro-N-[6-(1H-pyrrolo[2,3-b]pyridin-4-yloxy)-naphthalen-1-yl]-benzamide | $C_{24}H_{16}ClN_3O_2$ | 413.87 |

| Example No. | Structure & Name | Mol Formula | Mass |
|---|---|---|---|
| 200 | 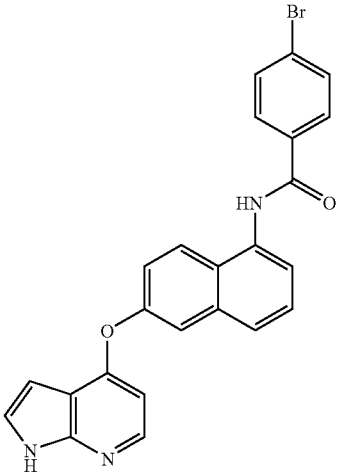<br>4-bromo-N-[6-(1H-pyrrolo[2,3-b]pyridin-4-yloxy)-naphthalen-1-yl]-benzamide | $C_{24}H_{16}BrN_3O_2$ | 458.32 |
| 201 | 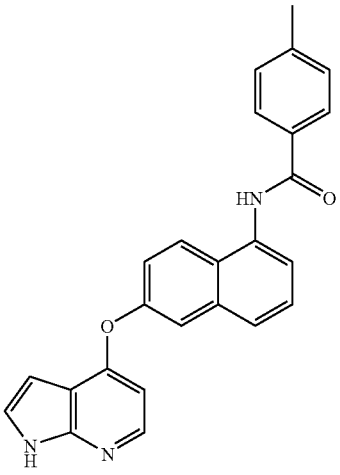<br>4-methyl-N-[6-(1H-pyrrolo[2,3-b]pyridin-4-yloxy)-naphthalen-1-yl]-benzamide | $C_{25}H_{19}N_3O_2$ | 393.45 |
| 202 | 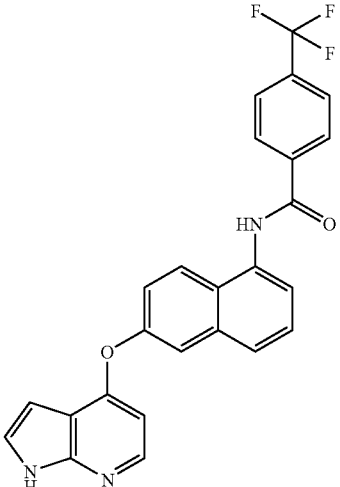<br>4-trifluoromethyl-N-[6-(1H-pyrrolo[2,3-b]pyridin-4-yloxy)-naphthalen-1-yl]-benzamide | $C_{25}H_{16}F_3N_3O_2$ | 447.42 |

| Example No. | Structure & Name | Mol Formula | Mass |
|---|---|---|---|
| 203 | 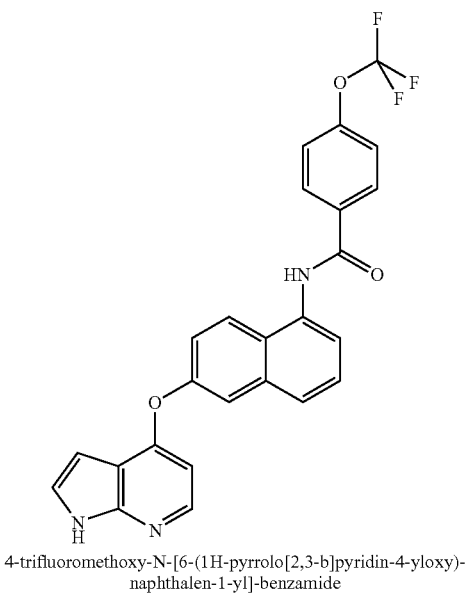<br>4-trifluoromethoxy-N-[6-(1H-pyrrolo[2,3-b]pyridin-4-yloxy)-naphthalen-1-yl]-benzamide | $C_{25}H_{16}F_3N_3O_3$ | 463.42 |
| 204 | 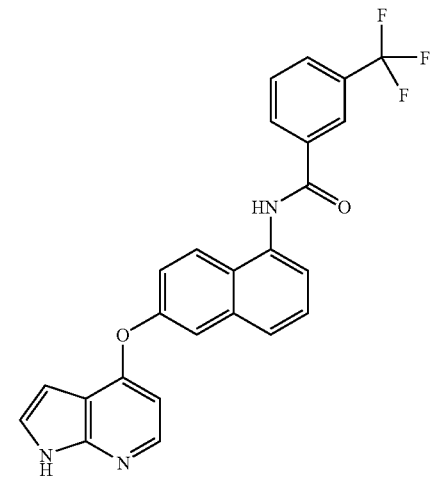<br>3-trifluoromethyl-N-[6-(1H-pyrrolo[2,3-b]pyridin-4-yloxy)-naphthalen-1-yl]-benzamide | $C_{25}H_{16}F_3N_3O_2$ | 447.42 |
| 205 | 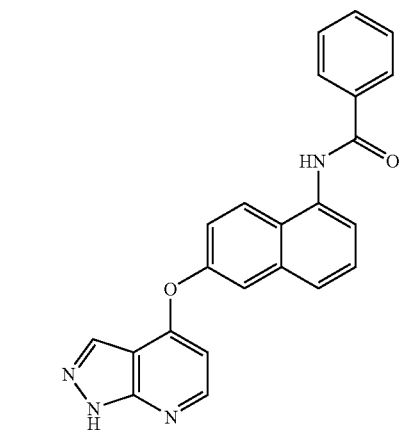<br>N-[6-(1H-Pyrazolo[3,4-b]pyridin-4-yloxy)-naphthalen-1-yl]-benzamide | $C_{23}H_{16}N_4O_2$ | 380.41 |

| Example No. | Structure & Name | Mol Formula | Mass |
|---|---|---|---|
| 206 | 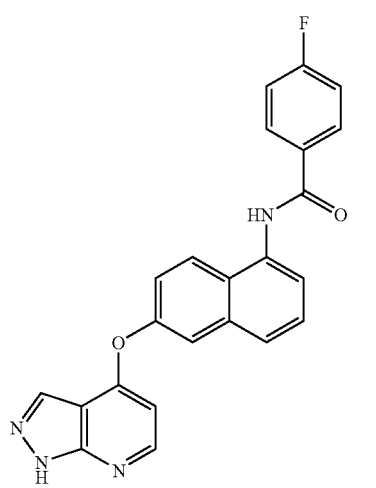<br>4-Fluoro-N-[6-(1H-pyrazolo[3,4-b]pyridin-4-yloxy)-naphthalen-1-yl]-benzamide | $C_{23}H_{15}FN_4O_2$ | 398.40 |
| 207 | 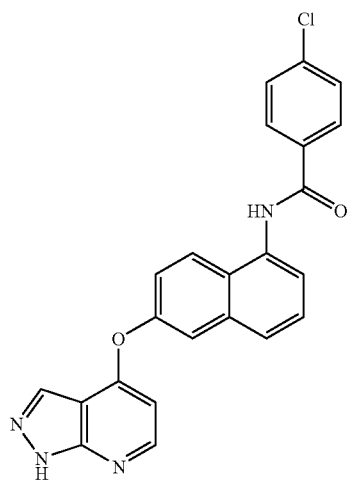<br>4-chloro-N-[6-(1H-pyrazolo[3,4-b]pyridin-4-yloxy)-naphthalen-1-yl]-benzamide | $C_{23}H_{15}ClN_4O_2$ | 414.85 |
| 208 | 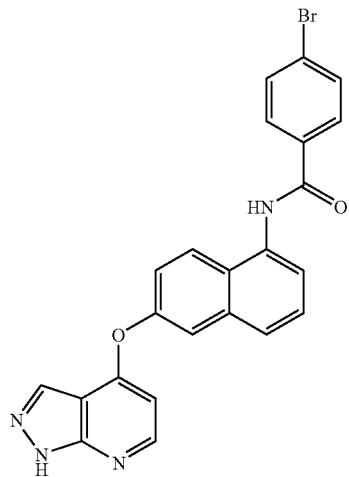<br>4-bromo-N-[6-(1H-pyrazolo[3,4-b]pyridin-4-yloxy)-naphthalen-1-yl]-benzamide | $C_{23}H_{15}BrN_4O_2$ | 459.31 |

| Example No. | Structure & Name | Mol Formula | Mass |
|---|---|---|---|
| 209 | 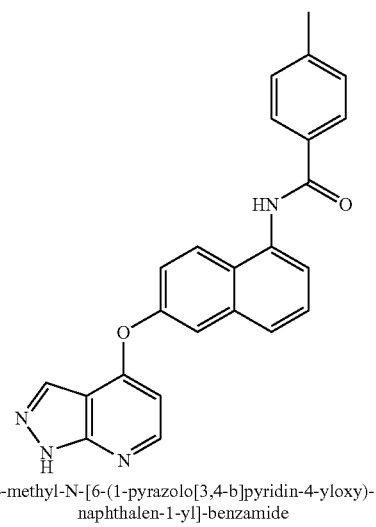<br>4-methyl-N-[6-(1-pyrazolo[3,4-b]pyridin-4-yloxy)-naphthalen-1-yl]-benzamide | $C_{24}H_{18}N_4O_2$ | 394.44 |
| 210 | 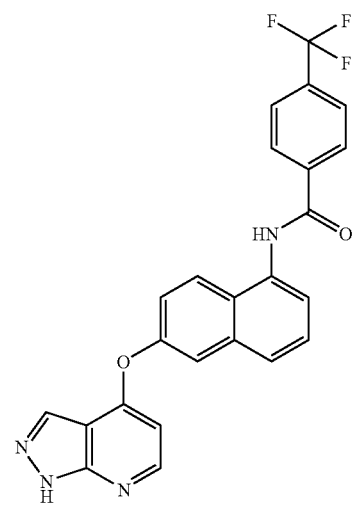<br>4-trifluoromethyl-N-[6-(1H-pyrazolo[3,4-b]pyridin-4-yloxy)-naphthalen-1-yl]-benzamide | $C_{24}H_{15}F_3N_4O_2$ | 448.41 |

| Example No. | Structure & Name | Mol Formula | Mass |
|---|---|---|---|
| 211 | 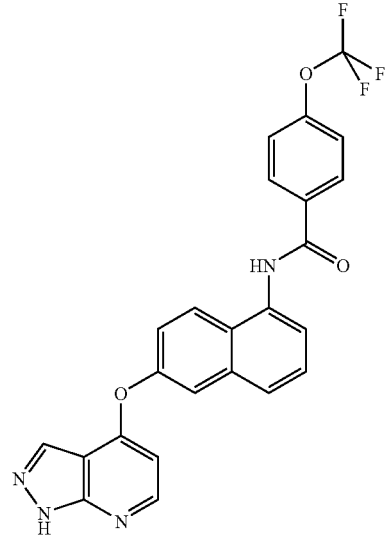<br>4-trifluoromethoxy-N-[6-(1H-pyrazolo[3,4-b]pyridin-4-yloxy)-naphthalen-1-yl]-benzamide | $C_{24}H_{15}F_3N_4O_3$ | 464.41 |
| 212 | 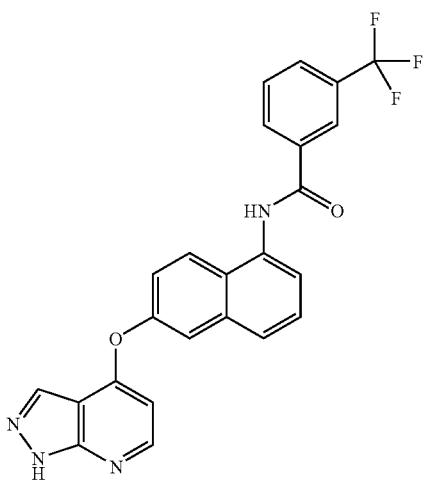<br>3-trifluoromethyl-N-[6-(1H-pyrazolo[3,4-b]pyridin-4-yloxy)-naphthalen-1-yl]-benzamide | $C_{24}H_{15}F_3N_4O_2$ | 448.41 |
| 213 | 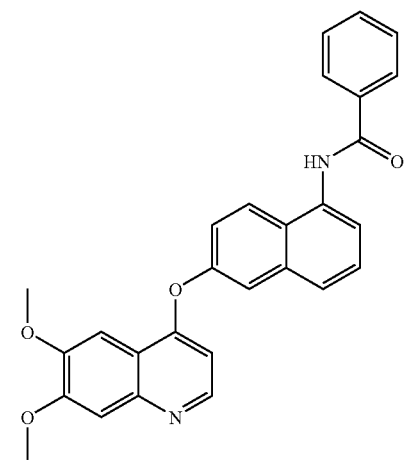<br>N-[6-(6,7-Dimethoxy-quinolin-4-yloxy)-naphthalen-1-yl]-benzamide | $C_{28}H_{22}N_2O_4$ | 450.50 |

| Example No. | Structure & Name | Mol Formula | Mass |
|---|---|---|---|
| 214 | 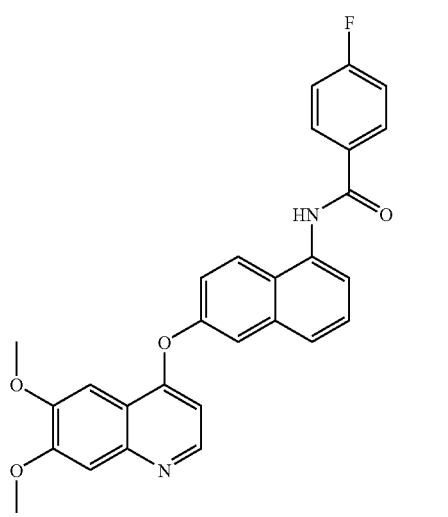<br>N-[6-(6,7-Dimethoxy-quinolin-4-yloxy)-naphthalen-1-yl]-4-fluoro-benzamide | $C_{28}H_{21}FN_2O_4$ | 468.49 |
| 215 | 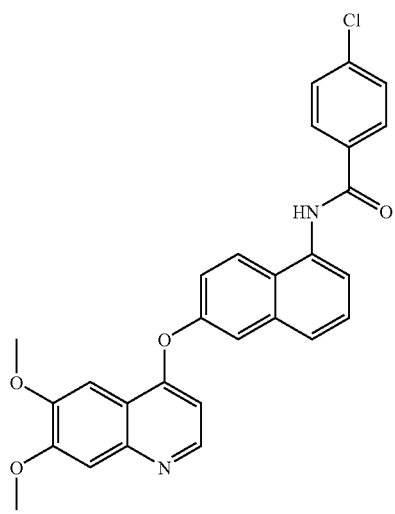<br>N-[6-(6,7-Dimethoxy-quinolin-4-yloxy)-naphthalen-1-yl]-4-chloro-benzamide | $C_{28}H_{21}ClN_2O_4$ | 484.94 |

| Example No. | Structure & Name | Mol Formula | Mass |
|---|---|---|---|
| 216 | 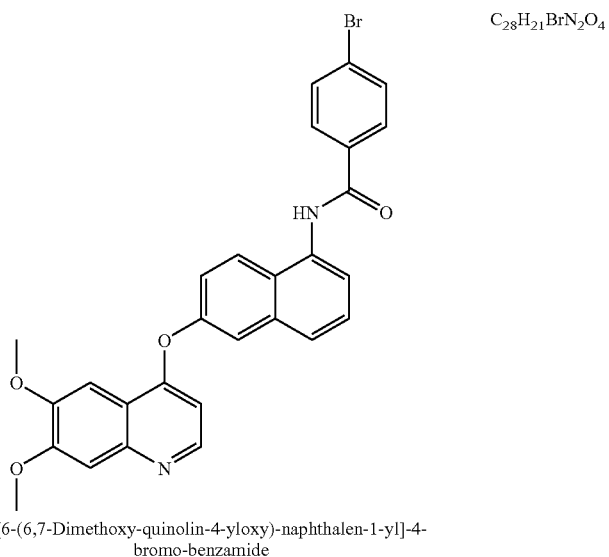<br>N-[6-(6,7-Dimethoxy-quinolin-4-yloxy)-naphthalen-1-yl]-4-bromo-benzamide | $C_{28}H_{21}BrN_2O_4$ | 529.39 |
| 217 | 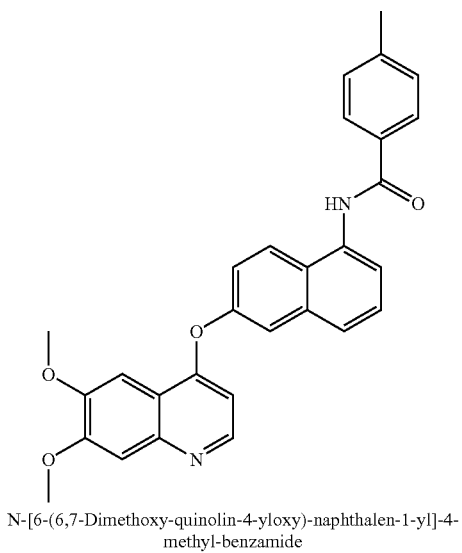<br>N-[6-(6,7-Dimethoxy-quinolin-4-yloxy)-naphthalen-1-yl]-4-methyl-benzamide | $C_{29}H_{24}N_2O_4$ | 464.53 |

| Example No. | Structure & Name | Mol Formula | Mass |
|---|---|---|---|
| 218 | 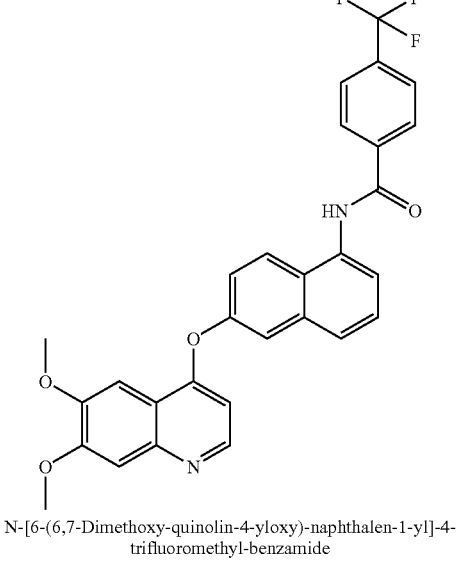<br>N-[6-(6,7-Dimethoxy-quinolin-4-yloxy)-naphthalen-1-yl]-4-trifluoromethyl-benzamide | $C_{29}H_{21}F_3N_2O_4$ | 518.50 |
| 219 | 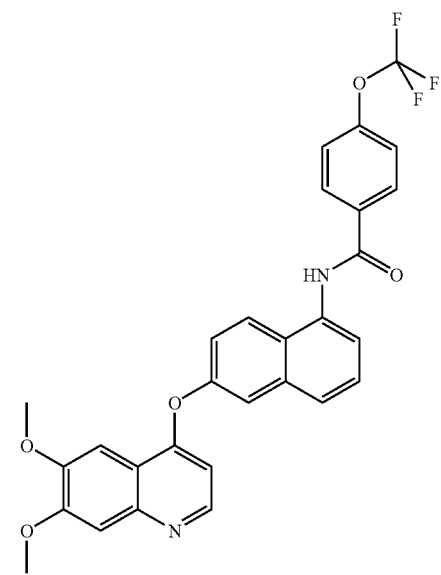<br>N-[6-(6,7-Dimethoxy-quinolin-4-yloxy)-naphthalen-1-yl]-4-trifluoromethoxy-benzamide | $C_{29}H_{21}F_3N_2O_5$ | 534.50 |

| Example No. | Structure & Name | Mol Formula | Mass |
|---|---|---|---|
| 220 | <br>N-[6-(6,7-Dimethoxy-quinolin-4-yloxy)-naphthalen-1-yl]-3-trifluoromethyl-benzamide | $C_{29}H_{21}F_3N_2O_4$ | 518.50 |
| 221 | 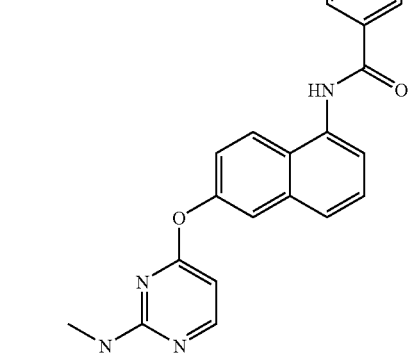<br>N-[6-(2-Methylamino-pyrimidin-4-yloxy)-naphthalen-1-yl]-benzamide | $C_{22}H_{18}N_4O_2$ | 370.41 |
| 222 | 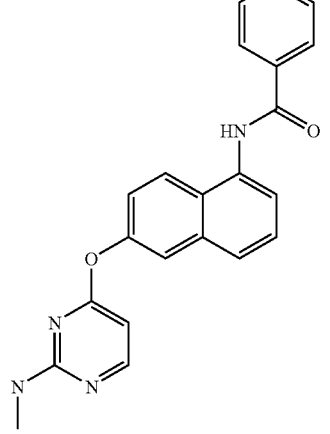<br>4-Fluoro-N-[6-(2-methylamino-pyrimidin-4-yloxy)-naphthalen-1-yl]-benzamide | $C_{22}H_{17}FN_4O_2$ | 388.40 |

| Example No. | Structure & Name | Mol Formula | Mass |
|---|---|---|---|
| 223 | 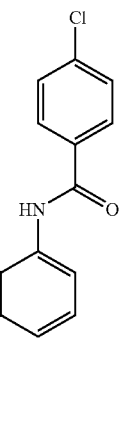<br>4-chloro-N-[6-(2-methylamino-pyrimidin-4-yloxy)-naphthalen-1-yl]-benzamide | $C_{22}H_{17}ClN_4O_2$ | 404.86 |
| 224 | 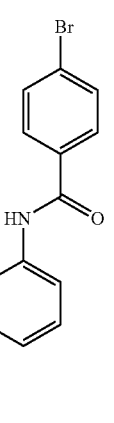<br>4-bromo-N-[6-(2-methylamino-pyrimidin-4-yloxy)-naphthalen-1-yl]-benzamide | $C_{22}H_{17}BrN_4O_2$ | 449.31 |
| 225 | 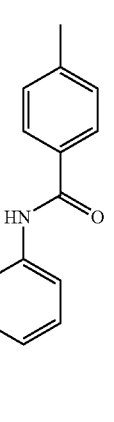<br>4-methyl-N-[6-(2-methylamino-pyrimidin-4-yloxy)-naphthalen-1-yl]-benzamide | $C_{23}H_{20}N_4O_2$ | 384.44 |

| Example No. | Structure & Name | Mol Formula | Mass |
|---|---|---|---|
| 226 | 4-Trifluoromethyl-N-[6-(2-methylamino-pyrimidin-4-yloxy)-naphthaolen-1-yl]-benzamide | C₂₃H₁₇F₃N₄O₂ | 438.41 |
| 227 | 4-Trifluoromethoxy-N-[6-(2-methylamino-pyrimidin-4-yloxy)-naphthalen-1-yl]-benzamide | C₂₃H₁₇F₃N₄O₃ | 454.41 |

| Example No. | Structure & Name | Mol Formula | Mass |
|---|---|---|---|
| 228 | 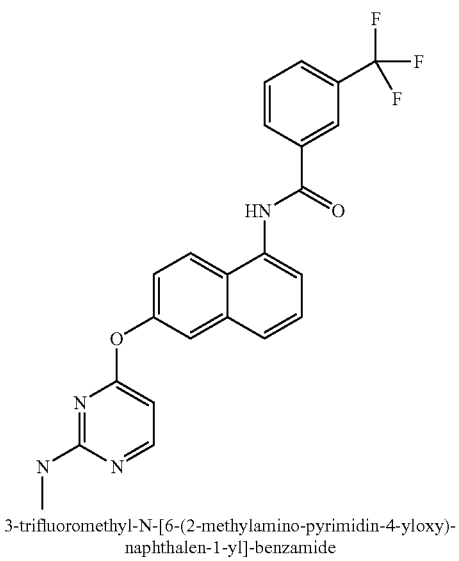<br>3-trifluoromethyl-N-[6-(2-methylamino-pyrimidin-4-yloxy)-naphthalen-1-yl]-benzamide | $C_{23}H_{17}F_3N_4O_2$ | 438.41 |
| 229 | 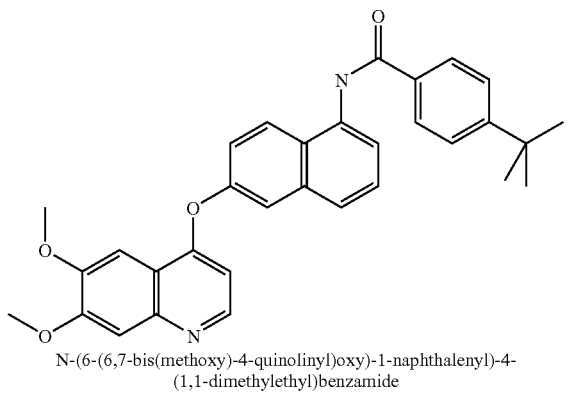<br>N-(6-(6,7-bis(methoxy)-4-quinolinyl)oxy)-1-naphthalenyl)-4-(1,1-dimethylethyl)benzamide | $C_{32}H_{30}N_2O_4$ | 506.22 |
| 230 | 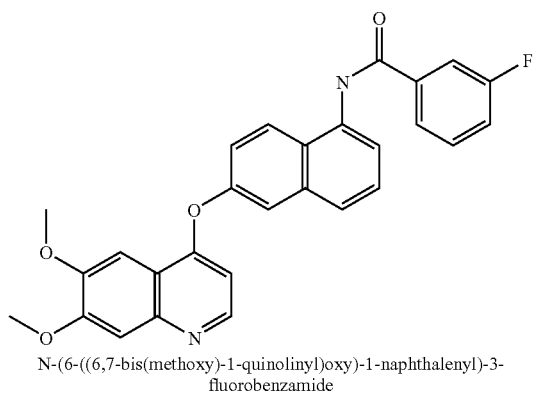<br>N-(6-((6,7-bis(methoxy)-1-quinolinyl)oxy)-1-naphthalenyl)-3-fluorobenzamide | $C_{28}H_{21}FN_2O_4$ | 468.15 |

| Example No. | Structure & Name | Mol Formula | Mass |
|---|---|---|---|
| 231 | 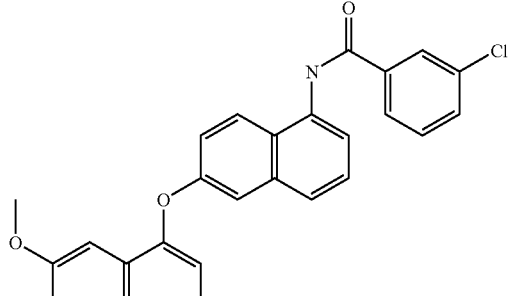<br>N-(6-((6,7-bis(methoxy)-1-quinolinyl)oxy)-1-naphthalenyl)-3-chlorobenzamide | $C_{28}H_{21}ClN_2O_4$ | 484.12 |
| 232 | 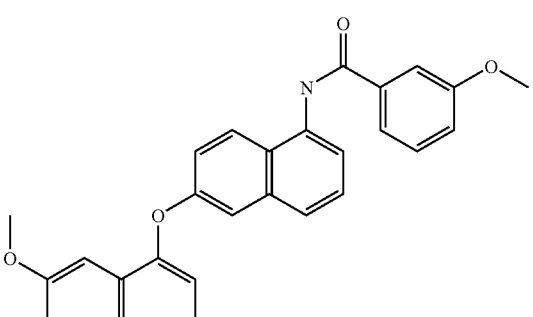<br>N-(6-((6,7-bis(methoxy)-4-quinolinyl)oxy)-1-naphthalenyl)-3-(methyloxy)benzamide | $C_{29}H_{24}N_2O_5$ | 480.17 |
| 233 | 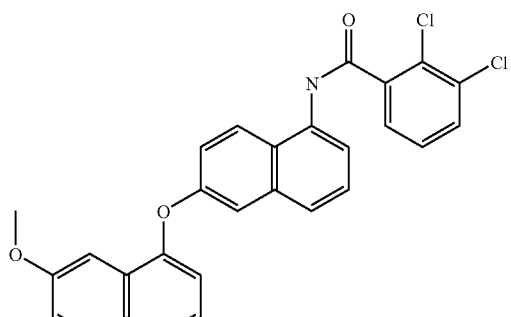<br>N-(6-((6,7-bis(methoxy)-4-quinolinyl)oxy)-1-naphthalenyl)-2,3-dichlorobenzamide | $C_{28}H_{20}Cl_2N_2O_4$ | 518.08 |
| 234 | 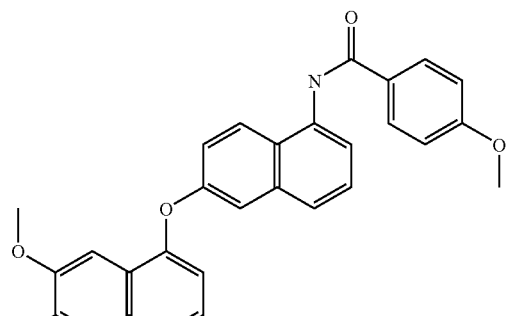<br>N-(6-((6,7-bis(methoxy)-4-quinolinyl)oxy)-1-naphthalenyl)-4-(methyloxy)benzamide | $C_{29}H_{24}N_2O_5$ | 480.17 |

| Example No. | Structure & Name | Mol Formula | Mass |
|---|---|---|---|
| 235 | 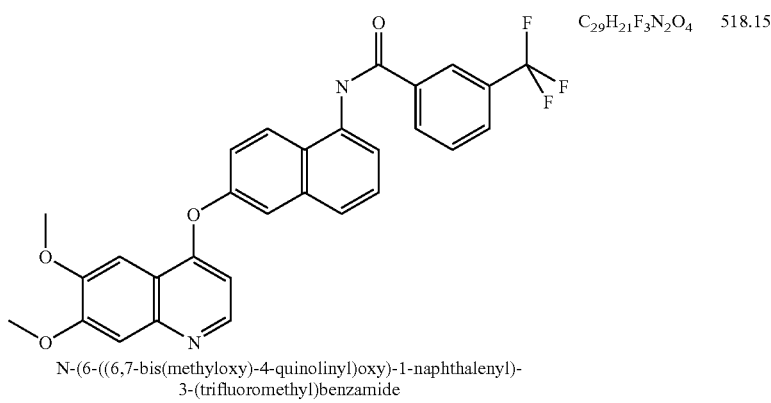<br>N-(6-((6,7-bis(methyloxy)-4-quinolinyl)oxy)-1-naphthalenyl)-3-(trifluoromethyl)benzamide | C$_{29}$H$_{21}$F$_3$N$_2$O$_4$ | 518.15 |
| 236 | 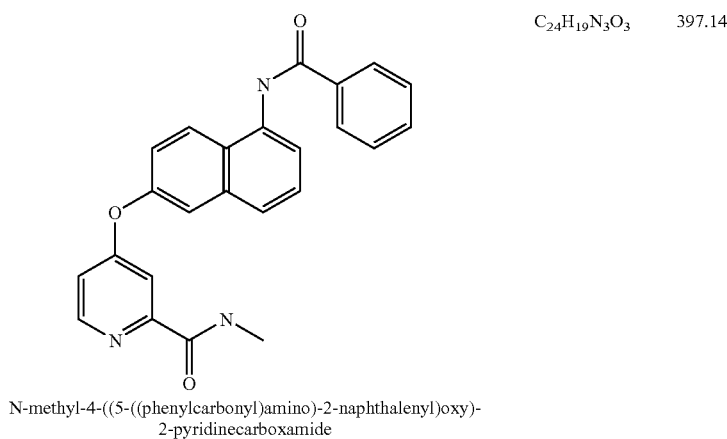<br>N-methyl-4-((5-((phenylcarbonyl)amino)-2-naphthalenyl)oxy)-2-pyridinecarboxamide | C$_{24}$H$_{19}$N$_3$O$_3$ | 397.14 |
| 237 | 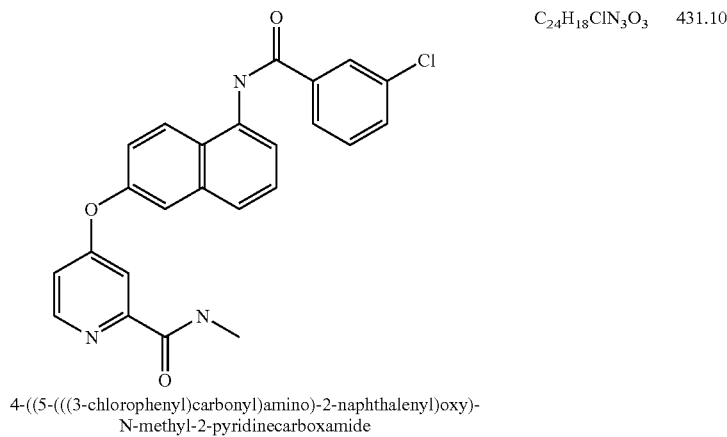<br>4-((5-(((3-chlorophenyl)carbonyl)amino)-2-naphthalenyl)oxy)-N-methyl-2-pyridinecarboxamide | C$_{24}$H$_{18}$ClN$_3$O$_3$ | 431.10 |

| Example No. | Structure & Name | Mol Formula | Mass |
|---|---|---|---|
| 238 | 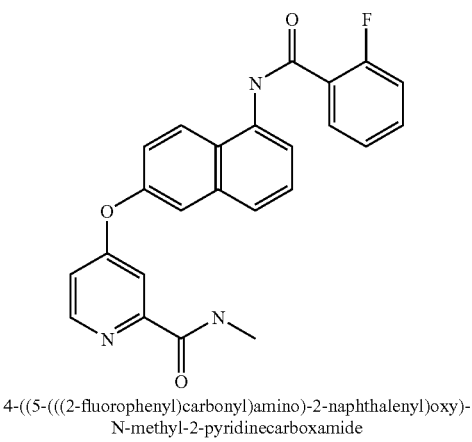<br>4-((5-(((2-fluorophenyl)carbonyl)amino)-2-naphthalenyl)oxy)-N-methyl-2-pyridinecarboxamide | $C_{24}H_{18}FN_3O_3$ | 415.13 |
| 239 | 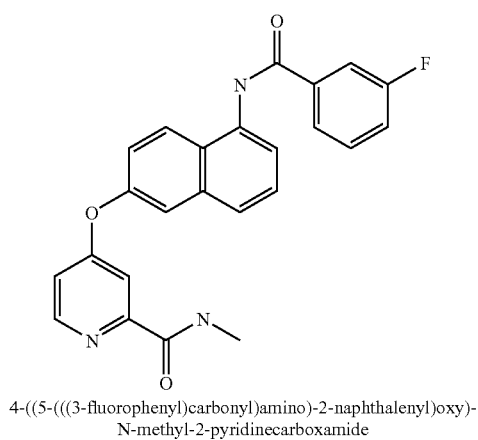<br>4-((5-(((3-fluorophenyl)carbonyl)amino)-2-naphthalenyl)oxy)-N-methyl-2-pyridinecarboxamide | $C_{24}H_{18}FN_3O_3$ | 415.13 |
| 240 | 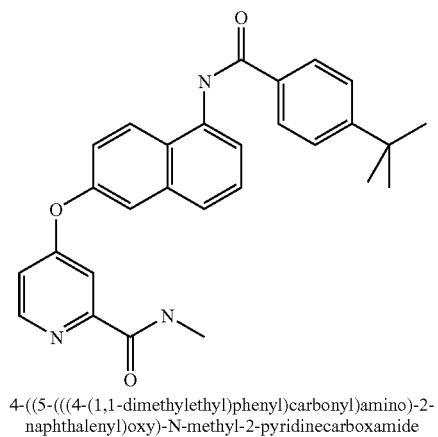<br>4-((5-(((4-(1,1-dimethylethyl)phenyl)carbonyl)amino)-2-naphthalenyl)oxy)-N-methyl-2-pyridinecarboxamide | $C_{28}H_{27}N_3O_3$ | 453.21 |

| Example No. | Structure & Name | Mol Formula | Mass |
|---|---|---|---|
| 241 | 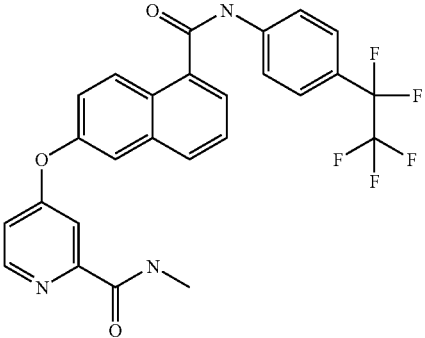 4-((5-(((4-(pentafluoro-ethyl)phenyl)carbonyl)amino)-2-naphthalenyl)oxy)-N-methyl-2-pyridinecarboxamide | $C_{26}H_{18}F_5N_3O_3$ | 515.44 |
| 242 | 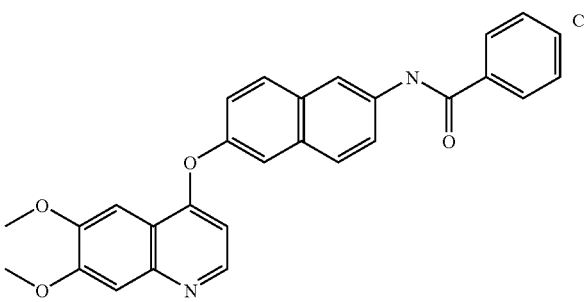 N-(6-((6,7-bis(methyloxy)-4-quinolinyl)methyl)-2-naphthalenyl)benzamide | $C_{29}H_{24}N_2O_3$ | 448.52 |

The following examples were prepared similar to that described above.

| Ex. No. | Structure & Name | Mol Formula | Mass | Mass (M + 1) |
|---|---|---|---|---|
| 243 | 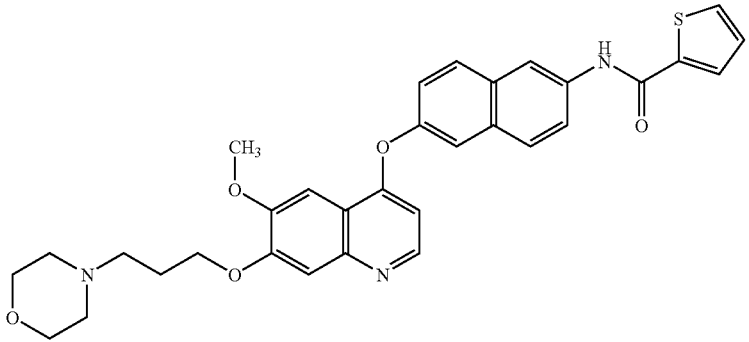 N-(6-(((6-(methoxy)-7-((3-(4-morpholinyl)propyl)oxy)-4-quinolinyl)oxy)-2-naphthalenyl)-2-thiophenecarboxamide | $C_{32}H_{31}N_3O_5S$ | 569 | 570 |

| Ex. No. | Structure & Name | Mol Formula | Mass | Mass (M + 1) |
|---|---|---|---|---|
| 244 | 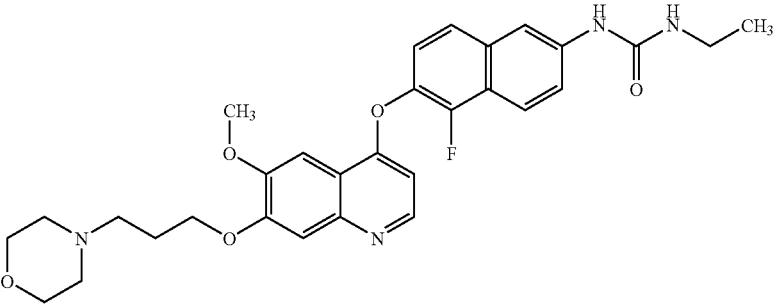<br>N-ethyl-N'-(5-fluoro-6-((6-(methoxy)-7-((3-(4-morpholinyl)propyl)oxy)-4-quinolinyl)oxy)-2-naphthalenyl)urea | $C_{30}H_{33}FN_4O_5$ | 548 | 549 |
| 245 | 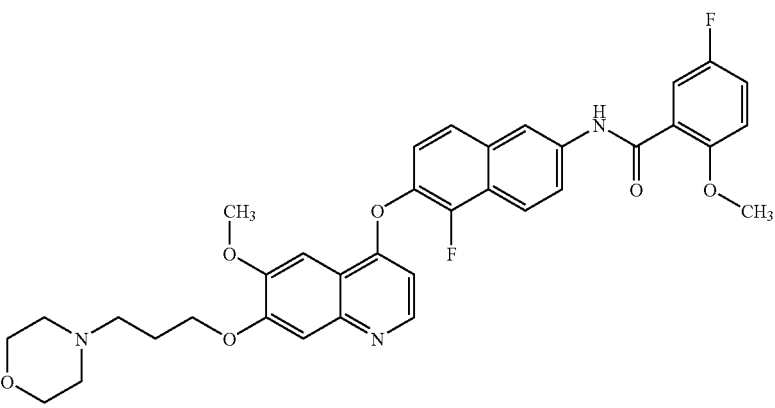<br>5-fluoro-N-(5-fluoro-6-((6-(methoxy)-7-((3-(4-morpholinyl)propyl)oxy)-4-quinolinyl)oxy)-2-naphthalenyl)-2-(methoxy)benzamide | $C_{35}H_{33}F_2N_3O_6$ | 629 | 630 |
| 246 | 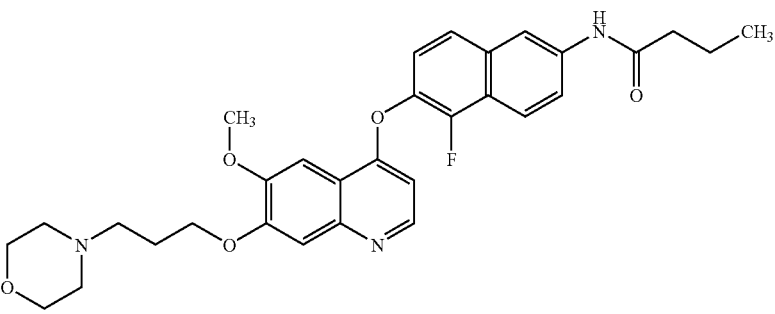<br>N-(5-fluoro-6-((6-(methoxy)-7-((3-(4-morpholinyl)propyl)oxy)-4-quinolinyl)oxy)-2-naphthalenyl)butanamide | $C_{31}H_{34}FN_3O_5$ | 547 | 548 |
| 247 | 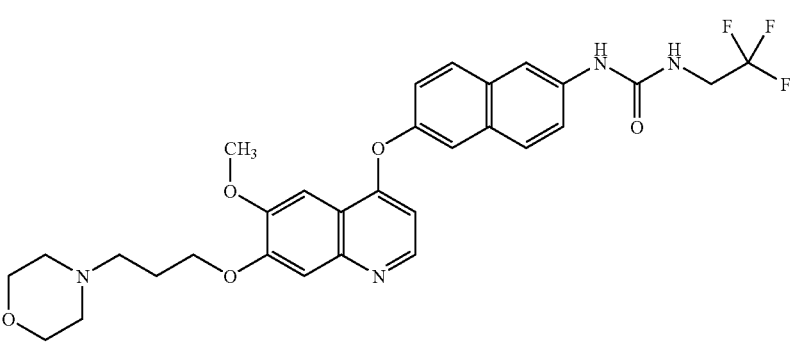<br>N-(5-fluoro-6-((6-(methoxy)-7-((3-(4-morpholinyl)propyl)oxy)-4-quinolinyl)oxy)-2-naphthalenyl)-N'-(2,2,2-trifluoroethyl)urea | $C_{30}H_{30}F_4N_4O_5$ | 602 | 603 |

| Ex. No. | Structure & Name | Mol Formula | Mass | Mass (M + 1) |
|---|---|---|---|---|
| 248 | 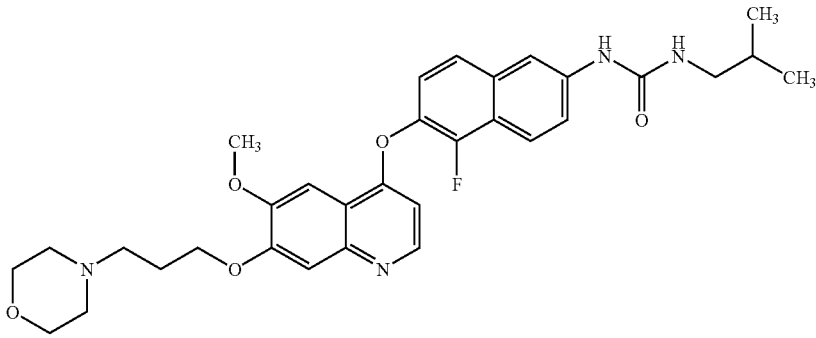<br>N-(5-fluoro-6-((6-(methoxy)-7-((3-(4-morpholinyl)propyl)oxy)-4-quinolinyl)oxy)-2-naphthalenyl)-N'-(2-methylpropyl)urea | $C_{32}H_{37}FN_4O_5$ | 576 | 577 |
| 249 | 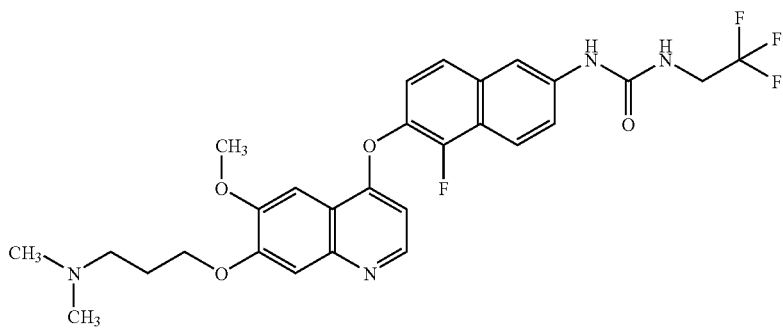<br>N-(6-((7-((3-(dimethylamino)propyl)oxy)-6-(methoxy)-4-quinolinyl)oxy)-5-fluoro-2-naphthalenyl)-N'-(2,2,2-trifluoroethyl)urea | $C_{28}H_{28}F_4N_4O_4$ | 560 | 561 |
| 250 | 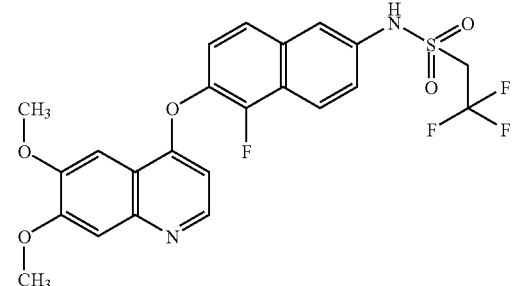<br>N-(6-((6,7-bis(methoxy)-4-quinolinyl)oxy)-5-fluoro-2-naphthalenyl)-2,2,2-trifluoroethanesulfonamide | $C_{23}H_{18}F_4N_2O_5S$ | 510 | 511 |
| 251 | 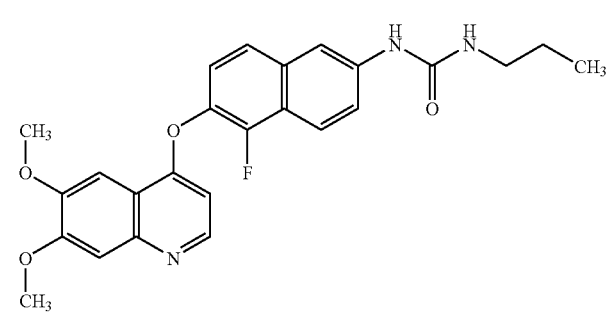<br>N-(6-((6,7-bis(methoxy)-4-quinolinyl)oxy)-5-fluoro-2-naphthalenyl)-N'-propylurea | $C_{25}H_{24}FN_3O_4$ | 449 | 450 |

| Ex. No. | Structure & Name | Mol Formula | Mass | Mass (M + 1) |
|---|---|---|---|---|
| 252 | 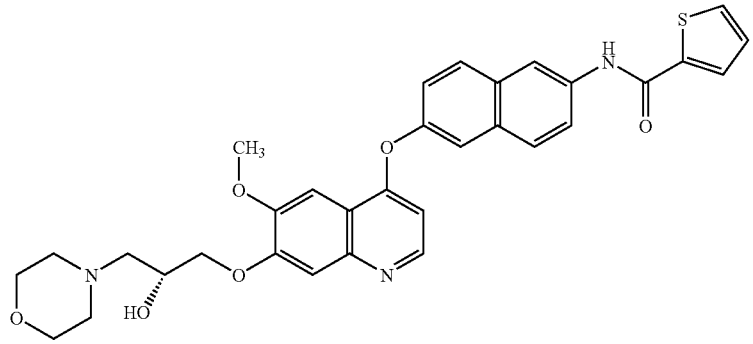<br>N-(6-((7-(((2R)-2-hydroxy-3-(4-morpholinyl)propyl)oxy)-6-(methoxy)-4-quinolinyl)oxy)-2-naphthalenyl)-2-thiophenecarboxamide | $C_{32}H_{31}N_3O_6S$ | 585 | 586 |
| 253 | 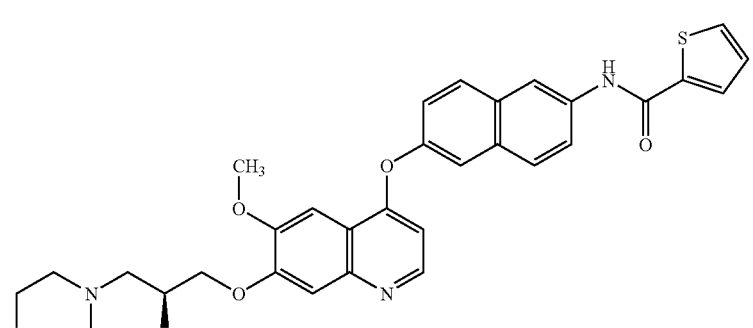<br>N-(6-((7-(((2S)-2-hydroxy-3-(4-morpholinyl)propyl)oxy)-6-(methoxy)-4-quinolinyl)oxy)-2-naphthalenyl)-2-thiophenecarboxamide | $C_{32}H_{31}N_3O_6S$ | 585 | 586 |
| 254 | 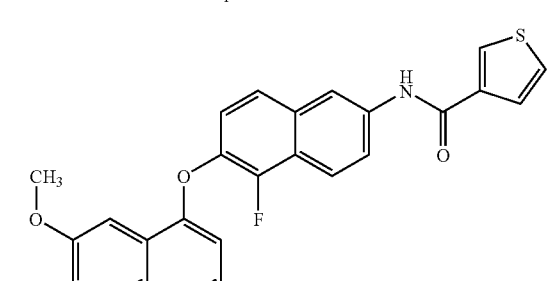<br>N-(5-fluoro-6-((7-hydroxy-6-(methoxy)-4-quinolinyl)oxy)-2-naphthalenyl)-3-thiophenecarboxamide | $C_{25}H_{17}FN_2O_4S$ | 460 | 461 |
| 255 | 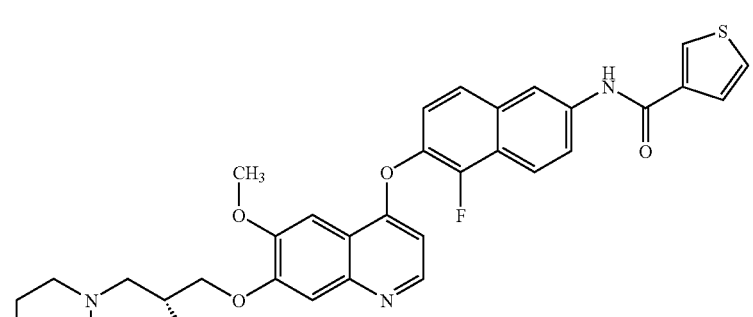<br>N-(5-fluoro-6-((7-(((2R)-2-hydroxy-3-(4-morpholinyl)propyl)oxy)-6-(methoxy)-4-quinolinyl)oxy)-2-naphthalenyl)-3-thiophenecarboxamide | $C_{32}H_{30}FN_3O_6S$ | 603 | 604 |

| Ex. No. | Structure & Name | Mol Formula | Mass | Mass (M + 1) |
|---|---|---|---|---|
| 256 | 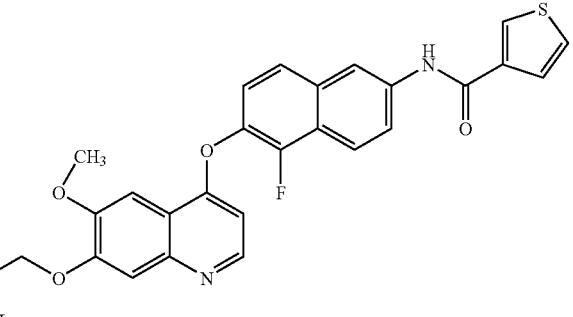<br>N-(5-fluoro-6-((7-(((2S)-2-hydroxy-3-(4-morpholinyl)propyl)oxy)-6-(methoxy)-4-quinolinyl)oxy)-2-naphthalenyl)-3-thiophenecarboxamide | $C_{32}H_{30}FN_3O_6S$ | 603 | 604 |

EXAMPLE 257

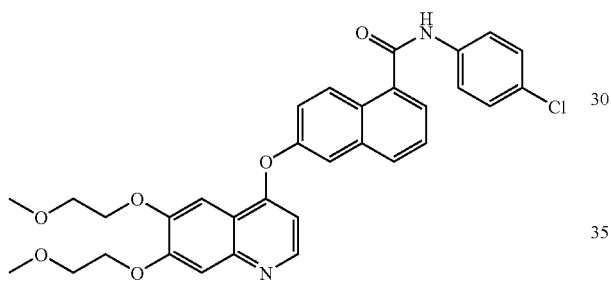

6-((6,7-bis((2-(methoxy)ethyl)oxy)-4-quinolinyl)oxy)-N-(4-chlorophenyl)-1-naphthalenecarboxamide

Step (a) Preparation of 4-chloro-6,7-dihydroxyquinoline

In a tube with a stirring bar was introduced 4-chloro-6,7-dimethoxyquinoline (1.5 g, 6.71 mmol) and 15 g of pyridinium hydrochloride. The tube was sealed and the mixture stirred at 200° C. for 1 h. The reaction was cooled to RT and a saturated solution of NaHCO$_3$ was added followed by EtOAc. The EtOAc layer was washed with a saturated solution of NaHCO$_3$, and the aqueous solution was back extracted with EtOAc. The combined organic layers were washed with brine, dried over Na$_2$SO$_4$ and concentrated under vacuum. The crude mixture was used in the next step.

Step (b) Preparation of 4-chloro-6,7-bis(2-methoxyethoxy)quinoline

A portion of the crude obtained in the previous step was dissolved in acetone (9.1 mL). Cs$_2$CO$_3$ (2.08 g, 6.37 mmol), 2-methoxyethylbromide (0.43 mL, 4.55 mmol) and TBAI (0.067 g, 0.182 mmol) were added to the reaction. The resulting slurry was heated to reflux for 24 h. The solvent was removed under vacuum and the resulting mixture partitioned between a saturated solution of NaHCO$_3$ and EtOAc. The EtOAc layer was washed with a saturated solution of NaHCO$_3$ and brine. The crude was purified by chromatography using 100% EtOAc.

Step (c) Preparation of 6-(6,7-bis(2-methoxyethoxy)quinolin-4-yloxy)-1-naphthoic acid The 6-(6,7-bis(2-methoxyethoxy)quinolin-4-yloxy)-1-naphthoic acid was obtained starting from the 4-chloro-6,7-bis(2-methoxyethoxy)quinoline (Step b) using the condition described in Example 801, Step d.

Step (d) Preparation of 6-((6,7-bis((2-(methoxy)ethyl)oxy)-4-quinolinyl)oxy)-N-(4-chlorophenyl)-1-naphthalenecarboxamide The title compound was obtained starting from 6-(6,7-bis(2-methoxyethoxy)quinolin-4-yloxy)-1-naphthoic acid (step c) using the conditions described in Example 560. M+H 573.1, Calc'd for $C_{32}H_{29}ClN_2O_6$–573.04.

EXAMPLE 258

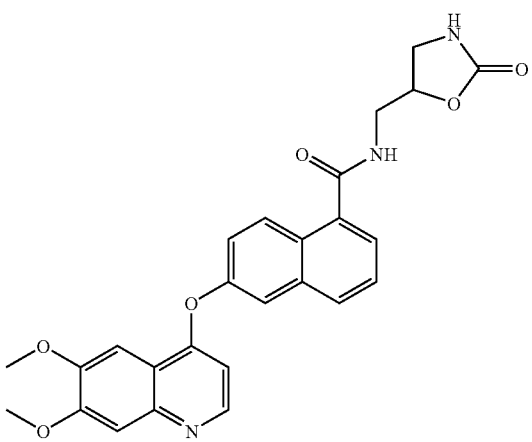

6-((6,7-bis(methoxy)-4-quinolinyl)oxy)-N-(((5R,S)-2-oxo-1,3-oxazolidin-5-yl)methyl)-1-naphthalenecarboxamide Step (a) Preparation of (R,S)-5-(azidomethyl)oxazolidin-2-one 5-(Chloromethyl)oxazolidin-2-one (1.36 g, 10 mmol) was dissolved in DMSO (20 mL). $NaN_3$ (6.5 g, 100 mmol) and TBAI (0.37 g, 1.0 mmol) were added and the resulting mixture was stirred at 70° C. overnight. The mixture was cooled to RT and the resulting solid was diluted with DCM and water. In a separatory funnel, layers were separated, the aqueous layer was extracted several times with DCM, and the combined organic layers were washed with water and brine. After evaporation, the crude was dissolved in EtOAc, and this solution washed with 1N HCl. The aqueous layer was neutralized with 6N NaOH and extracted several times with EtOAc to give the desired compound.

Step (b) Preparation of (R,S)-5-(aminomethyl)oxazolidin-2-one

The crude 5-(azidomethyl)oxazolidin-2-one (0.28 g) was dissolved in EtOH (8 mL) and Pd/C 10% (0.05 g) was added under Argon. The Argon atmosphere was replaced by $H_2$ and the mixture stirred under $H_2$ atmosphere for three days. The catalyst was removed by filtration, and the solvent removed under vacuum to give crude material.

Step (c) 6-((6,7-bis(methoxy)-4-quinolinyl)oxy)-N-(((5R,S)-2-oxo-1,3-oxazolidin-5-yl)methyl)-1-naphthalenecarboxamide The title compound was obtained using the conditions described in Example 560 starting from 6-(6,7-dimethoxyquinolin-4-yloxy)-1-naphthoyl chloride and the crude (R,S)-5-(aminomethyl)oxazolidin-2-one (step b). M+H 474.0, Calc'd for $C_{26}H_{23}N_3O_6$–473.48.

EXAMPLE 259

6-((6,7-bis(methoxy)-4-quinolinyl)oxy)-N-(2-((3-(dimethylamino)propyl)(methyl)amino)-5-(trifluoromethyl)phenyl)-1-naphthalenecarboxamide Step (a) Preparation of N-(3-(dimethylamino)propyl)-N-methyl-2-nitro-4-(trifluoromethyl)benzenamine To 4-fluoro-3-nitrobenzotrifluoride (1.00 g, 4.78 mmol) in THF (25 mL) was added $N^1,N^1,N^3$-trimethylpropane-1,3-diamine (0.84 mL, 5.7 mmol) and $NaHCO_3$ (1.1 g, 13 mmol). The resulting mixture was stirred for 1 h at RT, diluted with $CH_2Cl_2$, and washed with $H_2O$. The organic layer was dried ($MgSO_4$), filtered and concentrated to afford the title compound.

Step (b) Preparation of N1-(3-(dimethylamino)propyl)-N1-methyl-4-(trifluoromethyl)benzene-1,2-diamine To N-(3-(dimethylamino)propyl)-N-methyl-2-nitro-4-(trifluoromethyl)benzenamine (Step a, 1.42 g, 4.65 mmol) in MeOH (47 mL) was added Pd/C (10%, 493 mg, 0.465 mmol). The mixture was stirred overnight under an atmosphere of $H_2$. The mixture was filtered through a pad of Celite and concentrated to afford the title compound as a brown oil. M+H –276. Calc'd for $C_{13}H_{20}F_3N_3$–275.32.

Steps (c) Preparation of 6-((6,7-bis(methoxy)-4-quinolinyl)oxy)-N-(2-((3-(dimethylamino)propyl)(methyl)amino)-5-(trifluoromethyl)phenyl)-1-naphthalenecarboxamide Prepared according to Example 119, Step (b). M+H –633. Cal'd for $C_{35}H_{35}F_3N_4O_4$–632.68.

EXAMPLE 260

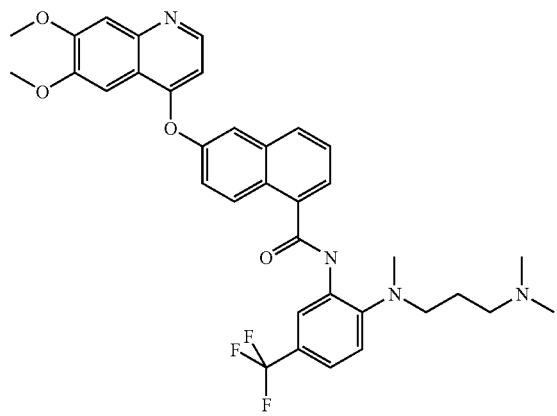

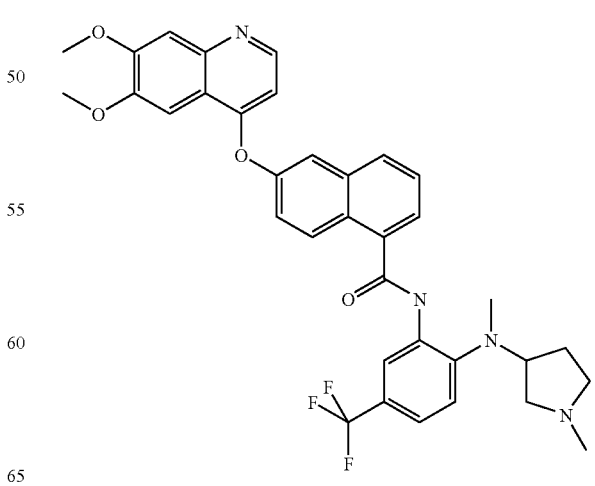

6-((6,7-bis(methoxy)-4-quinolinyl) oxy)-N-(2-(methyl((R,S)-1-methyl-3-pyrrolidinyl)amino)-5-(trifluoromethyl)phenyl)-1-naphthalenecarboxamide Step (a) Preparation of (R,S)N,1-dimethyl-N-(2-nitro-4-(trifluoromethyl)phenyl)pyrrolidin-3-amine To 4-fluoro-3-nitrobenzotrifluoride (5.00 g, 24.0 mmol) in THF (145 mL) was added (R,S)N,1-dimethylpyrrolidin-3-amine (3.72 mL, 29.0 mmol) and NaHCO$_3$ (5.52 g, 84.0 mmol). The resulting mixture was stirred overnight at RT, diluted with CH$_2$Cl$_2$, and washed with H$_2$O. The organic layer was dried (MgSO$_4$), filtered and concentrated to afford the title compound.

Step (b) Preparation of (R,S) N1-methyl-N1-(1-methylpyrrolidin-3-yl)-4-(trifluoromethyl)benzene-1,2-diamine To (R,S)N, 1-dimethyl-N-(2-nitro-4-(trifluoromethyl)phenyl)pyrrolidin-3-amine (7.25 g, 24.0 mmol) in MeOH (240 mL) was added Pd/C (10%, 1.3 g, 1.2 mmol). The mixture was stirred overnight under an atmosphere of H$_2$ The mixture was filtered through a pad of Celite and concentrated to afford the title compound as a brown oil. M+H −274. Cal'd for C$_{13}$H$_{18}$F$_3$N$_3$−273.30.

Step (c) Preparation of 6-((6,7-bis(methoxy)-4-quinolinyl)oxy)-N-(2-(methyl((R,S)-1-methyl-3-pyrrolidinyl)amino)-5-(trifluoromethyl)phenyl)-1-naphthalenecarboxamide The title compound was prepared according to Example 119, Step (b). M+H−631. Cal'd for C$_{35}$H$_{33}$F$_3$N$_4$O$_4$−630.66.

The following example was prepared similar to the procedures described in Example 114

| Example No. | Structure & Name | Mol Formula | Mass | M + H |
|---|---|---|---|---|
| 261 | 6-((6,7-bis(methoxy)-4-quinolinyl)oxy)-N-phenyl-1-naphthalenecarboxamide | C$_{28}$H$_{22}$N$_2$O$_4$ | 450.49 | 451.1 |

The following examples were prepared similar to the procedures described in Example 119 using either TEA or DIEA as the base.

| Example No. | Structure & Name | Mol Formula | Mass | M + H |
|---|---|---|---|---|
| 262 | 6-((6,7-bis(methoxy)-4-quinolinyl)oxy)-N-(4-methylphenyl)-1-naphthalenecarboxamide | C$_{29}$H$_{24}$N$_2$O$_4$ | 464.52 | 465.1 |

| Example No. | Structure & Name | Mol Formula | Mass | M + H |
|---|---|---|---|---|
| 263 | 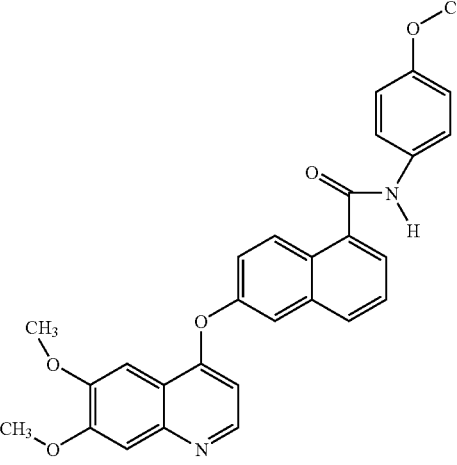<br>6-((6,7-bis(methoxy)-4-quinolinyl)oxy)-N-(4-(methoxy)phenyl)-1-naphthalenecarboxamide | $C_{29}H_{24}N_2O_5$ | 480.52 | 481.1 |
| 264 | 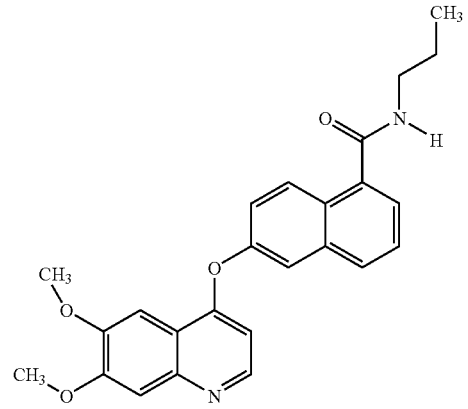<br>6-((6,7-bis(methoxy)-4-quinolinyl)oxy)-N-propyl-1-naphthalenecarboxamide | $C_{25}H_{24}N_2O_4$ | 416.48 | 417.2 |
| 265 | 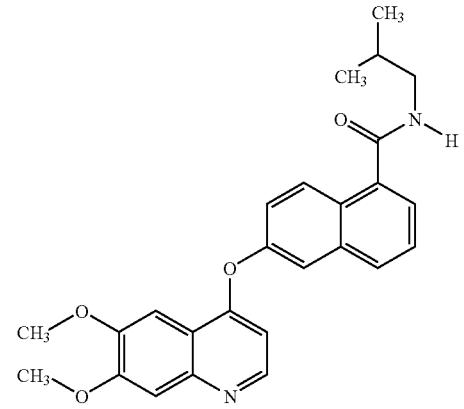<br>6-((6,7-bis(methoxy)-4-quinolinyl)oxy)-N-(2-methylpropyl)-1-naphthalenecarboxamide | $C_{26}H_{26}N_2O_4$ | 430.5 | 431.2 |

| Example No. | Structure & Name | Mol Formula | Mass | M + H |
|---|---|---|---|---|
| 266 | 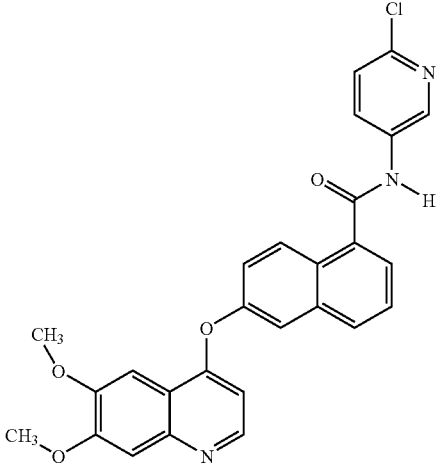<br>6-((6,7-bis(methoxy)-4-quinolinyl)oxy)-N-(6-Chloro-3-pyridinyl)-1-naphthalenecarboxamide | C$_{27}$H$_{20}$ClN$_3$O$_4$ | 485.93 | 486.1 |
| 267 | 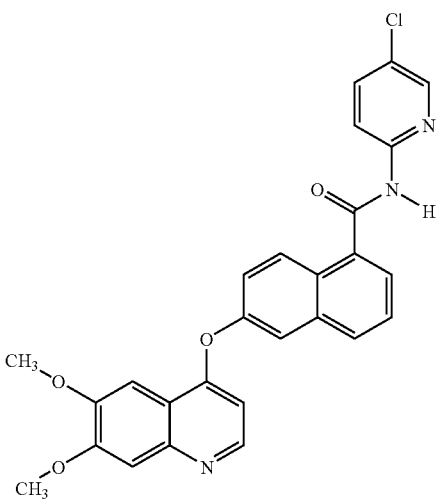<br>6-((6,7-bis(methoxy)-4-quinolinyl)oxy)-N-(5-chloro-2-pyridinyl)-1-naphthalenecarboxamide | C$_{27}$H$_{20}$ClN$_3$O$_4$ | 485.93 | 486.1 |
| 268 | 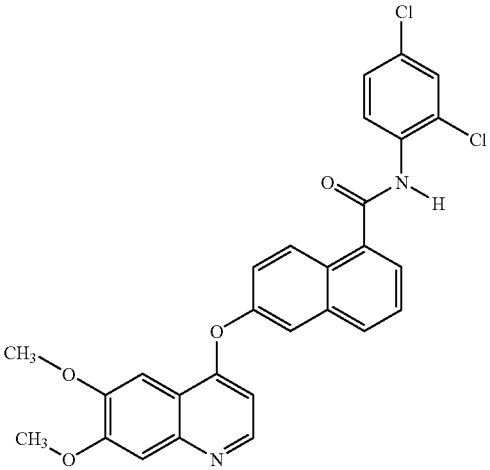<br>6-((6,7-bis(methoxy)-4-quinolinyl)oxy)-N-(2,4-dichlorophenyl)-1-naphthalenecarboxamide | C$_{28}$H$_{20}$Cl$_2$N$_2$O$_4$ | 519.38 | 519 |

-continued
| Example No. | Structure & Name | Mol Formula | Mass | M + H |
|---|---|---|---|---|
| 269 | 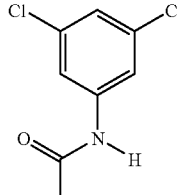<br>6-((6,7-bis(methoxy)-4-quinolinyl)oxy)-N-(3,5-dichlorophenyl)-1-naphthalenecarboxamide | $C_{28}H_{20}Cl_2N_2O_4$ | 519.38 | 519 |
| 270 | 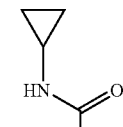<br>6-((6,7-bis(methoxy)-4-quinolinyl)oxy)-N-cyclopropyl-1-naphthalenecarboxamide | $C_{25}H_{22}N_2O_4$ | 414.45 | 415.2 |
EXAMPLE 271
6-((6,7-bis(methoxy)-4-quinolinyl)oxy)-N-((1S,2R)-2-fluorocyclopropyl)-1-naphthalenecarboxamide
EXAMPLE 272
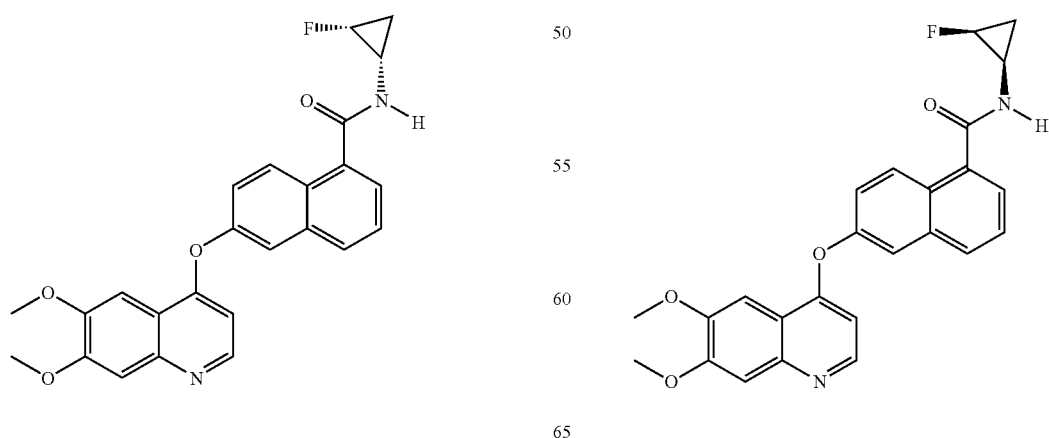

6-((6,7-bis(methoxy)-4-quinolinyl)oxy)-N-((1R,2S)-2-fluorocyclopropyl)-1-naphthalenecarboxamide 6-(6,7-Dimethoxyquinolin-4-yloxy)-1-naphthoyl chloride (200 mg, 0.50 mmol) was suspended in $CH_2Cl_2$ and TEA (210 μL, 1.5 mmol) was added. The mixture was blanketed with nitrogen, cis-2-fluorocyclopropylamine (131 mg, 0.54 mmol) was added and the reaction was stirred at RT for 1 h. The mixture was washed with water, dried with $Na_2SO_4$, filtered and concentrated in-vacuo. The residue was purified by column chromatography to give the title compounds. MS (ESI pos. ion) m/z: 433.2 (M+H). Calc'd for $C_{28}H_{21}FN_2O_4$–432.46.

EXAMPLE 273

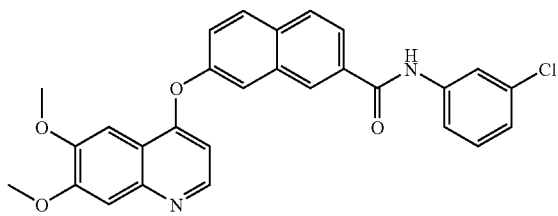

7-((6,7-bis(methoxy)-4-quinolinyl)oxy)-N-(3-chlorophenyl)-2-naphthalenecarboxamide Step (a) Preparation of 7-(6,7-dimethoxyquinolin-4-yloxy)naphthalen-2-ol To a solution of naphthalene-2,7-diol (8.95 g, 55.88 mmol) in NMP (50 mL) in a sealed tube, was added 4-chloro-6,7-dimethoxyquinoline (5.0 g, 22.35 mmol). KOH (1.40 g, 24.58 mmol) was added, followed by copper powder (0.71 g, 11.18 mmol). The tube was sealed and the solution was stirred and heated to 150° C. for 24 h. The reaction was cooled to RT, diluted with water and extracted with EtOAc 3×. The combined organic layer was washed with brine, dried over $MgSO_4$, filtered, and concentrated in vacuo. The crude material was purified by silica gel chromatography with 50% to 100% (95:5:0.5 EtOAc/MeOH/$NH_4OH$) in Hexanes to give the titled compound. MS (ESI, pos. ion) m/z: 348.2 (M+1).

Step (b) Preparation of 7-(6,7-dimethoxyquinolin-4-yloxy)naphthalen-2-yl trifluoromethanesulfonate To a solution of 7-(6,7-dimethoxyquinolin-4-yloxy)naphthalen-2-ol (Step a, 1.0 g, 2.88 mmol) in $CH_2Cl_2$ (40 mL) at 0° C., $Et_3N$ (0.40 mL, 2.88 mmol) was added. The reaction was stirred at 0° C. for 5 min and N-phenyltrifluoromethanesulfonimide (1.23 g, 3.45 mmol) was added. The reaction was stirred at 0° C. and gradually warmed to RT for 16 h. The solution was concentrated in vacuo. The crude material was purified by silica gel column chromatography with 75% EtOAc/Hexane to give the titled compound as a white solid. MS (ESI, pos. ion) m/z: 480.1 (M+1).

Step (c) Preparation of methyl 7-(6,7-dimethoxyquinolin-4-yloxy)-2-naphthoate

To a solution of 7-(6,7-dimethoxyquinolin-4-yloxy)naphthalen-2-yl trifluoromethanesulfonate (Step b, 1.0 g, 2.08 mmol) in DMF (10 mL) in a sealed tube, $Pd(OAc)_2$ (0.094, 0.416 mmol) was added, followed by DPPP (0.257 g, 0.624 mmol). CO(g) was bubbled through the mixture for 5 min, and MeOH (2 mL) and $Et_3N$ (0.58 mL, 4.16 mmol) was added. The tube was sealed and the mixture was stirred at 70° C. for 2 h. The reaction was diluted with water and extracted with EtOAc 3×. The combined organic layer was washed with water and brine, dried over $MgSO_4$, filtered and concentrated in vacuo. The crude material was taken on directly without purification. MS (ESI, pos. ion) m/z: 390.2 (M+1).

Step (d) Preparation of 7-(6,7-dimethoxyquinolin-4-yloxy)-2-naphthoic acid

To a solution of methyl 7-(6,7-dimethoxyquinolin-4-yloxy)-2-naphthoate (Step c, 0.809 g, 2.08 mmol) in EtOH (10 mL), 1N NaOH (3 mL) was added. The solution was stirred at 70° C. for 2 h. The reaction was cooled to RT and concentrated in vacuo. The crude material was taken up in water (50 mL) and acidified to pH=3 with 1N HCl. The solid was filtered and dried in vacuo. MS (ESI, pos. ion) m/z: 376.1 (M+1).

Step (e) Preparation of 7-((6,7-bis(methoxy)-4-quinolinyl)oxy)-N-(3-chlorophenyl)-2-naphthalenecarboxamide A slurry of 7-(6,7-dimethoxyquinolin-4-yloxy)-2-naphthoic acid (0.54 g, 1.44 mmol) in 10 mL of $C_2O_2Cl_2$ and 2 drops of DMF was stirred at RT. After 2 h, the solution was concentrated to dryness and placed under high vacuum overnight. A portion of the crude residue (0.075 g, 0.191 mmol) was dissolved in 1 mL of $CH_2Cl_2$. To the resulting solution was added DIPEA (0.133 mL, 0.764 mmol), 3-chloroaniline (0.024 mL, 0.229 mmol) and a catalytic amount of DMAP. The reaction was stirred under a $N_2$ atmosphere for 16 h. The reaction was diluted with EtOAc, and washed with saturated aqueous $NaHCO_3$. The organic layer was dried ($MgSO_4$), filtered and concentrated. The residue was passed through a medium-pressure silica gel column (solvent gradient: 95:5 $CH_2Cl_2$:MeOH; 90:10 $CH_2Cl_2$:MeOH) to afford the desired crude compound. The fractions were concentrated to dryness to afford a solid residue. The residue was triturated with $Et_2O$/Hexanes to afford the desired compound as a pale yellow solid. MS (ESI, pos. ion) m/z: 485.0 (M+1). Mass Calc'd for $C_{28}H_{21}ClN_2O_4$: 484.937.

The following examples were prepared similar to the procedures described in Example 273:

| Example No. | Structure & Name | Mol Formula | Mass | M + H |
|---|---|---|---|---|
| 274 | 7-((6,7-bis(methoxy)-4-quinolinyl) oxy)-N-(3,4-difluorophenyl)-2-naphthalenecarboxamide | $C_{28}H_{20}F_2N_2O_4$ | 486.47 | 487.3 |
| 275 | 7-((6,7-bis(methoxy)-4-quinolinyl) oxy)-N-(4-(trifluoromethyl)-2-pyridinyl)-2-naphthalenecarboxamide | $C_{28}H_{20}F_3N_3O_4$ | 519.48 | 520.2 |
| 276 | 6-((6,7-bis(methoxy)-4-quinolinyl)oxy)-N-methyl-1-naphthalenecarboxamide | $C_{23}H_{20}N_2O_4$ | 388.42 | 389.2 |

EXAMPLE 277

6-(6,7-dimethoxyquinolin-4-yloxy)quinoline-3-carboxylic acid

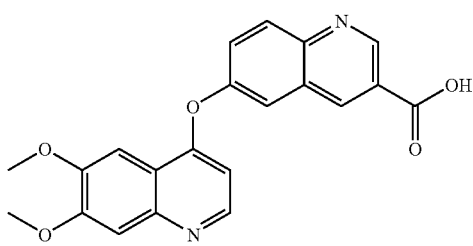

Step (a) Preparation of diethyl 2-((4-methoxyphenylamino)methylene)malonate

In a flask maintained under reduce pressure, p-methoxyaniline (35.1 g, 280 mmol) and diethyl 2-(methoxymethylene)malonate (73.97 g, 340 mmol) were stirred at 100° C. for two h. The crude mixture was used without further purification.

Step (b) Preparation of ethyl 4-chloro-6-methoxyquinoline-3-carboxylate

The crude reaction mixture obtained above (74 g) was dissolved in toluene (300 mL). POCl$_3$ (46.6 ml, 500 mmol) was added followed by PCl$_5$ (26 g, 125 mmol). The mixture was heated at reflux 6 h. Toluene and excess of POCl$_3$ were removed under vacuum. The residue was poured on a mixture of NaOH 1N and ice. The resulting brown precipitate was filtered off and washed with water, then with methanol to give an off-white solid.

Step (c) Preparation of ethyl 6-methoxyquinoline-3-carboxylate

To a solution of ethyl 4-chloro-6-methoxyquinoline-3-carboxylate (Step b, 18 g, 68 mmol) in EtOH (200 mL) stirred under $N_2$ was introduced Pd/C 10% (2 g). The $N_2$ atmosphere was replaced by $H_2$ and the mixture was vigorously stirred at RT under $H_2$ atmosphere (balloon) overnight. The mixture was diluted with DCM and filtered. The catalyst was washed several times with DCM. The solvents were removed under vacuum. The solid residue was suspended in EtOH and the filtered to give ethyl 6-methoxyquinoline-3-carboxylate.

Step (d) Preparation of 6-hydroxyquinoline-3-carboxylic acid hydrochloride salt A mixture of ethyl 6-methoxyquinoline-3-carboxylate (step e, 2.1 g, 9.1 mmol) and HBr 48% (in water) was heated at reflux for 72 h. The resulting solution was cooled at 0° C. The crystalline solid was filtered off, washed with ice-cold water and rinsed with acetone to give a green-yellow solid.

Step (e) Preparation of 6-(6,7-dimethoxyquinolin-4-yloxy)quinoline-3-carboxylic acid The title compound was prepared using a procedure similar to that described in Example 801, Step d.
The following examples were prepared similar to the procedure described in Example 273, Step e:

| Example No. | Structure & Name | Mol Formula | Mass | M + H |
|---|---|---|---|---|
| 278 | 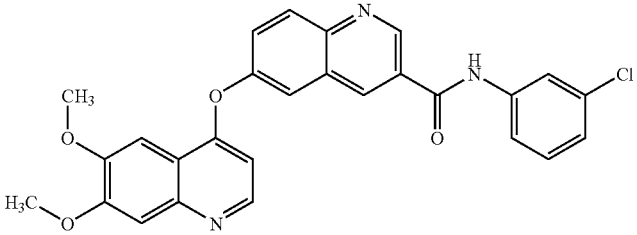<br>6-((6,7-bis(methoxy)-4-quinolinyl)oxy)-N-(3-chlorophenyl)-3-quinolinecarboxamide | $C_{27}H_{20}ClN_3O_4$ | 485.93 | 486.2 |
| 279 | 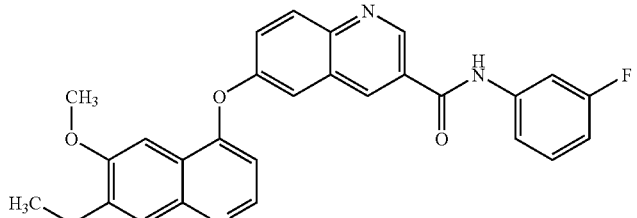<br>6-((6,7-bis(methoxy)-4-quinolinyl)oxy)-N-(3-fluorophenyl)-3-quinolinecarboxamide | $C_{27}H_{20}FN_3O_4$ | 469.47 | 470.2 |
| 280 | 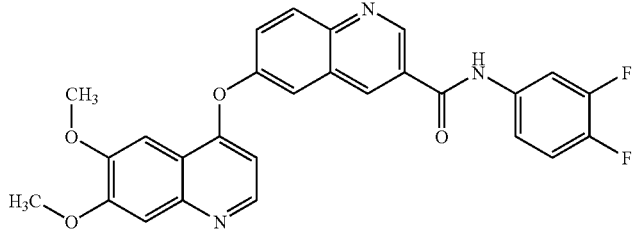<br>6-((6,7-bis(methoxy)-4-quinolinyl)oxy)-N-(3,4-difluorophenyl)-3-quinolinecarboxamide | $C_{27}H_{19}F_2N_3O_4$ | 487.46 | 488.2 |

| Example No. | Structure & Name | Mol Formula | Mass | M + H |
|---|---|---|---|---|
| 281 | 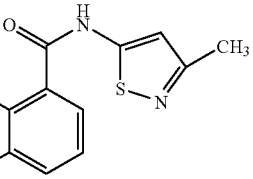<br>6-((6,7-bis(methoxy)-4-quinolinyl)oxy)-N-(1-ethyl-1H-pyrazol-5-yl)-1-naphthalenecarboxamide | $C_{27}H_{24}N_4O_4$ | 468.51 | 469.3 |
| 282 | 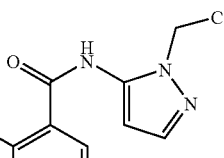<br>6-((6,7-bis(methoxy)-4-quinolinyl)oxy)-N-(3-methyl-5-isothiazolyl)-1-naphthalenecarboxamide | $C_{26}H_{21}N_3O_4S$ | 471.54 | 472 |
| 283 | 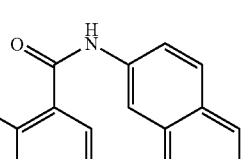<br>6-((6,7-bis(methoxy)-4-quinolinyl)oxy)-N-(2-naphthalenyl)-1-naphthalenecarboxamide | $C_{32}H_{24}N_2O_4$ | 500.55 | 501.1 |
| 284 | 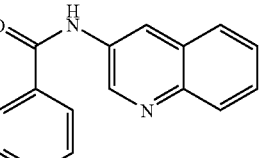<br>6-((6,7-bis(methoxy)-4-quinolinyl)oxy)-N-(3-quinolinyl)-1-naphthalenecarboxamide | $C_{31}H_{23}N_3O_4$ | 501.54 | 502.2 |

-continued
| Example No. | Structure & Name | Mol Formula | Mass | M + H |
|---|---|---|---|---|
| 285 | 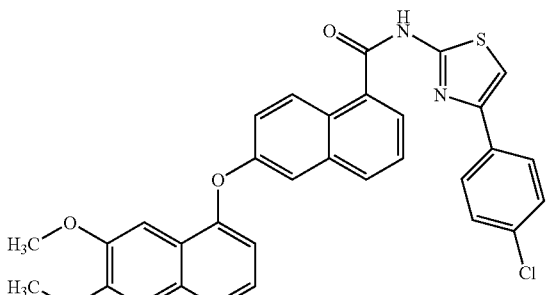<br>6-((6,7-bis(methoxy)-4-quinolinyl)oxy)-N-(4-(4-chlorophenyl)-1,3-thiazol-2-yl)-1-naphthalenecarboxamide | $C_{31}H_{22}ClN_3O_4S$ | 568.05 | 568 |
| 286 | 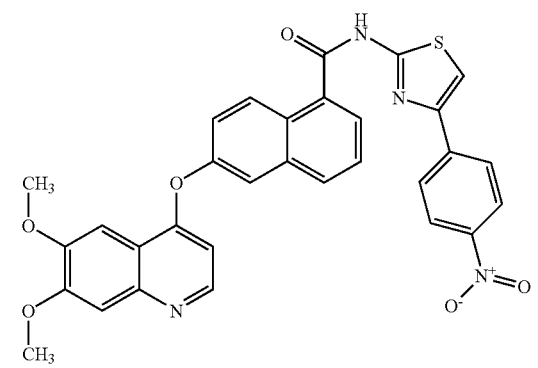<br>6-((6,7-bis(methoxy)-4-quinolinyl)oxy)-N-(4-(4-nitrophenyl)-1,3-thiazol-2-yl)-1-naphthalenecarboxamide | $C_{31}H_{22}N_4O_6S$ | 578.6 | 579.2 |
| 287 | 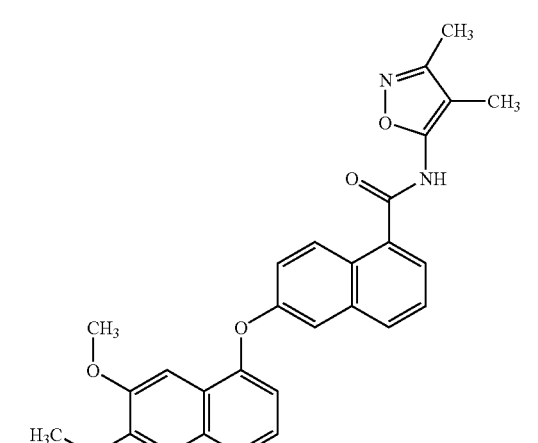<br>6-((6,7-bis(methoxy)-4-quinolinyl)oxy)-N-(3,4-dimethyl-5-isoxazolyl)-1-naphthalenecarboxamide | $C_{27}H_{23}N_3O_5$ | 469.5 | 470.1 |

| Example No. | Structure & Name | Mol Formula | Mass | M + H |
|---|---|---|---|---|
| 288 | 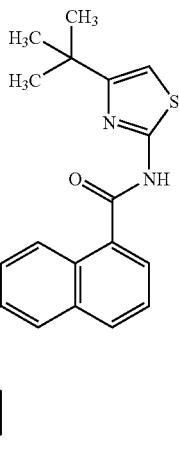<br>6-((6,7-bis(methoxy)-4-quinolinyl)oxy)-N-(4-(1,1-dimethylethyl)-1,3-thiazol-2-yl)-1-naphthalenecarboxamide | $C_{29}H_{27}N_3O_4S$ | 513.62 | 514.1 |
| 289 | 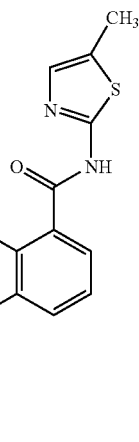<br>6-((6,7-bis(methoxy)-4-quinolinyl)oxy)-N-(5-methyl-1,3-thiazol-2-yl)-1-naphthalenecarboxamide | $C_{26}H_{21}N_3O_4S$ | 471.54 | 472 |
| 290 | 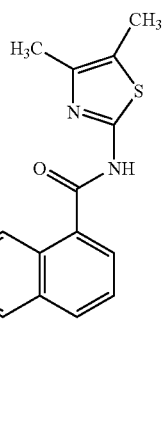<br>6-((6,7-bis(methoxy)-4-quinolinyl)oxy)-N-(4,5-dimethyl-1,3-thiazol-2-yl)-1-naphthalenecarboxamide | $C_{27}H_{23}N_3O_4S$ | 485.56 | 486 |

-continued
| Example No. | Structure & Name | Mol Formula | Mass | M + H |
|---|---|---|---|---|
| 291 | 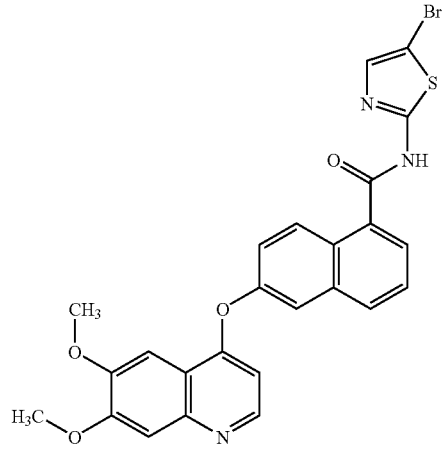 6-((6,7-bis(methoxy)-4-quinolinyl)oxy)-N-(5-bromo-1,3-thiazol-2-yl)-1-naphthalenecarboxamide | $C_{25}H_{18}BrN_3O_4S$ | 536.4 | 535.9 |
| 292 | 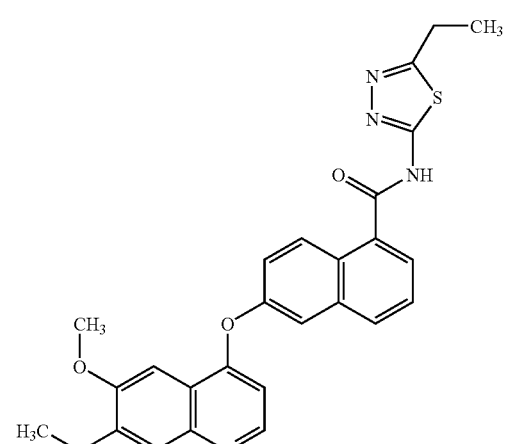 6-((6,7-bis(methoxy)-4-quinolinyl)oxy)-N-(5-ethyl-1,3,4-thiadiazol-2-yl)-1-naphthalenecarboxamide | $C_{26}H_{22}N_4O_4S$ | 486.55 | 487 |
| 293 | 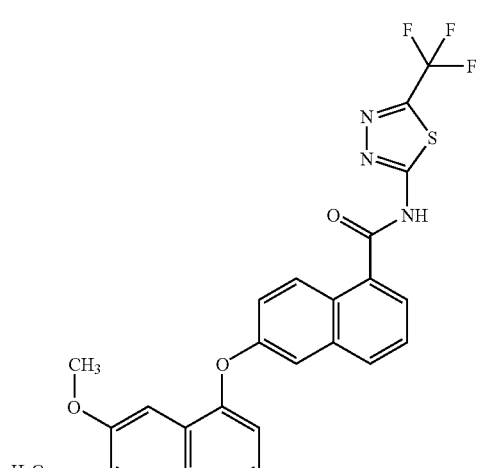 6-((6,7-bis(methoxy)-4-quinolinyl)oxy)-N-(5-(trifluoromethyl)-1,3,4-thiadiazol-2-yl)-1-naphthalenecarboxamide | $C_{25}H_{17}F_3N_4O_4S$ | 526.49 | 527 |

| Example No. | Structure & Name | Mol Formula | Mass | M + H |
|---|---|---|---|---|
| 294 | 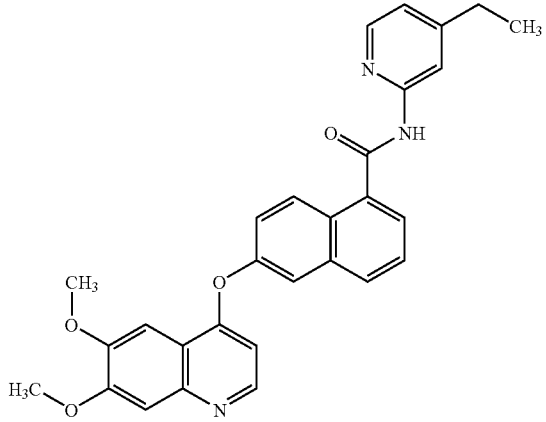<br>6-((6,7-bis(methoxy)-4-quinolinyl)oxy)-N-(4-ethyl-2-pyridinyl)-1-naphthalenecarboxamide | $C_{29}H_{25}N_3O_4$ | 479.53 | 480.1 |
| 295 | 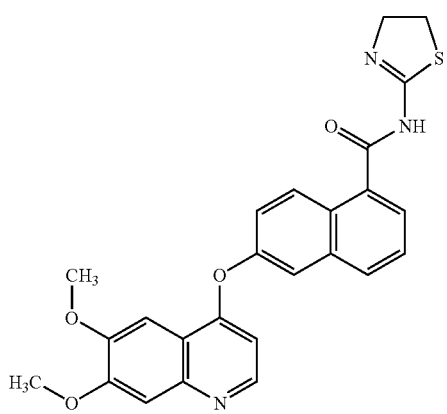<br>6-((6,7-bis(metnoxy)-4-quinolinyl)oxy)-N-(4,5-dihydro-1,3-thiazol-2-yl)-1-naphthalenecarboxamide | $C_{25}H_{21}N_3O_4S$ | 459.52 | 460 |
| 296 | 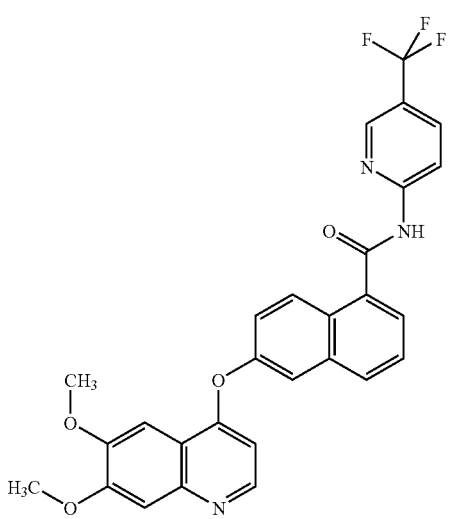<br>6-((6,7-bis(methoxy)-4-quinolinyl)oxy)-N-(5-(trifluoromethyl)-2-pyridinyl)-1-naphthalenecarboxamide | $C_{28}H_{20}F_3N_3O_4$ | 519.48 | 520 |

| Example No. | Structure & Name | Mol Formula | Mass | M + H |
|---|---|---|---|---|
| 297 | 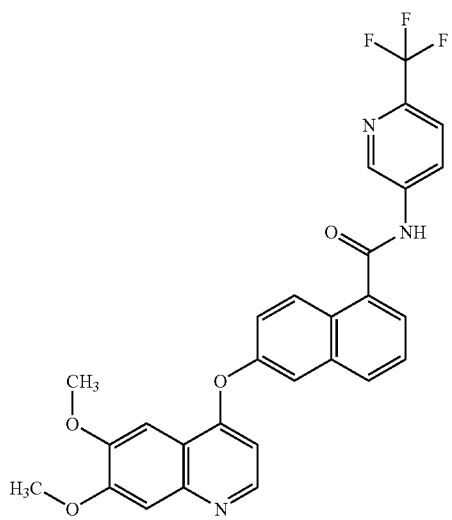<br>6-((6,7-bis(methoxy)-4-quinolinyl)oxy)-N-(6-(trifluoromethyl)-3-pyridinyl)-1-naphthalenecarboxamide | $C_{28}H_{20}F_3N_3O_4$ | 519.48 | 520 |
| 298 | 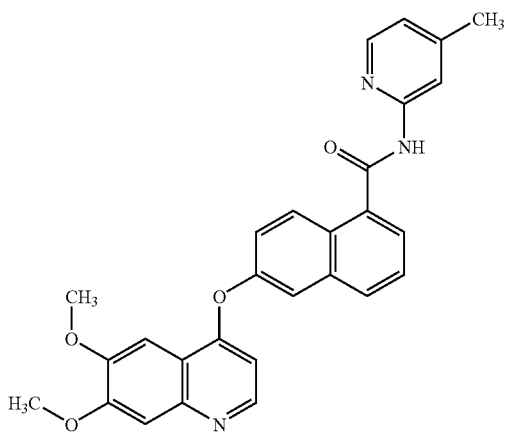<br>6-((6,7-bis(methoxy)-4-quinolinyl)oxy)-N-(4-methyl-2-pyridinyl)-1-naphthalenecarboxamide | $C_{28}H_{23}N_3O_4$ | 465.51 | 466 |
| 299 | 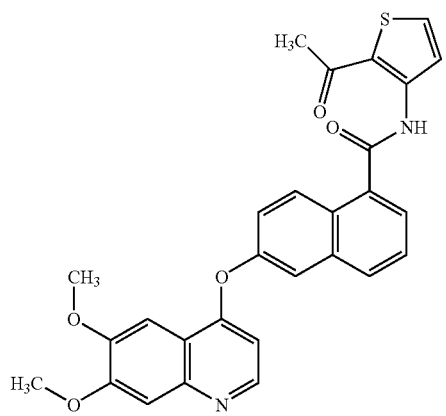<br>N-(2-acetyl-3-thienyl)-6-((6,7-bis(methoxy)-4-quinolinyl)oxy)-1-naphthalenecarboxamide | $C_{28}H_{22}N_2O_5S$ | 498.56 | 499.2 |

| Example No. | Structure & Name | Mol Formula | Mass | M + H |
|---|---|---|---|---|
| 300 | 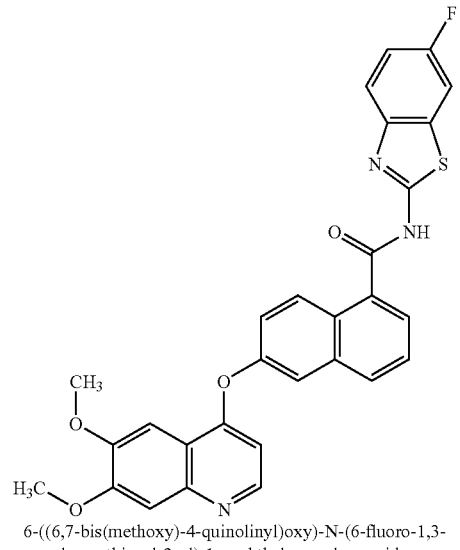6-((6,7-bis(methoxy)-4-quinolinyl)oxy)-N-(6-fluoro-1,3-benzothiazol-2-yl)-1-naphthalenecarboxamide | $C_{29}H_{20}FN_3O_4S$ | 525.56 | 526.1 |
| 301 | 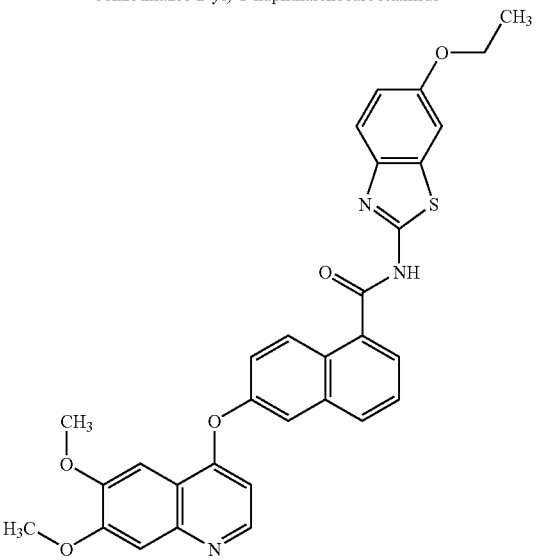6-((6,7-bis(methoxy)-4-quinolinyl)oxy)-N-(6-(ethoxy)-1,3-benzothiazol-2-yl)-1-naphthalenecarboxamide | $C_{31}H_{25}N_3O_5S$ | 551.62 | 552.1 |
| 302 | 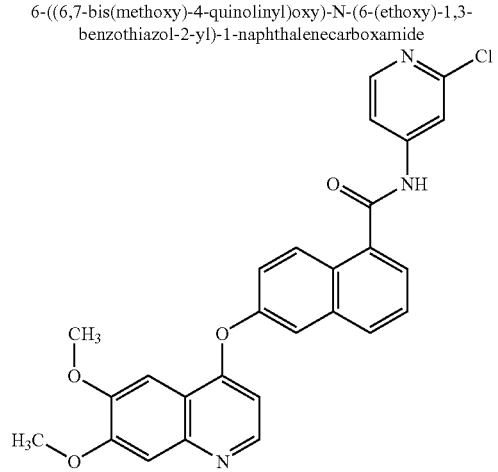6-((6,7-bis(methoxy)-4-quinolinyl)oxy)-N-(2-chloro-4-pyridinyl)-1-naphthalenecarboxamide | $C_{27}H_{20}ClN_3O_4$ | 485.93 | 486.1 |

-continued
| Example No. | Structure & Name | Mol Formula | Mass | M + H |
|---|---|---|---|---|
| 303 | 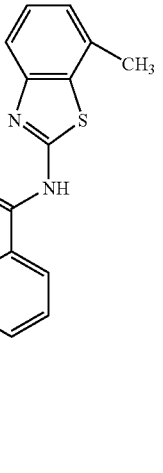<br>6-((6,7-bis(methoxy)-4-quinolinyl)oxy)-N-(7-methyl-1,3-benzothiazol-2-yl)-1-naphthalenecarboxamide | $C_{30}H_{23}N_3O_4S$ | 521.6 | 522.1 |
| 304 | 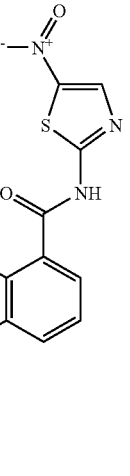<br>6-((6,7-bis(methoxy)-4-quinolinyl)oxy)-N-(5-nitro-1,3-thiazol-2-yl)-1-naphthalenecarboxamide | $C_{25}H_{18}N_4O_6S$ | 502.51 | 503.1 |
| 305 | 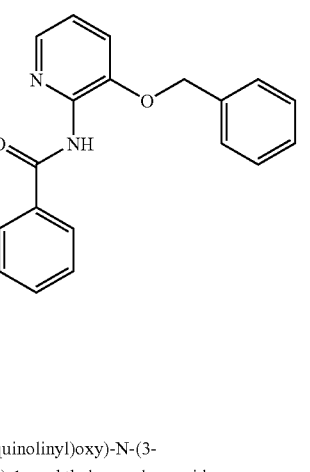<br>6-((6,7-bis(methoxy)-4-quinolinyl)oxy)-N-(3-((phenylmethyl)oxy)-2-pyridinyl)-1-naphthalenecarboxamide | $C_{34}H_{27}N_3O_5$ | 557.6 | 558.2 |

-continued
| Example No. | Structure & Name | Mol Formula | Mass | M + H |
|---|---|---|---|---|
| 306 | 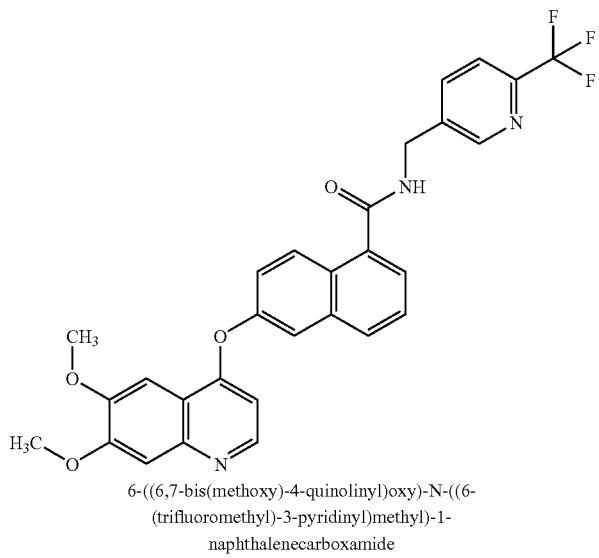<br>6-((6,7-bis(methoxy)-4-quinolinyl)oxy)-N-((6-(trifluoromethyl)-3-pyridinyl)methyl)-1-naphthalenecarboxamide | $C_{29}H_{22}F_3N_3O_4$ | 533.5 | 534.2 |
| 307 | 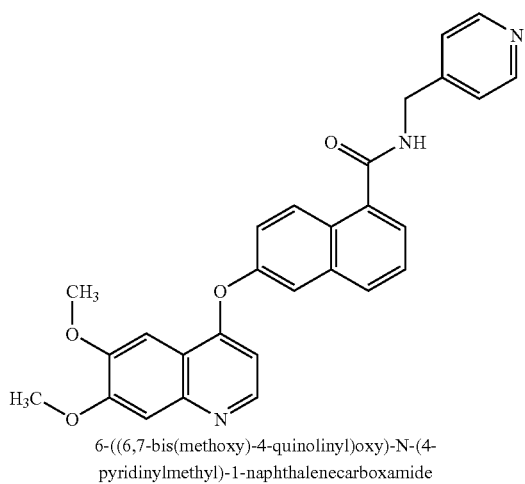<br>6-((6,7-bis(methoxy)-4-quinolinyl)oxy)-N-(4-pyridinylmethyl)-1-naphthalenecarboxamide | $C_{28}H_{23}N_3O_4$ | 465.51 | 466.2 |
| 308 | 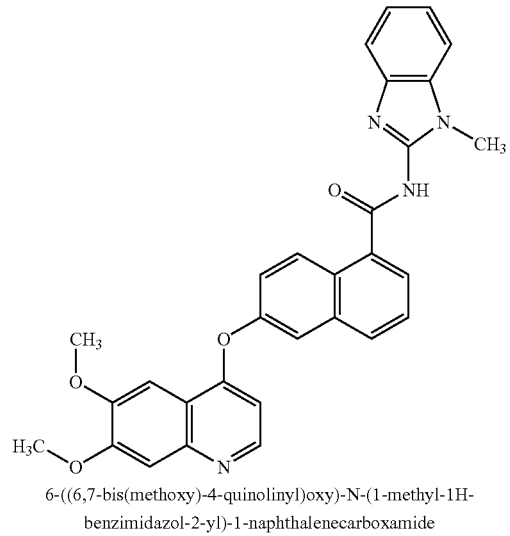<br>6-((6,7-bis(methoxy)-4-quinolinyl)oxy)-N-(1-methyl-1H-benzimidazol-2-yl)-1-naphthalenecarboxamide | $C_{30}H_{24}N_4O_4$ | 504.54 | 505.1 |

-continued
| Example No. | Structure & Name | Mol Formula | Mass | M + H |
|---|---|---|---|---|
| 309 | 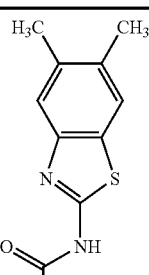 6-((6,7-bis(methoxy)-4-quinolinyl)oxy)-N-(5,6-dimethyl-1,3-benzothiazol-2-yl)-1-naphthalenecarboxamide | $C_{31}H_{25}N_3O_4S$ | 535.62 | 536.2 |
| 310 | 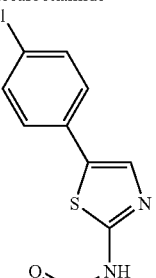 6-((6,7-bis(methoxy)-4-quinolinyl)oxy)-N-(5-(4-chlorophenyl)-1,3-thiazol-2-yl)-1-naphthalenecarboxamide | $C_{31}H_{22}ClN_3O_4S$ | 568.05 | 568.1 |
| 311 | 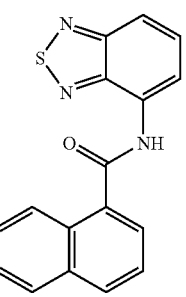 N-(2,1,3-benzothiadiazol-4-yl)-6-((6,7-bis(methoxy)-4-quinolinyl)oxy)-1-naphthalenecarboxamide | $C_{28}H_{20}N_4O_4S$ | 508.56 | 509.2 |

| Example No. | Structure & Name | Mol Formula | Mass | M + H |
|---|---|---|---|---|
| 312 | 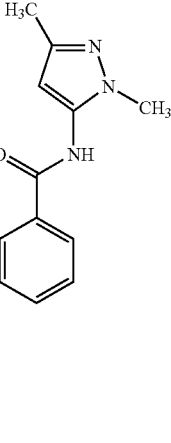<br>6-((6,7-bis(methoxy)-4-quinolinyl)oxy)-N-(1,3-dimethyl-1H-pyrazol-5-yl)-1-naphthalenecarboxamide | $C_{27}H_{24}N_4O_4$ | 468.51 | 469.2 |
| 313 | 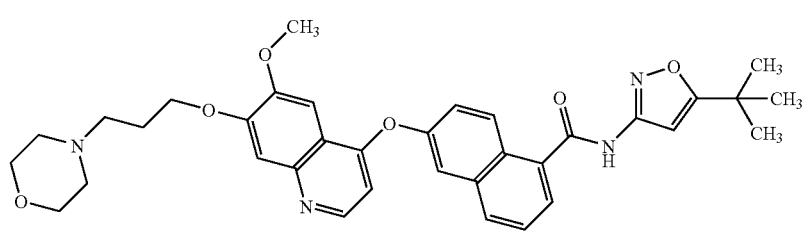<br>N-(5-(1,1-dimethylethyl)-3-isoxazolyl)-6-((6-(methoxy)-7-((3-(4-morpholinyl)propyl)oxy)-4-quinolinyl)oxy)-1-naphthalenecarboxamide | $C_{35}H_{38}N_4O_6$ | 610.71 | 611.3 |
| 314 | 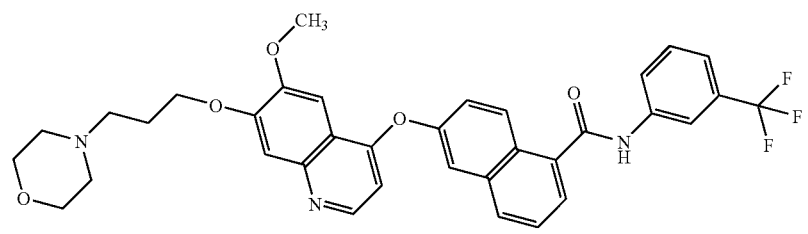<br>6-((6-(methoxy)-7-((3-(4-morpholinyl)propyl)oxy)-4-quinolinyl)oxy)-N-(3-(trifluoromethyl)phenyl)-1-naphthalenecarboxamide | $C_{35}H_{32}F_3N_3O_5$ | 631.65 | 632.2 |
| 315 | 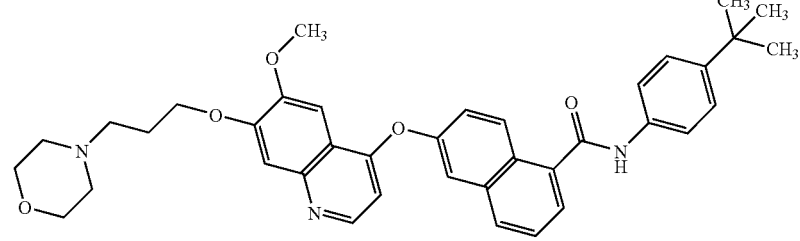<br>N-(4-(1,1-dimethylethyl)phenyl)-6-((6-(methoxy)-7-((3-(4-morpholinyl)propyl)oxy)-4-quinolinyl)oxy)-1-naphthalenecarboxamide | $C_{38}H_{41}N_3O_5$ | 619.76 | 620.3 |

| Example No. | Structure & Name | Mol Formula | Mass | M + H |
|---|---|---|---|---|
| 316 | 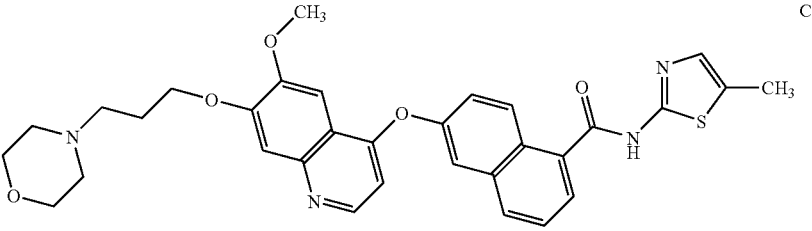<br>6-((6-(methoxy)-7-((3-(4-morpholinyl)propyl)oxy)-4-quinolinyl)oxy)-N-(5-methyl-1,3-thiazol-2-yl)-1-naphthalenecarboxamide | $C_{32}H_{32}N_4O_5S$ | 584.69 | 585.2 |
| 317 | 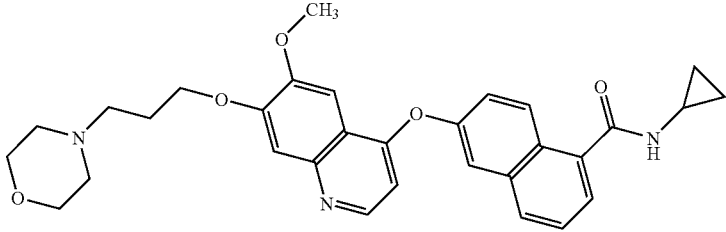<br>N-cyclopropyl-6-((6-(methoxy)-7-((3-(4-morpholinyl)propyl)oxy)-4-quinolinyl)oxy)-1-naphthalenecarboxamide | $C_{31}H_{33}N_3O_5$ | 527.62 | 528.2 |
| 318 | 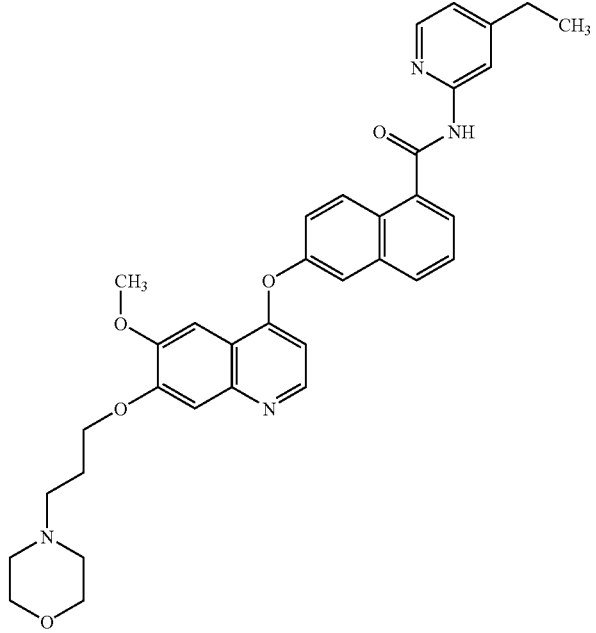<br>N-(4-ethyl-2-pyridinyl)-6-((6-(methoxy)-7-((3-(4-morpholinyl)propyl)oxy)-4-quinolinyl)oxy)-1-naphthalenecarboxamide | $C_{35}H_{36}N_4O_5$ | 592.69 | 593.3 |

| Example No. | Structure & Name | Mol Formula | Mass | M + H |
|---|---|---|---|---|
| 319 | 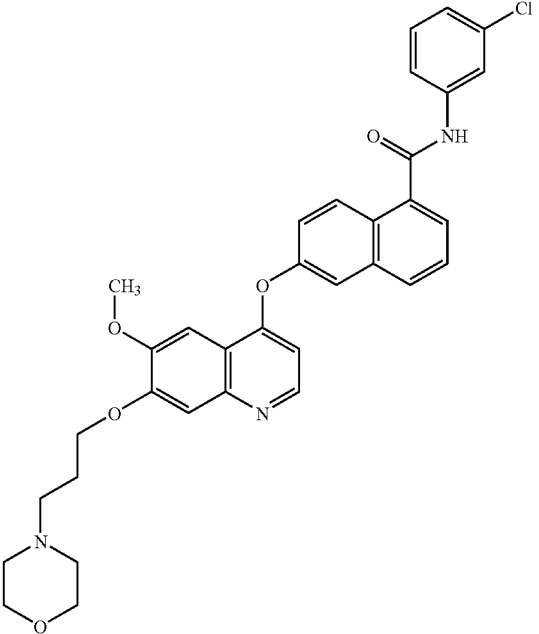<br>N-(3-chlorophenyl)-6-((6-(methoxy)-7-((3-(4-morpholinyl)propyl)oxy)-4-quinolinyl)oxy)-1-naphthalenecarboxamide | C₃₄H₃₂ClN₃O₅ | 598.1 | 598.2 |
| 320 | 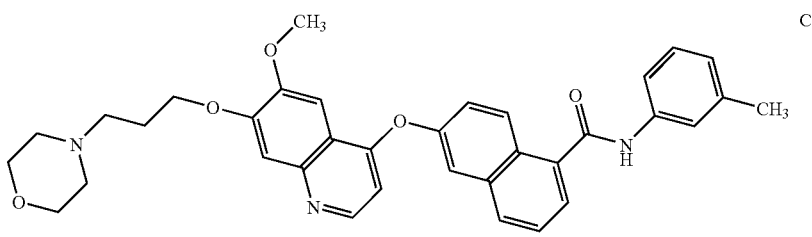<br>6-((6-(methoxy)-7-((3-(4-morpholinyl)propyl)oxy)-4-quinolinyl)oxy)-N-(3-methylphenyl)-1-naphthalenecarboxamide | C₃₅H₃₅N₃O₅ | 577.68 | 578.3 |
| 321 | 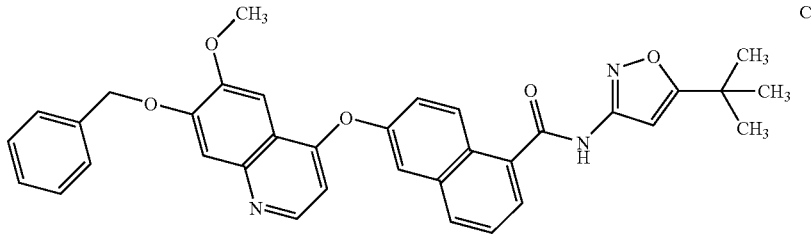<br>N-(5-(1,1-dimethylethyl)-3-isoxazolyl)-6-((6-(methoxy)-7-((phenylmethyl)oxy)-4-quinolinyl)oxy)-1-naphthalenecarboxamide | C₃₅H₃₁N₃O₅ | 573.65 | 574.2 |

| Example No. | Structure & Name | Mol Formula | Mass | M + H |
|---|---|---|---|---|
| 322 | 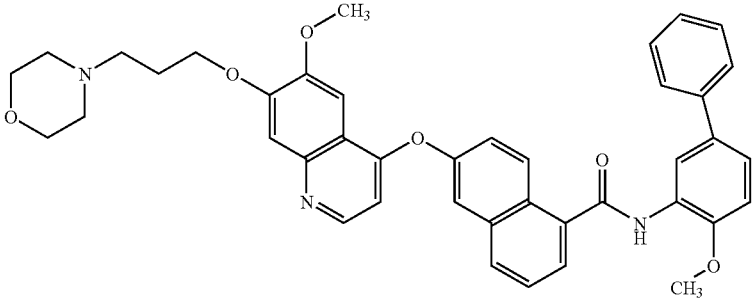
N-(4-(methoxy)-1,1'-biphenyl-3-yl)-6-((6-(methoxy)-7-((3-(4-morpholinyl)propyl)oxy)-4-quinolinyl)oxy)-1-naphthalenecarboxamide | $C_{41}H_{39}N_3O_6$ | 669.77 | 670.3 |
| 323 | 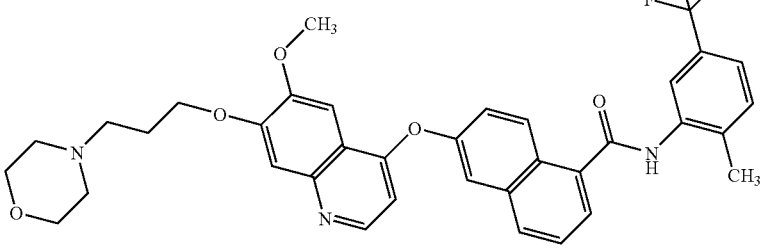
6-((6-(methoxy)-7-((3-(4-morpholinyl)propyl)oxy)-4-quinolinyl)oxy)-N-(2-methyl-5-(trifluoromethyl)phenyl)-1-naphthalenecarboxamide | $C_{36}H_{34}F_3N_3O_5$ | 645.67 | 646.6 |
| 324 | 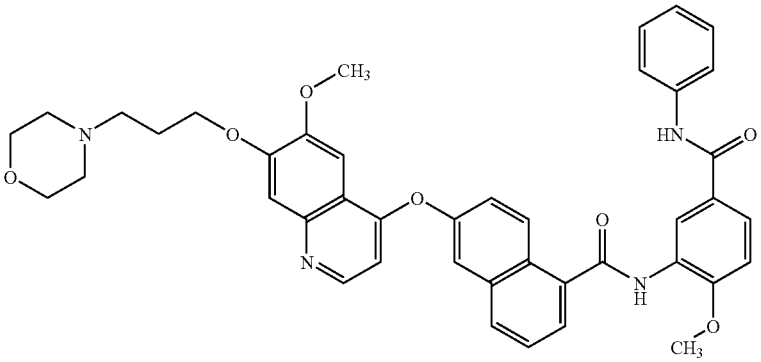
6-((6-(methoxy)-7-((3-(4-morpholinyl)propyl)oxy)-4-quinolinyl)oxy)-N-(2-(methoxy)-5-((phenylamino)carbonyl)phenyl)-1-naphthalenecarboxamide | $C_{42}H_{40}N_4O_7$ | 712.8 | 713.3 |
| 325 | 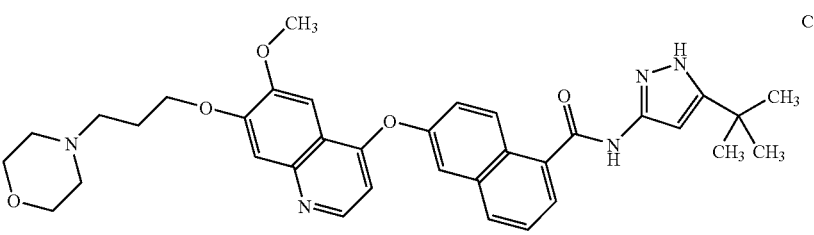
N-(5-(1,1-dimethylethyl)-1H-pyrazol-3-yl)-6-((6-(methoxy)-7-((3-(4-morpholinyl)propyl)oxy)-4-quinolinyl)oxy)-1-naphthalenecarboxamide | $C_{35}H_{39}N_5O_5$ | 609.72 | 610.2 |

| Example No. | Structure & Name | Mol Formula | Mass | M + H |
|---|---|---|---|---|
| 326 | 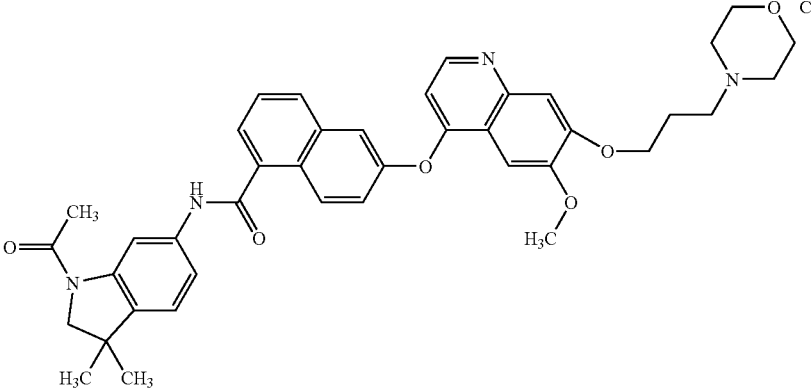<br>N-(1-acetyl-3,3-dimethyl-2,3-dihydro-1H-indol-6-yl)-6-((6-(methoxy)-7-((3-(4-morpholinyl)propyl)oxy)-4-quinolinyl)oxy)-1-naphthalenecarboxamide | C₄₀H₄₂N₄O₆ | 674.79 | 675.3 |
| 327 | 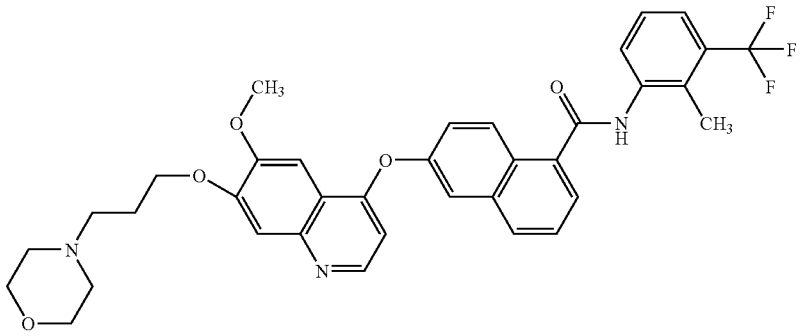<br>6-((6-(methoxy)-7-((3-(4-morpholinyl)propyl)oxy)-4-quinolinyl)oxy)-N-(2-methyl-3-(trifluoromethyl)phenyl)-1-naphthalenecarboxamide | C₃₆H₃₄F₃N₃O₅ | 645.67 | 646.2 |
| 328 | 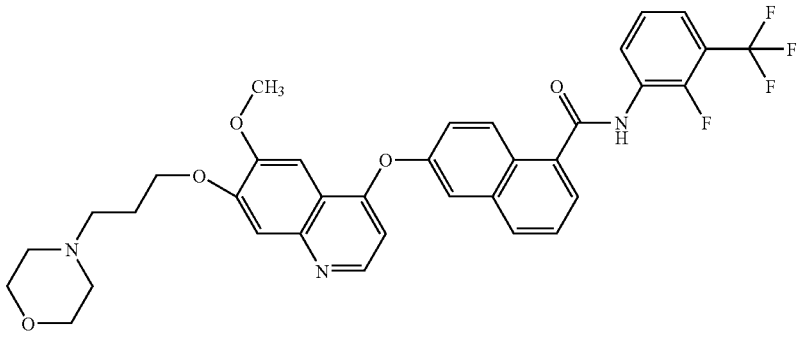<br>N-(2-fluoro-3-(trifluoromethyl)phenyl)-6-((6-(methoxy)-7-((3-(4-morpholinyl)propyl)oxy)-4-quinolinyl)oxy)-1-naphthalenecarboxamide | C₃₅H₃₁F₄N₃O₅ | 649.64 | 650.2 |

| Example No. | Structure & Name | Mol Formula | Mass | M + H |
|---|---|---|---|---|
| 329 | 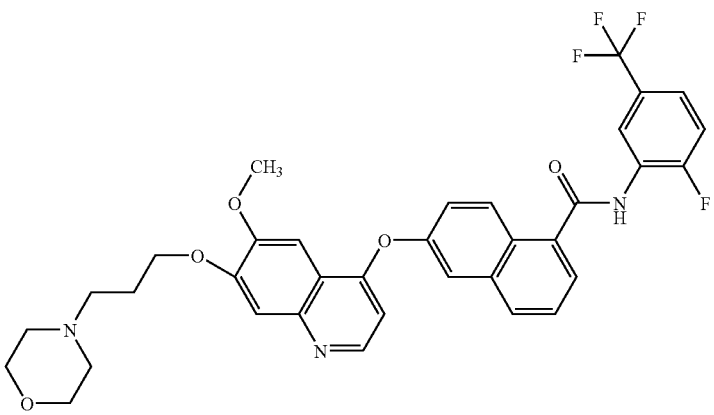<br>N-(2-fluoro-5-(trifluoromethyl)phenyl)-6-((6-(methoxy)-7-((3-(4-morpholinyl)propyl)oxy)-4-quinolinyl)oxy)-1-naphthalenecarboxamide | $C_{35}H_{31}F_4N_3O_5$ | 649.64 | 650.2 |
| 330 | 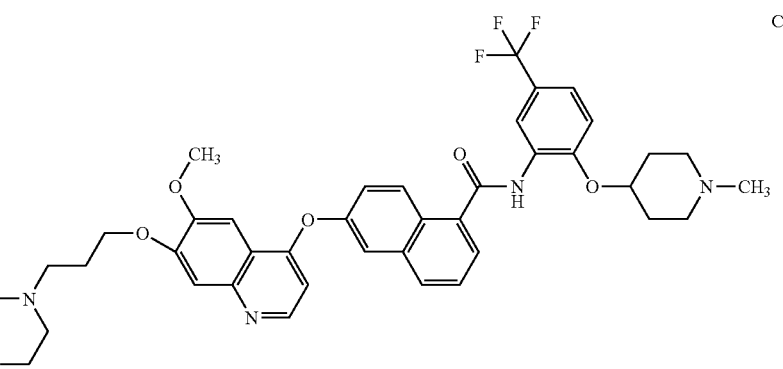<br>6-((6-(methoxy)-7-((3-(4-morpholinyl)propyl)oxy)-4-quinolinyl)oxy)-N-(2-((1-methyl-4-piperidinyl)oxy)-5-(trifluoromethyl)phenyl)-1-naphthalenecarboxamide | $C_{41}H_{43}F_3N_4O_6$ | 744.81 | 745.3 |
| 331 | 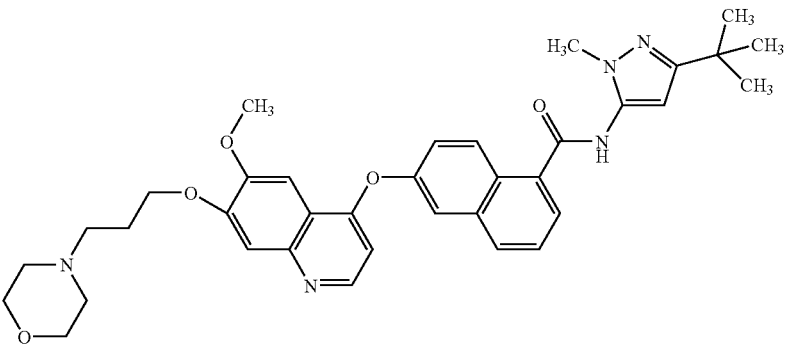<br>N-(3-(1,1-dimethylethyl)-1-methyl-1H-pyrazol-5-yl)-6-((6-(methoxy)-7-((3-(4-morpholinyl)propyl)oxy)-4-quinolinyl)oxy)-1-naphthalenecarboxamide | $C_{36}H_{41}N_5O_5$ | 623.75 | 624.3 |

| Example No. | Structure & Name | Mol Formula | Mass | M + H |
|---|---|---|---|---|
| 332 | 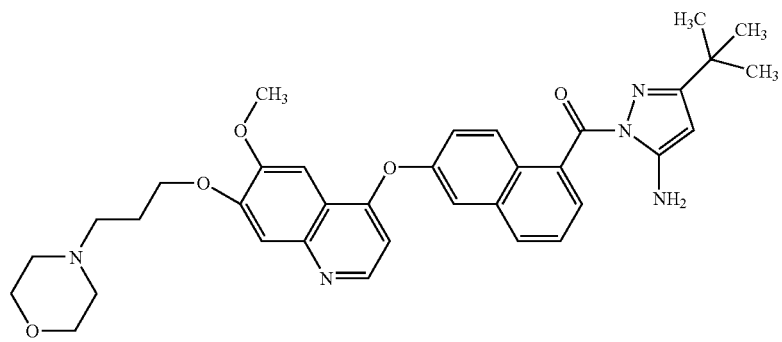<br>3-(1,1-dimethylethyl)-1-((6-((6-(methoxy)-7-((3-(4-morpholinyl)propyl)oxy)-4-quinolinyl)oxy)-1-naphthalenyl)carbonyl)-1H-pyrazol-5-amine | C₃₅H₃₉N₅O₅ | 609.72 | 610.2 |
| 333 | 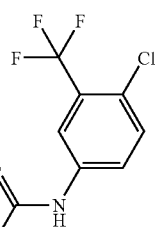<br>N-(4-chloro-3-(trifluoromethyl)phenyl)-6-((6-(methoxy)-7-((3-(4-morpholinyl)propyl)oxy)-4-quinolinyl)oxy)-1-naphthalenecarboxamide | C₃₅H₃₁ClF₃N₃O₅ | 666.09 | 666.5 |
| 334 | 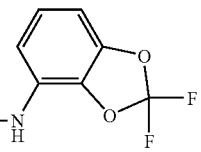<br>N-(2,2-difluoro-1,3-benzodioxol-4-yl)-6-((6-(methoxy)-7-((3-(4-morpholinyl)propyl)oxy)-4-quinolinyl)oxy)-1-naphthalenecarboxamide | C₃₅H₃₁F₂N₃O₇ | 643.64 | 644.5 |

| Example No. | Structure & Name | Mol Formula | Mass | M + H |
|---|---|---|---|---|
| 335 | 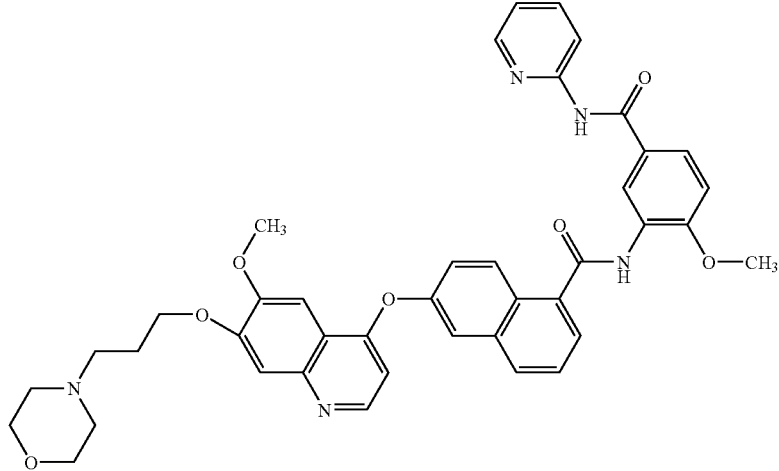  6-((6-(methoxy)-7-((3-(4-morpholinyl)propyl)oxy)-4-quinolinyl)oxy)-N-(2-(methoxy)-5-((2-pyridinylamino)carbonyl)phenyl)-1-naphthalenecarboxamide | $C_{41}H_{39}N_5O_7$ | 713.79 | 714.6 |
| 336 | 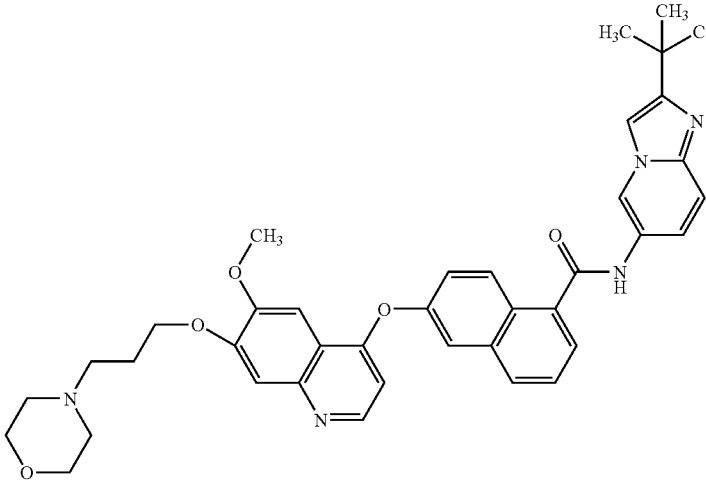  N-(2-(1,1-dimethylethyl)imidazo[1,2-a]pyridin-6-yl)-6-((6-(methoxy)-7-((3-(4-morpholinyl)propyl)oxy)-4-quinolinyl)oxy)-1-naphthalenecarboxamide | $C_{39}H_{41}N_5O_5$ | 659.78 | 660.6 |
| 337 | 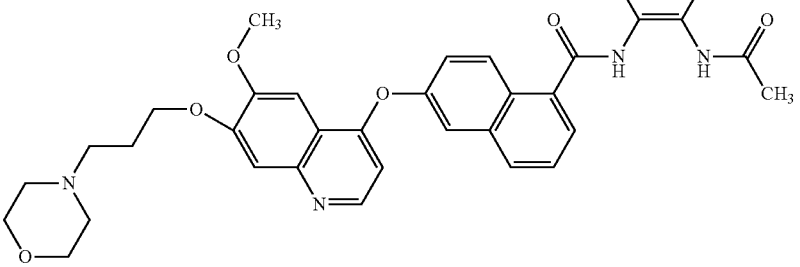  N-(2-(acetylamino)-5-(trifluoromethyl)phenyl)-6-((6-(methoxy)-7-((3-(4-morpholinyl)propyl)oxy)-4-quinolinyl)oxy)-1-naphthalenecarboxamide | $C_{37}H_{35}F_3N_4O_6$ | 688.7 | 689.5 |

-continued

| Example No. | Structure & Name | Mol Formula | Mass | M + H |
|---|---|---|---|---|
| 338 | 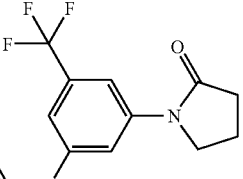<br>6-((6-(methoxy)-7-((3-(4-morpholinyl)propyl)oxy)-4-quinolinyl)oxy)-N-(3-(2-oxo-1-pyrrolidinyl)-5-(trifluoromethyl)phenyl)-1-naphthalenecarboxamide | $C_{39}H_{37}F_3N_4O_6$ | 714.74 | 715.5 |
| 339 | 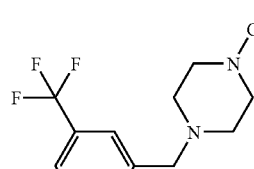<br>6-((6-(methoxy)-7-((3-(4-morpholinyl)propyl)oxy)-4-quinolinyl)oxy)-N-(3-((4-methyl-1-piperazinyl)methyl)-5-(trifluoromethyl)phenyl)-1-naphthalenecarboxamide | $C_{41}H_{44}F_3N_5O_5$ | 743.82 | 744.6 |
| 340 | 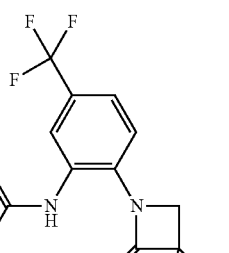<br>N-(2-(3,3-dimethyl-2-oxo-1-azetidinyl)-5-(trifluoromethyl)phenyl)-6-((6-(methoxy)-7-((3-(4-morpholinyl)propyl)oxy)-4-quinolinyl)oxy)-1-naphthalenecarboxamide | $C_{40}H_{39}F_3N_4O_6$ | 728.76 | 729.6 |

-continued

| Example No. | Structure & Name | Mol Formula | Mass | M + H |
|---|---|---|---|---|
| 341 | 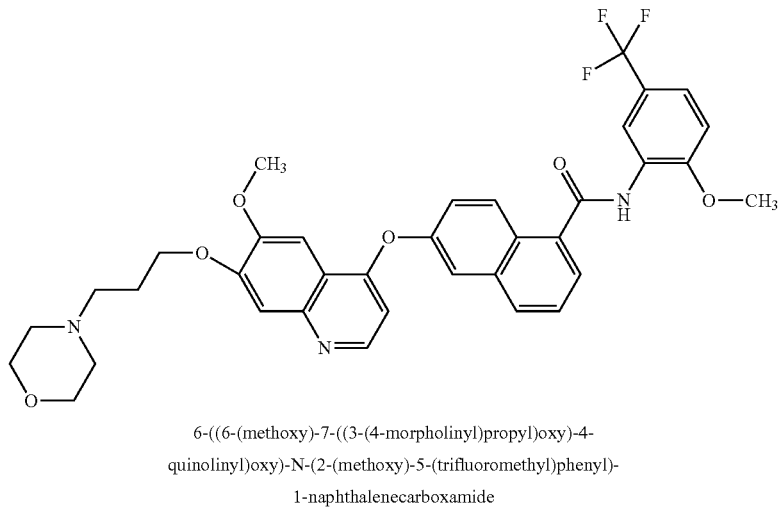<br>6-((6-(methoxy)-7-((3-(4-morpholinyl)propyl)oxy)-4-quinolinyl)oxy)-N-(2-(methoxy)-5-(trifluoromethyl)phenyl)-1-naphthalenecarboxamide | $C_{36}H_{34}F_3N_3O_6$ | 661.67 | 662.5 |
| 342 | 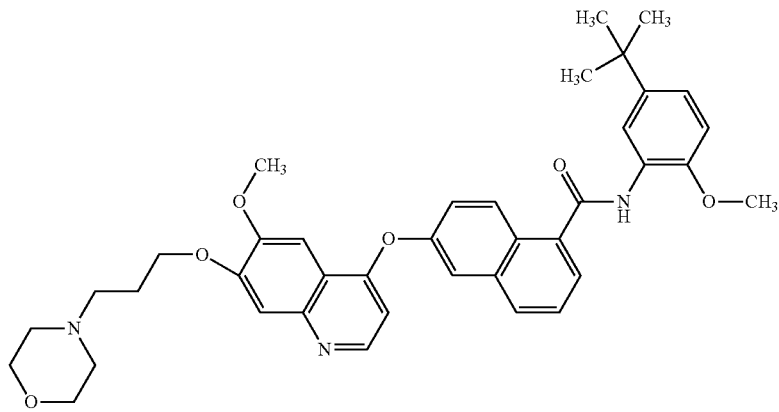<br>N-(5-(1,1-dimethylethyl)-2-(methoxy)phenyl)-6-((6-(methoxy)-7-((3-(4-morpholinyl)propyl)oxy)-4-quinolinyl)oxy)-1-naphthalenecarboxamide | $C_{39}H_{43}N_3O_6$ | 649.78 | 650.5 |
| 343 | 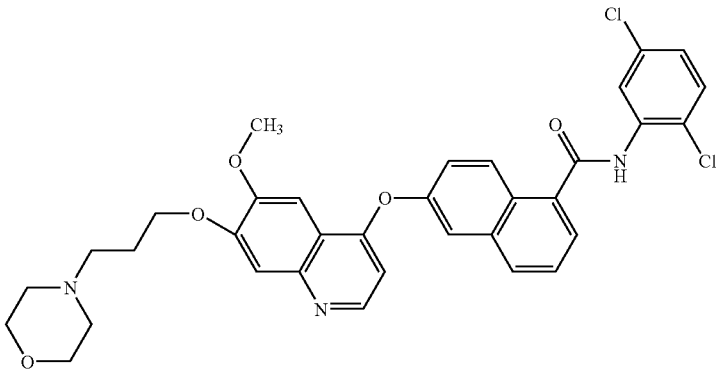<br>N-(2,5-dichlorophenyl)-6-((6-(methoxy)-7-((3-(4-morpholinyl)propyl)oxy)-4-quinolinyl)oxy)-1-naphthalenecarboxamide | $C_{34}H_{31}Cl_2N_3O_5$ | 632.54 | 632.4 |

| Example No. | Structure & Name | Mol Formula | Mass | M + H |
|---|---|---|---|---|
| 344 | 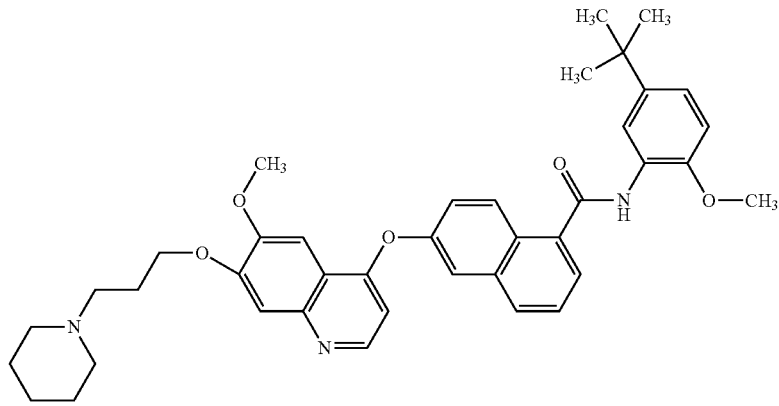<br>N-(5-(1,1-dimethylethyl)-2-(methoxy)phenyl)-6-((6-(methoxy)-7-((3-(1-piperidinyl)propyl)oxy)-4-quinolinyl)oxy)-1-naphthalenecarboxamide | $C_{40}H_{45}N_3O_5$ | 647.81 | 648.6 |
| 345 | 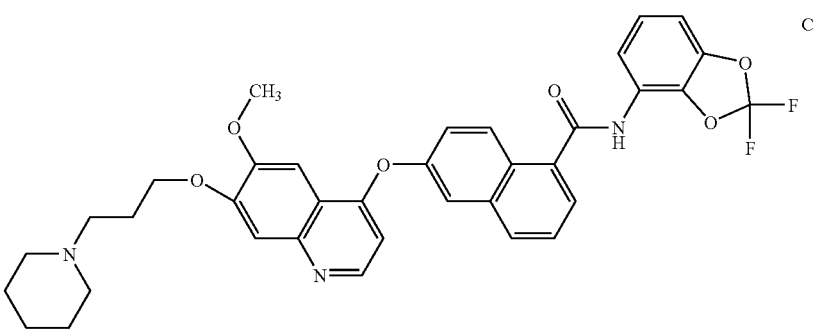<br>N-(2,2-difluoro-1,3-benzodioxol-4-yl)-6-((6-(methoxy)-7-((3-(1-piperidinyl)propyl)oxy)-4-quinolinyl)oxy)-1-naphthalenecarboxamid | $C_{36}H_{33}F_2N_3O_6$ | 641.67 | 642.5 |
| 346 | 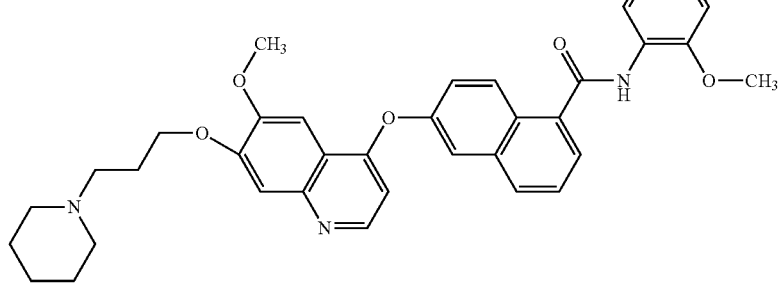<br>6-((6-(methoxy)-7-((3-(1-piperidinyl)propyl)oxy)-4-quinolinyl)oxy)-N-(2-(methoxy)-5-(trifluoromethyl)phenyl)-1-naphthalenecarboxamide | $C_{37}H_{36}F_3N_3O_5$ | 659.7 | 660.6 |

| Example No. | Structure & Name | Mol Formula | Mass | M + H |
|---|---|---|---|---|
| 347 | 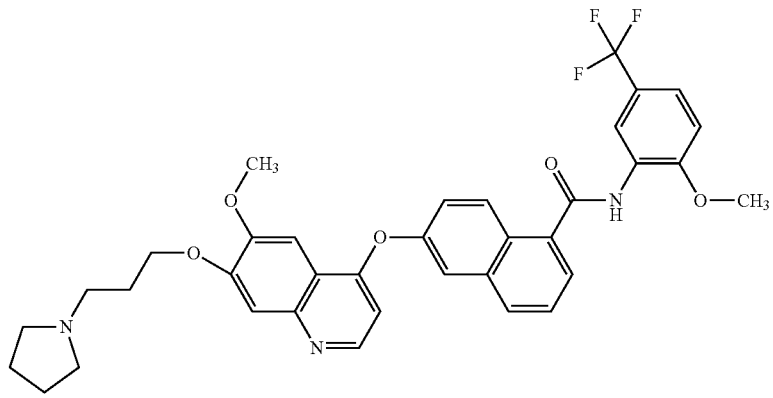<br>6-((6-(methoxy)-7-((3-(1-pyrrolidinyl)propyl)oxy)-4-quinolinyl)oxy)-N-(2-(methoxy)-5-(trifluoromethyl)phenyl)-1-naphthalenecarboxamide | $C_{36}H_{34}F_3N_3O_5$ | 645.67 | 646.5 |
| 348 | 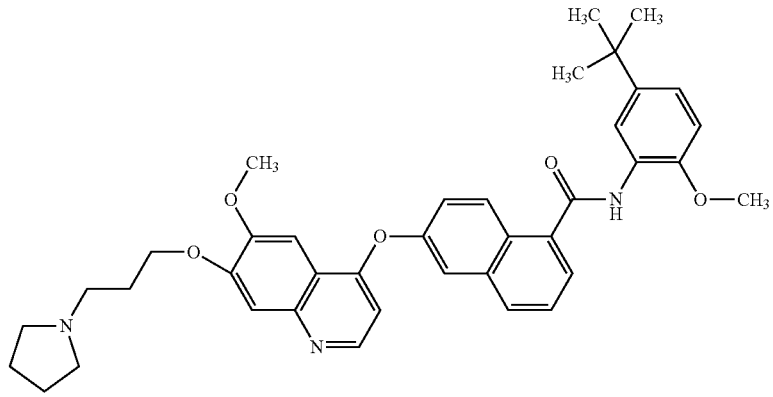<br>N-(5-(1,1-diniethylethyl)-2-(methoxy)phenyl)-6-((6-(methoxy)-7-((3-(1-pyrrolidinyl)propyl)oxy)-4-quinolinyl)oxy)-1-naphthalenecarboxamide | $C_{39}H_{43}N_3O_5$ | 633.78 | 634.6 |
| 349 | 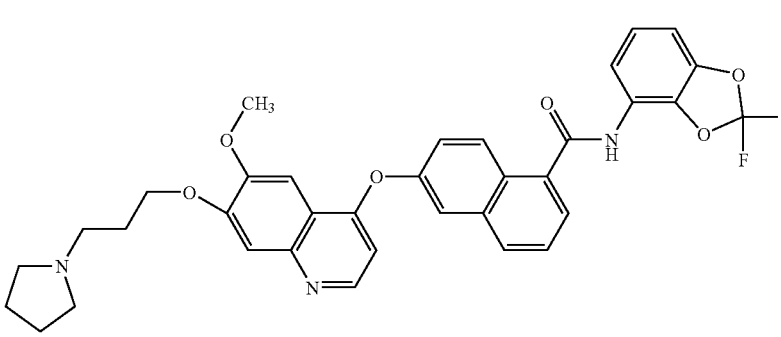<br>N-(2,2-difluoro-1,3-benzodioxol-4-yl)-6-((6-(methoxy)-7-((3-(1-pyrrolidinyl)propyl)oxy)-4-quinolinyl)oxy)-1-naphthalenecarboxamide | $C_{35}H_{31}F_2N_3O_6$ | 627.64 | 628.5 |

| Example No. | Structure & Name | Mol Formula | Mass | M + H |
|---|---|---|---|---|
| 350 | 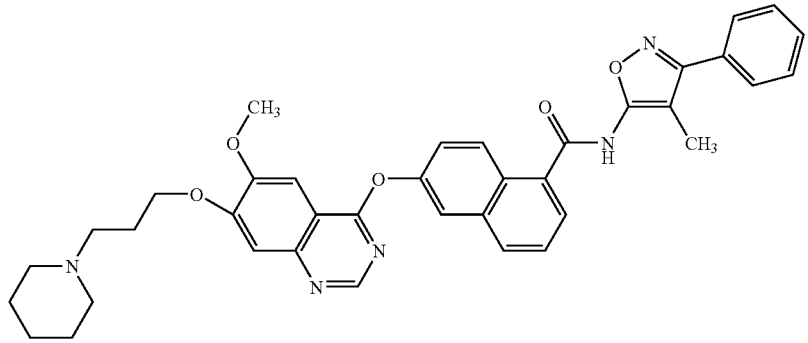                6-((6-(methoxy)-7-((3-(1-piperidinyl)propyl)oxy)-4-quinazolinyl)oxy)-N-(4-methyl-3-phenyl-5-isoxazolyl)-1-naphthalenecarboxamide | C₃₈H₃₇N₅O₅ | 643.74 | 644.3 |
| 351 | 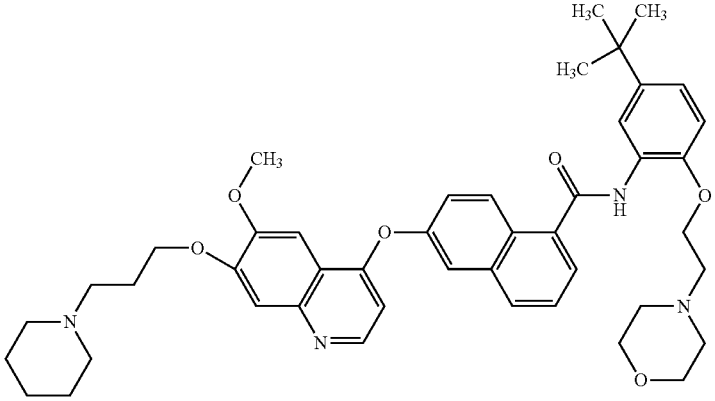                N-(5-(1,1-dimethylethyl)-2-((2-(4-morpholinyl)ethyl)oxy)phenyl)-6-((6-(methoxy)-7-((3-(4-morpholinyl)propyl)oxy)-4-quinolinyl)oxy)-1-naphthalenecarboxamide | C₄₄H₅₂N₄O₇ | 748.92 | 749.4 |
| 352 | 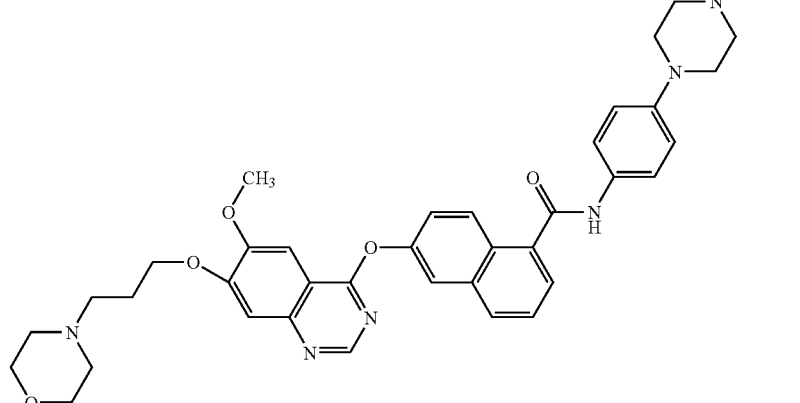                N-(4-(4-(1-methylethyl)-1-piperazinyl)phenyl)-6-((6-(methoxy)-7-((3-(1-piperidinyl)propyl)oxy)-4-quinazolinyl)oxy)-1-naphthalenecarboxamide | C₄₁H₄₈N₆O₄ | 688.87 | 689.3 |

| Example No. | Structure & Name | Mol Formula | Mass | M + H |
|---|---|---|---|---|
| 353 | 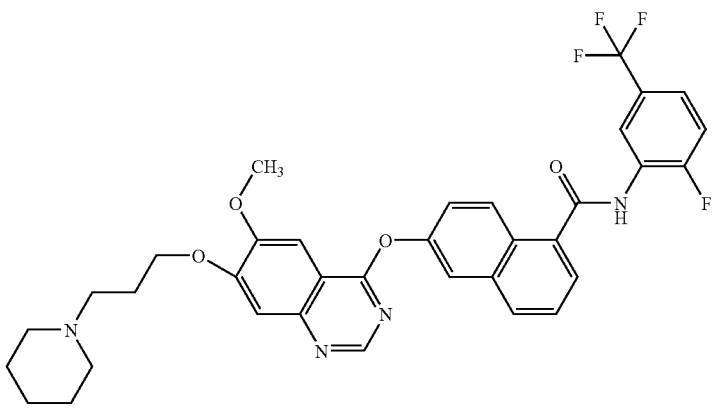<br>N-(2-fluoro-5-(trifluoromethyl)phenyl)-6-((6-(methoxy)-7-((3-(1-piperidinyl)propyl)oxy)-4-quinazolinyl)oxy)-1-naphthalenecarboxamide | $C_{35}H_{32}F_4N_4O_4$ | 648.65 | 649.5 |
| 354 | 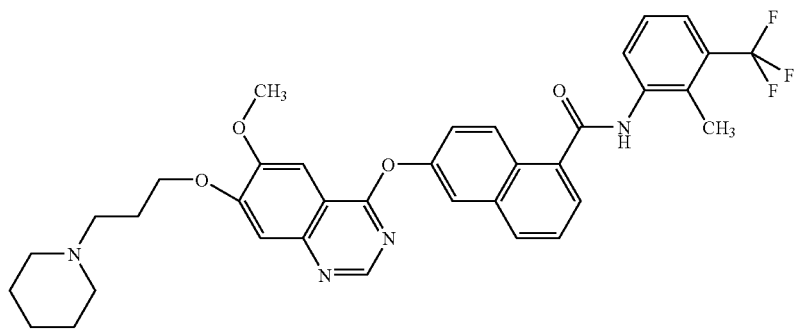<br>6-((6-(methoxy)-7-((3-(1-pipendinyl)propyl)oxy)-4-quinazolinyl)oxy)-N-(2-methyl-3-(trifluoromethyl)phenyl)-1-naphthalenecarboxamide | $C_{36}H_{35}F_3N_4O_4$ | 644.69 | 645.7 |
| 355 | 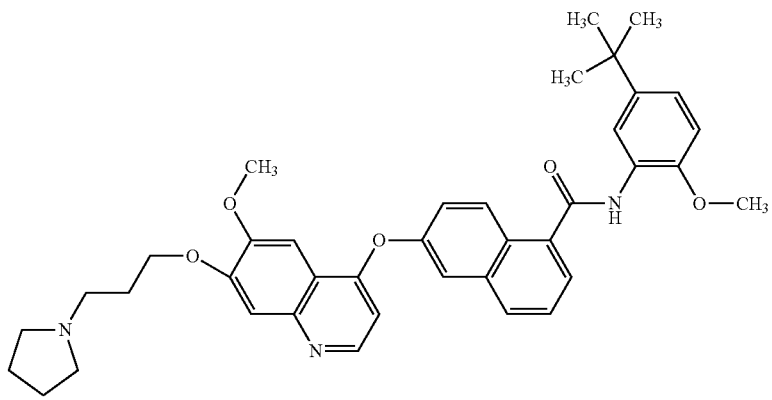<br>N-(5-(1,1-dimethylethyl)-2-(methoxy)phenyl)-6-((6-(methoxy)-7-((3-(1-pyrrolidinyl)propyl)oxy)-4-quinolinyl)oxy)-1-naphthalenecarboxamide | $C_{39}H_{43}N_3O_5$ | 633.78 | 634.6 |

| Example No. | Structure & Name | Mol Formula | Mass | M + H |
|---|---|---|---|---|
| 356 | 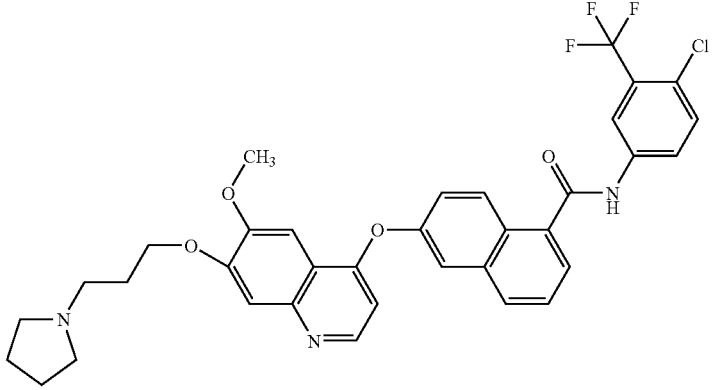<br>N-(4-chloro-3-(trifluoromethyl)phenyl)-6-((6-(methoxy)-7-((3-(1-pyrrolidinyl)propyl)oxy)-4-quinolinyl)oxy)-1-naphthalenecarboxamide | $C_{35}H_{31}ClF_3N_3O_4$ | 650.09 | 650.5 |

EXAMPLE 357

6-((6,7-bis(methoxy)-4-quinolinyl)oxy)-N-(2-(dimethylamino)ethyl)-1-naphthalenecarboxamide

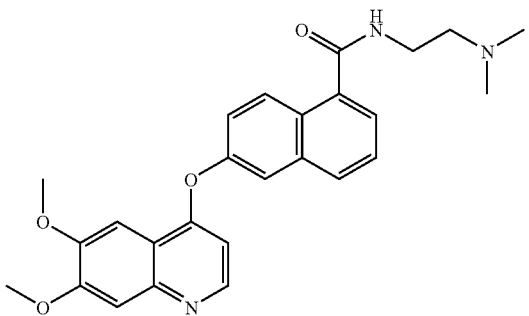

6-(6,7-Dimethoxyquinolin-4-yloxy)-1-naphthoic acid (80 mg, 0.213 mmol), 1-(3-dimethylaminopropyl)-3-ethylcarbodiimide hydrochloride (61 mg, 0.32 mmol) and HOAT (29 mg, 0.213 mmol) were added to a reaction tube, then dissolved in DMF (0.6 mL). A solution of N,N-dimethylethylenediamine (23 mg, 0.256 mmol) in DMF (0.6 mL) was added to the reaction, followed by Hunig's base (75 mg, 0.581 mmol). The mixture became yellow and clear within 15 min and was stirred at RT for 16 h. The mixture was concentrated under vacuum. The remaining yellow oil was purified by silica gel chromatography (2% to 3% 7N $NH_3$ in MeOH in $CH_2Cl_2$) to afford 6-((6,7-bis(methoxy)-4-quinolinyl)oxy)-N-(2-(dimethylamino)ethyl)-1-naphthalenecarboxamide as a white solid. MS (ESI, pos. ion) m/z: 446.1 (M+1). Calc'd for $C_{226}H_{27}N_3O_4$–445.52.

The following examples were prepared similar to the procedures described in Example 357.

| Example No. | Structure & Name | Mol Formula | Mass | M + H |
|---|---|---|---|---|
| 358 | 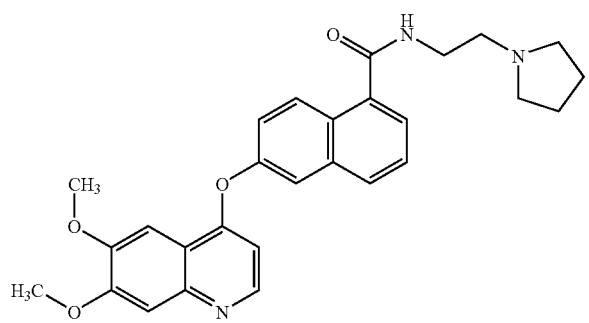<br>6-((6,7-bis(methoxy)-4-quinolinyl)oxy)-N-(2-(1-pyrrolidinyl)ethyl)-1-naphthalenecarboxamide | $C_{28}H_{29}N_3O_4$ | 471.55 | 472.1 |

| Example No. | Structure & Name | Mol Formula | Mass | M + H |
|---|---|---|---|---|
| 359 | 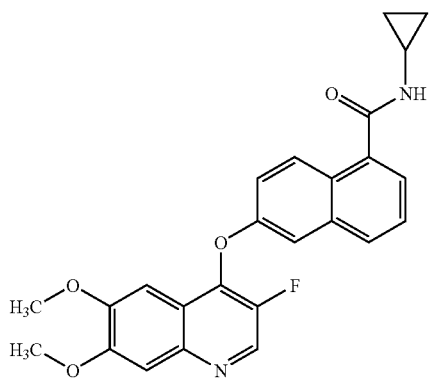<br>N-cyclopropyl-6-((3-fluoro-6,7-bis(methoxy)-4-quinolinyl)oxy)-1-naphthalenecarboxamide | $C_{25}H_{21}FN_2O_4$ | 432.45 | 433 |
| 360 | 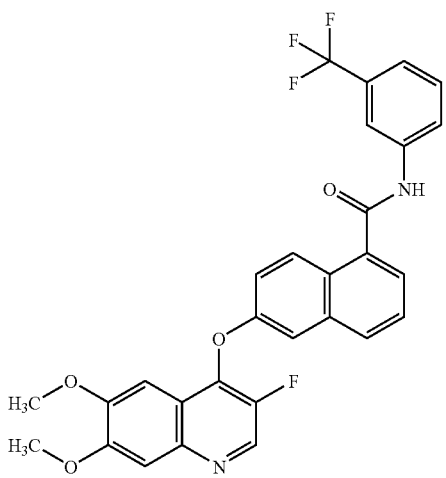<br>6-((3-fluoro-6,7-bis(methoxy)-4-quinolinyl)oxy)-N-(3-(trifluoromethyl)phenyl)-1-naphthalenecarboxamide | $C_{29}H_{20}F_4N_2O_4$ | 536.48 | 537 |
| 361 | 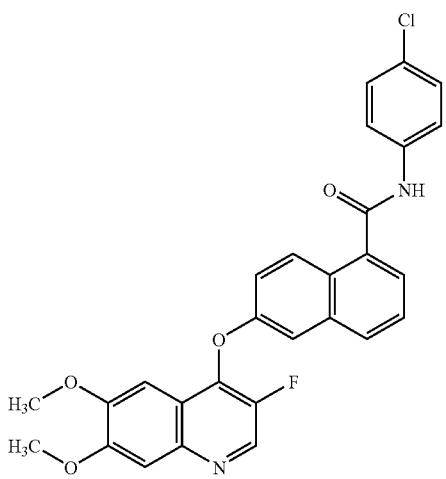<br>N-(4-chlorophenyl)-6-((3-fluoro-6,7-bis(methoxy)-4-quinolinyl)oxy)-1-naphthalenecarboxamide | $C_{28}H_{20}ClFN_2O_4$ | 502.93 | 503 |

| Example No. | Structure & Name | Mol Formula | Mass | M + H |
|---|---|---|---|---|
| 362 | 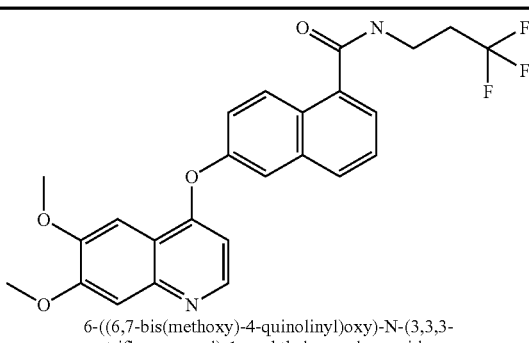<br>6-((6,7-bis(methoxy)-4-quinolinyl)oxy)-N-(3,3,3-trifluoropropyl)-1-naphthalenecarboxamide | $C_{25}H_{21}F_3N_2O_4$ | 470.44 | 471.1 |

EXAMPLE 363

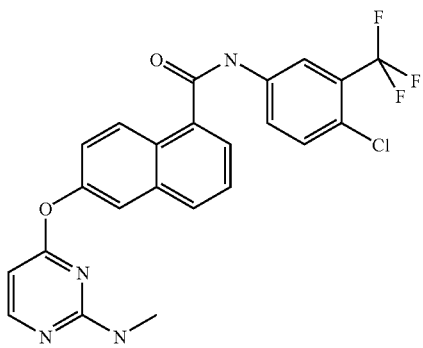

6-(2-Methylamino-pyrimidin-4-yloxy)-naphthalene-1-carboxylic acid (4-chloro-3-trifluoromethyl-phenyl)-amide

Step (a) Preparation of 6-(2-fluoropyrimidin-4-yloxy)-1-naphthoic Acid

To a solution of 6-hydroxy-1-napthoic acid (3.23 g, 17.2 mmol) in DMSO (8 mL), $Cs_2CO_3$ (16.8 g, 57.6 mmol) was added and stirred at RT 10 min. 2,4-Difluoropyrimidine (2 g, 17.2 mmol) was added and the reaction was stirred at RT for 12 h. The mixture was diluted with water and made pH 7 using 1 N HCl, at which point it is a foamy emulsion. The mixture sat without stirring 2 days and the resulting solid was filtered and rinsed with water and $Et_2O$ to yield the title compound as a pink solid.

Step (b) Preparation of 6-(2-(methylamino)pyrimidin-4-yloxy)-1-naphthoic acid 6-(2-Fluoropyrimidin-4-yloxy)-1-naphthoic acid (step a, 1 g, 3.53 mmol) was suspended in THF (10 mL) and warmed to partially dissolve. The mixture was cooled to RT and N-methylamine (2 M in THF, 8.9 mL, 17.7 mmol) was added. After 2 h, the solvent was concentrated in-vacuo. The residue was diluted with $H_2O$ and made pH 7 using 1 N HCl. The solid was filtered and rinsed with water and $Et_2O$ to yield the title compound as a pink solid.

Step (c) Preparation of N-(4-chloro-3-(trifluoromethyl)phenyl)-6-((2-(methylamino)-4-pyrimidinyl)oxy)-1-naphthalenecarboxamide This compound was prepared similar to the procedure described in Example 357. MS (ESI pos. ion) m/z: 473.0 (M+H). Calc'd for $C_{23}H_{16}ClF_3N_4O_2$=472.85.

The following examples were prepared similar to the procedures described in Example 357 and purified by column chromatography and/or crystallization.

| Example No. | Structure & Name | Mol Formula | Mass | M + H |
|---|---|---|---|---|
| 364 | 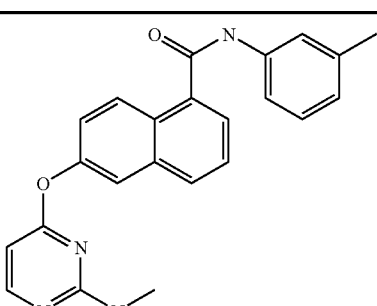<br>6-((2-(methylamino)-4-pyrimidinyl)oxy)-N-(3-methylphenyl)-1-naphthalenecarboxamide | $C_{23}H_{20}N_4O_2$ | 384.43 | 385.1 |

| Example No. | Structure & Name | Mol Formula | Mass | M + H |
|---|---|---|---|---|
| 365 | 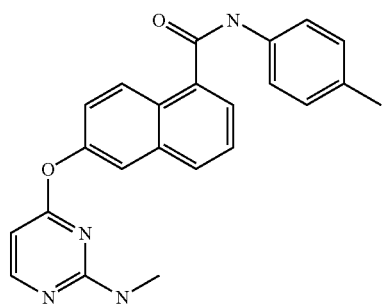[br]6-((2-(methylamino)-4-pyrimidinyl)oxy)-N-(4-methylphenyl)-1-naphthalenecarboxamide | $C_{23}H_{20}N_4O_2$ | 384.43 | 385.1 |
| 366 | 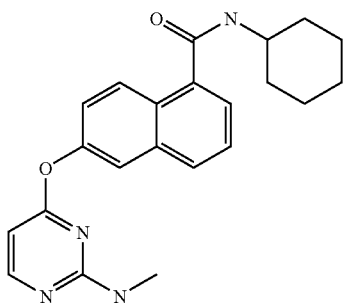[br]N-cyclohexyl-6-((2-(methylamino)-4-pyrimidinyl)oxy)-1-naphthalenecarboxamide | $C_{22}H_{24}N_4O_2$ | 376.45 | 377.2 |
| 367 | 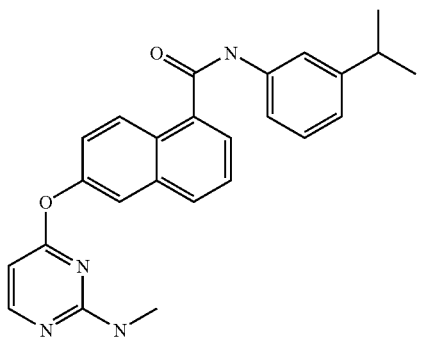[br]6-((2-(methylamino)-4-pyrimidinyl)oxy)-N-(3-(1-methylethyl)phenyl)-1-naphthalenecarboxamide | $C_{25}H_{24}N_4O_2$ | 412.49 | 413.1 |
| 368 | 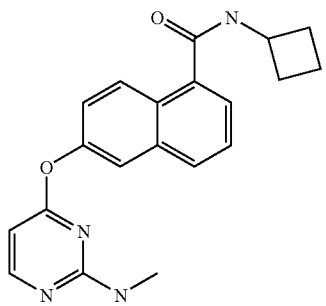[br]N-cyclobutyl-6-((2-(methylamino)-4-pyrimidinyl)oxy)-1-naphthalenecarboxamide | $C_{20}H_{20}N_4O_2$ | 348.40 | 349.1 |

| Example No. | Structure & Name | Mol Formula | Mass | M + H |
|---|---|---|---|---|
| 369 | 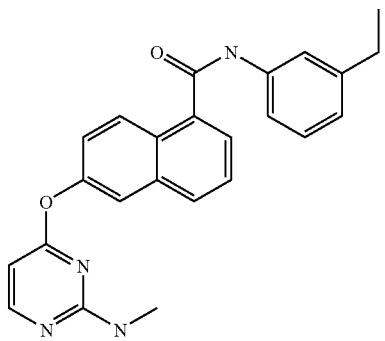<br>N-(3-ethylphenyl)-6-((2-(methylamino)-4-pyrimidinyl)oxy)-1-naphthalenecarboxamide | $C_{24}H_{22}N_4O_2$ | 398.46 | 399.1 |
| 370 | 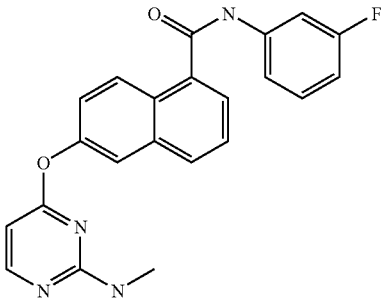<br>N-(3-fluorophenyl)-6-((2-(methylamino)-4-pyrimidinyl)oxy)-1-naphthalenecarboxamide | $C_{22}H_{17}FN_4O_2$ | 388.39 | 389.1 |
| 371 | 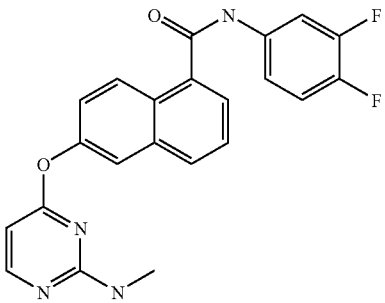<br>N-(3,4-difluorophenyl)-6-((2-(methylamino)-4-pyrimidinyl)oxy)-1-naphthalenecarboxamide | $C_{22}H_{16}F_2N_4O_2$ | 406.38 | 407.1 |
| 372 | 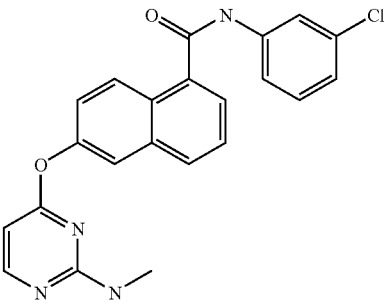<br>N-(3-chlorophenyl)-6-((2-(methylamino)-4-pyrimidinyl)oxy)-1-naphthalenecarboxamide | $C_{22}H_{17}ClN_4O_2$ | 404.85 | 405.1 |

| Example No. | Structure & Name | Mol Formula | Mass | M + H |
|---|---|---|---|---|
| 373 | 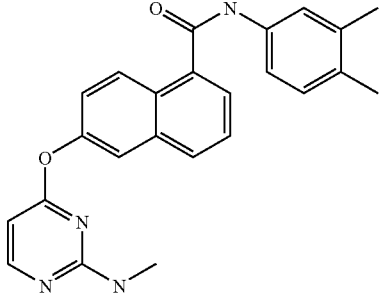<br>N-(3,4-dimethylphenyl)-6-((2-(methylamino)-4-pyrimidinyl)oxy)-1-naphthalenecarboxamide | $C_{24}H_{22}N_4O_2$ | 398.46 | 399.1 |
| 374 | 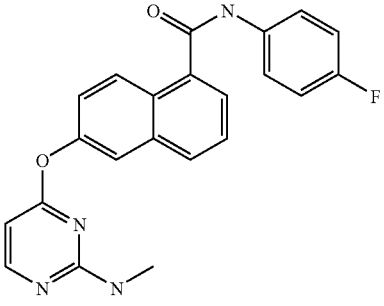<br>N-(4-fluorophenyl)-6-((2-(methylamino)-4-pyrimidinyl)oxy)-1-naphthalenecarboxamide | $C_{22}H_{17}FN_4O_2$ | 388.39 | 389.1 |
| 375 | 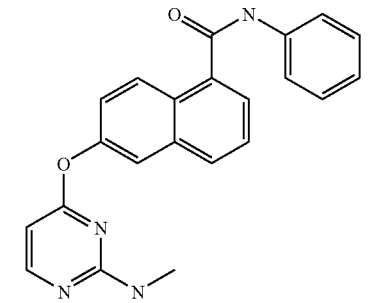<br>6-((2-(methylamino)-4-pyrimidinyl)oxy)-N-phenyl-1-naphthalenecarboxamide | $C_{22}H_{18}N_4O_2$ | 370.41 | 371.1 |
| 376 | 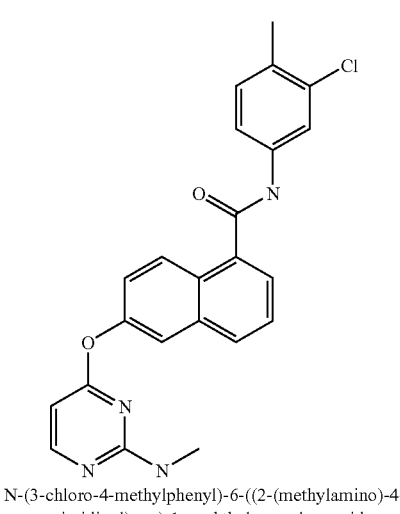<br>N-(3-chloro-4-methylphenyl)-6-((2-(methylamino)-4-pyrimidinyl)oxy)-1-naphthalenecarboxamide | $C_{23}H_{19}ClN_4O_2$ | 418.88 | 419.1 |

| Example No. | Structure & Name | Mol Formula | Mass | M + H |
|---|---|---|---|---|
| 377 | 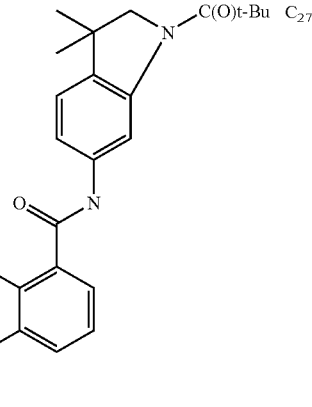 tert-butyl 3,3-dimethyl-6-(2-(2-(methylamino)pyrimidin-4-yloxy)-1-naphthamido)indoline-1-carboxylate | $C_{27}H_{27}N_5O_2$ | 453.55 | — |

EXAMPLE 378

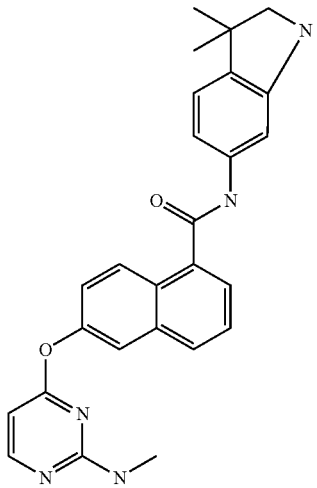

N-(3,3-dimethyl-2,3-dihydro-1H-indol-6-yl)-6-((2-(methylamino)-4-pyrimidinyl)oxy)-1-naphthalenecarboxamide To a cooled (ice bath) solution of tert-butyl 3,3-dimethyl-6-(2-(2-(methylamino)pyrimidin-4-yloxy)-1-naphthamido)indoline-1-carboxylate (theor. 76 mg, 0.17 mmol) in $CH_2Cl_2$ (1.5 mL), TFA (200 µL) was added, the reaction stirred and warmed to RT overnight. The mixture was concentrated in-vacuo and the residue dissolved in $CH_2Cl_2$, washed with 1 N NaOH, then brine and dried with $Na_2SO_4$. The mixture was filtered and evaporated. The residue was triturated with hexanes and the solid filtered to give the title compound as a white solid. MS (ESI pos. ion) m/z: 440.2 (M+H). Calc'd for $C_{26}H_{25}N_5O_2$—439.51.

EXAMPLE 379

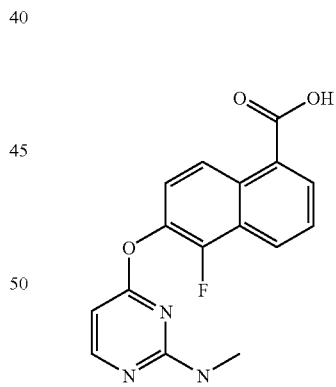

5-fluoro-6-(2-(methylamino)pyrimidin-4-yloxy)-1-naphthoic acid

The title compound was prepared similar to Example 363, steps a and b.

The following examples were prepared similar to the procedures described in Example 357 and purified by column chromatography and/or crystallization.

| Example No. | Structure & Name | Mol Formula | Mass | M + H |
|---|---|---|---|---|
| 380 | 5-fluoro-6-((2-(methylamino)-4-pyrimidinyl)oxy)-N-(3-chlorophenyl)-1-naphthalenecarboxamide | $C_{22}H_{16}ClFN_4O_2$ | 422.85 | 423.1 |
| 381 | 5-fluoro-6-((2-(methylamino)-4-pyrimidinyl)oxy)-N-(4-((trifluoromethyl)oxy)phenyl)-1-naphthalenecarboxamide | $C_{23}H_{16}F_4N_4O_3$ | 472.4 | 473.1 |
| 382 | 5-fluoro-6-((2-(methylamino)-4-pyrimidinyl)oxy)-N-(3-methylphenyl)-1-naphthalenecarboxamide | $C_{23}H_{19}FN_4O_2$ | 402.43 | 403.1 |
| 383 | N-(3-chloro-4-methylphenyl)-5-fluoro-6-((2-(methylamino)-4-pyrimidinyl)oxy)-1-naphthalenecarboxamide | $C_{23}H_{18}ClFN_4O_2$ | 436.87 | 437.1 |

-continued

| Example No. | Structure & Name | Mol Formula | Mass | M + H |
|---|---|---|---|---|
| 384 | 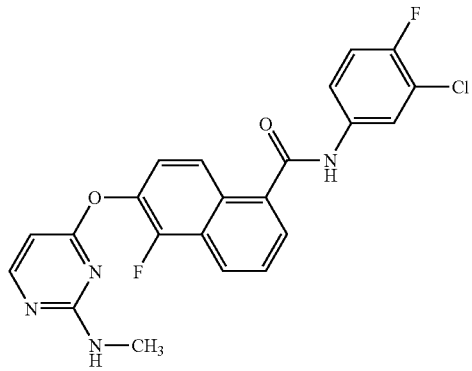<br>N-(3-chloro-4-fluorophenyl)-5-fluoro-6-((2-(methylamino)-4-pyrimidinyl)oxy)-1-naphthalenecarboxamide | $C_{22}H_{15}ClF_2N_4O_2$ | 440.84 | 441 |
| 385 | 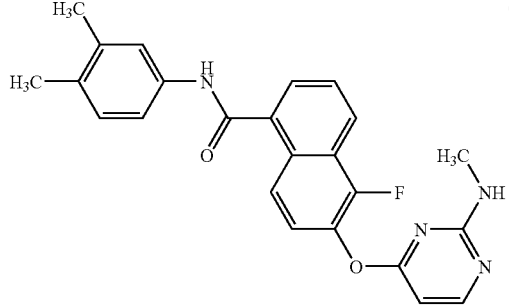<br>N-(3,4-dimethylphenyl)-5-fluoro-6-((2-(methylamino)-4-pyrimidinyl)oxy)-1-naphthalenecarboxamide | $C_{24}H_{21}FN_4O_2$ | 416.45 | 417.2 |
| 386 | 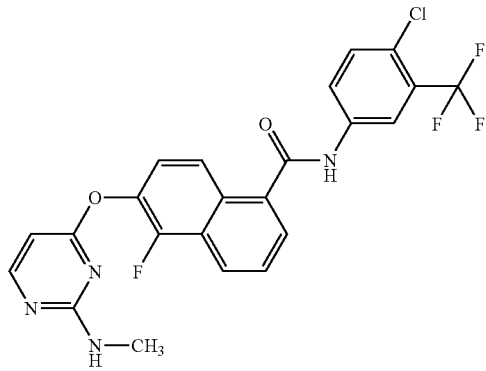<br>N-(4-chloro-3-(trifluoromethyl)phenyl)-5-fluoro-6-((2-(methylamino)-4-pyrimidinyl)oxy)-1-naphthalenecarboxamide | $C_{23}H_{15}ClF_4N_4O_2$ | 490.84 | 491.1 |

EXAMPLE 387

N-(3-(trifluoromethyl)phenyl)-6-((2-((1-methylethyl)amino)-4-pyrimidinyl)oxy)-1-naphthalenecarboxamide

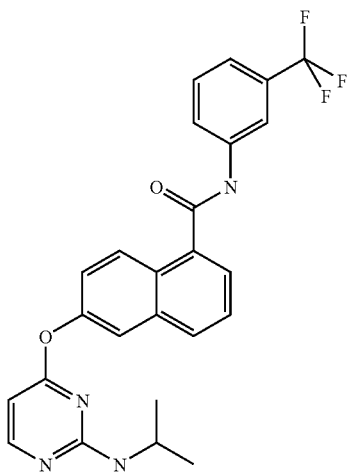

Step (a) Preparation of 6-(2-(isopropylamino)pyrimidin-4-yloxy)-1-naphthoic acid The title compound was prepared similar to the procedure described in Example 363 (b).

Step (b) Preparation of N-(3-(trifluoromethyl)phenyl)-6-((2-((1-methylethyl)amino)-4-pyrimidinyl)oxy)-1-naphthalenecarboxamide This compound was prepared similar to the procedure described in Example 357. MS (ESI pos. ion) m/z: 467.1 (M+H). Calc'd for $C_{25}H_{21}F_3N_4O_2$–466.46. The following examples were prepared similar to the procedures described in Example 387 and purified by column chromatography and/or crystallization.

| Example No. | Structure & Name | Mol Formula | Mass | M + H |
|---|---|---|---|---|
| 388 | 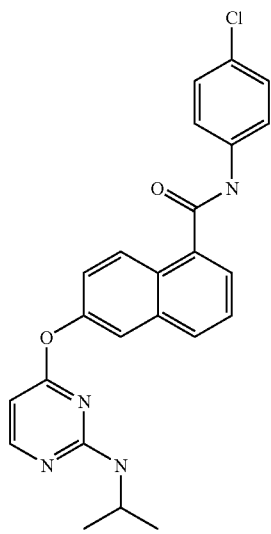<br>N-(4-chlorophenyl)-6-((2-((1-methylethyl)amino)-4-pyrimidinyl)oxy)-1-naphthalenecarboxamide | $C_{24}H_{21}ClN_4O_2$ | 432.90 | 433.0 |

-continued
| Example No. | Structure & Name | Mol Formula | Mass | M + H |
|---|---|---|---|---|
| 389 | 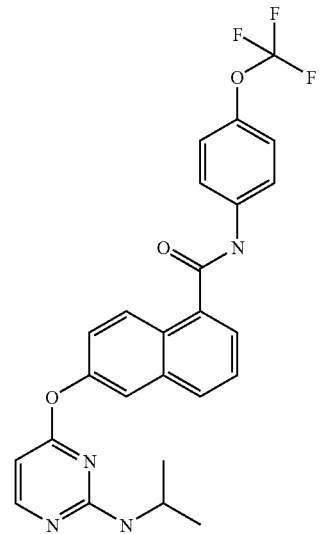<br>6-((2-((1-methylethyl)amino)-4-pyrimidinyl)oxy)-N-(4-((trifluoromethyl)oxy)phenyl)-1-naphthalenecarboxamide | $C_{25}H_{21}F_3N_4O_3$ | 482.45 | 483.1 |
| 390 | 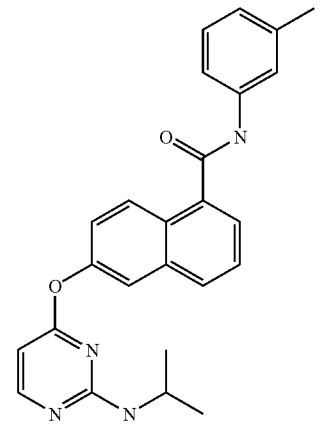<br>6-((2-((1-methylethyl)amino)-4-pyrimidinyl)oxy)-N-(3-methylphenyl)-1-naphthalenecarboxamide | $C_{25}H_{24}N_4O_2$ | 412.49 | 413.2 |
| 391 | 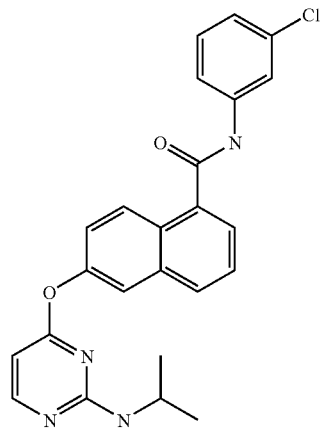<br>N-(3-chlorophenyl)-6-((2-((1-methylethyl)amino)-4-pyrimidinyl)oxy)-1-naphthalenecarboxamide | $C_{24}H_{21}ClN_4O_2$ | 432.90 | 433.0 |

| Example No. | Structure & Name | Mol Formula | Mass | M + H |
|---|---|---|---|---|
| 392 | 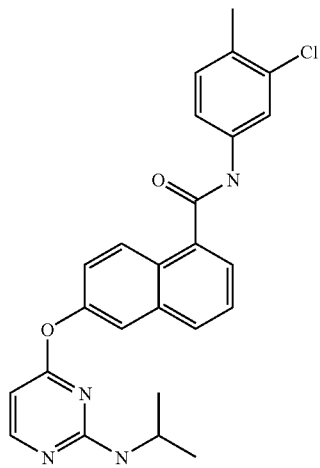<br>N-(3-chloro-4-methylphenyl)-6-((2-((1-methylethyl)amino)-4-pyrimidinyl)oxy)-1-naphthalenecarboxamide | $C_{25}H_{23}ClN_4O_2$ | 446.93 | 447.1 |
| 393 | 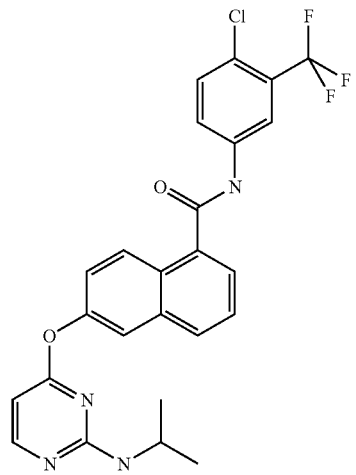<br>N-(4-chloro-3-(trifluoromethyl)phenyl)-6-((2-((1-methylethyl)amino)-4-pyrimidinyl)oxy)-1-naphthalenecarboxamide | $C_{25}H_{20}ClF_3N_4O_2$ | 500.90 | 501.1 |

-continued

| Example No. | Structure & Name | Mol Formula | Mass | M + H |
|---|---|---|---|---|
| 394 | 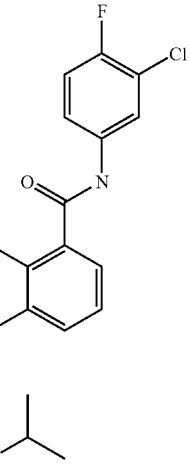<br>N-(3-chloro-4-fluorophenyl)-6-((2-((1-methylethyl)amino)-4-pyrimidinyl)oxy)-1-naphthalenecarboxamide | $C_{24}H_{20}ClFN_4O_2$ | 450.89 | 451.0 |
| 395 | 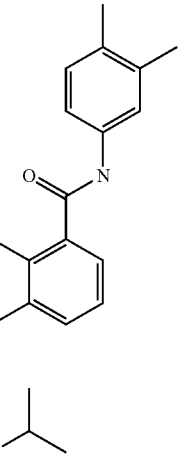<br>N-(3,4-dimethylphenyl)-6-((2-((1-methylethyl)amino)-4-pyrimidinyl)oxy)-1-naphthalenecarboxamide | $C_{26}H_{26}N_4O_2$ | 426.51 | 427.2 |

EXAMPLE 396

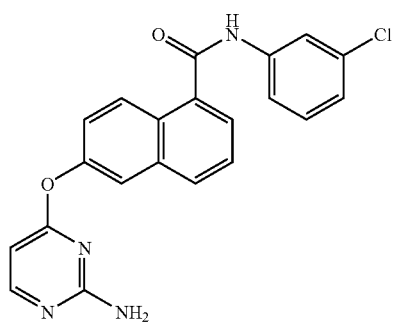

6-((2-amino-4-pyrimidinyl)oxy)-N-(3-chlorophenyl)-1-naphthalenecarboxamide

Step (a) Preparation of 6-(2-aminopyrimidin-4-yloxy)-1-naphthoic acid 6-(2-Fluoropyrimidin-4-yloxy)-1-naphthoic acid (1.2 g, 4.2 mmol) was dissolved in NH$_4$OH (37% water, 20 mL) and stirred at RT for 3h. Solvent was evaporated. A little bit of MeOH was added to the slurry followed by ether until the compound crashed out. Solid was filtered.

Step (b) Preparation of 6-(2-aminopyrimidin-4-yloxy)-N-4-chloro-1-naphthamide 6-(2-Aminopyrimidin-4-yloxy)-1-naphthoic acid (Step a, 82 mg, 0.29 mmol), 3-chloroaniline (0.046 mL, 0.43 mmol), HATU (166 mg, 0.43 mmol) and DIPEA (0.07 mL, 0.43 mmol) were stirred overnight in CHCl$_3$ (3 mL) at RT. The mixture was filtered and the solid was rinsed with CHCl$_3$, ether and MeOH. The title compound was obtained as an off-with solid. MS (ESI pos. ion) m/z: 391 (M+H). Calc'd for $C_{21}H_{15}ClN_4O_4$–390.82.

The following compounds were prepared similar to the procedures described in Example 396, step b.

| Example No. | Structure & Name | Mol Formula | Mass | M + H |
|---|---|---|---|---|
| 397 | 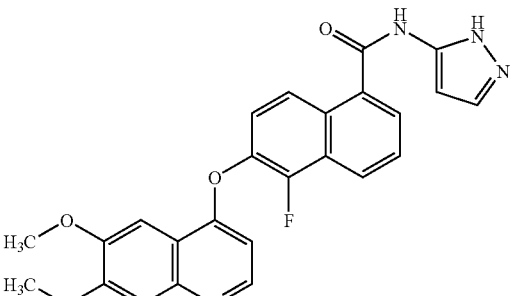<br>6-((6,7-bis(methoxy)-4-quinolinyl)oxy)-5-fluoro-N-(1H-pyrazol-5-yl)-1-naphthalenecarboxamide | $C_{25}H_{19}FN_4O_4$ | 458.45 | 459.1 |
| 398 | 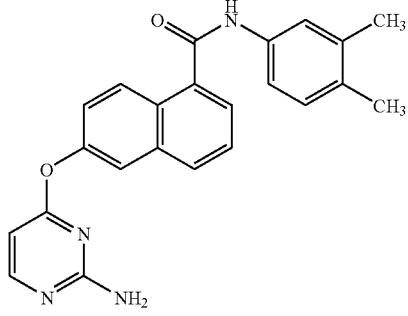<br>6-((2-amino-4-pyrimidinyl)oxy)-N-(3,4-dimethylphenyl)-1-naphthalenecarboxamide | $C_{23}H_{20}N_4O_2$ | 384.44 | 385.1 |
| 399 | 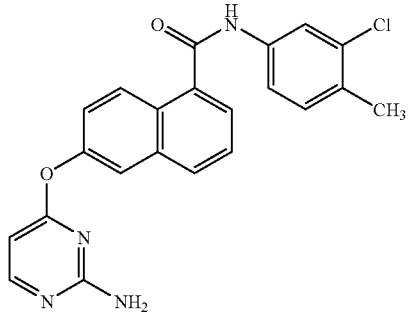<br>6-((2-amino-4-pyrimidinyl)oxy)-N-(3-chloro-4-methylphenyl)-1-naphthalenecarboxamide | $C_{22}H_{17}ClN_4O_2$ | 404.86 | 405 |
| 400 | 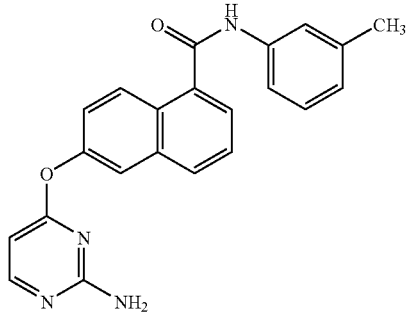<br>6-((2-amino-4-pyrimidinyl)oxy)-N-(3-(methyl)phenyl)-1-naphthalenecarboxamide | $C_{22}H_{18}N_4O_2$ | 370.41 | 371.1 |

-continued

| Example No. | Structure & Name | Mol Formula | Mass | M + H |
|---|---|---|---|---|
| 401 | 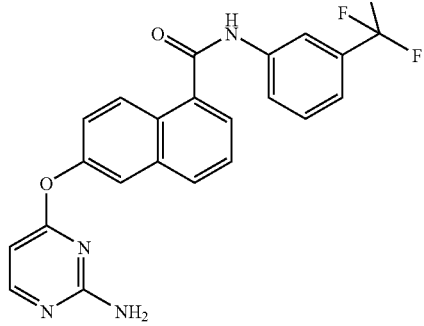<br>6-((2-amino-4-pyrimidinyl)oxy)-N-(3-(trifluoromethyl)phenyl)-1-naphthalenecarboxamide | $C_{22}H_{15}F_3N_4O_2$ | 424.38 | 425 |
| 402 | 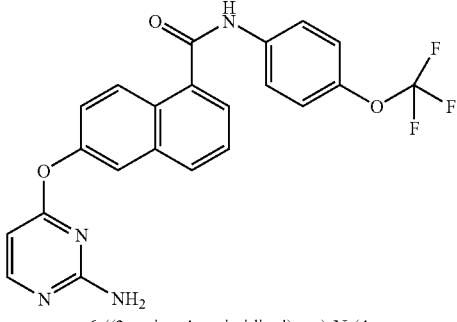<br>6-((2-amino-4-pyrimidinyl)oxy)-N-(4-((trifluoromethyl)oxy)phenyl)-1-naphthalenecarboxamide | $C_{22}H_{15}F_3N_4O_3$ | 440.38 | 441.1 |
| 403 | 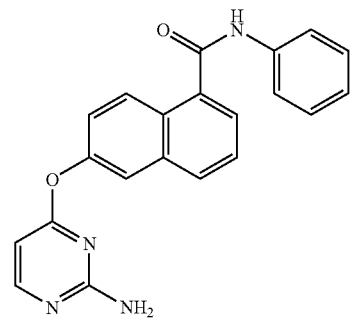<br>6-((2-amino-4-pyrimidinyl)oxy)-N-phenyl-1-naphthalenecarboxamide | $C_{21}H_{16}N_4O_2$ | 356.38 | 357.1 |
| 404 | 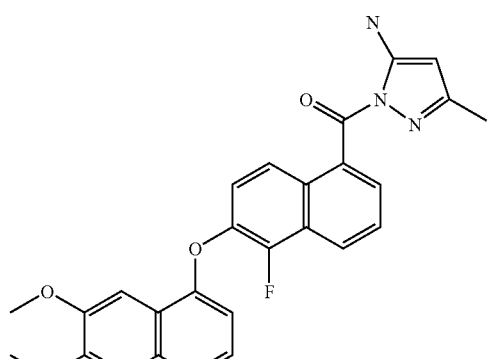<br>1-((6-((6,7-bis(methoxy)-4-quinolinyl)oxy)-5-fluoro-1-naphthalenyl)carbonyl)-3-methyl-1H-pyrazol-5-amine | $C_{26}H_{21}FN_4O_4$ | 472.47 | 473 |

EXAMPLE 405

N-(6-((6,7-bis(methoxy)-4-quinolinyl)oxy)-1-naphthalenyl)-N'-(2-fluorophenyl)urea

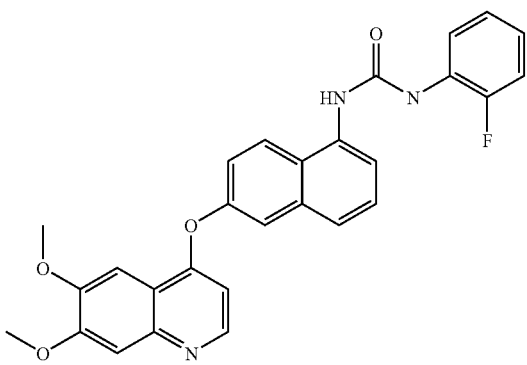

6-(6,7-Dimethoxyquinolin-4-yloxy)naphthalen-1-amine (50 mg, 0.144 mmol) and 2-fluorophenylisocyanate (20 mg, 0.144 mmol) were dissolved in THF (1 mL) then stirred at RT for 16 h. A precipitate formed in the mixture and was collected on a glass frit, washing with minimal THF then $CH_2Cl_2$ to give N-(6-((6,7-bis(methoxy)-4-quinolinyl)oxy)-1-naphthalenyl)-N'-(2-fluorophenyl)urea as an off-white solid. MS (ESI, pos. ion) m/z: 484.2 (M+1). Mass Calc'd for $C_{28}H_{22}FN_3O_4$: 483.50

The following examples were prepared similar to the procedures described in Example 405.

| Example No. | Structure & Name | Mol Formula | Mass | M + H |
|---|---|---|---|---|
| 406 | N-(7-((6,7-bis(methoxy)-4-quinolinyl)oxy)-2-naphthalenyl)-N'-(3-fluorophenyl)urea | $C_{28}H_{22}FN_3O_4$ | 483.5 | 484.1 |
| 407 | N-(6-((6,7-bis(methoxy)-4-quinolinyl)oxy)-1-naphthalenyl)-N'-(4-chlorophenyl)urea | $C_{28}H_{22}ClN_3O_4$ | 499.95 | 500.1 |
| 408 | N-(6-((6,7-bis(methoxy)-4-quinolinyl)oxy)-1-naphthalenyl)-N'-(4-(trifluoromethyl)phenyl)urea | $C_{29}H_{22}F_3N_3O_4$ | 533.5 | 534.2 |

| | | | | |
|---|---|---|---|---|
| 409 | 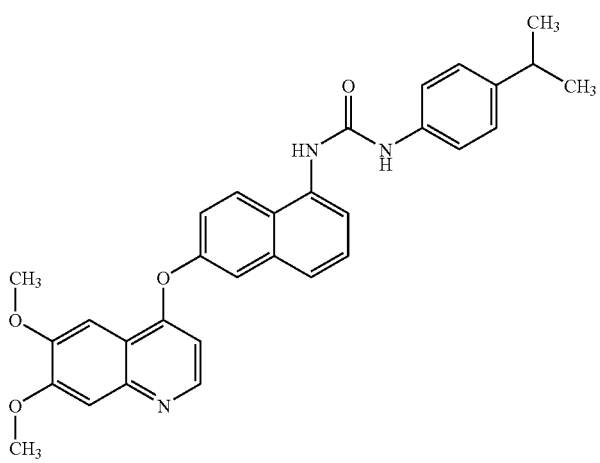<br>N-(6-((6,7-bis(methoxy)-4-quinolinyl)oxy)-1-naphthalenyl)-<br>N'-(4-(1-methylethyl)phenyl)urea | $C_{31}H_{29}N_3O_4$ | 507.59 | 508.2 |
| 410 | 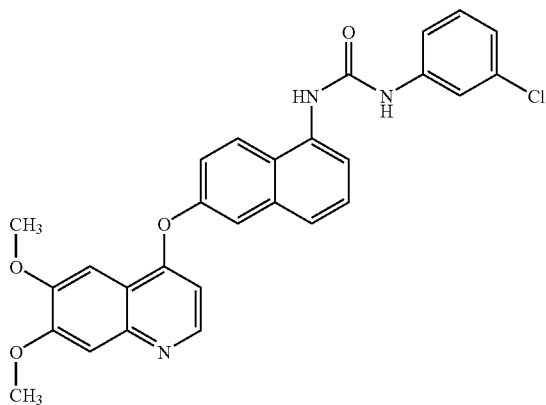<br>N-(6-((6,7-bis(methoxy)-4-quinolinyl)oxy)-1-<br>naphthalenyl)-N'-(3-chlorophenyl)urea | $C_{28}H_{22}ClN_3O_4$ | 499.95 | 500.1 |
| 411 | 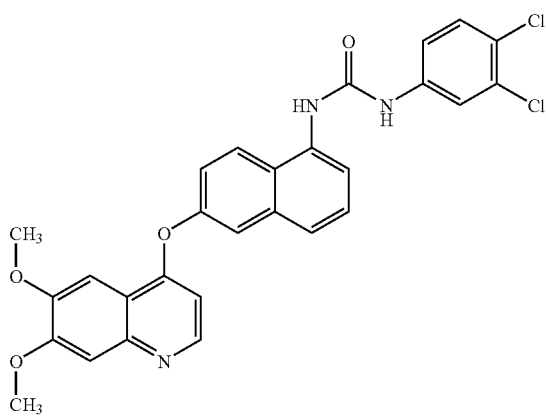<br>N-(6-((6,7-bis(methoxy)-4-quinolinyl)oxy)-1-<br>naphthalenyl)-N'-(3,4-dichlorophenyl)urea | $C_{28}H_{21}Cl_2N_3O_4$ | 534.4 | 534.1 |

-continued
| Ex. No. | Name & Structure | Mol Formula | Calc MW | [M + H]+ | [M − H]− |
|---|---|---|---|---|---|
| 412 | 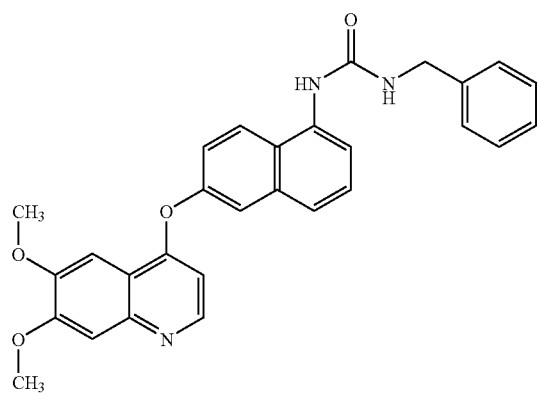<br>N-(6-((6,7-bis(methoxy)-4-quinolinyl)oxy)-1-naphthalenyl)-N'-(phenylmethyl)urea | C29H25N3O4 | 479.53 | 480.1 | |
| 413 | 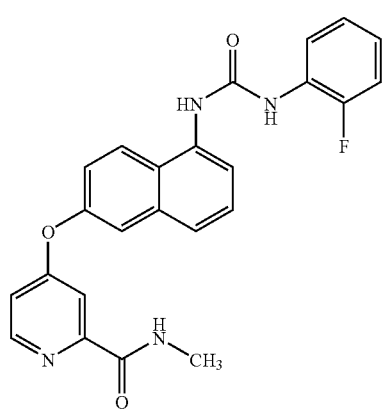<br>4-((5-((((2-fluorophenyl)amino) carbonyl)amino)-2-naphthalenyl)oxy)-N-methyl-2-pyridinecarboxamide | C24H19FN4O3 | 430.437 | | 429.2 |
| 414 | 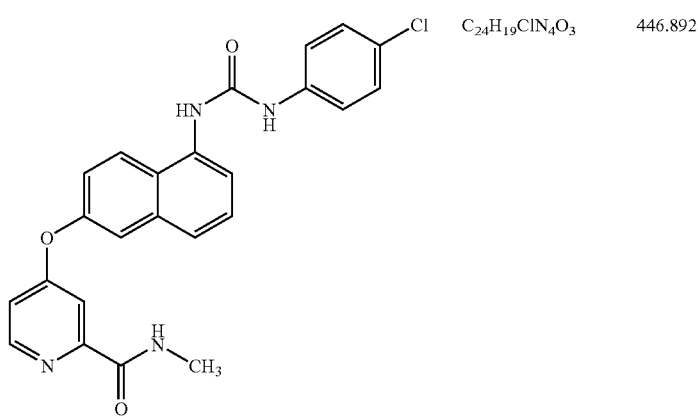<br>4-((5-((((4-chlorophenyl)amino) carbonyl)amino)-2-naphthalenyl)oxy)-N-methyl-2-pyridinecarboxamide | C24H19ClN4O3 | 446.892 | | 445.1 |

| | | | | |
|---|---|---|---|---|
| 415 | 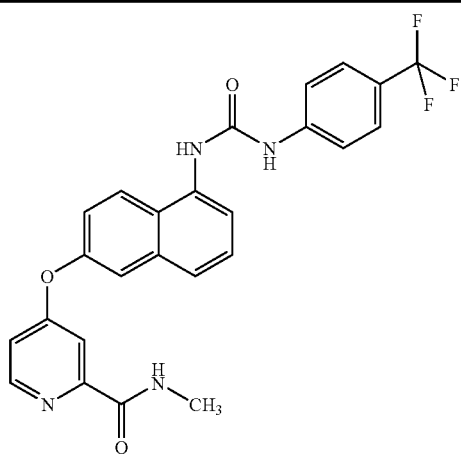<br>N-methyl-4-((5-((((4-(trifluoromethyl)phenyl)amino)carbonyl)amino)-2-naphthalenyl)oxy)-2-pyridinecarboxamide | $C_{25}H_{19}F_3N_4O_3$ | 480.444 | 479.1 |
| 416 | 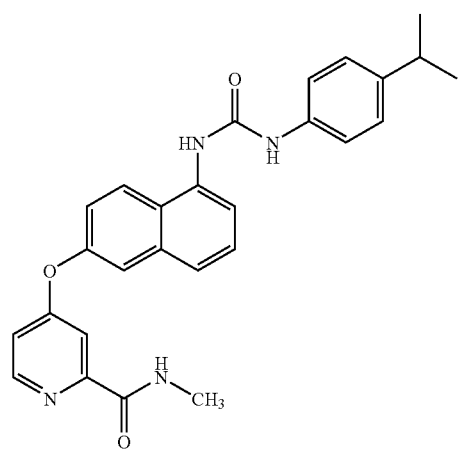<br>N-methyl-4-((5-((((4-(1-methylethyl)phenyl)amino)carbonyl)amino)-2-naphthalenyl)oxy)-2-pyridinecarboxamide | $C_{27}H_{26}N_4O_3$ | 454.527 | 453.2 |

EXAMPLE 417

N-(6-((6,7-bis(methoxy)-4-quinolinyl)oxy)-1-naphthalenyl)-N'-cyclopropylurea

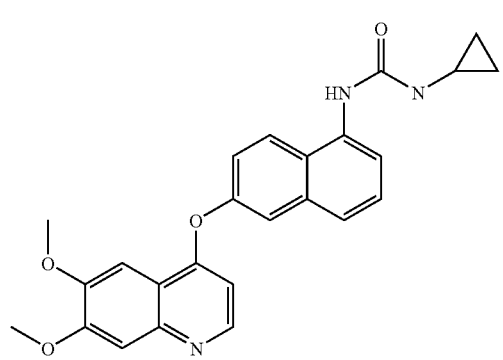

6-(6,7-Dimethoxyquinolin-4-yloxy)naphthalen-1-amine (80 mg, 0.231 mmol) was suspended in THF (1 mL), then added Hunig's base (33 mg, 0.254 mmol) and a solution of phenylchloroformate (36 mg, 0.231 mmol) in THF (0.5 mL). The reaction was stirred at RT for 16 h. A solution of cyclopropylamine (26 mg, 0.462 mmol) in THF (0.6 mL) was added to the mixture and the reaction was heated at 50° C. for 4 h. A precipitate formed and was collected on a glass frit, washed with THF then $CH_2Cl_2$. The tan solid was purified by preparative thin layer chromatography (8% MeOH in $CH_2Cl_2$) to give N-(6-((6,7-bis(methoxy)-4-quinolinyl)oxy)-1-naphthalenyl)-N'-cyclopropylurea as a white solid. MS (ESI, pos. ion) m/z: 430.2 (M+1). Mass Calc'd for $C_{25}H_{23}N_3O_4$: 429.47

The following examples were prepared similar to the procedures described in Example 417.

| Example No. | Structure & Name | Mol Formula | Mass | M + H |
|---|---|---|---|---|
| 418 | N-(6-((6,7-bis(methoxy)-4-quinolinyl)oxy)-1-naphthalenyl) N'-(cyclopropylmethyl)urea | $C_{26}H_{25}N_3O_4$ | 443.5 | 444.1 |
| 419 | N-(6-((6,7-bis(methoxy)-4-quinolinyl)oxy)-1-naphthalenyl)- N'-(1,3-thiazol-2-yl)urea | $C_{25}H_{20}N_4O_4S$ | 472.52 | 473.1 |
| 420 | N-(6-((6,7-bis(methoxy)-4-quinolinyl)oxy)-1-naphthalenyl)- N'-propylurea | $C_{25}H_{25}N_3O_4$ | 431.49 | 432.1 |

EXAMPLE 421

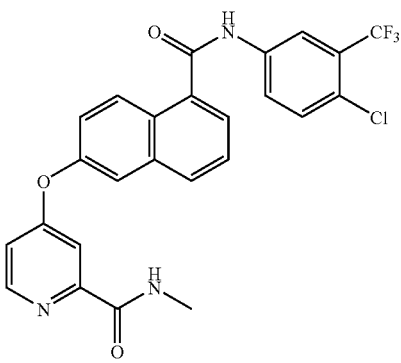

4-((5-(((4-chloro-3-(trifluoromethyl)phenyl)amino)carbonyl)-2-naphthalenyl)oxy)-N-methyl-2-pyridinecarboxamide Step (a) Preparation of 6-(2-(methylcarbamoyl)pyridine-4-yloxy)-1-napthoic acid $Cs_2CO_3$ (52.0 g, 160 mmol) was added to a solution of 6-hydroxy-1-naphthoic acid (10 g, 53.0 mmol) in DMSO (140 mL). After stirring vigorously for 15 min N-methyl-4-chloropicolinamide (10.8 g, 61.0 mmol) was introduced and the mixture was heated at 100° C. for 10 h. After cooling to RT, the mixture was filtered through a plug of silica gel (10:1:0.5; $CH_2Cl_2$, $CH_3OH$, AcOH). The filtrate was concentrated and triturated with EtOAc to provide the title compound as a slightly pink solid. MS (ESI, pos. ion) m/z: 323.3 (M+1). Mass Calc'd for $C_{18}H_{12}N_2O_4$: 322.31.

Step (b) Preparation of 6-(2-(methylcarbamoyl)pyridine-4-yloxy)-1-napthoyl Chloride To a suspension of 6-(2-methylcarbamoyl)pyridin-4-yloxy)-1-napthoic acid (Step a, 6.00 g, 18.6 mmol) in $CH_2Cl_2$ (100 μL) were added oxalyl chloride (5.2 mL, 60.5 mmol) and DMF (143 μL, 1.86 mmol). Stirring was continued 2 h at which point the resulting slurry was concentrated and azeotroped with benzene (3×25 mL) to provide the title compounds as a yellow powder. MS (methyl ester) (ESI, pos. ion) m/z: 337.3 (M+1). Mass Calc'd for $C_{19}H_{16}N_2O_4$: 336.34.

Step (c) Preparation of 4-((5-(((4-chloro-3-(trifluoromethyl)phenyl)amino)carbonyl)-2-naphthalenyl)oxy)-N-methyl-2-pyridinecarboxamide To a solution of 6-(2-methylcarbamoyl)pyridin-4-yloxy)-1-napthoyl chloride (Step b, 50 mg, 0.13 mmol) and 5-amino-2-chlorobenzotrifluoride (26 mg, 0.13 mmol) in 2 mL of $CH_2Cl_2$ was added TEA (93 μL, 0.66 mmol). The reaction was maintained at RT for 1 h before being concentrated and purified by silica gel column chromatography (50% acetone in hexanes) to give the title compound as a yellow solid. MS (ESI, pos. ion) m/z: 500.4 (M+1). Mass Calc'd for $C_{25}H_{17}ClF_3N_3O_3$: 499.87.

The following examples were prepared similar to the procedures described in Example 421.

| Example No. | Structure & Name | Mol Formula | Mass | M + H |
|---|---|---|---|---|
| 422 | ![structure] 4-((5-(((4-chlorophenyl)amino)carbonyl)-2-naphthalenyl)oxy)-N-methyl-2-pyridinecarboxamide | $C_{24}H_{18}ClN_3O_3$ | 431.87 | 432.4 |

-continued
| Example No. | Structure & Name | Mol Formula | Mass | M + H |
|---|---|---|---|---|
| 423 | 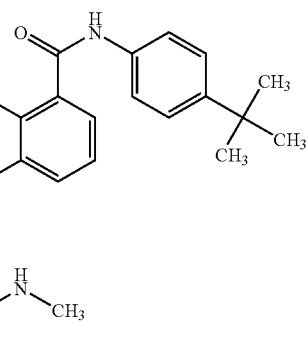 4-((5-(((4-(1,1-dimethylethyl)phenyl) amino)carbonyl)-2-naphthalenyl)oxy)-N-methyl-2-pyridinecarboxamide | $C_{28}H_{27}N_3O_3$ | 453.54 | 454.5 |
| 424 | 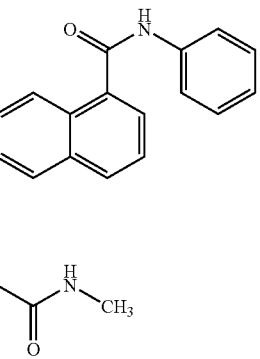 N-methyl-4-((5-((phenylamino)carbonyl)-2-naphthalenyl)oxy)-2-pyridinecarboxamide | $C_{24}H_{19}N_3O_3$ | 397.43 | 398.3 |
| 425 | 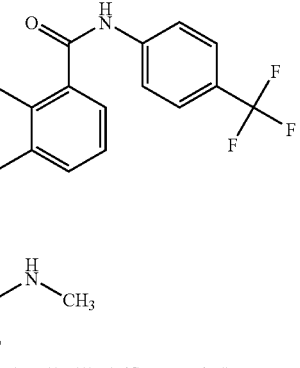 N-methyl-4-((5-(((4-(trifluoromethyl)phenyl)amino)carbonyl)-2-naphthalenyl)oxy)-2-pyridinecarboxamide | $C_{25}H_{18}F_3N_3O_3$ | 465.42 | 466.4 |

-continued
| Example No. | Structure & Name | Mol Formula | Mass | M + H |
|---|---|---|---|---|
| 426 | 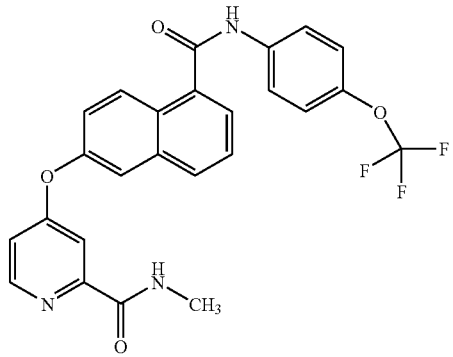<br>N-methyl-4-((5-(((4-((trifluoromethyl)oxy)phenyl)amino)carbonyl)-2-naphthalenyl) oxy)-2-pyridinecarboxamide | $C_{25}H_{18}F_3N_3O_4$ | 481.43 | 482.4 |
| 427 | 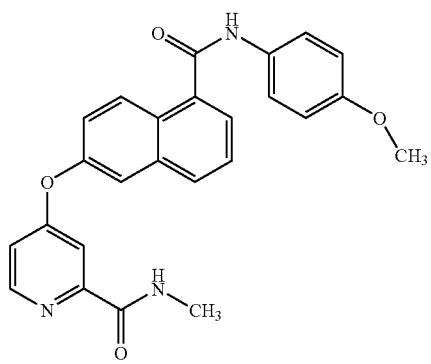<br>N-methyl-4-((5-(((4-(methoxy)phenyl) amino)carbonyl)-2-naphthalenyl)oxy)-2-pyridinecarboxamide | $C_{25}H_{21}N_3O_4$ | 427.45 | 428.1 |
| 428 | 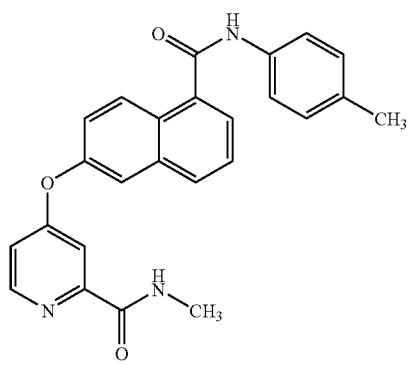<br>N-methyl-4-((5-(((4-methylphenyl) amino)carbonyl)-2-naphthalenyl)oxy)-2-pyridinecarboxamide | $C_{25}H_{21}N_3O_3$ | 411.46 | 412.1 |

| Example No. | Structure & Name | Mol Formula | Mass | M + H |
|---|---|---|---|---|
| 429 | 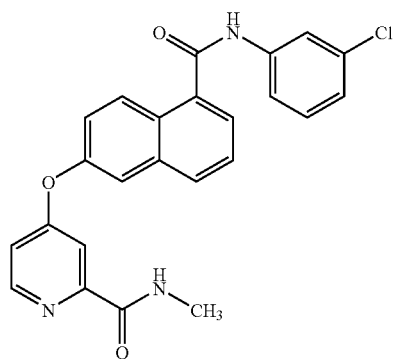<br>4-((5-(((3-chlorophenyl)amino)carbonyl)-2-naphthalenyl)oxy)-N-methyl-2-pyridinecarboxamide | $C_{24}H_{18}ClN_3O_3$ | 431.88 | 432.4 |
| 430 | 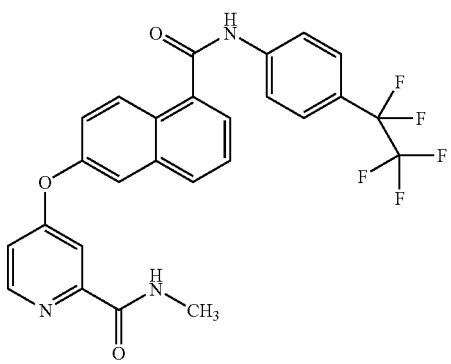<br>N-methyl-4-((5-(((4-(pentafluoroethyl)phenyl)amino)carbonyl)-2-naphthalenyl) oxy)-2-pyridinecarboxamide | $C_{26}H_{18}F_5N_3O_3$ | 515.43 | 516.1 |
| 431 | 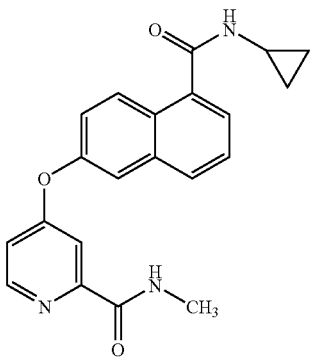<br>4-((5-((cyclopropylamino)carbonyl)-2-naphthalenyl)oxy)-N-methyl-2-pyridinecarboxamide | $C_{21}H_{19}N_3O_3$ | 361.4 | 362.3 |

| Example No. | Structure & Name | Mol Formula | Mass | M + H |
|---|---|---|---|---|
| 432 | 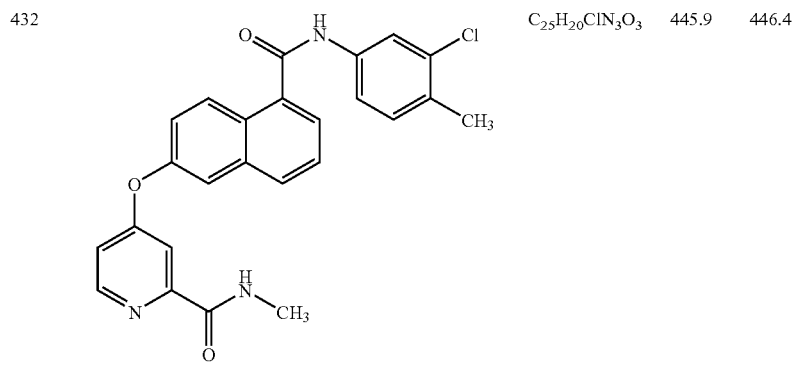 4-((5-(((3-chloro-4-methylphenyl) amino)carbonyl)-2-naphthalenyl)oxy)-N-methyl-2-pyridinecarboxamide | $C_{25}H_{20}ClN_3O_3$ | 445.9 | 446.4 |
| 433 | 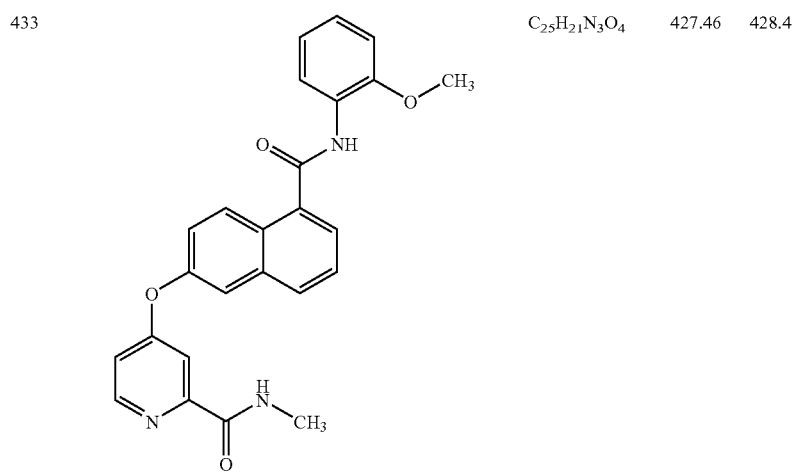 N-methyl-4-((5-(((2-(methoxy)phenyl) amino)carbonyl)-2-naphthalenyl)oxy)-2-pyridinecarboxamide | $C_{25}H_{21}N_3O_4$ | 427.46 | 428.4 |
| 434 | 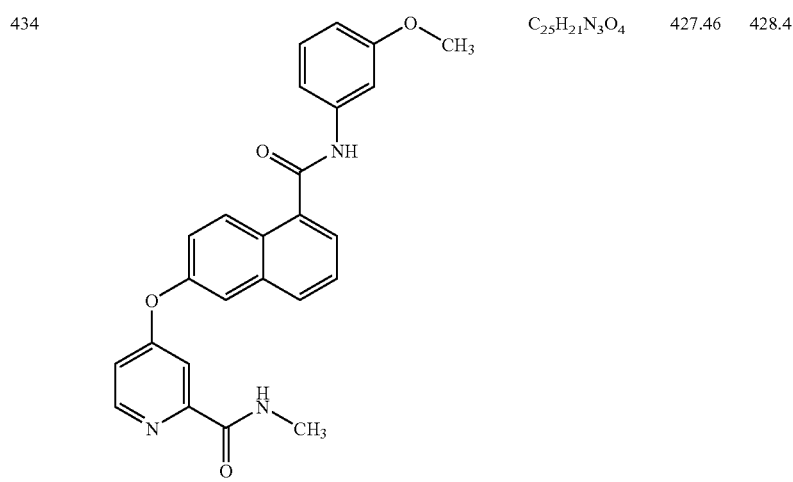 N-methyl-4-((5-(((3-(methoxy)phenyl) amino)carbonyl)-2-naphthalenyl)oxy)-2-pyridinecarboxamide | $C_{25}H_{21}N_3O_4$ | 427.46 | 428.4 |

| Example No. | Structure & Name | Mol Formula | Mass | M + H |
|---|---|---|---|---|
| 435 | 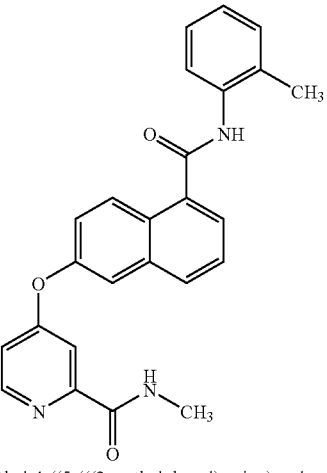<br>N-methyl-4-((5-(((2-methylphenyl)amino) carbonyl)-2-naphthalenyl)oxy)-2-pyridinecarboxamide | $C_{25}H_{21}N_3O_3$ | 411.46 | 412.4 |
| 436 | 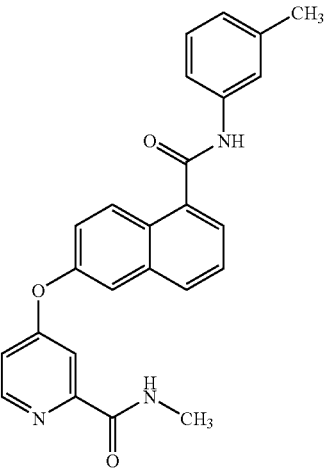<br>N-methyl-4-((5-(((3-methylphenyl)amino)carbonyl)-2-naphthalenyl)oxy)-2-pyridinecarboxamide | $C_{25}H_{21}N_3O_3$ | 411.46 | 412.4 |
| 437 | 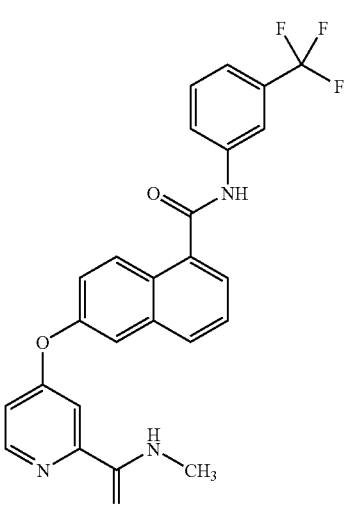<br>N-methyl-4-((5-(((3-(trifluoromethyl)phenyl)amino)carbonyl)-2-naphthalenyl)oxy)-2-pyridinecarboxamide | $C_{25}H_{18}F_3N_3O_3$ | 465.43 | 466.4 |

| Example No. | Structure & Name | Mol Formula | Mass | M + H |
|---|---|---|---|---|
| 438 | 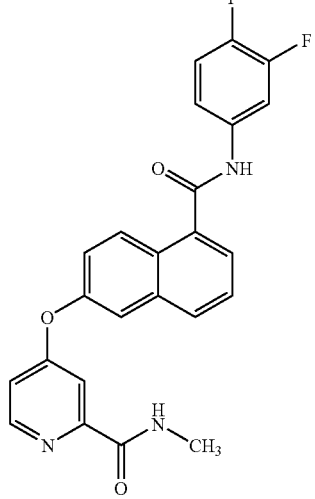<br>4-((5-(((3,4-difluorophenyl)amino)carbonyl)-2-naphthalenyl)oxy)-N-methyl-2-pyridinecarboxamide | $C_{24}H_{17}F_2N_3O_3$ | 433.41 | 434.2 |
| 439 | 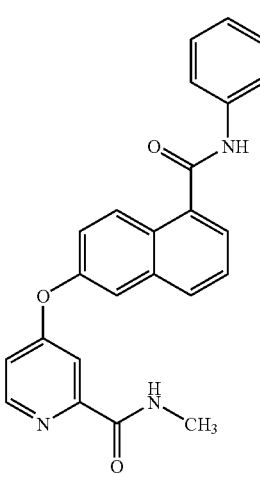<br>4-((5-(((3-ethynylphenyl)amino)carbonyl)-2-naphthalenyl)oxy)-N-methyl-2-pyridinecarboxamide | $C_{26}H_{19}N_3O_3$ | 421.45 | 422.2 |
| 440 | 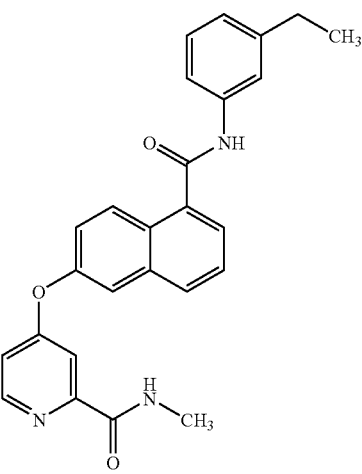<br>4-((5-(((3-ethylphenyl)amino)carbonyl)-2-naphthalenyl)oxy)-N-methyl-2-pyridinecarboxamide | $C_{26}H_{23}N_3O_3$ | 425.49 | 426.2 |

-continued
| Example No. | Structure & Name | Mol Formula | Mass | M + H |
|---|---|---|---|---|
| 441 | 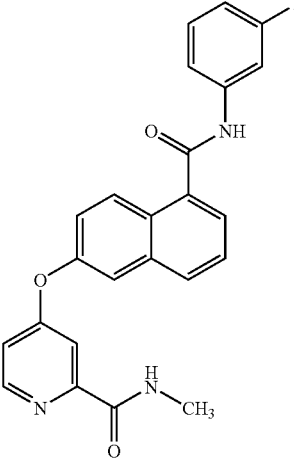 4-((5-(((3-bromophenyl)amino)carbonyl)-2-naphthalenyl)oxy)-N-methyl-2-pyridinecarboxamide | $C_{24}H_{18}BrN_3O_3$ | 476.33 | 477.1 |
| 442 | 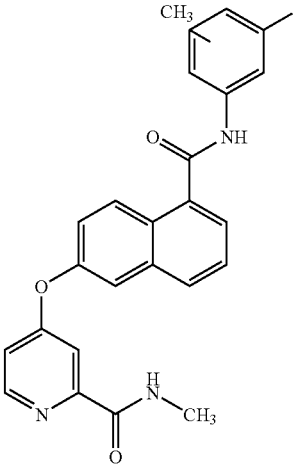 4-((5-(((3,5-dimethylphenyl)amino) carbonyl)-2-naphthalenyl)oxy)-N-methyl-2-pyridinecarboxamide | $C_{26}H_{23}N_3O_3$ | 425.49 | 426.2 |
| 443 | 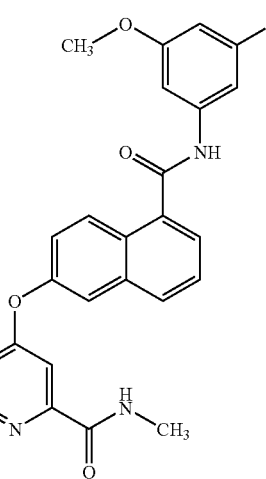 4-((5-(((3,5-bis(methoxy)phenyl) amino)carbonyl)-2-naphthalenyl)oxy)-N-methyl-2-pyridinecarboxamide | $C_{26}H_{23}N_3O_5$ | 457.48 | 458.2 |

-continued
| Example No. | Structure & Name | Mol Formula | Mass | M + H |
|---|---|---|---|---|
| 444 | 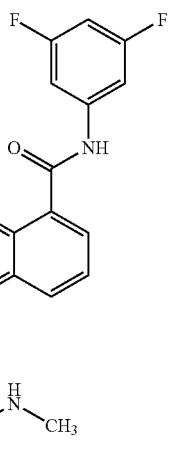  4-((5-(((3,5-difluorophenyl)amino) carbonyl)-2-naphthalenyl)oxy)-N-methyl-2-pyridinecarboxamide | $C_{24}H_{17}F_2N_3O_3$ | 433.41 | 434.2 |
| 445 | 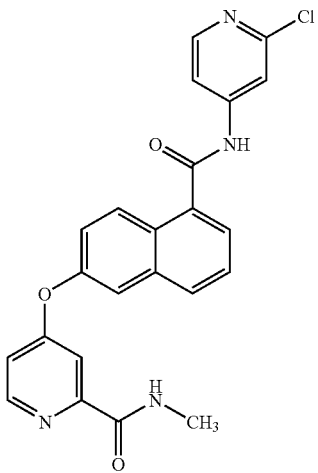  4-((5-(((2-chloro-4-pyridinyl)amino) carbonyl)-2-naphthalenyl)oxy)-N-methyl-2-pyridinecarboxamide | $C_{23}H_{17}ClN_4O_3$ | 432.87 | 433.1 |
| 446 | 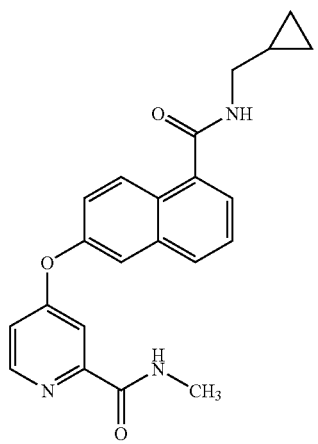  4-((5-(((cyclopropylmethyl)amino)carbonyl)-2-naphthalenyl)oxy)-N-methyl-2-pyridinecarboxamide | $C_{22}H_{21}N_3O_3$ | 375.43 | 376.1 |

| Example No. | Structure & Name | Mol Formula | Mass | M + H |
|---|---|---|---|---|
| 447 | 4-((5-((2,3-dihydro-1,4-benzodioxin-6-ylamino)carbonyl)-2-naphthalenyl)oxy)-N-methyl-2-pyridinecarboxamide | $C_{26}H_{21}N_3O_5$ | 455.47 | 456.1 |
| 448 | N-methyl-4-((5-((1,3-thiazol-2-ylamino)carbonyl)-2-naphthalenyl)oxy)-2-pyridinecarboxamide | $C_{21}H_{16}N_4O_3S$ | 404.45 | 405.1 |
| 449 | N-methyl-4-((5-(((3-((trifluoromethyl)oxy)phenyl)amino)carbonyl)-2-naphthalenyl)oxy)-2-pyridinecarboxamide | $C_{25}H_{18}F_3N_3O_4$ | 481.43 | 482.1 |

| Example No. | Structure & Name | Mol Formula | Mass | M + H |
|---|---|---|---|---|
| 450 | 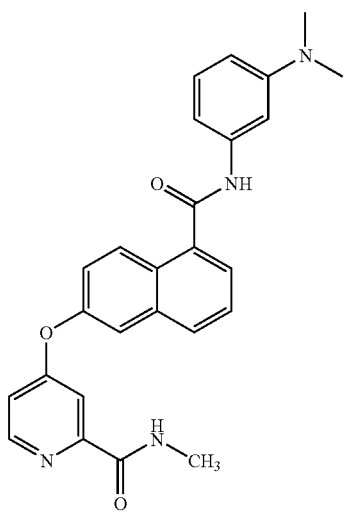<br>4-((5-(((3-(dimethylamino)phenyl)amino)carbonyl)-2-naphthalenyl)oxy)-N-methyl-2-pyridinecarboxamide | $C_{26}H_{24}N_4O_3$ | 440.5 | 441.1 |
| 451 | 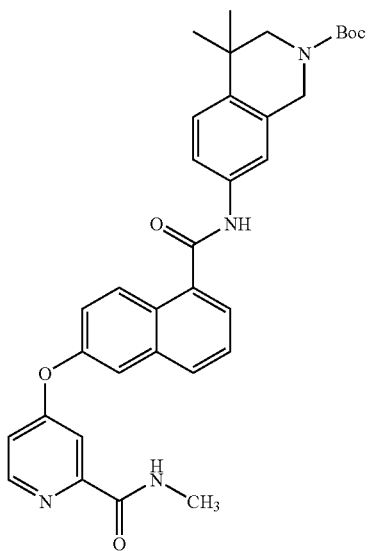<br>1,1-dimethylethyl 4,4-dimethyl-7-(((6-((2-((methylamino)carbonyl)-4-pyridinyl)oxy)-1-naphthalenyl)carbonyl)amino)-3,4-dihydro-2(1H)-isoquinolinecarboxylate | $C_{34}H_{36}N_4O_5$ | 580.68 | 581.1 |

| Example No. | Structure & Name | Mol Formula | Mass | M + H |
|---|---|---|---|---|
| 452 | 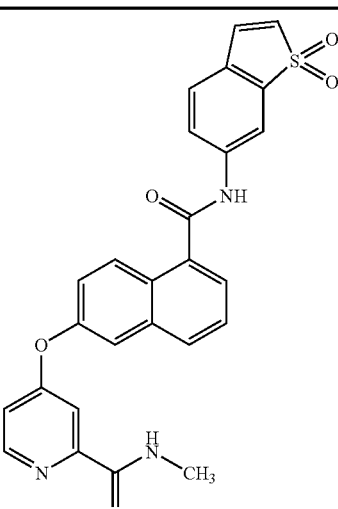<br>4-((5-(((1,1-dioxido-1-benzothien-6-yl)amino)carbonyl)-2-naphthalenyl)oxy)-N-methyl-2-pyridinecarboxamide | $C_{26}H_{19}N_3O_5S$ | 485.52 | 485.9 |

The following examples were prepared similar to the procedure described in Example 421, step c omitting the base and using THF as the solvent.

| Example No. | Structure & Name | Mol Formula | Mass | M + H |
|---|---|---|---|---|
| 453 | 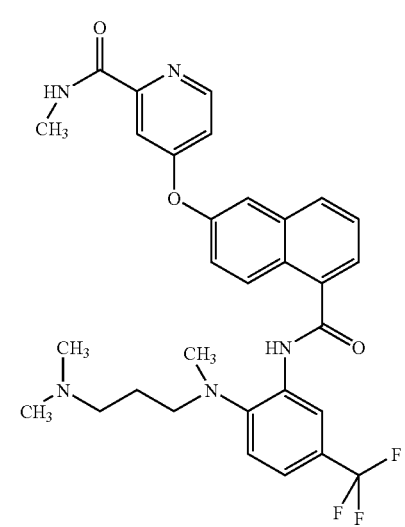<br>4-((5-(((2-((3-(dimethylamino)propyl)(methyl)amino)-5-(trifluoromethyl)phenyl)amino)carbonyl)-2-naphthalenyl)oxy)-N-methyl-2-pyridinecarboxamide | $C_{31}H_{32}F_3N_5O_3$ | 579.62 | 580.2 |

| Example No. | Structure & Name | Mol Formula | Mass | M + H |
|---|---|---|---|---|
| 454 | 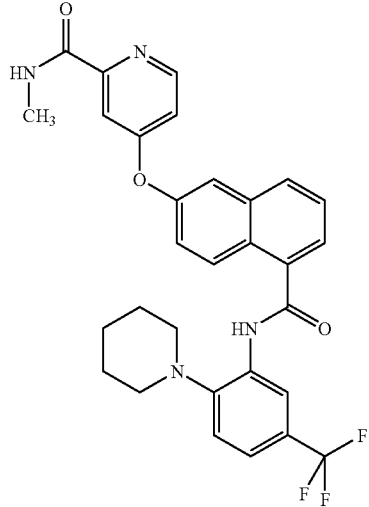<br>N-methyl-4-((5-(((2-(1-piperidinyl)-5-(trifluoromethyl)phenyl)amino)carbonyl)-2-naphthalenyl)oxy)-2-pyridinecarboxamide | $C_{30}H_{27}F_3N_4O_3$ | 548.56 | 549.2 |
| 455 | 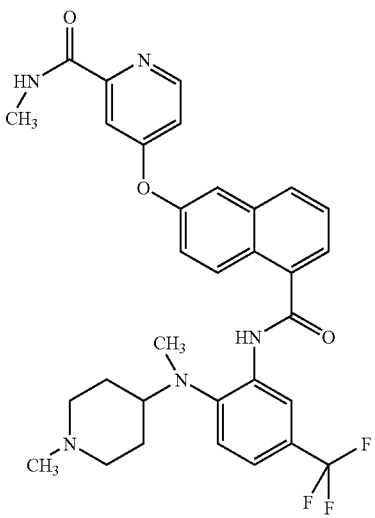<br>N-methyl-4-((5-(((2-(methyl(1-methyl-4-piperidinyl)amino)-5-(trifluoromethyl)phenyl)amino)carbonyl)-2-naphthalenyl)oxy)-2-pyridinecarboxamide | $C_{32}H_{32}F_3N_5O_3$ | 591.63 | 592.2 |

| Example No. | Structure & Name | Mol Formula | Mass | M + H |
|---|---|---|---|---|
| 456 | 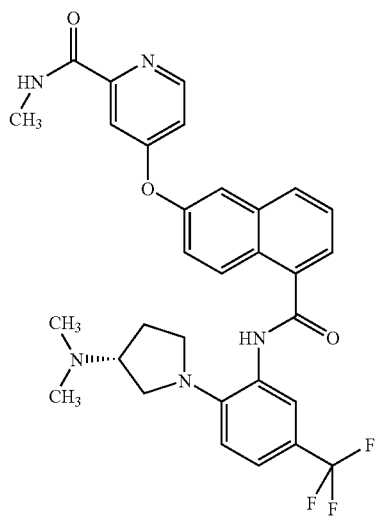<br>4-((5-(((2-((3R)-3-(dimethylamino)-1-pyrrolidinyl)-5-(trifluoromethyl)phenyl)amino)carbonyl)-2-naphthalenyl)oxy)-N-methyl-2-pyridinecarboxamide | $C_{31}H_{30}F_3N_5O_3$ | 577.6 | 578.2 |
| 457 | 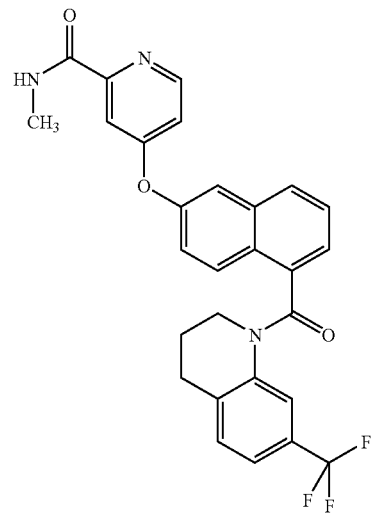<br>N-methyl-4-((5-((7-(trifluoromethyl)-3,4-dihydro-1(2H)-quinolinyl)carbonyl)-2-naphthalenyl)oxy)-2-pyridinecarboxamide | $C_{28}H_{22}F_3N_3O_3$ | 505.49 | 506.1 |

EXAMPLE 458

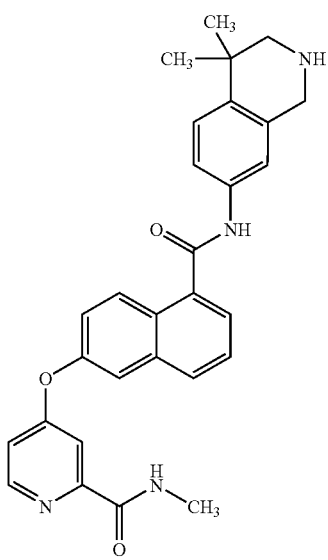

4-((5-(((4,4-dimethyl-1,2,3,4-tetrahydro-7-isoquinolinyl)amino)carbonyl)-2-naphthalenyl)oxy)-N-methyl-2-pyridinecarboxamide The title compound was prepared similar to the procedure described in Example 378 from 1,1-dimethylethyl 4,4-dimethyl-7-((((6-((2-((methylamino)carbonyl)-4-pyridinyl)oxy)-1-naphthalenyl)carbonyl)amino)-3,4-dihydro-2(1H)-isoquinolinecarboxylate. MS (ESI pos. ion) m/z: 481.1 (M+H). Calc'd for $C_{29}H_{28}N_4O_3$–480.57.

The following examples were prepared similar to the procedures described in Example 421, Step c using either TEA or DIEA as the base.

| Example No. | Structure & Name | Mol Formula | Mass | M + H |
|---|---|---|---|---|
| 459 | 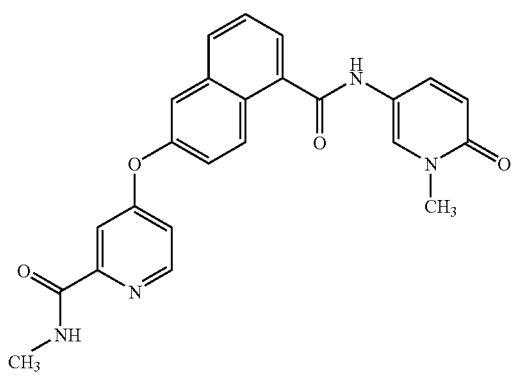<br>N-methyl-4-((5-(((1-methyl-6-oxo-1,6-dihydro-3-pyridinyl)amino)carbonyl)-2-naphthalenyl)oxy)-2-pyridinecarboxamide | $C_{24}H_{20}N_4O_4$ | 428.45 | 429.0 |
| 460 | 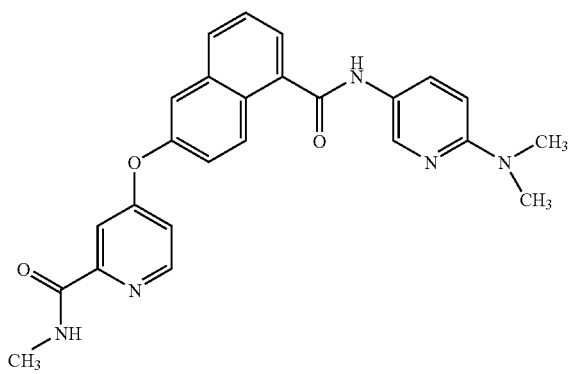<br>4-((5-(((6-(dimethylamino)-3-pyridinyl)amino)carbonyl)-2-naphthalenyl)oxy)-N-methyl-2-pyridinecarboxamide | $C_{25}H_{23}N_5O_3$ | 441.49 | 442.0 |

-continued
| Example No. | Structure & Name | Mol Formula | Mass | M + H |
|---|---|---|---|---|
| 461 | 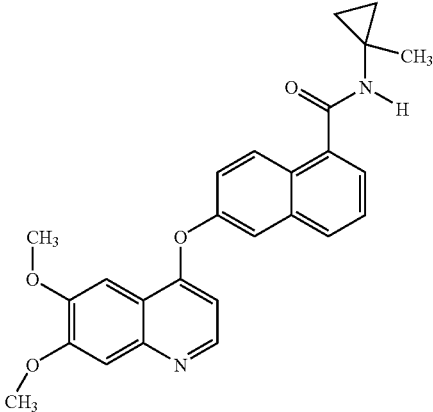<br>6-((6,7-bis(methoxy)-4-quinolinyl)oxy)-N-(1-methylcyclopropyl)-1-naphthalenecarboxamide | $C_{26}H_{24}N_2O_4$ | 428.49 | 429.2 |
| 462 | 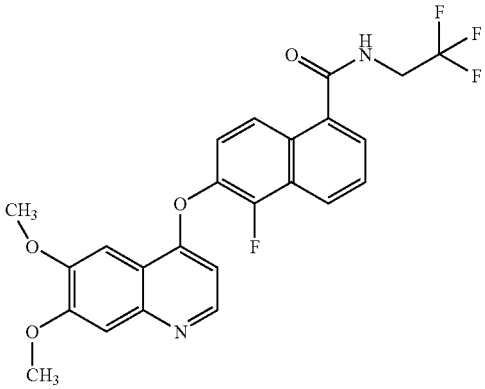<br>6-((6,7-bis(methoxy)-4-quinolinyl)oxy)-5-fluoro-N-(2,2,2-trifluoroethyl)-1-naphthalenecarboxamide | $C_{24}H_{18}F_4N_2O_4$ | 474.41 | 475 |
| 463 | 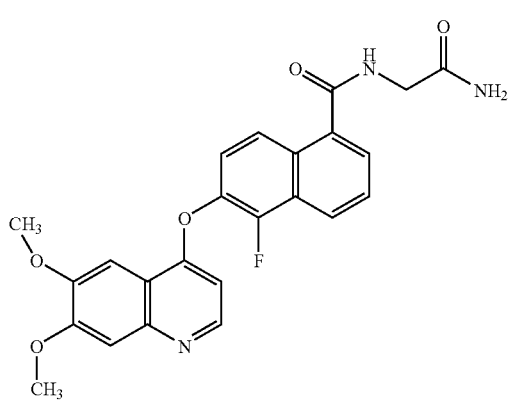<br>N-(2-amino-2-oxoethyl)-6-(6,7-dimethoxyquinolin-4-yloxy)-5-fluoro-1-naphthamide | $C_{24}H_{20}FN_3O_5$ | 449.44 | 450.1 |

| Example No. | Structure & Name | Mol Formula | Mass | M + H |
|---|---|---|---|---|
| 464 | 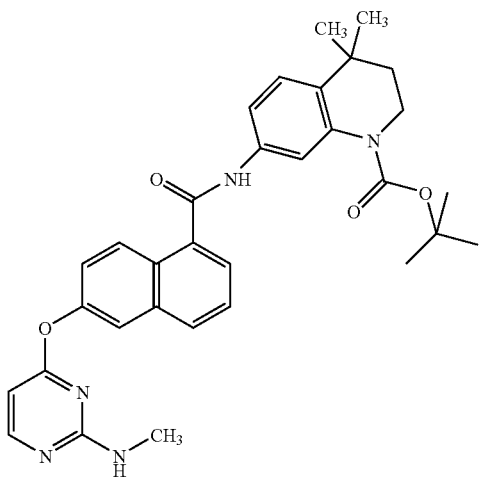<br>tert-butyl 4,4-dimethyl-7-(2-(2-(methylamino)pyrimidin-4-yloxy)-1-naphthamido)-3,4-dihydroquinoline-1(2H)-carboxylate | $C_{27}H_{27}N_5O_2$ | 553.67 | NA |
| 465 | 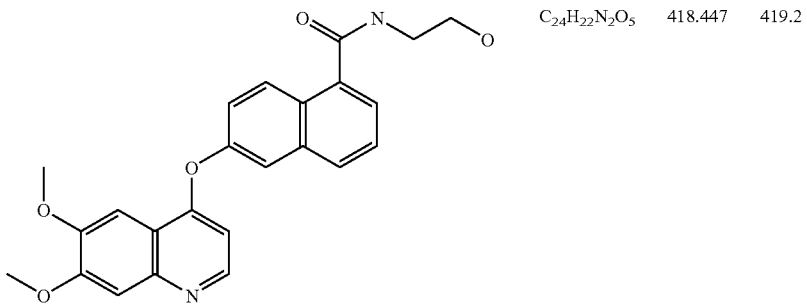<br>6-((6,7-bis(methoxy)-4-quinolinyl)oxy-N-(2-hydroxyethyl)-1-naphthalenecarboxamide | $C_{24}H_{22}N_2O_5$ | 418.447 | 419.2 |
| 466 | 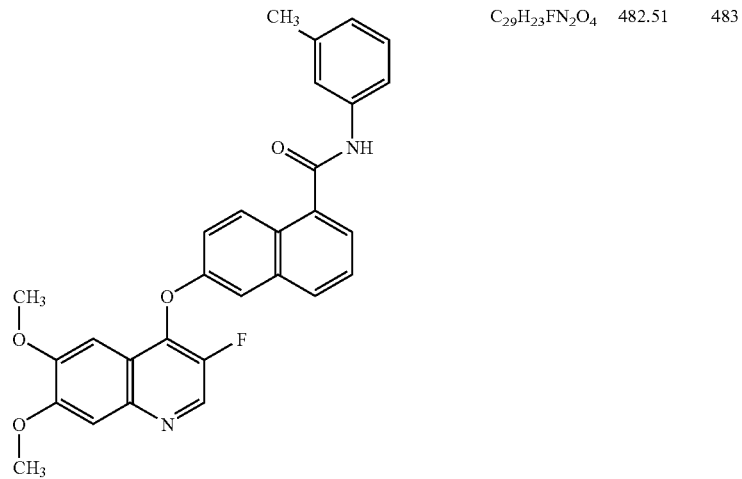<br>6-((3-fluoro-6,7-bis(methoxy)-4-quinolinyl)oxy)-N-(3-methylphenyl)-1-naphthalenecarboxamide | $C_{29}H_{23}FN_2O_4$ | 482.51 | 483 |

| Example No. | Structure & Name | Mol Formula | Mass | M + H |
|---|---|---|---|---|
| 467 | 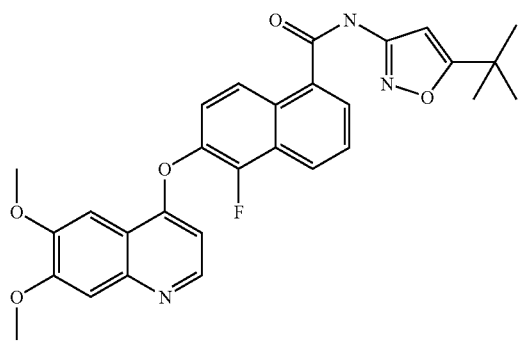<br>6-((6,7-bis(methoxy)-4-quinolinyl)oxy)-N-(5-(1,1-dimethylethyl)-3-isoxazolyl)-5-fluoro-1-naphthalenecarboxamide | $C_{29}H_{26}FN_3O_5$ | 515.53 | 516.2 |

The following example was prepared according to Example 421, Step C, but using chloroform as the solvent.

| Example No. | Structure & Name | Mol Formula | Mass | M + H |
|---|---|---|---|---|
| 468 | 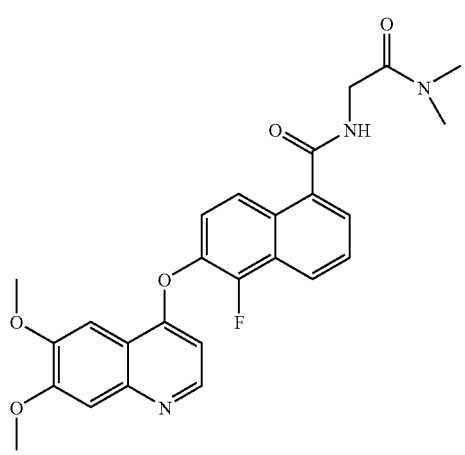<br>6-(6,7-dimethoxyquinolin-4-yloxy)-N-(2-(dimethylamino)-2-oxoethyl)-5-fluoro-1-naphthamide | $C_{26}H_{24}N_3O_5$ | 477.49 | 478.1 |

The following example was prepared according to Example 421, step C, but using chloroform as the solvent, omitting the base.

| Example No. # | Structure & Name | Mol Formula | Mass | M + H |
|---|---|---|---|---|
| 469 | 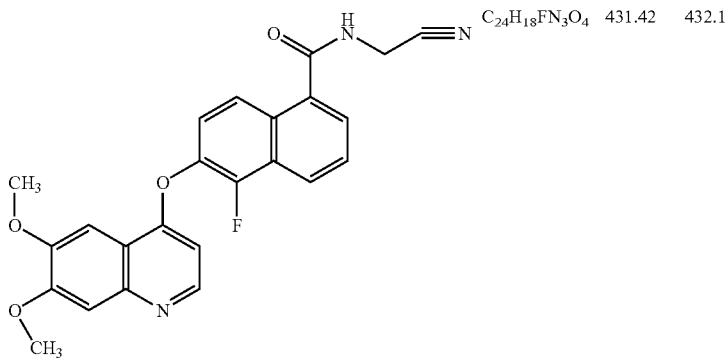<br>6-((6,7-bis(methoxy)-4-quinolinyl)oxy)-N-(cyanomethyl)-5-fluoro-1-naphthalenecarboxamide | $C_{24}H_{18}FN_3O_4$ | 431.42 | 432.1 |
The following example was prepared similar to Example 421, Step c, omitting the base.
| Example No. | Structure & Name | Mol Formula | Mass | M + H |
|---|---|---|---|---|
| 470 | 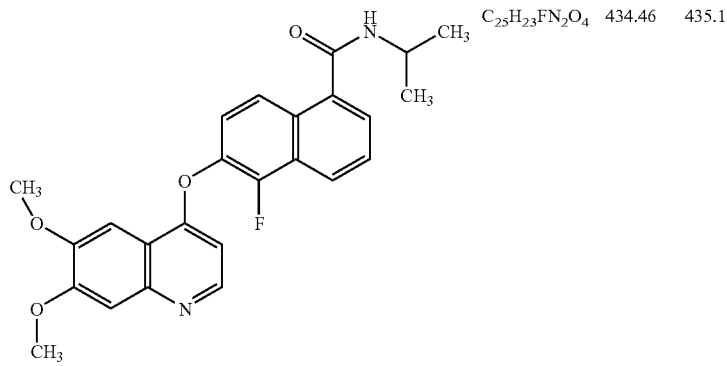<br>6-((6,7-bis(methoxy)-4-quinolinyl)oxy)-5-fluoro-N-(1-methylethyl)-1-napthalenecarboxamide | $C_{25}H_{23}FN_2O_4$ | 434.46 | 435.1 |

EXAMPLE 471

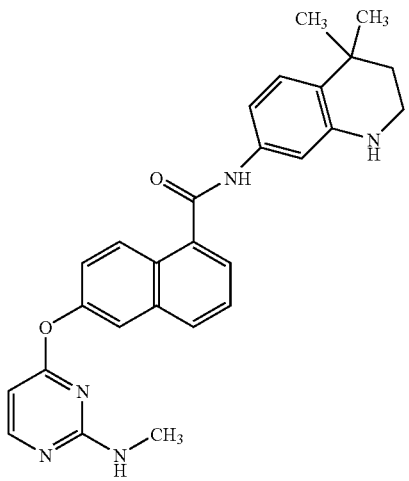

N-(4,4-dimethyl-1,2,3,4-tetrahydro-7-quinolinyl)-6-((2-(methylamino)-4-pyrimidinyl)oxy)-1-naphthalenecarboxamide The title compound was prepared similar to Example 378 using tert-butyl 4,4-dimethyl-7-(2-(2-(methylamino)pyrimidin-4-yloxy)-1-naphthamido)-3,4-dihydroquinoline-1(2H)-carboxylate as the starting material. MS (ESI pos. ion) m/z: 454.1 (M+H). Calc'd for $C_{27}H_{27}N_5O_2$–453.54.

EXAMPLE 472

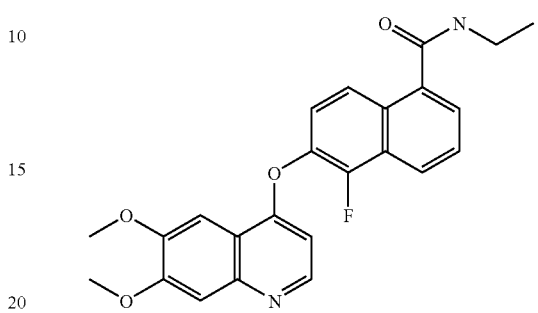

6-((6,7-bis(methoxy)-4-quinolinyl)oxy)-N-ethyl-5-fluoro-1-naphthalenecarboxamide 6-(6,7-Dimethoxyquinolin-4-yloxy)-5-fluoro-1-naphthoyl chloride (70 mg) was stirred in a solution of 2M $EtNH_2$ in THF (3 mL) at RT for 4 days. Solvent was evaporated and residue purified by prep plate using 5% MeOH in $CH_2Cl_2$ as the eluent. The solid obtained was rinsed with ether and dried to afford the title compound. MS (ESI pos. ion) m/z: 421.1 (M+H). Calc'd for $C_{24}H_{21}FN_2O_4$–420.43.

The following examples were prepared similar to the procedures described in Example 421, step c, omitting the base and using THF as the solvent.

| Example No. | Structure & Name | Mol Formula | Mass | M + H |
|---|---|---|---|---|
| 473 | ![structure] 6-((6,7-bis(methoxy)-4-quinolinyl)oxy)-N-(1-(1,3-thiazol-2-yl)ethyl)-1-naphthalenecarboxamide | $C_{27}H_{23}N_3O_4S$ | 485.56 | 486.1 |

| Example No. | Structure & Name | Mol Formula | Mass | M + H |
|---|---|---|---|---|
| 474 | 6-((6,7-bis(methoxy)-4-quinolinyl)oxy)-N-(2-(4-thiomorpholinyl)-5-(trifluoromethyl)phenyl)-1-naphthalenecarboxamide | C₃₃H₂₈F₃N₃O₄S | 619.66 | 620 |
| 475 | 6-((6,7-bis(methoxy)-4-quinolinyl)oxy)-N-(2-(1-oxido-4-thiomorpholinyl)-5-(trifluoromethyl)phenyl)-1-naphthalenecarboxamide | C₃₃H₂₈F₃N₃O₅S | 635.66 | 636 |

-continued

| Example No. | Structure & Name | Mol Formula | Mass | M + H |
|---|---|---|---|---|
| 476 | 6-((6,7-bis(methoxy)-4-quinolinyl)oxy)-N-(2-(1,1-dioxido-4-thiomorpholinyl)-5-(trifluoromethyl)phenyl)-1-naphthalenecarboxamide | $C_{33}H_{28}F_3N_3O_6S$ | 651.66 | 652.1 |

EXAMPLE 477

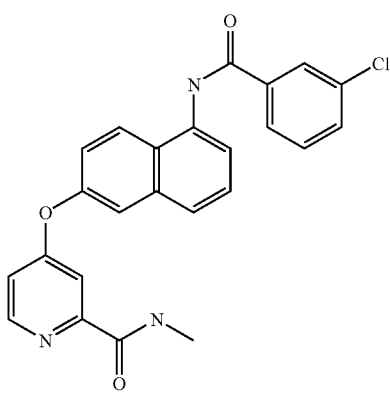

N-methyl-4-((5-(((3-chlorophenyl)carbonyl)amino)-2-naphthalenyl)oxy)-2-pyridinecarboxamide Step (a) Preparation of 4-(5-aminonaphthalen-2-yloxy)-N-methylpicolinamide To a solution of 5-amino-2-napthol (2.8 g, 17.6 mmol) in DMF (20 mL), NaH (60% in oil, 843 mg, 21.1 mmol) was added and stirred until the bubbling stopped. To the mixture 4-chloro-N-methylpicolinamide (Org. Proc. Res. & Dev., 2002, 6, 777-781) (1 g, 5.86 mmol) was added and the reaction heated to 90° C. for 22 h. The mixture was cooled to RT and diluted with CHCl$_3$ and washed with water. The emulsion was filtered thru a pad of Celite and the layers separated. The water was washed with CHCl$_3$ and the organic portions combined and washed with 1N NaOH and brine, dried with Na$_2$SO$_4$, filtered and evaporated. The residue was purified by column chromatography using hexanes and EtOAc as the eluent to give the title compound as a rose-colored solid.

Step (b) Preparation of N-methyl-4-((5-(((3-chlorophenyl)carbonyl)amino)-2-naphthalenyl)oxy)-2-pyridinecarboxamide To a suspension of 4-(5-aminonaphthalen-2-yloxy)-N-methylpicolinamide (40 mg, 0.14 mmol) and NaHCO$_3$ (33 mg, 0.44 mmol) in CH$_2$Cl$_2$, 3-chlorobenzoyl chloride (17 □L, 0.14 mmol) was added. The reaction was stirred at RT for 12 h then taken up into CHCl$_3$ and washed with water and brine, dried over Na$_2$SO$_4$, and filtered. The title compound was isolated after purification by column chromatography. MS (ESI pos. ion) m/z: 432.4 (M+H). Calc'd for C$_{24}$H$_{18}$ClN$_3$O$_3$– 431.87.

The following examples were prepared similar to the procedures described in Example 477 and purified by column chromatography and/or crystallization.

| Example # | Structure & Name | Mol Formula | Mass | M + H |
|---|---|---|---|---|
| 478 | 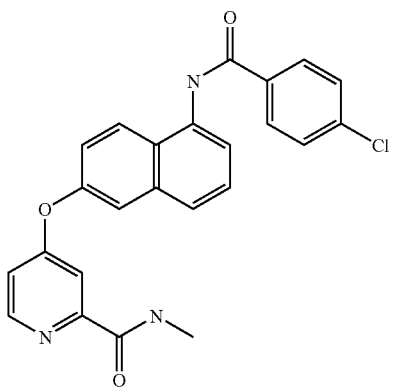<br>4-((5-(((4-chlorophenyl)carbonyl)amino)-2-naphthalenyl)oxy)-N-methyl-2-pyridinecarboxamide | $C_{24}H_{18}ClN_3O_3$ | 431.88 | 432.4 |
| 479 | 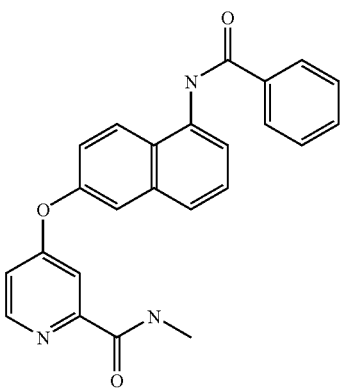<br>N-methyl-4-((5-((phenylcarbonyl)amino)-2-naphthalenyl)oxy)-2-pyridinecarboxamide | $C_{24}H_{19}N_3O_3$ | 397.43 | 398.4 |
| 480 | 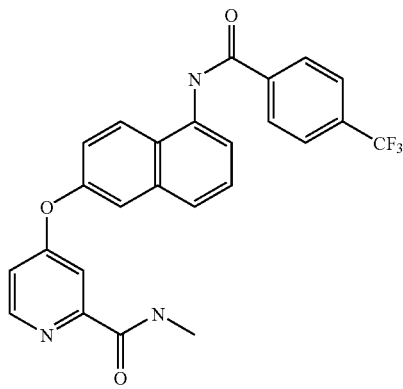<br>N-methyl-4-((5-(((4-(trifluoromethyl)phenyl)carbonyl)amino-2-naphthalenyl)oxy)-2-pyridinecarboxamide | $C_{25}H_{18}F_3N_3O_3$ | 465.43 | 466.4 |

| Example # | Structure & Name | Mol Formula | Mass | M + H |
|---|---|---|---|---|
| 481 | 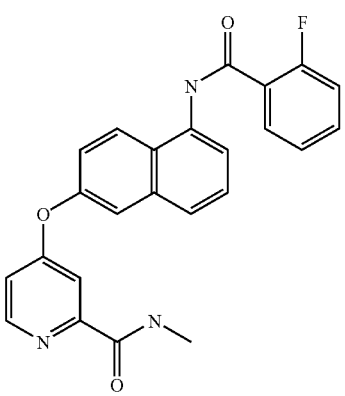4-((5-(((2-fluorophenyl)carbonyl)amino)-2-naphthalenyl)oxy)-N-methyl-2-pyridinecarboxamide | $C_{24}H_{18}FN_3O_3$ | 415.42 | 416.4 |
| 482 | 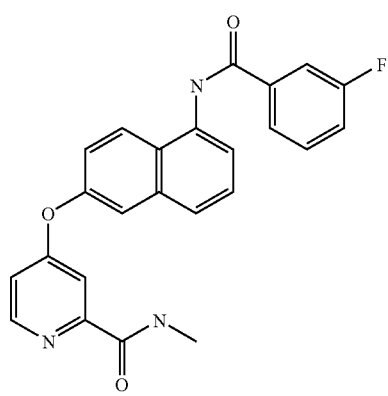4-((5-(((3-fluorophenyl)carbonyl)amino)-2-naphthalenyl)oxy)-N-methyl-2-pyridinecarboxamide | $C_{24}H_{18}FN_3O_3$ | 415.42 | 416.4 |
| 483 | 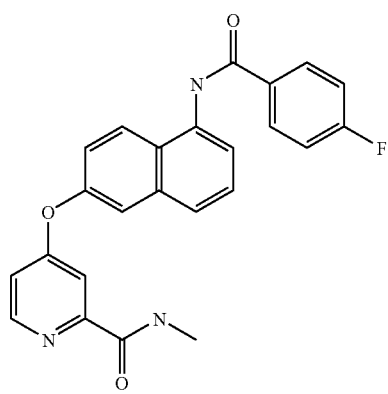4-((5-(((4-fluorophenyl)carbonyl)amino)-2-naphthalenyl)oxy)-N-methyl-2-pyridinecarboxamide | $C_{24}H_{18}FN_3O_3$ | 415.42 | 416.4 |

| Example # | Structure & Name | Mol Formula | Mass | M + H |
|---|---|---|---|---|
| 484 | 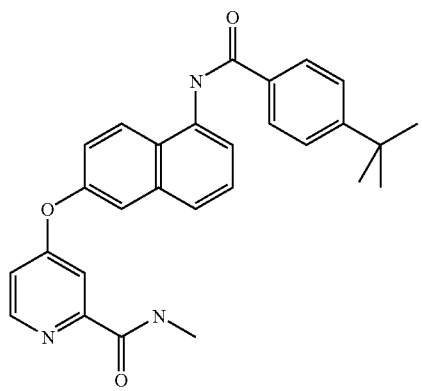<br>4-((5-(((4-(1,1-dimethylethyl)phenyl)carbonyl)amino)-2-naphthalenyl)oxy)-N-methyl-2-pyridinecarboxamide | $C_{28}H_{27}N_3O_3$ | 453.54 | 454.5 |
| 485 | 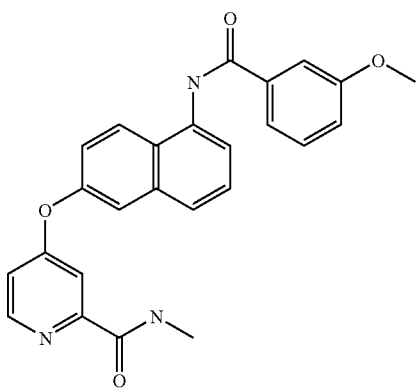<br>N-methyl-4-((5-(((3-(methoxy)phenyl)carbonyl)amino)-2-naphthalenyl)oxy)-2-pyridinecarboxamide | $C_{25}H_{21}N_3O_4$ | 427.46 | 428.1 |
| 486 | 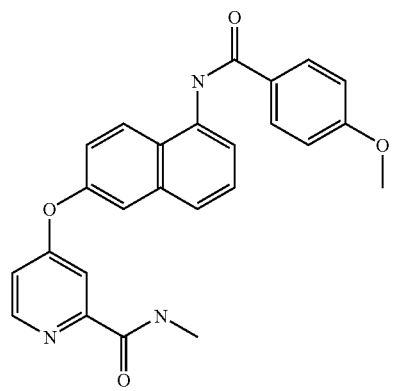<br>N-methyl-4-((5-(((4-(methoxy)phenyl)carbonyl)amino)-2-naphthalenyl)oxy)-2-pyridinecarboxamide | $C_{25}H_{21}N_3O_4$ | 427.46 | 428.1 |

-continued
| Example # | Structure & Name | Mol Formula | Mass | M + H |
|---|---|---|---|---|
| 487 | 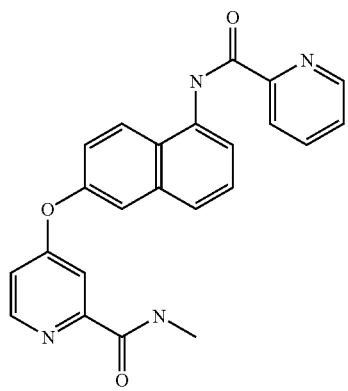  N-methyl-4-((5-((2-pyridinylcarbonyl)amino)-2-naphthalenyl)oxy)-2-pyridinecarboxamide | C₂₃H₁₈N₄O₃ | 398.42 | 399.1 |
| 488 | 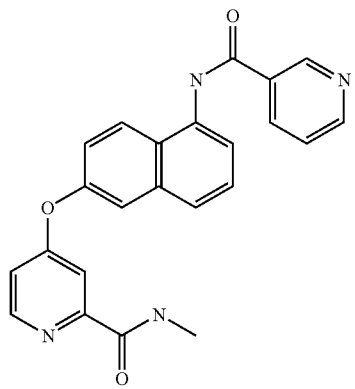  N-methyl-4-((5-((3-pyridinylcarbonyl)amino)-2-naphthalenyl)oxy)-2-pyridinecarboxamide | C₂₃H₁₈N₄O₃ | 398.42 | 399.1 |
| 489 | 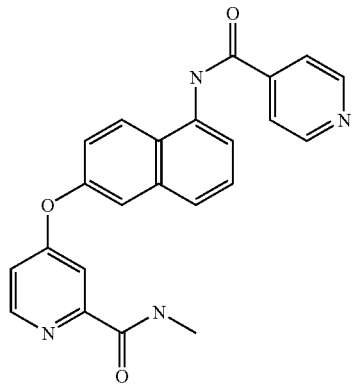  N-methyl-4-((5-((4-pyridinylcarbonyl)amino)-2-naphthalenyl)oxy)-2-pyridinecarboxamide | C₂₃H₁₈N₄O₃ | 398.42 | 399.1 |

| Example # | Structure & Name | Mol Formula | Mass | M + H |
|---|---|---|---|---|
| 490 | 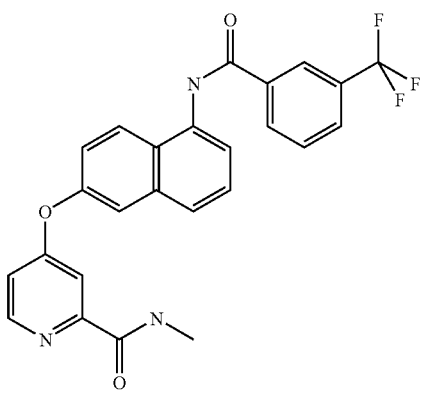<br>N-methyl-4-((5-(((3-(trifluoromethyl)phenyl)carbonyl)amino)-2-naphthalenyl)oxy)-2-pyridinecarboxamide | $C_{25}H_{18}F_3N_3O_3$ | 465.43 | 466.1 |
| 491 | 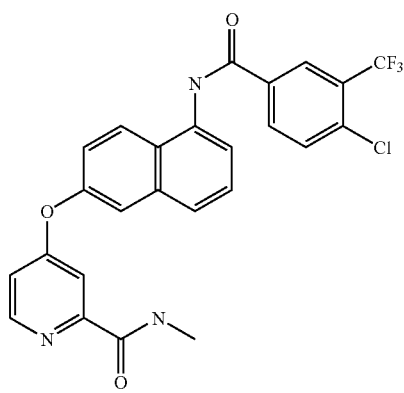<br>4-((5-(((4-chloro-3-(trifluoromethyl)phenyl)carbonyl)amino)-2-naphthalenyl)oxy)-N-methyl-2-pyridinecarboxamide | $C_{25}H_{17}ClF_3N_3O_3$ | 499.87 | 500 |
| 492 | 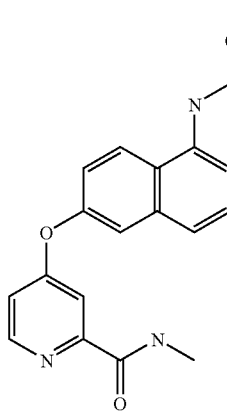<br>4-((5-(((4-chlorophenyl)acetyl)amino)-2-naphthalenyl)oxy)-N-methyl-2-pyridinecarboxamide | $C_{25}H_{20}ClN_3O_3$ | 445.9 | 446.1 |

| Example # | Structure & Name | Mol Formula | Mass | M + H |
|---|---|---|---|---|
| 493 | 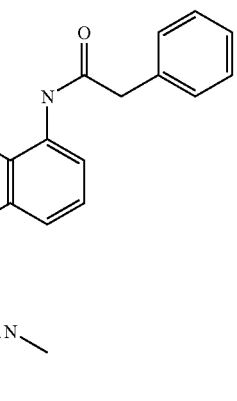<br>N-methyl-4-((5-((phenylacetyl)amino)-2-naphthalenyl)oxy)-2-pyridinecarboxamide | $C_{25}H_{21}N_3O_3$ | 411.46 | 412.1 |
| 494 | 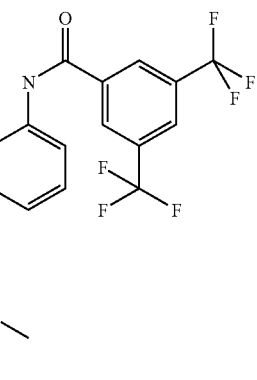<br>4-((5-(((3,5-bis(trifluoromethyl)phenyl)carbonyl)amino)-2-naphthalenyl)oxy)-N-methyl-2-pyridinecarboxamide | $C_{26}H_{17}F_6N_3O_3$ | 533.43 | 534.1 |
| 495 | 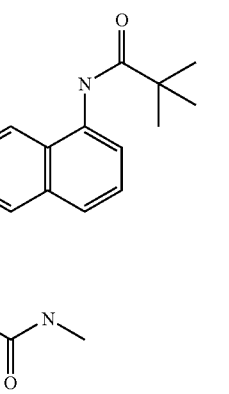<br>4-((5-((2,2-dimethylpropanyl)amino)-2-naphthalenyl)oxy)-N-methyl-2-pyridinecarboxamide | $C_{22}H_{23}N_3O_3$ | 377.44 | 378.2 |

-continued

| Example # | Structure & Name | Mol Formula | Mass | M + H |
|---|---|---|---|---|
| 496 | 4-((5-((cyclohexylcarbonyl)amino)-2-naphthalenyl)oxy)-N-methyl-2-pyridinecarboxamide | $C_{24}H_{25}N_3O_3$ | 403.48 | 404.2 |
| 497 | N-methyl-4-((5-(((4-methylphenyl)carbonyl)amino)-2-naphthalenyl)oxy)-2-pyridinecarboxamide | $C_{25}H_{21}N_3O_3$ | 411.46 | 412.1 |
| 498 | N-methyl-4-((5-(((3-methylphenyl)carbonyl)amino)-2-naphthalenyl)oxy)-2-pyridinecarboxamide | $C_{25}H_{21}N_3O_3$ | 411.46 | 412.1 |

| Example # | Structure & Name | Mol Formula | Mass | M + H |
|---|---|---|---|---|
| 499 | 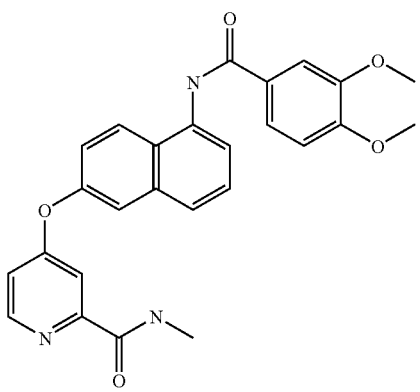<br>4-((5-(((3,4-bis(methoxy)phenyl)carbonyl)amino)-2-naphthalenyl)oxy)-N-methyl-2-pyridinecarboxamide | $C_{26}H_{23}N_3O_5$ | 457.48 | 458.1 |
| 500 | 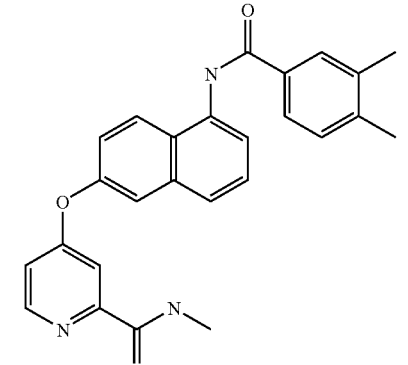<br>4-((5-(((3,4-dimethylphenyl)carbonyl)amino)-2-naphthalenyl)oxy)-N-methyl-2-pyridinecarboxamide | $C_{26}H_{23}N_3O_3$ | 425.49 | 426.1 |
| 501 | 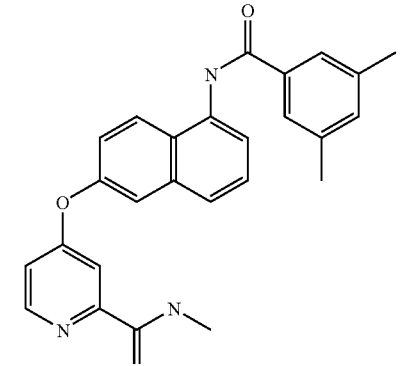<br>4-((5-(((3,5-dimethylphenyl)carbonyl)amino)-2-naphthalenyl)oxy)-N-methyl-2-pyridinecarboxamide | $C_{26}H_{23}N_3O_3$ | 425.49 | 426.1 |

-continued

| Example # | Structure & Name | Mol Formula | Mass | M + H |
|---|---|---|---|---|
| 502 | ![structure] N-methyl-4-((5-((1-naphthalenylcarbonyl)amino)-2-naphthalenyl)oxy)-2-pyridinecarboxamide | $C_{28}H_{21}N_3O_3$ | 447.49 | 448.1 |

EXAMPLE 503

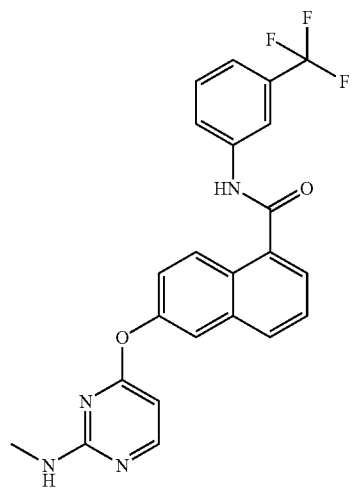

6-((2-(methylamino)-4-pyrimidinyl)oxy)-N-(3-(trifluoromethyl)phenyl)-1-naphthalenecarboxamide

Step (a) Preparation of 6-(2-chloropyrimidin-4-yloxy)-1-naphthoic acid

To a solution of 6-hydroxy-1-naphthoic acid (10.0 g, 53.1 mmol) in DMSO (60 mL) was added $Cs_2CO_3$ (51.9 g, 159.4 mmol). Bubbling was evident. The mixture was stirred at RT for 5 min, at which time 2,4-dichloropyrimidine (15.8 g, 16.3 mmol) was added. The reaction was stirred at RT and monitored by LCMS for the disappearance of starting material. EtOAc (1.0 L) was added, and the reaction was filtered to remove solid $Cs_2CO_3$. The mixture was extracted with 2N aqueous NaOH. The aqueous layer was washed with EtOAc, then acidified with 6N aqueous HCl to provide a white suspension. Filtration yielded a white solid.

Step (b) Preparation of 6-(2-chloropyrimidin-4-yloxy)-1-naphthoyl chloride

To a suspension of 6-(2-chloropyrimidin-4-yloxy)-1-naphthoic acid (Step a, 2.30 g, 7.65 mmol) in $CH_2Cl_2$ (50 mL) was added DMF (5 drops), followed by oxalyl chloride (0.734 mL, 8.41 mmol) dropwise. The mixture bubbled and was stirred at RT overnight. The reaction was filtered through a frit to remove any remaining solid and concentrated to afford the desired light-tan solid as its hydrochloride salt.

Step (c) Preparation of 6-(2-chloropyrimidin-4-yloxy)-N-(3-(trifluoromethyl)phenyl)-1-naphthamide To a suspension of the hydrochloride salt of 6-(2-chloropyrimidin-4-yloxy)-1-naphthoyl chloride (step b, 0.122 g, 0.34 mmol) in THF (3 mL) was added 3-(trifluoromethyl)benzenamine (0.047 mL, 0.38 mmol). The reaction was stirred at RT overnight. The mixture was concentrated and partitioned between EtOAc and 2N aqueous NaOH. Extraction with several portions of EtOAc was followed by washing of the organic layer with brine and drying with $MgSO_4$. The solution was filtered and concentrated to afford the desired compound.

Step (d) Preparation of 6-(2-chloropyrimidin-4-yloxy)-N-(3-(trifluoromethyl)phenyl)-1-naphthamide 6-(2-Chloropyrimidin-4-yloxy)-N-(3-(trifluoromethyl)phenyl)-1-naphthamide (0.075 g, 0.17 mmol) was stirred overnight at RT in a sealed tube with 2.0 M methylamine (3.0 mL) in THF. The reaction was concentrated, taken up in EtOAc, and washed with 2N aqueous NaOH. The mixture was washed with brine, dried with $MgSO_4$ and filtered. The concentrated mixture was purified by chromatography on silica gel to afford the desired product. MS (ESI, pos. ion) m/z: 439.0 (M+1). Mass Calc'd for $C_{23}H_{17}F_3N_4O_2$: 438.07.

The following examples were prepared similar to the procedures described in Example 503.
| Example No. | Structure & Example | Mol Formula | Mass | M + H |
|---|---|---|---|---|
| 504 | 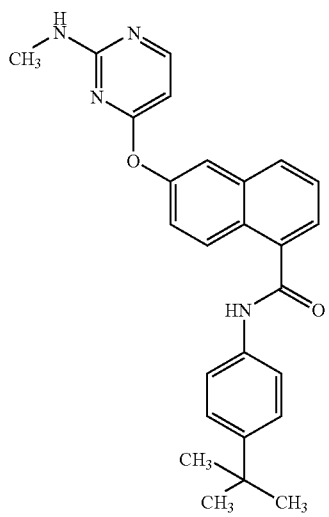<br>N-(4-(1,1-dimethylethyl)phenyl)-6-((2-(methylamino)-4-pyrimidinyl)oxy)-1-naphthalenecarboxamide | $C_{26}H_{26}N_4O_2$ | 426.52 | 427.2 |
| 505 | 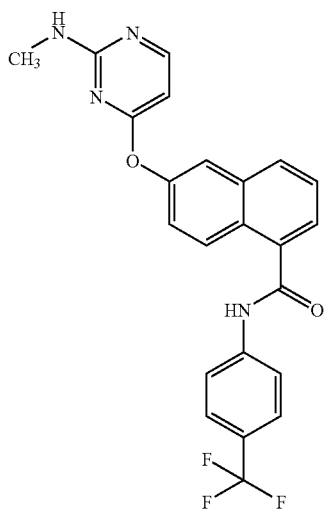<br>6-((2-(methylamino)-4-pyrimidinyl)oxy)-N-(4-(trifluoromethyl)phenyl)-1-naphthalenecarboxamide | $C_{23}H_{17}F_3N_4O_2$ | 438.41 | 439.0 |

-continued
| Example No. | Structure & Example | Mol Formula | Mass | M + H |
|---|---|---|---|---|
| 506 | 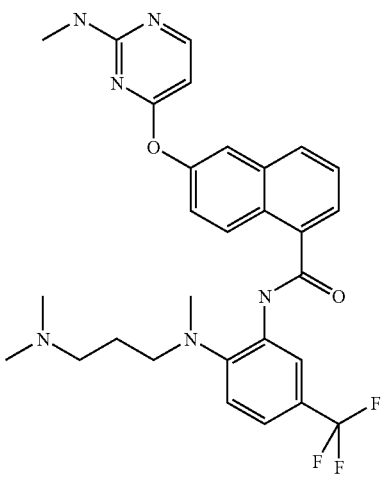<br>N-(2-((3-(dimethylamino)propyl)methyl)amino)-5-(trifluoromethyl)phenyl)-6-((2-(methylamino)-4-pyrimidinyl)oxy)-1-naphthalenecarboxamide | $C_{29}H_{31}F_3N_6O_2$ | 552.598 | 553.6 |
| 507 | 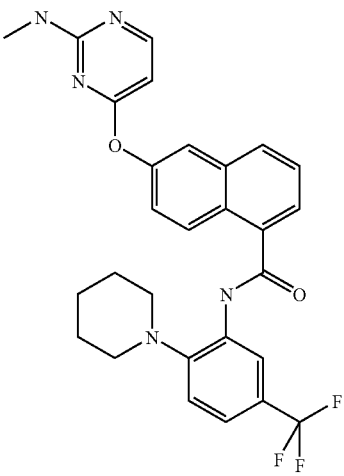<br>6-((2-(methylamino)-4-pyrimidinyl)oxy)-N-(2-(1-piperidinyl)-5-(trifluoromethyl)phenyl)-1-naphthalenecarboxamide | $C_{28}H_{26}F_3N_5O_2$ | 521.54 | 522 |

The following examples were prepared similar to the procedures described in Example 503, with heating to 60 C in Step d.

| Example No. | Structure & Name | Mol Formula | Mass | M + H |
|---|---|---|---|---|
| 508 | 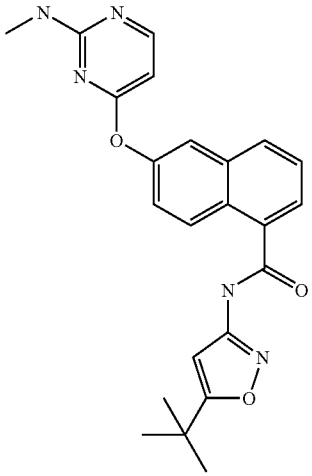<br>N-(5-(1,1-dimethylethyl)-3-isoxazolyl)-6-((2-(methylamino)-4-pyrimidinyl)oxy)-1-naphthalenecarboxamide | $C_{23}H_{23}N_5O_3$ | 417.47 | 418.1 |
| 509 | 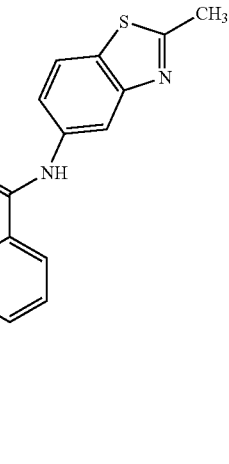<br>6-((2-(methylamino)-4-pyrimidinyl)oxy)-N-(2-methyl-1,3-benzothiazol-5-yl)-1-naphthalenecarboxamide | $C_{24}H_{19}N_5O_2S$ | 441.51 | 442.1 |
| 510 | 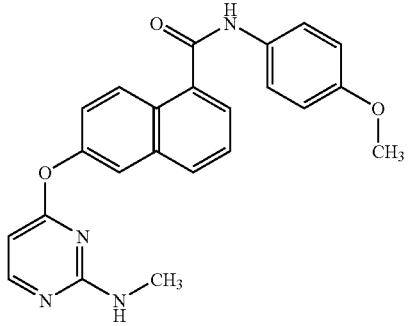<br>6-((2-(methylamino)-4-pyrimidinyl)oxy)-N-(4-(methoxy)phenyl)-1-naphthalenecarboxamide | $C_{23}H_{20}N_4O_3$ | 400.44 | 401.1 |

-continued
| Example No. | Structure & Name | Mol Formula | Mass | M + H |
|---|---|---|---|---|
| 511 | 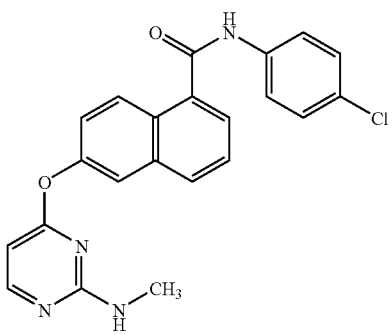<br>N-(4-chlorophenyl)-6-((2-(methylamino)-4-pyrimidinyl)oxy)-1-naphthalenecarboxamide | $C_{22}H_{17}ClN_4O_2$ | 404.86 | 405.1 |
| 512 | 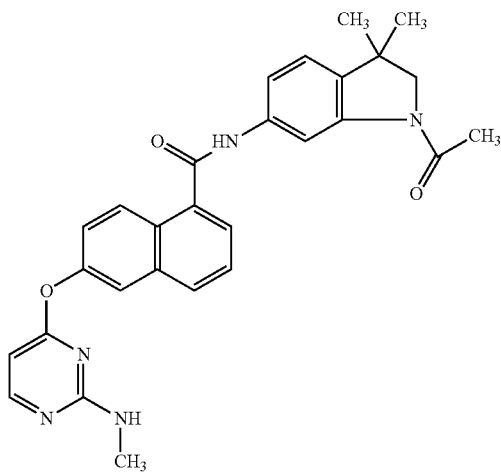<br>N-(1-acetyl-3,3-dimethyl-2,3-dihydro-1H-indol-6-yl)-6-((2-(methylamino)-4-pyrimidinyl)oxy)-1-naphthalenecarboxamide | $C_{28}H_{27}N_5O_3$ | 481.55 | 482.1 |
| 513 | 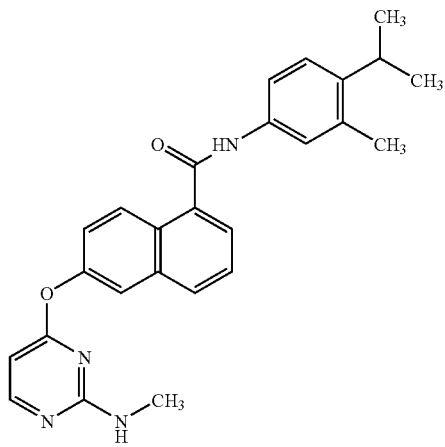<br>6-((2-(methylamino)-4-pyrimidinyl)oxy)-N-(3-methyl-4-(1-methylethyl)phenyl)-1-naphthalenecarboxamide | $C_{26}H_{26}N_4O_2$ | 426.52 | 427.2 |

-continued

| Example No. | Structure & Name | Mol Formula | Mass | M + H |
|---|---|---|---|---|
| 514 | 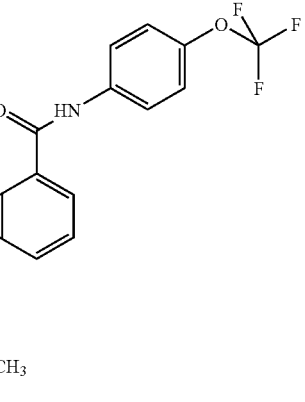<br>6-((2-(methylamino)-4-pyrimidinyl)oxy)-N-(4-((trifluoromethyl)oxy)phenyl)-1-naphthalenecarboxamide | $C_{23}H_{17}F_3N_4O_3$ | 454.41 | 455.1 |
| 515 | 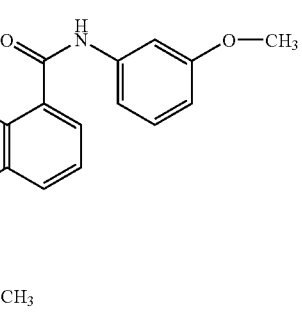<br>6-((2-(methylamino)-4-pyrimidinyl)oxy)-N-(3-(methoxy)phenyl)-1-naphthalenecarboxamide | $C_{23}H_{20}N_4O_3$ | 400.44 | 401.17 |

EXAMPLE 516

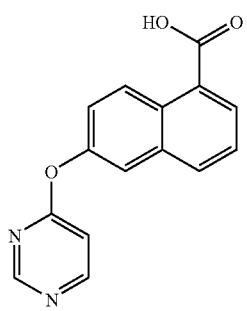

6-(pyrimidin-7-yloxy)-1-naphthoic acid

To a solution of 6-(2-chloropyrimidin-4-yloxy)-1-naphthoic acid (1.3 g, 4.3 μmmol) in a $CH_2Cl_2$/EtOAc/MeOH mixture were added ammonium formate (2.74 g, 43 mmol) and wet Pd/C. The mixture was stirred at RT overnight, filtered through a pad of Celite and evaporated to give the title compound as a brown solid.

The following examples were prepared similar to the procedures described in Example 357 and purified by column chromatography and/or crystallization.

| Example No. | Structure & Name | Mol Formula | Mass | M + H |
|---|---|---|---|---|
| 517 | 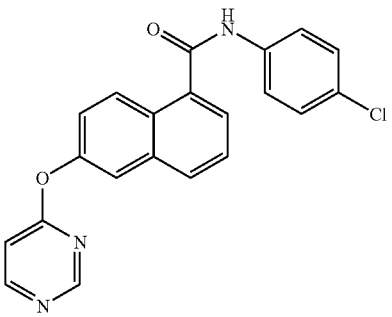<br>N-(4-chlorophenyl)-6-(4-pyrimidinyloxy)-1-naphthalenecarboxamide | $C_{21}H_{14}ClN_3O_2$ | 375.81 | 376.1 |
| 518 | 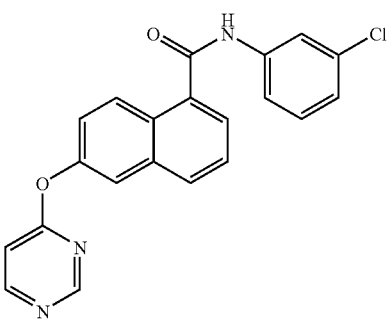<br>N-(3-chlorophenyl)-6-(4-pyrimidinyloxy)-1-naphthalenecarboxamide | $C_{21}H_{14}ClN_3O_2$ | 375.81 | 376.1 |
| 519 | 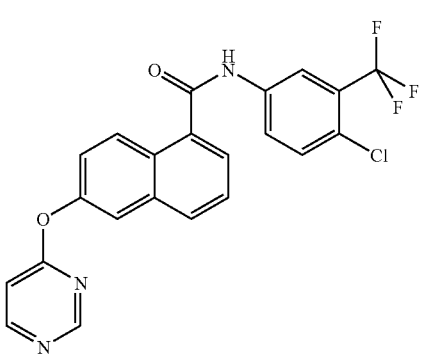<br>N-(4-chloro-3-(trifluoromethyl)phenyl)-6-(4-pyrimidinyloxy)-1-naphthalenecarboxamide | $C_{22}H_{13}ClF_3N_3O_2$ | 443.81 | 444.1 |
| 520 | 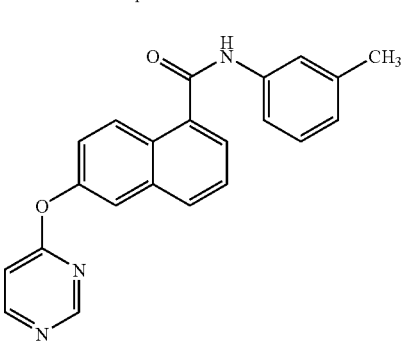<br>N-(3--methylphenyl)-6-(4-pyrimidinyloxy)-1-naphthalenecarboxamide | $C_{22}H_{17}N_3O_2$ | 355.39 | 356.2 |

-continued

| Example No. | Structure & Name | Mol Formula | Mass | M + H |
|---|---|---|---|---|
| 521 | 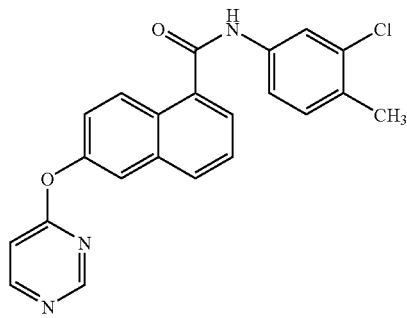<br>N-(3-chloro-4-methylphenyl)-6-(4-pyrimidinyloxy)-1-naphthalenecarboxamide | $C_{22}H_{16}ClN_3O_2$ | 389.84 | 390.1 |
| 522 | 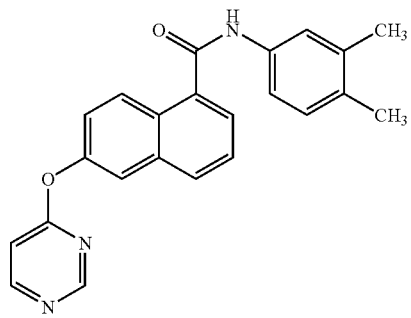<br>N-(3,4-dimethylphenyl)-6-(4-pyrimidinyloxy)-1-naphthalenecarboxamide | $C_{23}H_{19}N_3O_2$ | 369.42 | 370.1 |

EXAMPLE 523

6-(pyrimidin-4-yloxy)-N-(3-(trifluoromethyl)phenyl)-1-naphthamide

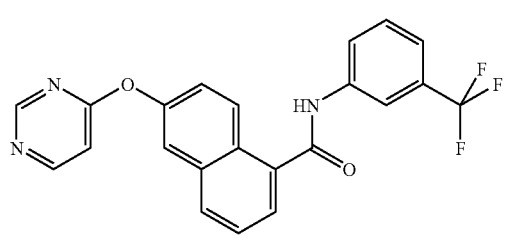

To a solution of 6-(2-chloropyrimidin-4-yloxy)-N-(3-(trifluoromethyl)phenyl)-1-naphthamide (0.075 g, 0.17 mmol) in EtOAc (3 mL) and methanol (0.5 mL) was added 10% Pd/C (20 mg). The flask was capped with a septum, and $H_2$ gas was introduced through a balloon/needle. Positive $H_2$ pressure was continued as the reaction was stirred vigorously overnight at RT. The reaction was filtered through Celite, concentrated, and purified by chromatography on silica to afford the desired product as a white solid. MS (ESI, pos. ion) m/z: 410.1 (M+1). Mass Calc'd for $C_{22}H_{14}F_3N_3O_2$: 409.36.

The following examples were prepared similar to the procedures described in Example 523:

| Example No. | Structure & Name | Mol Formula | Mass | M + H |
|---|---|---|---|---|
| 524 | 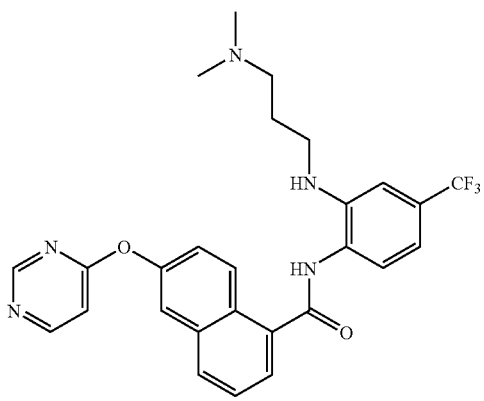<br>N-(2-((3-(dimethylamino)propyl)(methyl)amino)-5-(trifluoromethyl)phenyl)-6-(4-pyrimidinyloxy)-1-naphthalenecarboxamide | $C_{28}H_{28}F_3N_5O_2$ | 523.56 | 524.3 |

EXAMPLE 525

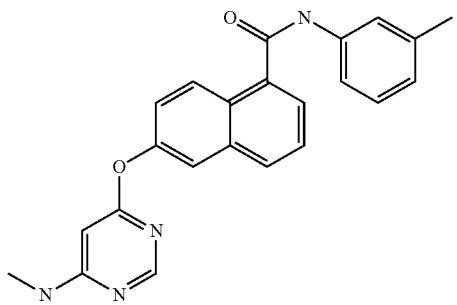

6-((6-(methylamino)-4-pyrimidinyl)oxy)-N-(3-methylphenyl)-1-naphthalenecarboxamide

Step (a) Preparation of 6-chloro-N-methylpyrimidin-4-amine

To an ice-bath cooled solution of 4,6-dichloropyrimidine (3 g, 20 mmol) in THF (5 mL), NEt₃ (5.6 mL, 40 mmol) was added followed by slow addition of N-methylamine (2 M in THF, 10 mL, 20 mmol). The mixture was warmed to RT and stirred overnight. The mixture was concentrated in-vacuo, the residue suspended in Et₂O and solid collected to give the title compound as a white solid.

Step (b) Preparation of 6-(6-(methylamino)pyrimidin-4-yloxy)-1-naphthoic acid The title compound was prepared similar to the procedure described in Example 783, Step (a), with the temperature of 70-100° C. (until the starting material is consumed).

Step (c) Preparation of 6-((6-(methylamino)-4-pyrimidinyl)oxy)-N-(3-methylphenyl)-1-naphthalenecarboxamide The title compound was prepared similar to the procedure described in Example 357. MS (ESI pos. ion) m/z: 385.2 (M+H). Calc'd for $C_{23}H_{20}N_4O_2$–384.43.

The following examples were prepared similar to the procedures described in Example 525 and purified by column chromatography and/or crystallization.

| Example No. | Structure & Name | Mol Formula | Mass | M + H |
|---|---|---|---|---|
| 526 | 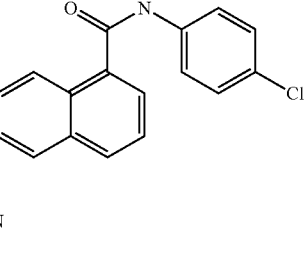<br>N-(4-chlorophenyl)-6-((6-(methylamino)-4-pyrimidinyl)oxy)-1-naphthalenecarboxamide | C$_{22}$H$_{17}$ClN$_4$O$_2$ | 404.85 | 405.1 |
| 527 | 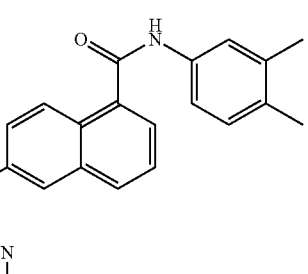<br>N-(3,4-dimethylphenyl)-6-((6-(methylamino)-4-pyrimidinyl)oxy)-1-naphthalenecarboxamide | C$_{24}$H$_{22}$N$_4$O$_2$ | 398.46 | 399.2 |
| 528 | 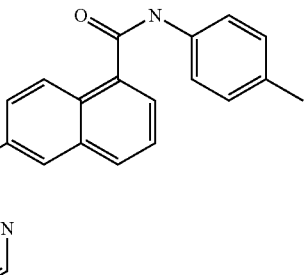<br>6-((6-(methylamino)-4-pyrimidinyl)oxy)-N-(4-methylphenyl)-1-naphthalenecarboxamide | C$_{23}$H$_{20}$N$_4$O$_2$ | 384.43 | 385.2 |
| 529 | 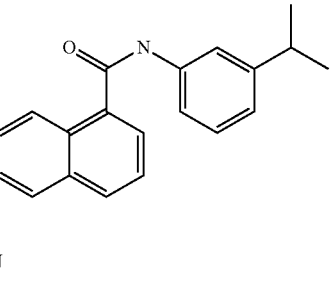<br>6-((6-(methylamino)-4-pyrimidinyl)oxy)-N-(3-(1-methylethyl)phenyl)-1-naphthalenecarboxamide | C$_{25}$H$_{24}$N$_4$O$_2$ | 412.49 | 413.2 |

| Example No. | Structure & Name | Mol Formula | Mass | M + H |
|---|---|---|---|---|
| 530 | 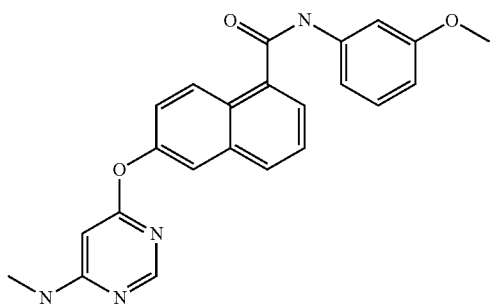<br>6-((6-(methylamino)-4-pyrimidinyl)oxy)-N-(3-(methoxy)phenyl)-1-naphthalenecarboxamide | $C_{23}H_{20}N_4O_3$ | 400.43 | 401.2 |
| 531 | 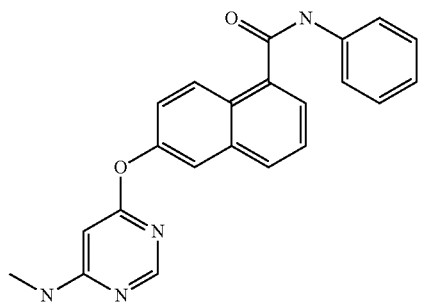<br>6-((6-(methylamino)-4-pyrimidinyl)oxy)-N-phenyl-1-naphthalenecarboxamide | $C_{22}H_{18}N_4O_2$ | 370.41 | 371.2 |
| 532 | 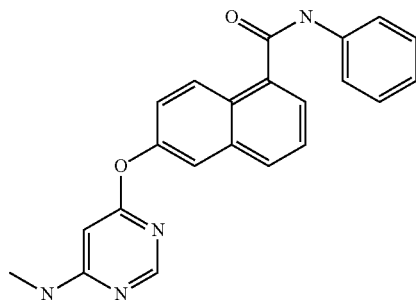<br>N-(3-chlorophenyl)-6-((6-(methylamino)-4-pyrimidinyl)oxy)-1-naphthalenecarboxamide | $C_{22}H_{17}ClN_4O_2$ | 404.85 | 405.1 |
| 533 | 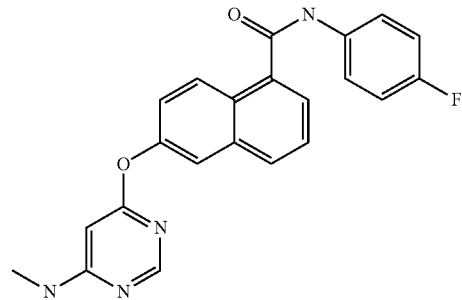<br>N-(4-fluorophenyl)-6-((6-(methylamino)-4-pyrimidinyl)oxy)-1-naphthalenecarboxamide | $C_{22}H_{17}FN_4O_2$ | 388.39 | 389.1 |

| Example No. | Structure & Name | Mol Formula | Mass | M + H |
|---|---|---|---|---|
| 534 | 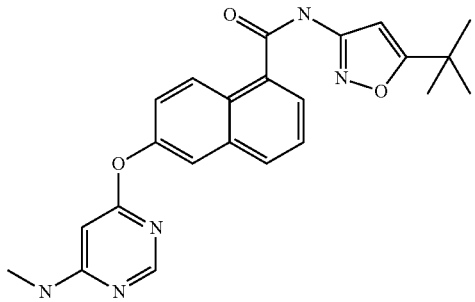<br>N-(5-(1,1-dimethylethyl)-3-isoxazolyl)-6-((6-(methylamino)-4-pyrimidinyl)oxy)-1-naphthalenecarboxamide | $C_{23}H_{23}N_5O_3$ | 417.46 | 418.2 |
| 535 | 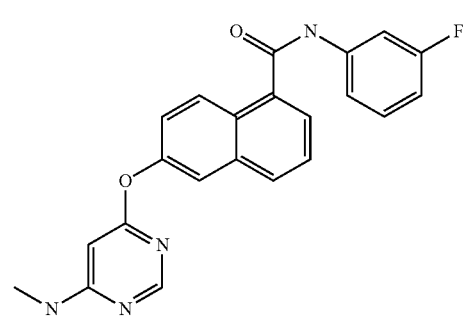<br>N-(3-fluorophenyl)-6-((6-(methylamino)-4-pyrimidinyl)oxy)-1-naphthalenecarboxamide | $C_{22}H_{17}FN_4O_2$ | 388.39 | 389.1 |
| 536 | 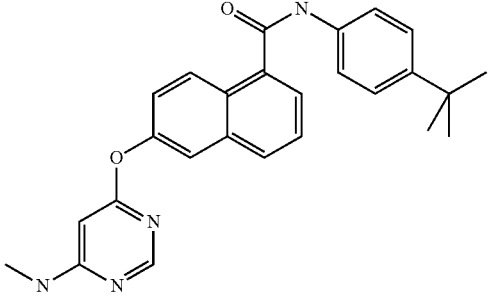<br>N-(4-(1,1-dimethylethyl)phenyl)-6-((6-(methylamino)-4-pyrimidinyl)oxy)-1-naphthalenecarboxamide | $C_{26}H_{26}N_4O_2$ | 426.51 | 427.2 |
| 537 | 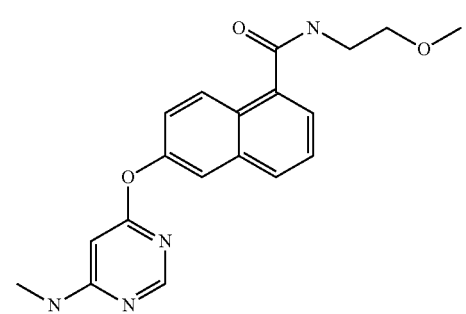<br>6-((6-(methylamino)-4-pyrimidinyl)oxy)-N-(2-(methoxy)ethyl)-1-naphthalenecarboxamide | $C_{19}H_{20}N_4O_3$ | 352.39 | 353.2 |

EXAMPLE 538

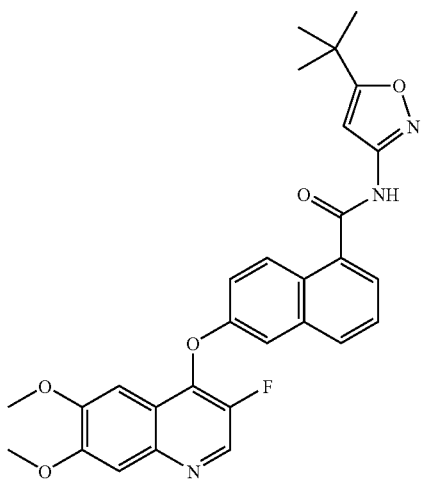

N-(5-(1,1-dimethylethyl)-3-isoxazolyl)-6-((3-fluoro-6,7-bis(methoxy)-4-quinolinyl)oxy)-1-naphthalenecarboxamide

Step (a) Preparation of 6-(3-fluoro-6,7-dimethoxyquinolin-4-yloxy)-1-naphthoic acid A resealable tube was charged with 4-chloro-3-fluoro-6,7-dimethoxyquinoline (prepared by the method described in WO 98/13350) (0.610 g, 2.52 mmol), 6-hydroxy-1-naphthoic acid (0.474 g, 2.52 mmol), palladium acetate (0.023 g, 0.101 mmol), 2-di-t-butylphosphino-2',4',6'-tri-1-propyl-1,1'-biphenyl (0.086 g, 0.202 mmol), potassium phosphate (2.14 g, 10.08 mmol), and DMF (12.6 mL, Aldrich). The system was flushed with argon and the tube was sealed. The mixture was stirred at 100° C. for 19 h then cooled to RT. Water (13 mL) was added, and the pH was adjusted to 6-7 with aqueous 6 N HCl solution. The resulting precipitate was filtered, washed with water, and purified by column chromatography on silica gel (eluting with 0-100% (50:50:2, EtOAc:hexane:AcOH)) to afford 6-(3-fluoro-6,7-dimethoxyquinolin-4-yloxy)-1-naphthoic acid as an off-white solid. MS (ESI, pos. ion) m/z: 394.0 (M+H). Mass Calc'd for $C_{22}H_{16}FNO_5$: 393.1

Step (b) Preparation of N-(5-(1,1-dimethylethyl)-3-isoxazolyl)-6-((3-fluoro-6,7-bis(methoxy)-4-quinolinyl)oxy)-1-naphthalenecarboxamide Pyridine (1.0 mL) was added to a mixture of 6-(3-fluoro-6,7-dimethoxyquinolin-4-yloxy)-1-naphthoyl chloride (prepared from 6-(3-fluoro-6,7-dimethoxyquinolin-4-yloxy)-1-naphthoic acid and oxalyl chloride by the procedure described in Example 273) (0.044 g, 0.107 mmol) and 3-amino-5-t-butylisoxazole (0.075 g, 0.535 mmol). The mixture stirred at 80° C. for 10 h and was then cooled to RT. The mixture was concentrated and the residue was purified by preparative thin layer chromatography on silica gel plates (eluting with 5% MeOH—$CH_2Cl_2$). Further purification via preparative thin layer chromatography on silica gel plates (eluting with 90:10:1 $CH_2Cl_2$:MeOHl:$NH_4OH$) afforded N-(5-(1,1-dimethylethyl)-3-isoxazolyl)-6-((3-fluoro-6,7-bis(methoxy)-4-quinolinyl)oxy)-1-naphthalenecarboxamide as an off-white solid. MS (ESI, pos. ion) m/z: 516.0 (M+H). Mass Calc'd for $C_{29}H_{26}FN_3O_5$: 515.5

The following examples were prepared similar to the procedures described in Example 538, Step b.

| Example No. | Structure & Name | Mol Formula | Mass | M + H |
|---|---|---|---|---|
| 539 | 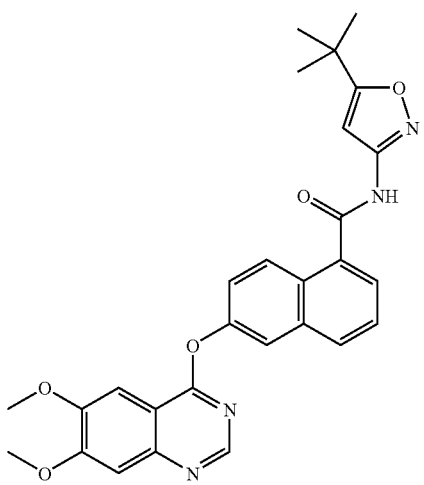<br>6-((6,7-bis(methoxy)-4-quinazolinyl)amino)-N-(5-(1,1-dimethylethyl)-3-isoxazolyl)-1-naphthalenecarboxamide | $C_{28}H_{27}N_5O_4$ | 497.55 | 498 |

-continued
| Example No. | Structure & Name | Mol Formula | Mass | M + H |
|---|---|---|---|---|
| 540 | 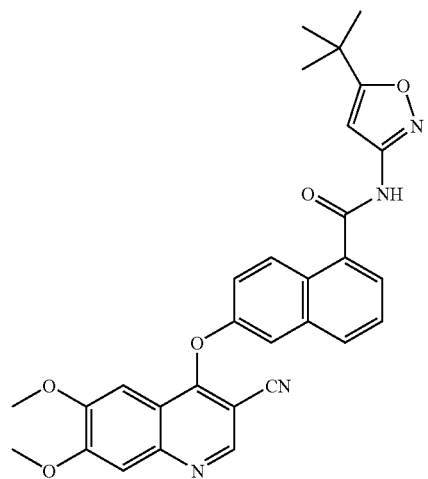<br>6-((3-cyano-6,7-bis(methoxy)-4-quinolinyl)oxy)-N-(5-(1,1-dimethylethyl)-3-isoxazolyl)-1-naphthalenecarboxamide | $C_{30}H_{26}N_4O_5$ | 522.56 | 523 |
| 541 | 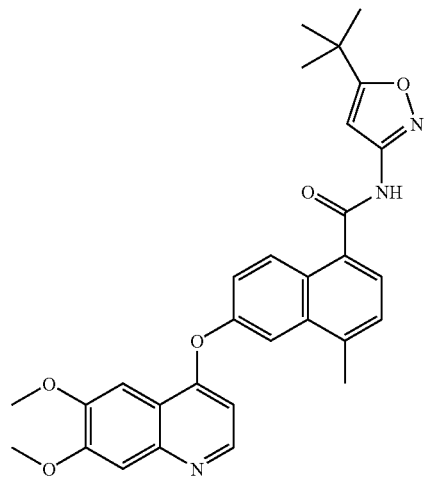<br>6-((6,7-bis(methoxy)-4-quinolinyl)oxy)-N-(5-(1,1-dimethylethyl)-3-isoxazolyl)-4-methyl-1-naphthalenecarboxamide | $C_{30}H_{29}N_3O_5$ | 511.57 | 512.3 |

| Example No. | Structure & Name | Mol Formula | Mass | M + H |
|---|---|---|---|---|
| 542 | 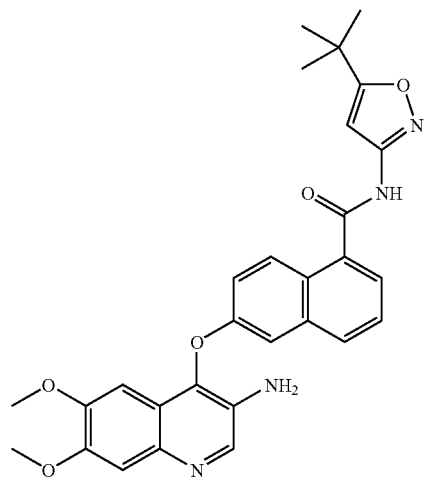<br>6-((3-amino-6,7-bis(methoxy)-4-quinolinyl)oxy)-N-(5-(1,1-dimethylethyl)-3-isoxazolyl)-1-naphthalenecarboxamide | $C_{29}H_{28}N_4O_5$ | 512.56 | 513.1 |
| 543 | 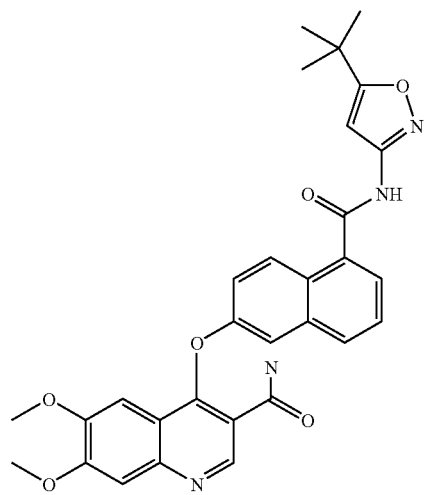<br>4-((5-(((5-(1,1-dimethylethyl)-3-isoxazolyl)amino)carbonyl)-2-naphthalenyl)oxy)-6,7-bis(methoxy)-3-quinolinecarboxamide | $C_{30}HN_4O_6$ | 540.573 | 541 |

| Example No. | Structure & Name | Mol Formula | Mass | M + H |
|---|---|---|---|---|
| 544 | 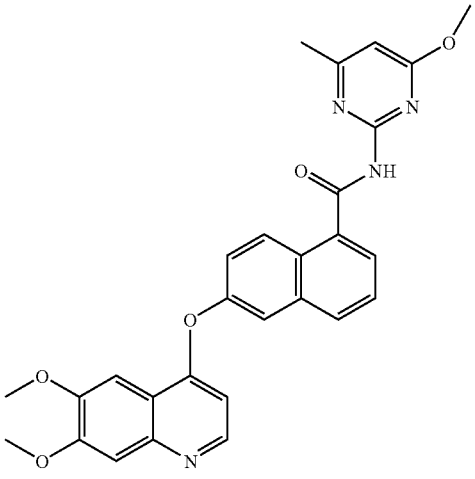<br>6-((6,7-bis(methoxy)-4-quinolinyl)oxy)-N-(4-methyl-6-(methoxy)-2-pyrimidinyl)-1-naphthalenecarboxamide | $C_{28}H_{24}N_4O_5$ | 496.52 | 497.1 |
| 545 | 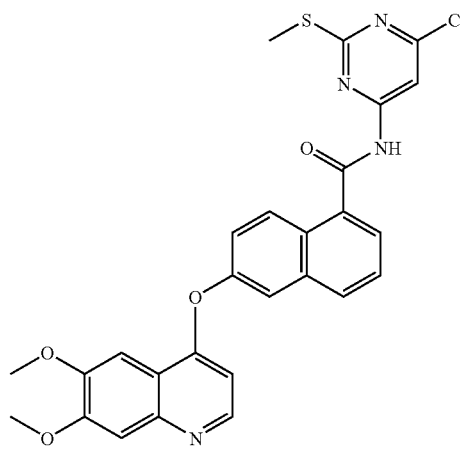<br>6-((6,7-bis(methoxy)-4-quinolinyl)oxy)-N-(6-chloro-2-(methylsulfanyl)-4-pyrimidinyl)-1-naphthalenecarboxamide | $C_{27}H_{21}ClN_4O_4S$ | 533.01 | 533 |
| 546 | 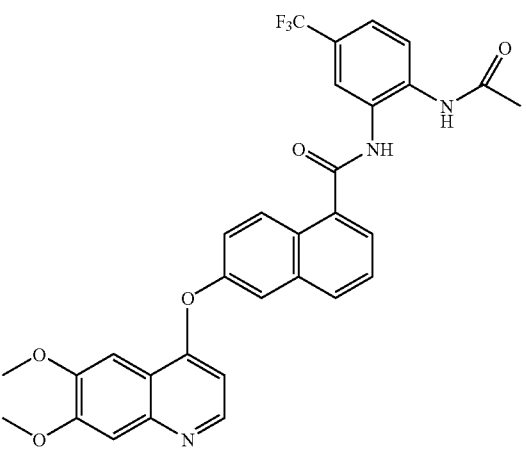<br>N-(2-(acetylamino)-5-(trifluoromethyl)phenyl)-6-((6,7-bis(methoxy)-4-quinolinyl)oxy)-1-naphthalenecarboxamide | $C_{31}H_{24}F_3N_3O_5$ | 575.54 | 576.5 |

| Example No. | Structure & Name | Mol Formula | Mass | M + H |
|---|---|---|---|---|
| 547 | 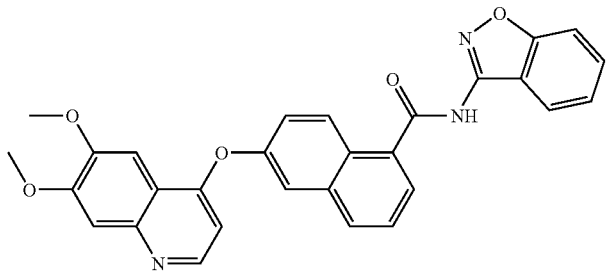<br>N-(1,2-benzisoxazol-3-yl)-6-((6,7-bis(methoxy)-4-quinolinyl)oxy)-1-napthalenecarboxamide | $C_{29}H_{21}N_3O_5$ | 491.5 | 492.1 |
| 548 | 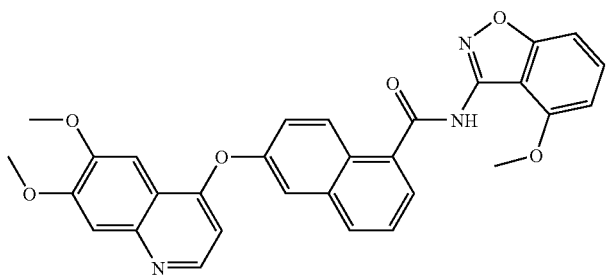<br>6-((6,7-bis(methoxy)-4-quinolinyl)oxy)-N-(4-(methoxy)-1,2-benzisoxazol-3-yl)-1-naphthalenecarboxamide | $C_{30}H_{23}N_3O_6$ | 521.53 | 522.4 |
| 549 | 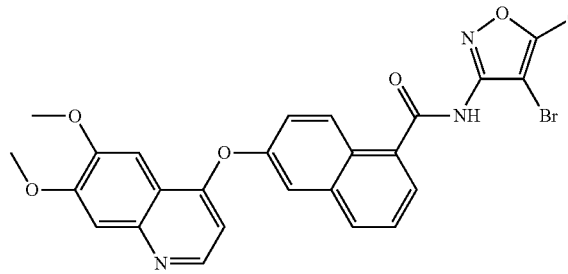<br>6-((6,7-bis(methoxy)-4-quinolinyl)oxy)-N-(4-bromo-5-methyl-3-isoxazolyl)-1-naphthalenecarboxamide | $C_{26}H_{20}BrN_3O_5$ | 534.36 | 534.3 |
| 550 | 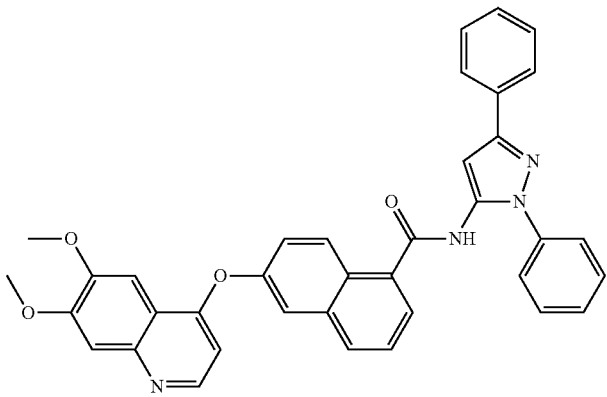<br>6-((6,7-bis(methoxy)-4-quinolinyl)oxy)-N-(1,3-diphenyl-1H-pyrazol-5-yl)-1-naphthalenecarboxamide | $C_{37}H_{28}N_4O_4$ | 592.65 | 593.5 |

-continued

| Example No. | Structure & Name | Mol Formula | Mass | M + H |
|---|---|---|---|---|
| 551 | N-(2-acetyl-5-(1,1-dimethylethyl)-3-thienyl)-6-((6,7-bis(methoxy)-4-quinolinyl)oxy)-1-naphthalenecarboxamide | $C_{32}H_{30}N_2O_5S$ | 554.66 | 555.5 |
| 552 | 4-((5-(((4-chlorophenyl)amino)carbonyl)-2-naphthalenyl)oxy)-7-(methoxy)-6-quinolinecarboxamide | $C_{28}H_{20}ClN_3O_4$ | 497.93 | 498.4 |
| 553 | 7-(methoxy)-4-((5-((2-pyridinylamino)carbonyl)-2-naphthalenyl)oxy)-6-quinolinecarboxamide | $C_{27}H_{20}N_4O_4$ | 464.47 | 465.4 |
| 554 | 7-(methoxy)-4-((5-((1,3-thiazol-2-ylamino)carbonyl)-2-naphthalenyl)oxy)-6-quinolinecarboxamide | $C_{25}H_{18}N_4O_4S$ | 470.50 | 471.3 |

-continued

| Example No. | Structure & Name | Mol Formula | Mass | M + H |
|---|---|---|---|---|
| 555 | 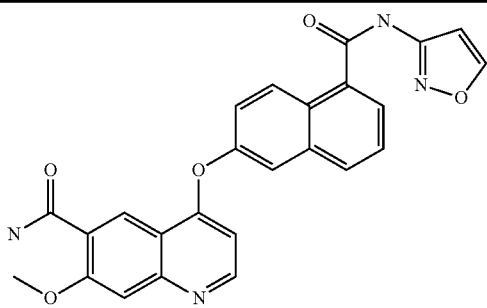<br>4-((5-((3-isoxazolylamino)carbonyl)-2-naphthalenyl)oxy)-7-(methoxy)-6-quinolinecarboxamide | $C_{25}H_{18}N_4O_5$ | 454.44 | 455.4 |

EXAMPLE 556

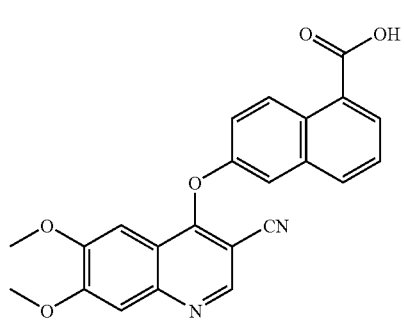

6-(3-cyano-6,7-dimethoxyquinolin-4-yloxy)-1-naphthoic acid

Step (a) Preparation of 4-chloro-3-cyano-6,7-dimethoxyquinoline

Copper (I) cyanide (0.301 g, 3.36 mmol) was added to a solution of 4-chloro-3-diazonium-6,7-dimethoxy quinoline tetrafluoroborate (prepared by the method described in WO 98/13350) (1.03 g, 3.05 mmol) in acetonitrile (30 mL). The reaction mixture stirred at RT for 2.5 h, then filtered. The filtrate was concentrated to afford 4-chloro-3-cyano-6,7-dimethoxyquinoline as a brown solid. MS (ESI, pos. ion) m/z: 249.0 (M+H). Mass Calc'd for $C_{12}H_9ClN_2O_2$: 248.

Step (b) Preparation of 6-(3-cyano-6,7-dimethoxyquinolin-4-yloxy)-1-naphthoic acid A resealable tube was charged with 6-hydroxy-1-naphthoic acid (0.596 g, 3.17 mmol), cesium carbonate (3.10 g, 9.51 mmol), and N,N-dimethylformamide (15 mL, Aldrich). The system was flushed with argon, the tube was sealed, and the mixture stirred at RT for 15 min. A solution of 4-chloro-3-cyano-6,7-dimethoxyquinoline (0.788 g, 3.17 mmol) in N,N-dimethylformamide (10 mL) was added (along with a 5 mL DMF rinse), and the system was again flushed with argon. The tube was sealed and the mixture stirred at 60° C. for 2 h. The mixture was diluted with water (30 mL) and 6 N HCl (aq) was added dropwise with stirring until the pH of the solution was 6-7. The resulting precipitate was filtered and washed with water. The filter cake was dried under vacuum to afford 6-(3-cyano-6,7-dimethoxyquinolin-4-yloxy)-1-naphthoic acid as a light brown solid. MS (ESI, pos. ion) m/z: 401.0 (M+H). Mass Calc'd for $C_{23}H_{16}N_2O_5$: 400.

EXAMPLE 557

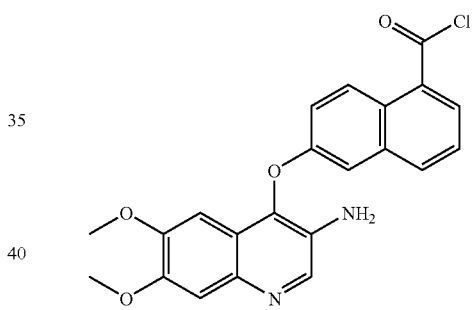

6-(3-amino-6,7-dimethoxyquinolin-4-yloxy)-1-naphthoyl chloride

Step (a) Preparation of 6-(6,7-dimethoxy-3-nitroquinolin-4-yloxy)-1-naphthoic acid A resealable tube was charged with 6-hydroxy-1-naphthoic acid (0.070 g, 0.37 mmol), cesium carbonate (0.364 g, 1.12 mmol), and DMF (2 mL, Aldrich). The system was flushed with argon, the tube was sealed, and the mixture stirred at RT for 15 min. 4-Chloro-6,7-dimethoxy-3-nitroquinoline (prepared by the method described in WO 98/13350) (0.100 g, 0.373 mmol) was added, and the system was again flushed with argon. The tube was sealed and the mixture stirred at RT for 4.5 h. The mixture was diluted with water (2 mL) and 6 N HCl (aq) was added dropwise with stirring until the pH of the solution was 5-6. The resulting precipitate was filtered and washed with water. The filter cake was dried under vacuum to afford 6-(6,7-dimethoxy-3-nitroquinolin-4-yloxy)-1-naphthoic acid as a yellow solid. MS (ESI, pos. ion) m/z: 421.1 (M+H). Mass Calc'd for $C_{22}H_{16}N_2O_7$: 420.

Step (b) Preparation of 6-(3-amino-6,7-dimethoxyquinolin-4-yloxy)-1-naphthoic acid Pd on carbon (5 wt %, 0.015 g) was added to a solution of 6-(6,7-dimethoxy-3-nitroquinolin-4-yloxy)-1-naphthoic acid (0.149 g, 0.354 mmol) in MeOH (30 mL). The system was purged with $H_2$ (g) and stirred under a $H_2$ atmosphere at RT for 21 h to afford a thick suspension. The pH of the reaction was adjusted to 6-7 with 2N NaOH (aq), and Pd on carbon (5 wt %, 0.025 g) was added to the resulting solution. The mixture was purged with $H_2$ then stirred under a $H_2$ atmosphere at RT for 3 days (additional Pd on carbon (5 wt %, 0.025 g) was added after the first and second days). The mixture was filtered through a pad of Celite and the filtrate was concentrated to afford 6-(3-amino-6,7-dimethoxyquinolin-4-yloxy)-1-naphthoic acid as a brown solid. MS (ESI, pos. ion) m/z: 391.1 (M+H). Mass Calc'd for $C_{22}H_{18}N_2O_5$: 390.

Step (c) Preparation of 6-(3-amino-6,7-dimethoxyquinolin-4-yloxy)-1-naphthoyl chloride The title compound was prepared similar to the procedure described in Example 801, Step e.

EXAMPLE 558

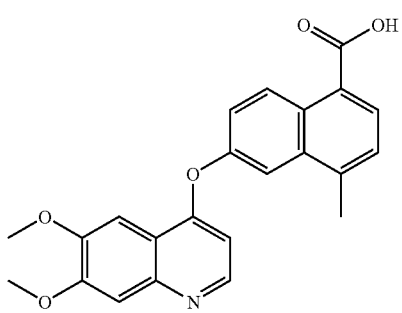

6-(6,7-dimethoxyquinolin-4-yloxy)-4-methyl-1-naphthoic acid

Step (a) Preparation of 6-(benzyloxy)-4-(dibenzylamino)-1-naphthoic acid

A freshly prepared solution of sodium chlorite (16.8 g, 186 mmol) in a 20% aqueous solution of sodium dihydrogen phosphate (155 mL) was added to a solution of 6-(benzyloxy)-4-(dibenzylamino)-1-naphthaldehyde (prepared by the method described in WO 03/014064) (8.50 g, 18.6 mmol) and 2-methyl-2-butene (27.2 g, 41 mL, 387 mmol) in t-butanol (186 mL). The mixture was stirred vigorously at RT for 1 h. The reaction mixture was diluted with a saturated aqueous solution of sodium sulfite (150 mL) and stirred for 15 min. The mixture was concentrated and then partitioned between $CH_2Cl_2$ and water. The aqueous phase was separated and extracted with $CH_2Cl_2$. The combined organic phases were washed with brine, dried over anhydrous sodium sulfate, filtered, and concentrated to afford a tan solid. This material was purified via column chromatography on silica gel (eluting with 0-50% EtOAc-hexane) to afford 6-(benzyloxy)-4-(dibenzylamino)-1-naphthoic acid as an orange brown solid. MS (ESI, pos. ion) m/z: 474.1 (M+H). Mass Calc'd for $C_{32}H_{27}NO_3$: 473.

Step (b) Preparation of Methyl 6-(benzyloxy)-4-(dibenzylamino)-1-naphthoate

Oxalyl chloride (2.60 g, 1.79 mL, 20.5 mmol) was added dropwise to a solution of 6-(benzyloxy)-4-(dibenzylamino)-1-naphthoic acid (3.236 g, 6.834 mmol) in dichloromethane (70 mL) and DMF (1 drop). The mixture stirred at RT for 1 h and was concentrated to afford a yellow solid. $CH_2Cl_2$ (60 mL) was added followed by the dropwise addition of MeOH (10 mL), and the mixture stirred at RT for 45 min. The mixture was concentrated to afford methyl 6-(benzyloxy)-4-(dibenzylamino)-1-naphthoate as a light brown solid. MS (ESI, pos. ion) m/z: 488.2 (M+H). Mass Calc'd for $C_{33}H_{29}NO_3$: 487.

Step (c) Preparation of Methyl-4-amino-6-hydroxy-1-naphthoate

Pd on carbon (5 wt %, 0.350 g) was added to a solution of methyl 6-(benzyloxy)-4-(dibenzylamino)-1-naphthoate (3.409 g, 6.834 mmol) in MeOH (70 mL). The system was evacuated and purged with argon and then stirred under a $H_2$ (g) atmosphere for 20 h. The mixture was filtered through a pad of Celite and concentrated to afford methyl-4-amino-6-hydroxy-1-naphthoate as a light brown solid. MS (ESI, pos. ion) m/z: 218.1 (M+H). Mass Calc'd for $C_{12}H_{11}NO_3$: 217.

Step (d) Preparation of Methyl 6-hydroxy-4-iodo-1-naphthoate

A solution of methyl-4-amino-6-hydroxy-1-naphthoate (0.500 g, 2.30 mmol) in THF (2.5 mL) was cooled to 0° C. and 3 N HCl (5.0 mL) was added. A solution of sodium nitrite (0.175 g, 2.53 mmol) in water (1.2 mL) was added and the mixture stirred at 0° C. for 15 min. A solution of potassium iodide (0.764 g, 4.60 mmol) in water (1.2 ml) was added and the mixture was stirred at 0° C. for 1 h. EtOAc was added and the solution was poured into water. The aqueous phase was separated and extracted with EtOAc. The combined organic phases were washed with brine, dried over anhydrous sodium sulfate, filtered and concentrated to afford a red-brown oil. This material was purified via column chromatography on silica gel (eluting with 0-50% EtOAc-hexane) to afford methyl 6-hydroxy-4-iodo-1-naphthoate as a tan solid. MS (ESI, pos. ion) m/z: 328.8 (M+H). Mass Calc'd for $C_{12}H_9IO_3$: 328.

Step (e) Preparation of Methyl 6-hydroxy-4-methyl-1-naphthoate

A resealable tube was charged with methyl 6-hydroxy-4-iodo-1-naphthoate (0.302 g, 0.920 mmol), toluene (5.0 ml), tetramethyltin (0.40 g, 0.30 mL, 2.2 mmol), and tetrakis (triphenylphosphine)palladium (0) (0.042 g, 0.036 mmol). The system was purged with argon and the tube was sealed. The mixture stirred at 90° C. for 24 h and was cooled to RT. The mixture was partitioned between EtOAc and water. The aqueous phase was separated and extracted with EtOAc. The combined organic phases were washed with brine, dried over anhydrous sodium sulfate, filtered and concentrated to afford an orange solid. This material was purified via column chromatography on silica gel (eluting with 0-50% ethyl acetate-hexane) to afford methyl 6-hydroxy-4-methyl-1-naphthoate as an orange brown solid. MS (ESI, pos. ion) m/z: 217.1 (M+H). Mass Calc'd for $C_{13}H_{12}O_3$: 216.

Step (f) Preparation of 6-(6,7-dimethoxyquinolin-4-yloxy)-4-methyl-1-naphthoic acid A resealable tube was charged with methyl 6-hydroxy-4-methyl-1-naphthoate (0.087 g, 0.402 mmol), cesium carbonate (0.393 g, 1.21 mmol), and DMF (2 mL). The system was flushed with argon, the tube was sealed, and the mixture stirred at RT for 15 min. 4-Chloro-6,7-dimethoxyquinoline (0.090 g, 0.40 mmol) was added, and the system was again flushed with argon. The tube was sealed and the mixture stirred at 100° C. for 18 h. Additional cesium carbonate (0.393 g, 1.21 mmol) was added and the system was again flushed with argon. The tube was sealed and the mixture stirred at 100° C. for 16 h. The mixture was partitioned between $CH_2Cl_2$ and water. The aqueous phase was separated and extracted with $CH_2Cl_2$. The aqueous phase was acidified to pH 5-6 with 6 N HCl (aq). The resulting precipitate was filtered and washed with water. The filter cake was dried under vacuum to afford 6-(6,7-dimethoxyquinolin-4-yloxy)-4-methyl-1-naphthoic acid as a light brown solid. MS (ESI, pos. ion) m/z: 390.1 (M+H). Mass Calc'd for $C_{23}H_{19}NO_5$: 389.

EXAMPLE 559

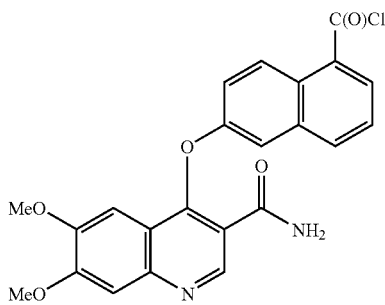

6-(3-carbamoyl-6,7-dimethoxyquinolin-4-yloxy)-1-naphthoyl chloride

Step (a) Preparation of 3-iodo-6,7-dimethoxyquinolin-4(1H)-one

A solution of iodine (14.84 g, 58.48 mmol) in KI (20% aq, 100 mL) was added to a solution of 6,7-dimethoxyquinolin-4(1H)-one (10.00 g, 48.73 mmol) in 2 N NaOH (aq, 100 mL), and the solution stirred at RT for 17 h. The mixture was acidified with AcOH and the resulting dark purple mixture was filtered and washed with water. The dark purple filter cake was recrystallized from water to afford an off-white suspension. This material was filtered and dried to afford 3-iodo-6,7-dimethoxyquinolin-4(1H)-one as an off-white solid. MS (ESI, pos. ion) m/z: 332.1 (M+H). Mass Calc'd for $C_{11}H_{10}INO_3$: 331.

Step (b) Preparation of 4-chloro-3-iodo-6,7-dimethoxyquinoline

Phosphorus oxychloride (6.743 g, 4.100 mL, 43.98 mmol) was added to a solution of 3-iodo-6,7-dimethoxyquinolin-4(1H)-one (13.237 g, 39.98 mmol) in DMF (100 mL). The mixture was stirred at 100° C. for 2 h then cooled to RT. The mixture was poured into ice water and the resulting precipitate was filtered and dried to afford 4-chloro-3-iodo-6,7-dimethoxyquinoline as a light brown solid. MS (ESI, pos. ion) m/z: 349.9 (M+H). Mass Calc'd for $C_{11}H_9ClINO_2$: 349.

Step (c) Preparation of 4-chloro-6,7-dimethoxyquinoline-3-carboxamide

A stainless steel cylinder was charged with 4-chloro-3-iodo-6,7-dimethoxyquinoline (0.200 g, 0.572 mmol), palladium (II) acetate (0.013 g, 0.057 mmol), 1,3-bis(diphenylphosphino)propane (0.047 g, 0.11 mmol), DMF (2 mL), and 1,1,1,3,3,3-hexamethyldisilazane S (0.37 g, 0.48 mL, 2.3 mmol). The cylinder was sealed and pressurized with CO gas at 30 psi. The system was heated at 100° C. for 1.5 h and then cooled to RT. The mixture was concentrated to afford an orange solid. This material was triturated with dichloromethane and the resulting precipitate was filtered and dried to afford 4-chloro-6,7-dimethoxyquinoline-3-carboxamide as an off-white solid. MS (ESI, pos. ion) m/z: 267.0 (M+H). Mass Calc'd for $Cl_2H_{11}ClN_2O_3$: 266.

Step (d) Preparation of 6-(3-carbamoyl-6,7-dimethoxyquinolin-4-yloxy)-1-naphthoic acid A resealable tube was charged with 6-hydroxy-1-naphthoic acid (0.035 g, 0.187 mmol), cesium carbonate (0.183 g, 0.561 mmol), and DMF (1.0 mL). The system was flushed with argon, the tube was sealed, and the mixture stirred at RT for 15 min. 4-Chloro-6,7-dimethoxyquinoline-3-carboxamide (0.050 g, 0.187 mmol) mL) was added (along with a 1 mL DMF rinse), and the system was again flushed with argon. The tube was sealed and the mixture stirred at 60° C. for 26 h. The reaction mixture was diluted with water (2.5 mL) and 6 N HCl (aq) was added dropwise with stirring until the pH of the solution was 5-6. The resulting precipitate was filtered and washed with water. The filter cake was dried under vacuum to afford 6-(3-carbamoyl-6,7-dimethoxyquinolin-4-yloxy)-1-naphthoic acid as a tan solid. MS (ESI, pos. ion) m/z: 419.0 (M+H). Mass Calc'd for $C_{23}H_{18}N_2O_6$: 418.

Step (e) Preparation of 6-(3-carbamoyl-6,7-dimethoxyquinolin-4-yloxy)-1-naphthoyl chloride The title compound was prepared similar to the procedure described in Example 682, Step b.

EXAMPLE 560

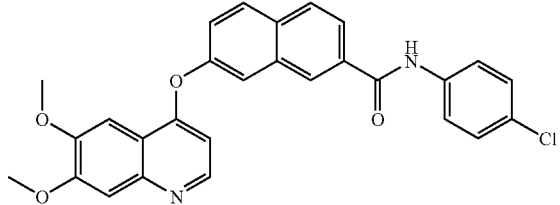

7-((6,7-bis(methoxy)-4-quinolinyl)oxy)-N-(4-chlorophenyl)-2-naphthalenecarboxamide A slurry of 7-(6,7-dimethoxyquinolin-4-yloxy)-2-naphthoic acid (0.54 g, 1.44 mmol) in 10 mL of $C_2O_2Cl_2$ and 2 drops of DMF was stirred at RT. After 2 h, the solution was concentrated to dryness and placed under high vacuum overnight. A portion of the crude residue (0.075 g, 0.191 mmol) was dissolved in 1 mL of $CH_2Cl_2$. To the resulting solution was added $Et_3N$ (0.106 mL, 0.76 mmol), 4-chloroaniline (0.036 g, 0.286 mmol) and a catalytic amount of DMAP. The reaction was stirred under a nitrogen atmosphere for 16 h. The reaction was diluted with $CH_2Cl_2$, washed with saturated aqueous $NaHCO_3$, and brine. The organic layer was dried ($MgSO_4$), filtered and concentrated. The residue was passed through a medium-pressure silica gel column (solvent gradient: 95:5 $CH_2Cl_2$:MeOH; 90:10 $CH_2Cl_2$:MeOH) to afford the desired crude compound. The fractions were concentrated to dryness to afford a solid residue. The residue was triturated with $Et_2$O/Hexanes to afford the desired compound as a pale yellow solid. MS (ESI, pos. ion) m/z: 485.0 (M+1). Mass Calc'd for $C_{28}H_{21}ClN_2O_4$: 484.937.

The following examples were prepared using that described for Example 560.

| Example No. | Structure & Name | Mol Formula | Mass | M + H |
|---|---|---|---|---|
| 561 | 7-((6,7-bis(methoxy)-4-quinolinyl)oxy)-N-(4-(1,1-dimethylethyl)phenyl)-2-naphthalenecarboxamide | $C_{32}H_{30}N_2O_4$ | 506.60 | 507.1 |
| 562 | 7-((6,7-bis(methoxy)-4-quinolinyl)oxy)-N-cyclopropyl-2-naphthalenecarboxamide | $C_{25}H_{22}N_2O_4$ | 414.46 | 415.1 |
| 563 | 7-((6,7-bis(methoxy)-4-quinolinyl)oxy)-N-(2-(methoxy)ethyl)-2-naphthalenecarboxamide | $C_{25}H_{24}N_2O_5$ | 432.47 | 433.1 |

| Example No. | Structure & Name | Mol Formula | Mass | M + H |
|---|---|---|---|---|
| 564 | 7-((6,7-bis(methoxy)-4-quinolinyl)oxy)-N-(3-methyl-4-(1-methylethyl)phenyl)-2-naphthalenecarboxamide | $C_{32}H_{30}N_2O_4$ | 506.6 | 507.1 |
| 565 | 7-((6,7-bis(methoxy)-4-quinolinyl)oxy)-N-(4-((trifluoromethyl)oxy)phenyl)-2-naphthalenecarboxamide | $C_{29}H_{21}F_3N_2O_5$ | 534.49 | 535.0 |
| 566 | 7-((6,7-bis(methoxy)-4-quinolinyl)oxy)-N-(3-(methoxy)phenyl)-2-naphthalenecarboxamide | $C_{29}H_{24}N_2O_5$ | 480.52 | 481.1 |
| 567 | 7-((6,7-bis(methoxy)-4-quinolinyl)oxy)-N-(3-isoxazolyl)-2-naphthalenecarboxamide | $C_{25}H_{19}N_3O_5$ | 441.44 | 442.0 |

| Example No. | Structure & Name | Mol Formula | Mass | M + H |
|---|---|---|---|---|
| 568 | 7-((6,7-bis(methoxy)-4-quinolinyl)oxy)-N-(3-fluorophenyl)-2-naphthalenecarboxamide | $C_{28}H_{21}FN_2O_4$ | 468.48 | 469.1 |
| 569 | 7-((6,7-bis(methoxy)-4-quinolinyl)oxy)-N-(3-pyridinyl)-2-naphthalenecarboxamide | $C_{27}H_{21}N_3O_4$ | 451.48 | 452.1 |
| 570 | 7-((6,7-bis(methoxy)-4-quinolinyl)oxy)-N-(1,3-thiazol-2-yl)-2-naphthalenecarboxamide | $C_{25}H_{19}N_3O_4S$ | 457.51 | 458.0 |
| 571 | 7-((6,7-bis(methoxy)-4-quinolinyl)oxy)-N-(3-((trifluoromethyl)oxy)phenyl)-2-naphthalenecarboxamide | $C_{29}H_{21}F_3N_2O_5$ | 534.49 | 535 |

| Example No. | Structure & Name | Mol Formula | Mass | M + H |
|---|---|---|---|---|
| 572 | 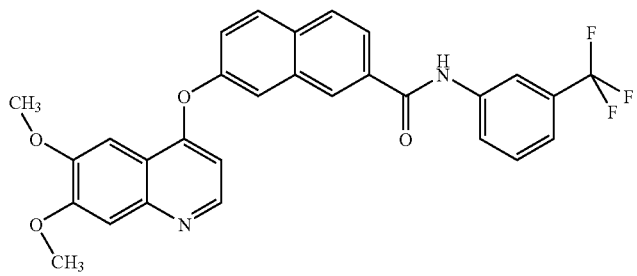
7-((6,7-bis(methoxy)-4-quinolinyl)oxy)-N-(3-(trifluoromethyl)phenyl)-2-naphthalenecarboxamide | $C_{29}H_{21}F_3N_2O_4$ | 518.49 | 519.0 |
| 573 | 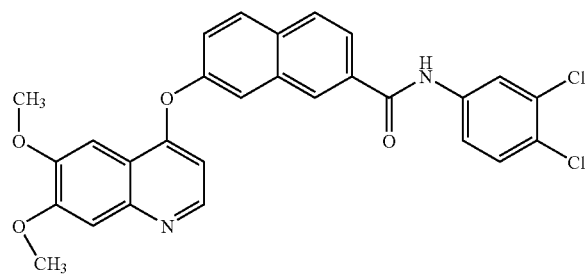
7-((6,7-bis(methoxy)-4-quinolinyl)oxy)-N-(3,4-dichlorophenyl)-2-naphthalenecarboxamide | $C_{28}H_{20}Cl_2N_2O_4$ | 519.38 | 520.9 |
| 574 | 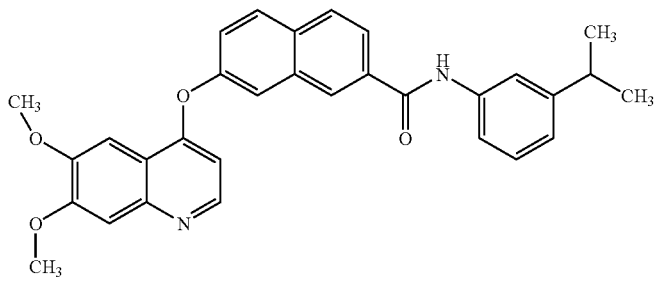
7-((6,7-bis(methoxy)-4-quinolinyl)oxy)-N-(3-(1-methylethyl)phenyl)-2-naphthalenecarboxamide | $C_{31}H_{28}N_2O_4$ | 492.57 | 493.1 |
| 575 | 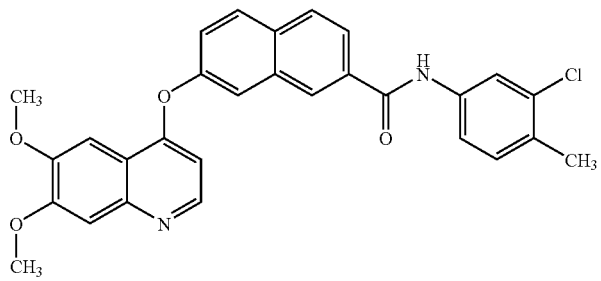
7-((6,7-bis(methoxy)-4-quinolinyl)oxy)-N-(3-chloro-4-methylphenyl)-2-naphthalenecarboxamide | $C_{29}H_{23}ClN_2O_4$ | 498.96 | 499.0 |

| Example No. | Structure & Name | Mol Formula | Mass | M + H |
|---|---|---|---|---|
| 576 | 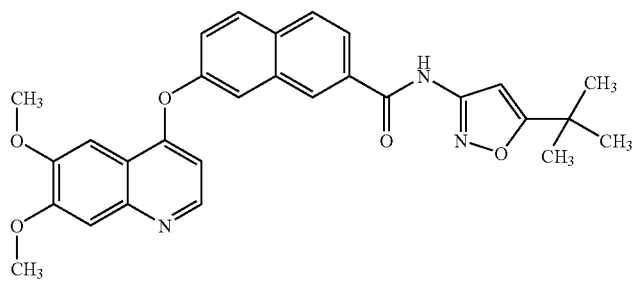<br>7-((6,7-bis(methoxy)-4-quinolinyl)oxy)-N-(5-(1,1-dimethylethyl)-3-isoxazolyl)-2-naphthalenecarboxamide | $C_{29}H_{27}N_{23}O_5$ | 497.55 | 498.1 |
| 577 | 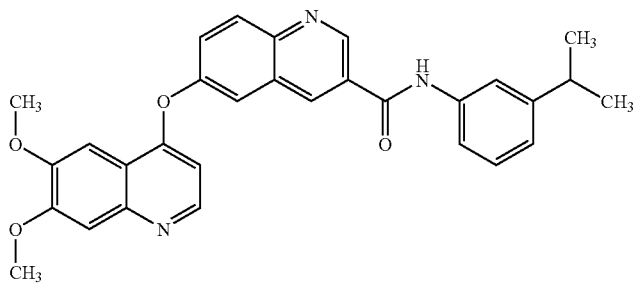<br>6-((6,7-bis(methoxy)-4-quinolinyl)oxy)-N-(3-(1-methylethyl)phenyl)-3-quinolinecarboxamide | $C_{30}H_{27}N_3O_4$ | 493.56 | 494.2 |
| 578 | 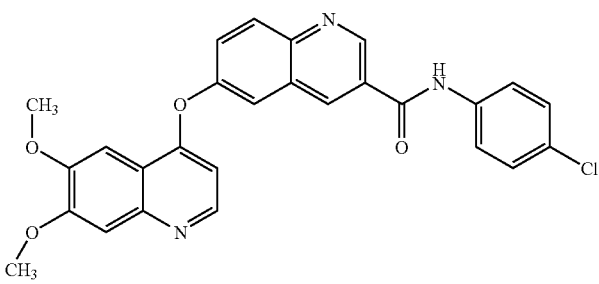<br>6-((6,7-bis(methoxy)-4-quinolinyl)oxy)-N-(4-chlorophenyl)-3-quinolinecarboxamide | $C_{27}H_{20}ClN_3O_4$ | 485.93 | 486.1 |
| 579 | 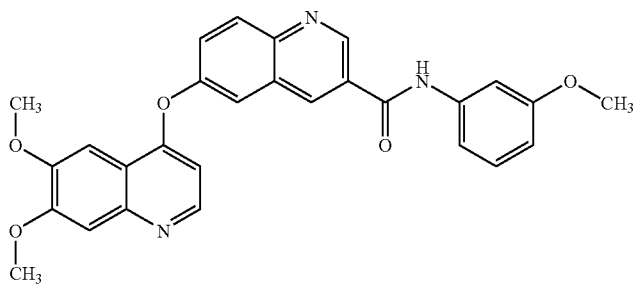<br>6-((6,7-bis(methoxy)-4-quinolinyl)oxy)-N-(3-(methoxy)phenyl)-3-quinolinecarboxamide | $C_{28}H_{23}N_3O_5$ | 481.51 | 482.2 |

| Example No. | Structure & Name | Mol Formula | Mass | M + H |
|---|---|---|---|---|
| 580 | 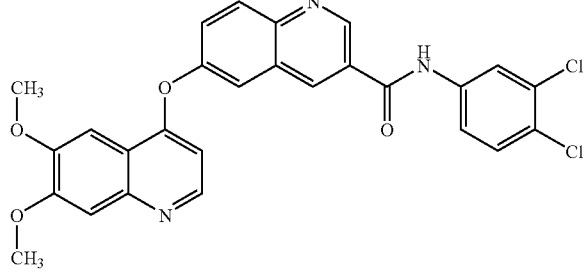<br>6-((6,7-bis(methoxy)-4-quinolinyl)oxy)-N-(3,4-dichlorophenyl)-3-quinolinecarboxamide | $C_{27}H_{19}Cl_2N_3O_4$ | 520.37 | 521.2 |
| 581 | 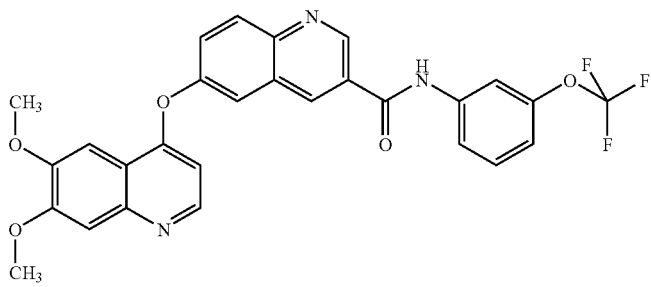<br>6-((6,7-bis(methoxy)-4-quinolinyl)oxy)-N-(3-((trifluoromethyl)oxy)phenyl)-3-quinolinecarboxamide | $C_{28}H_{20}F_3N_3O_5$ | 535.48 | 536.2 |
| 582 | 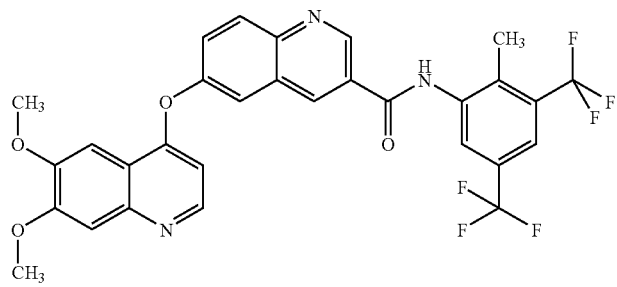<br>6-((6,7-bis(methoxy)-4-quinolinyl)oxy)-N-(2-methyl-3,5-bis(trifluoromethyl)phenyl)-3-quinolinecarboxamide | $C_{30}H_{21}F_6N_3O_4$ | 601.50 | 602.1 |
| 583 | 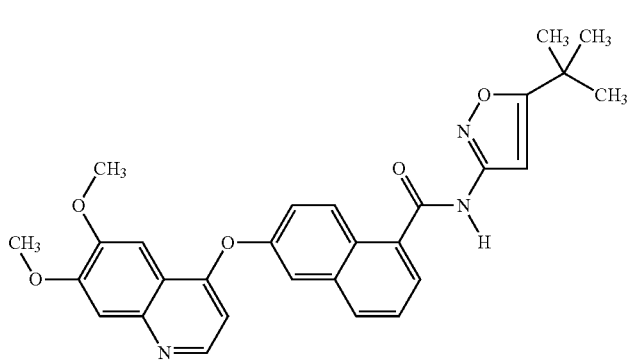<br>6-((6,7-bis(methoxy)-4-quinolinyl)oxy)-N-(5-(1,1-dimethylethyl)-3-isoxazolyl)-1-naphthalenecarboxamide | $C_{29}H_{27}N_3O_5$ | 497.55 | 49 |

-continued
| Example No. | Structure & Name | Mol Formula | Mass | M + H |
|---|---|---|---|---|
| 584 | 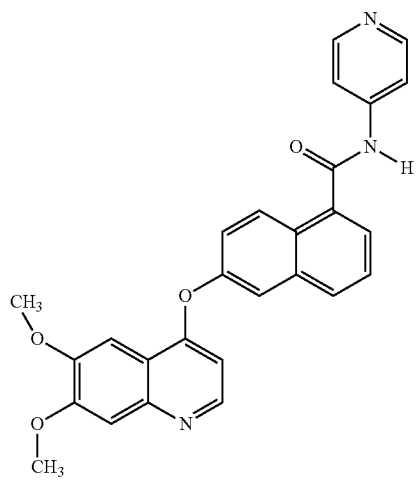<br>6-((6,7-bis(methoxy)-4-quinolinyl)oxy)-N-(4-pyridinyl)-1-naphthalenecarboxamide | $C_{27}H_{21}N_3O_4$ | 451.48 | 452.1 |
| 585 | 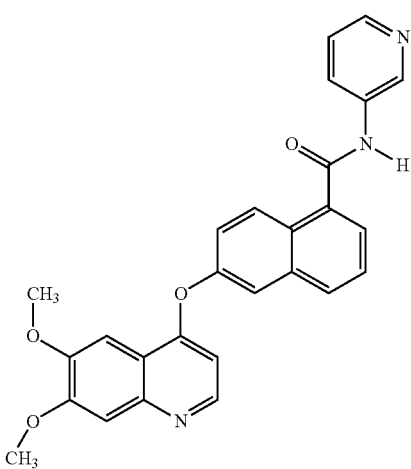<br>6-((6,7-bis(methoxy)-4-quinolinyl)oxy)-N-(3-pyridinyl)-1-naphthalenecarboxamide | $C_{27}H_{21}N_3O_4$ | 451.48 | 452.1 |
| 586 | 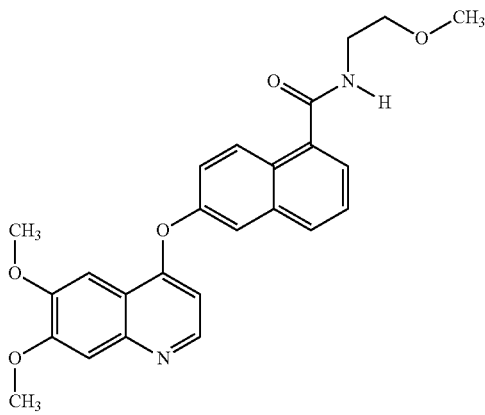<br>6-((6,7-bis(methoxy)-4-quinolinyl)oxy)-N-(2-(methoxy)ethyl)-1-naphthalenecarboxamide | $C_{25}H_{24}N_2O_5$ | 432.47 | 433.1 |

| Example No. | Structure & Name | Mol Formula | Mass | M + H |
|---|---|---|---|---|
| 587 | 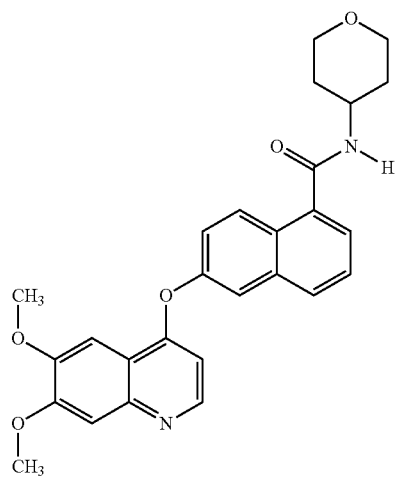<br>6-((6,7-bis(methoxy)-4-quinolinyl)oxy)-N-tetrahydro-2H-pyran-4-yl-1-naphthalenecarboxamide | $C_{27}H_{26}N_2O_5$ | 458.51 | 459.1 |
| 588 | 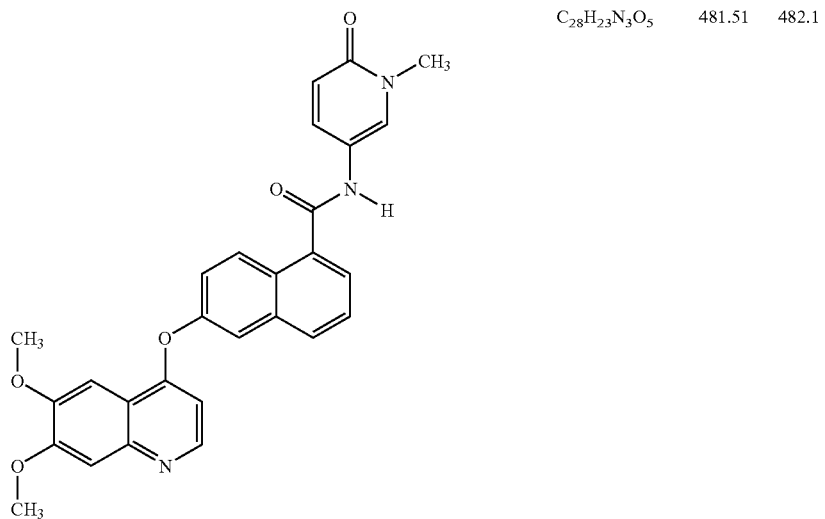<br>6-((6,7-bis(methoxy)-4-quinolinyl)oxy)-N-(1-methyl-6-oxo-1,6-dihydro-3-pyridinyl)-1-naphthalenecarboxamide | $C_{28}H_{23}N_3O_5$ | 481.51 | 482.1 |

| Example No. | Structure & Name | Mol Formula | Mass | M + H |
|---|---|---|---|---|
| 589 | 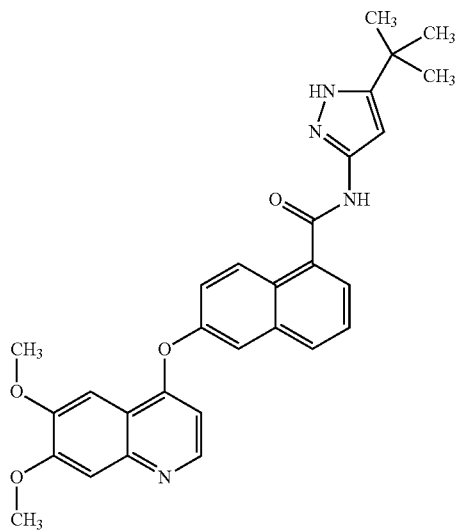<br>6-((6,7-bis(methoxy)-4-quinolinyl)oxy)-N-(5-(1,1-dimethylethyl)-1H-pyrazol-3-yl)-1-naphthalenecarboxamide | $C_{29}H_{28}N_4O_4$ | 496.56 | 497.2 |
| 590 | 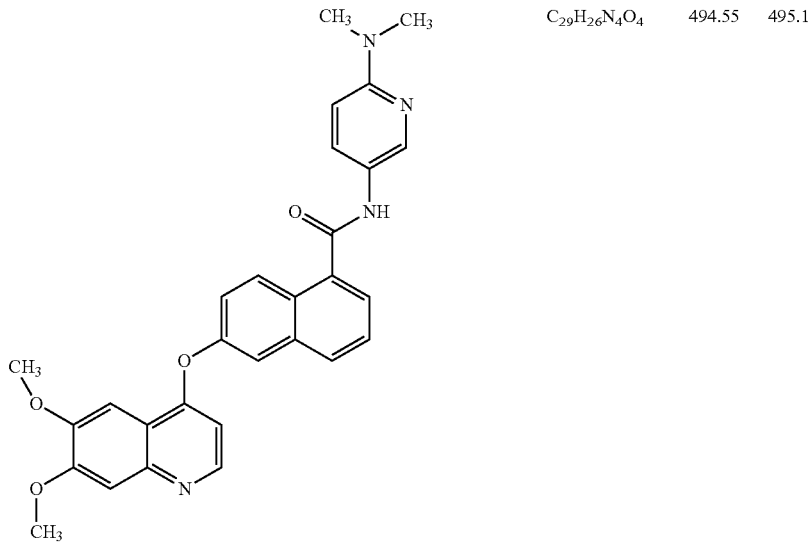<br>6-((6,7-bis(methoxy)-4-quinolinyl)oxy)-N-(6-(dimethylamino)-3-pyridinyl)-1-naphthalenecarboxamide | $C_{29}H_{26}N_4O_4$ | 494.55 | 495.1 |

| Example No. | Structure & Name | Mol Formula | Mass | M + H |
|---|---|---|---|---|
| 591 | 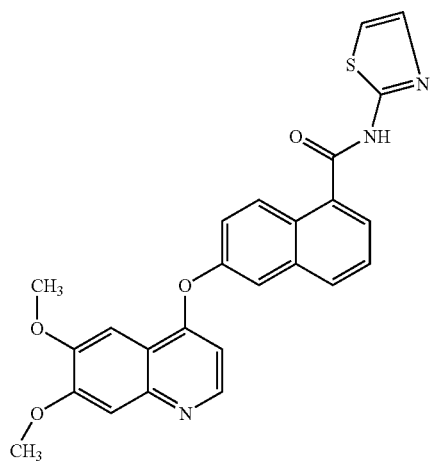<br>6-((6,7-bis(methoxy)-4-quinolinyl)oxy)-N-(1,3-thiazol-2-yl)-1-naphthalenecarboxamide | $C_{25}H_{19}N_3O_4S$ | 457.51 | 458 |
| 592 | 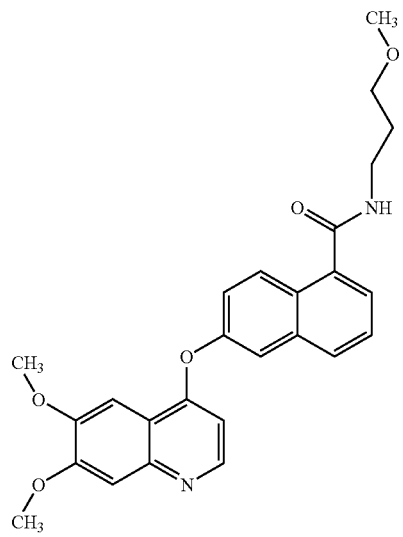<br>6-((6,7-bis(methoxy)-4-quinolinyl)oxy)-N-(3-(methoxy)propyl)-1-naphthalenecarboxamide | $C_{26}H_{26}N_2O_5$ | 446.5 | 477.1 |

| Example No. | Structure & Name | Mol Formula | Mass | M + H |
|---|---|---|---|---|
| 593 | 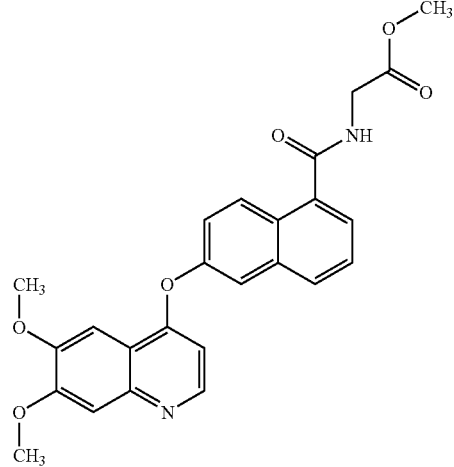<br>methyl N-((6-((6,7-bis(methoxy)-4-quinolinyl)oxy)-1-naphthalenyl)carbonyl)glycinate | $C_{25}H_{22}N_2O_6$ | 446.46 | 447.1 |
| 594 | 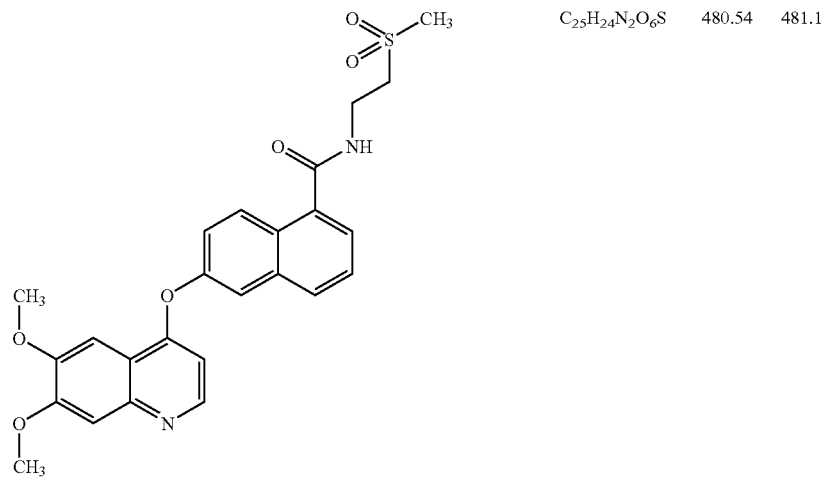<br>6-((6,7-bis(methoxy)-4-quinolinyl)oxy)-N-(2-(methylsulfonyl)ethyl)-1-naphthalenecarboxamide | $C_{25}H_{24}N_2O_6S$ | 480.54 | 481.1 |

| Example No. | Structure & Name | Mol Formula | Mass | M + H |
|---|---|---|---|---|
| 595 | 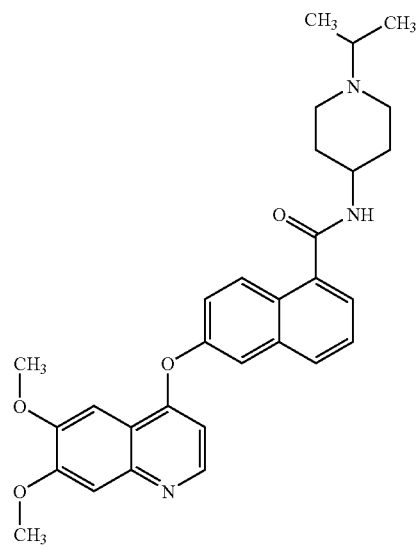<br>6-((6,7-bis(methoxy)-4-quinolinyl)oxy)-N-(1-(1-methylethyl)-4-piperidinyl)-1-naphthalenecarboxamide | $C_{30}H_{33}N_3O_4$ | 499.61 | 500.2 |
| 596 | 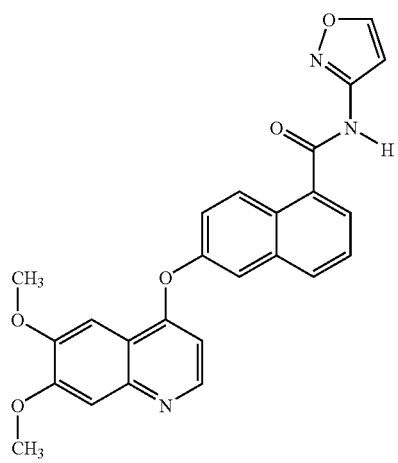<br>6-((6,7-bis(methoxy)-4-quinolinyl)oxy)-N-(3-isoxazolyl)-1-naphthalenecarboxamide | $C_{25}H_{19}N_3O_5$ | 441.44 | 442.1 |

| Example No. | Structure & Name | Mol Formula | Mass | M + H |
|---|---|---|---|---|
| 597 | 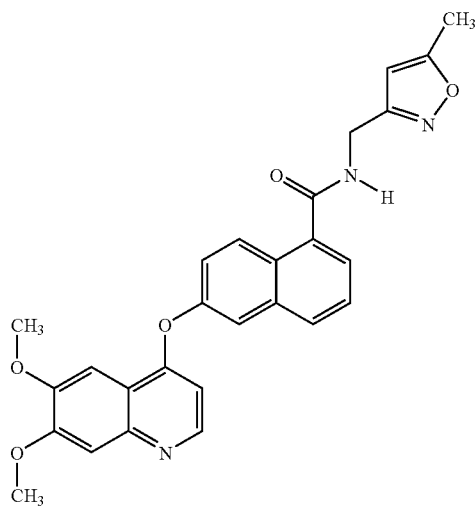<br>6-((6,7-bis(methoxy)-4-quinolinyl)oxy)-N-((5-methyl-3-isoxazolyl)methyl)-1-naphthalenecarboxamide | $C_{27}H_{23}N_3O_5$ | 469.5 | 470.1 |
| 598 | 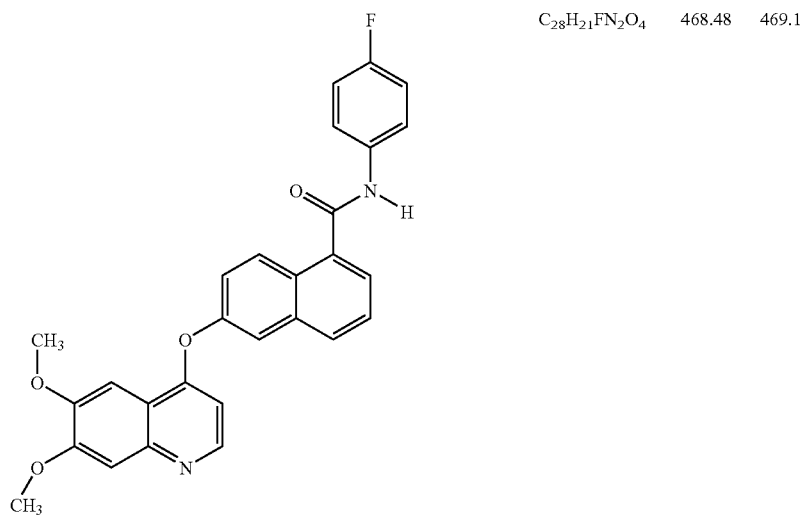<br>6-((6,7-bis(methoxy)-4-quinolinyl)oxy)-N-(4-fluorophenyl)-1-naphthalenecarboxamide | $C_{28}H_{21}FN_2O_4$ | 468.48 | 469.1 |

-continued
| Example No. | Structure & Name | Mol Formula | Mass | M + H |
|---|---|---|---|---|
| 599 | 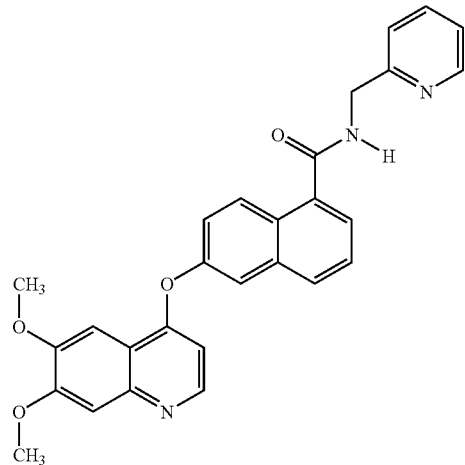<br>6-((6,7-bis(methoxy)-4-quinolinyl)oxy)-N-(2-pyridinylmethyl)-1-naphthalenecarboxamide | C$_{28}$H$_{23}$N$_3$O$_4$ | 465.51 | 466.2 |
| 600 | 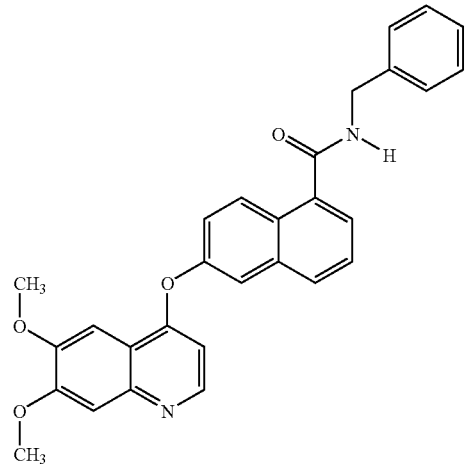<br>6-((6,7-bis(methoxy)-4-quinolinyl)oxy)-N-(phenylmethyl)-1-naphthalenecarboxamide | C$_{29}$H$_{24}$N$_2$O$_4$ | 464.52 | 46 |

| Example No. | Structure & Name | Mol Formula | Mass | M + H |
|---|---|---|---|---|
| 601 | 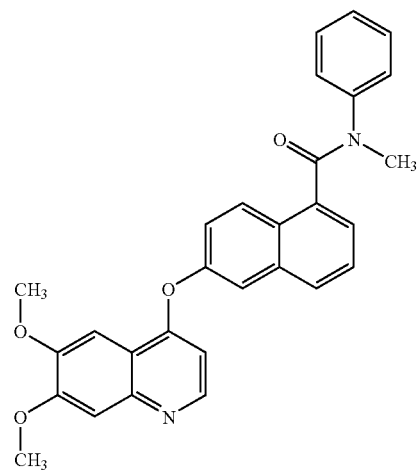 6-((6,7-bis(methoxy)-4-quinolinyl)oxy)-N-methyl-N-phenyl-1-naphthalenecarboxamide | C<sub>29</sub>H<sub>24</sub>N<sub>2</sub>O<sub>4</sub> | 464.52 | 465.2 |
| 602 | 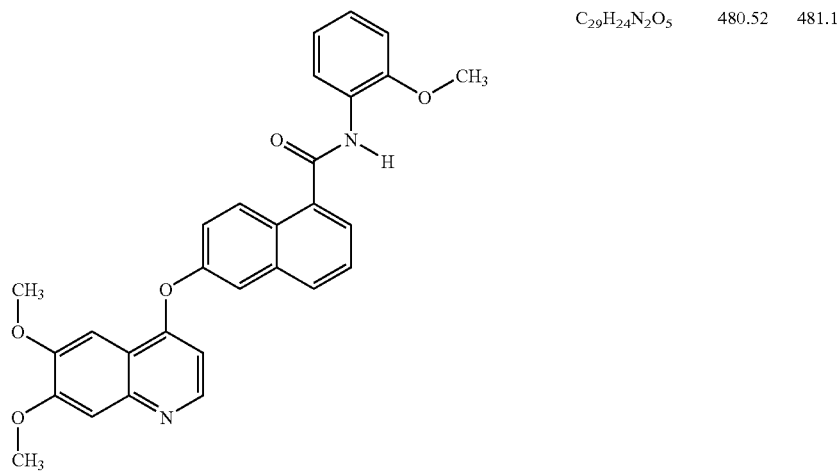 6-((6,7-bis(methoxy)-4-quinolinyl)oxy)-N-(2-(methoxy)phenyl)-1-naphthalenecarboxamide | C<sub>29</sub>H<sub>24</sub>N<sub>2</sub>O<sub>5</sub> | 480.52 | 481.1 |

-continued
| Example No. | Structure & Name | Mol Formula | Mass | M + H |
|---|---|---|---|---|
| 603 | 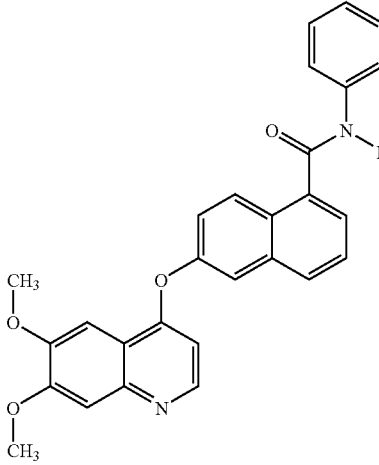<br>6-((6,7-bis(methoxy)-4-quinolinyl)oxy)-N-(3-chlorophenyl)-1-naphthalenecarboxamide | $C_{28}H_{21}ClN_2O_4$ | 484.94 | 485.1 |
| 604 | 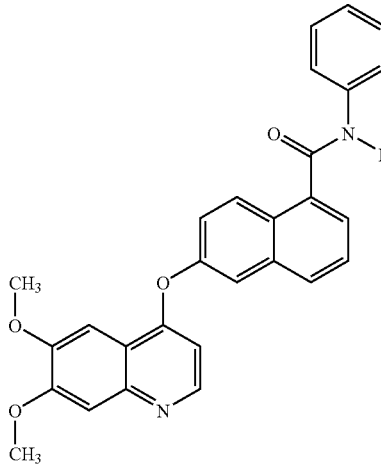<br>6-((6,7-bis(methoxy)-4-quinolinyl)oxy)-N-(3-fluorophenyl)-1-naphthalenecarboxamide | $C_{28}H_{21}FN_2O_4$ | 468.48 | 469.1 |
| 605 | 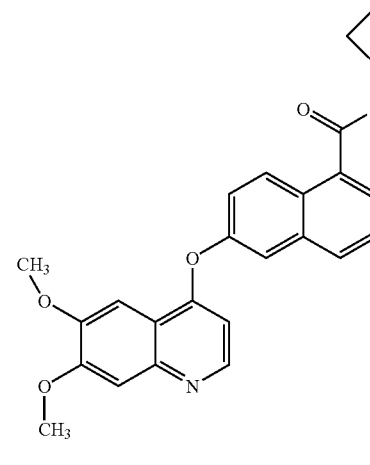<br>6-((6,7-bis(methoxy)-4-quinolinyl)oxy)-N-cyclobutyl-1-naphthalenecarboxamide | $C_{26}H_{24}N_2O_4$ | 428.49 | 429.1 |

| Example No. | Structure & Name | Mol Formula | Mass | M + H |
|---|---|---|---|---|
| 606 | 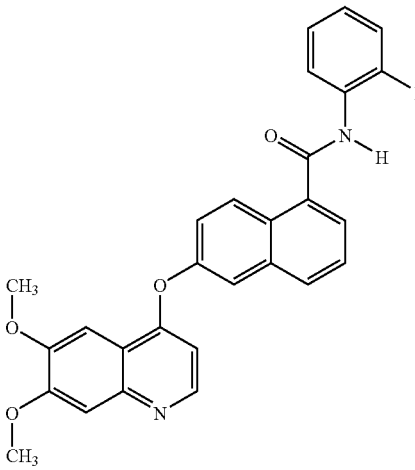<br>6-((6,7-bis(methoxy)-4-quinolinyl)oxy)-N-(2-fluorophenyl)-1-naphthalenecarboxamide | $C_{28}H_{21}FN_2O_4$ | 468.48 | 469 |
| 607 | 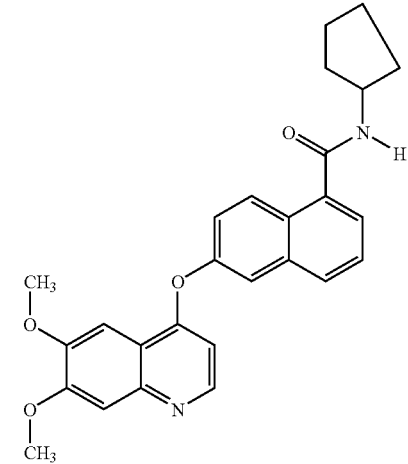<br>6-((6,7-bis(methoxy)-4-quinolinyl)oxy)-N-cyclopentyl-1-naphthalenecarboxamide | $C_{27}H_{26}N_2O_4$ | 442.51 | 443.1 |
| 608 | 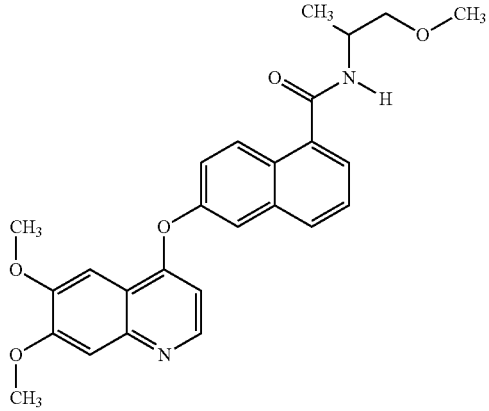<br>6-((6,7-bis(methoxy)-4-quinolinyl)oxy)-N-((R,S)-1-methyl-2-(methoxy)ethyl)-1-naphthalenecarboxamide | $C_{26}H_{26}N_2O_5$ | 446.5 | 447.1 |

-continued

| Example No. | Structure & Name | Mol Formula | Mass | M + H |
|---|---|---|---|---|
| 609 | 6-((6,7-bis(methoxy)-4-quinolinyl)oxy)-N,N-dipropyl-1-naphthalenecarboxamide | $C_{28}H_{30}N_2O_4$ | 458.56 | 459.2 |
| 610 | 6-((6,7-bis(methoxy)-4-quinolinyl)oxy)-N-(2-pyridinyl)-1-naphthalenecarboxamide | $C_{27}H_{21}N_3O_4$ | 451.48 | 452.1 |

The following examples were prepared similar to the procedures described in Example 560 and purified by column chromatography and/or crystallization.

| Example No. | Structure & Name | Mol Formula | Mass | M + H |
|---|---|---|---|---|
| 611 | 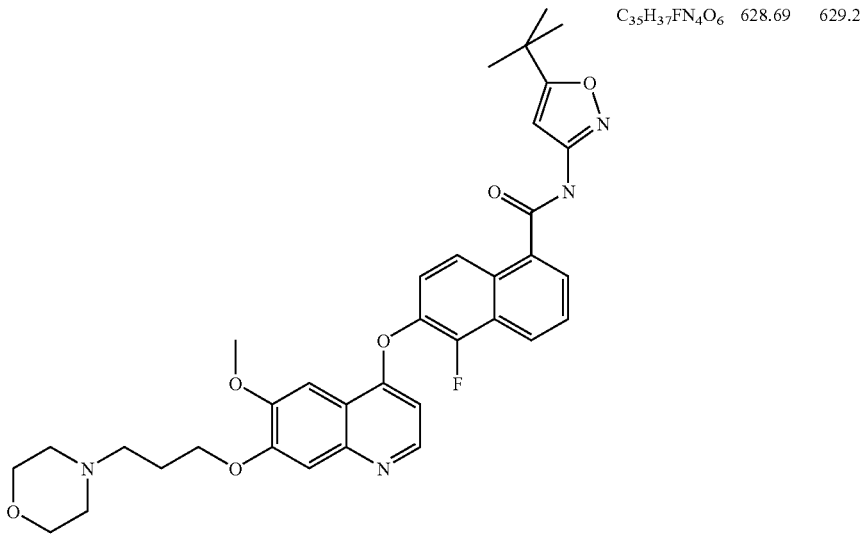<br>N-(5-(1,1-dimethylethyl)-3-isoxazolyl)-5-fluoro-6-((6-(methoxy)-7-((3-(4-morpholinyl)propyl)oxy)-4-quinolinyl)oxy)-1-naphthalenecarboxamide | $C_{35}H_{37}FN_4O_6$ | 628.69 | 629.2 |

EXAMPLE 612

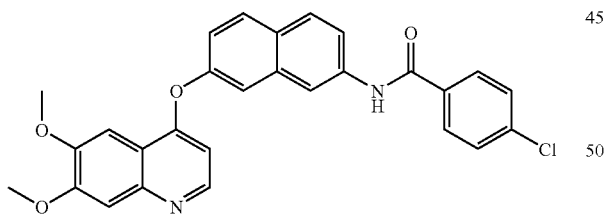

N-(7-((6,7-bis(methoxy) 4-quinolinyl)oxy)-2-naphthalenyl)-4-chlorobenzamide

Step (a) Preparation of 7-(6,7-dimethoxyquinolin-4-yloxy)naphthalen-2-amine

To a solution of 7-(6,7-dimethoxyquinolin-4-yloxy)naphthalen-2-yl trifluoromethanesulfonate (0.825 g, 1.72 mmol) in THF (30 mL), was added Pd(OAc)$_2$ (0.039, 0.17 mmol), followed by BINAP (0.1187 g, 0.19 mmol) and Cs$_2$CO$_3$ (0.784 g, 2.41 mmol). Diphenylmethanimine was added and the mixture was stirred at 65° C. for 16 h. The reaction was cooled to RT, treated with 1N HCl (12 mL) and stirred for 4 h. The mixture was diluted with water and extracted with EtOAc 3×. The aqueous extract was treated with NH$_4$OH until pH=12. This was extracted with EtOAc 3×. The combined organic layers were washed with water and brine, dried over MgSO$_4$, filtered and concentrated in vacuo. The crude material was taken on directly without purification. MS (ESI, pos. ion) m/z: 347.4 (M+1).

Step (b) Preparation of N-(7-((6,7-bis(methoxy)-4-quinolinyl)oxy)-2-naphthalenyl)-4-chlorobenzamide To a solution of 7-(6,7-dimethoxyquinolin-4-yloxy)naphthalen-2-amine (0.110 g, 0.31 mmol) in 10 ml of CH$_2$Cl$_2$ was added K$_2$CO$_3$ (0.086 g, 0.62 mmol). The mixture was cooled to 0° C. and 4-chlorobenzoyl chloride (44 mL, 0.34 mmol) was added. The solution was stirred for 16 h and allowed to gradually warm up to RT. The reaction was diluted with water and extracted with EtOAc 3×. The organic layer was dried (Na$_2$SO$_4$), filtered and concentrated. The residue was purified using a Gilson Prep HPLC system. The fractions were collected, combined, and extracted with EtOAc 3×. The organic layer was dried (Na$_2$SO$_4$), filtered and concentrated to afford the desired compound. MS (ESI, pos. ion) m/z: 485.0 (M+1). Mass Calc'd for C$_{29}$H$_{21}$ClN$_2$O$_4$: 484.937.

The following examples were prepared similar to the procedures described in Example 612.

| Example No. | Structure & Name | Mol Formula | Mass | M + H |
|---|---|---|---|---|
| 613 | 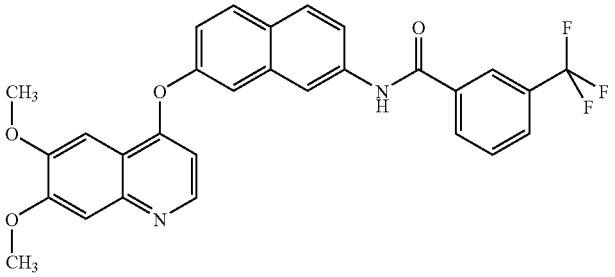<br>N-(7-((6,7-bis(methoxy)-4-quinolinyl)oxy)-2-naphthalenyl)-3-(trifluoromethyl)benzamide | $C_{29}H_{21}F_3N_2O_4$ | 518.49 | 519.1 |
| 614 | 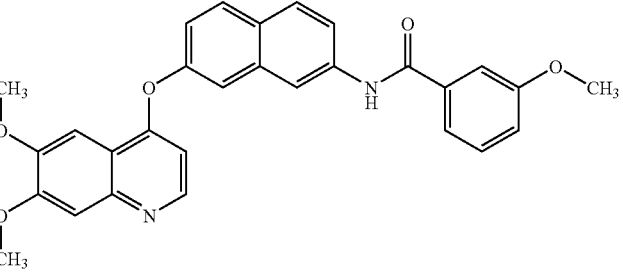<br>N-(7-((6,7-bis(methoxy)-4-quinolinyl)oxy)-2-naphthalenyl)-3-(methoxy)benzamide | $C_{29}H_{24}N_2O_5$ | 480.52 | 481.1 |
| 615 | 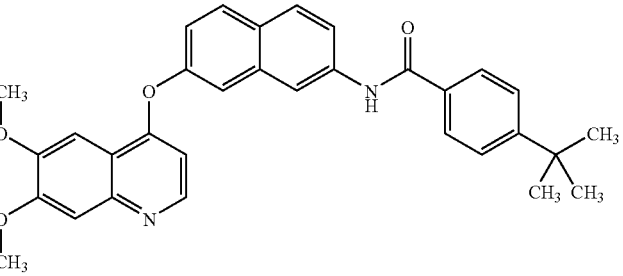<br>N-(7-((6,7-bis(methoxy)-4-quinolinyl)oxy)-2-naphthalenyl)-4-(1,1-dimethylethyl)benzamide | $C_{32}H_{30}N_2O_4$ | 506.6 | 507.2 |
| 616 | 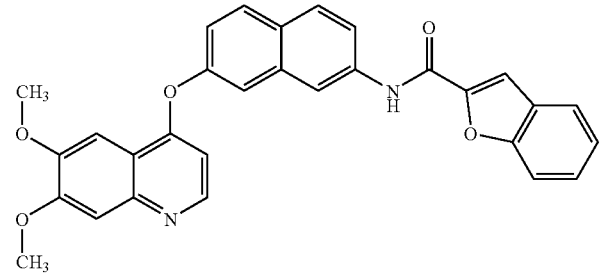<br>N-(7-((6,7-bis(methoxy)-4-quinolinyl)oxy)-2-naphthalenyl)-1-benzofuran-2-carboxamide | $C_{30}H_{22}N_2O_5$ | 490.51 | 491.1 |

-continued

| Example No. | Structure & Name | Mol Formula | Mass | M + H |
|---|---|---|---|---|
| 617 | 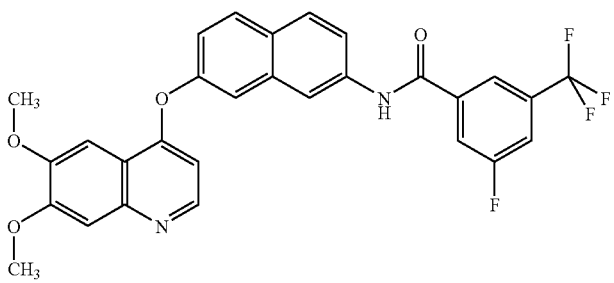<br>N-(7-((6,7-bis(methoxy)-4-quinolinyl)oxy)-2-naphthalenyl)-3-fluoro-5-(trifluoromethyl)benzamide | $C_{29}H_{20}F_4N_2O_4$ | 536.48 | 537.1 |
| 618 | 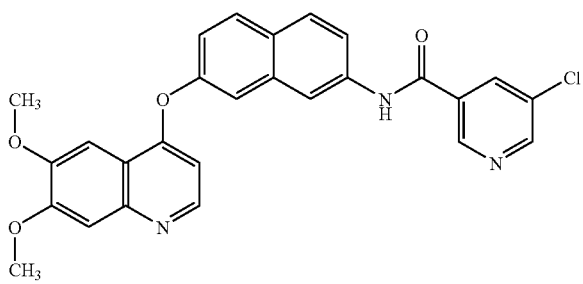<br>N-(7-((6,7-bis(methoxy)-4-quinolinyl)oxy)-2-naphthalenyl)-5-chloro-3-pyridinecarboxamide | $C_{27}H_{20}ClN_3O_4$ | 485.93 | 486.1 |
| 619 | 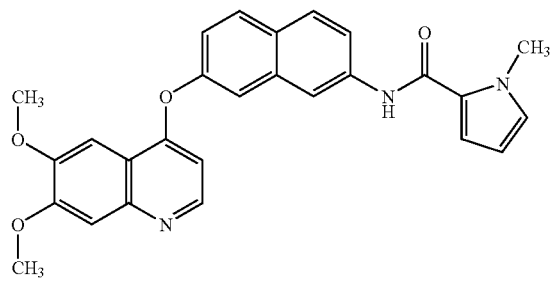<br>N-(7-((6,7-bis(methoxy)-4-quinolinyl)oxy)-2-naphthalenyl)-1-methyl-1H-pyrrole-2-carboxamide | $C_{27}H_{23}N_3O_4$ | 453.5 | 454.1 |
| 620 | 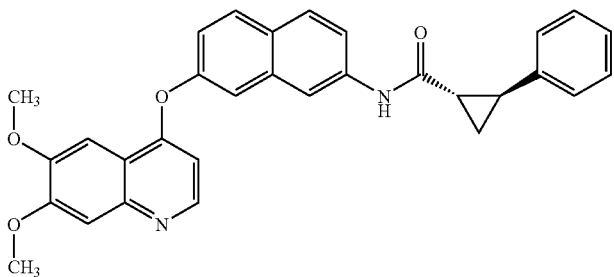<br>(1S,2S)-N-(7-((6,7-bis(methoxy)-4-quinolinyl)oxy)-2-naphthalenyl)-2-phenylcyclopropanecarboxamide | $C_{31}H_{26}N_2O_4$ | 490.56 | 491.2 |

| Example No. | Structure & Name | Mol Formula | Mass | M + H |
|---|---|---|---|---|
| 621 | 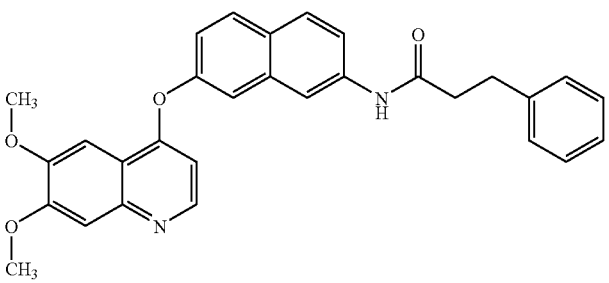<br>N-(7-((6,7-bis(methoxy)-4-quinolinyl)oxy)-2-naphthalenyl)-3-phenylpropanamide | $C_{30}H_{26}N_2O_4$ | 478.55 | 479.1 |
| 622 | 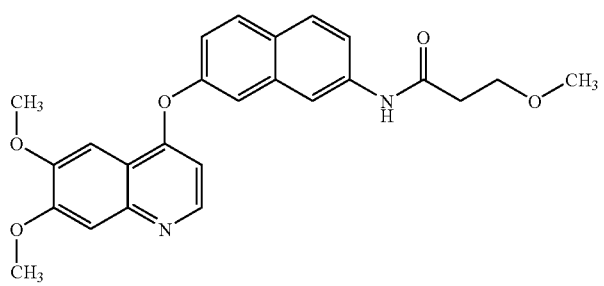<br>N-(7-((6,7-bis(methoxy)-4-quinolinyl)oxy)-2-naphthalenyl)-3-(methoxy)propanamide | $C_{25}H_{24}N_2O_5$ | 432.47 | 433.1 |
| 623 | 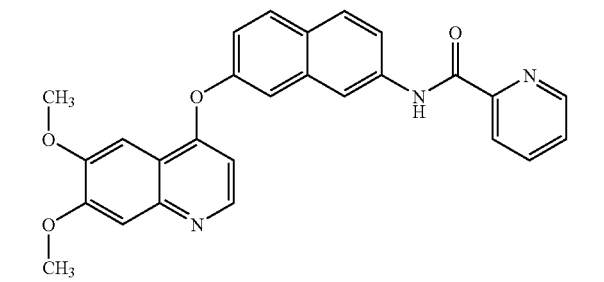<br>N-(7-((6,7-bis(methoxy)-4-quinolinyl)oxy)-2-naphthalenyl)-2-pyridinecarboxamide | $C_{27}H_{21}N_3O_4$ | 451.48 | 452.1 |
| 624 | 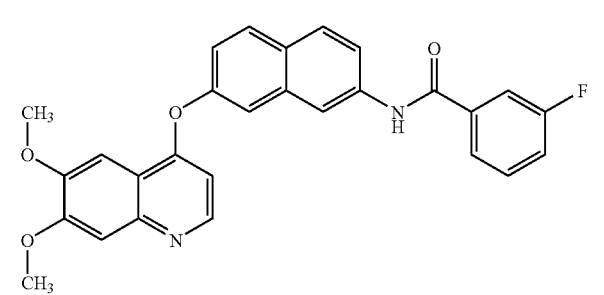<br>N-(7-((6,7-bis(methoxy)-4-quinolinyl)oxy)-2-naphthalenyl)-3-fluorobenzamide | $C_{28}H_{21}FN_2O_4$ | 468.48 | 469.1 |

| Example No. | Structure & Name | Mol Formula | Mass | M + H |
|---|---|---|---|---|
| 625 | 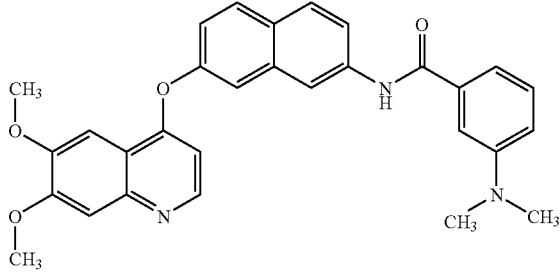<br>N-(7-((6,7-bis(methoxy)-4-quinolinyl)oxy)-2-naphthalenyl)-3-(dimethylamino)benzamide | $C_{30}H_{27}N_3O_4$ | 493.56 | 494.2 |
| 626 | 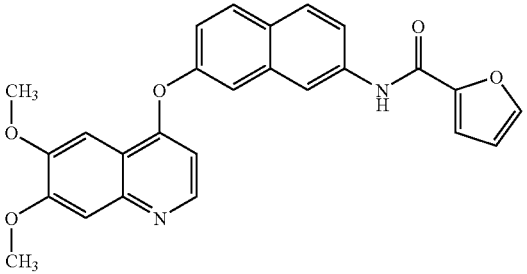<br>N-(7-((6,7-bis(methoxy)-4-quinolinyl)oxy)-2-naphthalenyl)-2-furancarboxamide | $C_{26}H_{20}N_2O_5$ | 440.45 | 441.1 |
| 627 | 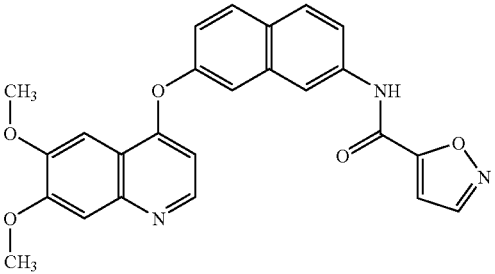<br>N-(7-((6,7-bis(methoxy)-4-quinolinyl)oxy)-2-naphthalenyl)-5-isoxazolecarboxamide | $C_{25}H_{19}N_3O_5$ | 441.44 | 442.1 |
| 628 | 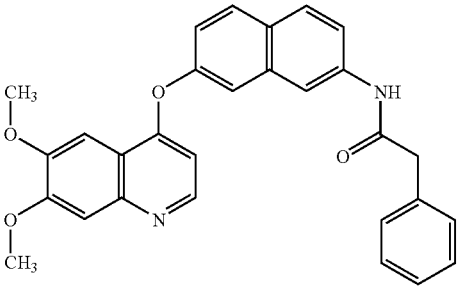<br>N-(7-((6,7-bis(methoxy)-4-quinolinyl)oxy)-2-naphthalenyl)-2-phenylacetamide | $C_{29}H_{24}N_2O_4$ | 464.52 | 465.3 |

| Example No. | Structure & Name | Mol Formula | Mass | M + H |
|---|---|---|---|---|
| 629 | 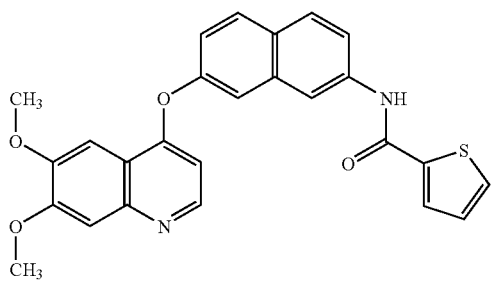<br>N-(7-((6,7-bis(methoxy)-4-quinolinyl)oxy)-2-naphthalenyl)-2-thiophenecarboxamide | $C_{26}H_{20}N_2O_4S$ | 456.52 | 457.4 |
| 630 | 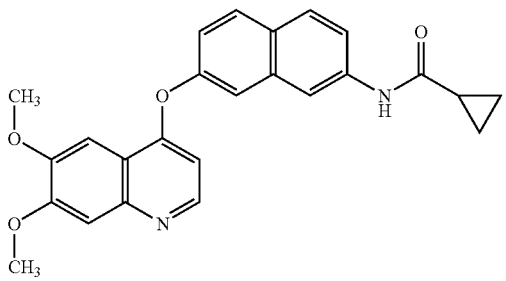<br>N-(7-((6,7-bis(methoxy)-4-quinolinyl)oxy)-2-naphthalenyl)cyclopropanecarboxamide | $C_{25}H_{22}N_2O_4$ | 414.46 | 41.0 |
| 631 | 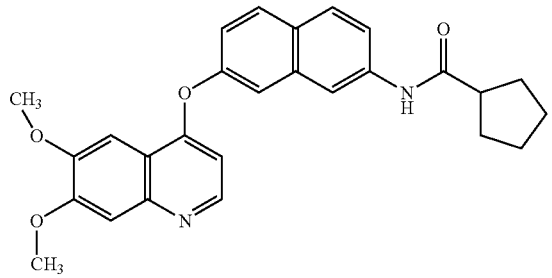<br>N-(7-((6,7-bis(methoxy)-4-quinolinyl)oxy)-2-naphthalenyl)cyclopentanecarboxamide | $C_{27}H_{26}N_2O_4$ | 442.51 | 443.2 |
| 632 | 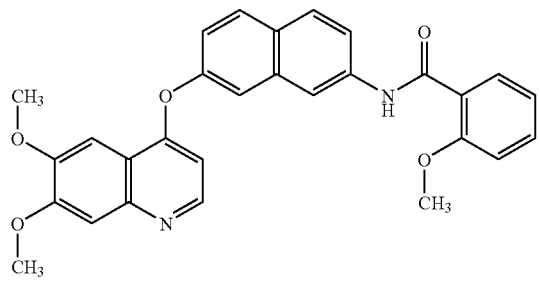<br>N-(7-((6,7-bis(methoxy)-4-quinolinyl)oxy)-2-naphthalenyl)-2-(methoxy)benzamide | $C_{29}H_{24}N_2O_5$ | 480.52 | 481.0 |

-continued

| Example No. | Structure & Name | Mol Formula | Mass | M + H |
|---|---|---|---|---|
| 633 | N-(7-((6,7-bis(methoxy)-4-quinolinyl)oxy)-2-naphthalenyl)-3-chlorobenzamide | C₂₈H₂₁ClN₂O₄ | 484.94 | 486.0 |
| 634 | N-(7-((6,7-bis(methoxy)-4-quinolinyl)oxy)-2-naphthalenyl)-4-(trifluoromethyl)benzamide | C₂₉H₂₁F₃N₂O₄ | 518.49 | 520.0 |
| 635 | N-(7-((6,7-bis(methoxy)-4-quinolinyl)oxy)-2-naphthalenyl)-3-(trifluoromethoxy)benzamide | C₂₉H₂₁F₃N₂O₅ | 534.48 | 535.4 |

EXAMPLE 636

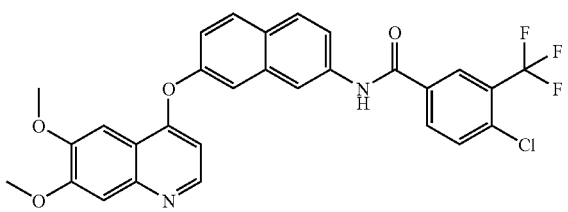

N-(7-((6,7-bis(methoxy)-4-quinolinyl)oxy)-2-naphthalenyl)-4-chloro-3-(trifluoromethyl)benzamide To a solution of 7-(6,7-dimethoxyquinolin-4-yloxy)naphthalen-2-amine (0.137 g, 0.40 mmol) in 10 mL of DMF was added EDCI (0.077 g, 0.40 mmol), HOBt (0.054 g, 0.40 mmol), and 4-chloro-3-(trifluoromethyl)benzoic acid (0.099 g, 0.44 mmol). DIPEA (0.140 mL, 0.80 mmol) was added and the solution was stirred for 16 h at RT under an atmosphere of nitrogen. The reaction was diluted with water and extracted with EtOAc 3×. The organic layer was washed with brine, dried (Na₂SO₄), filtered and concentrated. The residue was purified using a Gilson Prep HPLC system. The fractions were collected, combined, treated with NaHCO₃(aq) and extracted with EtOAc 3×. The organic layer was dried (Na₂SO₄), filtered and concentrated to afford the desired compound. MS (ESI, pos. ion) m/z: 553.0 (M+1). Mass Calc'd for C₂₉H₂₀ClF₃N₂O₄: 552.934.

The following examples were prepared similar to the procedures described in Example 636.

| Example No. | Structure & Name | Mol Formula | Mass | M + H |
|---|---|---|---|---|
| 637 | 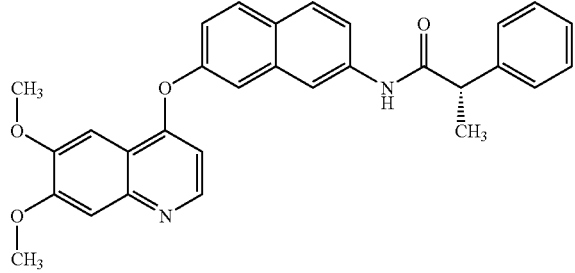<br>(2S)-N-(7-((6,7-bis(methoxy)-4-quinolinyl)oxy)-2-naphthalenyl)-2-phenylpropanamide | C₃₀H₂₆N₂O₄ | 478.55 | 479.2 |
| 638 | 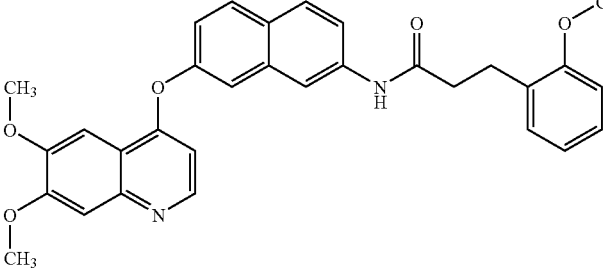<br>N-(7-((6,7-bis(methoxy)-4-quinolinyl)oxy)-2-naphthalenyl)-3-(2-(methoxy)phenyl)propanamide | C₃₁H₂₈N₂O₅ | 508.57 | 509.2 |
| 639 | 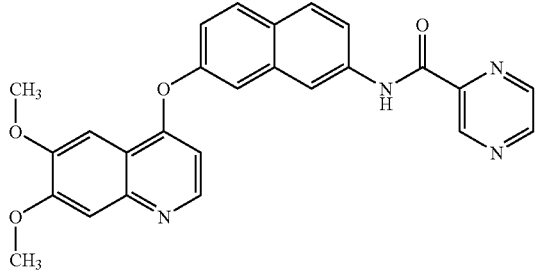<br>N-(7-((6,7-bis(methoxy)-4-quinolinyl)oxy)-2-naphthalenyl)-2-pyrazinecarboxamide | C₂₆H₂₀N₄O₄ | 452.47 | 453.1 |
| 640 | 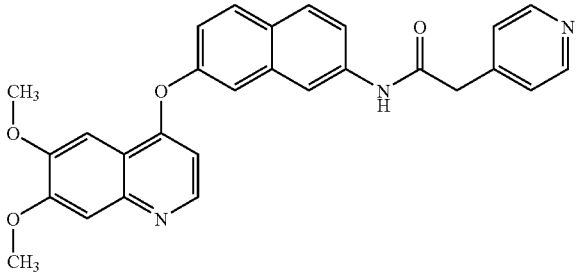<br>N-(7-((6,7-bis(methoxy)-4-quinolinyl)oxy)-2-naphthalenyl)-2-(4-pyridinyl)acetamide | C₂₈H₂₃N₃O₄ | 465.51 | 466.1 |

EXAMPLE 641

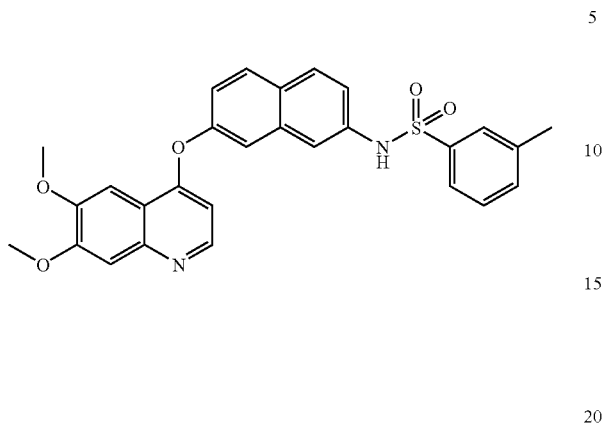

N-(7-((6,7-bis(methoxy)-4-quinolinyl)oxy)-2-naphthalenyl)-3-methylbenzenesulfonamide To a solution of 7-(6,7-dimethoxyquinolin-4-yloxy)naphthalen-2-amine (0.168 g, 0.48 mmol) in 20 mL of $CH_2Cl_2$ was added $K_2CO_3$ (0.134 g, 0.96 mmol), and pyridine (1 mL). The mixture was cooled to 0° C. and m-toluenesulfonyl chloride (0.110 g, 0.58 mmol) was added and the solution was stirred for 16 h at RT under an atmosphere of nitrogen. The reaction was diluted with water and extracted with $CH_2Cl_2$ 3×. The organic layer was washed with brine, dried ($Na_2SO_4$), filtered and concentrated. The residue was purified using a Gilson Prep HPLC system. The fractions were collected, combined, treated with $NaHCO_3$(aq) and extracted with EtOAc 3×. The organic layer was dried ($Na_2SO_4$), filtered and concentrated to afford the desired compound. MS (ESI, pos. ion) m/z: 501.0 (M+1). Mass Calc'd for $C_{28}H_{24}N_2O_5S$: 500.573.
The following examples were prepared similar to the procedures described in Example 641.

EXAPLE 643

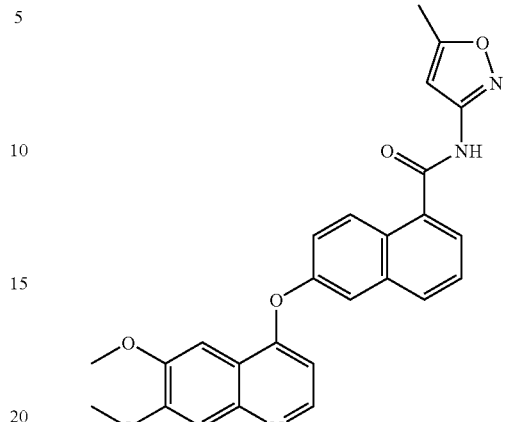

6-((6,7-bis(methoxy)-4-quinolinyl)oxy)-N-(5-methyl-3-isoxazolyl)-1-naphthalenecarboxamide A 16×100 mm resealable vial with stir-bar was charged with 1,2-dichloroethane (3.0 mL), 6-(6,7-dimethoxyquinolin-4-yloxy)-1-naphthoyl chloride (0.15 g, 0.38 mmol), and 5-amino-3-methylisoxazole (0.045 g, 0.46 mmol). To the suspension was added triethylamine (0.13 mL, 0.95 mmol) and N,N-dimethylaminopyridine (0.005 g, 0.04 mmol). The mixture stirred at 80° C. for 15 h and was then cooled to RT. The reaction mixture was concentrated and the residue was purified by column chromatography on silica gel (eluting with 2% methanol in dichloromethane) to afford 6-((6,7-bis(methoxy)-4-quinolinyl)oxy)-N-(5-methyl-3-isoxazolyl)-1-naphthalenecarboxamide as an off-white solid. MS (ESI, pos. ion) m/z: 456.1 (M+H). Mass Calc'd for $C_{29}H_{26}FN_3O_5$: 455.468

| Example No. | Structure & Name | Mol Formula | Mass | M + H |
|---|---|---|---|---|
| 642 | 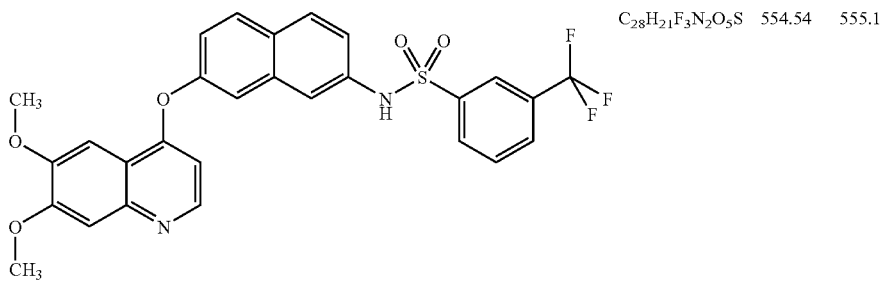<br>N-(7-((6,7-bis(methoxy)-4-quinolinyl)oxy)-2-naphthalenyl)-3-(trifluoromethyl)benzenesulfonamide | $C_{28}H_{21}F_3N_2O_5S$ | 554.54 | 555.1 |

The following examples were prepared similar to the procedures described in Example 643.
| Example No. | Structure & Name | Mol Formula | Mass | M + H |
|---|---|---|---|---|
| 644 | 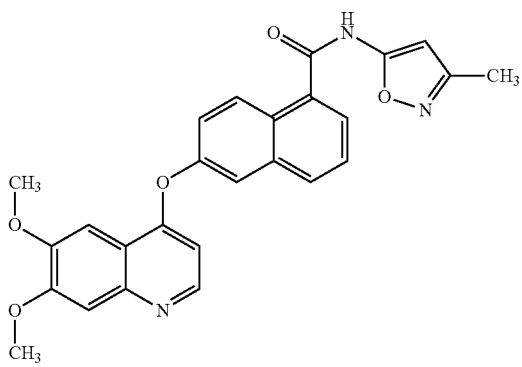<br>6-((6,7-bis(methoxy)-4-quinolinyl)oxy)-N-(3-methyl-5-isoxazolyl)-1-naphthalenecarboxamide | $C_{26}H_{21}N_3O_5$ | 455.47 | 456.1 |
| 645 | 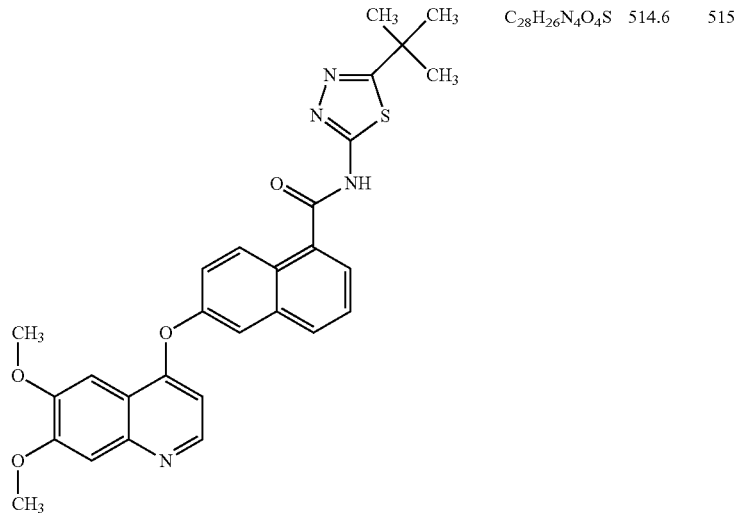<br>6-((6,7-bis(methoxy)-4-quinolinyl)oxy)-N-(5-(1,1-dimethylethyl)-1,3,4-thiadiazol-2-yl)-1-naphthalenecarboxamide | $C_{28}H_{26}N_4O_4S$ | 514.6 | 515 |

| Example No. | Structure & Name | Mol Formula | Mass | M + H |
|---|---|---|---|---|
| 646 | 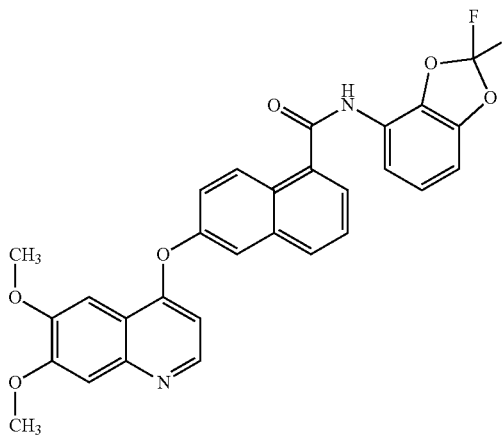<br>6-((6,7-bis(methoxy)-4-quinolinyl)oxy)-N-(2,2-difluoro-1,3-benzodioxol-4-yl)-1-naphthalenecarboxamide | $C_{29}H_{20}F_2N_2O_6$ | 530.48 | 531.2 |
| 647 | 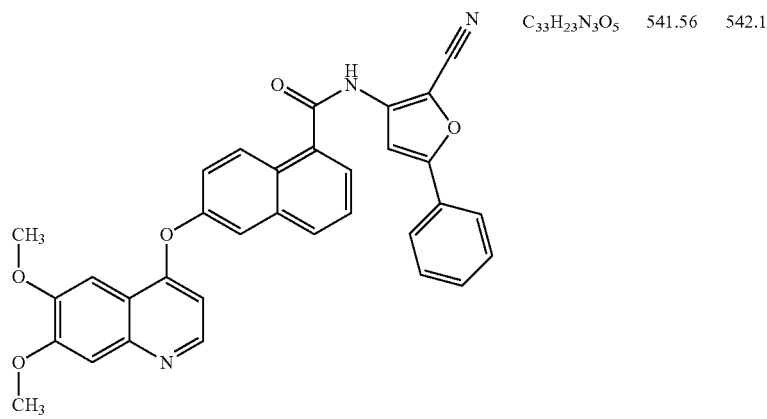<br>6-((6,7-bis(methoxy)-4-quinolinyl)oxy)-N-(2-cyano-5-phenyl-3-furanyl)-1-naphthalenecarboxamide | $C_{33}H_{23}N_3O_5$ | 541.56 | 542.1 |

-continued

| Example No. | Structure & Name | Mol Formula | Mass | M + H |
|---|---|---|---|---|
| 648 | 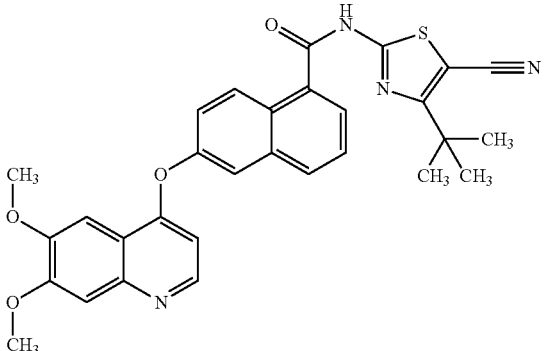<br>6-((6,7-bis(methoxy)-4-quinolinyl)oxy)-N-(5-cyano-4-(1,1-dimethylethyl)-1,3-thiazol-2-yl)-1-naphthalenecarboxamide | $C_{30}H_{26}N_4O_4S$ | 538.62 | 539.1 |
| 649 | 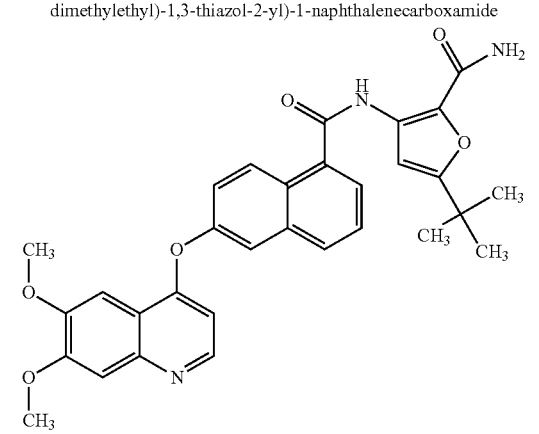<br>3-(((6-((6,7-bis(methoxy)-4-quinolinyl)oxy)-1-naphthalenyl)carbonyl)amino)-5-(1,1-dimethylethyl)-2-thiophenecarboxamide | $C_{31}H_{29}N_3O_5S$ | 555.65 | 556.2 |

The following example was prepared similar to the procedure described in Example 643, using 2-mercaptothiazoline in place of the amine.

| Example No. | Structure & Name | Mol Formula | Mass | M + H |
|---|---|---|---|---|
| 650 | 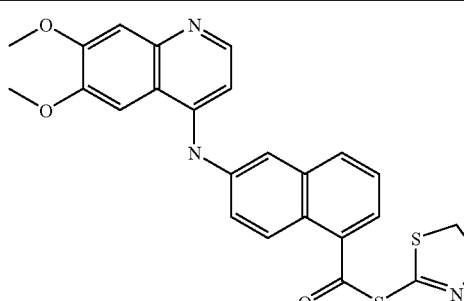<br>S-(4,5-dihydro-1,3-thiazol-2-yl) 6-((6,7-bis(methoxy)-4-quinolinyl)oxy)-1-naphthalenecarbothioate | $C_{25}H_{20}N_2O_4S_2$ | 476.57 | 477 |

EXAMPLE 651

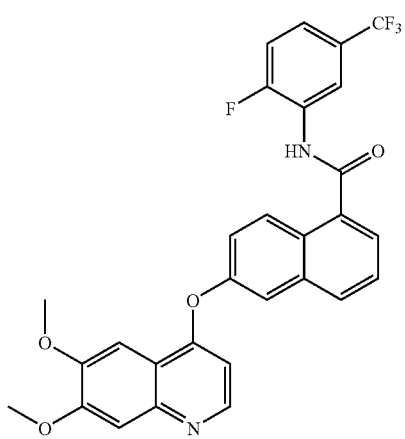

6-((6,7-bis(methoxy)-4-quinolinyl)oxy)-N-(2-fluoro-5-(trifluoromethyl)phenyl)-1-naphthalenecarboxamide Into a 16×100 mm vial was added 3-amino-4-fluorobenzotrifluoride (100 mg, 0.563 mmol), and dichloromethane (1 mL). To this was added 1.5 mL of a stock solution that is both 0.25M 6-(6,7-dimethoxyquinolin-4-yloxy)-1-naphthoyl chloride and 0.5M DMAP in dichloromethane. Reactions was stirred 24 h at RT. The mixture loaded directly onto silica column. Purified using 0 to 100% EtOAc in hexane. Best fractions were pooled, concentrated under reduced pressure to afford the title compound as a yellow oil. MS (ESI, pos. ion) m/z: 537 (M+1). Mass Calc'd for $C_{29}H_{20}F_4N_2O_4$: 536.47.

The following examples were prepared similar to that described in Example 651.

| Example No. | Structure & Name | Mol Formula | Mass | M + H | [M − H]− |
|---|---|---|---|---|---|
| 652 | 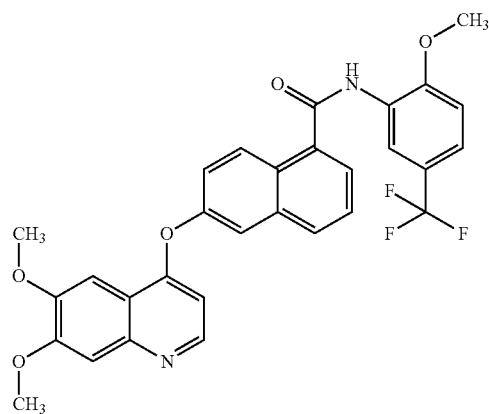<br>6-((6,7-bis(methoxy)-4-quinolinyl)oxy)-N-(2-(methoxy)-5-(trifluoromethyl)phenyl)-1-naphthalenecarboxamide | $C_{30}H_{23}F_3N_2O_5$ | 548.51 | 549 | N/A |
| 653 | 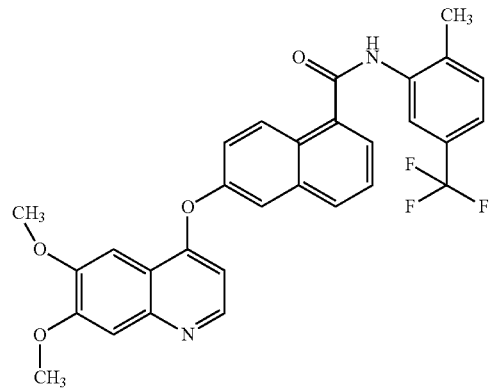<br>6-((6,7-bis(methoxy)-4-quinolinyl)oxy)-N-(2-methyl-5-(trifluoromethyl)phenyl)-1-naphthalenecarboxamide | $C_{30}H_{23}F_3N_2O_4$ | 532.52 | 533 | N/A |

| Example No. | Structure & Name | Mol Formula | Mass | M + H | [M − H]− |
|---|---|---|---|---|---|
| 654 | 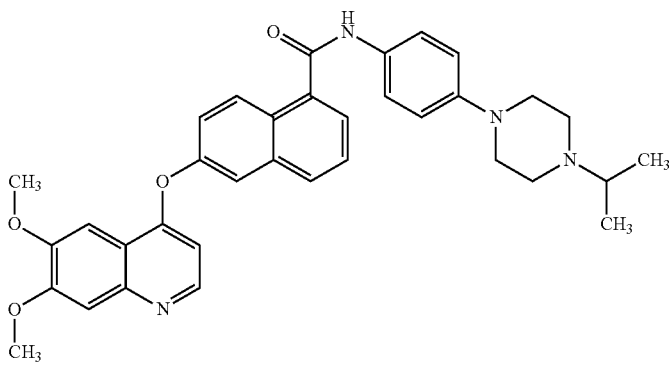  6-((6,7-bis(methoxy)-4-quinolinyl)oxy)-N-(4-(4-(1-methylethyl)-1-piperazinyl)phenyl)-1-naphthalenecarboxamide | C$_{35}$H$_{36}$N$_4$O$_4$ | 576.69 | M/2 = 289 | 575 |
| 655 | 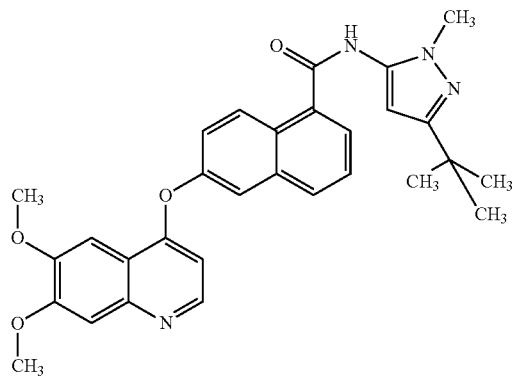  6-((6,7-bis(methoxy)-4-quinolinyl)oxy)-N-(3-(1,1-dimethylethyl)-1-methyl-1H-pyrazol-5-yl)-1-naphthalenecarboxamide | C$_{30}$H$_{30}$N$_4$O$_4$ | 510.59 | M/2 = 256 | 509 |
| 656 | 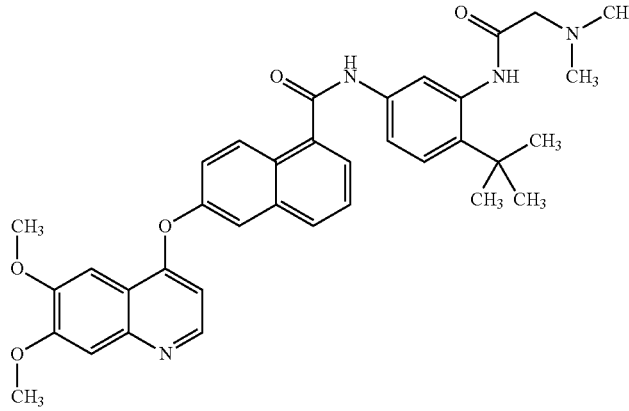  6-((6,7-bis(methoxy)-4-quinolinyl)oxy)-N-(4-(1,1-dimethylethyl)-3-((N,N-dimethylglycyl)amino)phenyl)-1-naphthalenecarboxamide | C$_{36}$H$_{38}$N$_4$O$_5$ | 606.72 | M/2 = 304 | 605 |

-continued

| Example No. | Structure & Name | Mol Formula | Mass | M + H | [M − H]− |
|---|---|---|---|---|---|
| 657 | 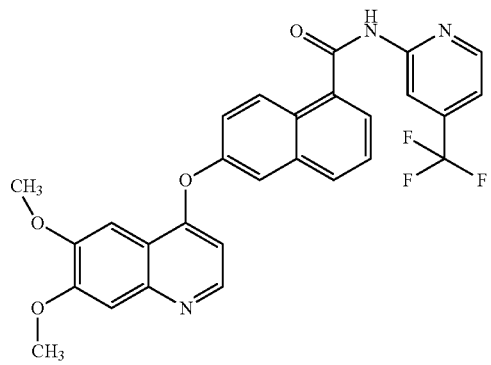<br>6-((6,7-bis(methoxy)-4-quinolinyl)oxy)-N-(4-(trifluoromethyl)-2-pyridinyl)-1-naphthalenecarboxamide | $C_{28}H_{20}F_3N_3O_4$ | 519.48 | 520 | N/A |
| 658 | 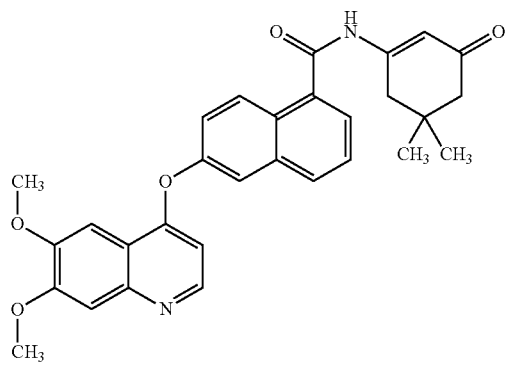<br>6-((6,7-bis(methoxy)-4-quinolinyl)oxy)-N-(5,5-dimethyl-3-oxo-1-cyclohexen-1-yl)-1-naphthalenecarboxamide | $C_{30}H_{28}N_2O_5$ | 496.56 | 497 | N/A |
| 659 | 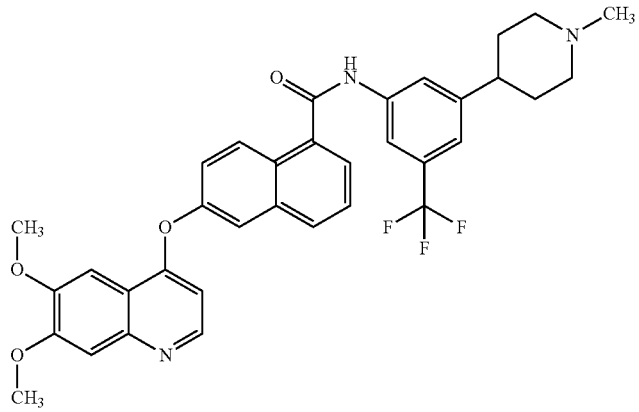<br>6-((6,7-bis(methoxy)-4-quinolinyl)oxy)-N-(3-(1-methyl-4-piperidinyl)-5-(trifluoromethyl)phenyl)-1-naphthalenecarboxamide | $C_{35}H_{32}F_3N_3O_4$ | 615.65 | M/2 = 308 | 614 |

EXAMPLE 660

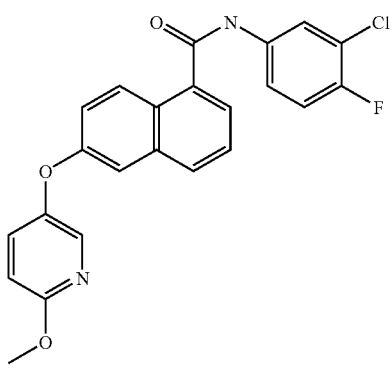

N-(3-chloro-4-fluorophenyl)-6-((6-(methoxy)-3-pyridinyl)oxy)-1-naphthalenecarboxamide

Step (a) Preparation of 6-methoxypyridin-3-ylboronic acid

To 5-bromo-2-methoxypyridine (8.25 g, 43.9 mmol) and triisopropylborate (10.3 g, 55.0 mmol) in THF (110 mL) at −80° C. was dropwise added n-BuLi (1.6M in hexanes, 30.1 mL, 48.2 mmol). The reaction mixture was gradually warmed to RT over 1 h and then stirred at RT for 16 h. The reaction mixture was quenched by addition of 1N aqueous HCl solution and stirred for 1 h. The aqueous layer was basified with 6N aqueous NaOH to pH=9, extracted with a mixture of EtOAc and Et$_2$O. The aqueous layer was acidified to pH=7 and extracted with EtOAc. The combined organic layers were dried over Na$_2$SO$_4$, filtered and concentrated in vacuo. This material was used in the next step without further purification.

Step (b) Preparation of methyl 6-(6-methoxypyridin-3-yloxy)-1-naphthoate

A solution/suspension of methyl 6-hydroxy-1-naphthoate (2.49 g, 12.3 mmol), 6-methoxypyridin-3-ylboronic acid (2.26 g, 14.8 mmol), copper acetate (2.46 g, 13.6 mmol), triethylamine (6.24 g, 61.7 mmol) and 4Å molecular sieves (2.00 g) in acetonitrile (120 mL) was stirred at RT for 16 h. The solids were filtered off. The filtrate was concentrated in vacuo. Water was added and extracted with EtOAc. The organic layer was washed with 1M aqueous NaOH solution, water, brine and dried over Na$_2$SO$_4$, filtered and concentrated in vacuo. Purification by silica gel chromatography afforded the title compound.

Step (c) Preparation of 6-(6-methoxypyridin-3-yloxy)-1-naphthoic acid

To a solution of 6-(6-methoxypyridin-3-yloxy)-1-naphthoate (480 mg, 1.55 mmol) in THF (155 mL) at RT was added 1M aqueous LiOH (31 mL). The reaction was stirred until the reaction was completed. THF was removed in vacuo. The aqueous layer was acidified using 6M aqueous HCl to pH=6-7 and extracted with EtOAc. The aqueous layer was further acidified to pH=5 and extracted with EtOAc. The combined organic layers were dried over Na$_2$SO$_4$, filtered and concentrated in vacuo to give the title compound, which was used without further purification.

Step (d) Preparation of 6-(6-methoxypyridin-3-yloxy)-1-naphthoyl chloride hydrochloride salt The title compound was prepared according to Example 273, Step a using 6-(6-methoxypyridin-3-yloxy)-1-naphthoic acid as starting material.

Step (e) Preparation of N-(3-chloro-4-fluorophenyl)-6-((6-(methoxy)-3-pyridinyl)oxy)-1-naphthalenecarboxamide To a stirred solution of 6-(6-methoxypyridin-3-yloxy)-1-naphthoyl chloride hydrochloride salt (225 mg, 0.64 mmol) and DIPEA (0.22 mL, 1.285 mmol) in DCM (5 mL) at RT was added 3-chloro-4-fluoroaniline (93.5 mg, 0.64 mmol). After stirring for 16 h, the reaction mixture was directly purified by silica gel chromatography (elution hexanes/EtOAC:85/15 to 35/65) to give the title compound as a tan solid. MS (ESI, pos. ion) m/z: 423.1 (M+1). Mass Calc'd for C$_{23}$H$_{16}$ClFN$_2$O$_3$: 422.84.

EXAMPLE 661

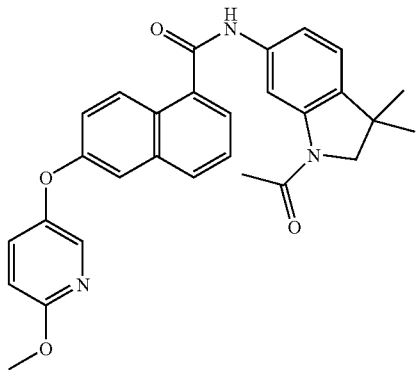

N-(1-acetyl-3,3-dimethyl-2,3-dihydro-1H-indol-6-yl)-6-((6-(methoxy)-3-pyridinyl)oxy)-1-naphthalenecarboxamide The title compound was prepared according to the experimental procedure described in example 660. MS (ESI, pos. ion) m/z: 482.2 (M+1). Mass Calc'd for C$_{29}$H$_{27}$N$_3$O$_4$: 481.55.

EXAMPLE 662

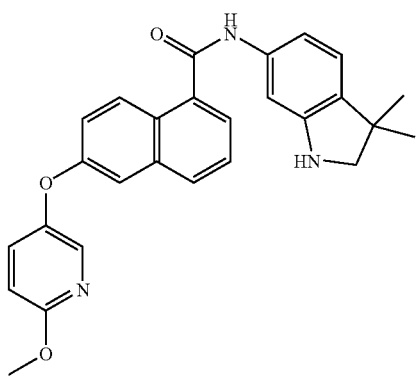

N-(3,3-dimethyl-2,3-dihydro-1H-indol-6-yl)-6-((6-(methoxy)-3-pyridinyl)oxy)-1-naphthalenecarboxamide To a solution of N-(1-acetyl-3,3-dimethyl-2,3-dihydro-1H-indol-6-yl)-6-((6-(methoxy)-3-pyridinyl)oxy)-1-naphthalenecarboxamide (482 mg, 0.48 mmol) in EtOH (5.5 mL) was added concentrated aqueous HCl solution (3.3 mL). The reaction mixture was heated at 55-65° C. for 4 h, cooled to RT. EtOH was removed in vacuo. The aqueous layer was basified to pH=7-8 by adding 6M aqueous NaOH solution. The title compound was isolated by filtration and dried under high vacuum. MS (ESI, pos. ion) m/z: 440.1 (M+1). Mass Calc'd for $C_{27}H_{25}N_3O_3$: 439.51.

EXAMPLE 663

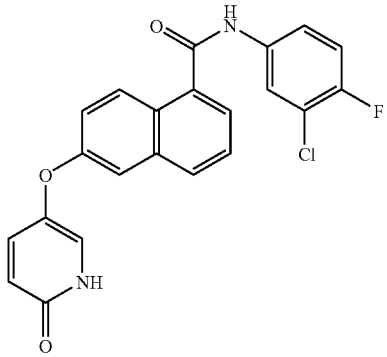

N-(3-chloro-4-fluorophenyl)-6-((6-oxo-1,6-dihydro-3-pyridinyl)oxy)-1-naphthalenecarboxamide To a stirred solution/suspension of N-(3-chloro-4-fluorophenyl)-6-((6-(methoxy)-3-pyridinyl)oxy)-1-naphthalenecarboxamide (167 mg, 0.39 mmol) in chloroform (4.7 mL) was added trimethylsilyl iodide (Aldrich, 221 mg, 1.10 mmol). The reaction mixture was heated at 70° C. (oil bath) for 2.5 h, cooled to RT and MeOH (1 mL) was added. After stirring for 15 min, the dark yellow solution was concentrated in vacuo and treated with concentrated aqueous $NH_4OH$ (3 mL). The title compound was isolated by filtration and dried under high vacuum. MS (ESI, pos. ion) m/z: 409.1 (M+1). Mass Calc'd for $C_{22}H_{14}ClFN_2O_3$: 408.81.

EXAMPLE 664

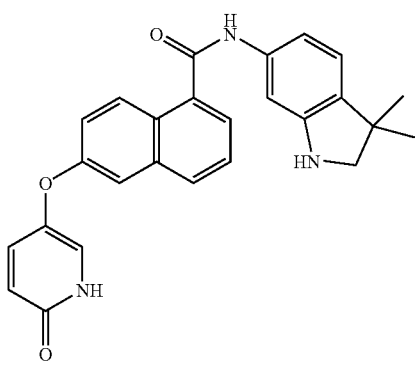

N-(3,3-dimethyl-2,3-dihydro-1H-indol-6-yl)-6-((6-oxo-1,6-dihydro-3-pyridinyl)oxy)-1-naphthalenecarboxamide The compound was prepared similarly to the procedure outlined above by using N-(3,3-dimethyl-2,3-dihydro-1H-indol-6-yl)-6-((6-(methoxy)-3-pyridinyl)oxy)-1-naphthalenecarboxamide as starting material:
MS (ESI, pos. ion) m/z: 426.2 (M+1). Mass Calc'd for $C_{26}H_{23}N_3O_3$: 425.49.

EXAMPLE 665

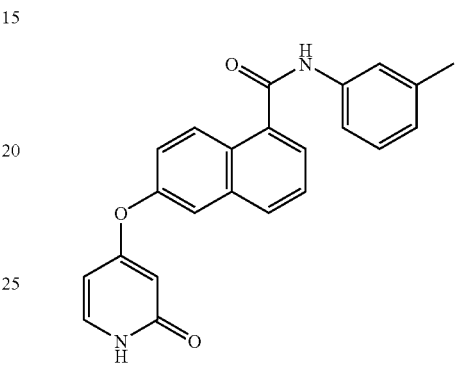

N-(3-methylphenyl)-6-((2-oxo-1,2-dihydro-4-pyridinyl)oxy)-1-naphthalenecarboxamide Step (a) Preparation of 6-(2-chloropyridin-4-yloxy)-1-napthoic acid 6-hydroxy-1-napthoic acid (3.2 g, 17 mmol) was reacted with 2,4-dichloropyridine (2.5 g, 17 mmol) and $Cs_2CO_3$ (16.6 g, 51 mmol) under the conditions of Example 421 step a to furnish the title compound as a brown solid. MS (ESI, pos. ion) m/z: 300.4 (M+1). Mass Calc'd for $C_{16}H_{10}ClNO_3$: 299.708.

Step (b) Preparation of 6-(2-oxo-1,2-dihydropyridi-4-yloxy)-1-napthoic acid

A mixture of 6-(2-chloropyridin-4-yloxy)-1-napthoic acid (100 mg, 0.33 mmol) and p-toluenesulfonic acid (12 mg, 0.06 mmol) in AcOH (4 mL) were heated in a sealed tube at 130° C. for 72 h.
The resulting suspension was filtered to provide the title compound as a white solid. MS (ESI, pos. ion) m/z: 282.1 (M+1). Mass Calc'd for $C_{16}H_{11}NO_4$: 281.263.

Step (c) Preparation of N-(3-methylphenyl)-6-((2-oxo-1,2-dihydro-4-pyridinyl)oxy)-1-naphthalenecarboxamide To a solution of 6-(2-oxo-1,2-dihydropyridi-4-yloxy)-1-napthoic acid (step b, 125 mg, 0.44 mmol), m-toluidine (53 mL, 0.48 mmol) and TBTU (143 mg, 0.44 mmol) in DMF (4.5 mL) at 0° C. was added DIPEA (195 μL, 1.1 mmol). The mixture was maintained at 0° C. for 15 minutes and then allowed to warm to ambient temperature where it was maintained for 10 h. The reaction was diluted with EtOAc (50 mL) and poured into sat'd $NaHCO_3$ (50 mL). The layers were separated and the aqueous phase was extracted with EtOAc (3×50 mL). The combined organic layers were washed with H₂O (3×100 mL), sat'd NaHCO₃ (3×100 mL) and brine. Concentration under reduced pressure and purification by silica gel chromatography (2-8% MeOH in CH₂Cl₂) provided the title compound as a white solid. MS (ESI, pos. ion) m/z: 371.1 (M+1). Mass Calc'd for $C_{23}H_{18}N_2O_3$: 370.401.

EXAMPLE 666

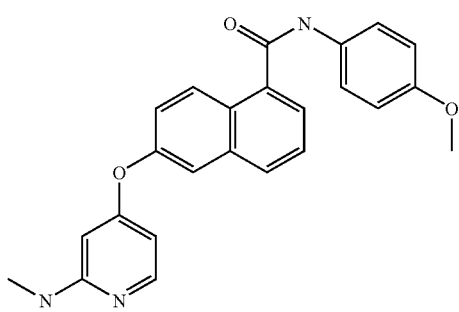

6-((2-(methylamino)-4-pyridinyl)oxy)-N-(4-(methoxy)phenyl)-1-naphthalenecarboxamide

Step (a) Preparation of 6-(2-chloropyridin-4-yloxy)-1-naphthoic acid

6-Hydroxynaphtoic acid (10.0 g, 53.1 mmol), 2,4-dichloropyridine (9.44 g, 63.8 mmol) and cesium carbonate (51.9 g, 159 mmol) were combined in DMSO (266 mL) and the reaction mixture was heated at 90° C. for 16 h. After cooling to RT, water was added and the aqueous layer was acidified to pH=4-5. The title compound was isolated by filtration and dried under vacuum.

Step (b) Preparation of 6-(2-methylaminopyridin-4-yloxy)-1-naphthoic acid

To melted methylamine hydrochloride (Aldrich, 73.7 g, 1090 mmol) at 235° C. (oil bath) was added 6-(2-chloropyridin-4-yloxy)-1-naphthoic acid (6.54 g, 21.8 mmol). The reaction mixture was stirred for 3 min and cooled to RT. The brownish solid was treated with EtOAc and water and stirred until all residue was either in solution or suspended. The precipitate was filtered off, washed with EtOAC and purified by silica gel chromatography using 0-100% of a 85:15:0.5 mixture of DCM:MeOH:AcOH. The product obtained was washed with water, filtered and dried under vacuum to give the title compound.

Step (c) Preparation of 6-((2-(methylamino)-4-pyridinyl)oxy)-N-(4-(methoxy)phenyl)-1-naphthalenecarboxamide 6-(2-Methylaminopyridin-4-yloxy)-1-naphthoic acid (170 mg, 0.58 mmol), p-anisidine (107 mg, 0.87 mmol), DIPEA (149 mg, 1.16 mmol) and TBTU (223 mg, 0.69 mmol) were combined in DMF (3.0 mL) and the reaction mixture was stirred at RT for 16 h, quenched by addition of a 6M aqueous NaOH solution. The precipitate was filtered off, treated with DCM, sonicated. The title compound was isolated by filtration. MS (ESI, pos. ion) m/z: 400.1 (M+1). Mass Calc'd for $C_{24}H_{21}N_3O_3$: 399.45.

The following compounds were prepared similarly to Example 665 isolated after purification by silica gel chromatography and/or crystallization:

| Example No. | Structure & Name | Mol Formula | Mass | M + H |
|---|---|---|---|---|
| 667 | 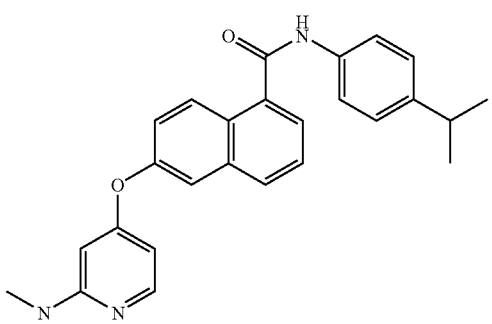<br>6-((2-(methylamino)-4-pyridinyl)oxy)-N-(4-(1-methylethyl)phenyl)-1-naphthalenecarboxamide | $C_{26}H_{25}N_3O_2$ | 411.50 | 412.1 |

-continued

| Example No. | Structure & Name | Mol Formula | Mass | M + H |
|---|---|---|---|---|
| 668 | 6-((2-(methylamino)-4-pyridinyl)oxy)-N-(4-((trifluoromethyl)oxy)phenyl)-1-naphthalenecarboxamide | $C_{24}H_{18}F_3N_3O_3$ | 453.42 | 454.4 |
| 669 | 6-((2-(methylamino)-4-pyridinyl)oxy)-N-(4-methylphenyl)-1-naphthalenecarboxamide | $C_{24}H_{21}N_3O_2$ | 383.45 | 384.4 |
| 670 | N-(4-chlorophenyl)-6-((2-(methylamino)-4-pyridinyl)oxy)-1-naphthalenecarboxamide | $C_{23}H_{18}ClN_3O_2$ | 403.87 | 404.4 |
| 671 | 6-((2-(methylamino)-4-pyridinyl)oxy)-N-(3-(methoxy)phenyl)-1-naphthalenecarboxamide | $C_{24}H_{21}N_3O_3$ | 399.45 | 400.2 |

-continued

| Example No. | Structure & Name | Mol Formula | Mass | M + H |
|---|---|---|---|---|
| 672 | 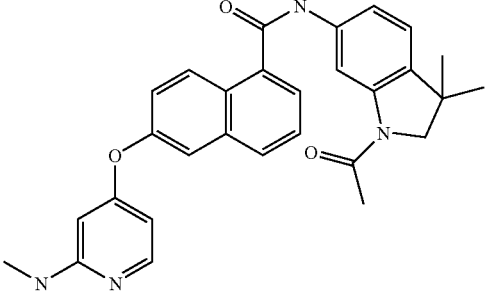<br>N-(1-acetyl-3,3-dimethyl-2,3-dihydro-2,3-1H-indol-6-yl)-6-((2-(methylamino)-4-pyridinyl)oxy)-1-naphthalenecarboxamide | $C_{29}H_{28}N_4O_3$ | 480.56 | 481.5 |
| 673 | 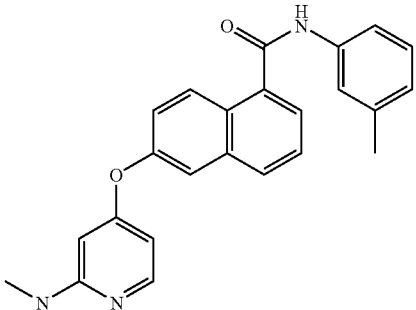<br>6-((2-methylamino)-4-pyridinyl)oxy)-N-(3-methylphenyl)-1-naphthalenecarboxamide | $C_{24}H_{21}N_3O_2$ | 383.45 | 384.2 |
| 674 | 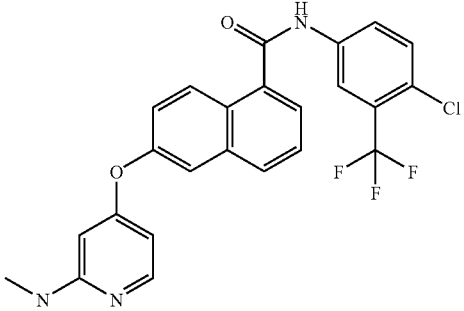<br>N-(4-chloro-3-(trifluoromethyl)phenyl)-6-((2-(methylamino)-4-pyridinyl)oxy)-1-naphthalenecarboxamide | $C_{24}H_{17}ClF_3N_3O_2$ | 471.86 | 472.1 |
| 675 | 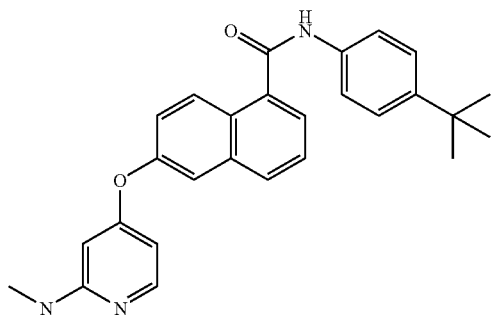<br>N-(4-(1,1-dimethylethyl)phenyl)-6-((2-(methylamino)-4-pyridinyl)oxy)-1-naphthalenecarboxamide | $C_{27}H_{27}N_3O_2$ | 425.53 | 426.5 |

-continued

| Example No. | Structure & Name | Mol Formula | Mass | M + H |
|---|---|---|---|---|
| 676 | 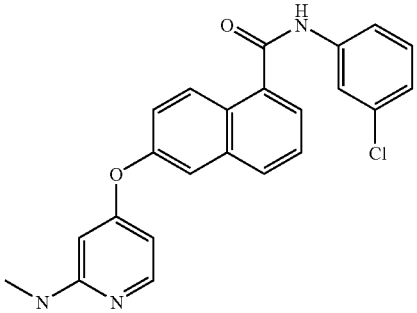<br>N-(3-chlorophenyl)-6-((2-(methylamino)-4-pyridinyl)oxy)-1-naphthalenecarboxamide | $C_{23}H_{18}ClN_3O_2$ | 403.87 | 404.1 |
| 677 | 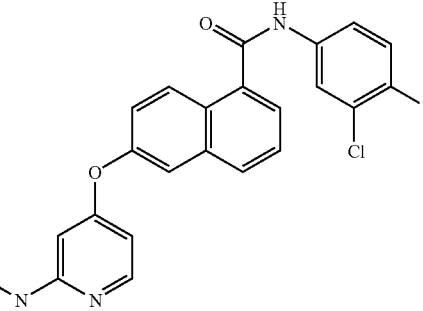<br>N-(3-chloro-4-fluorophenyl)-6-((2-(methylamino)-4-pyridinyl)oxy)-1-naphthalenecarboxamide | $C_{23}H_{17}ClFN_3O_2$ | 421.86 | 422.2 |
| 678 | 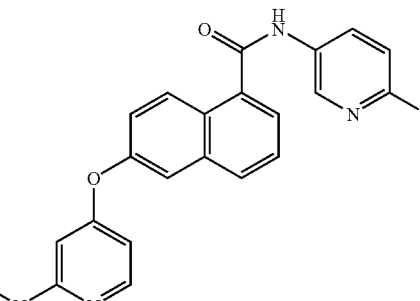<br>6-((2-(methylamino)-4-pyridinyl)oxy)-N-(6-(methoxy)-3-pyridinyl)-1-naphthalenecarboxamide | $C_{23}H_{20}N_4O_3$ | 400.44 | 401.2 |
| 679 | 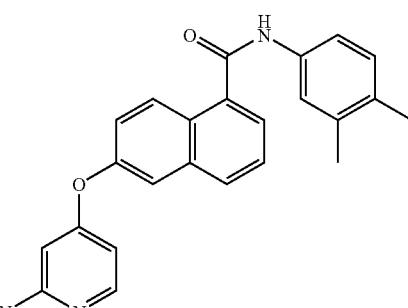<br>6-((2-(methylamino)-4-pyridinyl)oxy)-N-(3-methyl-4-(1-methylethyl)phenyl)-1-naphthalenecarboxamide | $C_{27}H_{27}N_3O_2$ | 425.53 | 426.0 |

EXAMPLE 680

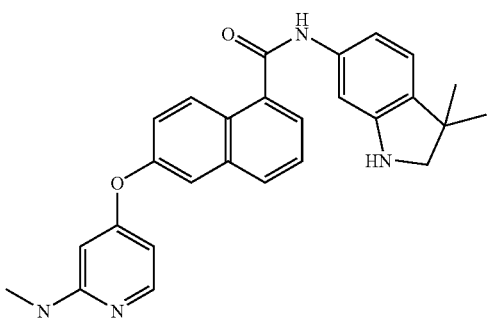

N-(3,3-dimethyl-2,3-dihydro-1H-indol-6-yl)-6-((2-(methylamino)-4-pyridinyl)oxy)-1-naphthalenecarboxamide The title compound was prepared from N-(1-acetyl-3,3-dimethyl-2,3-dihydro-1H-indol-6-yl)-6-((2-(methylamino)-4-pyridinyl)oxy)-1-naphthalenecarboxamide using the experimental procedure outlined in Example 662. MS (ESI, pos. ion) m/z: 439.2 (M+1). Mass Calc'd for $C_{27}H_{26}N_4O_2$: 438.53.

EXAMPLE 681

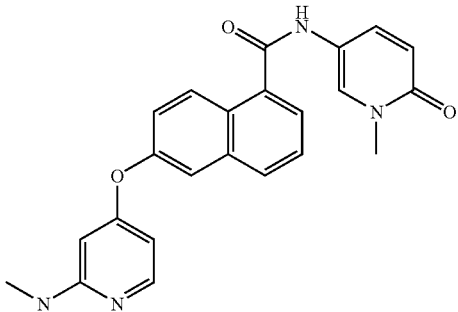

6-((2-(methylamino)-4-pyridinyl)oxy)-N-(1-methyl-6-oxo-1,6-dihydro-3-pyridinyl)-1-naphthalenecarboxamide

Step (a) Preparation of tert-butyl 6-methoxypyridin-3-ylcarbamate

To a stirring solution of 5-amino-2-methoxypyridine (8.00 g, 64.4 mmol) and triethylamine (11.7 mL, 83.8 mmol) in dioxane (32 mL) at 0° C. was added a solution of di-tert-butyl carbonate in dioxane (20 mL). The reaction mixture was allowed to warm to RT, stirred for 16 h. After concentration in vacuo, the residue was dissolved in 65 mL of EtOAc and 32 mL of a saturated aqueous NaHCO₃ solution and stirred at RT for 2 h. The layers were separated. The organic layer was washed with water and dried over Na₂SO₄, filtered and concentrated in vacuo to provide the title compound.

Step (b) Preparation of tert-butyl 1-methyl-6-oxo-1,6-dihydropyridin-3-ylcarbamate To a stirred solution of tert-butyl 6-methoxypyridin-3-ylcarbamate (14.4 g, 64.2 mmol) in MeOH (95 mL) was added methyl iodide (14.6 g, 103 mmol). The reaction mixture was heated at reflux for 16 h, cooled to RT and concentrated down. The residue was purified by silica gel chromatography to give the title compound.

Step (c) Preparation of 5-amino-1-methylpyridin-2(1H)-one hydrochloride

To a stirred solution of tert-butyl 1-methyl-6-oxo-1,6-dihydropyridin-3-ylcarbamate (1.20 g, 5.35 mmol) in dioxane (15 mL) at RT was added HCl (4M in dioxane, 5.35 mL, 21.4 mmol). The reaction mixture was heated at 70° C. for 9 h, cooled to RT and filtered to give the title compound.

Step (d) Preparation of 6-((2-(methylamino)-4-pyridinyl)oxy)-N-(1-methyl-6-oxo-1,6-dihydro-3-pyridinyl)-1-naphthalenecarboxamide The title compound was prepared according to the procedure outlined in example 666. MS (ESI, pos. ion) m/z: 401.0 (M+1). Mass Calc'd for $C_{23}H_{20}N_4O_3$: 400.44.

EXAMPLE 682

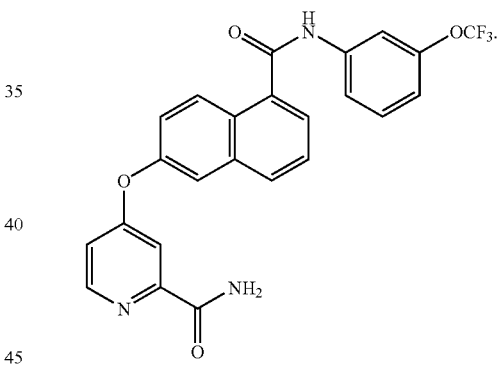

4-((5-(((3-(trifluoromethoxy)-phenyl)amino)carbonyl)-2-naphthalenyl)oxy)-2-pyridinecarboxamide

Step (a) Preparation of 6-(2-carbamoylpyridin-4-yloxy)-1-napthoic acid

6-Hydroxy-1-napthoic acid (2.5 g, 13 mmol) was reacted with 4-chloropicolinamide (WO 02/085857) (2.6 g, 15 mmol) under the conditions of Example 421 Step a to give the title compound as a brown solid. MS (ESI, pos. ion) m/z: 309.2 (M+1). Mass Calc'd for $C_{17}H_{12}N_2O_4$: 308.29.

Step (b) Preparation of 6-(2-carbamoylpyrdin-4-yloxy)-1-napthoyl chloride

A mixture of 6-(2-carbamoylpyridin-4-yloxy)-1-napthoic acid (Step a, 1.0 g, 3.2 mmol) and SOCl₂ (600 μL, 8.1 mmol) in toluene (25 mL, Aldrich) was heated at 110° C. for 7 h. The resulting solution was concentrated under reduced pressure and azeotroped from toluene (3×10 mL) to provide the title compounds as a yellow solid. MS (ESI, pos. ion) m/z: 327.5 (M+1). Mass Calc'd for $C_{17}H_{11}ClN_2O_3$: 326.73.

Step (c) Preparation 4-((5-(((3-((trifluoromethyl) oxy)phenyl)amino)carbonyl)-2-naphthalenyl)oxy)-2-pyridinecarboxamide 6-(2-carbamoylpyrdin-4-yloxy)-1-napthoyl chloride (step b, 150 mg g, 0.41 mmol) was reacted with 3-trifluoromethoxyaniline 56 µL, 0.41 mmol, Aldrich) under the conditions of Example 421 Step c to furnish the title compound as a yellow solid. MS (ESI, pos. ion) m/z: 468.1 (M+1). Mass Calc'd for $C_{24}H_{16}F_3N_3O_4$: 467.40.

The following compounds were prepared similarly to the procedure outlined in Example 421 step c using either TEA or DIEA as the base.

EXAMPLE 686

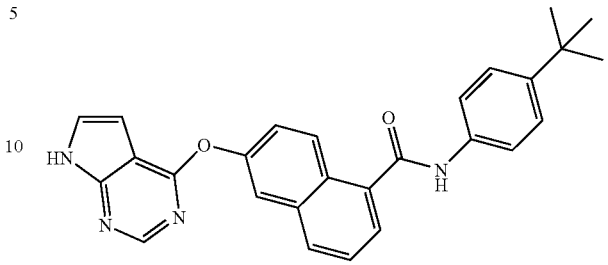

| Example No. | Structure & Name | Mol Formula | Mass | M + H |
|---|---|---|---|---|
| 683 | 4-((5-(((3-chlorophenyl)amino)carbonyl)-2-naphthalenyl)oxy)-2-pyridinecarboxamide | $C_{23}H_{16}ClN_3O_3$ | 417.85 | 418.1 |
| 684 | 4-((5-(((3-(methoxy)phenyl)amino)carbonyl)-2-naphthalenyl)oxy)-2-pyridinecarboxamide | $C_{24}H_{19}N_3O_4$ | 413.43 | 414.1 |
| 685 | 4-((5-(((3-methylphenyl)amino)carbonyl)-2-naphthalenyl)oxy)-2-pyridinecarboxamide | $C_{24}H_{19}N_3O_3$ | 397.43 | 398.1 |

N-(4-(1,1-dimethylethyl)phenyl)-6-(7H-pyrrolo[2,3-d]pyrimidin-4-yloxy)-1-naphthalenecarboxamide Step (a) Preparation of 6-(7H-pyrrolo[2,3-d]pyrimidin-4-yloxy)-1-naphthoic acid $Cs_2CO_3$ (23.4 g, 71.9 mmol) was added in one portion to a solution of 6-hydroxy-1-naphthoic acid (5.41 g, 28.7 mmol) and 6-chloro-7-deazapurine (3.68 g, 24.0 mmol) in DMSO (47.9 ml) at RT. The resulting mixture was heated to 100° C. and stirred for 14 hours. The mixture was cooled to RT and neutralized to a pH of 7 with 6N HCl. Solid material proceeded to crash out of solution. The entire mixture was centrifuged and the liquid was decanted. To the solid was added saturated aqueous $NaHCO_3$ and the resulting mixture was agitated over night on a rotating plate. The mixture was centrifuged again and decanted into a 1 L flask. The solution was acidified to neutral pH, centrifuged again and decanted. EtOAc was added to the solid material, the mixture centrifuged and the liquid was decanted to reveal the desired compound. MS (ESI, pos. ion) m/z: 306.1 (M+1). Mass Calc'd for $C_{18}H_{15}NO_3$: 305.08.

Step (b) Preparation of 6-(7H-pyrrolo[2,3-d]pyrimidin-4-yloxy)-1-naphthoyl chloride To a solution of 6-(7H-pyrrolo[2,3-d]pyrimidin-4-yloxy)-1-naphthoic acid (357 mg, 1.17 mmol) in DCM (11.7 mL) under an $N_2$ atmosphere, was added DMF (2 drops) followed by $(COCl)_2$ (143 μL, 1.64 mmol) dropwise. After stirring at RT for 4 hours, the reaction mixture became a yellow slurry. An aliquot was removed and placed in a vial containing 500 μl of 1M $MeNH_2$. After 5 min, the resulting solution was analyzed by LCMS to indicate complete conversion to the methylamine and that no acid was present in the reaction mixture. The slurry was concentrated to a yellow stable solid, which was taken directly to the next step of the reaction sequence.

Step (c) Preparation of N-(4-(1,1-dimethylethyl)phenyl)-6-(7H-pyrrolo[2,3-d]pyrimidin-4-yloxy)-1-naphthalenecarboxamide THF (1.3 mL) was added to 6-(7H-pyrrolo[2,3-d]pyrimidin-4-yloxy)-1-naphthoyl chloride (84.0 mg, 0.259 mmol) in a 10 mL round bottom flask, followed by 4-t-butyl aniline (62.4 μL, 0.389 mmol) and Hunig's base (45.1 μL, 0.259 mmol). The resulting solution was stirred for 14 h and then transferred to a 50 mL flask. To this solution was added ~5 g of silica gel. The resulting slurry was concentrated by reduced pressure. The impregnated silica gel was loaded into a dry pack column cartridge and the crude mixture was purified through Biotage chromatography (Hex:EtOAc). The collected product was repurified through trituration with DCM. MS (ESI, pos. ion) m/z: 437.1 (M+1). Mass Calc'd for $C_{18}H_{15}NO_3$: 436.51.

The following compounds were prepared similarly to the procedure outlined in Example 686.

| Example No. | Structure & Name | Mol Formula | Mass | M + H |
|---|---|---|---|---|
| 687 | 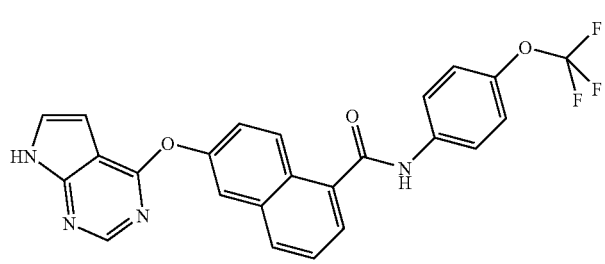<br>6-(7H-pyrrolo[2,3-d]pyrimidin-4-yloxy)-N-(4-((trifluoromethyl)oxy)phenyl)-1-naphthalenecarboxamide | $C_{24}H_{15}F_3N_4O_3$ | 464.4 | 465.1 |
| 688 | 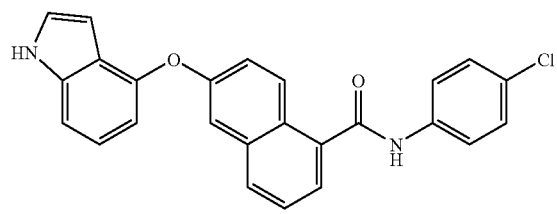<br>N-(4-chlorophenyl)-6-(7H-pyrrolo[2,3-d]pyrimidin-4-yloxy)-1-naphthalenecarboxamide | $C_{23}H_{15}ClN_4O_2$ | 414.85 | 415.0 |

| Example No. | Structure & Name | Mol Formula | Mass | M + H |
|---|---|---|---|---|
| 689 | 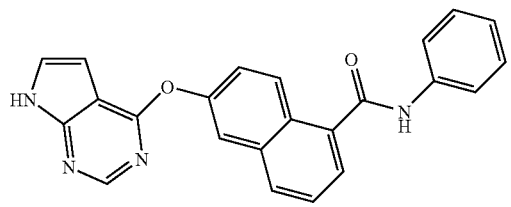<br>N-phenyl-6-(7H-pyrrolo[2,3-d]pyrimidin-4-yloxy)-1-naphthalenecarboxamide | C₂₃H₁₆N₄O₂ | 380.4 | 38.1 |
| 690 | 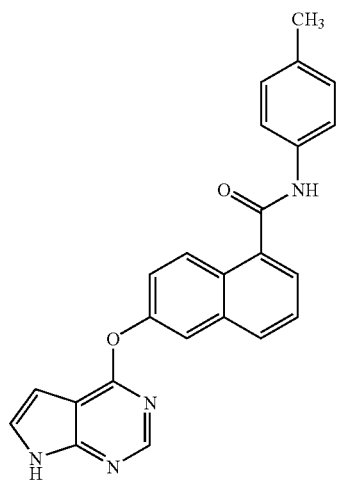<br>N-(4-methylphenyl)-6-(7H-pyrrolo[2,3-d]pyrimidin-4-yloxy)-1-naphthalenecarboxamide | C₂₄H₁₈N₄O₂ | 394.43 | 395.1 |
| 691 | 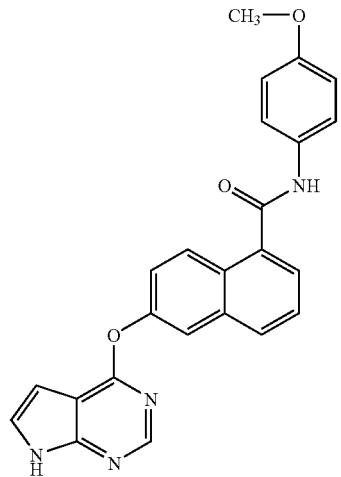<br>N-(4-(methoxy)phenyl)-6-(7H-pyrrolo[2,3-d]pyrimidin-4-yloxy)-1-naphthalenecarboxamide | C₂₄H₁₈N₄O₃ | 410.43 | 41 |

| Example No. | Structure & Name | Mol Formula | Mass | M + H |
|---|---|---|---|---|
| 692 | 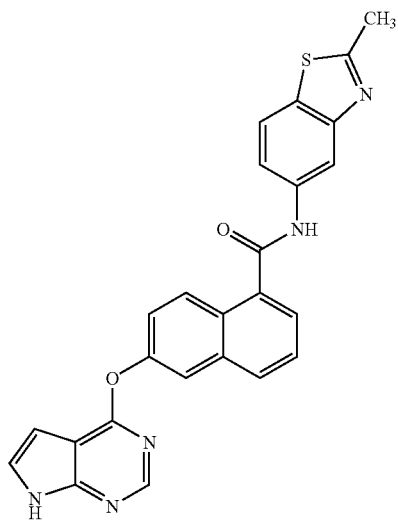<br>N-(2-methyl-1,3-benzothiazol-5-yl)-6-(7H-pyrrolo[2,3-d]pyrimidin-4-yloxy)-1-naphthalenecarboxamide | $C_{25}H_{17}N_5O_2S$ | 451.51 | 452.1 |
| 693 | 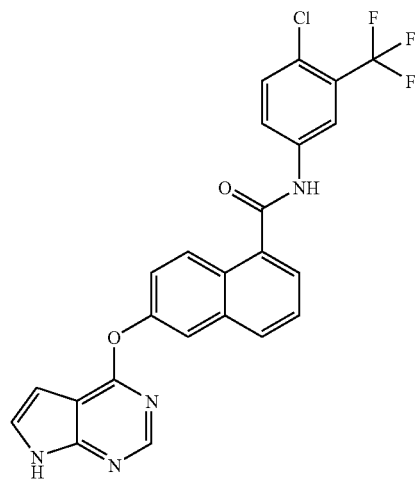<br>N-(4-chloro-3-(trifluoromethyl)phenyl)-6-(7H-pyrrolo[2,3-d]pyrimidin-4-yloxy)-1-naphthalenecarboxamide | $C_{24}H_{14}ClF_3N_4O_2$ | 482.85 | 483.0 |

| Example No. | Structure & Name | Mol Formula | Mass | M + H |
|---|---|---|---|---|
| 694 | 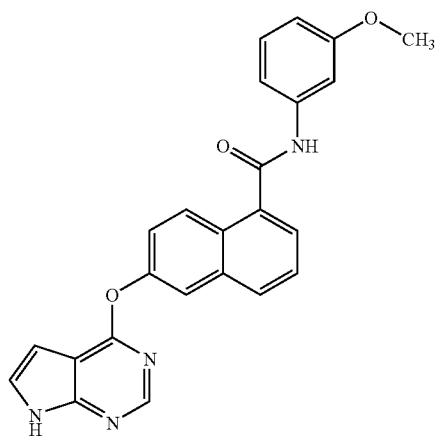<br>N-(3-methoxy)phenyl)-6-(7H-pyrrolo[2,3-d]pyrimidin-4-yloxy)-1-naphthalenecarboxamide | $C_{24}H_{18}N_4O_3$ | 410.43 | 411.1 |
| 695 | 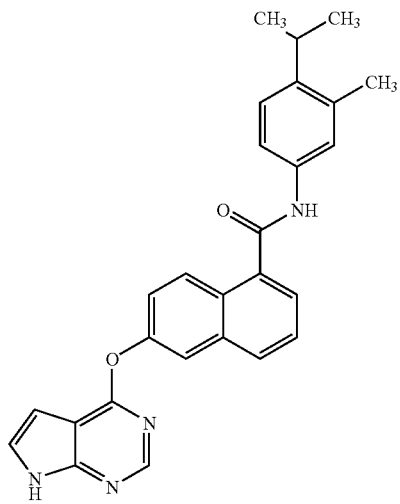<br>N-(3-methyl-4-(1-methylethyl)phenyl)-6-(7H-pyrrolo[2,3-d]pyrimidin-4-yloxy)-1-naphthalenecarboxamide | $C_{27}H_{24}N_4O_2$ | 436.51 | 437.1 |
| 696 | 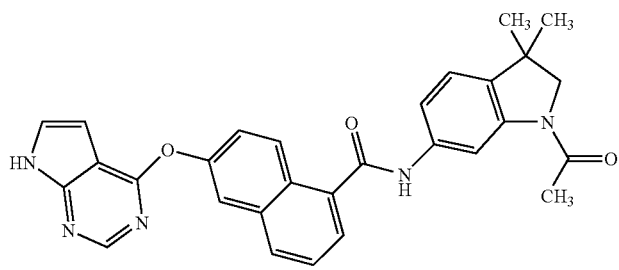<br>N-(1-acetyl-3,3-dimethyl-2,3-dihydro-1H-indol-6-yl)-6-(7H-pyrrolo[2,3-d]pyrimidin-4-yloxy)-1-naphthalenecarboxamide | $C_{29}H_{25}N_5O_3$ | 491.55 | 492.2 |

-continued

| Example No. | Structure & Name | Mol Formula | Mass | M + H |
|---|---|---|---|---|
| 697 | 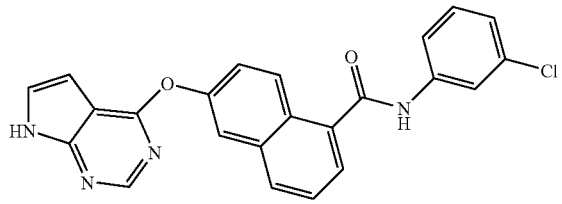<br>N-(3-chlorophenyl)-6-(7H-pyrrolo[2,3-d]pyrimidin-4-yloxy)-1-naphthalenecarboxamide | $C_{23}H_{15}ClN_4O_2$ | 414.85 | 415.0 |
| 698 | 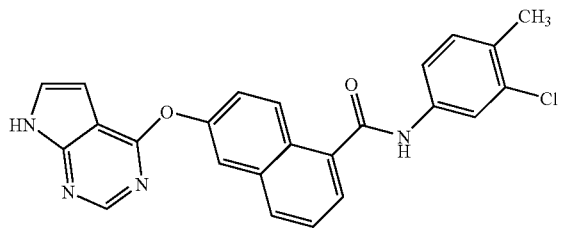<br>N-(3-chloro-4-methylphenyl)-6-(7H-pyrrolo[2,3-d]pyrimidin-4-yloxy)-1-naphthalenecarboxamide | $C_{24}H_{17}ClN_4O_2$ | 428.88 | 429.1 |
| 699 | 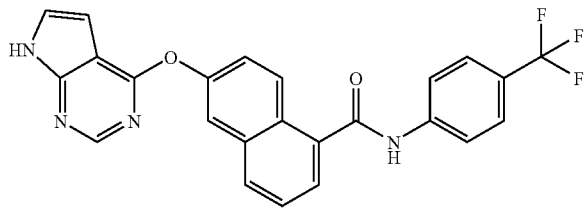<br>6-(7H-pyrrolo[2,3-d]pyrimidin-4-yloxy)-N-(4-(trifluoromethyl)phenyl)-1-naphthalenecarboxamide | $C_{24}H_{15}F_3N_4O_2$ | 448.4 | 449.1 |
| 700 | 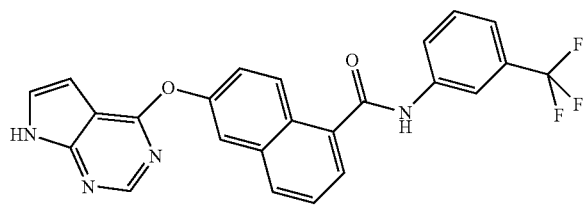<br>6-(7H-pyrrolo[2,3-d]pyrimidin-4-yloxy)-N-(3-(trifluoromethyl)phenyl)-1-naphthalenecarboxamide | $C_{24}H_{15}F_3N_4O_2$ | 448.4 | 449.0 |

| Example No. | Structure & Name | Mol Formula | Mass | M + H |
|---|---|---|---|---|
| 701 | 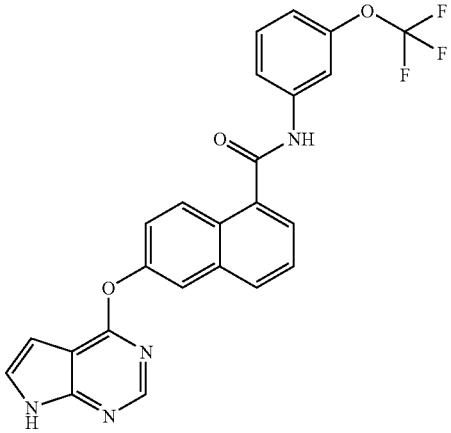<br>6-(7H-pyrrolo[2,3-d]pyrimidin-4-yloxy)-N-(3-((trifluoromethyl)oxy)phenyl)-1-naphthalenecarboxamide | $C_{24}H_{15}F_3N_4O_3$ | 464.4 | 465.1 |
| 702 | 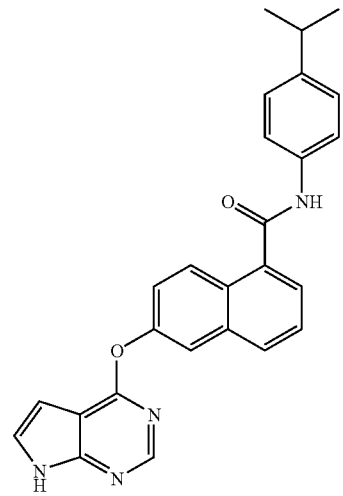<br>N-(4-(1-methylethyl)phenyl)-6-(7H-pyrrolo[2,3-d]pyrimidin-4-yloxy)-1-naphthalenecarboxamide | $C_{26}H_{22}N_4O_2$ | 422.49 | 423.1 |
| 703 | 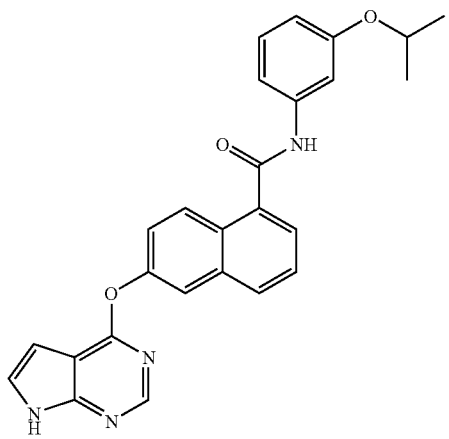<br>N-(3-((1-methylethyl)oxy)phenyl)-6-(7H-pyrrolo[2,3-d]pyrimidin-4-yloxy)-1-naphthalenecarboxamide | $C_{26}H_{22}N_4O_3$ | 438.49 | 4 |

| Example No. | Structure & Name | Mol Formula | Mass | M + H |
|---|---|---|---|---|
| 704 | 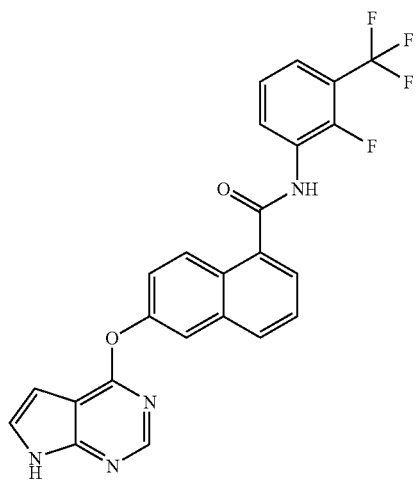<br>N-(2-fluoro-3-(trifluoromethyl)phenyl)-6-(7H-pyrrolo[2,3-d]pyrimidin-4-yloxy)-1-naphthalenecarboxamide | $C_{24}H_{14}F_4N_4O_2$ | 466.39 | 467.1 |
| 705 | 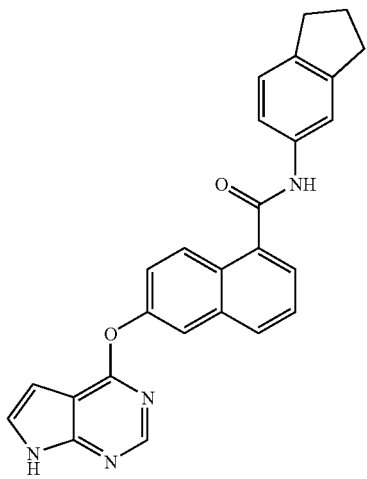<br>N-(2,3-dihydro-1H-inden-5-yl)-6-(7H-pyrrolo[2,3-d]pyrimidin-4-yloxy)-1-naphthalenecarboxamide | $C_{26}H_{20}N_4O_2$ | 420.47 | 421.1 |
| 706 | 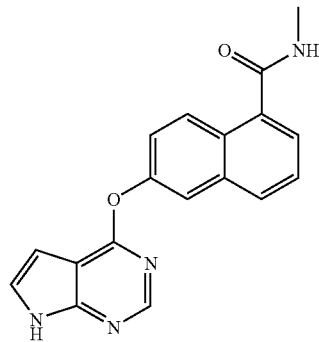<br>N-methyl-6-(7H-pyrrolo[2,3-d]pyrimidin-4-yloxy)-1-naphthalenecarboxamide | $C_{18}H_{14}N_4O_2$ | 318.33 | 319.1 |

-continued
| Example No. | Structure & Name | Mol Formula | Mass | M + H |
|---|---|---|---|---|
| 707 | 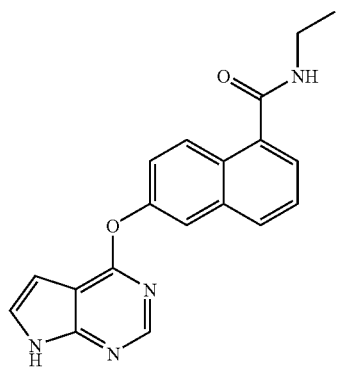<br>N-ethyl-6-(7H-pyrrolo[2,3-d]pyrimidin-4-yloxy)-1-naphthalenecarboxamide | $C_{19}H_{16}N_4O_2$ | 332.36 | 333.1 |
| 708 | 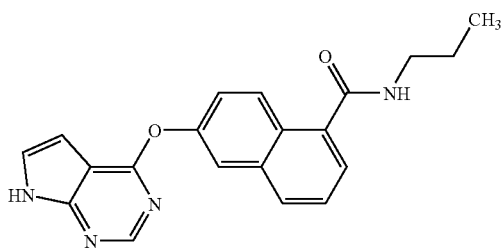<br>N-propyl-6-(7H-pyrrolo[2,3-d]pyrimidin-4-yloxy)-1-naphthalenecarboxamide | $C_{20}H_{18}N_4O_2$ | 346.39 | 347.1 |
| 709 | 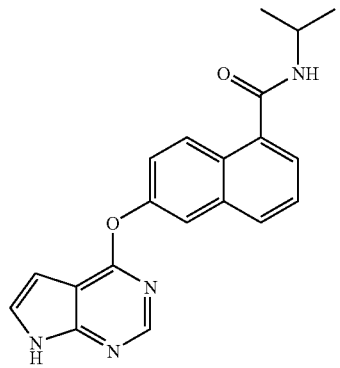<br>N-(1-methylethyl)-6-(7H-pyrrolo[2,3-d]pyrimidin-4-yloxy)-1-naphthalenecarboxamide | $C_{20}H_{18}N_4O_2$ | 346.39 | 347.1 |

| Example No. | Structure & Name | Mol Formula | Mass | M + H |
|---|---|---|---|---|
| 710 | 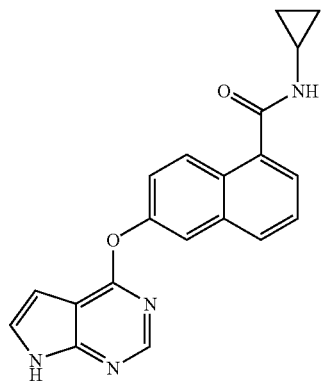<br>N-cyclopropyl-6-(7H-pyrrolo[2,3-d]pyrimidin-4-yloxy)-1-naphthalenecarboxamide | C$_{20}$H$_{16}$N$_4$O$_2$ | 344.37 | 345.1 |
| 711 | 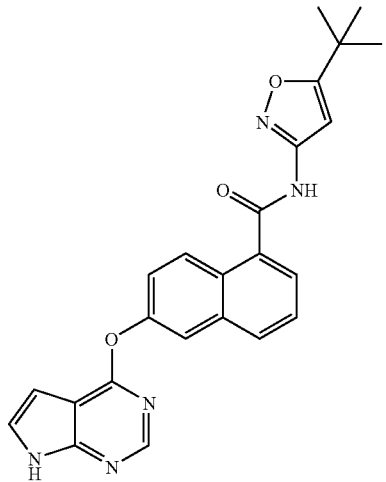<br>N-(5-(1,1-dimethylethyl)-3-isoxazolyl)-6-(7H-pyrrolo[2,3-d]pyrimidin-4-yloxy)-1-naphthalenecarboxamide | C$_{24}$H$_{21}$N$_5$O$_3$ | 427.46 | 428.1 |
| 712 | 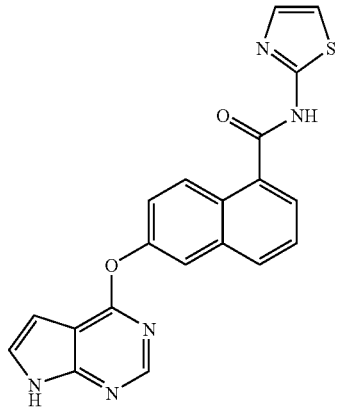<br>6-(7H-pyrrolo[2,3-d]pyrimidin-4-yloxy)-N-(1,3-thiazol-2-yl)-1-naphthalenecarboxamide | C$_{20}$H$_{13}$N$_5$O$_2$S | 387.42 | 388.0 |

-continued
| Example No. | Structure & Name | Mol Formula | Mass | M + H |
|---|---|---|---|---|
| 713 | 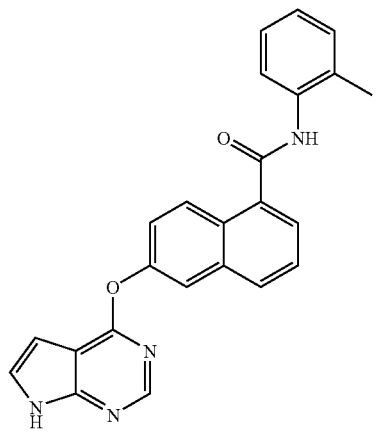<br>N-(2-methylphenyl)-6-(7H-pyrrolo[2,3-d]pyrimidin-4-yloxy)-1-naphthalenecarboxamide | $C_{24}H_{18}N_4O_2$ | 394.43 | 395.1 |
| 714 | 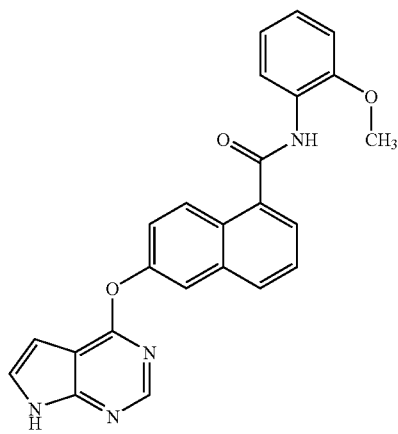<br>N-(2-(methoxy)phenyl)-6-(7H-pyrrolo[2,3-d]pyrimidin-4-yloxy)-1-naphthalenecarboxamide | $C_{24}H_{18}N_4O_3$ | 410.43 | 411.1 |
| 715 | 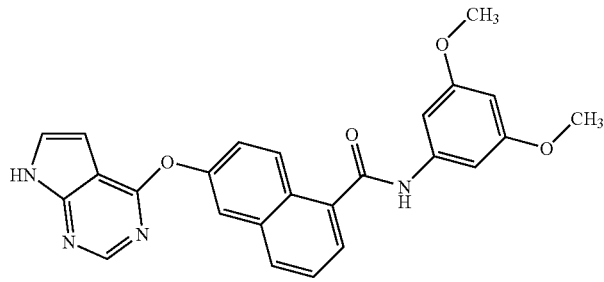<br>N-(3,5-bis(methoxy)phenyl)-6-(7H-pyrrolo[2,3-d]pyrimidin-4-yloxy)-1-naphthalenecarboxamide | $C_{25}H_{20}N_4O_4$ | 440.46 | 441.1 |

-continued
| Example No. | Structure & Name | Mol Formula | Mass | M + H |
|---|---|---|---|---|
| 716 | 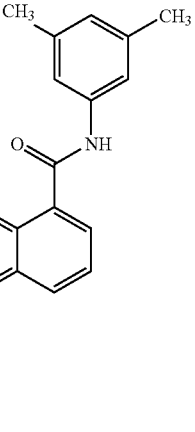<br>N-(3,5-dimethylphenyl)-6-(7H-pyrrolo[2,3-d]pyrimidin-4-yloxy)-1-naphthalenecarboxamide | $C_{25}H_{20}N_4O_2$ | 408.46 | 409.1 |
| 717 | 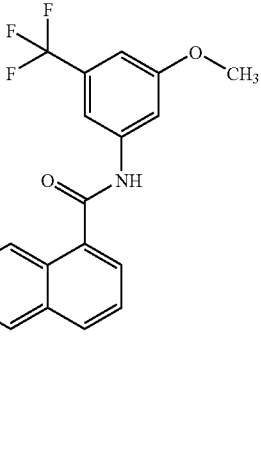<br>N-(3-(methoxy)-5-(trifluoromethyl)phenyl)-6-(7H-pyrrolo[2,3-d]pyrimidin-4-yloxy)-1-naphthalenecarboxamide | $C_{25}H_{17}F_3N_4O_3$ | 478.43 | 479.1 |
| 718 | 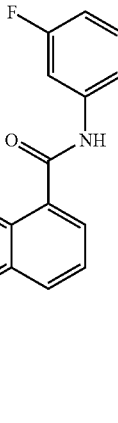<br>N-(3,5-difluorophenyl)-6-(7H-pyrrolo[2,3-d]pyrimidin-4-yloxy)-1-naphthalenecarboxamide | $C_{23}H_{14}F_2N_4O_2$ | 416.39 | 417.0 |

| Example No. | Structure & Name | Mol Formula | Mass | M + H |
|---|---|---|---|---|
| 719 | 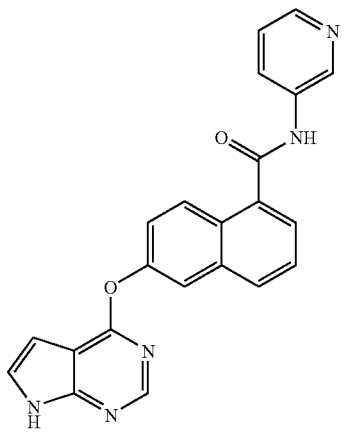<br>N-(3-pyridinyl)-6-(7H-pyrrolo[2,3-d]pyrimidin-4-yloxy)-1-naphthalenecarboxamide | $C_{22}H_{15}N_5O_2$ | 381.39 | 382.0 |
| 720 | 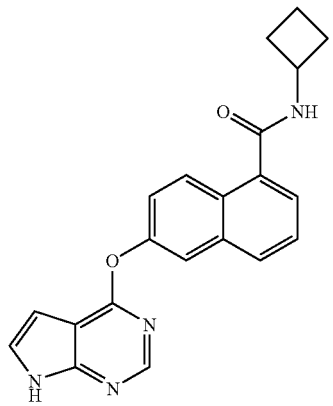<br>N-cyclobutyl-6-(7H-pyrrolo[2,3-d]pyrimidin-4-yloxy)-1-naphthalenecarboxamide | $C_{21}H_{18}N_4O_2$ | 358.4 | 359.0 |
| 721 | 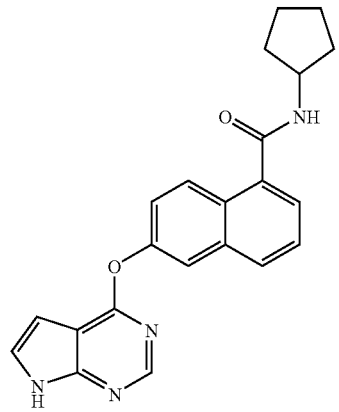<br>N-cyclopentyl-6-(7H-pyrrolo[2,3-d]pyrimidin-4-yloxy)-1-naphthalenecarboxamide | $C_{22}H_{20}N_4O_2$ | 372.43 | 373.1 |

-continued
| Example No. | Structure & Name | Mol Formula | Mass | M + H |
|---|---|---|---|---|
| 722 | 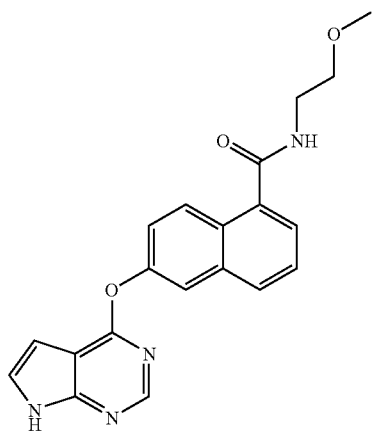<br>N-(2-methoxy)ethyl)-6-(7H-pyrrolo[2,3-d]pyrimidin-4-yloxy)-1-naphthalenecarboxamide | C$_{20}$H$_{18}$N$_4$O$_3$ | 362.39 | 363.0 |
| 723 | 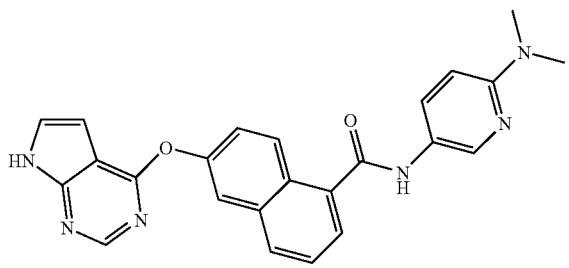<br>N-(6-(dimethylamino)-3-pyridinyl)-6-(7H-pyrrolo[2,3-d]pyrimidin-4-yloxy)-1-naphthalenecarboxamide | C$_{24}$H$_{20}$N$_6$O$_2$ | 424.46 | 42.1 |
| 724 | 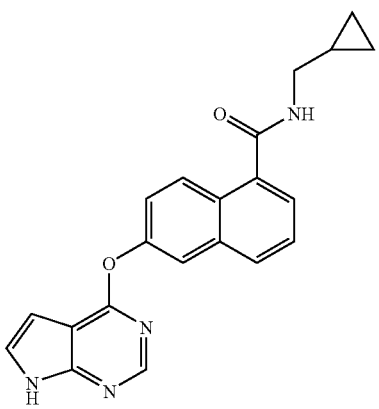<br>N-(cyclopropylmethyl)-6-(7H-pyrrolo[2,3-d]pyrimidin-4-yloxy)-1-naphthalenecarboxamide | C$_{21}$H$_{18}$N$_4$O$_2$ | 358.4 | 359.0 |

-continued

| Example No. | Structure & Name | Mol Formula | Mass | M + H |
|---|---|---|---|---|
| 725 | 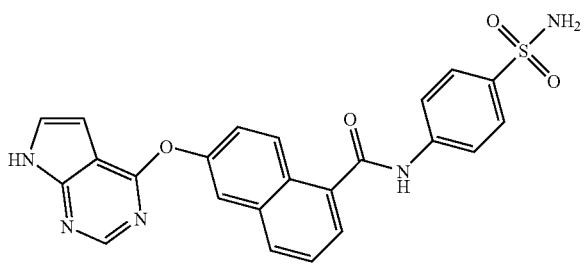<br>N-(4-(aminosulfonyl)phenyl)-6-(7H-pyrrolo[2,3-d]pyrimidin-4-yloxy)-1-naphthalenecarboxamide | $C_{23}H_{17}N_5O_4S$ | 459.48 | 460.0 |
| 726 | 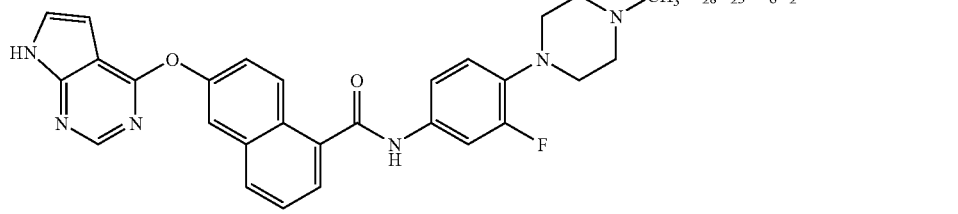<br>N-(3-fluoro-4-(4-methyl-1-piperazinyl)phenyl)-6-(7H-pyrrolo[2,3-d]pyrimidin-4-yloxy)-1-naphthalenecarboxamide | $C_{28}H_{25}FN_6O_2$ | 496.54 | 497.1 |
| 727 | 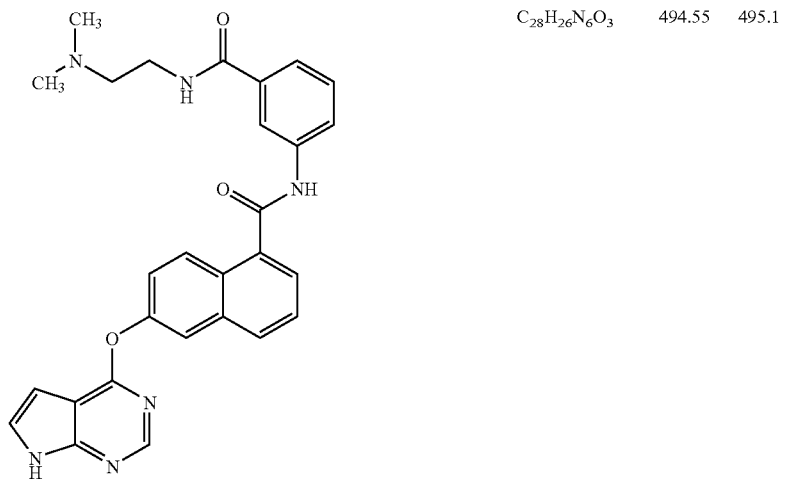<br>N-(3-(((2-dimethylamino)ethyl)amino)carbonyl)phenyl)-6-(7H-pyrrolo[2,3-d]pyrimidin-4-yloxy)-1-naphthalenecarboxamide | $C_{28}H_{26}N_6O_3$ | 494.55 | 495.1 |

| Example No. | Structure & Name | Mol Formula | Mass | M + H |
|---|---|---|---|---|
| 728 | 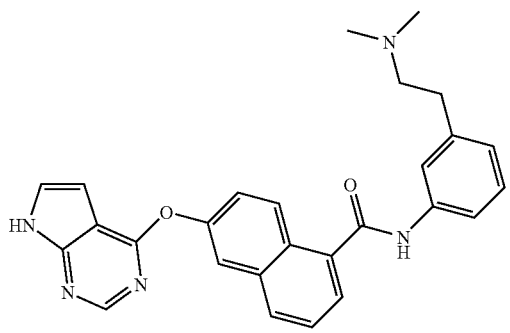<br>N-(3-(2-(dimethylamino)ethyl)phenyl)-6-(7H-pyrrolo[2,3-d]pyrimidin-4-yloxy)-1-naphthalenecarboxamide | $C_{27}H_{25}N_5O_2$ | 451.53 | 452.1 |
| 729 | 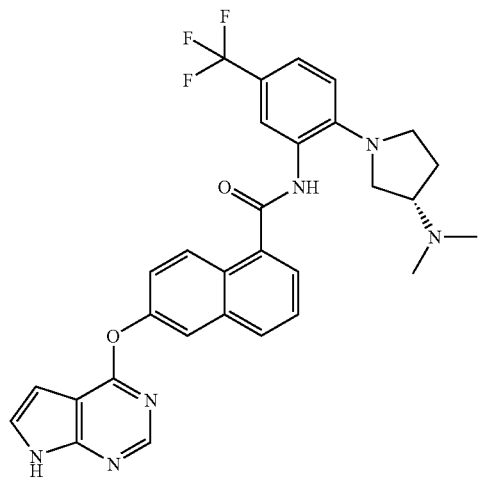<br>N-(2-((3S)-3-(dimethylamino)-1-pyrrolidinyl)-5-(trifluoromethyl)phenyl)-6-(7H-pyrrolo[2,3-d]pyrimidin-4-yloxy)-1-naphthalenecarboxamide | $C_{30}H_{27}F_3N_6O_2$ | 560.58 | 561.2 |
| 730 | 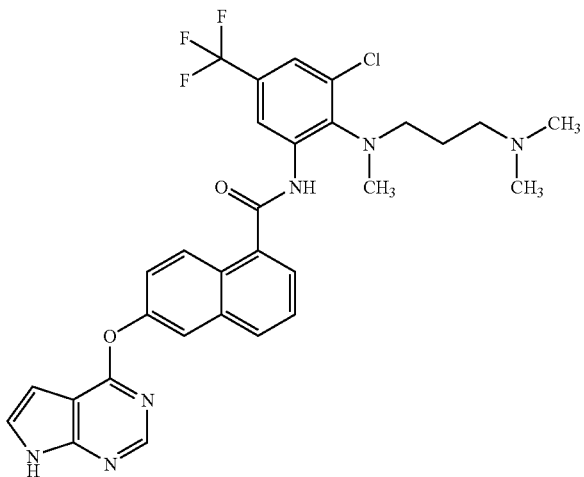<br>N-(3-chloro-2-((3-(dimethylamino)propyl)(methyl)amino)-5-(trifluoromethyl)phenyl)-6-(7H-pyrrolo[2,3-d]pyrimidin-4-yloxy)-1-naphthalenecarboxamide | $C_{30}H_{28}ClF_3N_6O_2$ | 597.04 | 597.2 |

| Example No. | Structure & Name | Mol Formula | Mass | M + H |
|---|---|---|---|---|
| 731 | 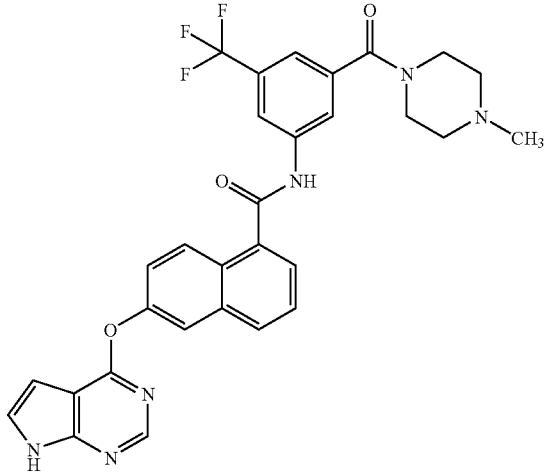<br>N-(3-((4-methyl-1-piperazinyl)carbonyl)-5-(trifluoromethyl)phenyl)-6-(7H-pyrrolo[2,3-d]pyrimidin-4-yloxy)-1-naphthalenecarboxamide | $C_{30}H_{25}F_3N_6O_3$ | 574.56 | 575.1 |

EXAMPLE 732

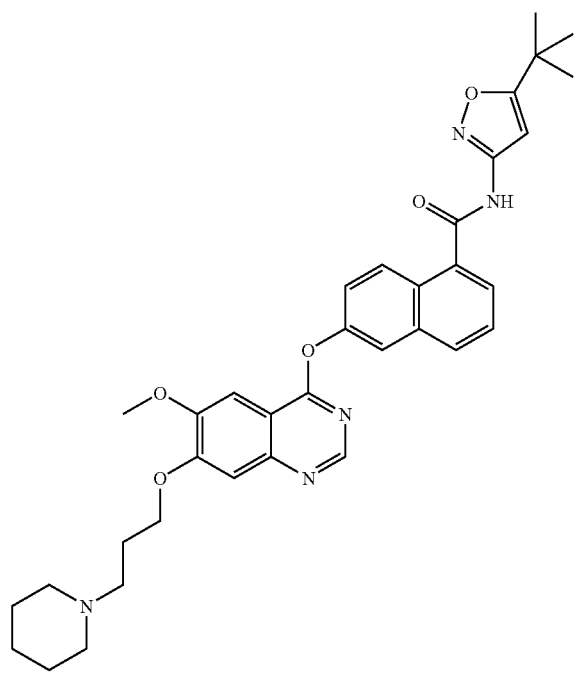

N-(5-(1,1-dimethylethyl)-3-isoxazolyl)-6-((6-(methoxy)-7-((3-(1-piperidinyl)propyl)oxy)-4-quinazolinyl)oxy)-1-naphthalenecarboxamide Step (a) Preparation of (6-methoxy-4-oxo-7-(3-piperidin-1-yl)propoxy)quinazolin-3(4H)-yl)methyl pivalate To a solution of (7-hydroxy-6-methoxy-4-oxoquinazolin-3(4H)-yl)methyl pivalate (2.0 g, 6.52 mmol, see J. Med. Chem., 47:871 (2004)) and 1-(2-chloropropyl)piperidine hydrochloride (1.4 g, 8.85 mmol) in DMF (13 mL), was added potassium carbonate (2.7 g, 19.59 mmol). The mixture was heated to 90° C. for 20 h. After cooling RT, the mixture was diluted with $H_2O$ (50 mL). The mixture was extracted with EtOAc (3×25 mL) and the organic extracts were washed with $H_2O$ and brine. The organic phase was dried over $MgSO_4$, filtered, and concentrated in vacuo to give the title compound as a light yellow solid. MS (ESI, pos. ion) m/z: 432 (M+1). Mass Calc'd for $C_{23}H_{33}CN_3O_5$: 431.2.

Step (b) Preparation of 6-methoxy-7-(3-piperidin-1-yl)propoxy)quinazoline-4(3H)-one Dissolve (6-methoxy-4-oxo-7-(3-piperidin-1-yl)propoxy)quinazolin-3(4H)-yl)methyl pivalate (1.9 g, 4.5 mmol))in a solution of ammonia in MeOH (2M, 45 mL). The solution was stirred at ambient temperature for 24 h, then diluted with $CH_2Cl_2$ (20 mL). The mixture was filtered and the filtrate was concentrated in vacuo. The crude mixture was triturated with $Et_2O/CH_2Cl_2$ (95:5) and the precipitate filtered and dried under vacuum to give title compound as a white solid. MS (ESI, pos. ion) m/z: 318 (M+1). Mass Calc'd for $C_{17}H_{23}N_3O_3$: 317.1.

Step (c) Preparation of 4-chloro-6-methoxy-7-(3-piperidin-1-yl)propoxy)quinazoline To a solution of 6-methoxy-7-(3-piperidin-1-yl)propoxy)quinazoline-4(3H)-one (1.53 g, 4.82 mmol) in thionyl chloride (11.3 mL), was added DMF (0.10 mL). The mixture was heated to 80° C. for 1.5 h. After cooling RT, the mixture was concentrated in vacuo then diluted with $CH_2Cl_2$. The solution was cooled to 0° C. in an ice bath followed by addition of $H_2O$ and aqueous saturated $NaHCO_3$ to adjust the pH of the mixture to 8. The mixture was extracted with $CH_2Cl_2$ (3×25 mL) and the organic extracts were washed with $H_2O$ and brine.

The organic phase was dried over MgSO$_4$, filtered, and concentrated in vacuo. The resulting residue was purified by silica gel column chromatography (92:8 CH$_2$Cl$_2$/MeOH) to yield the title compound as a light yellow solid. MS (ESI, pos. ion) m/z: 336 (M+1). Mass Calc'd for C$_{17}$H$_{22}$ClN$_3$O$_2$: 335.1.

Step (d) Preparation of 6-(6-methoxy-7-(3-(piperidin-1-yl)propoxy)quinazolin-4-yloxy)-1-naphthoic acid To a solution of 6-hydroxy-1-naphthoic acid (0.26 g, 1.36 mmol, 1.05 equiv) in DMSO (2 mL), was added potassium tert-butoxide (0.44 g, 3.90 mmol, 3.0 equiv). The solution was stirred at ambient temperature for a period of 15 minutes. To this solution was added, 4-chloro-6-methoxy-7-(3-piperidin-1-yl)propoxy)quinazoline (0.44 g, 1.30 mmol) in DMSO (1 mL). The reaction mixture was heated to 90° C. for 15 h. After cooling RT, the mixture was diluted with H$_2$O (10 mL) and acidified with 3N HCl to a pH of 5. The precipitate was isolated by filtration and vacuum dried to give the title compound as a light brown solid. MS (ESI, pos. ion) m/z: 488 (M+1). Mass Calc'd for C$_{28}$H$_{29}$N$_3$O$_5$: 487.2.

Step (e) Preparation of N-(5-(1,1-dimethylethyl)-3-isoxazolyl)-6-((6-(methoxy)-7-((3-(1-piperidinyl)propyl)oxy)-4-quinazolinyl)oxy)-1-naphthalenecarboxamide The compound was prepared according to Example 273, step e to afford the title compound as a light yellow solid. MS (ESI, pos. ion) m/z: 610.3 (M+1). Mass Calc'd for C$_{35}$H$_{39}$N$_5$O$_5$: 609.3.

The following examples were prepared similar to the procedures described in Example 732.

N-(3-chlorophenyl)-6-((6-(methoxy)-7-((3-(4-morpholinyl)propyl)oxy)-4-quinolinyl)oxy)-1-naphthalenecarboxamide Step (a) Preparation of 4-chloro-6-methoxyquinolin-7-ol To a solution of 7-(benzyloxy)-4-chloro-6-methoxyquinoline (WO98/13350A1)(2.0 g, 6.67 mmol) in TFA (13 mL), was added methansulfonic acid (0.95 mL, 13.3 mmol). The mixture was heated to reflux for 3 h. After cooling to RT, the mixture was concentrated in vacuo. The resulting residue was diluted with ice/H$_2$O and neutralized with cold 1N NaOH to a pH of 7. The resulting precipitate was stirred for 1 h at RT, filtered, and dried under high vacuum to give the title compound as a light yellow solid. MS (ESI, pos. ion) m/z: 210 (M+1). Mass Calc'd for C$_{10}$H$_8$ClNO$_2$: 209.0.

Step (b) Preparation of 4-(3-chloropropyl)morpholine

To a solution of 1-bromo-3-chloropropane (3.4 mL, 34.5 mmol) in DMF (40 mL), was added potassium carbonate (6.4 g, 69 mmol) and morpholine (2.0 mL, 23.0 mmol). The solution was stirred at RT for 15 h, then diluted with H$_2$O (150 mL). The mixture was extracted with EtOAc (3×25 mL) and the organic extracts were washed with H$_2$O and brine. The organic phase was dried over MgSO$_4$, filtered, and concentrated in vacuo to give title compound as a colorless oil. MS (ESI, pos. ion) m/z: 164 (M+1). Mass Calc'd for C$_7$H$_{14}$ClNO: 163.08.

Step (c) Preparation of 4-chloro-6-methoxy-7-(3-morpholinopropoxy)quinoline

To a solution of 4-chloro-6-methoxyquinolin-7-ol (1.0 g, 4.77 mmol) and 4-(3-chloropropyl)morpholine (0.86 g, 5.25 mmol)in DMF (9.5 mL), was added potassium carbonate (2.0 g, 14.3 mmol). The mixture was heated to 90° C. for 15 h. After cooling RT, the mixture was diluted with H$_2$O (30 mL). The mixture was extracted with EtOAc (3×25 mL) and the organic extracts were washed with H$_2$O and brine. The organic phase was dried over MgSO$_4$, filtered, and concen-

| Example No. | Structure & Name | Mol Formula | Mass | M + H |
|---|---|---|---|---|
| 733 | 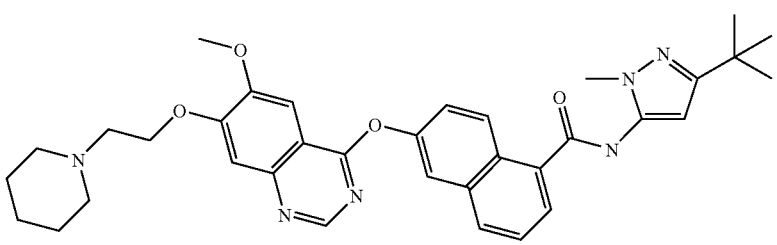 N-(3-(1,1-dimethylethyl)-1-methyl-1H-pyrazol-5-yl)-6-((6-(methoxy)-7-((2-(1-piperidinyl)ethyl)oxy)-4-quinazolinyl)oxy)-1-naphthalenecarboxamide | C$_{35}$H$_{40}$N$_6$O$_4$ | 608.73 | 609.3 |

EXAMPLE 734

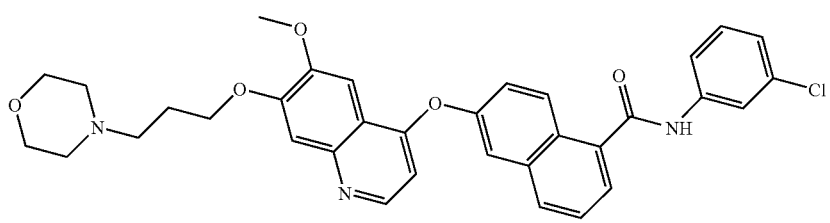

trated in vacuo. The resulting residue was purified by silica gel column chromatography (5% MeOH/CH$_2$Cl$_2$) to yield the title compounds as a light yellow solid. MS (ESI, pos. ion) m/z: 337 (M+1). Mass Calc'd for C$_{17}$H$_{22}$ClN$_2$O$_3$: 336.1.

Step (d) Preparation of 6-(6-methoxy-7-(3-morpholinopropoxy)quinolin-4-yloxy)-1-naphthoic acid The compound was prepared according to Example 732, step d to afford the title compound as a light brown solid. MS (ESI, pos. ion) m/z: 489 (M+1). Mass Calc'd for C$_{28}$H$_{28}$N$_2$O$_6$: 488.2.

Step (e) Preparation of N-(3-chlorophenyl)-6-((6-(methyloxy)-7-((3-(4-morpholinyl)propyl)oxy)-4-quinolinyl)oxy)-1-naphthalenecarboxamide The compound was prepared according to Example 273, step e to afford the title compound as a light yellow solid. MS (ESI, pos. ion) m/z: 598.2 (M+1). Mass Calc'd for C$_{34}$H$_{32}$ClN$_3$O$_5$: 597.2.

EXAMPLE 735

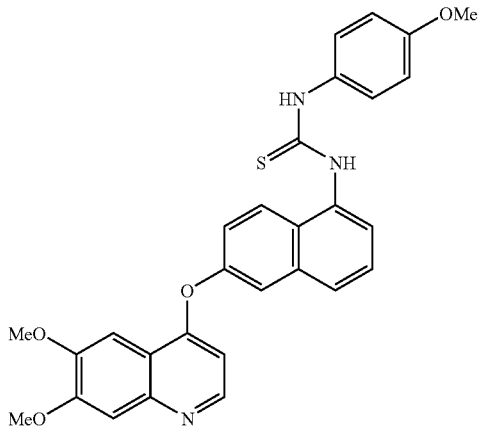

N-(6-((6,7-bis(methoxy)-4-quinolinyl)oxy)-1-naphthalenyl)-N'-(4-(methoxy)phenyl)thiourea Step (a) Preparation of 4-(5-isothiocyanatonaphthalen-2-yloxy)-6,7-dimethoxyquinoline Thiocarbonyl diimidazole (108 mg, 0.606 mmol) was added to a solution of 6-(6,7-dimethoxyquinolin-4-yloxy)naphthalen-1-amine (210, 0.606 mmol) and NEt$_3$ (84.5 μL, 0.606) in DCM (1.52 mL) in one portion at RT. After 15 minutes of stirring, LCMS and TLC indicated that the reaction was complete. The crude mixture was purified by silica gel chromatography (Hex:EtOAc). MS (ESI, pos. ion) m/z: 389.0 (M+1). Mass Calc'd for C$_{18}$H$_{15}$NO$_3$: 388.45.

Step (b) Preparation of N-(6-((6,7-bis(methoxy)-4-quinolinyl)oxy)-1-naphthalenyl)-N'-(4-(methoxy)phenyl)thiourea To a solution of 4-(5-isothiocyanatonaphthalen-2-yloxy)-6,7-dimethoxyquinoline (27 mg, 0.070 mmol) in DCM (348 μL) at RT was added 4-methoxyaniline (17.2 mg, 0.140 mmol) in one portion. After stirring for 14 h, the crude mixture was concentrated under reduced pressure and purified by silica gel chromatography. MS (ESI, pos. ion) m/z: 512.1. (M+1). Mass Calc'd for C$_{18}$H$_{15}$NO$_3$: 511.60.

The following examples were prepared similar to the procedures described in Example 735.

| Example No. | Structure & Name | Mol Formula | Mass | M + H |
|---|---|---|---|---|
| 736 | 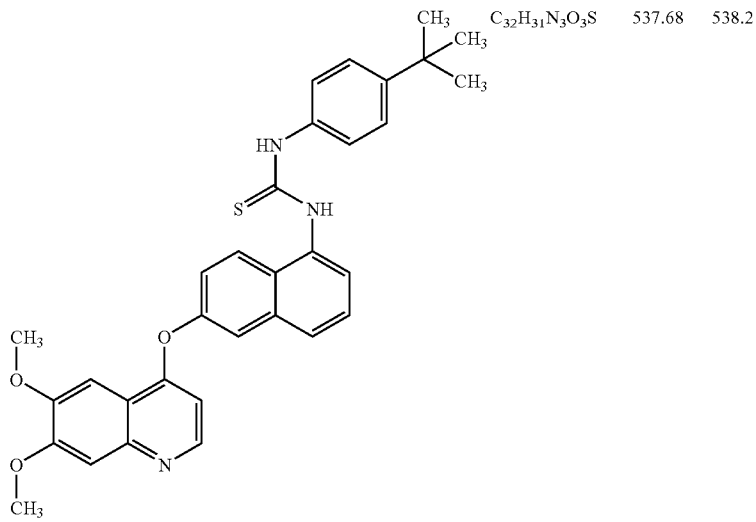<br>N-(6-((6,7-bis(methoxy)-4-quinolinyl)oxy)-1-naphthalenyl)-N'-(4-(1,1-dimethylethyl)phenyl)thiourea | C$_{32}$H$_{31}$N$_3$O$_3$S | 537.68 | 538.2 |

-continued

| Example No. | Structure & Name | Mol Formula | Mass | M + H |
|---|---|---|---|---|
| 737 | N-(6-((6,7-bis(methoxy)-4-quinolinyl)oxy)-1-naphthalenyl)-N'-(3-(methoxy)phenyl)thiourea | C29H25N3O4S | 511.6 | 512.2 |
| 738 | N-(6-((6,7-bis(methoxy)-4-quinolinyl)oxy)-1-naphthalenyl)-N'-(4-(trifluoromethyl)phenyl)thiourea | C29H22F3N3O3S | 549.57 | 550.1 |

EXAMPLE 739

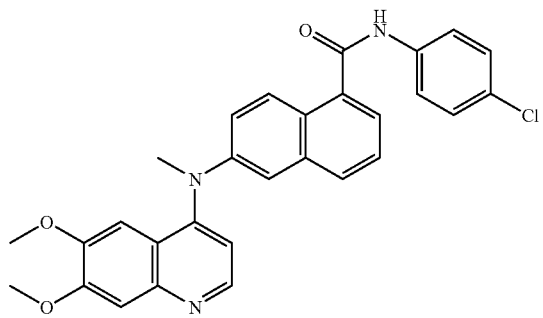

6-((6,7-bis(methoxy)-4-quinolinyl)(methyl)amino)-N-(4-chlorophenyl)-1-naphthalenecarboxamide Step (a) Preparation methyl-6-(trifluoromethylsulfonyloxy)-1-napthoate To a mixture of methyl-6-hydroxy-1-napthoate (1.5 g, 7.4 mmol) in dry $CH_2Cl_2$ (100 mL) at −78° C. was added diisoproylethylamine (3.8 mL, 21 mmol, Aldrich) and trifluoromethanesulfonic anhydride (1.4 mL, 8.1 mmol). The reaction was maintained at this temperature for 1 h at which point it was quenched by the addition of sat'd $NaHCO_3$ (50 mL). The mixture was warmed to ambient temperature and the aqueous layer was extracted with $CH_2Cl_2$ (3×50 mL). The combined organic layers were washed with brine, dried over $Na_2SO_4$ and concentrated in vacuo. The resulting brown residue was purified by silica gel column chromatography (10-30% acetone in hexanes) to give the title compound as a yellow solid. MS (ESI, pos. ion) m/z: 335.3 (M+1). Mass Calc'd for $C_{13}H_9F_3O_5S$: 334.27.

Step (b) Preparation methyl-6-amino-1-napthoate

To a solution of methyl-6-(trifluoromethylsulfonyloxy-1-napthoate (2.0 g, 6.0 mmol) in dimethoxyethane (10 mL) was added $Pd_2(dba)_3$ (55 mg, 0.06 mmol), 2-(dicyclohexylphosphino)biphenyl (84 mg, 0.23 mmol), $K_3PO_4$ (1.9 g, 8.9 mmol) and benzophenone imine (1.25 mL, 7.5 mmol). The mixture was heated at 90° C. for 10 h. After cooling to ambient temperature, 2N HCl (4 mL) was added the mixture was stirred vigorously for 1 h. EtOAc (5 mL) was added to the reaction and the mixture was basified to pH 14 with 6N NaOH. The aqueous layer was extracted with EtOAc (3×30 mL). The combined organic layers were washed with brine, dried over $Na_2SO_4$ and concentrated in vacuo. The resulting brown residue was purified by silica gel column chromatography (0-25% EtOAc in hexanes) to give the title compound as a orange oil. MS (ESI, pos. ion) m/z: 202.1 (M+1). Mass Calc'd for $C_{12}H_{11}NO_2$: 201.22.

Step (c) Preparation methyl-6-(6,7-dimethoxyquinolin-4-ylamino)-1-napthoate

To a mixture of methyl-6-amino-1-napthoate (300 mg, 1.5 mmol) and 4-chloro-6,7-dimethoxyquinoline (416 mg, 1.8 mmol) in a 20 mL sealed tube was added isopropyl alcohol (6 mL) and trifluoroacetic acid (287 µL, 3.7 mmol). The reaction vessel was sealed and heated at 90° C. for 1 h before being allowed to cool to ambient temperature. To the resulting thick yellow slurry was added isopropyl alcohol (6 mL). The reaction vessel was sealed and heated at 90° C. for 10 h. The mixture was then cooled to 0° C. and filtered. The resulting solid was washed well with cold $CH_3OH$ and dried in vacuo to provide the title compound as a yellow solid. MS (ESI, pos. ion) m/z: 389.3 (M+1). Mass Calc'd for $C_{23}H_{20}N_2O_4$: 388.42.

Step (d) Preparation methyl-6-(6,7-dimethoxyquinolin-4-yl)(methyl)amino)-1-napthoate To a suspension of methyl-6-(6,7-dimethoxyquinolin-4-ylamino)-1-napthoate (125 mg, 0.32 mmol) in DMF (3 mL) at 0° C. was added NaH (40 mg, 0.96 mmol, Aldrich). The resulting slurry was allowed to warm to ambient temperature and stir 0.5 h before being cooled to 0° C. and exposed to iodomethane (60 µL, 0.96 mmol). The mixture was allowed to warm to ambient temperature and stir for an additional 1 h before it was quenched with sat'd $NH_4Cl$ (10 mL) and extracted with $CH_2Cl_2$ (5×50 mL). The organic layer was washed with $H_2O$ (3×50 mL) then brine and dried over $Na_2SO_4$. Concentration and purification by silica gel chromatography (0-10% $CH_3OH$ in $CH_2Cl_2$) provided the title compound as a white solid. MS (ESI, pos. ion) m/z: 403.3 (M+1). Mass Calc'd for $C_{24}H_{22}N_2O_4$: 402.44.

Step (e) Preparation 6-(6,7-dimethoxyquinolin-4-yl)(methyl)amino)-1-napthoic acid To methyl-6-(6,7-dimethoxyquinolin-4-yl)(methyl)amino)-1-napthoate (275 mg, 0.68 mmol) in $CH_3OH$ (5 mL) was added 6 N NaOH (5 mL). The resulting mixture was maintained at RT for 10 h at which point the organics were removed in vacuo and the resulting mixture was diluted with $H_2O$ (5 mL) and acidified to pH 3 with 2N HCl. The resulting precipitate was collected by filtration and washed with $Et_2O$ (2×10 mL) to provide the title compound as a yellow solid. MS (ESI, pos. ion) m/z: 389.4 (M+1). Mass Calc'd for $C_{23}H_{20}N_2O_4$: 388.42.

Step (f) Preparation 6-(6,7-dimethoxyquinolin-4-yl) (methyl)amino)-1-napthoyl chloride 6-(6,7-dimethoxyquinolin-4-yl)(methyl)amino)-1-napthoic acid (60 mg g, 0.15 mmol) was reacted with oxalyl chloride (55 µL, 0.60 mmol) under the conditions of Example 421 Step b to give the title compound as a yellow solid. MS (ESI, pos. ion) m/z: 388.4 (M+MeOH). Mass Calc'd for $C_{24}H_{21}F_3NO_4$: 387.43.

Step (g) Preparation 6-((6,7-bis(methoxy)-4-quinolinyl)(methyl)amino)-N-(4-chlorophenyl)-1-naphthalenecarboxamide 6-(6,7-dimethoxyquinolin-4-yl)(methyl)amino)-1-napthoyl chloride (Step f, 63 mg, 0.15 mmol) was reacted with 4-chloroaniline (30 µL, 0.23 mmol) and TEA (85 µL, 0.61 mmol) under the conditions of Example 421 Step c to give the title compound as a white solid. MS (ESI, pos. ion) m/z: 497.8 (M+H). Mass Calc'd for $C_{30}H_{23}ClN_2O_3$: 496.98.

EXAMPLE 740

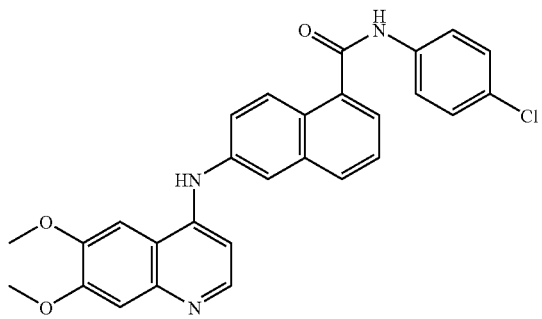

6-((6,7-bis(methoxy)-4-quinolinyl)amino)-N-(4-chlorophenyl)-1-naphthalenecarboxamide Step (a) Preparation of 6-(6,7-dimethoxynapthenlen-1-ylamino)1-napthoic acid Methyl-6-(6,7-dimethoxyquinolin-4-yl)(methyl)amino)-1-napthoate (275 mg, 0.68 mmol) in $CH_3OH$ (5 mL) was reacted with 6 N NaOH (5 mL) under the conditions of Example 739 Step e to give the title compound as a pale green powder. MS (ESI, pos. ion) m/z: 374.3 (M+1). Mass Calc'd for $C_{23}H_{19}NO_4$: 373.40.

Step (b) Preparation of 6-((6,7-bis(methoxy)-4-quinolinyl)amino)-N-(4-chlorophenyl)-1-naphthalenecarboxamide To a solution of 6-(6,7-dimethoxynapthenlen-1-ylamino) 1-napthoic acid (step a, 150 mg, 0.38 mmol), EDC (295 mg, 1.5 mmol), HOBt (208 mg, 1.5 mmol) and 4-chloroaniline (295 mg, 2.3 mmol) in DMF (8 mL, Aldrich) was added TEA (650 µL, 4.6 mmol). The reaction was maintained at RT for 10 h before being poured into $H_2O$ (20 mL). The aqueous layer was extracted with EtOAc (3×50 mL). The combined organic layers were washed with $H_2O$ (3×100 mL) then concentrated under reduced pressure. The resulting solid was triturated with $CH_2Cl_2$ to give the title compound as an off-white powder. MS (ESI, pos. ion) m/z: 484.4 (M+1). Mass Calc'd for $C_{28}H_{22}ClN_3O_3$: 483.95.

The following examples were prepared similar to the procedures described in Example 740.

| Example No. | Structure & Name | Mol Formula | Mass | M + H |
|---|---|---|---|---|
| 741 | 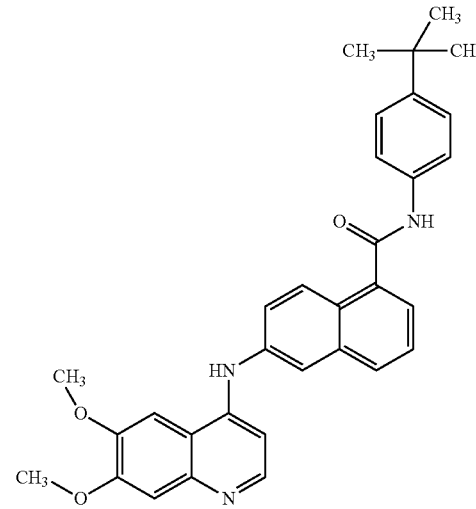<br>6-((6,7-bis(methoxy)-4-quinolinyl)amino)-N-(4-(1,1-dimethylethyl)phenyl)-1-naphthalenecarboxamide | $C_{32}H_{31}N_3O_3$ | 505.62 | 506.2 |
| 742 | 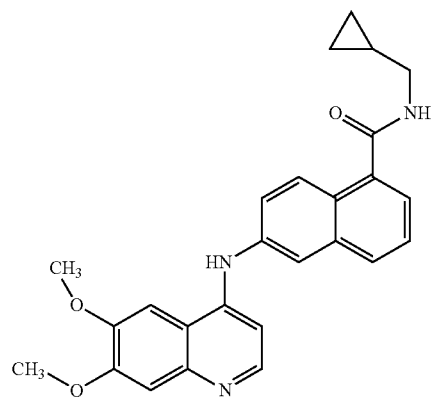<br>6-((6,7-bis(methoxy)-4-quinolinyl)amino)-N-(cyclopropylmethyl)-1-naphthalenecarboxamide | $C_{26}H_{25}N_3O_3$ | 427.5 | 428.1 |

EXAMLE 743

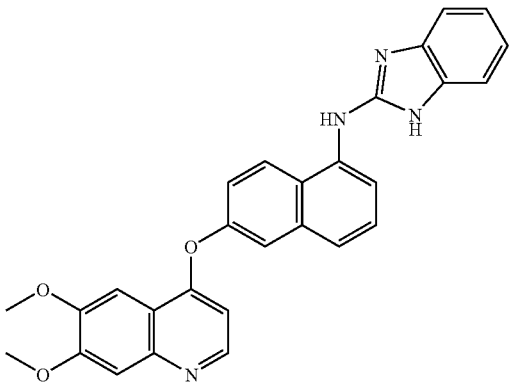

N-(6-((6,7-bis(methoxy)-4-quinolinyl)oxy)-1-naphthalenyl)-1H-benzimidazol-2-amine Thiocarbonyl diimidazole (113 mg, 0.65 mmol) was added to a solution of 6-(6,7-dimethoxyquinolin-4-yloxy)naphthalene-1-amine (150 mg, 0.43 mmol), in $CH_2Cl_2$ (5 mL) After stirring for 3 h, the mixture was concentrated and the derived residue was dissolved in MeCN (3 mL). A solution of 1,2-diphenylamine (50 mg, 0.46 mmol) in MeCN (1 mL, Aldrich) was added and the mixture was stirred for 10 min before the addition of EDC (75 mg, 0.39 mmol). The reaction was heated at 80° C. for 0.5 h before being cooled to ambient temperature, concentrated under reduced pressure and purified by silica gel chromatography (0-10% MeOH in $CH_2Cl_2$) to provide the title compound as a tan solid. MS (ESI, pos. ion) m/z: 463.2 (M+1). Mass Calc'd for $C_{28}H_{22}N_4O_3$: 462.50.

EXAMPLE 744

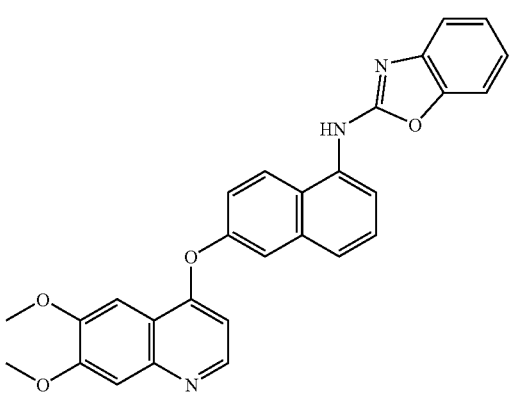

N-(6-((6,7-bis(methoxy)-4-quinolinyl)oxy)-1-naphthalenyl)-1,3-benzoxazol-2-amine Thiocarbonyl diimidazole (113 mg, 0.65 mmol) was added to a mixture of 6-(6,7-dimethoxyquinolin-4-yloxy)naphthalene-1-amine (150 mg, 0.43 mmol), in $CH_2Cl_2$ (5 mL) at ambient temperature. After stirring for 3 h, the mixture was concentrated and the derived isothiocyanate was dissolved in MeCN (2 mL). A solution of 2-aminophenol (50 mg, 0.45 mmol) in MeCN (2 mL) was added and the mixture was stirred for 48 h at which point EDC (125 mg, 0.65 mmol) was introduced. The reaction was heated at 80° C. for 2 h. After cooling to ambient temperature, the suspension was filtered and the resulting solid was washed well with MeOH to furnish the title as a tan solid. MS (ESI, pos. ion) m/z: 464.1 (M+1). Mass Calc'd for $C_{28}H_{21}N_3O_4$: 463.48.

EXAMPLE 745

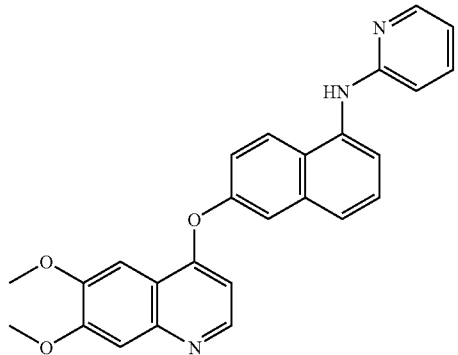

N-(6-((6,7-bis(methoxy)-4-quinolinyl)oxy)-1-naphthalenyl)-2-pyridinamine

To a solution of 6-(6,7-dimethoxyquinolin-4-yloxy)naphthalene-1-amine (150 mg, 0.43 mmol), 2-chloropyridine (45 µl, 0.47 mmol), and NaOtBu (52.0 g, 160 mmol) in dioxane (4 mL) were added $Pd_2(dba)_3$ (12 mg, 0.01 mmol) and 2-(dicyclohexylphosphino)-2'-4'-6'-tri-i-propyl-1,1'-biphenyl (25 mg, 0.05 mmol). The resulting mixture was heated at 100° C. for 3 h. After cooling to ambient temperature, the mixture was diluted with EtOAc (25 mL) and poured into sat'd $NaHCO_3$ (50 mL). The phases were separated and the aqueous phase was extracted with EtOAc (2×25 mL). The organic layers were combined, washed with brine, dried over $Na_2SO_4$ and concentrated in vacuo. The derived residue was purified by silica gel chromatography (0-10% $CH_3OH$ in $CH_2Cl_2$) to provide the title compound as a white solid. MS (ESI, pos. ion) m/z: 424.1 (M+1). Mass Calc'd for $C_{26}H_{21}N_3O_3$: 423.46.

The following examples were prepared similar to the procedures described in Example 745.

| Example No. | Structure & Name | Mol Formula | Mass | M + H |
|---|---|---|---|---|
| 746 | 6-((6,7-bis(methoxy)-4-quinolinyl)oxy)-N-phenyl-1-naphthalenamine | C₂₇H₂₂N₂O₃ | 422.48 | 423.2 |
| 747 | N-(6-((6,7-bis(methoxy)-4-quinolinyl)oxy)-1-naphthalenyl)-N-(2-pyridinyl)-2-pyridinamine | C₃₁H₂₄N₄O₃ | 500.56 | 501.2 |
| 748 | 6-((6,7-bis(methoxy)-4-quinolinyl)oxy)-N-(3-(methoxy)phenyl)-1-naphthalenamine | C₂₈H₂₄N₂O₄ | 452.51 | 453.2 |

-continued

| Example No. | Structure & Name | Mol Formula | Mass | M + H |
|---|---|---|---|---|
| 749 | 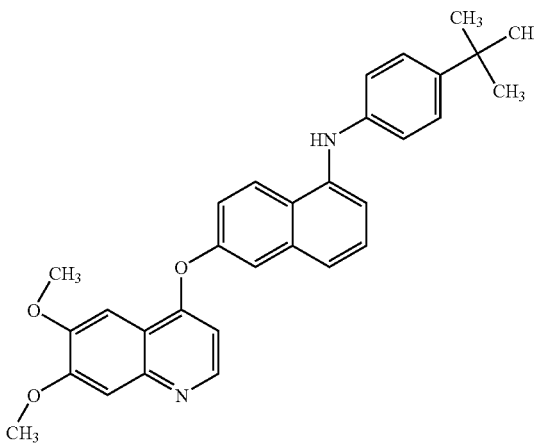<br>6-((6,7-bis(methoxy)-4-quinolinyl)oxy)-N-(4-(1,1-dimethylethyl)phenyl)-1-naphthalenamine | $C_{31}H_{30}N_2O_3$ | 478.59 | 479.2 |

EXAMPLE 750

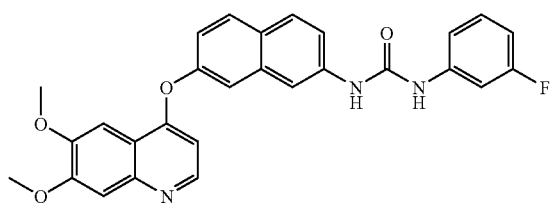

N-(7-((6,7-bis(methoxy)-4-quinolinyl)oxy)-2-naphthalenyl)-N'-(3-fluorophenyl)urea To a solution of 7-(6,7-dimethoxyquinolin-4-yloxy)naphthalen-2-amine (0.158 g, 0.45 mmol) in 20 mL of THF was added 3-fluorophenyl isocyanate (0.057 mL, 0.50 mmol). The solution was stirred for 16 h at RT under an atmosphere of nitrogen. The reaction was concentrated and the crude solid was treated with $CH_2Cl_2$. The resulting solid was collected by vacuum filtration and dried in vacuo to afford the desired compound. MS (ESI, pos. ion) m/z: 484.0 (M+1). Mass Calc'd for $C_{28}H_{22}FN_3O_4$: 483.497.

The following compounds were prepared in a manner similar to Example 421, step c, omitting the base and using excess ammonia (as either a 0.5 M solution in dioxane or a saturated solution on $CH_2Cl_2$).

| Example No. | Structure & Name | Mol Formula | Mass | M + H |
|---|---|---|---|---|
| 751 | 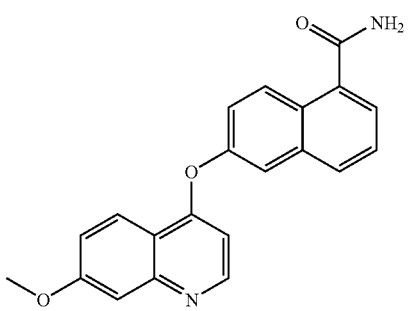<br>6-((7-(methoxy)-4-quinolinyl)oxy)-1-naphthalenecarboxamide | $C_{21}H_{16}N_2O_3$ | 344.37 | 345.1 |

-continued
| Example No. | Structure & Name | Mol Formula | Mass | M + H |
|---|---|---|---|---|
| 752 | 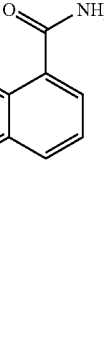<br>5-fluoro-6-((6-(methoxy)-7-((3-(4-morpholinyl)propyl)oxy)-4-quinolinyl)oxy)-1-naphthalenecarboxamide | $C_{28}H_{28}FN_3O_5$ | 505.54 | 506.2 |
| 753 | 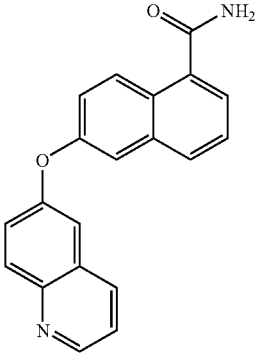<br>6-(6-quinolinyloxy)-1-naphthalenecarboxamide | $C_{20}H_{14}N_2O_2$ | 314.34 | 315.1 |
| 754 | 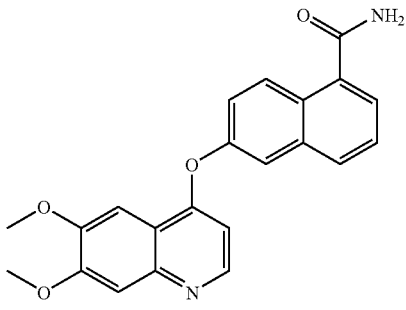<br>6-((6,7-bis(methoxy)-4-quinolinyl)oxy)-1-naphthalenecarboxamide | $C_{22}H_{18}N_2O_6$ | 374.39 | 375.1 |
| 755 | 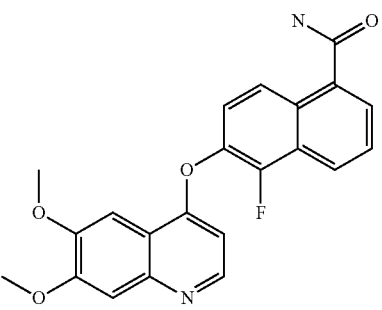<br>6-((6,7-bis(methoxy)-4-quinolinyl)oxy)-5-fluoro-1-naphthalenecarboxamide | $C_{22}H_{17}FN_2O_4$ | 392.38 | 393.1 |

| Example No. | Structure & Name | Mol Formula | Mass | M + H |
|---|---|---|---|---|
| 756 | 6-((6,7-bis(methoxy)-4-quinazolinyl)oxy)-1-naphthalenecarboxamide | $C_{21}H_{17}N_3O_4$ | 375.38 | 376.1 |
| 757 | 4-((5-(aminocarbonyl)-2-naphthalenyl)oxy)-7-(methoxy)-6-quinolinecarboxamide | $C_{22}H_{17}N_3O_4$ | 387.39 | 388.3 |
| 758 | 4-((5-(aminocarbonyl)-1-fluoro-2-naphthalenyl)oxy)-7-(methoxy)-6-quinolinecarboxamide | $C_{22}H_{16}FN_3O_4$ | 405.38 | 406.3 |

EXAMPL 759

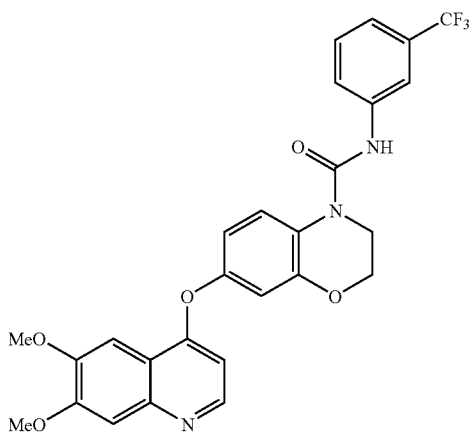

7-(6,7-dimethoxyquinolin-4-yloxy)-N-(3-(trifluoromethyl)phenyl)-2,3-dihydrobenzo[b][1,4]oxazine-4-carboxamide

Step (a) Preparation of 2-chloro-N-(2,4-dihydroxyphenyl)acetamide

To a solution of 4-aminoresorcinol hydrochloride (30 g, 0.1857 mol) in $CH_2Cl_2$, (460 mL) TEA (77.6 mL, 0.557 mol) was added at 0° C. To the resulting mixture, chloroacetyl chloride (14.78 mL, 0.1857 mol) was added drop wise and the solution was stirred for 60 h at RT. The crude product was washed through a plug of silica gel with $CH_2Cl_2$ and purified through column chromatography using 100% $CH_2Cl_2$→25%→50%→75% 90:10:1 $CH_2Cl_2$:MeOH:NH$_4$OH. The solution was concentrated in vacuo to give the title compound. MS (ESI, pos. ion) m/z: 202 (M+1). Mass calc'd for $C_8H_8ClNO_3$: 201.02.

Step (b) Preparation of 7-hydroxy-2H-benzo[b][1,4]oxazin-3(4H)-one

To a solution of 2-chloro-N-(2,4-dihydroxyphenyl)acetamide (20 g, 0.0995 mol) in $CH_2Cl_2$ (250 mL) sodium hydride (7.164 g, 0.2985 mol) was slowly added at RT. The resulting mixture was stirred for 6 h before water (10 mL) was slowly added. The solution was concentrated in vacuo and purified with column chromatography using 100% $CH_2Cl_2$→25%→40% 90:10:1 $CH_2Cl_2$:MeOH:NH$_4$OH to yield the title compound. MS (ESI, pos. ion) m/z: 166 (M+1). Mass cal'd for $C_8H_7NO_3$: 165.04.

Step (c) Preparation of 3,4-dihydro-2H-benzo[b][1,4]oxazin-7-ol

To a solution of 7-hydroxy-2H-benzo[b][1,4]oxazin-3(4H)-one (6 g, 36.36 mmol) in THF (50 mL) BH$_3$-THF (150 mL, 254.54 mmol) was slowly added at RT. The resulting reaction was stirred for 4 h at 60° C. before water (5 mL) was added. The solution was concentrated in vacuo and purified with column chromatography using 100% $CH_2Cl_2$→25%→50% 90:10:1 $CH_2Cl_2$:MeOH:NH$_4$OH to yield the title compound. MS (ESI, pos. ion) m/z: 152 (M+1). Mass calc'd for $C_8H_9NO_2$: 151.06.

Step (d) Preparation of 7-(6,7-dimethoxyquinolin-4-yloxy)-3,4-dihydro-2H-benzo[b][1,4]oxazine A solution of 3,4-dihydro-2H-benzo[b][1,4]oxazin-7-ol (2.5 g, 16.54 mmol), cesium carbonate (16.167, 49.62 mmol), and 4-chloro-6,7-dimethoxyquinoline (5.534 g, 24.81 mmol) in DMF (30 mL) was stirred for 15 h at 80° C. The solution was concentrated in vacuo and purified with column chromatography using 100% $CH_2Cl_2$→10% 90:10:1 $CH_2Cl_2$:MeOH:NH$_4$OH to yield the title compound. MS (ESI, pos. ion) m/z: 339 (M+1). Mass calc'd for $C_{19}H_{18}N_2O_4$: 338.13.

Step (e) Preparation of 7-(6,7-dimethoxyquinolin-4-yloxy)-N-(3-(trifluoromethyl)phenyl)-2,3-dihydrobenzo[b][1,4]oxazine-4-carboxamide To a solution of 7-(6,7-dimethoxyquinolin-4-yloxy)-3,4-dihydro-2H-benzo[b][1,4]oxazine (50 mg, 0.1478 mmol) in $CH_2Cl_2$ (1 mL) 1-isocyanato-3-(trifluoromethyl)benzene (31 μL, 0.2217 mmol) was added. The resulting mixture was stirred for 1 h at RT. The solution was concentrated in vacuo and purified with column chromatography using 100% $CH_2Cl_2$→15% 90:10:1 $CH_2Cl_2$:MeOH:NH$_4$OH to yield the title compound. MS (ESI, pos. ion) m/z: 526 (M+1). Mass calc'd for $C_{27}H_{22}F_3N_3O_5$: 525.15.

The following examples were prepared similar to the procedures described in Example 759.

| Example No. | Structure & Name | Mol Formula | Mass | M + H |
|---|---|---|---|---|
| 760 | 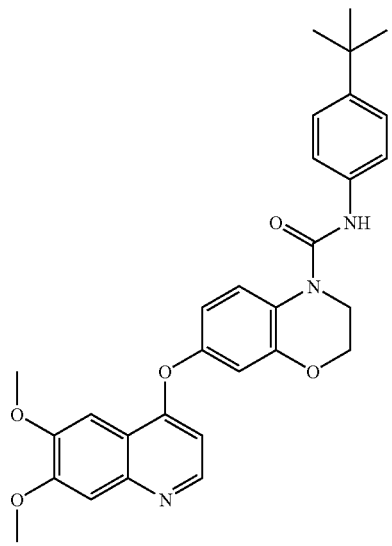<br>7-((6,7-bis(methyloxy)-4-quinolinyl)oxy)-N-(4-(1,1-dimethylethyl)phenyl)-2,3-dihydro-4H-1,4-benzoxazine-4-carboxamide | $C_{30}H_{31}N_3O_5$ | 513.59 | 514.1 |
| 761 | 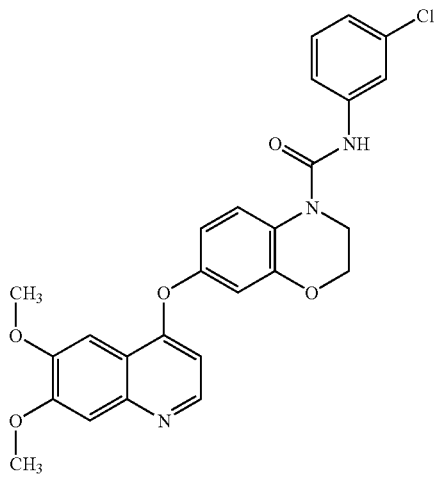<br>7-((6,7-bis(methyloxy)-4-quinolinyl)oxy)-N-(3-chlorophenyl)-2,3-dihydro-4H-1,4-benzoxazine-4-carboxamide | $C_{26}H_{22}ClN_3O_5$ | 491.93 | 492.1 |

| Example No. | Structure & Name | Mol Formula | Mass | M + H |
|---|---|---|---|---|
| 762 | 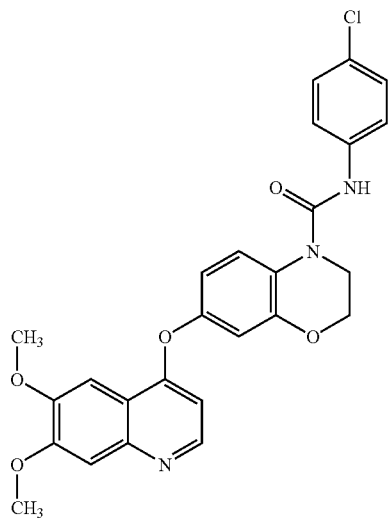<br>7-((6,7-bis(methyloxy)-4-quinolinyl)oxy)-N-(4-chlorophenyl)-2,3-dihydro-4H-1,4-benzoxazine-4-carboxamide | $C_{26}H_{22}ClN_3O_5$ | 491.93 | 492.1 |
| 763 | 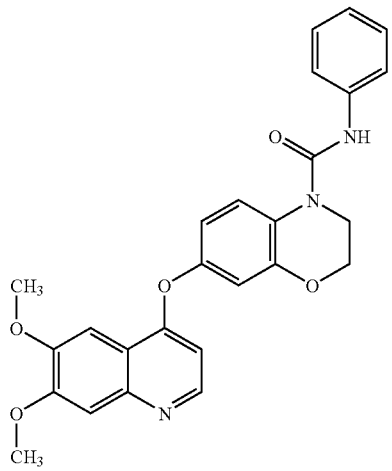<br>7-((6,7-bis(methyloxy)-4-quinolinyl)oxy)-N-phenyl-2,3-dihydro-4H-1,4-benzoxazine-4-carboxamide | $C_{26}H_{23}N_3O_5$ | 457.48 | 458.1 |

-continued
| Example No. | Structure & Name | Mol Formula | Mass | M + H |
|---|---|---|---|---|
| 764 | 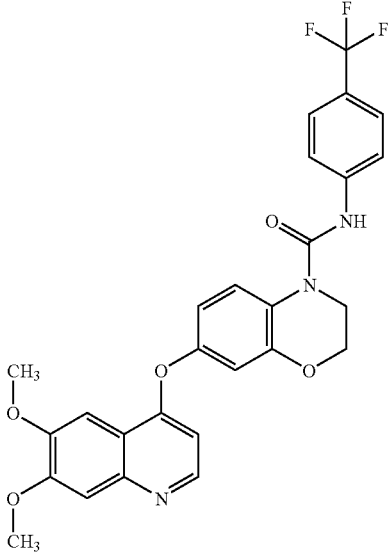<br>7-((6,7-bis(methyloxy)-4-quinolinyl)oxy)-N-(4-(trifluoromethyl)phenyl)-2,3-dihydro-4H-1,4-benzoxazine-4-carboxamide | $C_{27}H_{22}F_3N_3O_5$ | 525.48 | 526.1 |
| 765 | 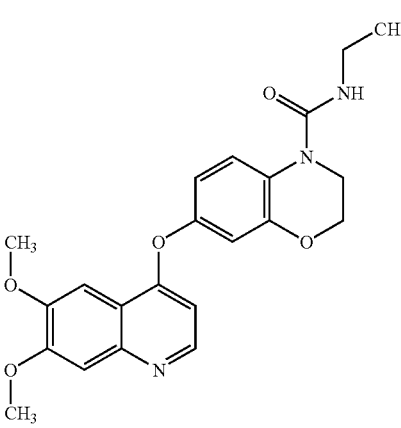<br>7-((6,7-bis(methyloxy)-4-quinolinyl)oxy)-N-ethyl-2,3-dihydro-4H-1,4-benzoxazine-4-carboxamide | $C_{22}H_{23}N_3O_5$ | 409.44 | 41 |

| Example No. | Structure & Name | Mol Formula | Mass | M + H |
|---|---|---|---|---|
| 766 | 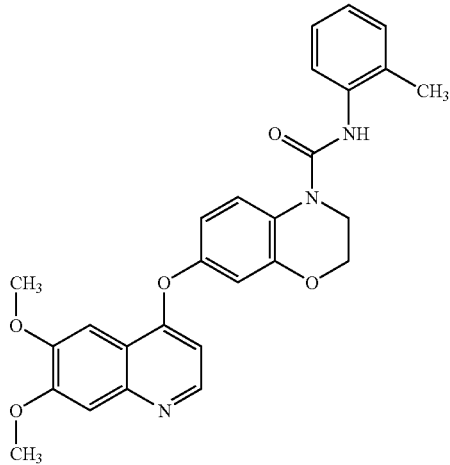<br>7-((6,7-bis(methyloxy)-4-quinolinyl)oxy)-N-(2-methylphenyl)-2,3-dihydro-4H-1,4-benzoxazine-4-carboxamide | $C_{27}H_{25}N_3O_5$ | 471.51 | 472.1 |
| 767 | 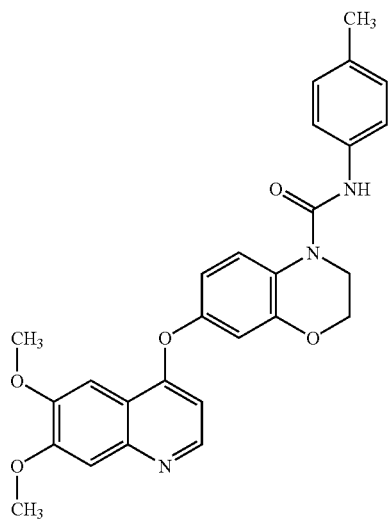<br>7-((6,7-bis(methyloxy)-4-quinolinyl)oxy)-N-(4-methylphenyl)-2,3-dihydro-4H-1,4-benzoxazine-4-carboxamide | $C_{27}H_{25}N_3O_5$ | 471.51 | 472 |

| Example No. | Structure & Name | Mol Formula | Mass | M + H |
|---|---|---|---|---|
| 768 | 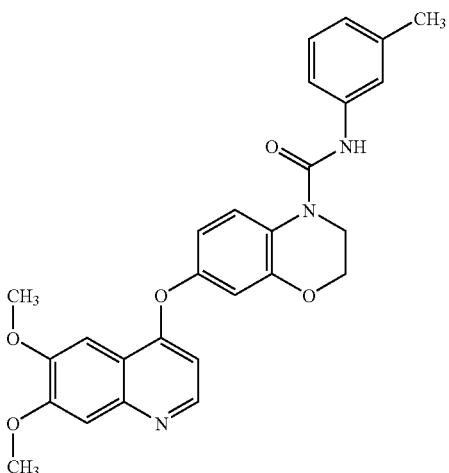<br>7-((6,7-bis(methyloxy)-4-quinolinyl)oxy)-N-(3-methylphenyl)-2,3-dihydro-4H-1,4-benzoxazine-4-carboxamide | $C_{27}H_{25}N_3O_5$ | 471.51 | 472.1 |
| 769 | 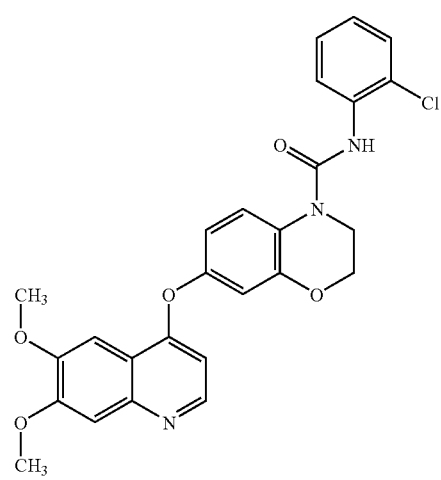<br>7-((6,7-bis(methyloxy)-4-quinolinyl)oxy)-N-(2-chlorophenyl)-2,3-dihydro-4H-1,4-benzoxazine-4-carboxamide | $C_{26}H_{22}ClN_3O_5$ | 491.93 | 492.1 |
| 770 | 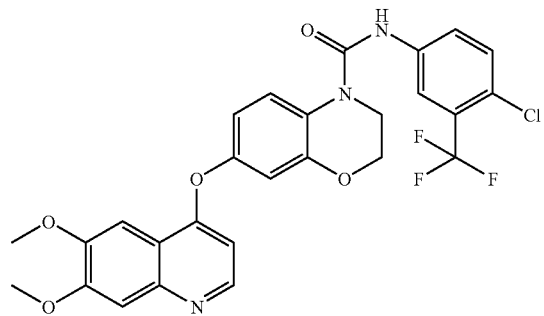<br>7-((6,7-bis(methyloxy)-4-quinolinyl)oxy)-N-(4-chloro-3-(trifluoromethyl)phenyl)-2,3-dihydro-4H-1,4-benzoxazine-4-carboxamide | $C_{27}H_{21}ClF_3N_3O_5$ | 559.93 | 560.1 |

-continued
| Example No. | Structure & Name | Mol Formula | Mass | M + H |
|---|---|---|---|---|
| 771 | 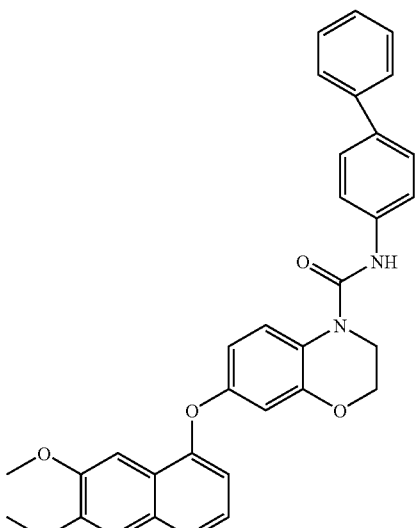<br>N-(1,1′-biphenyl-4-yl)-7-((6,7-bis(methyloxy)-4-quinolinyl)oxy)-2,3-dihydro-4H-1,4-benzoxazine-4-carboxamide | $C_{32}H_{27}N_3O_5$ | 533.58 | 534.1 |
| 772 | 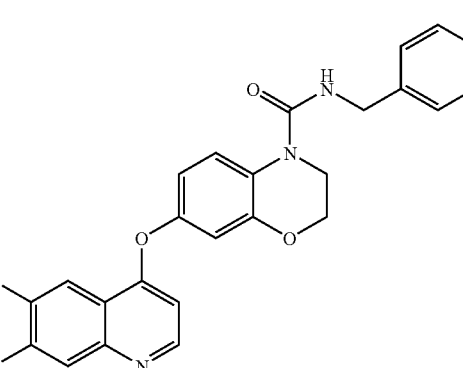<br>7-((6,7-bis(methyloxy)-4-quinolinyl)oxy)-N-(phenylmethyl)-2,3-dihydro-4H-1,4-benzoxazine-4-carboxamide | $C_{27}H_{25}N_3O_5$ | 471.51 | 472.1 |
| 773 | 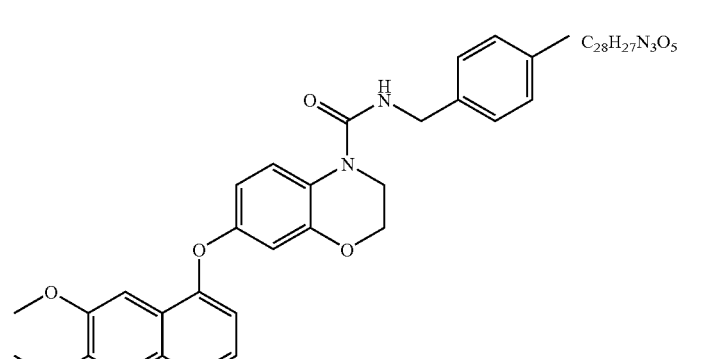<br>7-((6,7-bis(methyloxy)-4-quinolinyl)oxy)-N-((4-methylphenyl)methyl)-2,3-dihydro-4H-1,4-benzoxazine-4-carboxamide | $C_{28}H_{27}N_3O_5$ | 485.54 | 486.2 |

| Example No. | Structure & Name | Mol Formula | Mass | M + H |
|---|---|---|---|---|
| 774 | 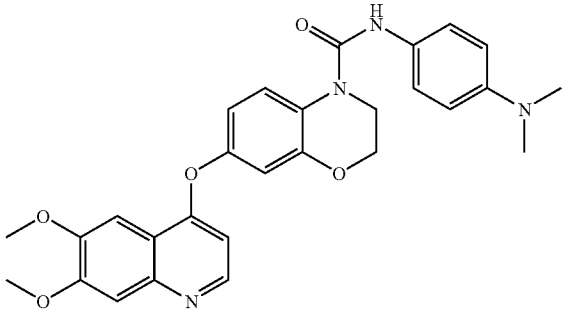<br>7-((6,7-bis(methyloxy)-4-quinolinyl)oxy)-N-(4-dimethylamino)phenyl)-2,3-dihydro-4H-1,4-benzoxazine-4-carboxamide | $C_{28}H_{28}N_4O_5$ | 500.55 | 501.1 |
| 775 | 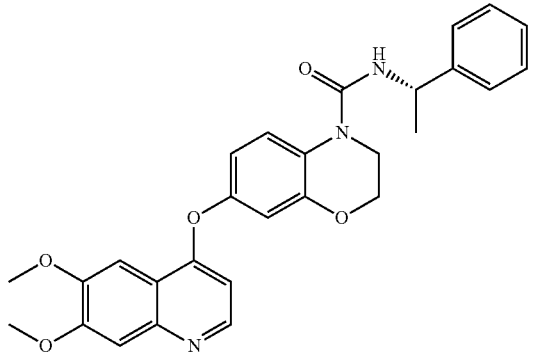<br>7-((6,7-bis(methyloxy)-4-quinolinyl)oxy)-N-((1S)-1-phenylethyl)-2,3-dihydro-4H-1,4-benzoxazine-4-carboxamide | $C_{28}H_{27}N_3O_5$ | 485.54 | 486.1 |
| 776 | 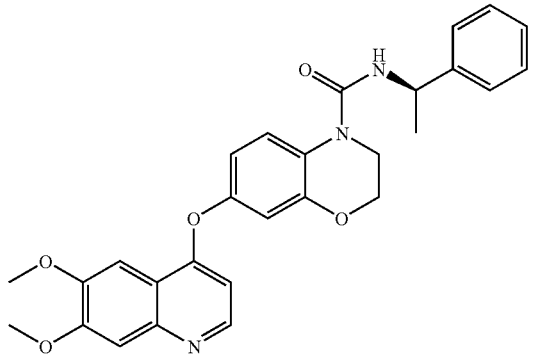<br>7-((6,7-bis(methyloxy)-4-quinolinyl)oxy)-N-((1R)-1-phenylethyl)-2,3-dihydro-4H-1,4-benzoxazine-4-carboxamide | $C_{28}H_{27}N_3O_5$ | 485.54 | 486. |

-continued

| Example No. | Structure & Name | Mol Formula | Mass | M + H |
|---|---|---|---|---|
| 777 | 7-((6,7-bis(methyloxy)-4-quinolinyl)oxy)-N-methyl-2,3-dihydro-4H-1,4-benzoxazine-4-carboxamide | C₂₁H₂₁N₃O₅ | 395.41 | 396.1 |
| 778 | 7-((6,7-bis(methyloxy)-4-quinolinyl)oxy)-N-(1-(1,3-thiazol-2-yl)ethyl)-2,3-dihydro-4H-1,4-benzoxazine-4-carboxamide | C₂₅H₂₄N₄O₅S | 492.55 | 493.1 |

EXAMPLE 779

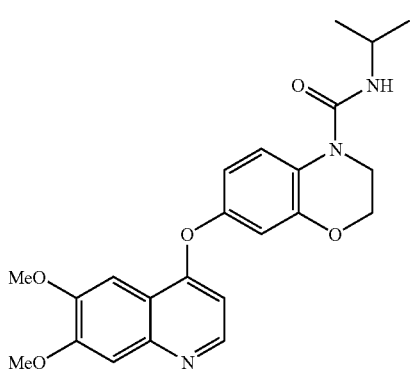

7-(6,7-dimethoxyquinolin-4-yloxy)-N-isopropyl-2,3-dihydrobenzo[b][1,4]oxazine-4-carboxamide Step (a) Preparation of 4-nitrophenyl 7-(6,7-dimethoxyquinolin-4-yloxy)-2,3-dihydrobenzo[b][1,4]oxazine-4-carboxylate To a solution of 7-(6,7-dimethoxyquinolin-4-yloxy)-3,4-dihydro-2H-benzo[b][1,4]oxazine (400 mg, 1.182 mmol) and p-nitrophenyl chloroformate (262 mg, 1.300 mmol) in THF (6 mL) DIPEA (245 μL, 1.419 mmol) was added drop wise at RT. The solution was stirred for 1 h at RT before the resulting mixture was concentrated in vacuo and the title compound was used in the following reaction without purification. MS (ESI, pos. ion) m/z: 504 (M+1). Mass cal'd for C₂₆H₂₁N₃O₈: 503.13.

Step (b) Preparation of 7-(6,7-dimethoxyquinolin-4-yloxy)-N-isopropyl-2,3-dihydrobenzo[b][1,4]oxazine-4-carboxamide To a solution of 4-nitrophenyl 7-(6,7-dimethoxyquinolin-4-yloxy)-2,3-dihydrobenzo[b][1,4]oxazine-4-carboxylate (190 mg, 0.3777 mmol) in THF (4 mL) isopropylamine (321 μL, 3.777 mmol) was added at RT. The reaction was stirred for 1 h at RT before the resulting mixture was concentrated in vacuo and purified by column chromatography using 100% CH₂Cl₂→10%→20% 90:10:1 CH₂Cl₂:MeOH:NH₄OH to 1 yield the title compound. MS (ESI, pos. ion) m/z: 424 (M+1). Mass cal'd for C₂₃H₂₅N₃O₅: 423.18

EXAMPLE 780

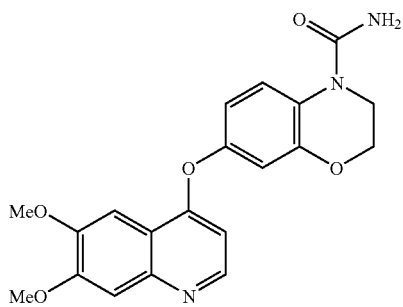

601

7-(6,7-dimethoxyquinolin-4-yloxy)-2,3-dihydrobenzo[b][1,4]oxazine-4-carboxamide

Preparation of 7-(6,7-dimethoxyquinolin-4-yloxy)-2,3-dihydrobenzo[b][1,4]oxazine-4-carboxamide To a solution of 7-(6,7-dimethoxyquinolin-4-yloxy)-3,4-dihydro-2H-benzo[b][1,4]oxazine (100 mg, 0.2955 mmol) in toluene (2 mL) trichloroacetyl isocyanate (39 μL, 0.325 mmol) was added at RT. The resulting reaction mixture was stirred for 2 h at 60° C. The solution was cooled to RT and 10% HCl/H$_2$O (5 mL) was added. The solution was concentrated in vacuo and purified with column chromatography using 100% CH$_2$Cl$_2$→10%→20%→30% 90:10:1 CH$_2$Cl$_2$:MeOH:NH$_4$OH to yield the title compound. MS (ESI, pos. ion) m/z: 382 (M+1). Mass cal'd for C$_{20}$H$_{19}$N$_3$O$_5$: 381.13.

EXAMPLE 781

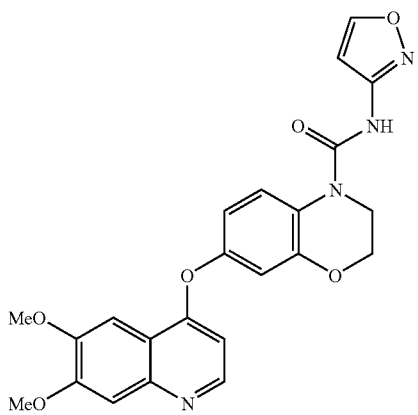

602

7-(6,7-dimethoxyquinolin-4-yloxy)-N-(isoxazol-3-yl)-2,3-dihydrobenzo[b][1,4]oxazine-4-carboxamide Step (a) Preparation of 4-nitrophenyl isoxazol-3-ylcarbamate A solution of 3-amino isoxazole (220 uL, 2.973 mmol) and p-nitrophenyl chloroformate (659 mg, 3.271 mmol) in THF (8 mL) was stirred for 15 min at RT before the solution was concentrated in vacuo. The title compound was used immediately in the following reaction without further purification. MS (ESI, pos. ion) m/z: 250 (M+1). Mass calc'd for C$_{10}$H$_7$N$_3$O$_5$: 249.18.

Step (b) Preparation of 7-(6,7-dimethoxyquinolin-4-yloxy)-N-(isoxazol-3-yl)-2,3-dihydrobenzo[b][1,4]oxazine-4-carboxamide To a solution of 7-(6,7-dimethoxyquinolin-4-yloxy)-3,4-dihydro-2H-benzo[b][1,4]oxazine (100 mg, 0.2955 mmol) and 4-nitrophenyl isoxazol-3-ylcarbamate (294 mg, 1.182 mmol) in CH$_2$Cl$_2$ (3 mL) DIPEA (269 μL, 2.069 mmol) was added at RT. The reaction mixture was stirred at 35° C. for 15 h before the solution was concentrated in vacuo and purified with column chromatography using 100% EtOAc→10%→30%→50% 19:1 EtOAc:MeOH to yield the title compound. MS (ESI, pos. ion) m/z: 449 (M+1). Mass calc'd for C$_{23}$H$_{20}$N$_4$O$_6$: 448.44.

The following compounds were prepared similar to the procedures described in Example 781.

| Example No. | Structure & Name | Mol Formula | Mass | M + H |
|---|---|---|---|---|
| 782 | 7-((6,7-bis(methyloxy)-4-quinolinyl)oxy)-N-(1,3-thiazol-2-yl)-2,3-dihydro-4H-1,4-benzoxazine-4-carboxamide | C$_{23}$H$_{20}$N$_4$O$_5$S | 464.5 | 465 |

EXAMPLE 783

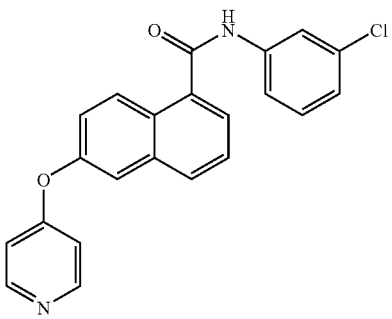

N-(3-chlorophenyl)-6-(4-pyridinyloxy)-1-naphthalenecarboxamide

Step (a) Preparation of 6-(pyridin-4-yloxy)-1-naphthoic acid

To a solution of 6-hydroxy-1-napthoic acid (2 g, 10.6 mmol) in DMSO (5 mL), $Cs_2CO_3$ (14 g, 42.4 mmol) was added and stirred at RT 10 min. 4-Chloropyridine hydrochloride (1.9 g, 12.7 mmol) was added in one portion and the reaction mixture heated to 140° C. for 12 h. The reaction mixture was cooled to RT, diluted with water and made pH 5 using 6 N HCl, at which point a brown precipitate crashed out. The solid was filtered and rinsed with water and hexanes to yield the title compound.

Step (b) Preparation of 6-(pyridin-4-yloxy)-1-naphthoyl chloride

This compound was prepared similar to the procedure described in Example 273 Step (a).

Step (c) Preparation of N-(3-chlorophenyl)-6-(4-pyridinyloxy)-1-naphthalenecarboxamide 6-(Pyridin-4-yloxy)-1-naphthoyl chloride (50 mg, 0.18 mmol) was suspended in $CH_2Cl_2$ and solid $NaHCO_3$ (excess) was added. The mixture was blanketed with nitrogen and 3-chloroaniline (18.6 µL, 0.18 mmol) was added and the reaction mixture stirred at RT for 1 h. The reaction mixture was diluted with $CHCl_3$ and water (using heat to dissolve the solids) and the organic layer further washed with brine, dried with $Na_2SO_4$, filtered and concentrated in-vacuo. The residue was crystallized from $CH_2Cl_2$/hexanes to give the title compound as a brown solid. MS (ESI pos. ion) m/z: 375.1 (M+H). Calc'd for $C_{22}H_{15}ClN_2O_2$–374.82.

The following compounds were prepared similar to the procedures described in Example 783 and purified by column chromatography and/or crystallization.

| Example No. | Structure & Name | Mol Formula | Mass | M + H |
|---|---|---|---|---|
| 784 | 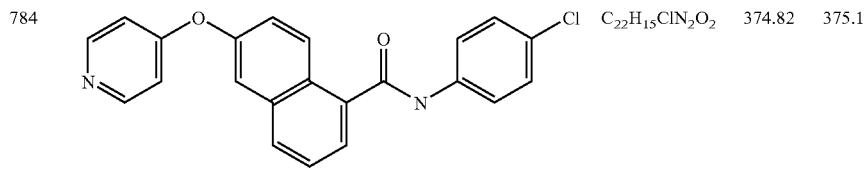<br>N-(4-chlorophenyl)-6-(4-pyridinyloxy)-1-naphthalenecarboxamide | $C_{22}H_{15}ClN_2O_2$ | 374.82 | 375.1 |
| 785 | 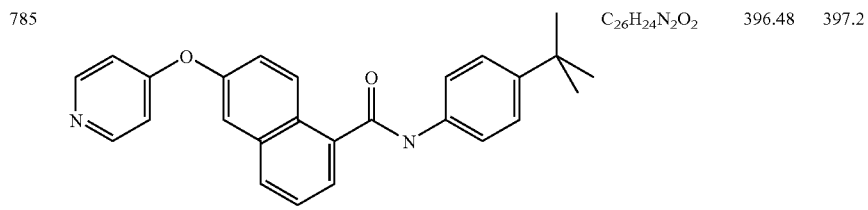<br>N-(4-(1,1-dimethylethyl)phenyl)-6-(4-pyridinyloxy)-1-naphthalenecarboxamide | $C_{26}H_{24}N_2O_2$ | 396.48 | 397.2 |

-continued

| Example No. | Structure & Name | Mol Formula | Mass | M + H |
|---|---|---|---|---|
| 786 | N-(3-methylphenyl)-6-(4-pyridinyloxy)-1-naphthalenecarboxamide | $C_{23}H_{18}N_2O_2$ | 354.40 | 355.1 |
| 787 | N-phenyl-6-(4-pyridinyloxy)-1-naphthalenecarboxamide | $C_{22}H_{16}N_2O_2$ | 340.38 | 341.1 |
| 788 | N-(3-chloro-4-methylphenyl)-6-(4-pyridinyloxy)-1-naphthalenecarboxamide | $C_{23}H_{17}ClN_2O_2$ | 388.85 | 389.1 |

-continued
| Example No. | Structure & Name | Mol Formula | Mass | M + H |
|---|---|---|---|---|
| 789 | 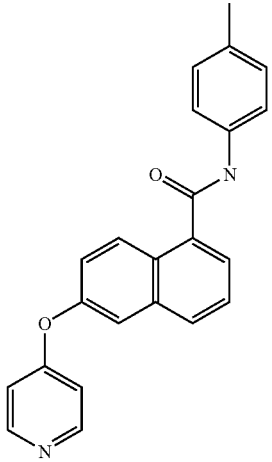 N-(4-methylphenyl)-6-(4-pyridinyloxy)-1-naphthalenecarboxamide | C₂₃H₁₈N₂O₂ | 354.40 | 355.1 |
| 790 | 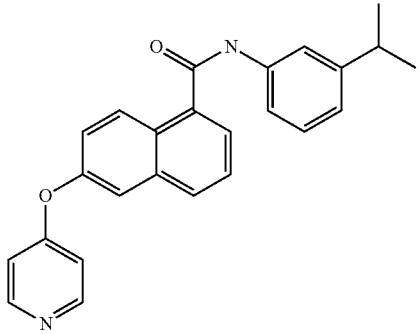 N-(3-(1-methylethyl)phenyl)-6-(4-pyridinyloxy)-1-naphthalenecarboxamide | C₂₅H₂₂N₂O₂ | 382.46 | 383.1 |
| 791 | 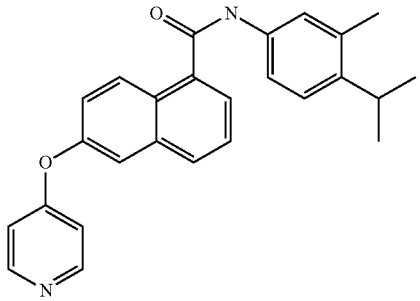 N-(3-methyl-4-(1-methylethyl)phenyl)-6-(4-pyridinyloxy)-1-naphthalenecarboxamide | C₂₆H₂₄N₂O₂ | 396.48 | 397.1 |

-continued
| Example No. | Structure & Name | Mol Formula | Mass | M + H |
|---|---|---|---|---|
| 792 | 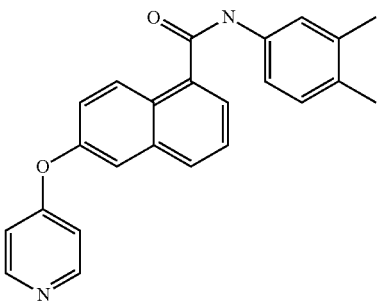<br>N-(3,4-dimethylphenyl)-6-(4-pyridinyloxy)-1-naphthalenecarboxamide | $C_{24}H_{20}N_2O_2$ | 368.43 | 369.1 |
| 793 | 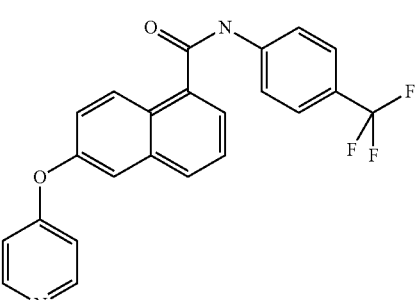<br>6-(4-pyridinyloxy)-N-(4-(trifluoromethyl)phenyl)-1-naphthalenecarboxamide | $C_{23}H_{15}F_3N_2O_2$ | 408.37 | 409.1 |
| 794 | 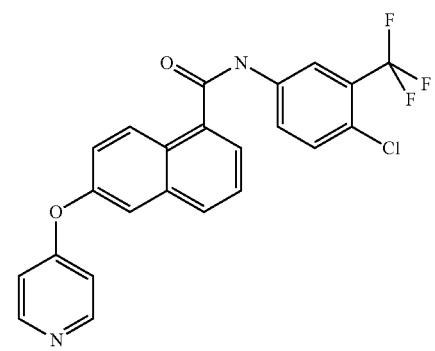<br>N-(4-chloro-3-(trifluoromethyl)phenyl)-6-(4-pyridinyloxy)-1-naphthalenecarboxamide | $C_{23}H_{14}ClF_3N_2O_2$ | 422.82 | 443.1 |

The following examples were prepared similar to the procedures described in Example 783 step c.

| Example No. | Structure & Name | Mol Formula | Mass | M + H |
|---|---|---|---|---|
| 795 | 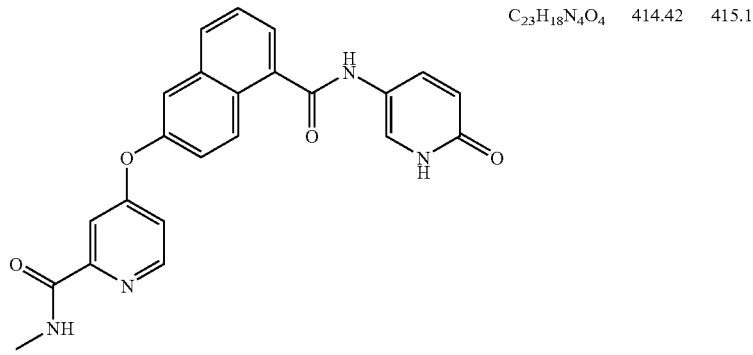<br>N-methyl-4-((5-(((6-oxo-1,6-dihydro-3-pyridinyl)amino)carbonyl)-2-naphthalenyl)oxy)-2-pyridinecarboxamide | $C_{23}H_{18}N_4O_4$ | 414.42 | 415.1 |

The following examples were prepared similar to the procedures described in Example 783, Step c, using 1.5-1.8 equiv amine.

| Example No. | Structure & Name | Mol Formula | Mass | M + H |
|---|---|---|---|---|
| 796 | 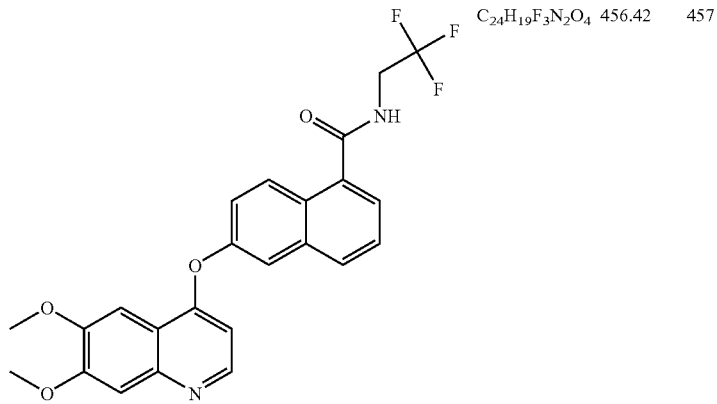<br>6-((6,7-bis(methyloxy)-4-quinolinyl)oxy)-N-(2,2,2-trifluoroethyl)-1-naphthalenecarboxamide | $C_{24}H_{19}F_3N_2O_4$ | 456.42 | 457 |

-continued
| Example No. | Structure & Name | Mol Formula | Mass | M + H |
|---|---|---|---|---|
| 797 | 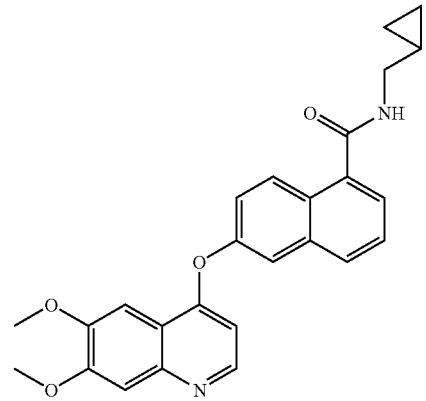 6-((6,7-bis(methyloxy)-4-quinolinyl)oxy)-N-(cyclopropylmethyl)-1-naphthalenecarboxamide | C$_{26}$H$_{24}$N$_2$O$_4$ | 428.49 | 429.1 |
| 798 | 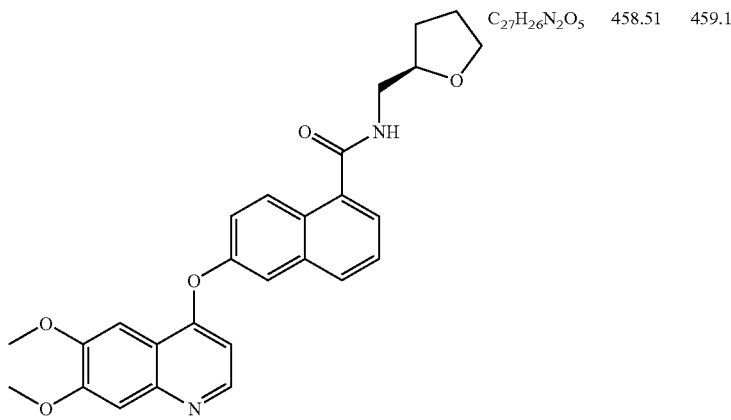 6-((6,7-bis(methyloxy)-4-quinolinyl)oxy)-N-((2R)-tetrahydro-2-furanylmethyl)-1-naphthalenecarboxamide | C$_{27}$H$_{26}$N$_2$O$_5$ | 458.51 | 459.1 |
| 799 | 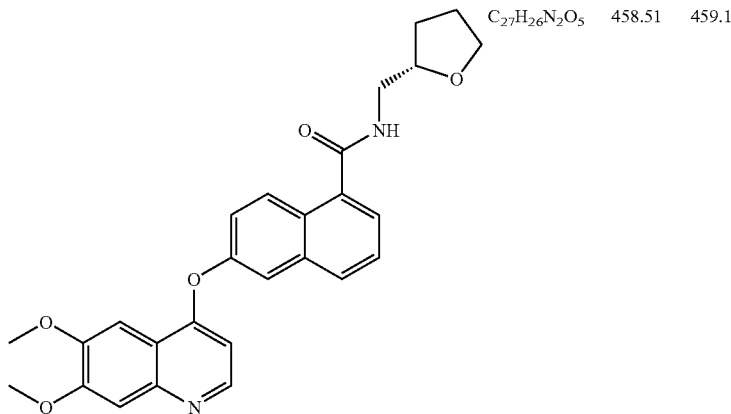 6-((6,7-bis(methyloxy)-4-quinolinyl)oxy)-N-((2S)-tetrahydro-2-furanylmethyl)-1-naphthalenecarboxamide | C$_{27}$H$_{26}$N$_2$O$_5$ | 458.51 | 459.1 |

-continued

| Example No. | Structure & Name | Mol Formula | Mass | M + H |
|---|---|---|---|---|
| 800 | 6-((6,7-bis(methyloxy)-4-quinolinyl)oxy)-N-ethyl-1-naphthalenecarboxamide | $C_{24}H_{22}N_2O_4$ | 402.45 | 403.2 |

EXAMPLE 801

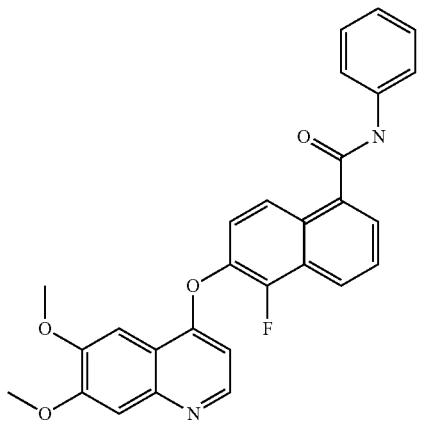

6-((6,7-bis(methyloxy)-4-quinolinyl)oxy)-5-fluoro-N-phenyl-1-naphthalenecarboxamide

Step (a) Preparation of methyl 6-hydroxy-1-naphthoate

To a cooled solution of 6-hydroxy-1-napthoic acid (TCI America) (50 g, 0.27 mmol) in methanol (500 mL), thionyl chloride (29 mL, 0.40 mmol) was added slowly. The temperature was maintained at 15 to 30° C. The reaction mixture was allowed to warm to RT and stirred O/N. The solvent was concentrated in-vacuo and the residue azeotroped with benzene. The title compound was obtained as a pink solid.

Step (b) Preparation of methyl 5-fluoro-6-hydroxy-1-naphthoate

To a stirred solution of methyl 6-hydroxy-1-naphthoate (25 g, 123.8 mmol) in anhydrous acetonitrile (130 mL), Select-Fluor (45 g, 127.5 mmol) was added and the reaction vessel sealed (sealed tube). The reaction mixture was heated to 85° C. for 3 d. The reaction mixture was allowed to cool to RT, diluted with ethyl acetate and washed with water, then brine, dried with $Na_2SO_4$, filtered and evaporated. The mixture was purified by column chromatography using methylene chloride as the eluent. The title compound was obtained as a tan solid.

Step (c) Preparation of 5-fluoro-6-hydroxy-1-naphthoic acid

Sodium hydroxide (116 g, 2.9 mol) was dissolved in 100 mL water and added to a solution of methyl 5-fluoro-6-hydroxy-1-naphthoate (8.56 g, 38.9 mmol) in methanol (200 mL). The mixture was refluxed at 80° C. for 2 h. The mixture was allowed to cool to RT, then poured into 6N HCl in ice. The pH was adjusted to 3 to give a fine purple/pink solid. The title compound was isolated by centrifuge (with some salts).

Step (d) Preparation of 6-(6,7-dimethoxyquinolin-4-yloxy)-5-fluoro-1-naphthoic acid To a solution of 5-fluoro-6-hydroxy-1-naphthoic acid (1 g, 4.87 mmol) in DMSO (5 mL), $Cs_2CO_3$ (4.75 g, 14.61 mmol) was added in one portion. The mixture was stirred at RT 10 min. To the suspension, 4-chloro-6,7-dimethoxyquinoline (1.09 g, 4.87 mmol) was added and the mixture heated to 140° C. O/N. The mixture was allowed to cool to RT, pH adjusted to 7 and the resulting solid filtered and rinsed with water. The title compound was obtained as a tan solid.

Step (e) Preparation of 6-(6,7-dimethoxyquinolin-4-yloxy)-5-fluoro-1-naphthoyl Chloride A suspension of 6-(6,7-dimethoxyquinolin-4-yloxy)-5-fluoro-1-naphthoic acid (1.23 g, 3.12 mmol) in thionyl chloride (3 mL, excess) was refluxed for 1.5 h. The reaction mixture was concentrated in-vacuo and azeotroped with toluene (×2) to give the title compound as a brown solid.

Step (f) Preparation of 6-((6,7-bis(methyloxy)-4-quinolinyl)oxy)-5-fluoro-N-phenyl-1-naphthalenecarboxamide The title compound was prepared similar to the procedure described in Example MHP-1 (c). The product was purified by column chromatography. MS (ESI pos. ion) m/z: 469.0 (M+H). Calc'd for $C_{28}H_{21}FN_2O_4$–468.48.

The following examples were prepared similar to the procedures described in Example 801 and purified by column chromatography and/or crystallization.

| Example No. | Structure & Name | Mol Formula | Mass | M + H |
|---|---|---|---|---|
| 802 | 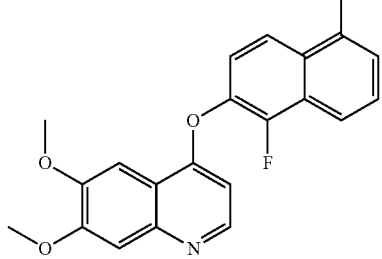<br>6-((6,7-bis(methyloxy)-4-quinolinyl)oxy)-5-fluoro-N-(2-(methyloxy)ethyl)-1-naphthalenecarboxamide | $C_{25}H_{23}FN_2O_5$ | 450.46 | 451.0 |
| 803 | 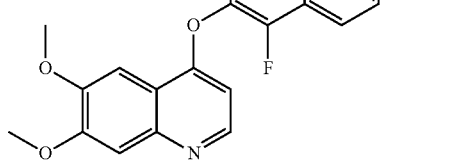<br>6-((6,7-bis(methyloxy)-4-quinolinyl)oxy)-N-cyclopropyl-5-fluoro-1-naphthalenecarboxamide | $C_{25}H_{21}FN_2O_4$ | 432.44 | 433.0 |
| 804 | 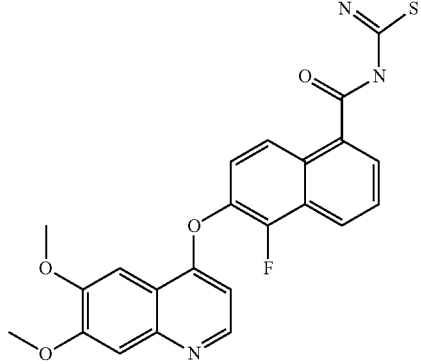<br>6-((6,7-bis(methyloxy)-4-quinolinyl)oxy)-5-fluoro-N-(1,3-thiazol-2-yl)-1-naphthalenecarboxamide | $C_{25}H_{18}FN_3O_4S$ | 475.49 | 476.0 |

-continued
| Example No. | Structure & Name | Mol Formula | Mass | M + H |
|---|---|---|---|---|
| 805 | 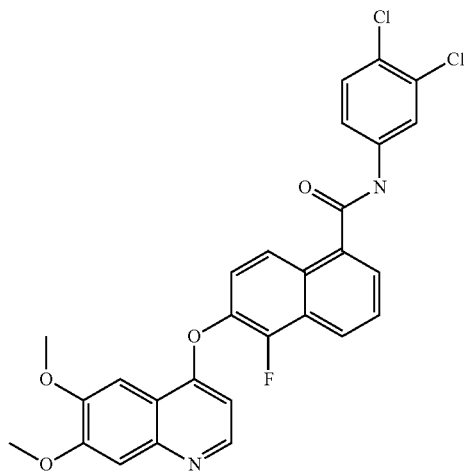<br>6-((6,7-bis(methyloxy)-4-quinolinyl)oxy)-N-(3,4-dichlorophenyl)-5-fluoro-1-naphthalenecarboxamide | $C_{28}H_{19}Cl_2FN_2O_4$ | 537.37 | 537.0 |
| 806 | 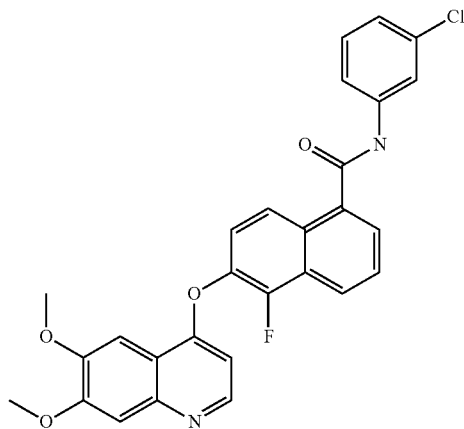<br>6-((6,7-bis(methyloxy)-4-quinolinyl)oxy)-N-(3-chlorophenyl)-5-fluoro-1-naphthalenecarboxamide | $C_{28}H_{20}ClFN_2O_4$ | 502.92 | 503.1 |
| 807 | 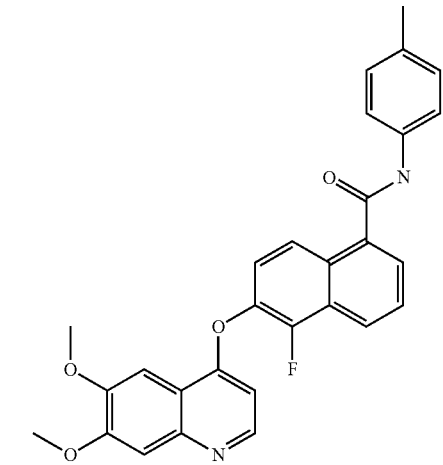<br>6-((6,7-bis(methyloxy)-4-quinolinyl)oxy)-5-fluoro-N-(4-methylphenyl)-1-naphthalenecarboxamide | $C_{29}H_{23}FN_2O_4$ | 482.50 | 4 |

-continued

| Example No. | Structure & Name | Mol Formula | Mass | M + H |
|---|---|---|---|---|
| 808 | 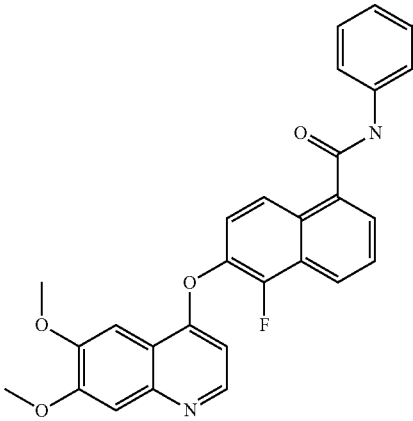<br>6-((6,7-bis(methyloxy)-4-quinolinyl)oxy)-5-fluoro-N-(3-fluorophenyl)-1-naphthalenecarboxamide | C$_{28}$H$_{20}$F$_2$N$_2$O$_4$ | 486.47 | 487.1 |
| 809 | 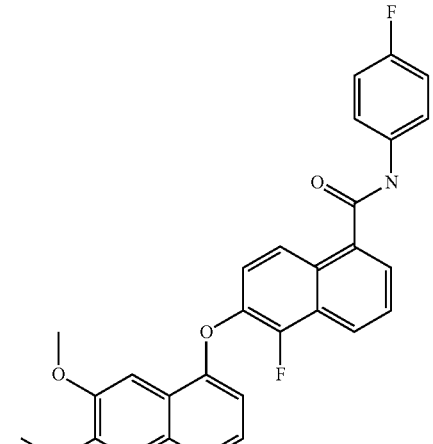<br>6-((6,7-bis(methyloxy)-4-quinolinyl)oxy)-5-fluoro-N-(4-fluorophenyl)-1-naphthalenecarboxamide | C$_{28}$H$_{20}$F$_2$N$_2$O$_4$ | 486.47 | 487.1 |
| 810 | 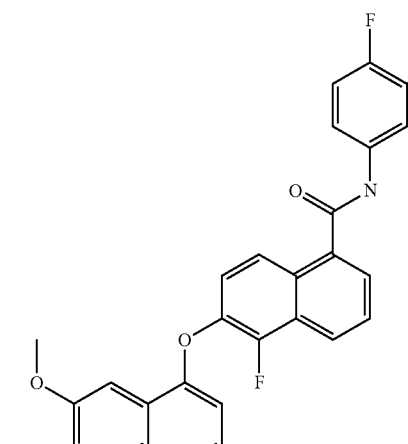<br>6-((6,7-bis(methyloxy)-4-quinolinyl)oxy)-N-(3,4-difluorophenyl)-5-fluoro-1-naphthalenecarboxamide | C$_{28}$H$_{19}$F$_3$N$_2$O$_4$ | 504.46 | 505.1 |

-continued
| Example No. | Structure & Name | Mol Formula | Mass | M + H |
|---|---|---|---|---|
| 811 | 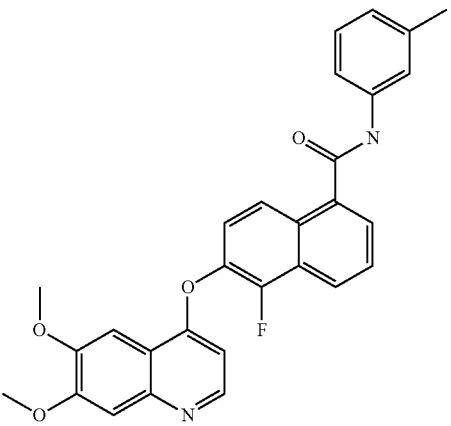<br>6-((6,7-bis(methyloxy)-4-quinolinyl)oxy)-5-fluoro-N-(3-methylphenyl)-1-naphthalenecarboxamide | C$_{29}$H$_{23}$FN$_2$O$_4$ | 482.50 | 483.2 |
| 812 | 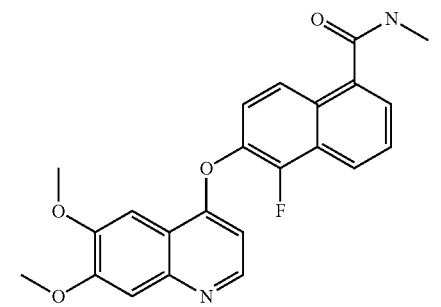<br>6-((6,7-bis(methyloxy)-4-quinolinyl)oxy)-5-fluoro-N-methyl-1-naphthalenecarboxamide | C$_{23}$H$_{19}$FN$_2$O$_4$ | 406.41 | 407.1 |
| 813 | 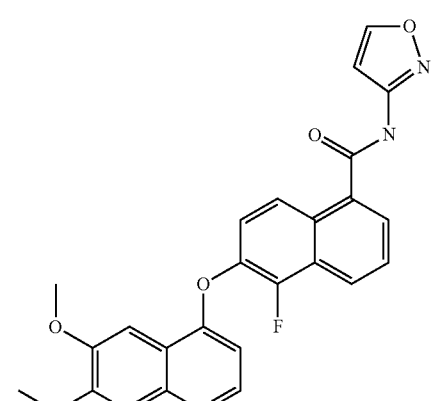<br>6-((6,7-bis(methyloxy)-4-quinolinyl)oxy)-5-fluoro-N-(3-isoxazolyl)-1-naphthalenecarboxamide | C$_{25}$H$_{18}$FN$_3$O$_5$ | 459.43 | 460. |

| Example No. | Structure & Name | Mol Formula | Mass | M + H |
|---|---|---|---|---|
| 814 | 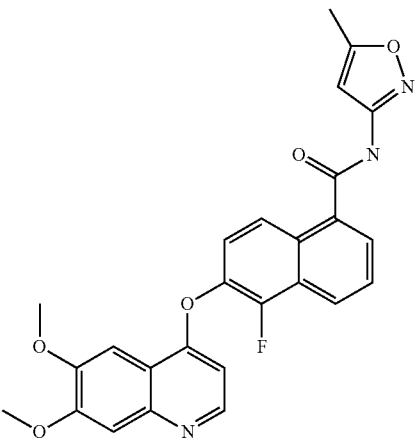<br>6-((6,7-bis(methyloxy)-4-quinolinyl)oxy)-5-fluoro-N-(5-methyl-3-isoxazolyl)-1-naphthalenecarboxamide | $C_{26}H_{20}FN_3O_5$ | 473.45 | 474.2 |
| 815 | 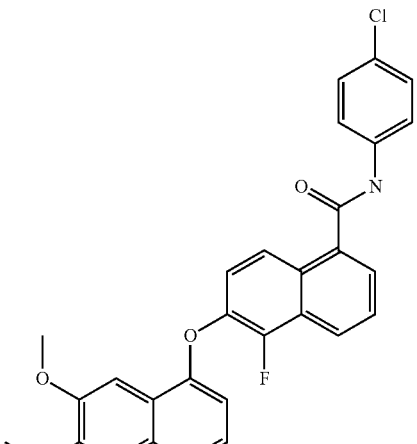<br>6-((6,7-bis(methyloxy)-4-quinolinyl)oxy)-N-(4-chlorophenyl)-5-fluoro-1-naphthalenecarboxamide | $C_{28}H_{20}ClFN_2O_4$ | 502.92 | 503 |

EXAMPLE 816

N-(4-chlorophenyl)-5-fluoro-6-((6-(methyloxy)-7-((3-(4-morpholinyl) propyl)oxy)-4-quinolinyl)oxy)-1-naphthalenecarboxamide

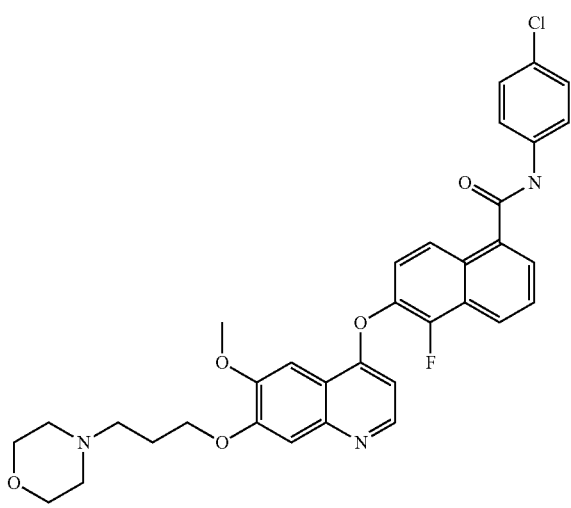

Step (a) Preparation of 5-fluoro-6-(6-methoxy-7-(3-morpholinopropoxy)quinolin-4-yloxy)-1-naphthoic acid In a microwave tube, 5-fluoro-6-hydroxy-1-naphthoic acid (300 mg, 1.48 mmol) and $Cs_2CO_3$ (1.45 g, 4.44 mmol) in DMSO (1.5 mL) were stirred for 3 min at RT. 4-Chloro-6-methoxy-7-(3-morpholinopropoxy)quinoline (500 mg, 1.48 mmol) was added and the vessel sealed. The mixture was subjected to the microwave (Personal Chemistry) at 160° C. for 15 min, then 30 min. The vessel was opened and the mixture stirred with a spatula, resealed and heated another 5 minutes. The reaction mixture made pH 7 with 1N HCl and evaporated. The residual solid was taken up into MeOH and filtered and evaporated. The solid was then taken up into and $CH_2Cl_2$/MeOH mixture and filtered. The filtrate was evaporated to dryness and triturated with ethyl acetate/hexanes and the title compound collected as a yellow solid.

Step (b) Preparation of N-(4-chlorophenyl)-5-fluoro-6-((6-(methyloxy)-7-((3-(4-morpholinyl)propyl)oxy)-4-quinolinyl)oxy)-1-naphthalenecarboxamide The title compound was prepared similar to Example 421, Steps b and c. MS (ESI pos. ion) m/z: 616.1 (M+H). Calc'd for $C_{34}H_{31}ClFN_3O_5$–616.08.

The following examples were prepared similar to the procedures described in Example 816

| Example No. | Structure & Name | Mol Formula | Mass | M + H |
|---|---|---|---|---|
| 817 | 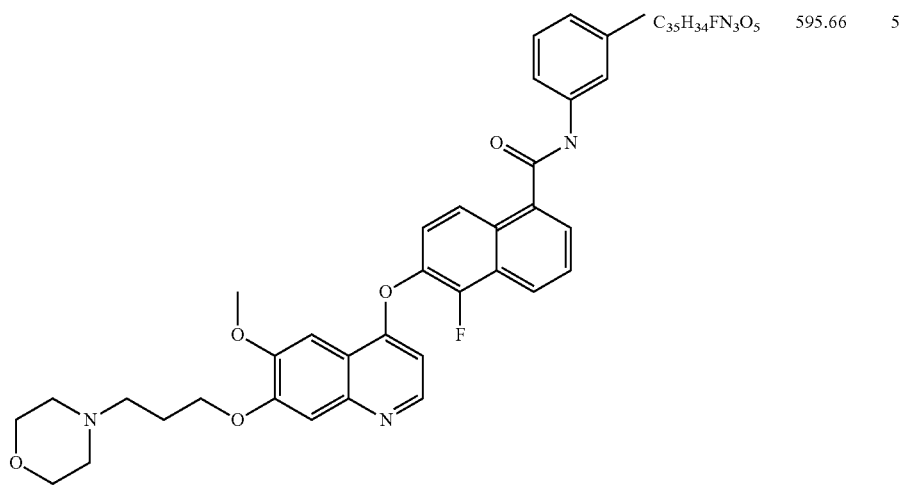<br>5-fluoro-6-((6-(methyloxy)-7-((3-(4-morpholinyl)propyl)oxy)-4-quinolinyl)oxy)-N-(3-methylphenyl)-1-naphthalenecarboxamide | $C_{35}H_{34}FN_3O_5$ | 595.66 | 5 |

| Example No. | Structure & Name | Mol Formula | Mass | M + H |
|---|---|---|---|---|
| 818 | 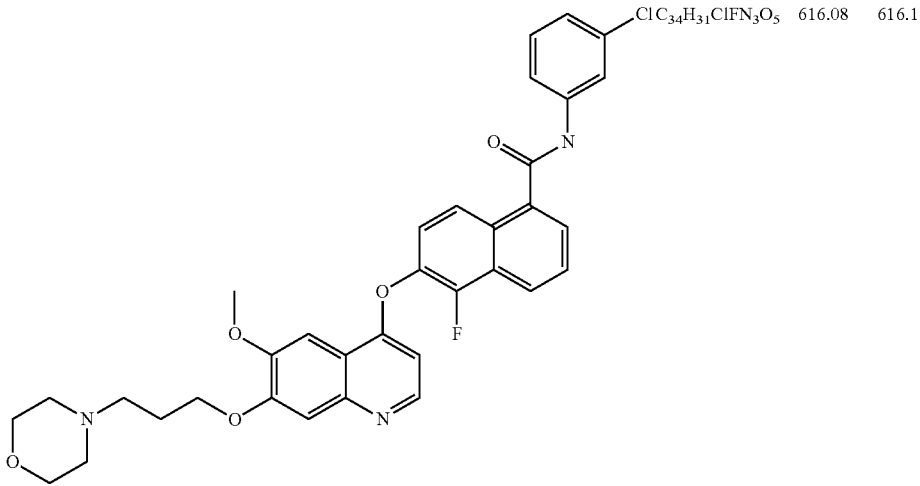 N-(3-chlorophenyl)-5-fluoro-6-((6-(methyloxy)-7-((3-(4-morpholinyl)propyl)oxy)-4-quinolinyl)oxy)-1-naphthalenecarboxamide | C$_{34}$H$_{31}$ClFN$_3$O$_5$ | 616.08 | 616.1 |

EXAMPLE 819

4-((5-((cyclopropylamino)carbonyl)-2-naphthalenyl)oxy)-7-(methyloxy)-6-quinolinecarboxamide Step (a) Preparation of 4-chloro-7-methoxyquinoline-6-carboxamide The synthesis of this compound follows the procedure described in the following patent (patent No. WO 00/050405, Application No. WO 2000-GB579).

Step (b) Preparation of 6-(6-carbamoyl-7-methoxyquinolin-4-yloxy)-1-naphthoic acid The title compound was synthesized in a manner similar to that described in Example 801, Step d.

Step (c) Preparation of 6-(6-carbamoyl-7-methoxyquinolin-4-yloxy)-1-naphthoyl chloride The title compound was synthesized in a manner similar to that described in Example 801, Step e.

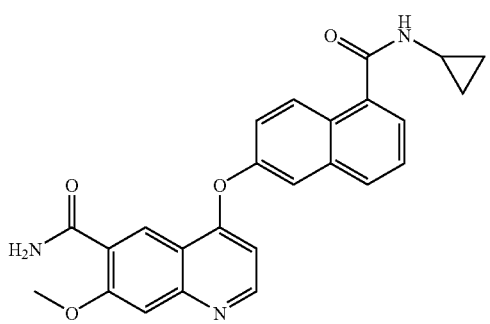

Step (d) Preparation of 4-((5-((cyclopropylamino)carbonyl)-2-naphthalenyl)oxy)-7-(methyloxy)-6-quinolinecarboxamide The title compound was synthesized in a manner similar to that described in Example 273, Step e. MS (ESI pos. ion) m/z: 469.0 (M+H). Calc'd for C$_{28}$H$_{21}$FN$_2$O$_4$–468.48.

The following examples were prepared similar to the procedures described in Example 819, Step d.

| Example No. | Structure & Name | Mol Formula | Mass | M + H |
|---|---|---|---|---|
| 820 | 4-((5-((cyclopropylamino)carbonyl)-1-fluoro-2-naphthalenyl)oxy)-7-(methyloxy)-6-quinolinecarboxamide | $C_{25}H_{20}FN_3O_4$ | 445.45 | 446.4 |

EXAMPLE 821

4-((5-((cyclopropylamino)carbonyl)-2-naphthalenyl)oxy)-N-methyl-7-(methyloxy)-6-quinolinecarboxamide

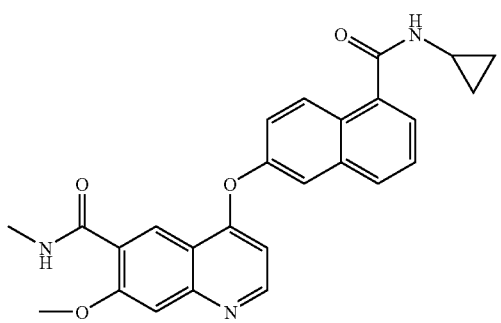

Step (a) Preparation of 4-chloro-7-methoxy-N-methylquinoline-6-carboxamide

The synthesis of this compound follows the procedure described in the following patent (patent No. WO 00/050405, Application No. WO 2000-GB579).

Step (b) 6-(7-methoxy-6-(methylcarbamoyl)quinolin-4-yloxy)-1-naphthoic acid

The title compound was synthesized in a manner similar to that described in Example 801, Step d.

Step (c) Preparation of 4-((5-((cyclopropylamino)carbonyl)-2-naphthalenyl)oxy)-N-methyl-7-(methyloxy)-6-quinolinecarboxamide The title compound was synthesized in a manner similar to that described in Example 273, Step e.
The following examples were prepared similar to the procedures described in Example 821.

| Example No. | Structure & Name | Mol Formula | Mass | M + H |
|---|---|---|---|---|
| 822 | N-methyl-7-(methyloxy)-4-((5-(((2-(methyloxy)ethyl)amino)carbonyl)-2-naphthalenyl)oxy)-6-quinolinecarboxamide | $C_{26}H_{25}N_3O_5$ | 459.5 | 460.2 |

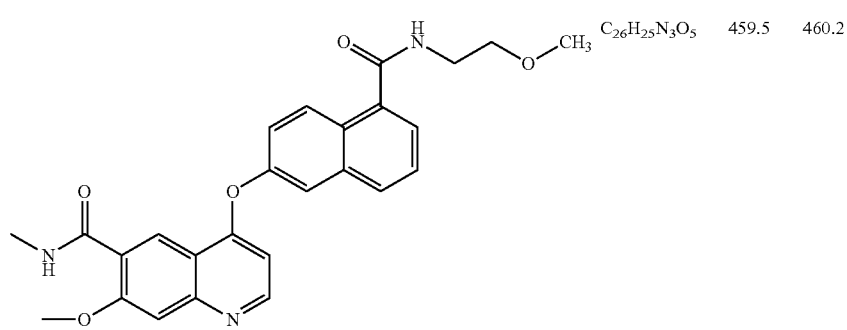

| Example No. | Structure & Name | Mol Formula | Mass | M + H |
|---|---|---|---|---|
| 823 | 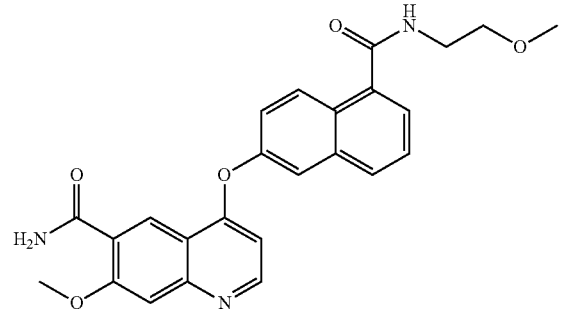<br>7-(methyloxy)-4-((5-(((2-(methyloxy)ethyl)amino)carbonyl)-2-naphthalenyl)oxy)-6-quinolinecarboxamide | C$_{25}$H$_{23}$N$_3$O$_5$ | 445.47 | 446.1 |

The following examples were prepared similar to the procedures described in Example Ex 120 and purified by column chromatography and/or crystallization.

| Example No. | Structure & Name | Mol Formula | Mass | M + H |
|---|---|---|---|---|
| 824 | 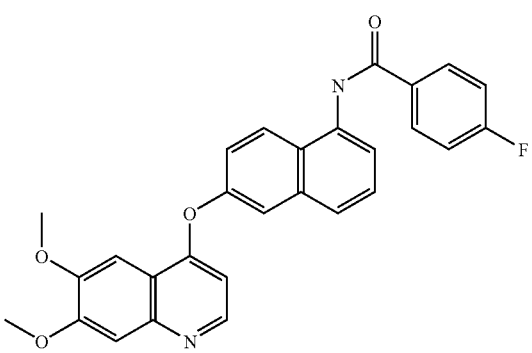<br>N-(6-((6,7-bis(methyloxy)-4-quinolinyl)oxy)-1-naphthalenyl)-4-fluorobenzamide | C$_{28}$H$_{21}$FN$_2$O$_4$ | 468.48 | 469.2 |
| 825 | 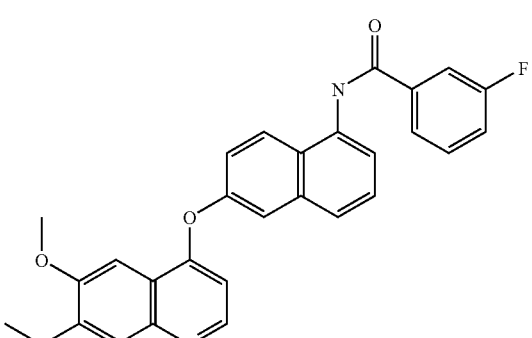<br>N-(6-((6,7-bis(methyloxy)-4-quinolinyl)oxy)-1-naphthalenyl)-3-fluorobenzamide | C$_{28}$H$_{21}$FN$_2$O$_4$ | 468.48 | 469.2 |

-continued

| Example No. | Structure & Name | Mol Formula | Mass | M + H |
|---|---|---|---|---|
| 826 | 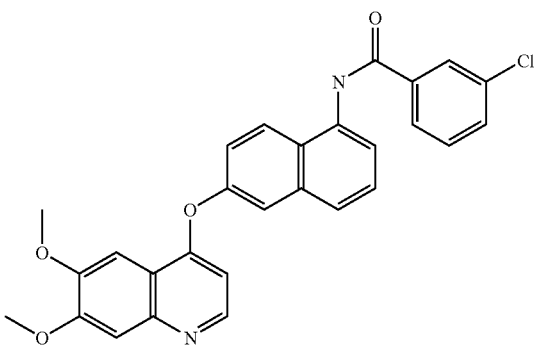 N-(6-((6,7-bis(methyloxy)-4-quinolinyl)oxy)-1-naphthalenyl)-3-chlorobenzamide | C<sub>28</sub>H<sub>21</sub>ClN<sub>2</sub>O<sub>4</sub> | 484.93 | 485.0 |
| 827 | 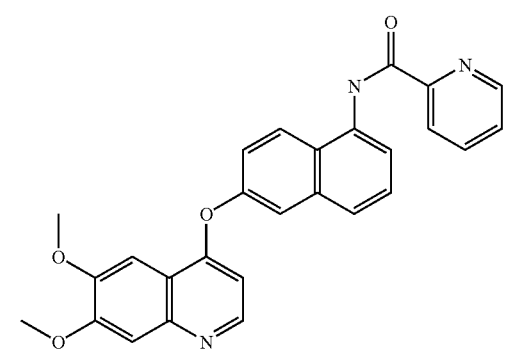 N-(6-((6,7-bis(methyloxy)-4-quinolinyl)oxy)-1-naphthalenyl)-2-pyridinecarboxamide | C<sub>27</sub>H<sub>21</sub>N<sub>3</sub>O<sub>4</sub> | 451.48 | 452.0 |
| 828 | 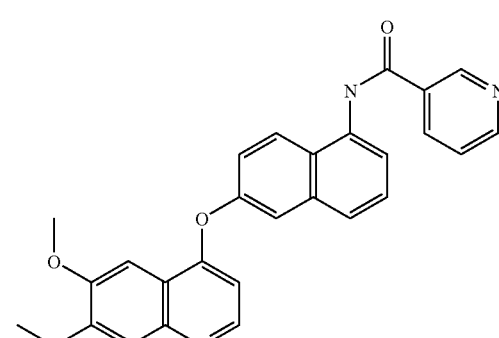 N-(6-((6,7-bis(methyloxy)-4-quinolinyl)oxy)-1-naphthalenyl)-3-pyridinecarboxamide | C<sub>27</sub>H<sub>21</sub>N<sub>3</sub>O<sub>4</sub> | 451.48 | 452.0 |

| Example No. | Structure & Name | Mol Formula | Mass | M + H |
|---|---|---|---|---|
| 829 | 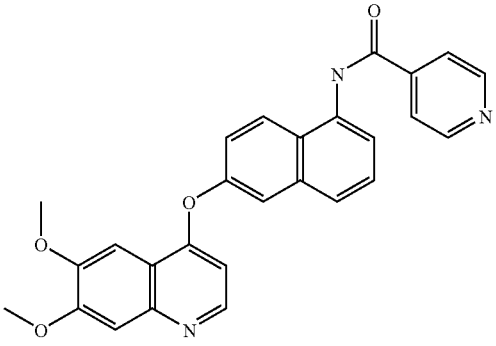<br>N-(6-((6,7-bis(methyloxy)-4-quinolinyl)oxy)-1-naphthalenyl)-4-pyridinecarboxamide | C₂₇H₂₁N₃O₄ | 451.48 | 452.0 |
| 830 | 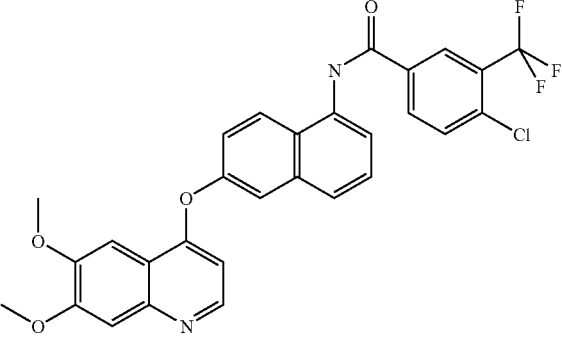<br>N-(6-((6,7-bis(methyloxy)-4-quinolinyl)oxy)-1-naphthalenyl)-4-chloro-3-(trifluoromethyl)benzamide | C₂₉H₂₀ClF₃N₂O₄ | 552.93 | 553.1 |
| 831 | 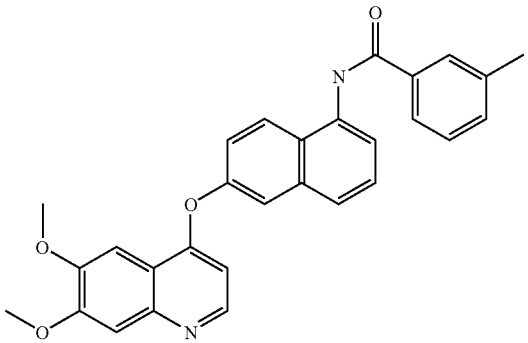<br>N-(6-((6,7-bis(methyloxy)-4-quinolinyl)oxy)-1-naphthalenyl)-3-methylbenzamide | C₂₉H₂₄N₂O₄ | 464.51 | 465.1 |

| Example No. | Structure & Name | Mol Formula | Mass | M + H |
|---|---|---|---|---|
| 832 | 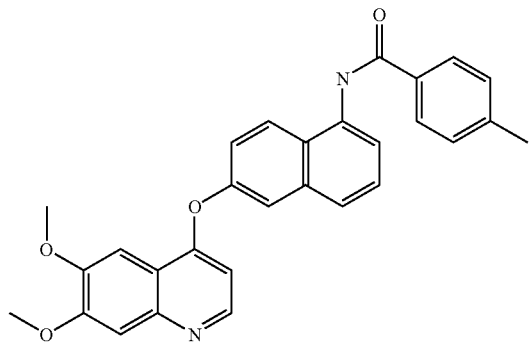<br>N-(6-((6,7-bis(methyloxy)-4-quinolinyl)oxy)-1-naphthalenyl)-4-methylbenzamide | $C_{29}H_{24}N_2O_4$ | 464.51 | 465.1 |
| 833 | 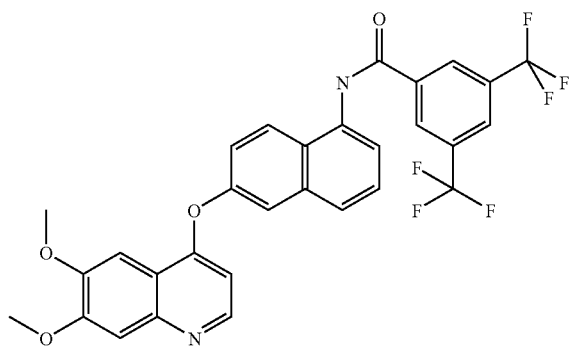<br>N-(6-((6,7-bis(methyloxy)-4-quinolinyl)oxy)-1-naphthalenyl)-3,5-bis(trifluoromethyl)benzamide | $C_{30}H_{20}F_6N_2O_4$ | 586.48 | 587.1 |
| 834 | 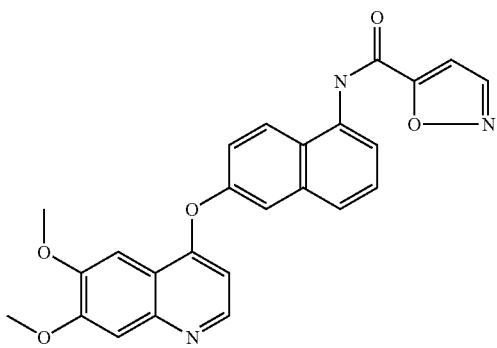<br>N-(6-((6,7-bis(methyloxy)-4-quinolinyl)oxy)-1-naphthalenyl)-5-isoxazolecarboxamide | $C_{25}H_{19}N_3O_5$ | 441.44 | 442.1 |

-continued
| Example No. | Structure & Name | Mol Formula | Mass | M + H |
|---|---|---|---|---|
| 835 | 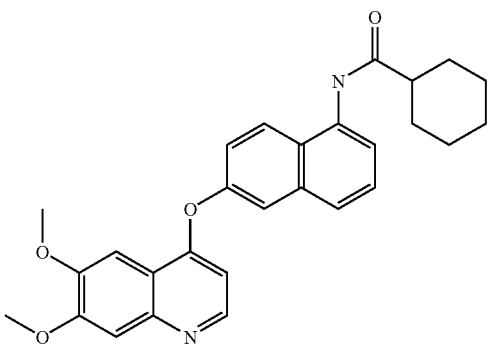<br>N-(6-((6,7-bis(methyloxy)-4-quinolinyl)oxy)-1-naphthalenyl)cyclohexanecarboxamide | $C_{28}H_{28}N_2O_4$ | 456.53 | 457.2 |
| 836 | 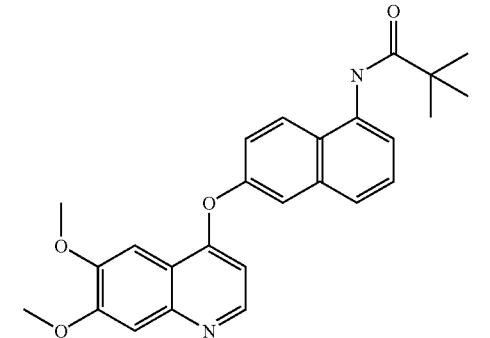<br>N-(6-((6,7-bis(methyloxy)-4-quinolinyl)oxy)-1-naphthalenyl)-2,2-dimethylpropanamide | $C_{26}H_{26}N_2O_4$ | 430.50 | 431.2 |
| 837 | 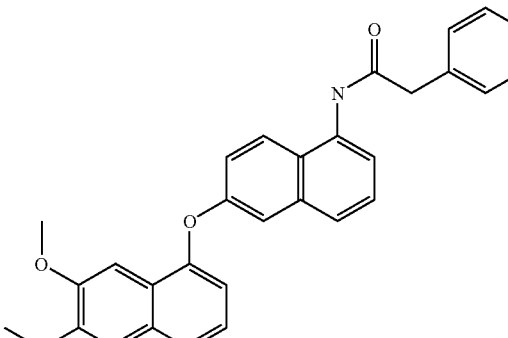<br>N-(6-((6,7-bis(methyloxy)-4-quinolinyl)oxy)-1-naphthalenyl)-2-phenylacetamide | $C_{29}H_{24}N_2O_4$ | 464.51 | 465.1 |

| Example No. | Structure & Name | Mol Formula | Mass | M + H |
|---|---|---|---|---|
| 838 | 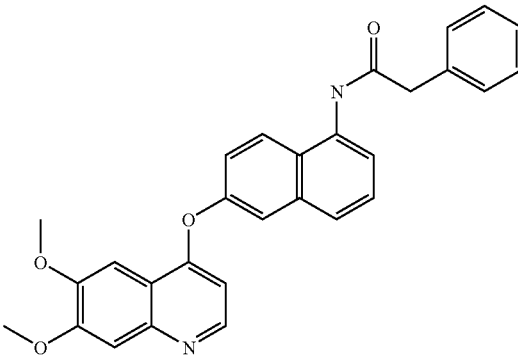 N-(6-((6,7-bis(methyloxy)-4-quinolinyl)oxy)-1-naphthalenyl)-2-(4-chlorophenyl)acetamide | $C_{29}H_{23}ClN_2O_4$ | 498.96 | 499.1 |
| 839 | 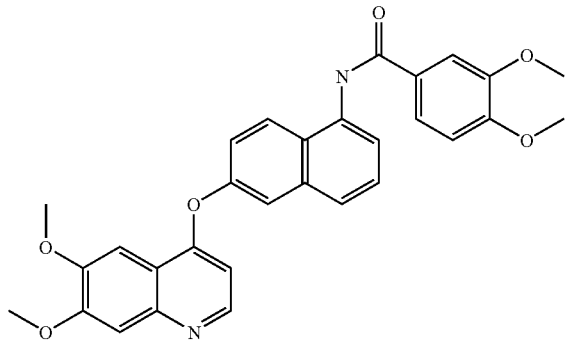 N-(6-((6,7-bis(methyloxy)-4-quinolinyl)oxy)-1-naphthalenyl)-3,4-bis(methyloxy)benzamide | $C_{30}H_{26}N_2O_6$ | 510.54 | 511.1 |
| 840 | 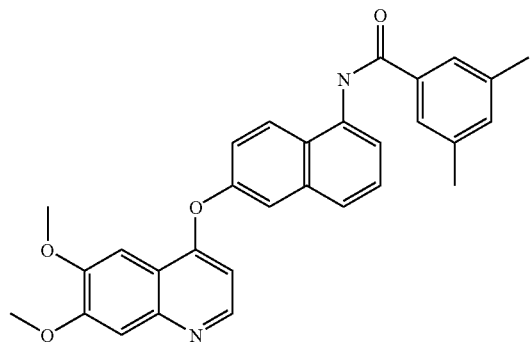 N-(6-((6,7-bis(methyloxy)-4-quinolinyl)oxy)-1-naphthalenyl)-3,5-dimethylbenzamide | $C_{30}H_{26}N_2O_4$ | 478.54 | 479.2 |

| Example No. | Structure & Name | Mol Formula | Mass | M + H |
|---|---|---|---|---|
| 841 | 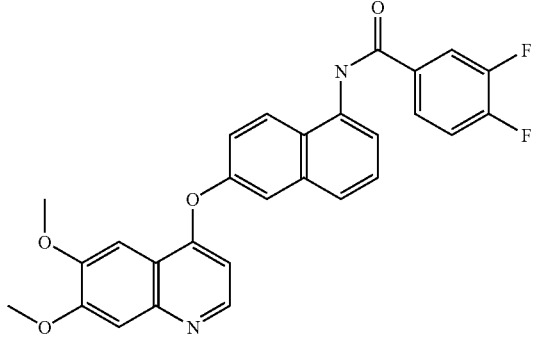 N-(6-((6,7-bis(methyloxy)-4-quinolinyl)oxy)-1-naphthalenyl)-3,4-difluorobenzamide | C$_{28}$H$_{20}$F$_2$N$_2$O$_4$ | 486.47 | 487.1 |
| 842 | 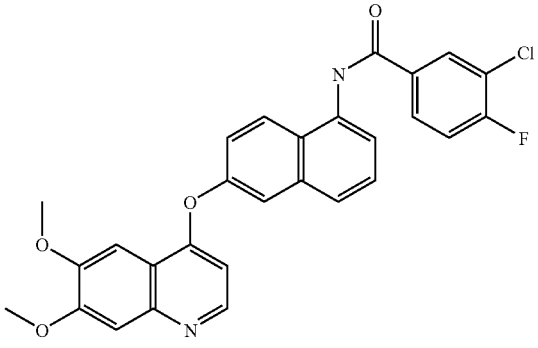 N-(6-((6,7-bis(methyloxy)-4-quinolinyl)oxy)-1-naphthalenyl)-3-chloro-4-fluorobenzamide | C$_{28}$H$_{20}$ClFN$_2$O$_4$ | 502.92 | 503. |
| 843 | 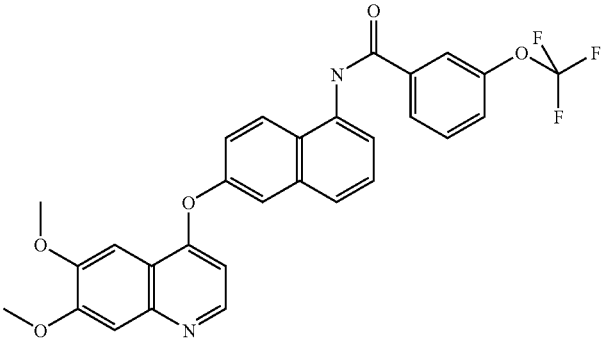 N-(6-((6,7-bis(methyloxy)-4-quinolinyl)oxy)-1-naphthalenyl)-3-((trifluoromethyl)oxy)benzamide | C$_{29}$H$_{21}$F$_3$N$_2$O$_5$ | 534.48 | 535.1 |

| Example No. | Structure & Name | Mol Formula | Mass | M + H |
|---|---|---|---|---|
| 844 | 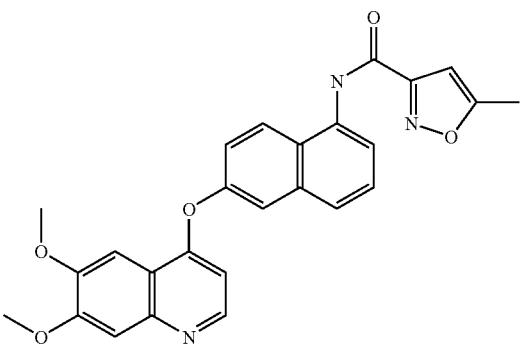 N-(6-((6,7-bis(methyloxy)-4-quinolinyl)oxy)-1-naphthalenyl)-5-methyl-3-isoxazolecarboxamide | C<sub>26</sub>H<sub>21</sub>N<sub>3</sub>O<sub>5</sub> | 455.46 | 456.1 |
| 845 | 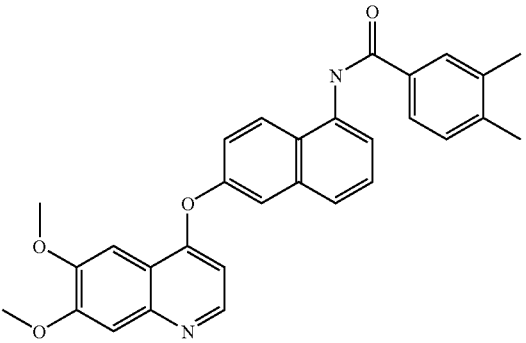 N-(6-((6,7-bis(methyloxy)-4-quinolinyl)oxy)-1-naphthalenyl)-3,4-dimethylbenzamide | C<sub>30</sub>H<sub>26</sub>N<sub>2</sub>O<sub>4</sub> | 478.54 | 479.2 |
| 846 | 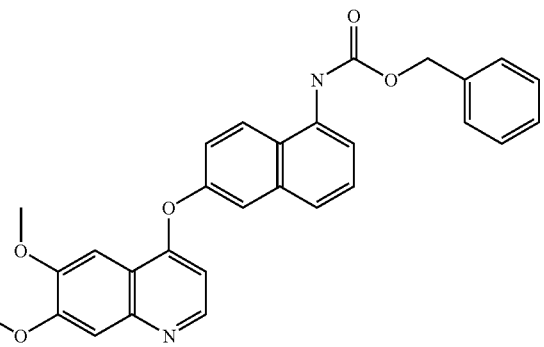 Phenylmethyl 6-((6,7-bis(methyloxy)-4-quinolinyl)oxy)-1-naphthalenylcarbamate | C<sub>29</sub>H<sub>24</sub>N<sub>2</sub>O<sub>5</sub> | 480.51 | 481.1 |

| Example No. | Structure & Name | Mol Formula | Mass | M + H |
|---|---|---|---|---|
| 847 | N-(6-(((6,7-bis(methyloxy)-4-quinolinyl)oxy)-1-naphthalenyl)-4-chlorobenzamide | C$_{28}$H$_{21}$ClN$_2$O$_4$ | 484.94 | 485.1 |
| 848 | N-(6-(((6,7-bis(methyloxy)-4-quinolinyl)oxy)-1-naphthalenyl)-2-chlorobenzamide | C$_{28}$H$_{21}$ClN$_2$O$_4$ | 484.94 | 485.1 |
| 849 | N-(6-(((6,7-bis(methyloxy)-4-quinolinyl)oxy)-1-naphthalenyl)-2-fluorobenzamide | C$_{28}$H$_{21}$FN$_2$O$_4$ | 468.48 | 469.1 |

| Example No. | Structure & Name | Mol Formula | Mass | M + H |
|---|---|---|---|---|
| 850 | 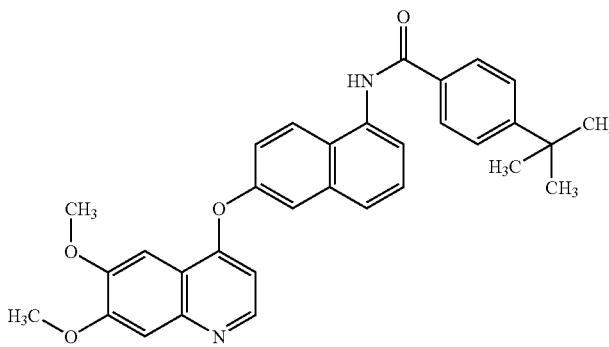<br>N-(6-((6,7-bis(methyloxy)-4-quinolinyl)oxy)-1-naphthalenyl)-4-(1,1-dimethylethyl)benzamide | C₃₂H₃₀N₂O₄ | 506.6 | 507.4 |
| 851 | 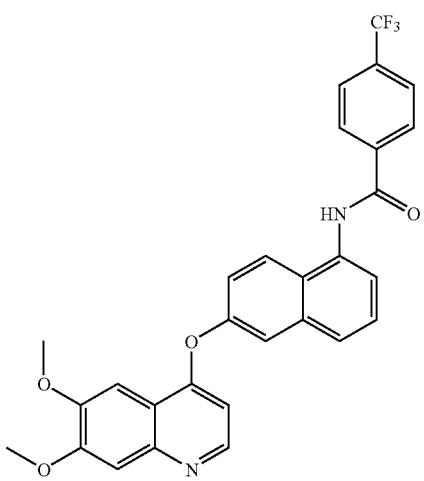<br>N-(6-((6,7-bis(methyloxy)-4-quinolinyl)oxy)-1-naphthalenyl)-4-(trifluoromethyl)benzamide | C₂₉H₂₁F₃N₂O₄ | 518.49 | 519.3 |
| 852 | 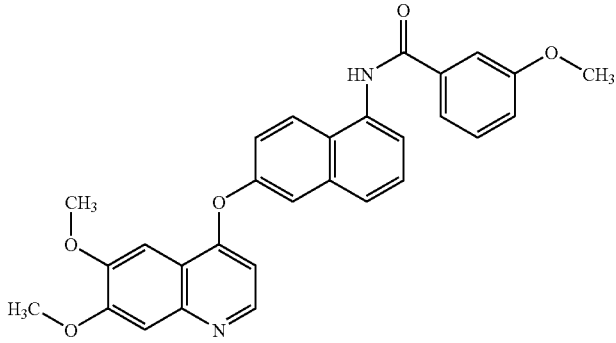<br>N-(6-((6,7-bis(methyloxy)-4-quinolinyl)oxy)-1-naphthalenyl)-3-(methyloxy)benzamide | C₂₉H₂₄N₂O₅ | 480.52 | 481.3 |

-continued

| Example No. | Structure & Name | Mol Formula | Mass | M + H |
|---|---|---|---|---|
| 853 | N-(6-((6,7-bis(methyloxy)-4-quinolinyl)oxy)-1-naphthalenyl)-2,3-dichlorobenzamide | C$_{28}$H$_{20}$Cl$_2$N$_2$O$_4$ | 519.38 | 521.4 |
| 854 | N-(6-((6,7-bis(methyloxy)-4-quinolinyl)oxy)-1-naphthalenyl)-4-(methyloxy)benzamide | C$_{29}$H$_{24}$N$_2$O$_5$ | 480.52 | 481.1 |
| 855 | N-(6-((6,7-bis(methyloxy)-4-quinolinyl)oxy)-1-naphthalenyl)-3-(trifluoromethyl)benzamide | C$_{29}$H$_{21}$F$_3$N$_2$O$_4$ | 518.49 | 519.3 |

EXAMPLE 856

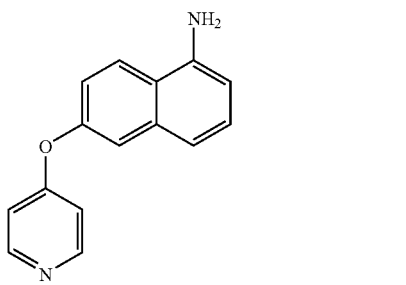

6-(pyridin-4-yloxy)naphthalen-1-amine

Preparation of
6-(pyridin-4-yloxy)naphthalen-1-amine

The title compound was prepared in a manner similar to that described in Example 120 Step a.
The following compounds were prepared in a manner similar to that described in Example 120 Step b.

EXAMPLE 859

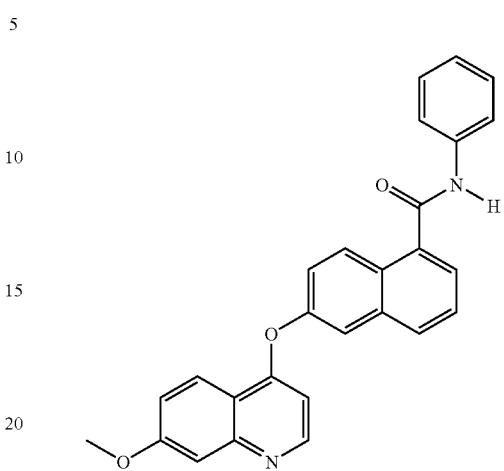

| Example No. | Structure & Name | Mol Formula | Mass | M + H |
|---|---|---|---|---|
| 857 | 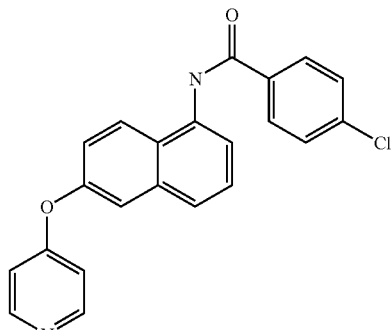<br>4-chloro-N-(6-(4-pyridinyloxy)-1-naphthalenyl)benzamide | $C_{22}H_{15}ClN_2O_2$ | 374.82 | 375.1 |
| 858 | 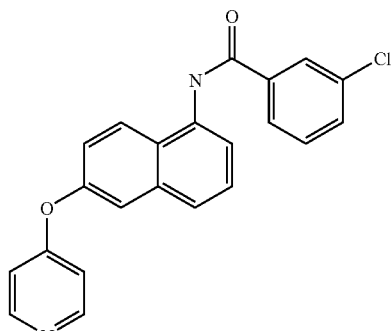<br>3-chloro-N-(6-(4-pyridinyloxy)-1-naphthalenyl)benzamide | $C_{22}H_{15}ClN_2O2$ | 374.82 | 375.0 |

6-((7-(methoxy)-4-quinolinyl)oxy)-N-phenyl-1-naphthalenecarboxamide

Step (a) Preparation of 7-methoxyquinolin-4-ol

To a solution of 1-(2-amino-4-methoxyphenyl)ethanone [J Med Chem, 32(4):807-826 (1989)] (7.32 g, 44.3 mmol) in dioxane (150 mL), NaOt-Bu (9.8 g, 102 mmol) was added and stirred at RT for 30 min. The color changed from lime green to dark green. Ethyl formate (23.64 mL, 292 mmol) was added with an additional 20 mL dioxane. The reaction mixture was stirred at RT 18 h after which the mixture was poured into water (20 mL) and the pH adjusted to 7 with 2N HCl. The solution was evaporated a little. The red solid was filtered and rinsed with water. The solid was triturated with 1:1 EtOAc: hexanes and then filtered to give the title compound as a brown solid.

Step (b) Preparation of 4-chloro-7-methoxyquinoline

To a solution of $POCl_3$ (11 mL, excess), 7-methoxyquinolin-4-ol (1.87 g, 10.67 mmol) was added and heated from RT to 90° C. The mixture was allowed to cool to RT, concentrated in-vacuo and cooled in an ice bath during the slow adjustment to pH 7 by alternating ice and 1N NaOH. The solid was filtered and rinsed with water. The title compound was isolated as a tan solid.

Step (c) Preparation of 6-(7-methoxyquinolin-4-yloxy)-1-naphthoic acid

The title compound was prepared similar to the procedure described in Example 760 step (d). Workup: The reaction mixture was filtered through a pad of Celite® using 95:5:0.5 ($CH_2Cl_2$: MeOH:Acetic acid) as the eluent and concentrated in-vacuo before pH adjustment.

Step (d) Preparation of 6-(7-methoxyquinolin-4-yloxy)-1-naphthoyl chloride

The title compound was prepared similar to the procedure described in Example 273.

Step (e) Preparation of 6-((7-(methyloxy)-4-quinolinyl)oxy)-N-phenyl-1-naphthalenecarboxamide The title compound was prepared similar to the procedure described in Example 783 Step (c). MS (ESI pos. ion) m/z: 421.0 (M+H). Calc'd for $C_{27}H_{20}N_2O_3$–420.46.

The following examples were prepared similar to the procedures described in Example 859 and purified by column chromatography and/or crystallization.

| Example No. | Structure & Name | Mol Formula | Mass | M + H |
|---|---|---|---|---|
| 860 | 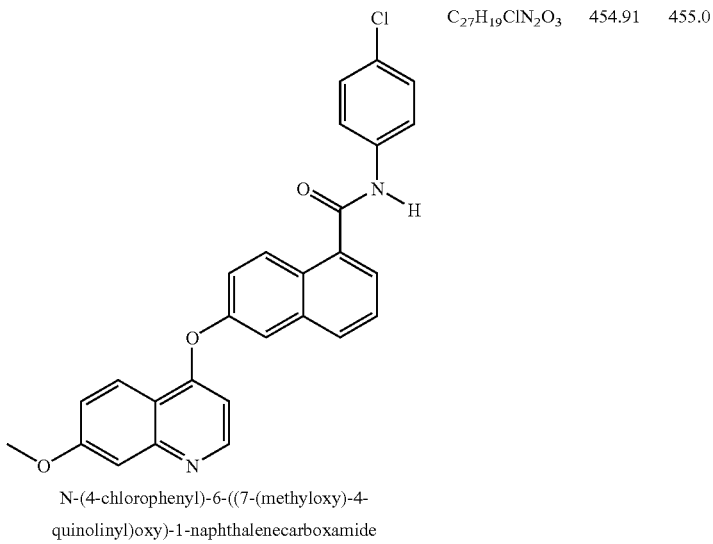<br>N-(4-chlorophenyl)-6-((7-(methyloxy)-4-quinolinyl)oxy)-1-naphthalenecarboxamide | $C_{27}H_{19}ClN_2O_3$ | 454.91 | 455.0 |

| Example No. | Structure & Name | Mol Formula | Mass | M + H |
|---|---|---|---|---|
| 861 | 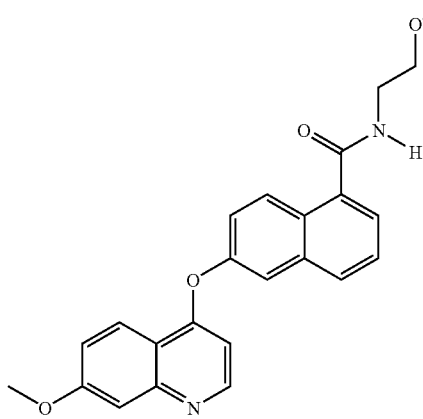<br>N-(2-(methyloxy)ethyl)-6-((7-(methyloxy)-4-quinolinyl)oxy)-1-naphthalenecarboxamide | $C_{24}H_{22}N_2O_4$ | 402.44 | 403. |
| 862 | 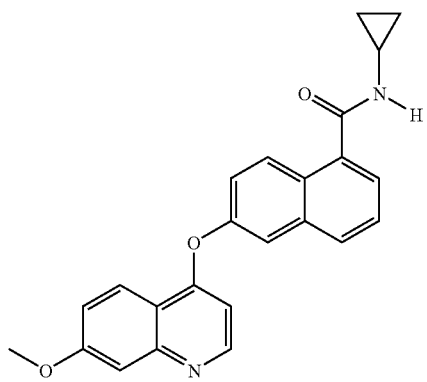<br>N-cyclopropyl-6-((7-(methyloxy)-4-quinolinyl)oxy)-1-naphthalenecarboxamide | $C_{24}H_{20}N_2O_3$ | 384.43 | 385.1 |
| 863 | 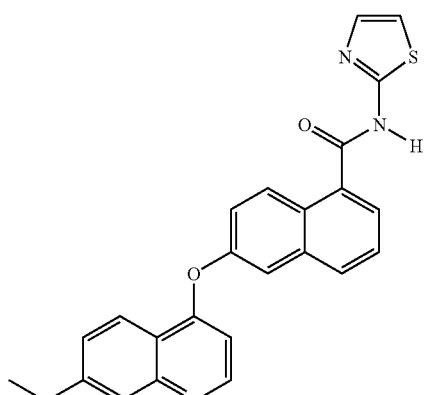<br>6-((7-(methyloxy)-4-quinolinyl)oxy)-N-(1,3-thiazol-2-yl)-1-naphthalenecarboxamide | $C_{24}H_{17}N_3O_3S$ | 427.48 | 428.0 |

EXAMPLE 864

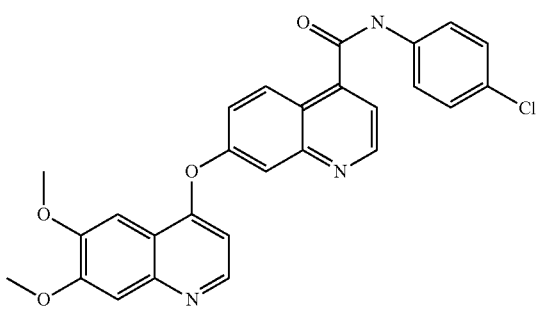

7-((6,7-bis(methyloxy)-4-quinolinyl)oxy)-N-(4-chlorophenyl)-4-quinolinecarboxamide-

Step (a) Preparation of methyl 7-methoxyquinoline-4-carboxylate

The following reagents were placed in a glass jacket inside of a Parr bomb: 4-chloro-7-methoxyquinoline (2 g, 10.33 mmol), Pd(OAC)$_2$ (225 mg, 1.0 mmol), 1,3-diphenylphosphino propane [DPPE] (618 mg, 1.55 mmol), DMF (15 mL), MeOH (3 mL) and TEA (2.87 mL, 20.66 mmol) and the vessel sealed. The vessel was pressurized to 50 psi CO and stirred at 70° C. (internal temperature) for 19 h. The vessel was allowed to cool to RT, carefully opened and the contents transferred to a round bottom flask and concentrated in-vacuo. A solution of 2:1 EtOAc:hexanes was added to the residual solid and the solid filtered (and discarded). The filtrate was evaporated and the residue purified by column chromatography using a mixture of EtOAc/hexanes as the eluent. The title compound was obtained as a yellow solid.

Step (b) Preparation of 7-hydroxyquinoline-4-carboxylic acid

To a cooled (0° C.) solution of methyl 7-methoxyquinoline-4-carboxylate (378 mg, 1.74 mmol) in CH$_2$Cl$_2$, BBr$_3$ (9 mL, excess) was added and the reaction mixture stirred and warmed to RT. After 4 days, the mixture was poured into ice and the yellow solid collected as the title compound.

Step (c) Preparation of 7-(6,7-dimethoxyquinolin-4-yloxy)quinoline-4-carboxylic acid The title compound was prepared similar to the procedure described in Example 783 step (a) using 7-hydroxyquinoline-4-carboxylic acid as the reagent.

Step (d) Preparation of 7-((6,7-bis(methoxy)-4-quinolinyl)oxy)-N-(4-chlorophenyl)-4-quinolinecarboxamide The title compound was prepared similar to the procedure described in Example 357. MS (ESI pos. ion) m/z: 486.1 (M+H). Calc'd for C$_{27}$H$_{20}$ClN$_3$O$_4$–485.92.

The following examples were prepared similar to the procedures described in Example 864 and purified by column chromatography and/or crystallization.

| Example No. | Structure & Name | Mol Formula | Mass | M + H |
|---|---|---|---|---|
| 865 | 7-((6,7-bis(methyloxy)-4-quinolinyl)oxy)-N-cyclopropyl-4-quinolinecarboxamide | C$_{24}$H$_{21}$N$_3$O$_4$ | 415.44 | 416.2 |
| 866 | 7-((6,7-bis(methyloxy)-4-quinolinyl)oxy)-N-(2-(methyloxy)ethyl)-4-quinolinecarboxamide | C$_{24}$H$_{23}$N$_3$O$_5$ | 433.46 | 434.2 |

EXAMPLE 867

6-((6,7-bis(methoxy)-4-quinazolinyl)oxy)-N-phenyl-1-naphthalenecarboxamide

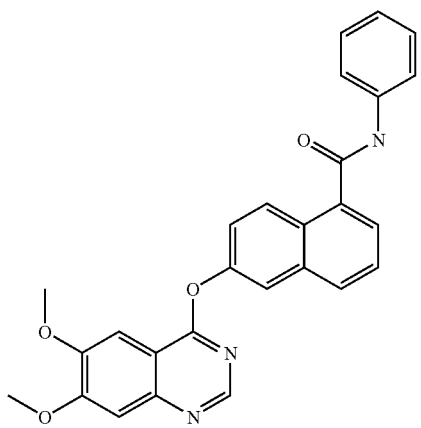

Step (a) Preparation of 6-(6,7-dimethoxyquinazolin-4-yloxy)-1-naphthoic acid The title compound was prepared similar to the procedure described in Example 477 Step (a) using 4-chloro-6,7-dimethoxyquinazoline as the reagent and $K_2CO_3$ as the base.

Step (b) Preparation of 6-((6,7-bis(methyloxy)-4-quinazolinyl)oxy)-N-phenyl-1-naphthalenecarboxamide The title compound was prepared similar to the procedure described in Example 357. MS (ESI pos. ion) m/z: 452.1 (M+H). Calc'd for $C_{27}H_{21}N_3O_4$–451.48.

The following examples were prepared similar to the procedures described in 867 and purified by column chromatography and/or crystallization.

| Example No. | Structure and Name | Mol Formula | Mass | M + H |
|---|---|---|---|---|
| 868 | 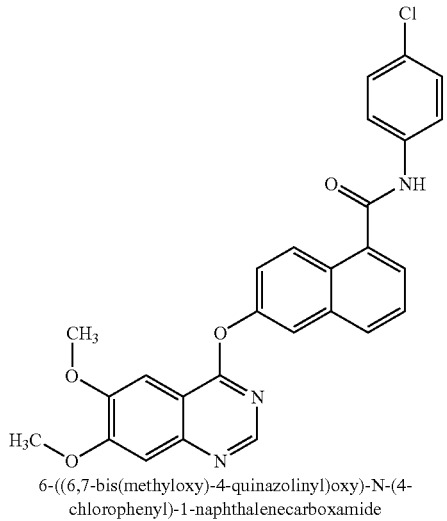<br>6-((6,7-bis(methyloxy)-4-quinazolinyl)oxy)-N-(4-chlorophenyl)-1-naphthalenecarboxamide | $C_{27}H_{20}ClN_3O_4$ | 485.92 | 486.1 |
| 869 | 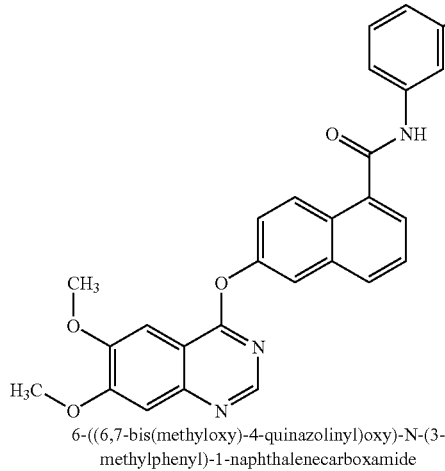<br>6-((6,7-bis(methyloxy)-4-quinazolinyl)oxy)-N-(3-methylphenyl)-1-naphthalenecarboxamide | $C_{28}H_{23}N_3O_4$ | 465.50 | 466.2 |

| Example No. | Structure and Name | Mol Formula | Mass | M + H |
|---|---|---|---|---|
| 870 | 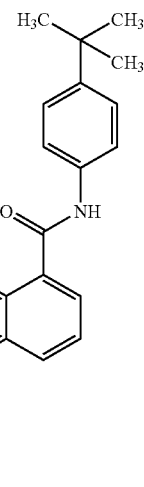 6-((6,7-bis(methyloxy)-4-quinazolinyl)oxy)-N-(4-(1,1-dimethylethyl)phenyl)-1-naphthalenecarboxamide | $C_{31}H_{29}N_3O_4$ | 507.58 | 508.2 |
| 871 | 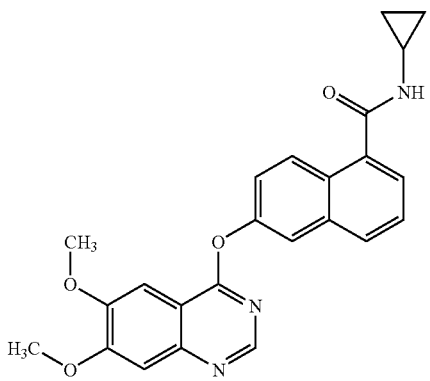 6-((6,7-bis(methyloxy)-4-quinazolinyl)oxy)-N-cyclopropyl-1-naphthalenecarboxamide | $C_{24}H_{21}N_3O_4$ | 415.44 | 416.2 |
| 872 | 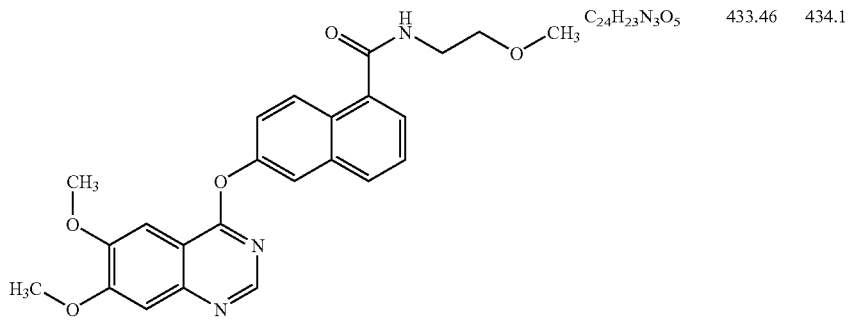 6-((6,7-bis(methyloxy)-4-quinazolinyl)oxy)-N-(2-(methyloxy)ethyl)-1-naphthalenecarboxamide | $C_{24}H_{23}N_3O_5$ | 433.46 | 434.1 |

| Example No. | Structure and Name | Mol Formula | Mass | M + H |
|---|---|---|---|---|
| 873 | ![structure] 6-((6,7-bis(methyloxy)-4-quinazolinyl)oxy)-N-methyl-1-naphthalenecarboxamide | $C_{22}H_{19}N_3O_4$ | 389.40 | 390.1 |
| 874 | ![structure] 6-((6,7-bis(methyloxy)-4-quinazolinyl)oxy)-N-(3-isoxazolyl)-1-naphthalenecarboxamide | $C_{24}H_{18}N_4O_5$ | 442.42 | 443.1 |

EXAMPLE 875

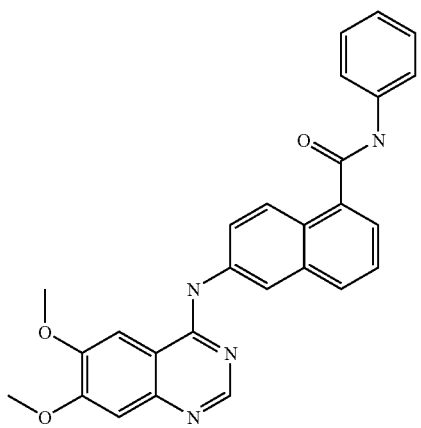

6-((6,7-bis(methyloxy)-4-quinazolinyl)amino)-N-phenyl-1-naphthalenecarboxamide

Step (a) Preparation of Methyl 6-(6,7-dimethoxyquinazolin-4-ylamino)-1-naphthoate The following reagents were combined in a flask and placed in a RT oil bath that was then heated to 90° C.: 4-Chloro-6,7-dimethoxyquinazoline (954 mg, 4.24 mmol), methyl 6-amino-1-naphthoate (857 mg, 4.24 mmol), TFA (098 mL, 12.7 mmol), and isopropanol (12 mL). The reaction was done before the bath reached the desired temperature. The mixture was diluted with water and made pH basic with 6N NaOH. The solid was filtered and rinsed with water and Et₂O. The title compound was obtained as a pink solid.

Step (b) Preparation of 6-(6,7-dimethoxyquinazolin-4-ylamino)-1-naphthoic acid Methyl 6-(6,7-dimethoxyquinazolin-4-ylamino)-1-naphthoate (500 mg, 1.28 mmol) was stirred with 6N NaOH (10 mL) and MeOH (10 mL) at 70° C. for 3 h. The mixture was poured into 6N HCl/ice and the pH adjusted to 7. The solid was collected and rinsed with water, stirred with MeOH (5 mL) and filtered again. The title compound was obtained (crude) as a yellow solid.

Step (c) Preparation of 6-((6,7-bis(methyloxy)-4-quinazolinyl)amino)-N-phenyl-1-naphthalenecarboxamide The title compound was prepared similar to the procedure described in Example 357. MS (ESI pos. ion) m/z: 451.1 (M+H). Calc'd for $C_{27}H_{22}N_4O_3$–450.49.

The following examples were prepared similar to the procedures described in Example 875 and purified by column chromatography and/or crystallization.

| Example No. | Structure & Name | Mol Formula | Mass | M + H |
|---|---|---|---|---|
| 876 | 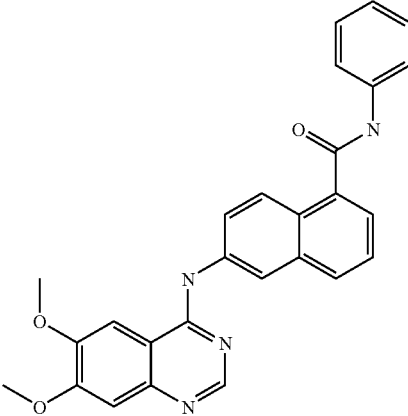<br>6-((6,7-bis(methyloxy)-4-quinazolinyl) amino)-N-(3-chlorophenyl)-1-naphthalenecarboxamide | $C_{27}H_{21}ClN_4O_3$ | 484.94 | 485.1 |
| 877 | 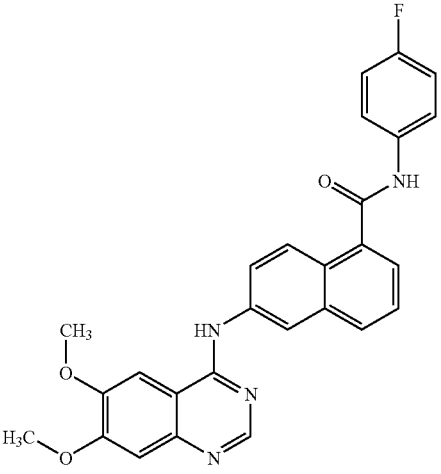<br>6-((6,7-bis(methyloxy)-4-quinazolinyl) amino)-N-(4-fluorophenyl)-1-naphthalenecarboxamide | $C_{27}H_{21}FN_4O_3$ | 468.49 | 469.1 |
| 878 | 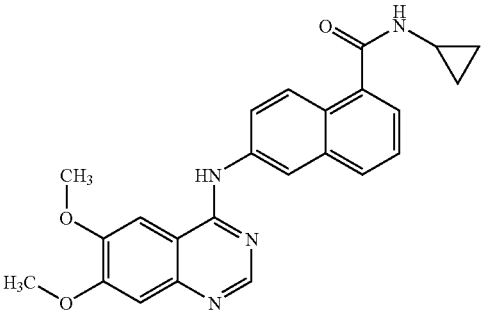<br>6-((6,7-bis(methyloxy)-4-quinazolinyl) amino)-N-cyclopropyl-1-naphthalenecarboxamide | $C_{24}H_{22}N_4O_3$ | 414.46 | 415.2 |

-continued

| Example No. | Structure & Name | Mol Formula | Mass | M + H |
|---|---|---|---|---|
| 879 | 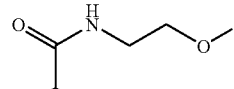<br>6-((6,7-bis(methyloxy)-4-quinazolinyl) amino)-N-(2-(methyloxy)ethyl)-1-naphthalenecarboxamide | $C_{24}H_{24}N_4O_4$ | 432.48 | 433.1 |

EXAMPLE 880

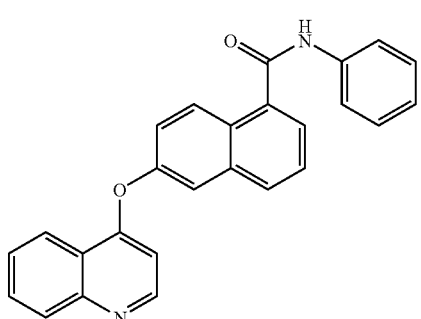

N-(4-chlorophenyl)-6-(4-quinolinyloxy)-1-naphthalenecarboxamide

Step (a) Preparation of 6-(quinolin-4-yloxy)-1-naphthoic acid

The title compound was prepared similar to the procedure described in Example 801 Step (d).

Step (b) Preparation of 6-(quinolin-4-yloxy)-1-naphthoyl chloride

The title compound was prepared similar to the procedure described in Example 273 Step (a).

Step (c) Preparation of N-(4-chlorophenyl)-6-(4-quinolinyloxy)-1-naphthalenecarboxamide The title compound was prepared similar to the procedure described in Example 783 Step (c). MS (ESI pos. ion) m/z: 425.1 (M+H). Calc'd for $C_{26}H_{17}ClN_2O_2$–424.88.

The following examples were prepared similar to the procedures described in Example 880 and purified by column chromatography and/or crystallization.

| Example No. | Structure & Name | Formula | Calc MW | M + H |
|---|---|---|---|---|
| 881 | N-phenyl-6-(4-quinolinyloxy)-1-naphthalenecarboxamide | $C_{26}H_{18}N_2O_2$ | 390.44 | 391.1 |

-continued
| Example No. | Structure & Name | Formula | Calc MW | M + H |
|---|---|---|---|---|
| 882 | 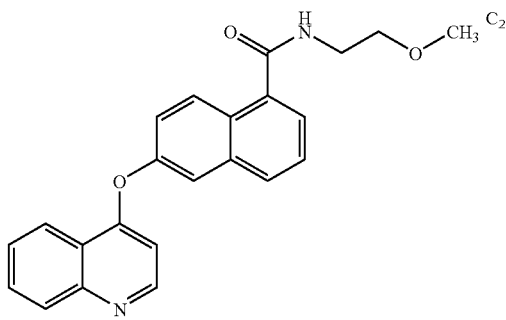<br>N-(2-(methyloxy)ethyl)-6-(4-quinolinyloxy)-1-naphthalenecarboxamide | $C_{23}H_{20}N_2O_3$ | 372.42 | 373.2 |
| 883 | 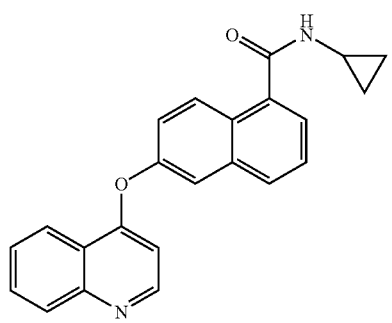<br>N-cyclopropyl-6-(4-quinolinyloxy)-1-naphthalenecarboxamide | $C_{23}H_{18}N_2O_2$ | 354.41 | 355.2 |
| 884 | 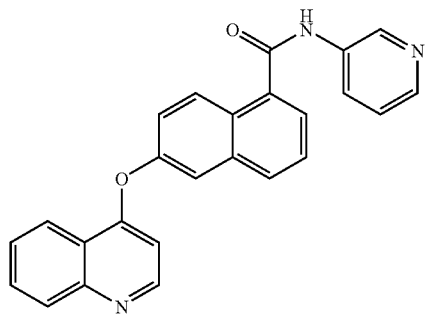<br>N-(3-pyridinyl)-6-(4-quinolinyloxy)-1-naphthalenecarboxamide | $C_{25}H_{17}N_3O_2$ | 391.43 | 392.1 |
| 885 | 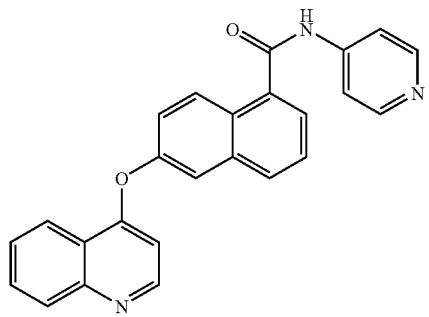<br>N-(4-pyridinyl)-6-(4-quinolinyloxy)-1-naphthalenecarboxamide | $C_{25}H_{17}N_3O_2$ | 391.43 | 392.1 |

EXAMPLE 886

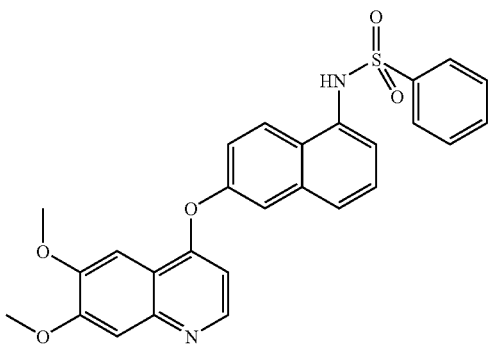

N-(6-((6,7-bis(methyloxy)-4-quinolinyl)oxy)-1-naphthalenyl)benzenesulfonamide 6-(6,7-Dimethoxyquinolin-4-yloxy)naphthalen-1-amine (50 mg, 0.144 mmol) and benzenesulfonylchloride (25 mg, 0.144 mmol) were dissolved in pyridine (0.6 mL) then stirred at RT for 3 days. The reaction mixture was concentrated under vacuum. The crude material was purified by silica gel chromatography (2% to 4% MeOH in DCM) to give N-(6-((6,7-bis(methyloxy)-4-quinolinyl)oxy)-1-naphthalenyl)benzenesulfonamide as a tan solid. MS (ESI pos. ion) m/z: 487.1 (+H). Calc'd for $C_{27}H_{22}N_2O_{5}S$–486.55.

The following examples were prepared similar to the procedures described in Example 890.

| Example No. | Structure & Name | Mol Formula | Mass | M + H |
|---|---|---|---|---|
| 887 | 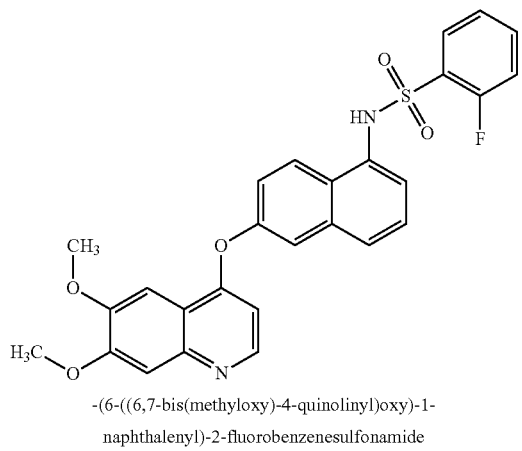<br>-(6-((6,7-bis(methyloxy)-4-quinolinyl)oxy)-1-naphthalenyl)-2-fluorobenzenesulfonamide | $C_{27}H_{21}FN_2O_5S$ | 504.54 | 505.1 |
| 888 | 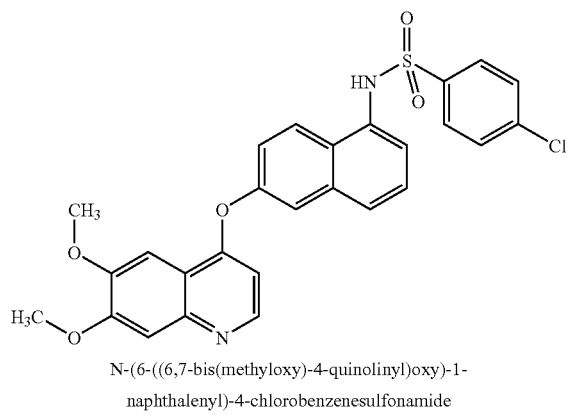<br>N-(6-((6,7-bis(methyloxy)-4-quinolinyl)oxy)-1-naphthalenyl)-4-chlorobenzenesulfonamide | $C_{27}H_{21}ClN_2O_5S$ | 520.99 | 521.4 |

-continued
| Example No. | Structure & Name | Mol Formula | Mass | M + H |
|---|---|---|---|---|
| 889 | 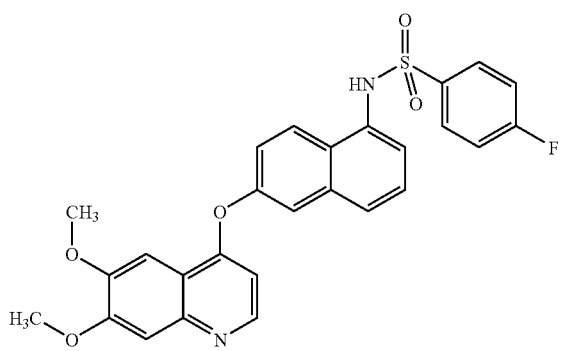<br>N-(6-((6,7-bis(methyloxy)-4-quinolinyl)oxy)-1-naphthalenyl)-4-fluorobenzenesulfonamide | C$_{27}$H$_{21}$FN$_2$O$_5$S | 504.54 | 505.2 |
| 890 | 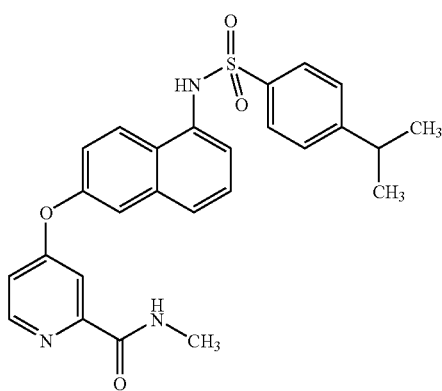<br>N-methyl-4-((5-(((4-(1-methylethyl)phenyl)sulfonyl)amino)-2-naphthalenyl)oxy)-2-pyridinecarboxamide | C$_{26}$H$_{25}$N$_3$O$_4$S | 475.566 | 476.2 |
| 891 | 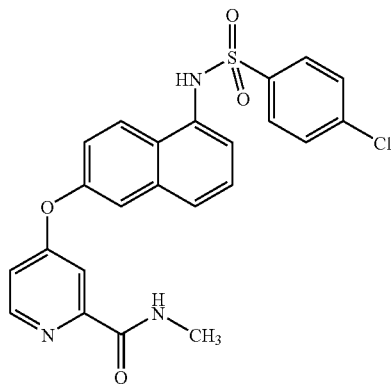<br>4-((5-(((4-chlorophenyl)sulfonyl)amino)-2-naphthalenyl)oxy)-N-methyl-2-pyridinecarboxamide | C$_{23}$H$_{18}$ClN$_3$O$_4$S | 467.931 | 468.1 |

-continued

| Example No. | Structure & Name | Mol Formula | Mass | M + H |
|---|---|---|---|---|
| 892 | 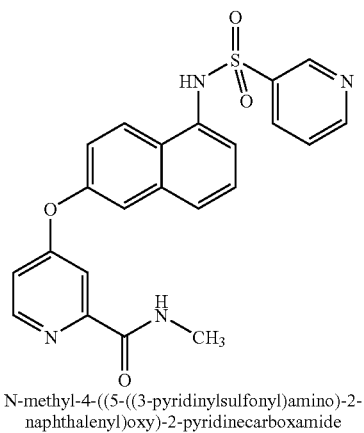<br>N-methyl-4-((5-((3-pyridinylsulfonyl)amino)-2-naphthalenyl)oxy)-2-pyridinecarboxamide | $C_{22}H_{18}N_4O_4S$ | 434.474 | 435.2 |

EXAMPLE 893

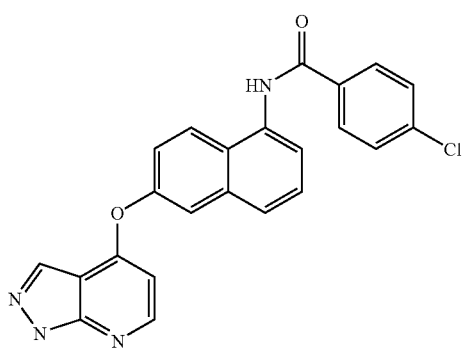

4-chloro-N-(6-(1H-pyrazolo[3,4b]pyridin-4-yloxy)-1-naphthalenyl)benzamide

Step (a) Preparation of 4-iodo-1H-pyrazolo[3,4-b]pyridine

A 1M solution of hydrazine in tetrahydrofuran (150 mL) was added slowly to 2-fluoro-4-iodopyridine-3-carboxaldehyde (10 g, 39.84 mmol) to give a clear solution. The reaction mixture was stirred at RT for 16 h. The mixture was concentrated in vacuo and the remaining solid was triturated with DCM to give the title compound as a pale yellow solid (8 g). The DCM filtrate was also washed with saturated sodium bicarbonate and brine. The organic layer was dried over sodium sulfate and concentrated under vacuum. The crude material was purified by trituration with DCM to give additional 4-iodo-1H-pyrazolo[3,4-b]pyridine as a yellow solid. MS (ESI, pos. ion) m/z: 245.9 (M+1).

Step (b) Preparation of 6-(1H-pyrazolo[3,4-b]pyridin-4-yloxy)naphthalen-1-amine 5-Aminonaphthalen-2-ol (356 mg, 2.24 mmol) was dissolved in DMF (2.5 mL) then cooled to 0° C. Sodium hydride (94 mg) was added slowly and the stirring was continued for 15 min at 0° C. 4-Iodo-1H-pyrazolo[3,4-b]pyridine (274 mg, 1.12 mmol) was then added slowly and the reaction was heated at 100° C. for 16 h, followed by 4.5 h at 120° C. The mixture was partitioned between water and EtOAc then washed with water, 1N aqueous NaOH, and brine. The organic layer was dried over sodium sulfate and concentrated in vacuo to give 6-(1H-pyrazolo[3,4-b]pyridin-4-yloxy)naphthalen-1-amine as a brown solid MS (ESI, pos. ion) m/z: 277.1 (M+1).

Step (c) Preparation of 4-chloro-N-(6-(1H-pyrazolo[3,4-b]pyridin-4-yloxy)-1-naphthalenyl)benzamide 6-(1H-Pyrazolo[3,4-b]pyridin-4-yloxy)naphthalen-1-amine (25 mg, 0.09 mmol), 4-chlorobenzoic acid (16 mg, 0.10 mmol) and TBTU (35 mg, 0.108 mmol) were dissolved in DMF (0.75 mL). Hunig's base (18 mg, 0.14 mmol) was then added and the reaction mixture was stirred at RT for 16 h. Additional 4-chlorobenzoic acid (6 mg, 0.036 mmol) and TBTU (12 mg, 0.036 mmol) were added to the reaction and stirring was continued for 3 days. The reaction mixture was concentrated in vacuo. The remaining dark brown residue was purified by silica gel chromatography (0% to 2% MeOH in DCM) to yield 4-chloro-N-(6-(1H-pyrazolo[3,4-b]pyridin-4-yloxy)-1-naphthalenyl)benzamide as an off-white solid. MS (ESI, pos. ion) m/z: 415.0 (M+1). MS (ESI pos. ion) m/z: 415.0 (M+H). Calc'd for $C_{23}H_{15}ClN_4O_2$–414.85.

The following example was prepared similar to the procedures described in Example 114.

| Example No. | Structure & Name | Mol Formula | Mass | M + H |
|---|---|---|---|---|
| 894 | 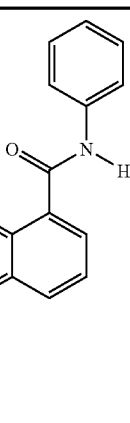<br>6-((6,7-bis(methoxy)-4-quinolinyl)oxy)-N-phenyl-1-naphthalenecarboxamide | $C_{28}H_{22}N_2O_4$ | 450.49 | 451.1 |

EXAMPLE 895

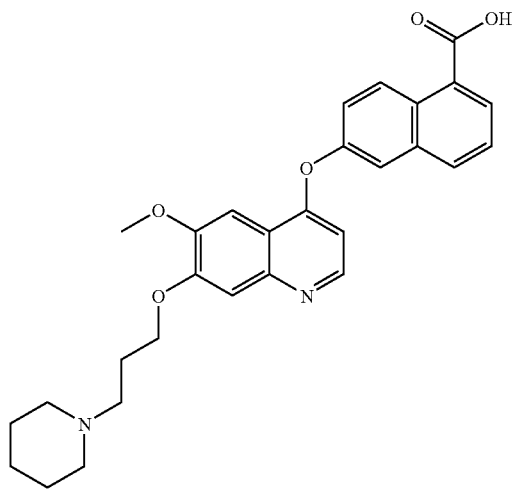

6-(6-methoxy-7-(3-(piperidin-1-yl)propoxy)quinolin-4-yloxy)-1-naphthoic acid

Step (a) Preparation of 4-chloro-7-(3-chloropropoxy)-6-methoxyquinoline

To a solution of 4-chloro-6-methoxyquinolin-7-ol (5.7 g, 0.027 mole) and 1-bromo-3-chloropropane (13.2 mL, 0.14 mole) in DMF (150 mL), was added potassium carbonate (30 g, 0.27 mole). The mixture was stirred at RT for 20 h. The mixture was concentrated in vacuo then diluted with $H_2O$ (100 mL). The mixture was extracted with EtOAc (3×50 mL) and the organic extracts were washed with $H_2O$ and brine. The organic phase was dried over $MgSO_4$, filtered, and concentrated in vacuo. The resulting residue was purified by silica gel column chromatography (5% $MeOH/CH_2Cl_2$) to yield the title compounds as a light yellow solid. MS (ESI, pos. ion) m/z: 286 (M+1). Mass Calc'd for $C_{13}H_{13}Cl_2NO_2$: 285.0.

Step (b) Preparation of 4-chloro-6-methoxy-7-(3-(piperidin-1-yl)propoxy)quinoline To a solution of 4-chloro-7-(3-chloropropoxy)-6-methoxyquinoline (3.1 g, 0.0108 mole) NaI (2.4 g, 0.0162 mole), and potassium carbonate (7.5 g, 0.054 mole in DMF (100 mL), was added piperidine (6.4 mL, 0.065 mole). The mixture was heated to 70° C. for 16 h. The mixture was concentrated in vacuo then diluted with $H_2O$ (100 mL). The mixture was extracted with EtOAc (3×50 mL) and the organic extracts were washed with $H_2O$ and brine. The organic phase was dried over $MgSO_4$, filtered, and concentrated in vacuo. The resulting residue was purified by silica gel column chromatography (7.5% $MeOH/CH_2Cl_2$) to yield the title compounds as a light yellow solid. MS (ESI, pos. ion) m/z: 335 (M+1). Mass Calc'd for $C_{18}H_{23}ClN_2O_2$: 334.1.

Step (c) Preparation of 6-(6-methoxy-7-(3-(piperidin-1-yl)propoxy)quinolin-4-yloxy)-1-naphthoic acid The compound was prepared according to Example 732, step d to afford the title compound as a light brown solid. MS (ESI, pos. ion) m/z: 487 (M+1). Mass Calc'd for $C_{29}H_{30}N_2O_5$: 486.2.

900) 6-(6-methoxy-7-(3-pyrrolidinopropoxy)quinolin-4-yloxy)-1-naphthoic acid was prepared similar to Example 899.

901) 6-(7-(Benzyloxy)-6-methoxyquinolin-4-yloxy)-1-naphthoic acid was prepared using a procedure similar to that described in Example 732, Step d:

The following compounds were prepared by methods previously described:

| Example No. | Structure & Name | Mol Formula | Mass | M + H |
|---|---|---|---|---|
| 896 | 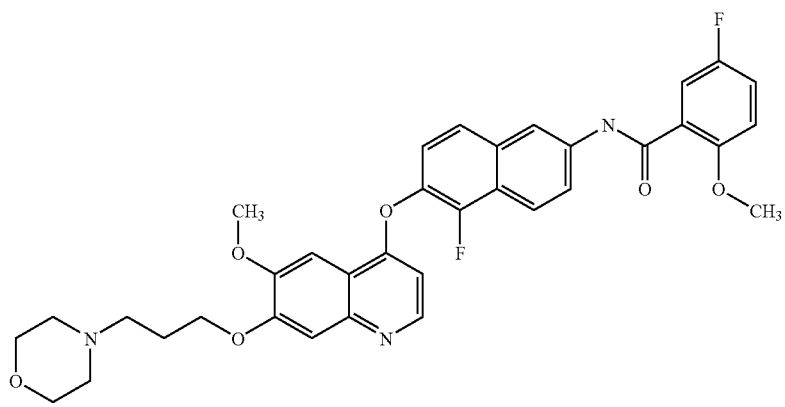  5-fluoro-N-(5-fluoro-6-((6-(methoxy)-7-((3-(4-morpholinyl)propyl)oxy)-4-quinolinyl)oxy)-2-naphthalenyl)-2-(methoxy)benzamide | $C_{35}H_{33}F_2N_3O_6$ | 629 | 630 |
| 897 | 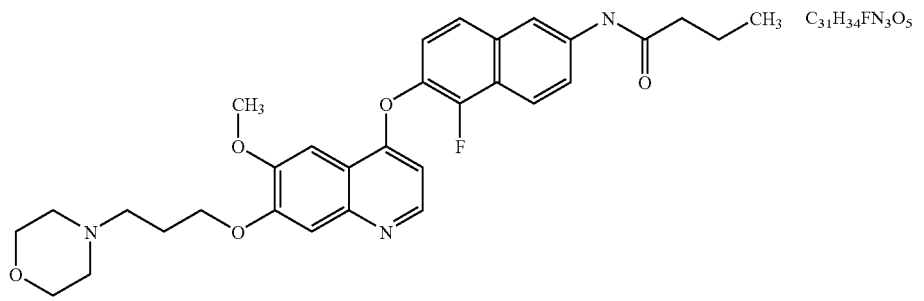  N-(5-fluoro-6-((6-(methoxy)-7-((3-(4-morpholinyl)propyl)oxy)-4-quinolinyl)oxy)-2-naphthalenyl)butanamide | $C_{31}H_{34}FN_3O_5$ | 547 | 54 |
| 898 | 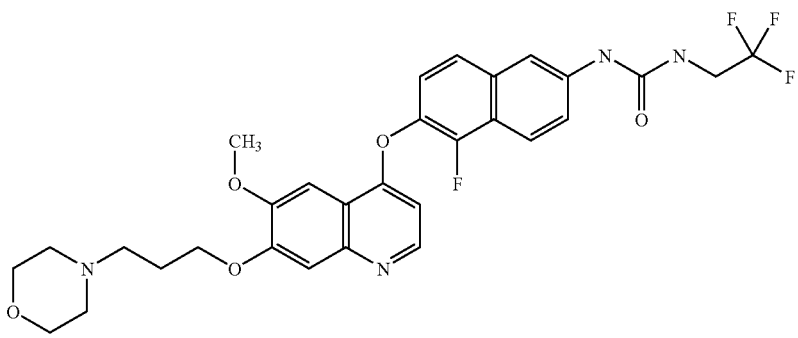  N-(5-fluoro-6-((6-(methoxy)-7-((3-(4-morpholinyl)propyl)oxy)-4-quinolinyl)oxy)-2-naphthalenyl)-N'-(2,2,2-trifluoroethyl)urea | $C_{30}H_{30}F_4N_4O_5$ | 602 | 603 |

| Example No. | Structure & Name | Mol Formula | Mass | M + H |
|---|---|---|---|---|
| 899 | 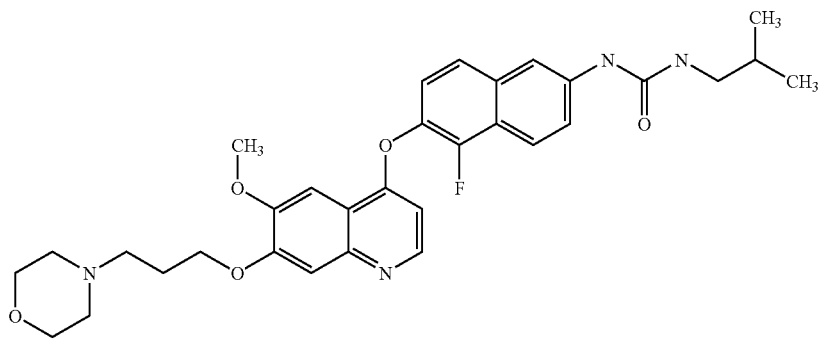 N-(5-fluoro-6-((6-(methoxy)-7-((3-(4-morpholinyl)propyl)oxy)-4-quinolinyl)oxy)-2-naphthalenyl)-N'-(2-methylpropyl)urea | $C_{32}H_{37}FN_4O_5$ | 576 | 577 |
| 900 | 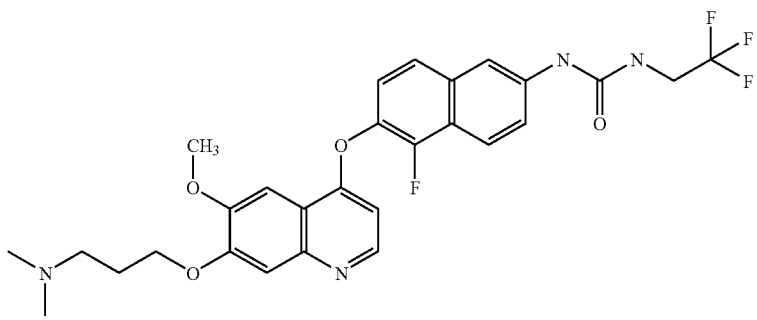 N-(6-((7-((3-(dimethylamino)propyl)oxy)-6-(methoxy)-4-quinolinyl)oxy)-5-fluoro-2-naphthalenyl)-N'-(2,2,2-trifluoroethyl)urea | $C_{28}H_{28}F_4N_4O_4$ | 560 | 561 |
| 901 | 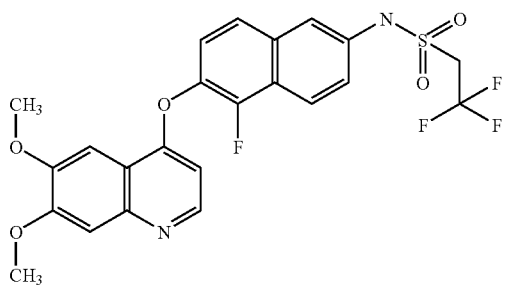 N-(6-((6,7-bis(methyloxy)-4-quinolinyl)oxy)-5-fluoro-2-naphthalenyl)-2,2,2-trifluoroethanesulfonamide | $C_{23}H_{18}F_4N_2O_5S$ | 510 | 511 |
| 902 | 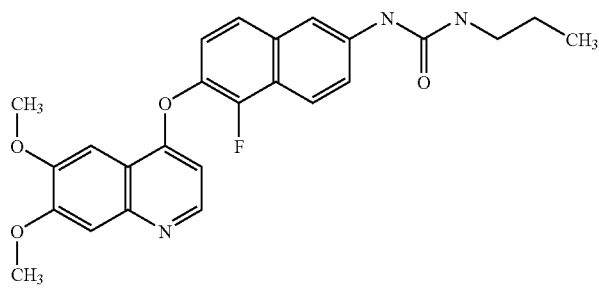 N-(6-((6,7-bis(methyloxy)-4-quinolinyl)oxy)-5-fluoro-2-naphthalenyl)-N'-propylurea | $C_{25}H_{24}FN_3O_4$ | 449 | 450 |

| Example No. | Structure & Name | Mol Formula | Mass | M + H |
|---|---|---|---|---|
| 903 | 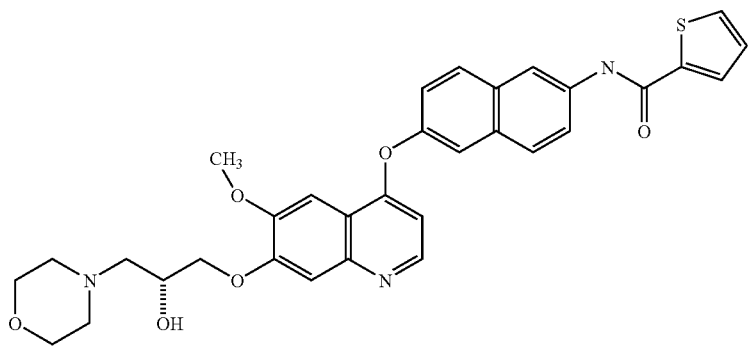<br>N-(6-((7-(((2R)-2-hydroxy-3-(4-morpholinyl)propyl)oxy)-6-(methoxy)-4-quinolinyl)oxy)-2-naphthalenyl)-2-thiophenecarboxamide | $C_{32}H_{31}N_3O_6S$ | 585 | 586 |
| 904 | 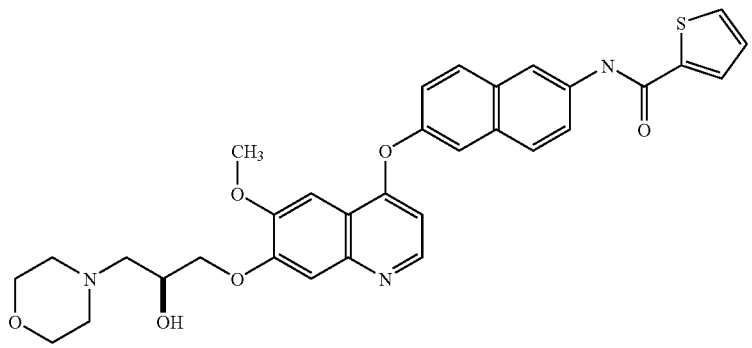<br>N-(6-((7-(((2S)-2-hydroxy-3-(4-morpholinyl)propyl)oxy)-6-(methoxy)-4-quinolinyl)oxy)-2-naphthalenyl)-2-thiophenecarboxamide | $C_{32}H_{31}N_3O_6S$ | 585 | 586 |
| 905 | 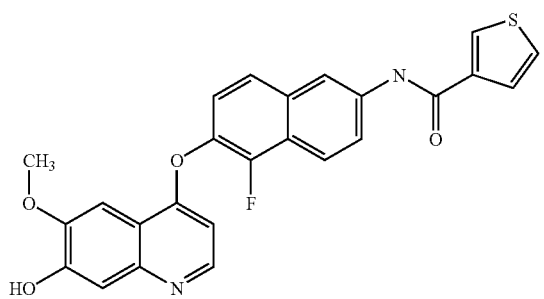<br>N-(5-fluoro-6-((7-hydroxy-6-(methyloxy)-4-quinolinyl)oxy)-2-naphthalenyl)-3-thiophenecarboxamide | $C_{25}H_{17}FN_2O_4S$ | 460 | 461 |

| Example No. | Structure & Name | Mol Formula | Mass | M + H |
|---|---|---|---|---|
| 906 | N-(5-fluoro-6-((7-(((2R)-2-hydroxy-3-(4-morpholinyl)propyl)oxy)-6-(methoxy)-4-quinolinyl)oxy)-2-naphthalenyl)-3-thiophenecarboxamide | $C_{32}H_{30}FN_3O_6S$ | 603 | 604 |
| 907 | N-(5-fluoro-6-((7-(((2S)-2-hydroxy-3-(4-morpholinyl)propyl)oxy)-6-(methoxy)-4-quinolinyl)oxy)-2-naphthalenyl)-3-thiophenecarboxamide | $C_{32}H_{30}FN_3O_6S$ | 603 | 604 |

Other compounds included in this invention are set forth in Tables 3-6 below.

TABLE 3

| # | R |
|---|---|
| 914. | 4-$CF_3$-phenyl |
| 915. | 4-fluorophenyl |
| 916. | 3-$CF_3$-phenyl |
| 917. | 3-chlorophenyl |
| 918. | 4-chloro-3-methylphenyl |
| 919. | 4-F-3-$CF_3$-phenyl |

TABLE 3-continued

| # | R |
|---|---|
| 920. | 2-pyridyl |
| 921. | 3-isoxazolyl |
| 922. | 2-thiazolyl |
| 923. | cyclopropyl |
| 924. | methoxyethyl |
| 925. | H |
| 926. | methyl |

TABLE 4
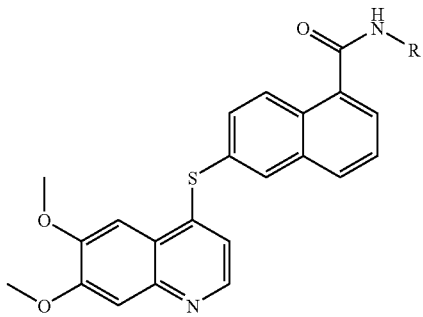
| # | R |
|---|---|
| 927. | 4-Cl-phenyl |
| 928. | 4-fluorophenyl |
| 929. | 4-CF$_3$-phenyl |
| 930. | 2-pyridyl |
| 931. | 3-isoxazolyl |
| 932. | 2-thiazolyl |
| 933. | cyclopropyl |
| 934. | methoxyethyl |
| 935. | H |
| 936. | methyl |
TABLE 5
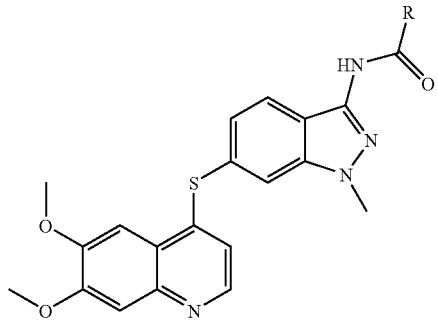
| # | R |
|---|---|
| 937. | 3-CH$_3$-phenyl |
| 938. | 4-chlorophenyl |
| 939. | 3-CF$_3$-phenyl |
| 940. | 4-F-3-Cl-phenyl |
| 941. | phenyl-NH— |
| 942. | 4-methylphenylamino |
TABLE 6
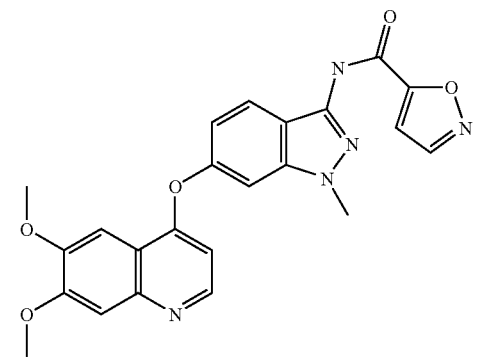
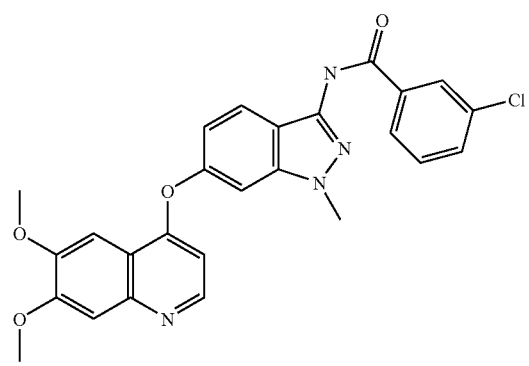

TABLE 6-continued
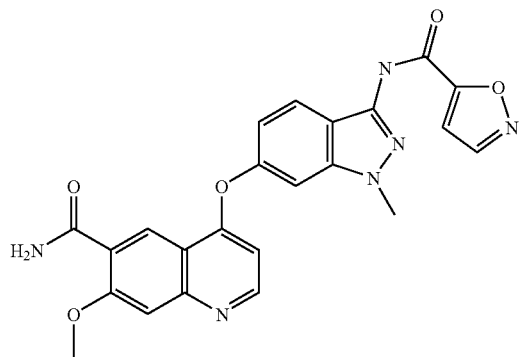
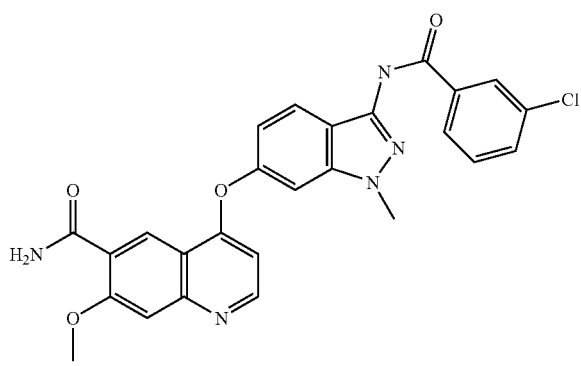
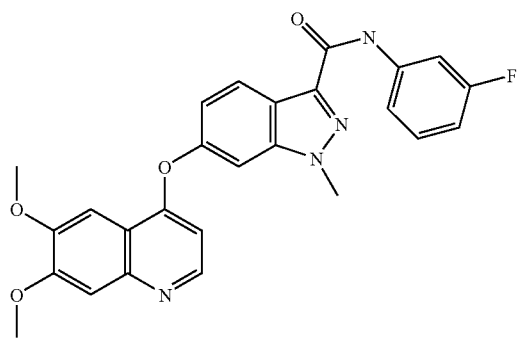
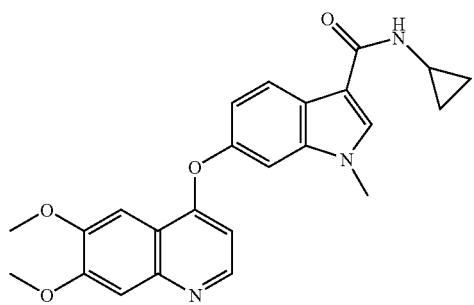

TABLE 6-continued
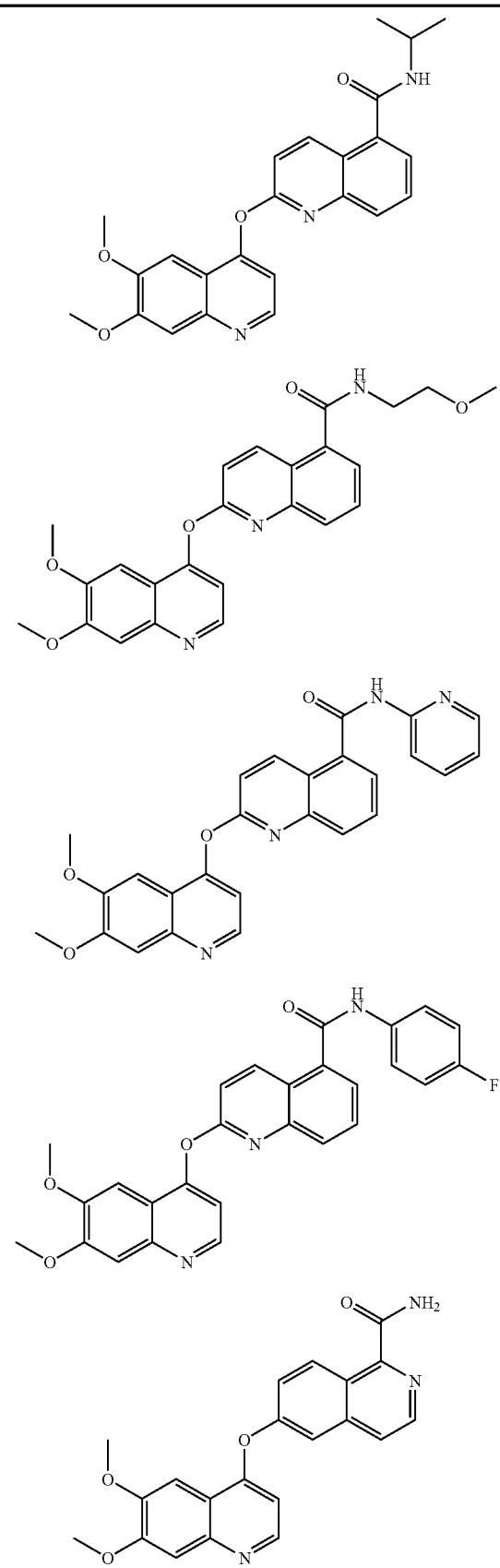

TABLE 6-continued
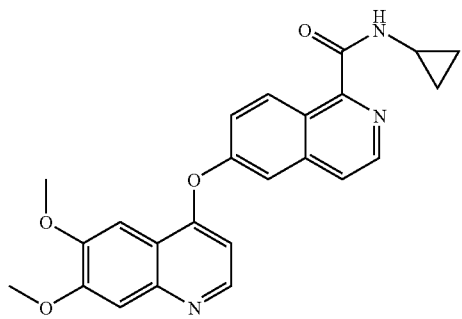
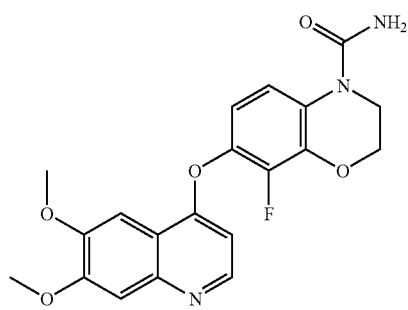
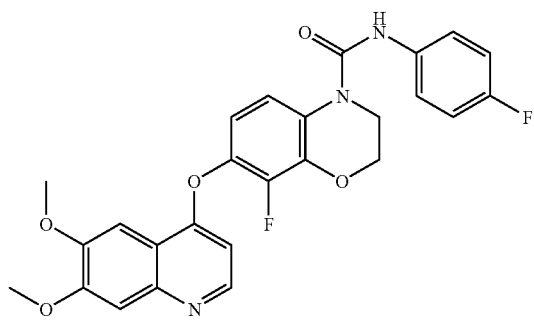
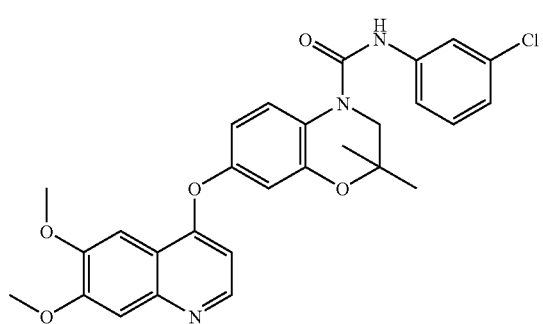

TABLE 6-continued
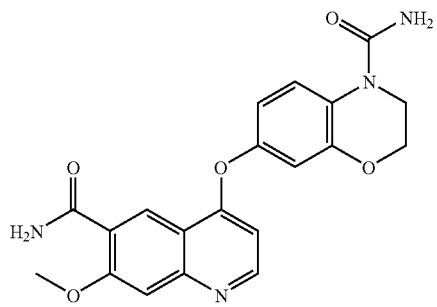
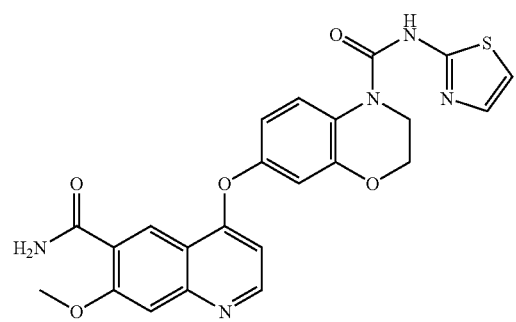
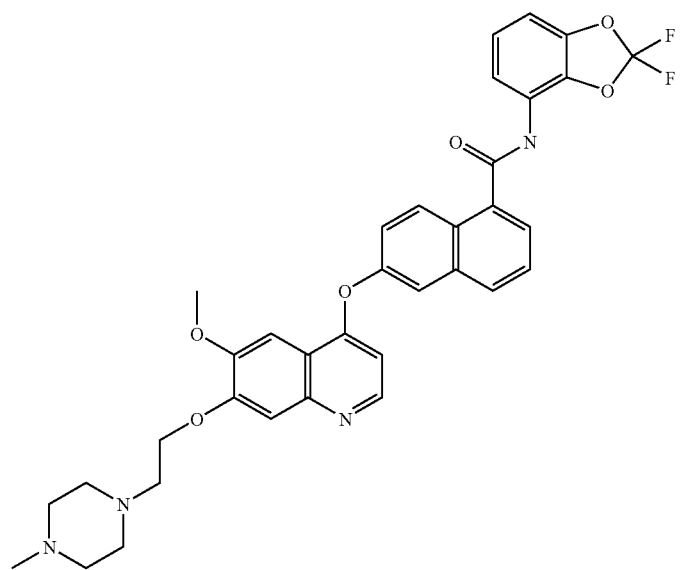
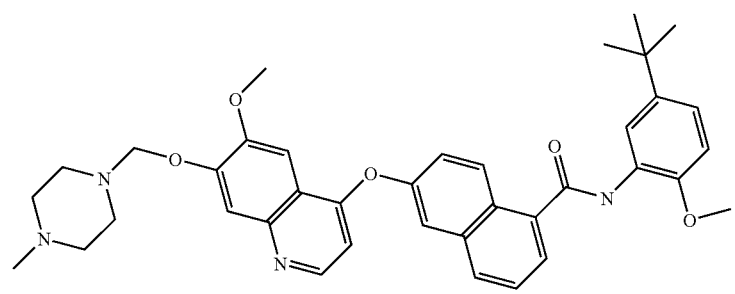

TABLE 6-continued
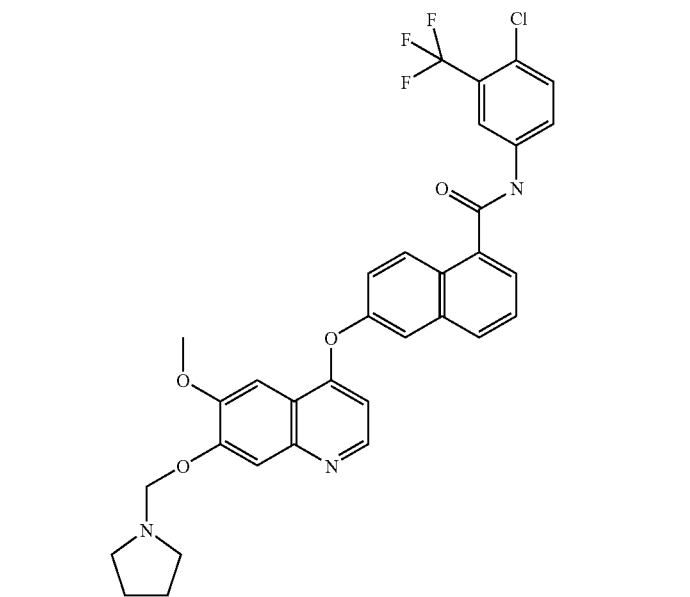
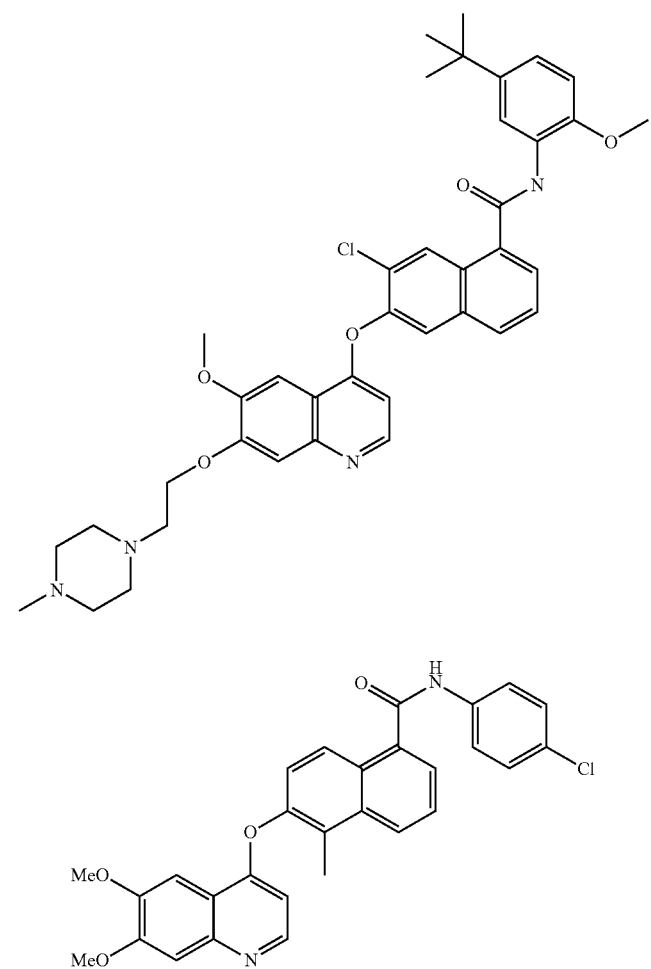

TABLE 6-continued

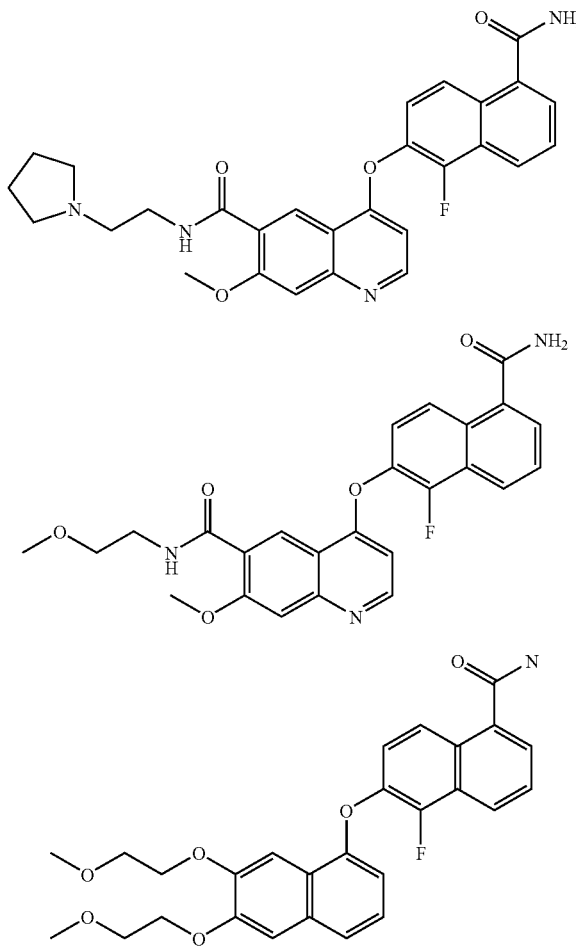

Preparation of 6-chloro-N¹-(3-(dimethylamino)propyl)-N¹-methyl-4-(trifluoromethyl)benzene-1,2-diamine A heterogeneous mixture of 1-chloro-2-fluoro-3-nitro-5-(trifluoromethyl)benzene (1.25 mL, 8.2 mmol), $K_2CO_3$ (3.44 g, 24.6 mmol), $N^1,N^1N^3$-trimethylpropane-1,3-diamine (1.26 mL, 8.61 mmol) and THF were allowed to stir at RT for 45 min. The THF was removed under reduced pressure and reconstituted in EtOAc (50 ml). The organic layer was washed with water (20 ml), brine (20 ml), dried over anhydrous sodium sulfate, filtered and concentrated to an oil. The concentrated oil was taken up in EtOH (20 ml) to which Raney nickel (2.5 g wet, washed) was added. The reduction was monitored and after 1 h, another portion of Raney nickel (3.8 g, wet, washed) was added. The reaction was allowed to stir for an additional 30 min., and filtered through Celite, washed with EtOH (10 mL) and concentrated. The crude residue was purified via flash chromatography (silica gel, gradient elution 0 to 25% MeOH in $CH_2Cl_2$) to afford 6-chloro-$N^2$-(3-(dimethylamino)propyl)-$N^1$-methyl-4-(trifluoromethyl)benzene-1,2-diamine as a yellow oil. MS m/z=310.1 [M+H]⁺. Calc'd for $C_{13}H_{19}ClF_3N_3$: 309.8.

Preparation 1 of 1-(6-amino-3,3-dimethylindolin-1-yl)ethanone

The title compound was prepared according to a procedure described in U.S. Patent Publication No. 2003/0203922.

Preparation of 4-(2-nitro-4-(trifluoromethyl)phenyl)thiomorpholine

To a solution of 1-fluoro-2-nitro-4-(trifluoromethyl)benzene (7.00 g, 33.48 mmol) in THF (250 ml) at RT was added thiomorpholine (3.45 g, 33.48 mmol) and sodium bicarbonate (3.66 g, 43.52 mmol). The vessel was purged with nitrogen and stirred at RT for 48 h. After removal of solvent under reduced pressure, the mixture was taken up in EtOAc and filtered. The organics were washed with water, then brine and dried with magnesium sulfate. Filtration and concentration provided the title compound as a bright orange solid. MS m/z: 293.1 (M+H⁺); calc MW=292.28.

Preparation of the sulfoxide of 4-(2-nitro-4-(trifluoromethyl)phenyl)thiomorpholine To a solution of 4-(2-nitro-4-(trifluoromethyl)phenyl)thiomorpholine (2.0 g, 6.84 mmol) in MeOH (60 mL) and water (15 ml) was added $NaIO_4$ (1.61 g, 7.53 mmol). The mixture was allowed to stir at RT for 12 h, at which time it was filtered to remove white solid precipitates. Concentration afforded the title compound as an orange solid. MS m/z: 309 (M+H$^+$); calc'd MW=308.28.

Preparation of sulfone of 4-(2-nitro-4-(trifluoromethyl)phenyl)thiomorpholine To a solution of the sulfoxide of 4-(2-nitro-4-(trifluoromethyl)phenyl)thiomorpholine (170 mg, 0.55 mmol) in MeOH (50 mL) was added KMnO$_4$ (96 mg, 0.61 mmol). The reaction was stirred at RT for 15 min and then quenched by the addition of aqueous saturated sodium bisulfate (20 mL). The reaction was filtered and concentrated to provide the sulfone product. MS m/z: 325 (M+H$^+$); calc'd MW=324.28.

The nitro groups of Examples 625-627 were reduced to the corresponding amine by conventional methods, such as be hydrogenation in the presence of a palladium catalyst. The reduction product of Example 625 was found to have a MS (m/z)=263.1 (M+H$^+$); calc'd MW=262.30, and the reduction product of Example 627 was found to have a MS (m/z)=295.1 (M+H$^+$); calc'd MW=294.30.

Preparation of (4-methylpiperazin-1-yl)(3-nitro-5-trifluoromethyl)phenyl)-methanone A solution of thionyl chloride (30 ml) and 3-nitro-5-(trifluoromethyl)benzoic acid (10 g) was heated to reflux for 2 h. The reaction mixture was concentrated under reduced pressure and treated with toluene (10 ml) which was then removed under reduced pressure to afford 3-nitro-5-(trifluoromethyl) benzoyl chloride.

To a solution of 3-nitro-5-(trifluoromethyl)benzoyl chloride (2.35 g, 9.3 mmol) in CH$_2$Cl$_2$ (40 mL) at RT was added N-methylpiperazine (1.26 mL, 9.3 mmol) and the mixture was allowed to stir for 30 min. The reaction was concentrated under reduced pressure, taken up in 1 M HCl (50 ml) and the aqueous layer was washed with Et$_2$O (2×20 ml). The aqueous layer was basified to a pH of about 9 with 6 N NaOH, and the aqueous layer was extracted with Et$_2$O (3×50 mL). The organic extracts were combined and washed with water (1×20 mL) followed by brine (1×20 mL), and dried over anhydrous sodium sulfate, filtered and concentrated under reduced pressure to afford (4-methylpiperazin-1-yl)(3-nitro-5-trifluoromethyl)phenyl)-methanone as an tan oil, which was used without further purification.

Preparation of (3-amino-5-(trifluoromethyl)phenyl)(4-methylpiperazin-1-yl)methanone To an argon purged solution of (4-methylpiperazin-1-yl(3-nitro-5-trifluoromethyl)phenyl)-methanone (1.03 g, 3.25 mmol) was added Pd/C (344 mg, 0.32 mmol, 10%). The mixture was placed under an atmosphere of H$_2$ for 5 h. The reaction was purged with argon and filtered through Celite. The filtrate was concentrated under reduced pressure to afford (3-amino-5-(trifluoromethyl)phenyl)(4-methylpiperazin-1-yl)methanone as an off-white solid. MS m/z=288.1 [M+H]$^+$. Calc'd for C$_{13}$H$_{16}$F$_3$N$_3$O: 287.3.

Preparation of tert-butyl 7-amino-4,4-dimethyl-3,4-dihydroisoquinoline-2(1H)-carboxylate The title compound was prepared according to the procedure in WO 2004085425.

Preparation of tert-butyl 3,3-dimethyl-6-nitroindoline-1-carboxylate

To a cooled (ice-bath) solution of 3,3-dimethyl-6-nitroindoline (U.S. Patent Publication No. 2003/0203922) (846 mg, 4.4 mmol) in CH$_2$Cl$_2$ (6 mL), triethylamine (2.45 mL, 17.6 mmol) and BOC anhydride (1.01 mL, 4.4 mmol) were added. The reaction mixture was stirred and allowed to warm to RT for 18 h. The mixture was washed with water and brine, dried with Na$_2$SO$_4$, filtered and evaporated. The mixture was purified by column chromatography (using EtOAc:hexanes as the eluent) and the title compound isolated as a brown solid.

Preparation of tert-butyl 6-amino-3,3-dimethylindoline-1-carboxylate tert-butyl 6-amino-3,3-dimethylindoline-1-carboxylate To a mixture of tert-butyl 6-amino-3,3-dimethylindoline-1-carboxylate (500 mg, 1.9 mmol) in MeOH (25 mL), under nitrogen, Pd/C (wet w/MeOH) was added and the atmosphere changed to hydrogen. The reaction mixture was stirred at RT for 3 h. The reaction mixture was filtered through a pad of celite and evaporated to give the title compound as a thick liquid.

Preparation of 1-isopropyl-4-(4-nitrophenyl)piperazine

To a vial was added 4-fluoronitrobenzene (1.41 g, 1.06 mL, 0.01 mol), DIEA (1.92 mL, 0.011 mmol), isopropylpiperazine (1.41 g, 0.011 mmol), and DMF (10 mL). Mixture was heated at 100° C. for 48 h in a sealed tube. The reaction mixture was cooled to RT and concentrated. The residue was purified via silica gel column chromatography (gradient elution with 0 to 10% MeOH in DCM) to afford 1-isopropyl-4-(4-nitrophenyl)piperazine.

Preparation of 4-(4-isopropylpiperazin-1-yl)benzenamine

10% Palladium on carbon (0.05 g) was added to a solution of the nitroaniline (0.001 mol) in EtOH (50 mL) under a H$_2$(g) atmosphere (via balloon). The reaction mixture stirred at RT overnight and was then filtered through celite. The filtrate was concentrated to afford a dark yellow oil, purified on silica column chromatography using isocratic 100% (90/10/1) (CH$_2$Cl$_2$/CH$_3$OH/NH$_4$OH). MS m/z=220 M+H. Calc'd for C$_{13}$H$_{21}$N$_3$:219.3.

Preparation of 2-tert-butyl-5-nitrobenzenamine

Concentrated sulfuric acid (1 L) was cooled to −10° C. with a dry ice-isopropanol bath in a 2 L 3-necked round bottom flask fitted with a mechanical stirrer and temperature probe. The 2-t-butylaniline (109 g, 730 mmol) was added, giving a clumpy solid. Once the temperature of the mixture was stabilized at −10° C., the potassium nitrate (101 g, 1001 mmol) was added portion wise, as a solid, over a 4-hour period, maintaining the temperature between −20 and −5° C. Once all of the potassium nitrate was added, the reaction was left to stir overnight with gradual warming to RT. The reaction was quenched by diluting with water and then extracting three times with EtOAc. The EtOAc extracts were washed multiple times with saturated NaHCO$_3$, until gas evolution ceased, then with brine. The EtOAc extracts were then combined, dried over anhydrous Na$_2$SO$_4$, filtered and concentrated under reduced pressure giving a black oil. The oil was eluted through a column of silica gel with EtOAc: hexanes gradient 5-50%. Solvent evaporation afforded 2-tert-butyl-5-nitrobenzenamine as a red solid.

Preparation of 2-bromo-N-(2-tert-butyl-5-nitrophenyl)acetamide 2-tert-Butyl-5-nitrobenzenamine (70 g, 359 mmol) and a catalytic amount of DMAP were dissolved into THF (1.5 L) under $N_2$. Triethylamine (109 g, 1077 mmol) was added and the solution was cooled to 0° C. Bromoacetyl bromide (207 g, 1023 mmol) was then added and the reaction was stirred at RT for 16 h. The reaction was then partially concentrated under reduced pressure, treated with water, and extracted three times with EtOAc. The EtOAc extracts were washed with brine, combined, dried over $Na_2SO_4$ and concentrated to a black oil. This oil was purified using silica chromatography, 95:5:0.5 $CH_2Cl_2$:MeOH:$NH_4OH$, giving 2-bromo-N-(2-tert-butyl-5-nitrophenyl)acetamide as a brown solid.

Preparation of N-(2-tert-butyl-5-nitrophenyl)-2-(dimethylamino)acetamide

2-Bromo-N-(2-tert-butyl-5-nitrophenyl)acetamide (80 g, 253, mmol) and potassium carbonate (70 g, 506 mmol) were combined in THF (1.75 L), and the mixture was cooled to 0° C. N,N-Dimethylamine (40 ml of a 2 M solution in THF, 800 mmol) was then added to the mixture through an addition funnel over a 30-min period. The mixture was then stirred at RT for 16 h. The mixture was then filtered and the filtrate was concentrated. The crude material was purified by silica chromatography using 50% EtOAc:hexanes as the eluent to give N-(2-tert-butyl-5-nitrophenyl)-2-(dimethylamino)acetamide as a brown solid.

Preparation of N-(5-amino-2-tert-butylphenyl)-2-dimethylamino)acetamide

To a solution of N-(2-tert-butyl-5-nitrophenyl)-2-(dimethylamino)acetamide (25.8 g, $O_2$ mmol) in 1,4-dioxane (200 ml) was added 10% Pd/C (2.5 g) as a slurry in a minimal amount of EtOH. The mixture was evacuated and purged with $H_2$, and then stirred at RT for 16 h. The reaction was then purged with $N_2$ and filtered through celite. The filtrate was concentrated and purified using silica chromatography, 97.5:2.5:0.25 to 95:5:0.5 $CH_2Cl_2$:MeOH:$NH_4OH$, to afford N-(5-amino-2-tert-butylphenyl)-2-dimethylamino)acetamide as a brown solid. MS (m/z)=250.2 (M+H$^+$); Calculated for $C_{14}H_{23}N_3O$: 249.4.

Preparation of 1-(2-Fluoro-4-nitrophenyl)-4-methylpiperazine

N-Methylpiperazine (30 mL, 27.1 g, 0.268 mol) was cooled in ice/water while adding 3,4-difluoronitrobenzene (2.0 g, 0.0126 mol) with stirring. The mixture was then heated at 100° C. overnight, evaporated to remove all excess N-methylpiperazine and the residue dissolved in 1M—hydrochloric acid (30 mL). After washing twice with 20 mL portions of DCM the solution was basified with 5 M—sodium hydroxide (10 mL). The product was extracted into DCM (twice with 20 mL), dried over sodium sulphate and evaporated giving 1.50 g yellow oil which solidified on standing

Preparation of 1-(2-Fluoro-4-aminophenyl)-4-methylpiperazine

The title compound was obtained by hydrogenation over 10% Pd/C of 1-(2-Fluoro-4-nitrophenyl)-4-methylpiperazine in EtOH.

Preparation of 1-methyl-4-[(4-nitrophenyl)acetyl]piperazine

4-Nitrophenylacetic acid (2.00 g, 0.011 mol) was dissolved in anhydrous THF (20 mL) with gradual addition of thionyl chloride (1.03 mL, 0.0143 mol) and a catalytic amount of DMF (2 drops) at RT and stirred for 24 h. On completion, the reaction was quenched in situ with N-methylpiperazine (3.85 g, 0.038 mol) added dropwise in a solution of DCM (20 mL) at RT and stirred overnight to give a beige suspension. The solvent was removed in vacuo and the residue partitioned between DCM (30 mL) and sodium hydroxide (1N, 30 mL). The organic layer was washed twice, dried over sodium sulphate and filtered. Removal of the solvent in vacuo yielded the title compound as an amber oil, 1.50 g (solidified on standing).

Preparation of 4-(4-methylpiperazin-1-yl)carbonylmethylaniline

A solution of 1-methyl-4-[(4-nitrophenyl)acetyl]piperazine (1.5 g, 5.70 mmol) in EtOH (30 mL) was reduced over palladium/charcoal (10% wt, 50% wet, 150 mg) with hydrogen under atmospheric pressure and RT for 18 h. The catalyst was separated by filtration through Celite® and the solvent evaporated to the title compound as a brown oil, 1.12 g.

Preparation of 4-[2-(4-methyl-piperazin-1-yl)ethyl]aniline 4-(4-Methylpiperazin-1-yl)carbonylmethylaniline (596 mg, 2.55 mmol) was treated in anhydrous THF (20 mL) under nitrogen with lithium aluminum hydride (291 mg, 2.67 mmol) overnight. The reaction was quenched with water (3×0.29 mL), 15% sodium hydroxide (3×0.29 mL) and again water (3×0.29 mL). The resulting precipitate was removed by filtration. Evaporation of the filtrate afforded the title compound as an orange oil, 380 mg.

Preparation of 3-(2-(dimethylamino)ethyl)benzenamine

The title compound was prepared using a procedure similar to that described in Example 444.

Preparation of N-(2-dimethylaminoethyl)-3-nitrobenzamide

3-Nitrobenzoyl chloride (2 g, 10.77 mmol) was loaded into a round bottomed flask, placed under a $N_2$ atmosphere and dissolved in anhydrous DCM (10 mL). The mixture was cooled to 0° C. and N,N-dimethylethylenediamine (0.98 mL, 8.98 mmol) was added to the reaction. The reaction was allowed to warm to RT and left to stir for 18 h. After 18 h the reaction had given a precipitate which was isolated by filtration and washed with DCM to give 2.28 g of a white solid, which was partitioned between DCM and a saturated aqueous NaHCO$_3$ solution. The organic layer was removed under reduced pressure and the aqueous layer was then re-extracted DCM. The organic layers were combined, dried over $Na_2SO_4$ and the solvent was removed under reduced pressure to afford the title compound as a yellow solid.

Preparation of 3-(N-(2-dimethylaminoethylcarbamoyl))aniline

Palladium on carbon (200 mg, 10% w/w) was loaded to a three-necked flask and EtOH (1 mL) was added. This was then fitted with a three-way tap with balloon. The flask was then placed under vacuum then purged with nitrogen, this was repeated twice more. The amide (2.0 g, 8.4 mmol) was dissolved in EtOH (20 mL), this was then added to the reaction. The reaction was then placed under vacuum and purged with nitrogen three more times. It was then placed under vacuum again then purged with hydrogen, this was repeated once more leaving the balloon filled with hydrogen. The reaction was left at RT overnight under a hydrogen atmosphere. The reaction solution was then filtered through a Celite® plug washing with EtOH. The filtrates were combined and solvent removed to give the title compounds as a clear colourless oil.

Preparation of tert-butyl 4-(3-amino-5-(trifluoromethyl)phenyl)-5,6-dihydropyridine-1(2H)-carboxylate Into a 50 mL round bottom flask was placed 3-bromo-5-(trifluoromethyl)benzenamine (1 g, 4.16 mmol) and DMF (10 mL). To this was added tert-butyl 4-(4,4,5,5-tetramethyl-1,3,2-dioxaborolan-2-yl)-5,6-dihydropyridine-1(2H)-carboxylate (1.67 g, 5.4 mmol), palladium dichlorodiphenylphosphinoferrocene (183 mg, 0.24 mmol), potassium carbonate (2.29 g, 16.6 mmol). Allowed to heat at 80° C. with stirring for 20 h. Work up: Reaction cooled to RT, solvents removed under reduced pressure. Purified via silica column using 0 to 8% MeOH gradient in DCM. Best fractions pooled, solvents removed under reduced pressure. Affords a clear oil. LC-MS (+) shows mass 343 (N+H) as expected for $C_{17}H_{21}F_3N_2O_2$, mw 342.36.

Preparation of 3-(1-methyl-1,2,3,6-tetrahydropyridin-4-yl)-5-(trifluoromethyl)benzenamine Into a 100 mL round bottom flask was placed LAH (1.518 g, 40 mmol) and suspended in THF (30 mL). Flask placed into an ice bath. Tert-butyl 4-(3-amino-5-(trifluoromethyl)phenyl)-5,6-dihydropyridine-1(2H)-carboxylate (1.368 g, 4 mmol) is added to THF (10 mL) and this solution is in turn added dropwise to the LAH suspension at 0° C. 15 min after addition was complete, flask is equipped with reflux condensor and allowed to reflux 15 h with stirring. Work up: Water (1.5 g) is added dropwise, then 15% NaOH(aq)(w/w)(1.5 g), followed by water (3 g). White precipitate forms after 20 h of stirring, filtered solids, removed solvent under reduced pressure. No further purification done. LC-MS (+) shows mass 257 (M+H), as expected for $C_{13}H_{15}F_3N_2$, mw 256.27.

Preparation of 3-(1-methylpiperidin-4-yl)-5-(trifluoromethyl)benzenamine

Into a 100 mL round bottom flask was placed 3-(1-methyl-1,2,3,6-tetrahydropyridin-4-yl)-5-(trifluoromethyl)benzenamine (2.05 g, 8 mmol) and EtOH (40 mL). Flask sparged with argon, then 10% Palladium on carbon (100 mg) is added. Argon removed and replaced with hydrogen via balloon, stirs overnight at RT. Work up: Filtered reaction mixture through Celite® under inert atmosphere. Removed solvents under reduced pressure. Purified via silica column using 0 to 100% 90/10/1 (DCM/MeOH/NH$_4$OH) gradient in DCM. Affords a pale yellow oil. LC-MS (+) shows mass 259 (M+H), as expected for $C_{13}H_{17}F_3N_2$, mw 258.28.

Preparation of $N^2,N^2$-dimethylpyridine-2,5-diamine

2-Chloro-5-nitropyridine (3.57 g, 22.5 mmol), dimethylamine hydrochloride (5.50 g, 67.5 mmol) and diisopropylethylamine (13.7 mL, 78.7 mmol) were combined in DMSO (15 mL) and the reaction mixture was heated at 80° C. for 4 h. After cooling to RT, water was added and the desired N,N-dimethyl-5-nitropyridin-2-amine was isolated by filtration and used in the next step without further purification.

Palladium on carbon (200 mg) was added to a solution of N,N-dimethyl-5-nitropyridin-2-amine (1.29 g, 7.75 mmol) in EtOH (40 mL) and EtOAc (40 mL). The resulting mixture was stirred for 16 h under a H$_2$ atmosphere, filtered and concentrated in vacuo to give the title compound.

Preparation of N,1-dimethyl-N-(2-nitro-4-(trifluoromethyl)phenyl)piperidin-4-amine To a solution of 1-fluoro-2-nitro-4-(trifluoromethyl)benzene (7.5 g, 36 mmol) in THF (180 mL) was added N,1-dimethylpiperidin-4-amine (5.5 g, 43 mmol) and NaHCO$_3$ (6.0 g, 71 mmol). The mixture was stirred at RT and monitored by LCMS for disappearance of starting material. The reaction was filtered, concentrated, and partitioned between H$_2$O and CH$_2$Cl$_2$. The aqueous layer was extracted several times with CH$_2$Cl$_2$, and the organics combined. The organics were washed with brine, dried with MgSO$_4$, filtered, and concentrated to afford the desired product.

Preparation of N1-methyl-N1-(1-methylpiperidin-4-yl)-4-(trifluoromethyl)benzene-1,2-diamine To a solution of N,1-dimethyl-N-(2-nitro-4-(trifluoromethyl)phenyl)piperidin-4-amine (11.3 g, 35.6 mmol) in MeOH (260 mL) at RT was added 10% Pd/C (1.89 g). H$_2$ gas was bubbled through the solution for 5 minutes and the reaction was stirred under an atmosphere of H$_2$ gas. The reaction was monitored by LCMS, and H$_2$ gas was added periodically until consumption of starting material. The mixture was filtered through Celite® with MeOH and concentrated to afford the desired product.

Preparation of 1-Methylcyclopropylamine Hydrochloride

The title compound was prepared according to the method described in patent WO 02/010116 A2.

Preparation of 4-methoxy-3-nitrobenzoyl Chloride 4-methoxy-3-nitrobenzoic acid (10.0 g, 0.051 mol), and thionyl chloride (25 g, 0.212 mol), were refluxed together for 24 h. The reaction mixture was cooled to RT and concentrated to dryness. The off-white solid was carried onto the next step.

Preparation of 4-methoxy-3-nitro-N-(pyridin-2-yl)benzamide 4-methoxy-3-nitrobenzoyl chloride (1.08 g, 0.005 mol), 2-aminopyridine (0.94 g, 0.01 mol) and DIPEA (1.8 mL, 0.01 mol) were allowed to stir in DCM (10 mL) for 48 h to form 4-methoxy-3-nitro-N-(pyridin-2-yl)benzamide. Intermediate was purified via silica column chromatography using 0 to 100% EtOAc in hexane.

Preparation of 3-amino-4-methoxy-N-(pyridine-3-yl)benzamide

Into a 100 mL round bottom flask was placed 4-methoxy-3-nitro-N-(pyridin-2-yl)benzamide (0.735 g, 2.69 mmol), 10% Palladium on carbon (250 mg), EtOH (50 mL), and acetic acid (10 mL) under inert atmosphere. Atmosphere then exchanged with hydrogen (via balloon) and allowed to stir 24 h at RT. Reaction mixture was filtered through Celite®, concentrated under reduced pressure, then purified via silica column chromatography using 0 to 100% EtOAc in hexane. MS m/z=244 [M+H]$^+$. Calc'd for $C_{13}H_{13}N_3O_2$: 243.3.

Preparation of 1-methyl-4-(2-nitro-4-(trifluoromethyl)phenoxy)piperidine 1-methylpiperidin-4-ol (2.99 mmol, 344.4 mg) was added to a suspension of potassium tert-butoxide in THF (5 mL) and stirred at RT for 30 minutes. 2-fluoro-5-trifluoromethyl nitrobenzene (2.39 mmol, 500 mg) was then added and the reaction mixture was stirred an additional 5 h at RT, at which time LC-MS showed complete conversion to the desired product. The reaction mixture was concentrated and the dark brown residue was taken up in methylene chloride (25 mL). This was washed with water (3×20 mL), dried over sodium sulfate, filtered and concentrated to give the crude product as a yellow oil. Crude material (>90% purity) was taken to the next step without further purification LC-MS: 305.1 (M+H)

Preparation of 2-(1-methylpiperidin-4-yloxy)-5-(trifluoromethyl)benzenamine

10% Palladium on carbon (100 mg) was put into a 100 mL round bottom flask and flushed thoroughly with nitrogen. EtOAc (30 mL) was slowly added to the flask, followed by addition of 1-methyl-4-(2-nitro-4-(trifluoromethyl)phenoxy)piperidine (800 mg crude) as a solution in MeOH (3 mL). The flask was evacuated and purged with hydrogen gas several times and then allowed to stir at RT under hydrogen for 18 h. The flask was then evacuated and purged with nitrogen several times. The reaction mixture was filtered through celite and concentrated to give 2-(1-methylpiperidin-4-yloxy)-5-(trifluoromethyl)benzenamine as a yellow solid. (>90% purity) was used without further purification (617.4 mg, 94% for 2 steps). LC-MS: 275.1 (M+H)

Synthesis of 3-((4-methylpiperazin-1-yl)methyl)-5-(trifluoromethyl)-benzenamine

To LAH (1.84 g, 48.5 mmol) in THF (50 ml) at RT was added (4-methylpiperazin-1-yl)(3-nitro-5-trifluoromethyl)phenyl)-methanone (1.54 g, 4.85 mmol) in THF (10 mL). The resulting mixture was refluxed for 5 h. The reaction mixture was cooled to 0° C. at which point water (1.84 mL), 15% aq. NaOH (1.84 mL and water (3.68 mL) were successively added. The resulting mixture was allowed to stir at RT for 1 h. The mixture was filtered through celite, concentrated under reduced pressure and purified via flash chromatography (silica gel, 0 to 25% MeOH in $CH_2Cl_2$, gradient elution) to afford 3-((4-methylpiperazin-1-yl)methyl)-5-(trifluoromethyl)benzenamine as a colorless oil. MS m/z=274 [M+H]$^+$. Calc'd for $C_{13}H_{18}F_3N_3$: 273.3.

Preparation of 1-(3-amino-5-(trifluoromethyl)phenyl)pyrrolidin-2-one.

Into a 16 by 100 mm vial sparged with argon was added 3-amino-5-bromobenzotrifluoride (1 g, 4.16 mmol), 2-pyrrolidinone (425 mg, 5 mmol), N,N'-dimethylethylenediamine (37 mg, 0.416 mmol), potassium carbonate (1.15 g, 8.33 mmol), copper(1)iodide (80 mg, 0.416 mmol), and toluene (1 mL). Vial capped, heated with stirring at 85° C. for 24 h. Reaction cooled to RT, solvent removed under reduced pressure, reconstituted in DCM and filtered through silica. Affords a gray solid. MS m/z=245 [M+H]$^+$. Calc'd for $C_{11}H_{11}F_3N_2O$: 244.2

Preparation of 3-chloro-2,2-dimethyl-N-(2-nitro-4-(trifluoromethyl)phenyl)propanamide To a solution of 2-nitro-4-(trifluoromethyl)benzenamine (3.00 g, 14.9 mmol, 1.0 equiv) in $CH_2Cl_2$ (90 mL) at 25° C., was added 3-chloro-2,2-dimethylpropanoyl chloride (3.9 mL, 29.8 mmol, 2.0 equiv) followed by triethylamine (4.2 mL, 29.8 mmol, 2.0 equiv). The solution was heated to 40° C. After 48 h, the solution was washed with water (50 mL), and brine (50 mL). After concentration in vacuo, the residue was purified by silica gel chromatography (1:10 hexanes:EtOAc to 1:5 hexanes:EtOAc) to afford 3-chloro-2,2-dimethyl-N-(2-nitro-4-(trifluoromethyl)phenyl)propanamide. MS—No (MH$^+$) observed.

Preparation of 3,3-dimethyl-1-(2-nitro-4-(trifluoromethyl)phenyl)azetidin-2-one

To a mixture of 3-chloro-2,2-dimethyl-N-(2-nitro-4-(trifluoromethyl)phenyl)propanamide (3.24 g, 10.0 mmol, 1.0 equiv) in acetone (100 mL) was added $K_2CO_3$ (3.5 g, 25.0 mmol, 2.5 equiv). The mixture was heated to 50° C. for 48 h. After filtering, the solvent was removed in vacuo and the resulting residue purified by silica gel chromatography (1:10 hexanes:EtOAc to 1:5 hexanes:EtOAc) to afford lactam 3. MS (MH$^+$) 289.1; Calculated 289.1 for $C_{12}H_{12}F_3N_2O_3$.

Preparation of 1-(2-amino-4-(trifluoromethyl)phenyl-3,3-dimethylazetidin-2-one

A mixture of 3,3-dimethyl-1-(2-nitro-4-(trifluoromethyl)phenyl)azetidin-2-one (1.67 g, 5.8 mmol, 1.0 equiv) and 10% Pd/C (300 mg) in MeOH (30 mL) was exposed to an atmosphere of $H_2$. After consumption of the starting material, the mixture was filtered and concentrated to afford 1-(2-amino-4-(trifluoromethyl)phenyl-3,3-dimethylazetidin-2-one, which was advanced without further purification. MS (MH$^+$) 259.1; Calculated 259.1 for $C_{12}H_{14}F_3N_2O$.

Preparation of (R)-1-(2-nitro-4-(trifluoromethyl) phenyl)-N,N-dimethylpyrrolidin-3-amine To a solution of 1-fluoro-2-nitro-4-(trifluoromethyl)benzene (0.67 mL, 4.78 mmol) in THF (25 mL) was added (R)-N,N-dimethylpyrrolidin-3-amine (0.66 g, 5.74 mmol) and $NaHCO_3$ (1.1 g, 13.15 mmol). The reaction was stirred at RT and monitored by LCMS for disappearance of starting material and formation of product. The mixture was concentrated, diluted with $CH_2Cl_2$, washed with $H_2O$ and then brine. Drying with $MgSO_4$ was followed by filtration and concentration to afford the product as an orange oil.

Preparation of R)-1-(2-amino-4-(trifluoromethyl) phenyl)-N,N-dimethylpyrrolidin-3-amine To a solution of (R)-N,N-dimethyl-1-(2-nitro-4-(trifluoromethyl)phenyl)pyrrolidin-3-amine (1.75 g, 5.77 mmol) in MeOH (60 mL) was added 10% Pd/C (0.30 g, 0.29 mmol). $H_2$ gas was bubbled through the solution for 5 minutes, and the reaction was stirred at RT under an atmosphere of $H_2$ gas. The reaction was monitored by LCMS for disappearance of starting material and formation of product. The mixture was filtered through celite with MeOH, and concentrated to afford the product as an orange/red oil.

Preparation of 1-(thiazol-2-yl)ethanamine

To a solution 1-(thiazol-2-yl)ethanone (5 g, 0.039 mol) in MeOH (100 mL) ammonium acetate (37.88 g, 0.492 mol) was added at RT and stirred for 20 min. To the resulting mixture, sodium cyanoborohydride (1.73 g, 0.028 mol) was added and the solution was stirred for 1 week at RT. Upon quenching with 6 M HCl (30 mL), the crude product was extracted with $CH_2Cl_2$ and purified through column chromatography using 100% $CH_2Cl_2 \rightarrow 20\%$ 90:10:1 $CH_2Cl_2$:MeOH:$NH_4OH$. The solution was concentrated in vacuo to give the title compound. MS (ESI, pos. ion) m/z: 129 (M+1). Mass calc'd for $C_5N_2S_1H_8$: 128.2.

Although the pharmacological properties of the compounds of Formulas I-VII vary with structural change, in general, activity possessed by compounds of Formulas I-VII may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of Lck kinase at doses less than 10 µM. Compounds of the present invention showed inhibition of c-Met kinase at doses less than 10 µM. Compounds of the present invention also showed inhibition of VEGFR kinase at doses less than 10 µM.

Biological Testing

The efficacy of the compounds of the invention as inhibitors of Lck, VEGFR and/or HGF related activity are demonstrated as follows.

c-Met Receptor Assay

Cloning, Expression and Purification of c-Met Kinase Domain

A PCR product covering residues 1058-1365 of c-Met (c-Met kinase domain) is generated from Human Liver QuickClone™ cDNA (Invitrogen) using forward primer 5'-ATTGACGGATCCATGCTAAATCCA-GAGCTGGTCCAGGCA-3' (SEQ ID NO. 1) and reverse primer 5'-ACAACAGAATTCAATACGGAGCGACA-CATTTTACGTT-3' (SEQ ID NO. 2). The PCR product is cloned into a modified pFastBac1 expression vector (harboring the gene for *S. japonicum* glutathione S-transferase immediately upstream of the multiple cloning site) using standard molecular biological techniques. The GST-c-Met kinase domain fusion (GST-Met) gene is transposed into full-length baculovirus DNA using the BacToBac™ system (Invitrogen). High5 cells are infected with the recombinant baculovirus for 72 h at 27° C. The infected cells are harvested by centrifugation and the pellet is stored at −80° C. The pellet is resuspended in buffer A (50 mM HEPES, pH 8.0, 0.25 M NaCl, 10 mM 2-mercaptoethanol, 10% (w/v) glycerol, 0.5% (v/v) protease inhibitor cocktail (Sigma P8340), stirred at 4° C. to homogeneity, and the cells are disrupted by microfluidization (Microfluidics) at 10,000 psi. The resulting lysate is centrifuged at 50,000×g for 90 min at 4° C., and the supernatant is adsorbed onto 10 mL of glutathione sepharose™ 4B (Amersham) by batch method. The slurry is rocked gently overnight at 4° C. The glutathione resin is harvested by centrifugation and washed three times with 40 mL buffer A by batch method. The resin is washed three times with buffer B (buffer A adjusted to 0.1 M NaCl, less protease inhibitors). The protein is eluted with buffer B containing 25 mM reduced glutathione. Eluted fractions are analyzed by SDS-PAGE and concentrated to <10 mL (~10 mg/mL total protein). The concentrated protein is separated by Superdex™ 200 (Amersham) size exclusion chromatography in buffer C (25 mM Tris, pH 7.5, 0.1 M NaCl, 10 mM 2-mercaptoethanol, 10% glycerol). The fractions are analyzed by SDS-PAGE and the appropriate fractions are pooled and concentrated to ~1 mg/mL. The protein is aliquotted and stored at −80° C.

Alternative Purification of Human GST-cMET from Baculovirus Cells

Baculovirus cells are broken in 5× (volume/weight) of Lysis Buffer (50 mM HEPES, pH 8.0, 0.25 M NaCl, 5 mM mercaptoethanol, 10% glycerol plus Complete Protease Inhibitors (Roche #10019600), 1 tablet per 50 mL buffer). The lysed cell suspension is centrifuged at 100,000×g (29, 300 rpm) in a Beckman ultracentrifuge Ti45 rotor for 1 h. The supernatant is incubated with 10 ml of Glutathione Sepharose 4B from Amersham Biosciences (#27-4574-01). Incubation is carried out overnight in a cold room (approximately 8° C.). The resin and supernatant is poured into an appropriately sized disposable column and the flow through supernatant was collected. The resin is washed with 10 column volumes (100 mL) of Lysis Buffer. The GST-cMET is eluted with 45 mL of 10 mM Glutathione (Sigma #G-4251) in Lysis Buffer. The elution is collected as 15 mL fractions. Aliquots of the elution fractions are run on SDS PAGE (12% Tris Glycine gel, Invitrogen, #EC6005BOX). The gel is stained with 0.25% Coomassie Blue stain. Fractions with GST-cMET are concentrated with a Vivaspin 20 mL Concentrator (#VS2002; 10.00 MW cutoff) to a final volume less than 2.0 ml. The concentrated GST-cMET solution is applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET is eluted with an isocratic run of the above buffer, with the eluent collected in 1.0 mL fractions. Fractions with significant $OD_{280}$ readings are run on another 12% Tris Glycine gel. The peak tubes with GST-cMET are pooled and the $OD_{280}$ is read with the column buffer listed above as the blank buffer.

Phosphorylation of the purified GST-cMET is performed by incubating the protein for 3 h at RT with the following:

|   | Final concentration |
|---|---|
| a) 100 mM ATP (Sigma #A7699) | 25 mM |
| b) 1.0M $MgCl_2$ (Sigma #M-0250) | 100 mM |
| c) 200 mM Sodium Orthovanadate (Sigma #S-6508) | 15 mM |
| d) 1.0M Tris-HCl, pH 7.00 (in house) | 50 mM |
| e) $H_2O$ | |
| f) GST-cMET | 0.2-0.5 mg/mL |

After incubation, the solution is concentrated in a Vivaspin 20 mL Concentrator to a volume less than 2.00 mL. The solution is applied to the same Superdex 75 16/60 column used above after re-equilibration. The GST-cMET is eluted as described above. The elution fractions corresponding to the first eluted peak on the chromatogram are run on a 12% Tris Glycine gel, as above, to identify the fractions with GST-cMET. Fractions are pooled and the $OD_{280}$ is read with the column buffer used as the blank.

A Kinase reaction Buffer is prepared as follows:

|  |  |  | Per 1 L |
|---|---|---|---|
| 60 mM HEPES $p$H 7.4 | 1M stock | 16.7 X | 60 mL |
| 50 mM NaCl | 5M stock | 100 X | 10 mL |
| 20 mM MgCl$_2$ | 1M stock | 50 X | 20 mL |
| 5 mM MnCl$_2$ | 1M stock | 200 X | 5 mL |

When the assay is carried out, freshly add:

| 2 mM DTT | 1M stock | 500 X |
|---|---|---|
| 0.05% BSA | 5% stock | 100 X |
| 0.1 mM Na$_3$OV$_4$ | 0.1M stock | 1000 X |

The HTRF Buffer Contains:
50 mM Tris-HCl (pH 7.5), 100 mM NaCl, 0.1% BSA, 0.05% Tween 20.5 mM EDTA
Fresh add SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration:
  0.1 nM final Eu-PT66
  11 nM final SA-APC
Methods:
1. Dilute GST-cMet (P) enzyme in kinase buffer as follows:
Prepare 8 nM GST-cMet (P) working solution (7.32 μM to 8 nM, 915 X, 10 μL to 9.15 mL). In a 96 well clear plate [Costar # 3365] add 100 μL in eleven columns, in one column add 100 μL kinase reaction buffer alone.
2. Assay Plate Preparation:
Use Biomek FX to transfer 10 μL 8 nM GST-cMet (P) enzyme, 48.4 μL kinase reaction buffer, 1.6 μL compound (in DMSO) (Start concentration at 10 mM, 1 mM and 0.1 mM, sequential dilution 1:3 to reach 10 test points) in a 96 well costar clear plate [Costar # 3365], mix several times. Then incubate the plate at RT for 30 min.
3. Prepare Gastrin and ATP working solution in kinase reaction buffer as follows:
Prepare 4 μM Gastrin and 16 μM ATP working solution

|  |  | Per 10 mL |
|---|---|---|
| Gastrin 4 μM stock | (500 μM to 4 μM, 125 X) | 80 μL |
| ATP 16 μM stock | (1000 μM to 16 μM, 62.5 X) | 160 μL |

Use Biomek FX to add 20 μl ATP and Gastrin Working Solution to the Assay Plate to Start Reaction, Incubate the Plate at RT for 1 h 4. Transfer 5 μL reaction product at the end of 1 h into 80 μL HTRF buffer in black plate [Costar # 3356], read on Discover after 30 min incubation.
Assay Condition Summary:

| K$_M$ ATP* | 6 μM |
|---|---|
| [ATP] | 4 μM |
| K$_M$ Gastrin/p(EY) | 3.8 μM |
| [gastrin] | 1 μM |
| [enzyme] | 1 nM |

K$_M$ ATP, K$_M$ gastrin for various enzymes were determined by HTRF/$^{33}$P labeling and HTRF methods.

c-Met Cell-Based Autophosphorylation Assay

Hunan PC3 and mouse CT26 cells are available obtained from ATCC. The cells were cultured in a growth medium containing RPMI 1640, penicillin/streptomycin/glutamine (1×) and 5% FBS. 2×10$^4$ cells in medium were plated per well in a 96 well plate and incubated at 37° C. overnight. The cells were serum-starved by replacing the growth media with basic medium (DMEM low glucose+0.1 BSA, 120 μL per well) at 37° C. for 16 h. Compounds (either 1 mM and 0.2 mM) in 100% DMSO were serially:diluted (1:3) 3333 fold on a 96 well plate, diluting 1:3 with DMSO from column 1 to 11 (columns 6 and 12 receive no compound). Compound samples (2.4 μL per well) were diluted with basic medium (240 μL) in a 96 well plate. The cells were washed once with basic medium (GIBCO, DMEM 11885-076) then compound solution was added (100 μL). The cells were incubated at 37° C. for 1 h. A (2 mg/mL) solution of CHO-HGF (7.5 μL) was diluted with 30 mL basic medium to provide a final concentration of 500 ng/nL. This HGF-containing media (120 μL) was transferred to a 96 well plate. Compounds (1.2 μL) was added to the HGF-containing media and mixed well. The mixture of media/HGF/compound (100 μL) was added to the cells (final HGF concentration ~250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 μL, Roche Protease inhibitor (Complete, # 1-697-498) 2 tablets, Phosphatase Inhibitor II (Sigma, #P-5726) 200 μL, and a sodium vanadate solution (containing 900 μL PBS, 100 μL 300 mM NaVO$_3$, 6 μL H$_2$O$_2$ (30% stock) and stirred at RT for 15 min) (90 μL). The cells were washed once with ice cold 1×PBS (GIBCO, #14190-136), then lysis buffer (60 μL) was added and the cells were incubated on ice for 20 min.

The IGEN assay was performed as follows: Dynabeads M-280 streptavidin beads were pre-incubated with biotinylated anti-human HGFR (240 μL anti-human-HGFR (R&D system, BAF527 or BAF328)@100 μg/mL+360 μL Beads (IGEN #10029+5.4 μL buffer —PBS/1% BSA/0.1% Tween20) by rotating for 30 min at RT. Antibody beads (25 μL) were transferred to a 96 well plate. Cell lysate solution (25 μL) was transferred added and the plate was shaken at RT for 1 h. Anti-phosphotyrosine 4G10 (Upstate 05-321) (19.7 μL antibody+6 mL 1×PBS) (12.5 μL) was added to each well, then incubated for 1 h at RT. Anti-mouse IgG ORI-Tag (ORI-GEN #110087) (24 μL Antibody+6 mL buffer) (12.5 μL) was added to each well, then incubated at RT for 30 min. 1×PBS (175 μL) was added to each well and the electrochemiluminescence was read by an IGEN M8. Raw data was analyzed using a 4-parameter fit equation in XLFit. IC$_{50}$ values are then determined using Grafit software. Examples 3-4, 9, 25-27, 37-38, 41, 85, 91-93, 87-88, 90, 107-108, 111, 114-115 and 133 exhibited activity in PC3 cells with IC$_{50}$ values less than 1.0 μM. Examples 1, 34, 9, 25-27, 38, 40, 46, 50-51, 53-54, 64, 66, 70, 73, 76, 85, 88-91, 92-93, 87-90, 104-105, 107 and 109-111 exhibited activity in CT26 cells with IC$_{50}$ values less than 1.0 μM.

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+ antibiotics, and spun at 1000 rpm for 10 min. Prior to centrifugation of the cells, a small amount is collected for a cell count. After centrifugation, the medium is discarded, and the cells are resuspended in the appropriate volume of DMEM+ 10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 µL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 µL of each compound dilution are diluted further in a total of 1 mL DMEM+ 10% FBS+antibiotics (400× dilution). Medium containing 0.25% DMSO is also prepared for the 0 µM compound sample. At the 22 h timepoint, the medium is removed from the cells, and 100 µL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/nL or bFGF at 220 ng/mL for 50 ng/mL or 20 ng/mL final concentrations, respectively, are prepared since 10 µL of each will be added to the cells (110 µL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Examples 114-117 and 120-121 inhibited VEGF-stimulated HUVEC proliferation at a level below 500 nM.

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+5% Isofluorane). An otohoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After 24 h in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A.G. Heinz, Irvine Calif.) mounted on a Nikon SMZ-U stereo microscope (A.G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:

0.1% BSA in PBS vehicle: 0.025 g of BSA was added to 25.0 mL of sterile 1× phosphate buffered saline, gently shaken until fully dissolved, and filtered at 0.2 µM. Individual 1.0 mL samples were aliquoted into 25 single-use vials, and stored at −20° C. until use. For the rHu-bFGF disks, a vial of this 0.1% BSA solution was allowed to thaw at RT. Once thawed, 10 µL of a 100 mM stock solution of DTT was added to the 1 ml BSA vial to yield a final concentration of 1 mM DTT in 0.1% BSA.

rHu-VEGF Dilutions: Prior to the disk implant surgery, 23.8 µL of the 0.1% BSA vehicle above was added to a 10 µg rHu-VEGF lyophilized vial yielding a final concentration of 10 µM.

rHu-bFGF: Stock concentration of 180 ng/µL: R&D rHu-bFGF: Added 139 µL of the appropriate vehicle above to the 25 µg vial lyophilized vial. 13.3 µL of the [180 ng/µL]

stock vial and added 26.6 μL of vehicle to yield a final concentration of 3.75 μM concentration.

Nitro-cellulose disk preparation: The tip of a 20-gauge needle was cut off square and beveled with emery paper to create a punch. This tip was then used to cut out ≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 μM rHu-VEGF (R&D Systems, Minneapolis, Minn.), or 3.75 μM rHu-bFGF (R&D Systems, Minneapolis, Minn.) and allowed to soak for 45-60 min before use. Each nitrocellulose filter disk absorbs approximately 0.1 μL of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention will be active at doses less than 150 mpk.

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at doses less than 100 mpk.

LCK-Homogeneous Time Resolved Fluorescent (HTRF) Kinase Assay:

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 μL of compound in 100% DMSO, 15 μL of ATP and biotinylated Gastrin, and 15 μL of LCK KD GST (225-509) for a final volume of 40 μL. The final concentration of gastrin is 1.2 μM. The final concentration of ATP is 0.5 μM (Km app=0.6 μM+/−0.1) and the final concentration of LCK is 250 μM. Buffer conditions are as follows: 50 mM HEPES pH 7.5, 50 mM NaCl, 20 mM MgCl, 5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Human Mixed Lymphocyte Reaction (huMLR):

The purpose of this assay is to test the potency of T cell activation inhibitors in an in vitro model of allogeneic T cell stimulation. Human peripheral blood lymphocytes (hPBL; $2\times10^5$/well) are incubated with mitomycin C-treated B lymphoblastoid cells (JY cell line; $1\times10^5$/well) as allogeneic stimulators in the presence or absence of dilutions of potential inhibitor compound in 96-well round-bottom tissue culture plates. These cultures are incubated at 37° C. in 5% $CO_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter. Examples 289, 314, 325, 342, 467, 541, 583, 589, 611, 657, 732, and 816, for example, inhibited T-cell activation with $IC_{50}$'s below 100 nM.

Jurkat Proliferation/Survival Assay:

The purpose of this assay is to test the general anti-proliferative/cytotoxic effect of compounds on the Jurkat human T cell line. Jurkat cells ($1\times10^5$/well) are plated in 96-well flat-bottom tissue culture plates with or without compound dilutions and cultured for 72 h at 37° C. in 5% $CO_2$. Viable cell number is determined during the last 4 h of culture by adding 10 μL/well WST-1 dye. WST-1 dye conversion relies on active mitochondrial electron transport for reduction of the tetrazolium dye. The dye conversion is read by OD at 450-600 nm.

Anti-CD3/CD28-Induced T Cell IL-2 Secretion and Proliferation Assay:

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates ($1\times10^5$ T cells/well). Cells are cultured for ~20 h at 37° C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and $^3$H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urolcinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan);

drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

FORMULATIONS

Also embraced within this invention is a class of pharmaceutical compositions comprising the active compounds of Formula I-VII in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg, or between about 0.01 and about 20 mg/kg, or between about 0.01 and about 10 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, EtOH, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

What is claimed is:

1. A method of treating cancer in a subject, said method comprising administering an effective amount of a compound of Formula I'

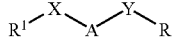

I' wherein R is selected from
- a) substituted or unsubstituted aryl,
- b) substituted or unsubstituted heterocyclyl,
- c) substituted or unsubstituted cycloalkyl,
- d) substituted or unsubstituted cycloalkenyl,
- e) H,
- f) substituted or unsubstituted alkyl,
- g) substituted or unsubstituted alkenyl,
- h) substituted or unsubstituted alkynyl,
- i) alkylaminocarbonyl,
- j) aminocarbonyl, and
- k) cyano;

wherein $R^1$ is

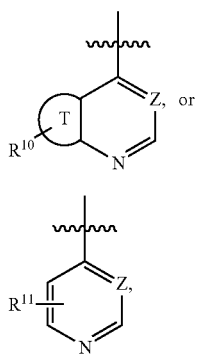

a)

b)

wherein ring T is selected from phenyl and 5-6-membered heteroaryl; wherein Z is selected from N or $CR^x$; wherein $R^x$ is selected from H, CN, $NH_2$, F, alkylcarbonylamino, and alkylaminocarbonyl; wherein $R^{10}$ is one or more substituents selected from H, $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocycly-loxy-$C_{1-6}$-alkoxy, cycloalkyloxy-$C_{1-6}$-alkoxy, aryloxy, heterocyclyloxy, and cycloalkyloxy; wherein $R^{11}$ is selected from amino, alkylamino, alkoxy, aminocarbonyl, alkylaminocarbonyl and H;

wherein A is

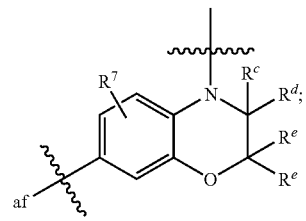

wherein X is selected from O, S, $NR^2$ and $CR^3R^4$;
wherein Y is selected from —$NR^b(CR^3R^4)_p$—, —$NR^bC(=O)(CR^3R^4)_p$—, —$NR^bC(=O)NR^b(CR^3R^4)_p$—, —$NR^bC(=O)(CR^3R^4)_pO$—, —$NR^bC(=O)O(CR^3R^4)_p$—, —$NR^bC(=S)(CR^3R^4)_p$—, —$NR^bC(=NR^a)(CR^3R^4)_p$—, —$NR^bSO_2$—$(CR^3R^4)_p$—, —$OC(=O)(CR^3R^4)_p$—, —$O(CR^3R^4)_p$—, —$(CR^3R^4)_p$—$S(=O)_t$—, —$(CR^3R^4)_p$—, —$S(=O)_2NR^b(CR^3R^4)_p$—, —$S(=O)_t(CR^3R^4)_p$—, —$C(=O)(CR^3R^4)_p$—, —$C(=O)S(CR^3R^4)_p$—, —$C(=NR^a)NR^b(CR^3R^4)_p$—, —$C(=S)NH(CR^3R^4)_p$— and —$C(=O)NR^b(CR^3R^4)_p$—; wherein Y is in either direction;

wherein $R^a$ and $R^b$ is each independently selected from H, alkyl, heterocyclyl, aryl, arylalkyl, heterocyclylalkyl, cycloalkyl, cycloalkylalkyl, alkenyl, alkynyl, $R^5R^5N$—(C=O)—, and $R^5$—(=O)—; wherein each of $R^a$ and $R^b$ is optionally substituted;

wherein $R^c$, $R^d$, $R^e$ and $R^f$ is each independently selected from H, and $C_{1-3}$-alkyl; wherein each of $R^c$, $R^d$, $R^e$ and $R^f$ is optionally substituted;

wherein $R^2$ is selected from H, alkyl, haloalkyl, aryl, heterocyclyl, arylalkyl, heterocyclylalkyl, cycloalkyl, cycloalkylalkyl, alkenyl, alkynyl and $R^5$-carbonyl;

wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;

wherein $R^5$ is selected from H, alkyl, haloalkyl, arylalkyl, heterocyclylalkyl, cycloalkylalkyl, aryl, heterocyclyl, alkenyl, alkynyl and cycloalkyl;

wherein $R^6$ is selected from cyano, —$OR^2$, —$SR^2$, halo, —$SO_2R^2$, —$C(=O)R^2$, —$SO_2NR^2R^5$, —$NR^5C(=O)OR^2$, —$NR^5C(=O)NR^5R^2$, —$NR^5C(=O)R^2$, —$CO_2R^2$, —$C(=O)NR^2R^5$ and —$NR^2R^5$;

wherein $R^7$ is selected from H, halo and $C_{1-3}$-alkyl;

wherein $R^{10}$ is one or more substituents selected from $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$- alkoxy, heterocyclyloxy-$C_{1-6}$-alkoxy, cycloalkyloxy-$C_{1-6}$-alkoxy, aryloxy, heterocyclyloxy, and cycloalkyloxy;

wherein p is 0, 1, 2, or 3; and wherein t is 0, 1 or 2;

wherein each alkyl, aryl, heteroaryl, cycloalkyl, alkenyl, alkynyl, heterocyclyl, and alkoxy moiety of any R, $R^1$, $R^2$, $R^3$, $R^4$, $R^5$, $R^a$ and $R^b$ is optionally substituted with one or more groups selected from halo, —$NH_2$, —OH, —$CO_2H$, ($C_1$-$C_6$)alkylamino, ($C_1$-$C_6$)alkyl, $C_1$-$C_6$) alkoxy, $C_1$-$C_6$)haloalkyl, di($C_1$-$C_6$)alkylamino, ($C_1$-$C_6$) alkylamino-($C_1$-$C_6$)alkyl, ($C_1$-$C_6$)hydroxyalkylamino, ($C_1$-$C_6$)alkylamino-($C_1$-$C_6$)alkylamino, phenyl, and heterocyclyl;

and pharmaceutically acceptable derivatives thereof;

provided R is not methyl when Y is —$CO_2$— or —O—.

2. The method of claim 1 comprising a combination with other active agents selected from antibiotic-type agents, alkylating agents, antimetabolite agents, hormonal agents, immunological agents, interferon-type agents and miscellaneous agents.

3. A method of treating angiogenesis in a subject, said method comprising administering an effective amount of a compound of Formula I'

    I' wherein R is selected from
  a) substituted or unsubstituted aryl,
  b) substituted or unsubstituted heterocyclyl,
  c) substituted or unsubstituted cycloalkyl,
  d) substituted or unsubstituted cycloalkenyl,
  e) H,
  f) substituted or unsubstituted alkyl,
  g) substituted or unsubstituted alkenyl,
  h) substituted or unsubstituted alkynyl,
  i) alkylaminocarbonyl,
  j) aminocarbonyl, and
  k) cyano;
wherein $R^1$ is

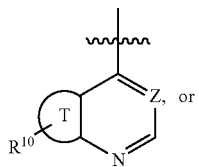    a)

or

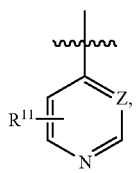    b)

wherein ring T is selected from phenyl and 5-6-membered heteroaryl; wherein Z is selected from N or $CR^x$; wherein $R^x$ is selected from H, CN, $NH_2$, F, alkylcarbonylamino, and alkylaminocarbonyl; wherein $R^{10}$ is one or more substituents selected from H, $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy; wherein $R^{11}$ is selected from amino, alkylamino, alkoxy, aminocarbonyl, alkylaminocarbonyl and H;

wherein A is

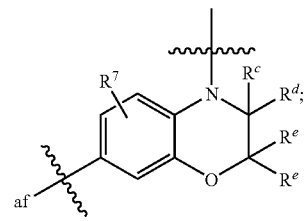

wherein X is selected from O, S, $NR^2$ and $CR^3R^4$;

wherein Y is selected from —$NR^b(CR^3R^4)_p$—, —$NR^bC(=O)(CR^3R^4)_p$—, —$NR^bC(=O)NR^b(CR^3R^4)_p$—, —$NR^bC(=O)(CR^3R^4)_pO$—, —$NR^bC(=O)O(CR^3R^4)_p$—, —$NR^bC(=S)(CR^3R^4)_p$—, —$NR^bC(=NR^a)(CR^3R^4)_p$—, —$NR^bSO_2$—$(CR^3R^4)_p$—, —OC(=O)(CR^3R^4)_p$—, —$O(CR^3R^4)_p$—, —$(CR^3R^4)_pS(=O)_t$—, —$(CR^3R^4)_p$—, —$S(=O)_2NR^b(CR^3R^4)_p$—, —$S(=O)_t(CR^3R^4)_p$—, —$C(=O)(CR^3R^4)_p$—, —$C(=O)S(CR^3R^4)_p$—, —$C(=NR^a)NR^b(CR^3R^4)_p$—, —$C(=S)NH(CR^3R^4)_p$— and —$C(=O)NR^b(CR^3R^4)_p$—; wherein Y is in either direction;

wherein $R^a$ and $R^b$ is each independently selected from H, alkyl, heterocyclyl, aryl, arylalkyl, heterocyclylalkyl, cycloalkyl, cycloalkylalkyl, alkenyl, alkynyl, $R^5R^5N$—(C=O)—, and $R^5$—(=O)—; wherein each of $R^a$ and $R^b$ is optionally substituted;

wherein $R^c$, $R^d$, $R^e$ and $R^f$ is each independently selected from H, and $C_{1-3}$-alkyl; wherein each of $R^c$, $R^d$, $R^e$ and $R^f$ is optionally substituted;

wherein $R^2$ is selected from H, alkyl, haloalkyl, aryl, heterocyclyl, arylalkyl, heterocyclylalkyl, cycloalkyl, cycloalkylalkyl, alkenyl, alkynyl and $R^5$-carbonyl;

wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;

wherein $R^5$ is selected from H, alkyl, haloalkyl, arylalkyl, heterocyclylalkyl, cycloalkylalkyl, aryl, heterocyclyl, alkenyl, alkynyl and cycloalkyl;

wherein $R^6$ is selected from cyano, —$OR^2$, —$SR^2$, halo, —$SO_2R^2$, —$C(=O)R^2$, —$SO_2NR^2R^5$, —$NR^5C(=O)OR^2$, —$NR^5C(=O)NR^5R^2$, —$NR^5C(=O)R^2$, —$CO_2R^2$, —$C(=O)NR^2R^5$ and —$NR^2R^5$;

wherein $R^7$ is selected from H, halo and $C_{1-3}$-alkyl;

wherein $R^{10}$ is one or more substituents selected from $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy;

wherein p is 0, 1, 2, or 3; and wherein t is 0, 1 or 2;

wherein each alkyl, aryl, heteroaryl, cycloalkyl, alkenyl, alkynyl, heterocyclyl, and alkoxy moiety of any R, $R^1$, $R^2$, $R^3$, $R^4$, $R^5$, $R^a$ and $R^b$ is optionally substituted with one or more groups selected from halo, —$NH_2$, —OH, —$CO_2H$, ($C_1$-$C_6$)alkylamino, ($C_1$-$C_6$)alkyl, $C_1$-$C_6$ alkoxy, $C_1$-$C_6$)haloalkyl, di($C_1$-$C_6$)alkylamino, ($C_1$-$C_6$) alkylamino-($C_1$-$C_6$)alkyl, ($C_1$-$C_6$)hydroxyalkylamino, ($C_1$-$C_6$)alkylamino-($C_1$-$C_6$)alkylamino, phenyl, and heterocyclyl;

and pharmaceutically acceptable derivatives thereof;

provided R is not methyl when Y is —$CO_2$— or —O—.

4. A method of treating proliferation-related disorders in a mammal, said method comprising administering an effective amount of a compound of Formula I'

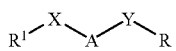
I' wherein R is selected from
  a) substituted or unsubstituted aryl,
  b) substituted or unsubstituted heterocyclyl,
  c) substituted or unsubstituted cycloalkyl,
  d) substituted or unsubstituted cycloalkenyl,
  e) H,
  f) substituted or unsubstituted alkyl,
  g) substituted or unsubstituted alkenyl,
  h) substituted or unsubstituted alkynyl,
  i) alkylaminocarbonyl,
  j) aminocarbonyl, and
  k) cyano;
wherein $R^1$ is

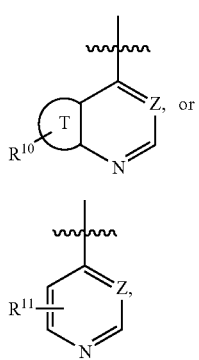

wherein ring T is selected from phenyl and 5-6-membered heteroaryl; wherein Z is selected from N or $CR^x$; wherein $R^x$ is selected from H, CN, $NH_2$, F, alkylcarbonylamino, and alkylaminocarbonyl; wherein $R^{10}$ is one or more substituents selected from H, $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy; wherein $R^{11}$ is selected from amino, alkylamino, alkoxy, aminocarbonyl, alkylaminocarbonyl and H;

wherein A is

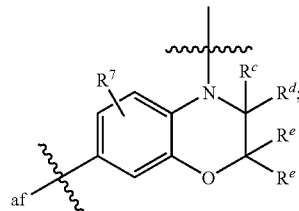

wherein X is selected from O, S, $NR^2$ and $CR^3R^4$;
wherein Y is selected from —$NR^b(CR^3R^4)_p$—, —$NR^bC(=O)(CR^3R^4)_p$—, —$NR^bC(=O)NR^b(CR^3R^4)_p$—, —$NR^bC(=O)(CR^3R^4)_pO$—, —$NR^bC(=O)O(CR^3R^4)_p$—, —$NR^bC(=S)(CR^3R^4)_p$—, —$NR^bC(=NR^a)(CR^3R^4)_p$—, —$NR^bSO_2$—$(CR^3R^4)_p$—, —$OC(=O)(CR^3R^4)_p$—, —$O(CR^3R^4)_p$—, —$(CR^3R^4)_p$—$S(=O)_t$—, —$(CR^3R^4)_p$—, —$S(=O)_2NR^b(CR^3R^4)_p$—, —$S(=O)_t(CR^3R^4)_p$—, —$C(=O)(CR^3R^4)_p$—, —$C(=O)S(CR^3R^4)_p$—, —$C(=NR^a)NR^b(CR^3R^4)_p$—, —$C(=S)NH(CR^3R^4)_p$— and —$C(=O)NR^b(CR^3R^4)_p$—; wherein Y is in either direction;
wherein $R^a$ and $R^b$ is each independently selected from H, alkyl, heterocyclyl, aryl, arylalkyl, heterocyclylalkyl, cycloalkyl, cycloalkylalkyl, alkenyl, alkynyl, $R^5R^5N$—(C=O)—, and $R^5$—(=O)—; wherein each of $R^a$ and $R^b$ is optionally substituted;
wherein $R^c$, $R^d$, $R^e$ and $R^f$ is each independently selected from H, and $C_{1-3}$-alkyl; wherein each of $R^c$, $R^d$, $R^e$ and $R^f$ is optionally substituted;
wherein $R^2$ is selected from H, alkyl, haloalkyl, aryl, heterocyclyl, arylalkyl, heterocyclylalkyl, cycloalkyl, cycloalkylalkyl, alkenyl, alkynyl and $R^5$-carbonyl;
wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;
wherein $R^5$ is selected from H, alkyl, haloalkyl, arylalkyl, heterocyclylalkyl, cycloalkylalkyl, aryl, heterocyclyl, alkenyl, alkynyl and cycloalkyl;
wherein $R^6$ is selected from cyano, —$OR^2$, —$SR^2$, halo, —$SO_2R^2$, —$C(=O)R^2$, —$SO_2NR^2R^5$, —$NR^5C(=O)OR^2$, —$NR^5C(=O)NR^5R^2$, —$NR^5C(=O)R^2$, —$CO_2R^2$, —$C(=O)NR^2R^5$ and —$NR^2R^5$;
wherein $R^7$ is selected from H, halo and $C_{1-3}$-alkyl;
wherein $R^{10}$ is one or more substituents selected from $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy;
wherein p is 0, 1, 2, or 3; and
wherein t is 0, 1 or 2;
wherein each alkyl, aryl, heteroaryl, cycloalkyl, alkenyl, alkynyl, heterocyclyl, and alkoxy moiety of any R, $R^1$, $R^2$, $R^3$, $R^4$, $R^5$, $R^a$ and $R^b$ is optionally substituted with one or more groups selected from halo, —$NH_2$, —OH, —$CO_2H$, ($C_1$-$C_6$)alkylamino, ($C_1$-$C_6$)alkyl, $C_1$-$C_6$) alkoxy, $C_1$-$C_6$)haloalkyl, di($C_1$-$C_6$)alkylamino, ($C_1$-$C_6$) alkylamino-($C_1$-$C_6$)alkyl, ($C_1$-$C_6$)hydroxyalkylamino, ($C_1$-$C_6$)alkylamino-($C_1$-$C_6$)alkylamino, phenyl, and heterocyclyl;

and pharmaceutically acceptable derivatives thereof;

provided R is not methyl when Y is —CO$_2$— or —O—.

5. A method of reducing blood flow in a tumor in a subject, said method comprising administering an effective amount of a compound of Formula I'

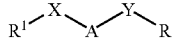

wherein R is selected from
- a) substituted or unsubstituted aryl,
- b) substituted or unsubstituted heterocyclyl,
- c) substituted or unsubstituted cycloalkyl,
- d) substituted or unsubstituted cycloalkenyl,
- e) H,
- f) substituted or unsubstituted alkyl,
- g) substituted or unsubstituted alkenyl,
- h) substituted or unsubstituted alkynyl,
- i) alkylaminocarbonyl,
- j) aminocarbonyl, and
- k) cyano;

wherein R$^1$ is a) 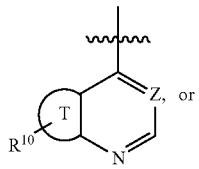

b) 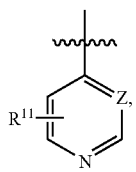

wherein ring T is selected from phenyl and 5-6-membered heteroaryl; wherein Z is selected from N or CR$^x$; wherein R$^x$ is selected from H, CN, NH$_2$, F, alkylcarbonylamino, and alkylaminocarbonyl; wherein R$^{10}$ is one or more substituents selected from H, C$_{1-6}$-alkoxy, C$_{1-6}$-haloalkoxy, C$_{1-6}$-alkylamino-C$_{1-6}$-alkoxy, aryl-C$_{1-6}$-alkoxy, heterocyclyl-C$_{1-6}$-alkoxy, cycloalkyl-C$_{1-6}$-alkoxy, heterocyclyl-C$_{1-6}$-(hydroxyalkoxy), cycloalkyl-C$_{1-6}$-(hydroxyalkoxy), aryl-C$_{1-6}$-(hydroxyalkoxy), C$_{1-6}$-alkoxyalkoxy, aryloxy-C$_{1-6}$-alkoxy, heterocyclyloxy-C$_{1-6}$-alkoxy, cycloalkyloxy-C$_{1-6}$-alkoxy, aryloxy, heterocyclyloxy, and cycloalkyloxy; wherein R$^{11}$ is selected from amino, alkylamino, alkoxy, aminocarbonyl, alkylaminocarbonyl and H;

wherein A is

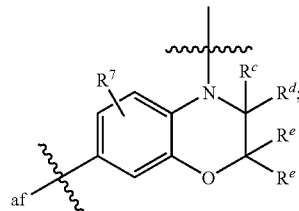

wherein X is selected from O, S, NR$^2$ and CR$^3$R$^4$;

wherein Y is selected from —NR$^b$(CR$^3$R$^4$)$_p$—, —NR$^b$C(=O)(CR$^3$R$^4$)$_p$—, —NR$^b$C(=O)NR$^b$(CR$^3$R$^4$)$_p$—, —NR$^b$C(=O)(CR$^3$R$^4$)$_p$O—, NR$^b$C(=O)O(CR$^3$R$^4$)$_p$—, —NR$^b$C(=S)(CR$^3$R$^4$)$_p$—, NR$^b$C(=NR$^a$)(CR$^3$R$^4$)$_p$—, —NR$^b$SO$_2$—(CR$^3$R$^4$)$_p$—, —OC(=O)(CR$^3$R$^4$)$_p$—, —O(CR$^3$R$^4$)$_p$—, —(CR$^3$R$^4$)$_p$—S(=O)$_t$—, —(CR$^3$R$^4$)$_p$—, —S(=O)$_2$NR$^b$(CR$^3$R$^4$)$_p$—, —S(=O)$_t$(CR$^3$R$^4$)$_p$—, —C(=O)(CR$^3$R$^4$)$_p$—, —C(=O)S(CR$^3$R$^4$)$_p$—, —C(=NR$^a$)NR$^b$(CR$^3$R$^4$)$_p$—, —C(=S)NH(CR$^3$R$^4$)$_p$— and —C(=O)NR$^b$(CR$^3$R$^4$)$_p$—; wherein Y is in either direction;

wherein R$^a$ and R$^b$ is each independently selected from H, alkyl, heterocyclyl, aryl, arylalkyl, heterocyclylalkyl, cycloalkyl, cycloalkylalkyl, alkenyl, alkynyl, R$^5$R$^5$N—(C=O)—, and R$^5$—(=O)—; wherein each of R$^a$ and R$^b$ is optionally substituted;

wherein R$^c$, R$^d$, R$^e$ and R$^f$ is each independently selected from H, and C$_{1-3}$-alkyl; wherein each of R$^c$, R$^d$, R$^e$ and R$^f$ is optionally substituted;

wherein R$^2$ is selected from H, alkyl, haloalkyl, aryl, heterocyclyl, arylalkyl, heterocyclylalkyl, cycloalkyl, cycloalkylalkyl, alkenyl, alkynyl and R$^5$-carbonyl;

wherein R$^3$ and R$^4$ is each independently selected from H, alkyl, aryl, heterocyclyl, arylalkyl, heterocyclylalkyl, haloalkyl, cycloalkyl, cycloalkylalkyl, R$^6$ and alkyl substituted with R$^6$;

wherein R$^5$ is selected from H, alkyl, haloalkyl, arylalkyl, heterocyclylalkyl, cycloalkylalkyl, aryl, heterocyclyl, alkenyl, alkynyl and cycloalkyl;

wherein R$^6$ is selected from cyano, —OR$^2$, —SR$^2$, halo, —SO$_2$R$^2$, —C(=O)R$^2$, —SO$_2$NR$^2$R$^5$, —NR$^5$C(=O)OR$^2$, —NR$^5$C(=O)NR$^5$R$^2$, —NR$^5$C(=O)R$^2$, —CO$_2$R$^2$, —C(=O)NR$^2$R$^5$ and —NR$^2$R$^5$;

wherein R$^7$ is selected from H, halo and C$_{1-3}$-alkyl;

wherein R$^{10}$ is one or more substituents selected from C$_{1-6}$-alkoxy, C$_{1-6}$-haloalkoxy, C$_{1-6}$-alkylamino-C$_{1-6}$-alkoxy, aryl-C$_{1-6}$-alkoxy, heterocyclyl-C$_{1-6}$-alkoxy, cycloalkyl-C$_{1-6}$-alkoxy, heterocyclyl-C$_{1-6}$-(hydroxyalkoxy), cycloalkyl-C$_{1-6}$-(hydroxyalkoxy), aryl-C$_{1-6}$-(hydroxyalkoxy), C$_{1-6}$-alkoxyalkoxy, aryloxy-C$_{1-6}$-alkoxy, heterocyclyloxy-C$_{1-6}$-alkoxy, cycloalkyloxy-C$_{1-6}$-alkoxy, aryloxy, heterocyclyloxy, and cycloalkyloxy;

wherein p is 0, 1, 2, or 3; and wherein t is 0, 1 or 2;

wherein each alkyl, aryl, heteroaryl, cycloalkyl, alkenyl, alkynyl, heterocyclyl, and alkoxy moiety of any R, R$^1$, R$^2$, R$^3$, R$^4$, R$^5$, R$^a$ and R$^b$ is optionally substituted with one or more groups selected from halo, —NH$_2$, —OH, —CO$_2$H, (C$_1$-C$_6$)alkylamino, (C$_1$-C$_6$)alkyl, C$_1$-C$_6$)alkoxy, C$_1$-C$_6$)haloalkyl, di(C$_1$-C$_6$)alkylamino, (C$_1$-C$_6$)alkylamino-(C$_1$-C$_6$)alkyl, (C$_1$-C$_6$)hydroxyalkylamino, (C$_1$-C$_6$)alkylamino-(C$_1$-C$_6$)alkylamino, phenyl, and heterocyclyl;

and pharmaceutically acceptable derivatives thereof;

provided R is not methyl when Y is —CO$_2$— or —O—.

6. A method of reducing tumor size in a subject, said method comprising administering an effective amount of a compound of Formula I'

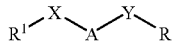  I' wherein R is selected from
a) substituted or unsubstituted aryl,
b) substituted or unsubstituted heterocyclyl,
c) substituted or unsubstituted cycloalkyl,
d) substituted or unsubstituted cycloalkenyl,
e) H,
f) substituted or unsubstituted alkyl,
g) substituted or unsubstituted alkenyl,
h) substituted or unsubstituted alkynyl,
i) alkylaminocarbonyl,
j) aminocarbonyl, and
k) cyano;

wherein R$^1$ is a) 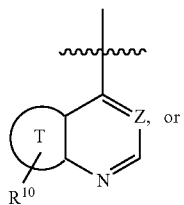

or b) 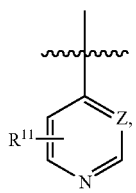

wherein ring T is selected from phenyl and 5-6-membered heteroaryl; wherein Z is selected from N or CR$^x$; wherein R$^x$ is selected from H, CN, NH$_2$, F, alkylcarbonylamino, and alkylaminocarbonyl; wherein R$^{10}$ is one or more substituents selected from H, C$_{1-6}$-alkoxy, C$_{1-6}$-haloalkoxy, C$_{1-6}$-alkylamino-C$_{1-6}$-alkoxy, aryl-C$_{1-6}$-alkoxy, heterocyclyl-C$_{1-6}$-alkoxy, cycloalkyl-C$_{1-6}$-alkoxy, heterocyclyl-C$_{1-6}$-(hydroxyalkoxy), cycloalkyl-C$_{1-6}$-(hydroxyalkoxy), aryl-C$_{1-6}$(hydroxyalkoxy), C$_{1-6}$-alkoxyalkoxy, aryloxy-C$_{1-6}$-alkoxy, heterocyclyloxy-C$_{1-6}$-alkoxy, cycloalkyloxy-C$_{1-6}$-alkoxy, aryloxy, heterocyclyloxy, and cycloalkyloxy; wherein R$^{11}$ is selected from amino, alkylamino, alkoxy, aminocarbonyl, alkylaminocarbonyl and H;

wherein A is

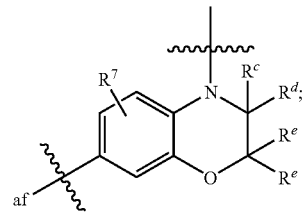

wherein X is selected from O, S, NR$^2$ and CR$^3$R$^4$;
wherein Y is selected from —NR$^b$(CR$^3$R$^4$)$_p$—, —NR$^b$C(=O)(CR$^3$R$^4$)$_p$—, —NR$^b$C(=O)NR$^b$(CR$^3$R$^4$)$_p$—, —NR$^b$C(=O)(CR$^3$R$^4$)$_p$O—, —NR$^b$C(=O)O(CR$^3$R$^4$)$_p$—, —NR$^b$C(=S)(CR$^3$R$^4$)$_p$—, —NR$^b$C(=NR$^a$)(CR$^3$R$^4$)$_p$—, —NR$^b$SO$_2$—(CR$^3$R$^4$)$_p$—, —OC(=O)(CR$^3$R$^4$)$_p$—, —O(CR$^3$R$^4$)$_p$—, —(CR$^3$R$^4$)$_p$—S(=O)$_t$—, —(CR$^3$R$^4$)$_p$—, —S(=O)$_2$NR$^b$(CR$^3$R$^4$)$_p$—, —S(=O)$_t$(CR$^3$R$^4$)$_p$—, —C(=O)(CR$^3$R$^4$)$_p$—, —C(=O)S(CR$^3$R$^4$)$_p$—, —C(=NR$^a$)NR$^b$(CR$^3$R$^4$)$_p$—, —C(=S)NH(CR$^3$R$^4$)$_p$— and —C(=O)NR$^b$(CR$^3$R$^4$)$_p$—; wherein Y is in either direction;

wherein R$^a$ and R$^b$ is each independently selected from H, alkyl, heterocyclyl, aryl, arylalkyl, heterocyclylalkyl, cycloalkyl, cycloalkylalkyl, alkenyl, alkynyl, R$^5$R$^5$N—(C=O)—, and R$^5$—(=O)—; wherein each of R$^a$ and R$^b$ is optionally substituted;

wherein R$^c$, R$^d$, R$^e$ and R$^f$ is each independently selected from H, and C$_{1-3}$-alkyl; wherein each of R$^c$, R$^d$, R$^e$ and R$^f$ is optionally substituted;

wherein R$^2$ is selected from H, alkyl, haloalkyl, aryl, heterocyclyl, arylalkyl, heterocyclylalkyl, cycloalkyl, cycloalkylalkyl, alkenyl, alkynyl and R$^5$-carbonyl;

wherein R$^3$ and R$^4$ is each independently selected from H, alkyl, aryl, heterocyclyl, arylalkyl, heterocyclylalkyl, haloalkyl, cycloalkyl, cycloalkylalkyl, R$^6$ and alkyl substituted with R$^6$;

wherein R$^5$ is selected from H, alkyl, haloalkyl, arylalkyl, heterocyclylalkyl, cycloalkylalkyl, aryl, heterocyclyl, alkenyl, alkynyl and cycloalkyl;

wherein R$^6$ is selected from cyano, —OR$^2$, —SR$^2$, halo, —SO$_2$R$^2$, —C(=O)R$^2$, —SO$_2$NR$^2$R$^5$, —NR$^5$C(=O)OR$^2$, —NR$^5$C(=O)NR$^5$R$^2$, —NR$^5$C(=O)R$^2$, —CO$_2$R$^2$, —C(=O)NR$^2$R$^5$ and —NR$^2$R$^5$;

wherein R$^7$ is selected from H, halo and C$_{1-3}$-alkyl;
wherein R$^{10}$ is one or more substituents selected from C$_{1-6}$-alkoxy, C$_{1-6}$-haloalkoxy, C$_{1-6}$-alkylamino-C$_{1-6}$-alkoxy, aryl-C$_{1-6}$-alkoxy, heterocyclyl-C$_{1-6}$-alkoxy, cycloalkyl-C$_{1-6}$-alkoxy, heterocyclyl-C$_{1-6}$-(hydroxyalkoxy), cycloalkyl-C$_{1-6}$-(hydroxyalkoxy), aryl-C$_{1-6}$-(hydroxyalkoxy), C$_{1-6}$-alkoxyalkoxy, aryloxy-C$_{1-6}$-alkoxy, heterocyclyloxy-C$_{1-6}$-alkoxy, cycloalkyloxy-C$_{1-6}$-alkoxy, aryloxy, heterocyclyloxy, and cycloalkyloxy;

wherein p is 0, 1, 2, or 3; and
wherein t is 0, 1 or 2;
wherein each alkyl, aryl, heteroaryl, cycloalkyl, alkenyl, alkynyl, heterocyclyl, and alkoxy moiety of any R, R$^1$, R$^2$, R$^3$, R$^4$, R$^5$, R$^a$ and R$^b$ is optionally substituted with one or more groups selected from halo, —NH$_2$, —OH, —CO$_2$H, (C$_1$-C$_6$)alkylamino, (C$_1$-C$_6$)alkyl, C$_1$-C$_6$)alkoxy, C$_1$-C$_6$)haloalkyl, di(C$_1$-C$_6$)alkylamino, (C$_1$-C$_6$)alkylamino-(C$_1$-C$_6$)alkyl, (C$_1$-C$_6$)hydroxyalkylamino, (C$_1$-C$_6$)alkylamino-(C$_1$-C$_6$)alkylamino, phenyl, and heterocyclyl;

and pharmaceutically acceptable derivatives thereof;

provided R is not methyl when Y is —CO$_2$— or —O—.

7. A method of treating diabetic retinopathy in a subject, said method comprising administering an effective amount of a compound of Formula I'

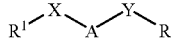

wherein R is selected from
a) substituted or unsubstituted aryl,
b) substituted or unsubstituted heterocyclyl,
c) substituted or unsubstituted cycloalkyl,
d) substituted or unsubstituted cycloalkenyl,
e) H,
f) substituted or unsubstituted alkyl,
g) substituted or unsubstituted alkenyl,
h) substituted or unsubstituted alkynyl,
i) alkylaminocarbonyl,
j) aminocarbonyl, and
k) cyano;

wherein R$^1$ is a) 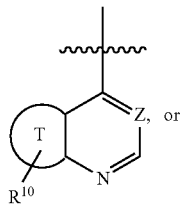

b) 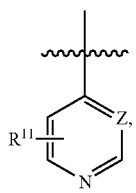

wherein ring T is selected from phenyl and 5-6-membered heteroaryl; wherein Z is selected from N or CR$^x$; wherein R$^x$ is selected from H, CN, NH$_2$, F, alkylcarbonylamino, and alkylaminocarbonyl; wherein R$^{10}$ is one or more substituents selected from H, C$_{1-6}$-alkoxy, C$_{1-6}$-haloalkoxy, C$_{1-6}$-alkylamino-C$_{1-6}$-alkoxy, aryl-C$_{1-6}$-alkoxy, heterocyclyl-C$_{1-6}$-alkoxy, cycloalkyl-C$_{1-6}$-alkoxy, heterocyclyl-C$_{1-6}$-(hydroxyalkoxy), cycloalkyl-C$_{1-6}$—(hydroxyalkoxy), aryl-C$_{1-6}$-(hydroxyalkoxy), C$_{1-6}$-alkoxyalkoxy, aryloxy-C$_{1-6}$-alkoxy, heterocyclyloxy-C$_{1-6}$-alkoxy, cycloalkyloxy-C$_{1-6}$-alkoxy, aryloxy, heterocyclyloxy, and cycloalkyloxy; wherein R$^{11}$ is selected from amino, alkylamino, alkoxy, aminocarbonyl, alkylaminocarbonyl and H;

wherein A is

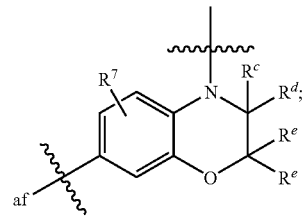

wherein X is selected from O, S, NR$^2$ and CR$^3$R$^4$;
wherein Y is selected from NR$^b$(CR$^3$R$^4$)$_p$—, —NR$^b$C(=O)(CR$^3$R$^4$)$_p$—, —NR$^b$C(=O)NR$^b$(CR$^3$R$^4$)$_p$—, —NR$^b$C(=O)(CR$^3$R$^4$)$_p$O—, —NR$^b$C(=O)O(CR$^3$R$^4$)$_p$—, —NR$^b$C(=S)(CR$^3$R$^4$)$_p$—, —NR$^b$C(=NR$^a$)(CR$^3$R$^4$)$_p$—, —NR$^b$SO$_2$—(CR$^3$R$^4$)$_p$—, —OC(=O)(CR$^3$R$^4$)$_p$—, —O(CR$^3$R$^4$)$_p$—, —(CR$^3$R$^4$)$_p$—S(=O)$_t$—, —(CR$^3$R$^4$)$_p$—, —S(=O)$_2$NR$^b$(CR$^3$R$^4$)$_p$—, —S(=O)$_t$(CR$^3$R$^4$)$_p$—, —C(=O)(CR$^3$R$^4$)$_p$—, —C(=O)S(CR$^3$R$^4$)$_p$—, —C(=NR$^a$)NR$^b$(CR$^3$R$^4$)$_p$—, —C(=S)NH(CR$^3$R$^4$)$_p$— and —C(=O)NR$^b$(CR$^3$R$^4$)$_p$—; wherein Y is in either direction;

wherein R$^a$ and R$^b$ is each independently selected from H, alkyl, heterocyclyl, aryl, arylalkyl, heterocyclylalkyl, cycloalkyl, cycloalkylalkyl, alkenyl, alkynyl, R$^5$R$^5$N—(C=O)—, and R$^5$—(=O)—; wherein each of R$^a$ and R$^b$ is optionally substituted;

wherein R$^c$, R$^d$, R$^e$ and R$^f$ is each independently selected from H, and C$_{1-3}$-alkyl; wherein each of R$^c$, R$^d$, R$^e$ and R$^f$ is optionally substituted;

wherein R$^2$ is selected from H, alkyl, haloalkyl, aryl, heterocyclyl, arylalkyl, heterocyclylalkyl, cycloalkyl, cycloalkylalkyl, alkenyl, alkynyl and R$^5$-carbonyl;

wherein R$^3$ and R$^4$ is each independently selected from H, alkyl, aryl, heterocyclyl, arylalkyl, heterocyclylalkyl, haloalkyl, cycloalkyl, cycloalkylalkyl, R$^6$ and alkyl substituted with R$^6$;

wherein R$^5$ is selected from H, alkyl, haloalkyl, arylalkyl, heterocyclylalkyl, cycloalkylalkyl, aryl, heterocyclyl, alkenyl, alkynyl and cycloalkyl;

wherein R$^6$ is selected from cyano, —OR$^2$, —SR$^2$, halo, —SO$_2$R$^2$, —C(=O)R$^2$, —SO$_2$NR$^2$R$^5$, —NR$^5$C(=O)OR$^2$, —NR$^5$C(=O)NR$^5$R$^2$, —NR$^5$C(=O)R$^2$, —CO$_2$R$^2$, —C(=O)NR$^2$R$^5$ and —NR$^2$R$^5$;

wherein R$^7$ is selected from H, halo and C$_{1-3}$-alkyl;
wherein R$^{10}$ is one or more substituents selected from C$_{1-6}$-alkoxy, C$_{1-6}$-haloalkoxy, C$_{1-6}$-alkylamino-C$_{1-6}$-alkoxy, aryl-C$_{1-6}$-alkoxy, heterocyclyl-C$_{1-6}$-alkoxy, cycloalkyl-C$_{1-6}$-alkoxy, heterocyclyl-C$_{1-6}$-(hydroxyalkoxy), cycloalkyl-C$_{1-6}$-(hydroxyalkoxy), aryl-C$_{1-6}$-(hydroxyalkoxy), C$_{1-6}$-alkoxyalkoxy, aryloxy-C$_{1-6}$-alkoxy, heterocyclyloxy-C$_{1-6}$-alkoxy, cycloalkyloxy-C$_{1-6}$-alkoxy, aryloxy, heterocyclyloxy, and cycloalkyloxy;

wherein p is 0, 1, 2, or 3; and
wherein t is 0, 1 or 2;

wherein each alkyl, aryl, heteroaryl, cycloalkyl, alkenyl, alkynyl, heterocyclyl, and alkoxy moiety of any R, R$^1$, R$^2$, R$^3$, R$^4$, R$^5$, R$^a$ and R$^b$ is optionally substituted with one or more groups selected from halo, —NH$_2$, —OH, —CO$_2$H, (C$_1$-C$_6$)alkylamino, (C$_1$-C$_6$)alkyl, C$_1$-C$_6$)alkoxy, C$_1$-C$_6$)haloalkyl, di(C$_1$-C$_6$)alkylamino, (C$_1$-C$_6$)alkylamino-(C$_1$-C$_6$)alkyl, (C$_1$-C$_6$)hydroxyalkylamino, (C$_1$-C$_6$)alkylamino-(C$_1$-C$_6$)alkylamino, phenyl, and heterocyclyl;

and pharmaceutically acceptable derivatives thereof;
provided R is not methyl when Y is —$CO_2$— or —O—.

8. Method of claim 1 wherein R is selected from H, 6-10 membered aryl, 4-10 membered heterocyclyl, 4-6 membered cycloalkyl, $C_{1-6}$-alkyl, $C_{2-6}$-alkenyl and $C_{2-6}$-alkynyl; wherein R is substituted or unsubstituted.

9. Method of claim 1 wherein R is optionally substituted phenyl or optionally substituted naphthyl.

10. Method of claim 1 wherein R is a substituted or unsubstituted heterocyclyl ring selected from pyrrolidinyl, pyrrolyl, imidazolyl, pyrazolyl, pyrazinyl, pyrimidinyl, pyridyl, quinolinyl, isoquinolinyl, tetrahydrofuryl, 2,3-dihydrothiazolyl, 2,3-dihydrobenzofuryl, 2,3-dihydro-1,4-benzodioxinyl, 1,3-benzodioxolyl, benzisoxazolyl, benzthiazolyl, benzimidazolyl, benzothiadiazolyl, indolinyl, imidazo[1,2-a]pyridyl, isoxazolyl, isothiazolyl, oxazolyl, thiazolyl, thiadiazolyl, furanyl, and thienyl.

11. Method of claim 1 wherein R is 4-6 membered cycloalkyl selected from 1-methyl-cyclopropyl, cyclopropyl, 2-fluorocyclopropyl, cyclobutyl, cyclopentyl and cyclohexyl.

12. Method of claim 1 wherein R is selected from methyl, trifluoromethyl, ethyl, propyl, butyl and pentyl.

13. Method of claim 1 wherein R is selected from cyclohexenyl, ethenyl and propenyl.

14. Method of claim 1 wherein R is H.

15. Method of claim 1 wherein R is dimethylamino.

16. Method of claim 1 wherein $R^1$ is selected from

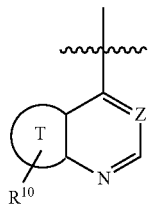

wherein ring T is selected from phenyl and 5-6-membered heteroaryl; wherein Z is selected from N or CH; wherein $R^{10}$ is one or more substituents selected from $R^8O$—; and wherein $R^8$ is selected from $C_{1-6}$-alkyl, $C_{1-6}$-haloalkyl, $C_{1-6}$-alkylamino-$C_{1-6}$-alkyl, aryl-$C_{1-6}$-alkyl, heterocyclyl-$C_{1-6}$-alkyl, cycloalkyl-$C_{1-6}$-alkyl, heterocyclyl-$C_{1-6}$-(hydroxyalkyl), cycloalkyl-$C_{1-6}$-(hydroxyalkyl), aryl-$C_{1-6}$-(hydroxyalkyl), $C_{1-6}$-alkoxyalkyl, aryloxy-$C_{1-6}$-alkyl, heterocyclyloxy-$C_{1-6}$-alkyl, cycloalkyloxy-$C_{1-6}$-alkyl, aryl, heterocyclyl, and cycloalkyl.

17. Method of claim 1 wherein $R^1$ is selected from

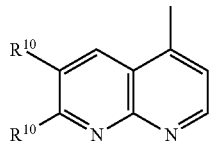 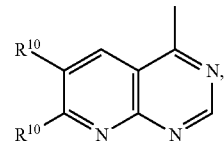

-continued

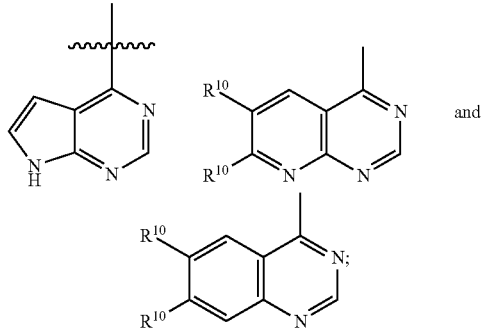

and wherein $R^{10}$ is selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), phenyl-$C_{1-3}$-(hydroxyalkoxy), $C_{1-2}$-alkoxy-$C_{1-3}$-alkoxy, phenyloxy-$C_{1-3}$-alkoxy, 5-6 membered heterocylyloxy-$C_{1-4}$-alkoxy, cycloalkyloxy-$C_{1-3}$-alkoxy, 5-6 membered heterocyclyloxy, and $C_{3-6}$-cycloalkyloxy.

18. Method of claim 1 wherein $R^1$ is selected from pyrrolo[2,3-d]pyrimidin-4-yl, pyrazolo[3,4-b]pyridine-4-yl, 2-aminocarbonyl-4-pyridyl, 2-methylaminocarbonyl-4-pyridyl, 2-methylaminopyrimidin-4-yl, 2-aminopyrimidin-4-yl, 6,7-dimethoxy-4-quinolinyl, 6-methoxy-7-(dimethylaminopropoxy)-4-quinolinyl, 6-methoxy-7-(4-morpholinylpropoxy)-4-quinolinyl, 6,7-dimethoxy-4-quinazolinyl, and 6-methoxy-7-(dimethylaminopropoxy)-4-quinazolinyl.

19. Method of claim 1 wherein Y is selected from —NH$(CH_2)_p$—, —NHC(=O)$(CH_2)_p$—, —NHC(=O)$(CH_2)_p$—, —NHC(=O)O$(CH_2)_p$—, —$(CH_2)_p$—NHC(=O)—, —NHC(=O)NH—, —C(=O)O—, —$NHSO_2$—, and —C(=O)NH$(CH_2)_p$—; and wherein p is 0, 1, or 2.

20. Method of claim 1 wherein Y is selected from —NH—, —NH$CH_2$—, —NH$(CH_2)_3$—, —NH$(CH_2)_3$—, —NHC(=O)$CH_2$—, —NHC(=O)$(CH_2)_2$—, —NHC(=O)—, —NHC(=O)$CH_2$O—, —NHC(=O)O$CH_2$—, —NHC(=O)NH—, —$(CH_2)$NHC(=O)—, —C(=O)O—, —$NHSO_2$—, and —C(=O)NH$CH_2$—.

21. Method of claim 1 wherein R is selected from ethyl, isopropyl, $(CH_3)_3CCH_2$—, ethenyl, and an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; wherein A is naphthyl; wherein X is —O— or —$CH_2$—; wherein Y is selected from —NHC(=O)—, —NHC(=O)$(CH_2)$—, —NHC(=O)$(CH_2)_2$—, —$(CH_2)_p$—NHC(=O)—, —NHC(=O)N— and —$NHSO_2$—; and wherein $R^1$ is selected from 6,7-dimethoxy-4-quinolinyl, 6-methoxy-7-(dimethylaminopropoxy)-4-quinolinyl, 6,7-dimethoxy-4-quinazolinyl, and 6-methoxy-7-(dimethylaminopropoxy)-4-quinazolinyl; and pharmaceutically acceptable derivatives thereof.

* * * * *

SEQUENCE LISTING

<160> NUMBER OF SEQ ID NOS: 2

<210> SEQ ID NO 1
<211> LENGTH: 39
<212> TYPE: DNA
<213> ORGANISM: Homo sapiens

<400> SEQUENCE: 1
attgacggat ccatgctaaa tccagagctg gtccaggca        39

```
<210> SEQ ID NO 2
<211> LENGTH: 37
<212> TYPE: DNA
<213> ORGANISM: Homo sapiens

<400> SEQUENCE: 2
acaacagaat tcaatacgga gcgacacatt ttacgtt                                    37
```